US012655105B2

(12) United States Patent
Donaldson et al.

(10) Patent No.: US 12,655,105 B2
(45) Date of Patent: *Jun. 16, 2026

(54) BIPHENYL AND PHENYLPYRIDINE COMPOUNDS

(71) Applicant: Pfizer Inc., New York, NY (US)

(72) Inventors: Joyann Susan Donaldson, Poway, CA (US); Rebecca Anne Gallego, San Diego, CA (US); Jacqui Elizabeth Hoffman, San Diego, CA (US); Mehran Jalaie, San Diego, CA (US); Justin Ian Montgomery, Ledyard, CT (US); Sacha Ninkovic, La Jolla, CA (US); Gwenaella Christine Rescourio, San Diego, CA (US); Jillian Elyse Spangler, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/286,812

(22) Filed: Jul. 31, 2025

(65) Prior Publication Data

US 2026/0028316 A1 Jan. 29, 2026

Related U.S. Application Data

(63) Continuation of application No. 18/971,728, filed on Dec. 6, 2024.

(60) Provisional application No. 63/719,173, filed on Nov. 12, 2024, provisional application No. 63/637,461, filed on Apr. 23, 2024, provisional application No. 63/607,470, filed on Dec. 7, 2023.

(51) Int. Cl.

| | |
|---|---|
| ***C07D 209/54*** | (2006.01) |
| ***A61K 31/40*** | (2006.01) |
| ***A61K 31/4025*** | (2006.01) |
| ***A61K 31/403*** | (2006.01) |
| ***A61K 31/407*** | (2006.01) |
| ***A61K 31/4155*** | (2006.01) |
| ***A61K 31/4245*** | (2006.01) |
| ***A61K 31/438*** | (2006.01) |
| ***A61K 31/445*** | (2006.01) |
| ***A61K 45/06*** | (2006.01) |
| ***C07D 207/16*** | (2006.01) |
| ***C07D 211/60*** | (2006.01) |
| ***C07D 221/20*** | (2006.01) |
| ***C07D 403/12*** | (2006.01) |
| ***C07D 413/12*** | (2006.01) |
| ***C07D 491/107*** | (2006.01) |

(52) U.S. Cl.

CPC ............ *C07D 209/54* (2013.01); *A61K 31/40* (2013.01); *A61K 31/4025* (2013.01); *A61K 31/403* (2013.01); *A61K 31/407* (2013.01); *A61K 31/4155* (2013.01); *A61K 31/4245* (2013.01); *A61K 31/438* (2013.01); *A61K 31/445* (2013.01); *A61K 45/06* (2013.01); *C07D 207/16* (2013.01); *C07D 211/60* (2013.01); *C07D 221/20* (2013.01); *C07D 403/12* (2013.01); *C07D 413/12* (2013.01); *C07D 491/107* (2013.01)

(58) Field of Classification Search

CPC .. A61K 31/40; A61K 31/4025; A61K 31/403; A61K 31/407; A61K 31/4155; A61K 31/4245; A61K 31/438; A61K 31/445; A61K 45/06; A61P 35/00; C07D 207/16; C07D 209/54; C07D 211/60; C07D 221/20; C07D 401/12; C07D 403/12; C07D 413/12; C07D 491/107

See application file for complete search history.

(56) References Cited

FOREIGN PATENT DOCUMENTS

| | | | |
|---|---|---|---|
| WO | 2013/106643 | A2 | 7/2013 |
| WO | 2019/060693 | A1 | 3/2019 |
| WO | 2019/140387 | A1 | 7/2019 |
| WO | 2019/236483 | A1 | 12/2019 |
| WO | 2019/238816 | A1 | 12/2019 |
| WO | 2019/238817 | A1 | 12/2019 |
| WO | 2019/238886 | A1 | 12/2019 |
| WO | 2020/092907 | A1 | 5/2020 |

(Continued)

OTHER PUBLICATIONS

Abbas, E., et al., "Design, synthesis, cytotoxicity, and molecular docking studies of novel thiazolyl-hydrazone derivatives as histone lysine acetyl-transferase inhibitors and apoptosis inducers," Arch Pharm, 2022, 355(7):1-16.

(Continued)

*Primary Examiner* — Savitha M Rao
(74) *Attorney, Agent, or Firm* — Beau Burton

(57) ABSTRACT

The invention relates to compounds of Formula (I):

(I)

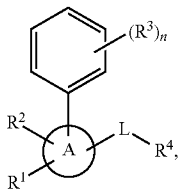

and pharmaceutically acceptable salts thereof to their use in medicine; to compositions containing them; to processes for their preparation; and to intermediates used in such processes. The compounds the present invention may be useful in the treatment, prevention, suppression and amelioration diseases, disorders, and conditions such as cancers.

16 Claims, No Drawings

Specification includes a Sequence Listing.

(56) References Cited

FOREIGN PATENT DOCUMENTS

WO 2020/207395 A1 10/2020

OTHER PUBLICATIONS

Arede, L. and Pina, C., "Buffering noise: KAT2A modular contributions to stabilization of transcription and cell identity in cancer and development," Experimental Hematology, 2021, 93:25-37.
Buckley, D., et al., "Targeting the von Hippel—Lindau E3 Ubiquitin Ligase Using Small Molecules To Disrupt the VHL/HIF-1alphia Interaction," Journal of the American Chemical Society, 2012, 134:4465-4468.
Chang, H and Yeh, MK, "Clinical development of liposome-based drugs: formulation, characterization, and therapeutic efficacy," International Journal of Nanomedicine, 2012, 7:49-60.
Chen Y-J, et al., "A SAGA Complex-Specific Dependency in Multiple Myeloma Orchestrates Oncogenic Transcriptional Programs," Blood, 2023, 142(1):5712.
Dalvie, D., et al., "Assessment of Three Human in Vitro Systems in the Generation of Major Human Excretory and Circulating Metabolites," Chemical Research in Toxicology, 2009, 22(2):357-368.
Finnin, B. and Morgan, T., et al., "Transdermal Penetration Enhancers, Limitations, and Potential," Journal of Pharmaceutical Sciences, 1999, 88(10):955-958.
Hu, Z., et al., "Genomic characterization of genes encoding histone acetylation modulator proteins identifies therapeutic targets for cancer treatment," Nature Communications, 2019, 10(1):733-749.
International Search Report, mailed on Apr. 22, 2025 for WO Application No. PCT/IB2024/062321, 4 pages.
Itoh, Y., et al., "Protein Knockdown Using Methyl Bestatin-Ligand Hybrid Molecules: Design and Synthesis of Inducers of Ubiquitination-Mediated Degradation of Cellular Retinoic Acid-Binding Proteins," Journal of American Chemical Society, 2010, 132:5820-5826.
Mares, A., et al., "Extended pharmacodynamic responses observed upon PROTAC-mediated degradation of RIPK2," Communications Biology, 2020, 3:1-13.
Mustachio L., et al., "Targeting the SAGA and ATAC Transcriptional Coactivator Complexes in MYC-Driven Cancers," Cancer Research, 2020, 80(10):1905-1911.
Pacifico, R., et al., "Discovery of a new class of triazole based inhibitors of acetyl transferase KAT2A," Journal of Enzyme Inhibition and Medicinal Chemistry, 2022, 37(1):1987-1994.
Paulekuhn, G., et al., "Trends in Active Pharmaceutical Ingredient Salt Selection based on Analysis of the Orange Book Database," Journal of Medicinal Chemistry, 2007, 50:6665-6672.
Rautio, J., et al., "The expanding role of prodrugs in contemporary drug design and development," Nature Reviews Drug Discovery, 2018, 17(8):559-587.
Riss, A., et al., "Subunits of ADA-two-A-containing (ATAC) or Spt-Ads-Gcn5-acetyltrasferase (SAGA) Coactivator Complexes Enhance the Acetyltransferase Activity of GCN5," The Journal of Biological Chemistry, 2015, 290 (48):28997-29009.
Soares, P., et al., "Group-Based Optimization of Potent and Cell-Active Inhibitors of the von Hippel-Lindau (VHL) E3 Ubiquitin Ligase: Structure-Activity Relationships Leading to the Chemical Probe (2S,4R)-1-((S)-2-(1-Cyanocyclopropanecarboxamido)-3,3-dimethylbutanoyl)-4-hydroxy-N-(4-(4-methylthiazol-5-yl)benzyl)pyrrolidine-2-carboxamide (VH298)," Journal of Medicinal Chemistry, 2018, 61:599-618.
Tinworth, C., et al., "PROTAC-Mediated Degradation of Bruton's Tyrosine Kinase Is Inhibited by Covalent Binding," ACS Chemical Biology, 2019, 14:342-347.
Written Opinion, mailed on Apr. 22, 2025 for WO Application No. PCT/IB2024/062321, 8 pages.
Zhang, J., et al., "Single amino acid-based PROTACs trigger degradation of the oncogenic kinase BCR-ABL in chronic myeloid leukemia (CML)," Journal of Biological Chemistry, 2023, 299(8):104994.

SEQUENCE LISTING

Sequence total quantity: 3
SEQ ID NO: 1 moltype = AA length = 861
FEATURE Location/Qualifiers
source 1..861
mol_type = protein
organism = Homo sapiens
SEQUENCE: 1
MASHHHHHHD YDGATTENLY FQGSMAEPSQ APTPAPAAQP RPLQSPAPAP TPTPAPSPAS 60
APIPTPTPAP APAPAAAPAG STGTGGPGVG SGGAGSGGDP ARPGLSQQQR ASQRKAQVRG 120
LPRAKKLEKL GVFSACKANE TCKCNGWKNP KPPTAPRMDL QQPAANLSEL CRSCEHPLAD 180
HVSHLENVSE DEINRLLGMV VDVENLFMSV HKEEDTDTKQ VYFYLFKLLR KCILQMTRPV 240
VEGSLGSPPF EKPNIEQGVL NFVQYKFSHL APRERQTMFE LSKMFLLCLN YWKLETPAQF 300
RQRSQAEDVA TYKVNYTRWL CYCHVPQSCD SLPRYETTHV FGRSLLRSIF TVTRRQLLEK 360
FRVEKDKLVP EKRTLILTHF PKFLSMLEEE IYGANSPIWE SGFTMPPSEG TQLVPRPASV 420
SAAVVPSTPI FSPSMGGGSN SSLSLDSAGA EPMPGEKRTL PENLTLEDAK RLRVMGDIPM 480
ELVNEVMLTI TDPAAMLGPE TSLLSANAAR DETARLEERR GIIEFHVIGN SLTPKANRRV 540
LLWLVGLQNV FSHQLPRMPK EYIARLVFDP KHKTLALIKD GRVIGGICFR MFPTQGFTEI 600
VFCAVTSNEQ VKGYGTHLMN HLKEYHIKHN ILYFLTYADE YAIGYFKKQG FSKDIKVPKS 660
RYLGYIKDYE GATLMECELN PRIPYTELSH IIKKQKEIIK KLIERKQAQI RKVYPGLSCF 720
KEGVRQIPVE SVPGIRETGW KPLGKEKGKE LKDPDQLYTT LKNLLAQIKS HPSAWPFMEP 780
VKKSEAPDYY EVIRFPIDLK TMTERLRSRY YVTRKLFVAD LQRVIANCRE YNPPDSEYCR 840
CASALEKFFY FKLKEGGLID K 861

SEQ ID NO: 2 moltype = AA length = 855
FEATURE Location/Qualifiers
source 1..855
mol_type = protein
organism = Homo sapiens
SEQUENCE: 2
MASHHHHHHD YDGATTENLY FQGSSEAGGA GPGGCGAGAG AGAGPGALPP QPAALPPAPP 60
QGSPCAAAAG GSGACGPATA VAAAGTAEGP GGGGSARIAV KKAQLRSAPR AKKLEKLGVY 120
SACKAEESCK CNGWKNPNPS PTPPRADLQQ IIVSLTESCR SCSHALAAHV SHLENVSEEE 180
MNRLLGIVLD VEYLFTCVHK EEDADTKQVY FYLFKLLRKS ILQRGKPVVE GSLEKKPPFE 240
KPSIEQGVNN FVQYKFSHLP AKERQTIVEL AKMFLNRINY WHLEAPSQRR LRSPNDDISG 300
YKENYTRWLC YCNVPQFCDS LPRYETTQVF GRTLLRSVFT VMRRQLLEQA RQEKDKLPLE 360
KRTLILTHFP KFLSMLEEEV YSQNSPIWDQ DFLSASSRTS QLGIQTVINP PPVAGTISYN 420
STSSSLEQPN AGSSSPACKA SSGLEANPGE KRKMTDSHVL EEAKKPRVMG DIPMELINEV 480
MSTITDPAAM LGPETNFLSA HSARDEAARL EERRGVIEFH VVGNSLNQKP NKKILMWLVG 540
LQNVFSHQLP RMPKEYITRL VFDPKHKTLA LIKDGRVIGG ICFRMFPSQG FTEIVFCAVT 600
SNEQVKGYGT HLMNHLKEYH IKHDILNFLT YADEYAIGYF KKQGFSKEIK IPKTKYVGYI 660
KDYEGATLMG CELNPRIPYT EFSVIIKKQK EIIKKLIERK QAQIRKVYPG LSCFKDGVRQ 720
IPIESIPGIR ETGWKPSGKE KSKEPRDPDQ LYSTLKSILQ QVKSHQSAWP FMEPVKRTEA 780
PGYYEVIRFP MDLKTMSERL KNRYYVSKKL FMADLQRVFT NCKEYNPPES EYYKCANILE 840
KFFFSKIKEA GLIDK 855

SEQ ID NO: 3 moltype = AA length = 21
FEATURE Location/Qualifiers
source 1..21
mol_type = protein
organism = synthetic construct
SEQUENCE: 3
ARTKQTARKS TGGKAPRKQL A 21

BIPHENYL AND PHENYLPYRIDINE COMPOUNDS

REFERENCE TO SEQUENCE LISTING

This application is being filed electronically via Patent Center and includes an electronically submitted sequence listing in .xml format. The .xml file contains a sequence listing entitled "PC073057B_Sequence_Listing_ST26.xml" created on Oct. 16, 2025, and having a size of 5,376 bytes. The sequence listing contained in this .xml file is part of the specification and is hereby incorporated by reference herein in its entirety.

BACKGROUND OF THE INVENTION

The present invention relates to novel biphenyl and phenylpyridine compounds. The invention also relates to the preparation of the compounds, intermediates useful in the preparation of the compounds, compositions containing the compounds, and uses of the compounds as KAT2A and KAT2B inhibitors and in the treatment of KAT2A and KAT2B related diseases, such as cancers.

Histone lysine acetyltransferases (HATs) are a group of enzymes responsible for the regulation of essential cell-biological processes, such as DNA repair, replication, and gene transcription. Abbas, Eman M. H. et al. *Archiv der Pharmazie* vol. 355(7) (2022). Lysine acetyltransferase 2A (KAT2A, also known as general control nonderepressible 5 (GCN5)) and lysine acetyltransferase 2B (KAT2B, also known as p300/CBP associated factor (PCAF)) are part of the HAT family.

KAT enzymes perform important regulatory functions in cancer, and thus, are frequently targeted by mutations, translocations, and amplifications. Hu, Z., et al., *Nat Commun.* 10(1):733 (2019). KAT2A and KAT2B are paralogous catalytic subunits in two distinct multiprotein histone modifying complexes, Spt-Ada-Gcn5-Acetyltransferase (SAGA) and Ada-Two-A-Containing (ATAC). KAT2A and KAT2B function as lysine acetyltransferases within these multiprotein complexes to post-translationally modify histones as well as other non-histone proteins, governing their function in biological processes such as transcriptional co-activators.

Outside of the KAT modules, SAGA and ATAC are distinct in composition, reflecting unique functions. Riss, A., et al., *J Biol Chem,* 290(48) (2015): 28997-9009. SAGA and ATAC are targeted to genomic loci through interactions with sequence specific transcription factors and may be stabilized at certain regions through interactions of "reader" domains with specific histone modifications. Due to the divergent subunit composition of both complexes including unique histone reader domain-contain proteins, these complexes may be recruited to specific regions of the genome. Distinct biochemical activates driven by additional subunits of the SAGA complex (e.g., USP22 deubiquitinating enzyme) indicate the potential for unique regulatory functions of SAGA versus ATAC complexes at these sites of recruitment.

In cancer, both SAGA and ATAC have been reported to modify the function of critical regulators of oncogenesis including MYC, E2F, and p53. Mustachio, L. M., Cancer-research vol. 80(10) (2020): 1905-1911. Members of the SAGA complex are found to be upregulated in up to 50% of multiple myeloma cancers. Chen, YJ blood, 603 (2023). KAT2A has been identified as a vulnerability in forms of acute myeloid leukemia and high KAT2A expression has been associated with bad prognosis in breast cancer, non-small cell lung carcinoma, and colon cancer. Arede, L. & Pina C., Experimental hematology, 93 (2021): 25-37. In computational analysis of DepMap CRISPR screening, cancer-specific dependencies of KAT2A and KAT2B network with components of both SAGA and ATAC complexes, suggesting the importance of both complexes in cancer.

Many HAT inhibitors lack of selectivity towards members of the HAT family and, therefore, selectivity for a specific enzyme, for example, KAT2A, is still an outstanding issue.

Accordingly, there remains a need for KAT2 inhibitors that may be useful for the treatment of cancer.

SUMMARY OF THE INVENTION

The present invention provides, in part, compounds of Formula (I), and pharmaceutically acceptable salts thereof, collectively a compound of the invention. Such compounds may inhibit the activity of KAT2A or KAT2B and may be useful in the treatment, prevention, suppression, and amelioration of diseases such as cancers, disorders and conditions mediated by the inhibition of KAT2A or KAT2B, or a combination thereof.

Also provided are pharmaceutical compositions, comprising the compounds or salts of the invention, alone or in combination with additional anticancer therapeutic agents. The present invention also provides, in part, methods for preparing such compounds, pharmaceutically acceptable salts and compositions of the invention, and methods of using the foregoing.

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

According to an embodiment of the invention there is provided a compound of Formula (I):

(I)

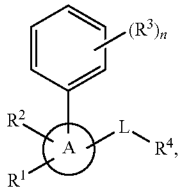

or a pharmaceutically acceptable salt thereof, wherein:

Ring A is phenyl or 5-6 membered N-containing heteroaryl consisting of one or two N atoms and carbon atoms as ring members;

L is a linking group of formula:

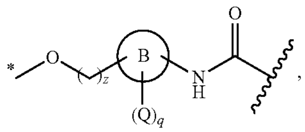

where:

the asterisk * represents the point of attachment to Ring A and the wave line ∿∿∿ represents the point of attachment to $R^4$, z is 0 or 1, q is 0, 1, or 2, each Q is independently —OH, —$CH_3$, or halogen, and Ring B is a $C_3$-$C_6$ cycloalkyl;

one of $R^1$ and $R^2$ is H or halogen and the other one of $R^1$ and $R^2$ is a group of formula (E1-1), (E1-2), (E1-3), (E2-1), (E2-2), or (E3-1):

(E1-1)

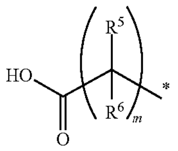

(E1-2)

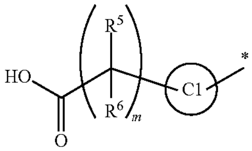

(E1-3)

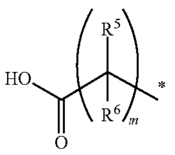

(E2-1)

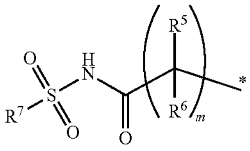

(E2-2)

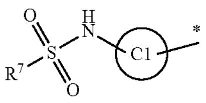

(E3-1)

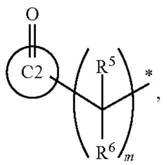

where each asterisk * represents the point of connection to Ring A, m is 0 or 1, $R^5$ and $R^6$ are each independently (i) H, (ii) halogen, (iii) $C_1$-$C_6$ alkyl optionally substituted with 1 to 3 halogens and 1 to 3 —OH, (iv) $C_1$-$C_3$ deuterated alkyl, (v) $C_2$-$C_6$ alkenyl, or (vi) $C_2$-$C_6$ alkynyl, or $R^5$ and $R^6$ together form a $C_3$-$C_6$ cycloalkyl or a 4-6 membered heterocycloalkyl comprising at least one heteroatom selected from the group consisting of N, O, and S, $R^7$ is selected from the group consisting of $C_1$-$C_6$ alkyl optionally substituted with 1 to 3 halogens, $C_3$-$C_5$ cycloalkyl optionally substituted with (i) 1 to 4 halogens or (ii) $C_1$-$C_3$ alkyl optionally substituted with 1 to 3 halogens, and —$NR^8R^9$, wherein $R^3$ and $R^9$ are each independently H or $C_1$-$C_6$ alkyl, or $R^3$ and $R^9$ together form a 4-6 membered N-containing heterocycloalkyl ring optionally substituted with 1 to 4 halogens, Ring C1 is 5-6 membered N-containing heteroaryl optionally substituted with one group selected from (i) $C_1$-$C_3$ alkyl optionally substituted with 1 to 4 halogens, (ii) $C_2$-$C_3$ hydroxyalkyl, and (iii) $C_3$-$C_4$ cycloalkyl, and Ring C2 is 5-6 membered N-containing heterocyclic ring optionally substituted with one group selected from (i) $C_1$-$C_3$ alkyl optionally substituted with 1 to 4 halogens, (ii) $C_2$-$C_3$ hydroxyalkyl, and (iii) $C_3$-$C_4$ cycloalkyl;

n is 1, 2, or 3;

each $R^3$ is independently selected from the group consisting of (i) halogen, (ii) $C_1$-$C_6$ alkyl optionally substituted with 1 to 3 halogens, (iii) $C_2$-$C_6$ alkenyl, (iv) $C_2$-$C_6$ alkynyl, and (v) $C_3$-$C_6$ cycloalkyl optionally substituted with 1 to 4 halogens; and $R^4$ is a 3-6 membered N-containing heterocycloalkyl optionally substituted with 1 to 4 substituents independently selected from the group consisting of:

halogen,

—OH,

—CN, $C_1$-$C_3$ alkyl optionally substituted with 1 to 3 halogens, a spirocyclic $C_3$-$C_6$ cycloalkyl optionally substituted with (i) 1 to 3 halogens or (ii) $C_1$-$C_3$ alkyl optionally substituted with 1 to 3 halogens, and a spirocyclic 3-6 membered heterocycloalkyl comprising at least one heteroatom selected from the group consisting of N, O, and S, and optionally substituted with (i) 1 to 3 halogens or (ii) $C_1$-$C_3$ alkyl optionally substituted with 1 to 3 halogens, wherein the point of attachment to linking group L is at a carbon atom.

Described below are embodiments of the invention, where for convenience Embodiment 1 (E1) is identical to the embodiment of Formula (I) provided above.

It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of the embodiments of the invention and the Examples included herein. It is to be understood that this invention is not limited to specific synthetic methods of making that may of course vary. It is to be also understood that the terminology used herein is for the purpose of describing specific embodiments only and is not intended to be limiting.

E1 A compound of Formula (I) or a pharmaceutically acceptable salt thereof, as defined above.

E2 A compound of embodiment E1 or a pharmaceutically acceptable salt thereof, having formula (II):

(II)

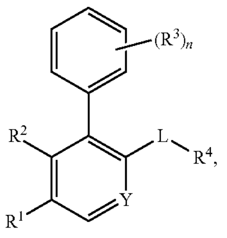

wherein:

Y is N or CH, preferably Y is CH; and n is 1, 2, or 3, preferably n is 1 or 2.

E3 A compound of embodiment E1 or E2, or a pharmaceutically acceptable salt thereof, wherein $R^2$ is H.

E4 A compound of embodiment E1 or E2, or a pharmaceutically acceptable salt thereof, wherein $R^1$ is H.

E5 A compound according to any one of embodiments E1 to E4, or a pharmaceutically acceptable salt thereof, wherein:

n is 1; and $R^3$ is $C_1$-$C_6$ alkyl optionally substituted with 1 to 3 halogens or a $C_3$-$C_6$ cycloalkyl optionally substituted with 1 to 4 halogens, preferably $R^3$ is a $C_1$-$C_3$ alkyl optionally substituted with 1 to 3 halogens or a $C_3$-$C_4$ cycloalkyl optionally substituted with 1 to 4 halogens, more preferably $R^3$ is $—CH_2CH_3$, $—CH_2CF_3$, $—CH(CH_3)_2$, cyclopropyl, or cyclobutyl, and even more preferably $R^3$ is cyclobutyl.

E6 A compound according to embodiment E1, or a pharmaceutically acceptable salt thereof, having formula (II-a1) or (II-b1):

(II-a1)

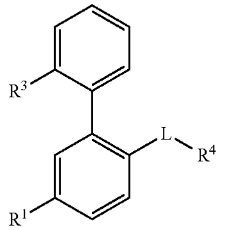

(II-b1)

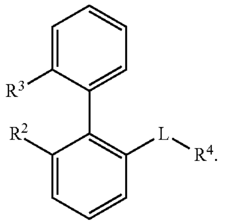

E7 A compound according to any one of embodiments E1 to E4, or a pharmaceutically acceptable salt thereof, wherein:

n is 2;

one $R^3$ is $R^{3A}$ and is selected from the group consisting of a $C_1$-$C_6$ alkyl optionally substituted with 1 to 3 halogens and a $C_3$-$C_6$ cycloalkyl optionally substituted with 1 to 4 halogens, preferably $R^{3A}$ is selected from the group consisting of a $C_1$-$C_3$ alkyl optionally substituted with 1 to 3 halogens and a $C_3$-$C_4$ cycloalkyl optionally substituted with 1 to 4 halogens, more preferably $R^{3A}$ is selected from the group consisting of $—CH_2CH_3$, $—CH_2CF_3$, $—CH(CH_3)_2$, cyclopropyl, and cyclobutyl, and even more preferably $R^{3A}$ is cyclobutyl; and the other $R^3$ is $R^{3B}$ and is halogen, preferably $R^{3B}$ is F.

E8 A compound according to embodiment E1, or a pharmaceutically acceptable salt thereof, having formula (II-a2) or (II-b2):

(II-a2)

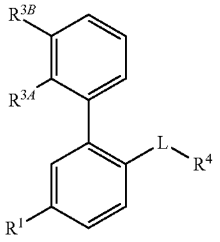

(II-b2)

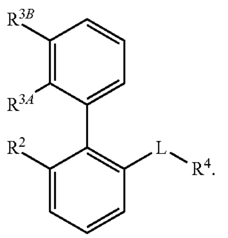

E9 A compound according to any one of embodiments E1 to E8, or a pharmaceutically acceptable salt thereof, wherein $R^4$ is a group of formula (E4-1), (E4-2), (E4-3), (E4-4), (E4-5), (E4-6), (E5-1), (E5-2), (E5-3), (E5-4), (E5-5), (E5-6), (E5-7), (E5-8), or (E5-9):

(E4-1)

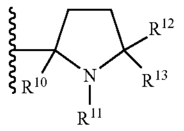

(E4-2)

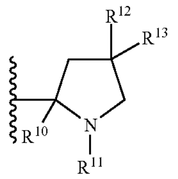

(E4-3)

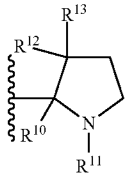

(E4-4)

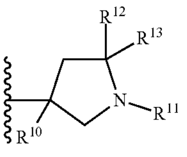

(E4-5)

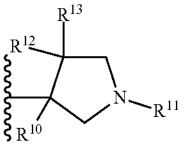

-continued (E4-6)

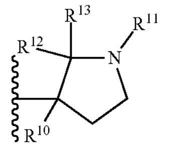

(E5-1)

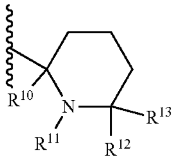

(E5-2)

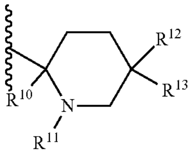

(E5-3)

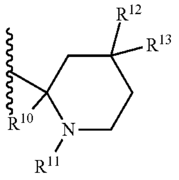

(E5-4)

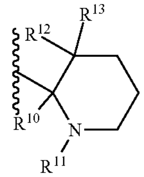

(E5-5)

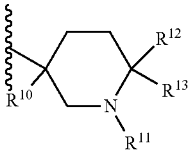

(E5-6)

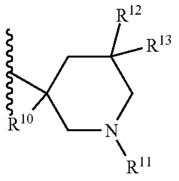

(E5-7)

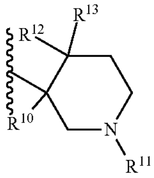

(E5-8)

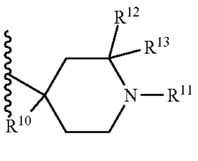

-continued (E5-9)

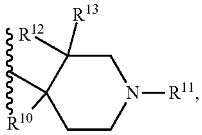

wherein:

the wave line represents the point of attachment to linking group L;

$R^{10}$ is (i) H, (ii) halogen, (iii) —OH, (iv) —CN, or (v) $C_1$-$C_3$ alkyl optionally substituted or halogen;

$R^{11}$ is (i) H, (ii) $C_1$-$C_3$ alkyl optionally substituted with 1 to 3 halogens, (iii) $C_2$-$C_3$ hydroxyalkyl, or (iv) $C_1$-$C_3$ deuterated alkyl; and $R^{12}$ and $R^{13}$ are each independently (i) H, (ii) halogen, or (iii) $C_1$-$C_3$ alkyl optionally substituted with 1 to 3 halogens, with the proviso that when $R^{12}$ and $R^{13}$ are adjacent to the ring N of $R^4$, $R^{12}$ and $R^{13}$ are not halogen, or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens;

or $R^{12}$ and $R^{13}$ together form a 3-6 membered heterocycloalkyl comprising at least one heteroatom selected from the group consisting of N, O, and S, and optionally substituted with (i) 1 to 3 halogens or (ii) $C_1$-$C_3$ alkyl optionally substituted with 1 to 3 halogens, with the proviso that when $R^{12}$ and $R^{13}$ are adjacent to the ring N of $R^4$ and form a 3-6 membered heterocycloalkyl, said 3-6 membered heterocycloalkyl is not attached to the $R^4$ ring by a heteroatom.

The proviso "when $R^{10}$ is adjacent to the ring N of $R^4$, $R^{10}$ is not OH or halogen" means that $R^{10}$ in formulae (E4-1), (E4-2), (E4-3), (E5-1), (E5-2), (E5-3), and (E5-4) is not OH or halogen.

The proviso "when $R^{12}$ and $R^{13}$ are adjacent to the ring N of $R^4$, $R^{12}$ and $R^{13}$ are not halogen" means that $R^{12}$ and $R^{13}$ in (E4-1), (E4-4), (E4-6), (E5-1), (E5-5), and (E5-8), are not halogen.

The proviso "when $R^{12}$ and $R^{13}$ are adjacent to the ring N of $R^4$ and form a 3-6 membered heterocycloalkyl, said 3-6 membered heterocycloalkyl is not attached to the $R^4$ ring by a heteroatom" means that $R^{12}$ and $R^{13}$ in (E4-1), (E4-4), (E4-6), (E5-1), (E5-5), and (E5-8), do not form 3-6 membered heterocycloalkyl that attaches to the $R^4$ ring by a heteroatom.

E10 A compound according to embodiment E9, or a pharmaceutically acceptable salt thereof, wherein $R^4$ is a group of formula (E4-2), (E4-4), (E5-6), or (E5-8), wherein:

$R^{10}$ is H or halogen, preferably $R^{10}$ is H or F, with the proviso that when $R^{10}$ is adjacent to the ring N of $R^4$, $R^{10}$ is not halogen;

$R^{11}$ is H, $C_1$-$C_3$ alkyl optionally substituted with 1 to 3 halogens, or $C_1$-$C_3$ deuterated alkyl, preferably $R^{11}$ is H or $C_1$-$C_3$ alkyl, more preferably $R^{11}$ is H, —$CH_3$, or $CD_3$; and $R^{12}$ and $R^{13}$ are each independently H, halogen, or $C_1$-$C_3$ alkyl optionally substituted with 1 to 3 halogens, preferably $R^{12}$ and $R^{13}$ are each $C_1$-$C_3$ alkyl optionally substituted with 1 to 3 halogens, more preferably $R^{12}$ and $R^{13}$ are each —$CH_3$, with the proviso that when $R^{12}$ and $R^{13}$ are adjacent to the ring N of $R^4$, $R^{12}$ and $R^{13}$ are not halogen, or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens, or $R^{12}$ and $R^{13}$ together form a 3-6 membered heterocycloalkyl comprising at least one heteroatom selected from the group consisting of N, O, and S, and optionally substituted with (i) 1 to 3 halogens or (ii) $C_1$-$C_3$ alkyl optionally substituted with 1 to 3 halogens, with the proviso that when $R^{12}$ and $R^{13}$ are adjacent to the ring N of $R^4$ and form a 3-6 membered heterocycloalkyl, said 3-6 membered heterocycloalkyl is not attached to the $R^4$ ring by a heteroatom, preferably $R^{12}$ and $R^{13}$ together form a $C_4$-$C_5$ cycloalkyl optionally substituted with 1 to 3 halogens or $R^{12}$ and $R^{13}$ together form a 4-6 membered heterocycloalkyl comprising at least one heteroatom selected from the group consisting of N and 0, more preferably $R^{12}$ and $R^{13}$ together form a $C_4$-$C_5$ cycloalkyl or $R^{12}$ and $R^{13}$ together form a 6 membered heterocycloalkyl comprising O.

E11 A compound according to any one of embodiments E1 to E10, or a pharmaceutically acceptable salt thereof, wherein $R^4$ is selected from the group consisting of:

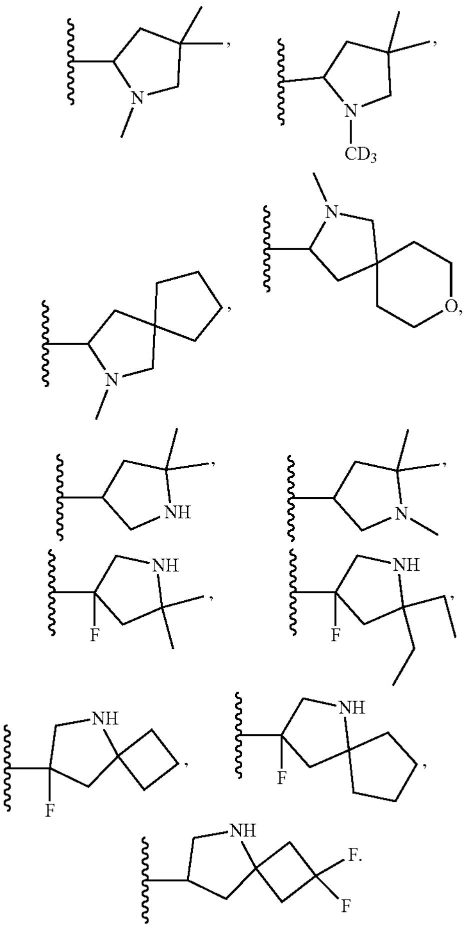

and

E12 A compound according to any one of embodiments E1 to E10, or a pharmaceutically acceptable salt thereof, wherein $R^4$ is selected from the group consisting of:

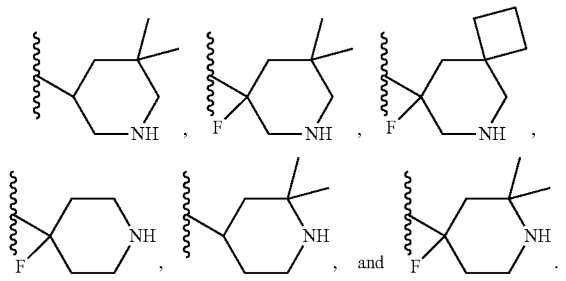

and

E13 A compound according to any one of embodiments E1 to E12, or a pharmaceutically acceptable salt thereof, wherein L is a linking group selected from the group consisting of L1, L2, and L3:

(L1)

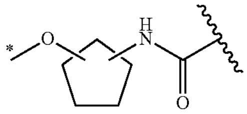

(L2)

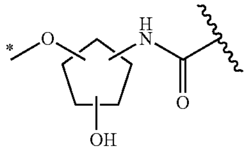

(L3)

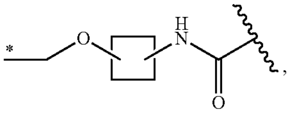

where the asterisk * represents the point of attachment to Ring A and the wave line represents the point of attachment to $R^4$.

E14 A compound according to embodiment E13, or a pharmaceutically acceptable salt thereof, wherein L is a linking group selected from the group consisting of L1', L2', and L3':

(L1')

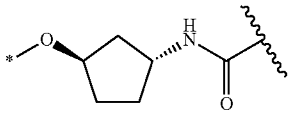

(L2')

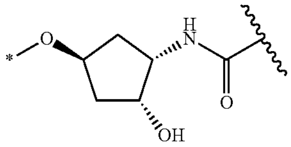

-continued (L3')

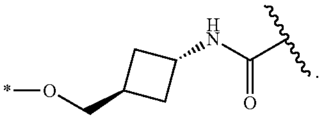

E15 A compound according to any one of embodiments E1 to E14, or a pharmaceutically acceptable salt thereof, wherein:

one of $R^1$ and $R^2$ is H or halogen and the other one of $R^1$ and $R^2$ is a group of formula (E1-1), (E1-2a), (E1-2b), (E1-3), (E2-1), (E2-2a), (E2-2b), or (E3-1a):

(E1-1)

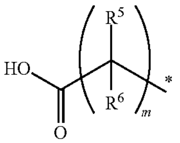

(E1-2a)

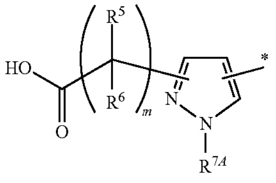

(E1-2b)

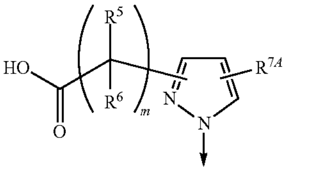

(E1-3)

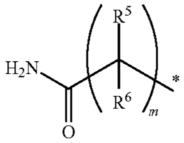

(E2-1)

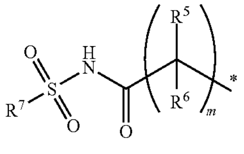

(E2-2a)

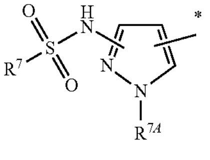

(E2-2b)

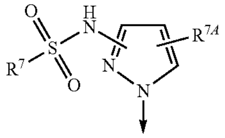

-continued (E3-1a)

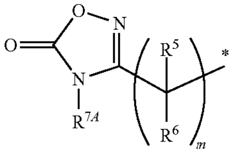

wherein:

each asterisk * represents the point of connection of the other one of $R^1$ and $R^2$ to the Ring A;

m is 0 or 1;

$R^5$ and $R^6$ are each independently (i) H, (ii) halogen, (iii) $C_1$-$C_6$ alkyl optionally substituted with 1 to 3 halogens and 1 to 3 —OH, (iv) $C_2$-$C_6$ alkenyl, or (v) $C_{2-6}$ alkynyl, or $R^5$ and $R^6$ together form a $C_3$-$C_6$ cycloalkyl or a 4-6 membered heterocycloalkyl comprising at least one heteroatom selected from the group consisting of N, O, and S;

$R^7$ is selected from the group consisting of $C_1$-$C_6$ alkyl optionally substituted with 1 to 3 halogens, $C_3$-$C_4$ cycloalkyl optionally substituted with 1 to 4 halogens or a $C_1$-$C_3$ alkyl optionally substituted with 1 to 3 halogens, and —$NR^8R^9$, wherein $R^3$ and $R^9$ are each independently H or $C_1$-$C_6$ alkyl or $R^3$ and $R^9$ together form a 4-6 membered N-containing heterocycloalkyl ring optionally substituted with 1 to 4 halogens; and $R^{7A}$ is (i) H, (ii) $C_1$-$C_3$ alkyl optionally substituted with 1 to 3 halogens, (iii) $C_2$-$C_3$ hydroxyalkyl, or (iv) $C_3$-$C_4$ cycloalkyl.

E16 A compound according to embodiment E15, or a pharmaceutically acceptable salt thereof, wherein:

$R^5$ and $R^6$ are each independently H, halogen, or $C_1$-$C_6$ alkyl optionally substituted with 1 to 3 halogens, or $R^5$ and $R^6$ together form a $C_3$-$C_5$ cycloalkyl or a 4-5 membered heterocycloalkyl comprising at least one heteroatom selected from the group consisting of N, O, and S, preferably $R^5$ and $R^6$ are each independently H, halogen, or $C_1$-$C_3$ alkyl optionally substituted with 1 to 3 halogens, more preferably $R^5$ and $R^6$ are each independently H or $C_1$-$C_3$ alkyl, and even more preferably, $R^5$ and $R^6$ are each independently H or —$CH_3$;

$R^7$ is selected from the group consisting of $C_1$-$C_3$ alkyl optionally substituted with 1 to 3 halogens, $C_3$-$C_4$ cycloalkyl optionally substituted with 1 to 4 halogens or a $C_1$-$C_3$ alkyl optionally substituted with 1 to 3 halogens, —$NR^8R^9$, wherein $R^3$ and $R^9$ are each independently H or $C_1$-$C_3$ alkyl or $R^3$ and $R^9$ together form a 4-5 membered N-containing heterocycloalkyl ring optionally substituted with 1 to 4 halogens, preferably $R^7$ is $C_1$-$C_3$ alkyl, $C_3$-$C_4$ cycloalkyl optionally substituted with 1 to 4 halogens or $C_1$-$C_3$ alkyl, or —$NR^8R^9$, more preferably $R^7$ is —$CH_3$, —$CH_2CH_3$, —$CH(CH_3)_2$, cyclopropyl, cyclopropyl substituted with —$CH_3$, —$NH_2$, —$N(CH_3)_2$, —$N(CH_2CH_3)(CH_3)$, or —$NR^8R^9$, where $R^8$ and $R^9$ together form azetidine optionally substituted with 1 to 3 halogens; and $R^{7A}$ is (i) H, (ii) $C_1$-$C_3$ alkyl optionally substituted with 1 to 3 halogens, (iii) $C_2$-$C_3$ hydroxyalkyl, or (iv) $C_3$-$C_4$ cycloalkyl, preferably $R^{7A}$ is H, $C_1$-$C_3$ alkyl, or $C_3$-$C_4$ cycloalkyl, more preferably $R^{7A}$ is H, $—CH_3$, $—CH_2CH_3$, $—CH(CH_3)_2$, or cyclopropyl.

E17 A compound according to embodiment E15 or E16, or a pharmaceutically acceptable salt thereof, wherein one of $R^1$ and $R^2$ is H and the other one of $R^1$ and $R^2$ is a group of formula (E1-1), (E1-2a), (E1-3), (E2-1), (E2-2b), or (E3-1).

E18 A compound according to any one of embodiments E1 to E17, or a pharmaceutically acceptable salt thereof, wherein one of $R^1$ and $R^2$ is H and the other one of $R^1$ and $R^2$ is selected from the group consisting of:

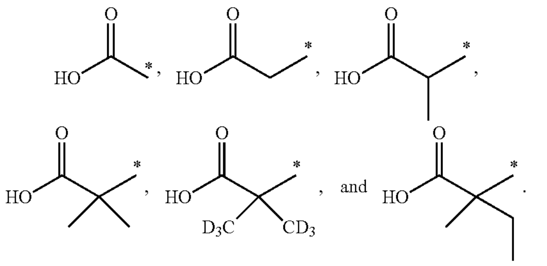

E19 A compound according to any one of embodiments E1 to E17, or a pharmaceutically acceptable salt thereof, wherein one of $R^1$ and $R^2$ is H and the other one of $R^1$ and $R^2$ is selected from the group consisting of:

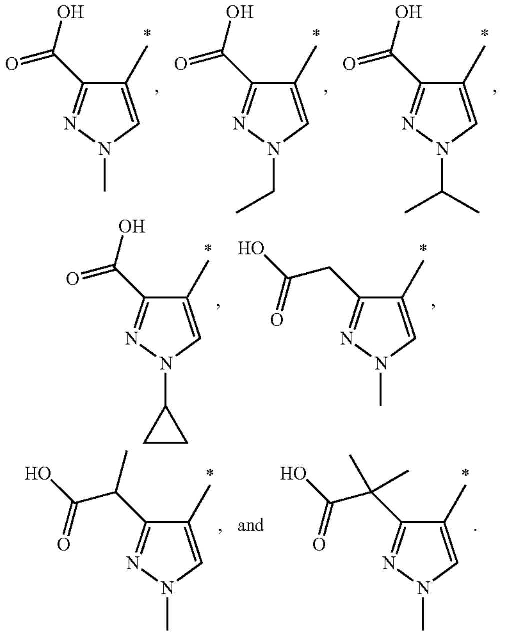

E20 A compound according to any one of embodiments E1 to E17, or a pharmaceutically acceptable salt thereof, wherein one of $R^1$ and $R^2$ is H and the other one of $R^1$ and $R^2$ is:

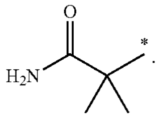

E21 A compound according to any one of embodiments E1 to E17, or a pharmaceutically acceptable salt thereof, wherein one of $R^1$ and $R^2$ is H and the other one of $R^1$ and $R^2$ is selected from the group consisting of:

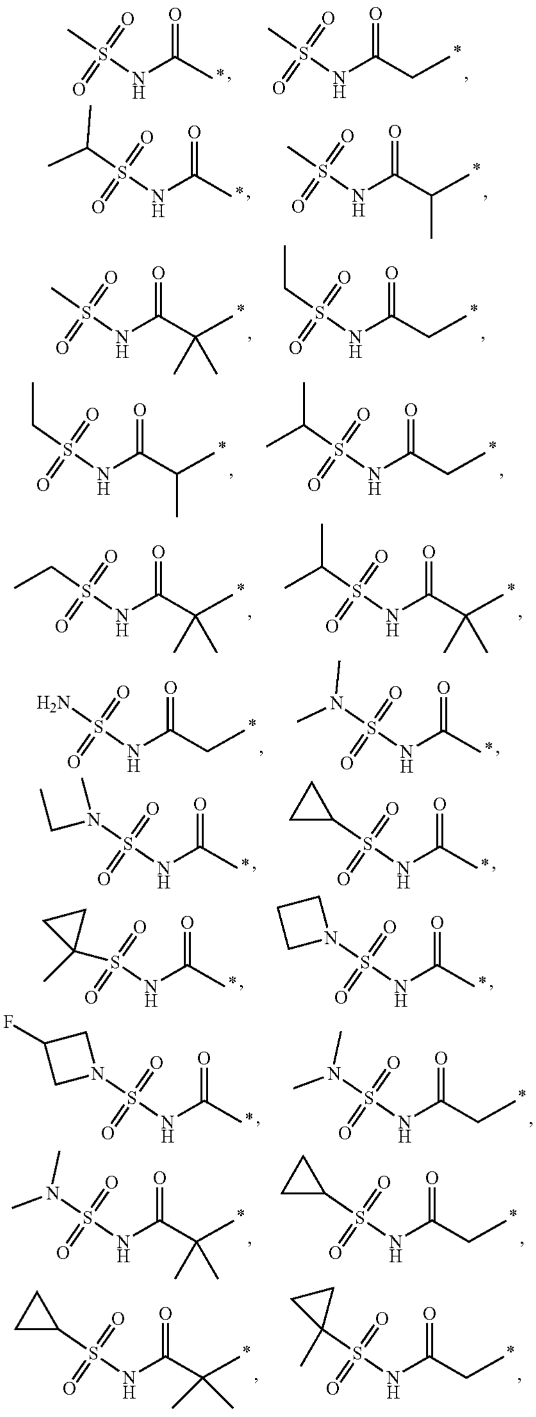

-continued

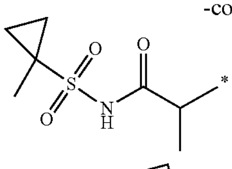
,
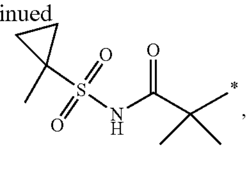
,
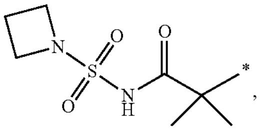
,
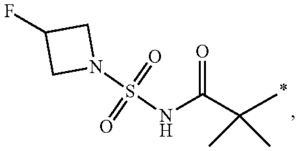
, and
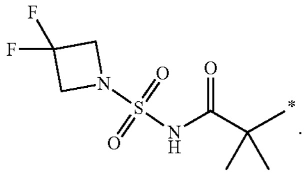
.

E22 A compound according to any one of embodiments E1 to E17, or a pharmaceutically acceptable salt thereof, wherein one of $R^1$ and $R^2$ is H and the other one of $R^1$ and $R^2$ is:

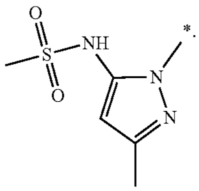
.

E23 A compound according to any one of embodiments E1 to E17, or a pharmaceutically acceptable salt thereof, wherein one of $R^1$ and $R^2$ is H and the other one of $R^1$ and $R^2$ is:

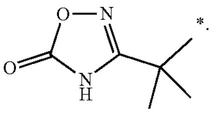
.

E24 A compound according to embodiment E1 or E2, or a pharmaceutically acceptable salt thereof, having formula (IA):

(IA)

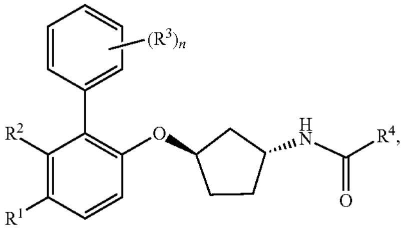
, wherein:

one of $R^1$ and $R^2$ is H and the other one of $R^1$ and $R^2$ is a group of formula (E1-1), (E1-2a), (E1-2b), (E2-1), (E2-2b), or (E3-1a):

(E1-1)

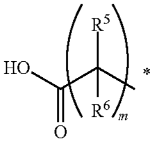

(E1-2a)

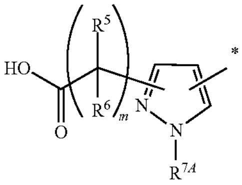

(E1-2b)

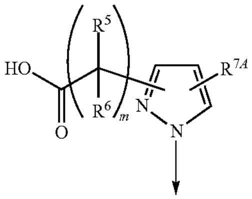

(E2-1)

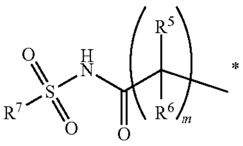

(E2-2b)

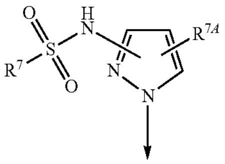

(E3-1a)

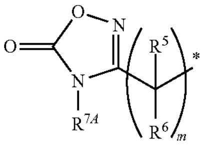

where each asterisk * represents the point of connection of the other one of $R^1$ and $R^2$ to the Ring A, m is 0 or 1, $R^5$ and $R^6$ are each independently (i) H, (ii) halogen, (iii) $C_1$-$C_6$ alkyl optionally substituted with 1 to 3 halogens and 1 to 3 —OH, (iv) $C_2$-$C_6$ alkenyl, or (v) $C_{2-6}$ alkynyl, or $R^5$ and $R^6$ together form a $C_3$-$C_6$ cycloalkyl or a 4-6 membered heterocycloalkyl comprising at least one heteroatom selected from the group consisting of N, O, and S, $R^7$ is selected from the group consisting of $C_1$-$C_6$ alkyl optionally substituted 1 to 3 halogens, $C_3$-$C_4$ cycloalkyl optionally substituted with 1 to 4 halogens or $C_1$-$C_3$ alkyl optionally substituted with 1 to 3 halogens, and —$NR^8R^9$, where $R^3$ and $R^9$ are each independently H or $C_1$-$C_6$ alkyl or $R^3$ and $R^9$ together form a 4-6 membered N-containing heterocycloalkyl ring optionally substituted with 1 to 4 halogens, and $R^{7A}$ is (i) H, (ii) $C_1$-$C_3$ alkyl optionally substituted with 1 to 3 halogens, (iii) $C_2$-$C_3$ hydroxyalkyl, or (iv) $C_3$-$C_4$ cycloalkyl; and $R^4$ is a group of formula (E4-2), (E4-4), (E5-6), or (E5-8):

(E4-2)

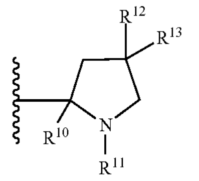

(E4-4)

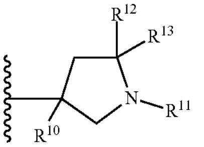

(E5-6)

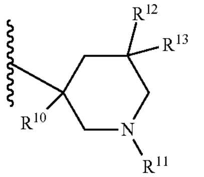

(E5-8)

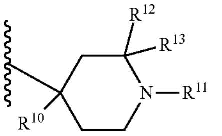

where the wave line ∿∿∿ represents the point of attachment to linking group L, $R^{10}$ is H, halogen, —OH, —CN, or $C_1$-$C_3$ alkyl optionally substituted with 1 to 3 halogens, with the proviso that when $R^{10}$ is adjacent to the ring N of $R^4$, $R^{10}$ is not OH or halogen, $R^{11}$ is H, $C_1$-$C_3$ alkyl, $C_1$-$C_3$ alkyl optionally substituted with 1 to 3 halogens, $C_2$-$C_3$ hydroxyalkyl, or $C_1$-$C_3$ deuterated alkyl, and $R^{12}$ and $R^{13}$ are each independently H, halogen, or $C_1$-$C_3$ alkyl optionally substituted with 1 to 3 halogens, with the proviso that when $R^{12}$ and $R^{13}$ are adjacent to the ring N of $R^4$, $R^{12}$ and $R^{13}$ are not halogen, or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens, or $R^{12}$ and $R^{13}$ together form a 3-6 membered heterocycloalkyl comprising at least one heteroatom selected from the group consisting of N, O, and S, and optionally substituted with (i) 1 to 3 halogens or (ii) $C_1$-$C_3$ alkyl optionally substituted with 1 to 3 halogens, with the proviso that when $R^{12}$ and $R^{13}$ are adjacent to the ring N of $R^4$ and form a 3-6 membered heterocycloalkyl, said 3-6 membered heterocycloalkyl is not attached to the $R^4$ ring by a heteroatom.

E25 A compound according to embodiment E24, or a pharmaceutically acceptable salt thereof, having formula (IA-1):

(IA-1)

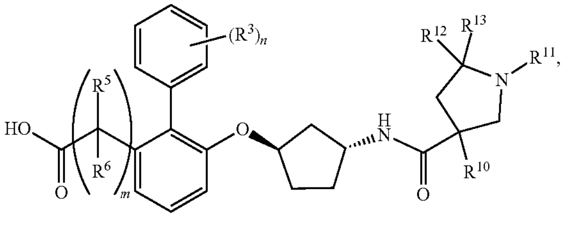

wherein:

m is 0 or 1;

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, or $C_1$-$C_3$ alkyl optionally substituted with 1 to 3 halogens;

$R^{10}$ is H or halogen;

$R^{11}$ is H or $C_1$-$C_3$ alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E26 A compound according to embodiment E25, or a pharmaceutically acceptable salt thereof, having formula (IA-1a) or (IA-1b):

(IA-1a)

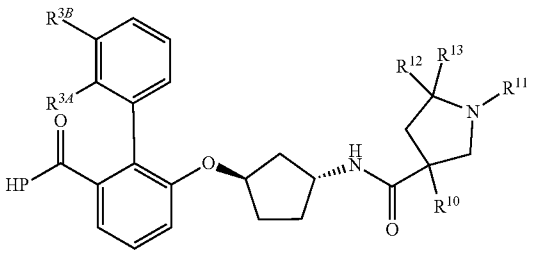

(IA-1b)

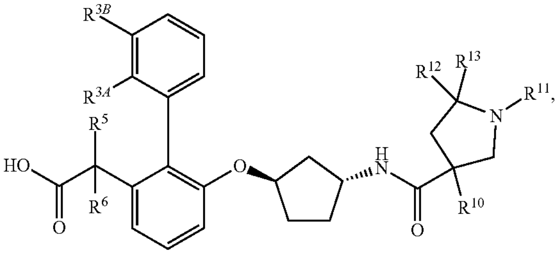

wherein:

$R^{3A}$ is $C_1$-$C_6$ alkyl or $C_3$-$C_4$ cycloalkyl;

$R^{3B}$ is halogen, preferably $R^{3B}$ is F;

$R^5$ and $R^6$ are each independently H or $C_1$-$C_3$ alkyl, preferably $R^5$ and $R^6$ are each independently H, —$CH_3$, or —$CH_2CH_3$;

$R^{10}$ is H or halogen, preferably $R^{10}$ is H or F; and $R^{11}$, $R^{12}$, and $R^{13}$ are each $C_1$-$C_3$ alkyl.

E27 A compound according to embodiment E26, or a pharmaceutically acceptable salt thereof, wherein $R^{3A}$ is cyclobutyl and $R^{3B}$ is F.

E28 A compound according to embodiment E26, or a pharmaceutically acceptable salt thereof, having formula (IA-1a).

E29 A compound according to any one of embodiments E25 to E28, or a pharmaceutically acceptable salt thereof, wherein $R^{10}$ and $R^{11}$ are each H.

E30 A compound according to any one of embodiments E25 to E28, or a pharmaceutically acceptable salt thereof, wherein $R^{12}$ and $R^{13}$ are each —$CH_3$.

E31 A compound according to embodiment E25, which is:

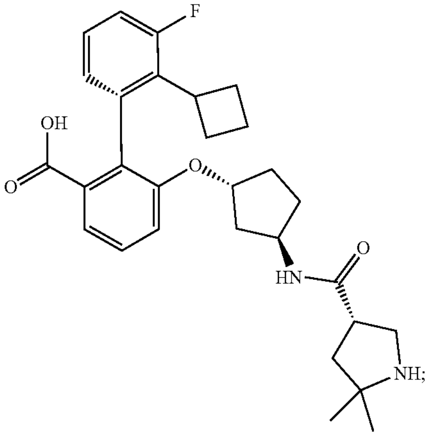

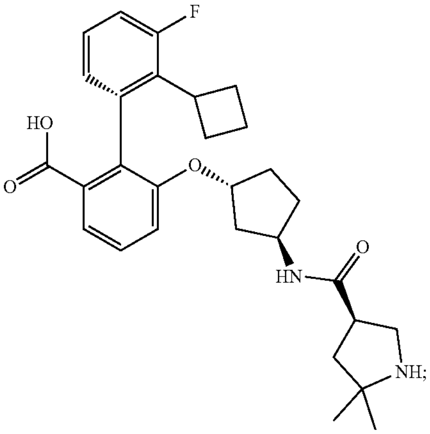

-continued

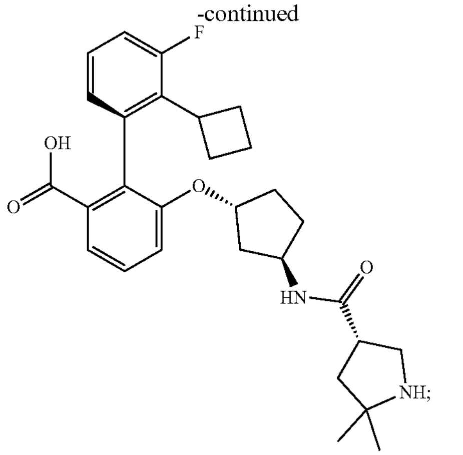

or

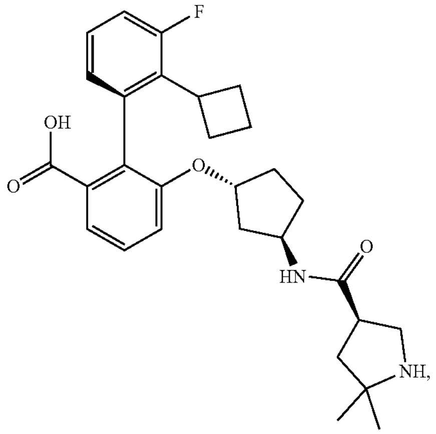

or a pharmaceutically acceptable salt thereof.

E32 A compound according to embodiment E24, or a pharmaceutically acceptable salt thereof, having formula (IA-2):

(IA-2)

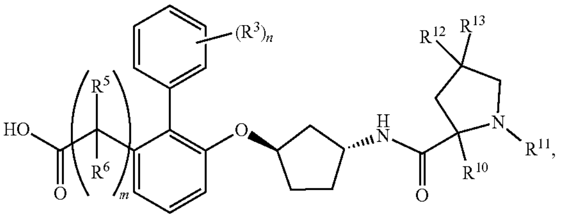

wherein:

m is 0 or 1;

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, or $C_1$-$C_3$ alkyl optionally substituted with 1 to 3 halogens;

$R^{10}$ is H or $C_1$-$C_3$ alkyl;

$R^{11}$ is H or $C_1$-$C_3$ alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E33 A compound according to embodiment E32, or a pharmaceutically acceptable salt thereof, having formula (IA-2a) or (IA-2b):

(IA-2a)

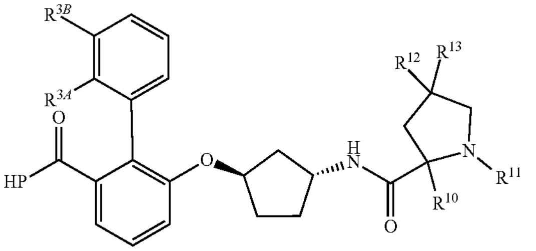

(IA-2b)

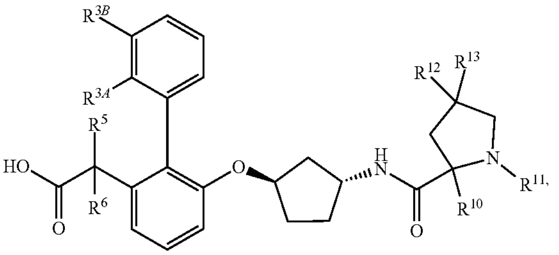

wherein:

$R^{3A}$ is $C_1$-$C_6$ alkyl or $C_3$-$C_4$ cycloalkyl, preferably $R^{3A}$ is —$CH_2CH_3$, —$CH(CH_3)_2$, or $C_3$-$C_4$ cycloalkyl;

$R^{3B}$ is halogen, preferably $R^{3B}$ is F;

$R^5$ and $R^6$ are each independently H or $C_1$-$C_3$ alkyl, preferably $R^5$ and $R^6$ are each independently H, —$CH_3$, or —$CH_2CH_3$;

$R^{10}$ is H or $C_1$-$C_3$ alkyl, preferably $R^{10}$ is H; and $R^{11}$, $R^{12}$, and $R^{13}$ are each $C_1$-$C_3$ alkyl.

E34 A compound according to embodiment E33, or a pharmaceutically acceptable salt thereof, wherein $R^{3A}$ is —$CH(CH_3)_2$ or cyclobutyl and $R^{3B}$ is F.

E35 A compound according to embodiment E33, or a pharmaceutically acceptable salt thereof, having formula (IA-2b), wherein $R^5$ and $R^6$ are each H.

E36 A compound according to any one of embodiments E32 to E35, or a pharmaceutically acceptable salt thereof, wherein $R^{10}$ is H.

E37 A compound according to any one of embodiments E32 to E36, or a pharmaceutically acceptable salt thereof, wherein $R^{11}$, $R^{12}$, and $R^{13}$ are each —$CH_3$.

E38 A compound according to embodiment E32, which is:

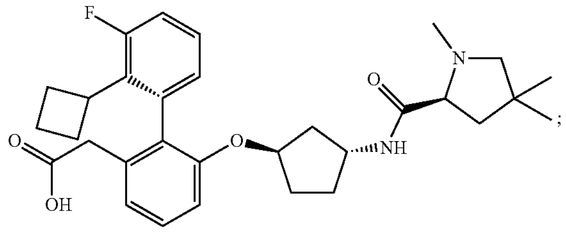

-continued

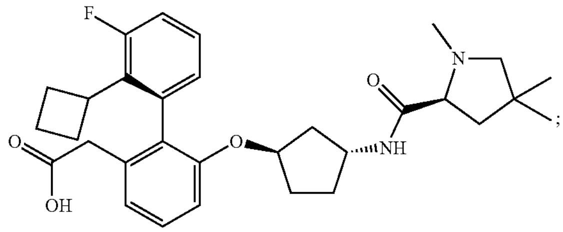

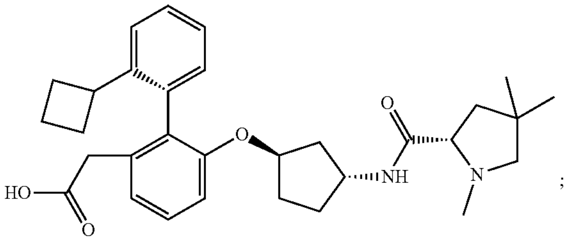

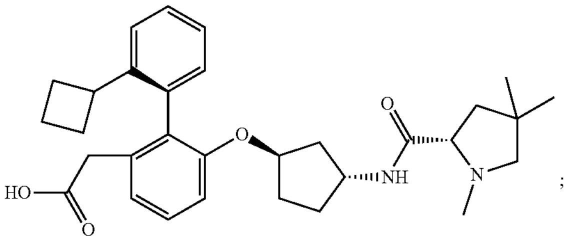

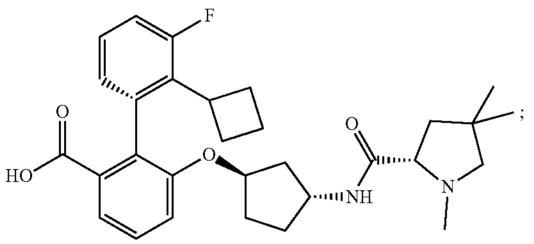

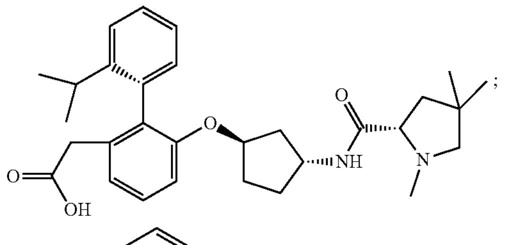

or

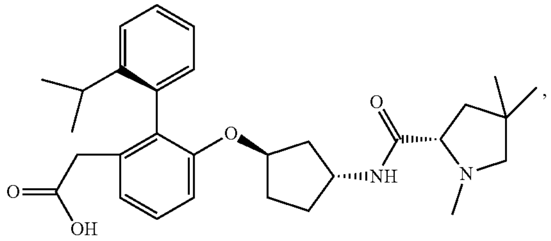

or a pharmaceutically acceptable salt thereof.

E39 A compound according to embodiment E24, or a pharmaceutically acceptable salt thereof, having formula (IA-3) or (IA-3'):

(IA-3)

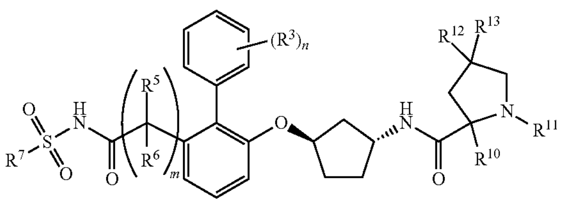

(IA-3')

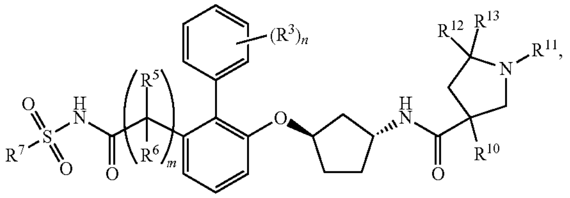

wherein:

m is 0 or 1;

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, or $C_1$-$C_3$ alkyl optionally substituted with 1 to 3 halogens;

$R^7$ is selected from the group consisting of $C_1$-$C_3$ alkyl, $C_3$-$C_4$ cycloalkyl optionally substituted with 1 to 4 halogens or a $C_1$-$C_3$ alkyl optionally substituted with 1 to 3 halogens, and $-NR^{38}R^9$, wherein $R^3$ and $R^9$ are each independently H or $C_1$-$C_3$ alkyl or $R^3$ and $R^9$ together form a 4-5 membered N-containing heterocycloalkyl ring optionally substituted with 1 to 4 halogens;

$R^{10}$ in formula (IA-3) is H or $C_1$-$C_3$ alkyl and $R^{10}$ in formula (IA-3') is H or halogen;

$R^{11}$ is H or $C_1$-$C_3$ alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E40 A compound according to embodiment E39, or a pharmaceutically acceptable salt thereof, having formula (IA-3a), (IA-3b), (IA-3c), or (IA-3d):

(IA-3a)

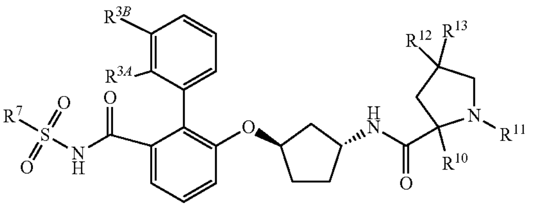

-continued (IA-3b)

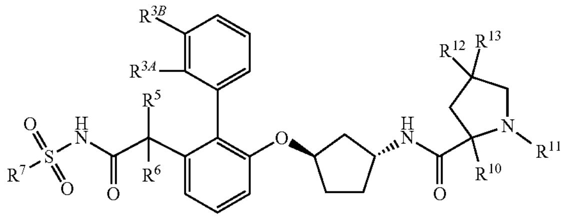

(IA-3c)

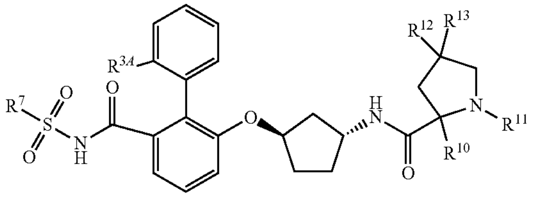

(IA-3d)

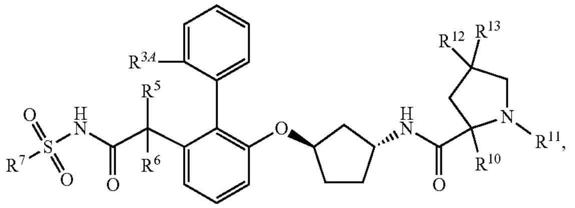

wherein:

$R^{3A}$ is $C_1$-$C_6$ alkyl or $C_3$-$C_4$ cycloalkyl, preferably $R^{3A}$ is $-CH_2CH_3$, $-CH(CH_3)_2$, or $C_3$-$C_4$ cycloalkyl;

$R^{3B}$ is halogen, preferably $R^{3B}$ is F;

$R^5$ and $R^6$ are each independently H or $C_1$-$C_3$ alkyl, preferably $R^5$ and $R^6$ are each independently H, $-CH_3$, or $-CH_2CH_3$;

$R^{10}$ is H or $C_1$-$C_3$ alkyl, preferably $R^{10}$ is H; and $R^{11}$ is H or $C_1$-$C_3$ alkyl;

$R^{12}$ and $R^{13}$ are each $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E41 A compound according to embodiment E40, or a pharmaceutically acceptable salt thereof, wherein $R^{3A}$ is cyclobutyl and $R^{3B}$ is F.

E42 A compound according to embodiment E40 or E41, or a pharmaceutically acceptable salt thereof, having formula (IA-3b) or (IA-3d), wherein $R^5$ and $R^6$ are each H.

E43 A compound according to any one of embodiments E39 to E42, or a pharmaceutically acceptable salt thereof, wherein $R^7$ is $-CH_3$, $-CH_2CH_3$, $-CH(CH_3)_2$, cyclopropyl, cyclopropyl substituted with $-CH_3$, $-NH_2$, $-N((CH)_3)_2$, $-N(CH_3)(CH_2CH_3)$, or azetidine optionally substituted with 1, 2, or 3 F.

E44 A compound according to any one of embodiments E39 to E43, or a pharmaceutically acceptable salt thereof, wherein $R^{10}$ is H and $R^{11}$ is $-CH_3$.

E45 A compound according to any one of embodiments E39 to E44, or a pharmaceutically acceptable salt thereof, wherein $R^{12}$ and $R^{13}$ are each $-CH_3$.

E46 A compound according to any one of embodiments E39 to E44, or a pharmaceutically acceptable salt thereof, wherein $R^{12}$ and $R^{13}$ together form a cyclopentyl.

E47 A compound according to embodiment E39, which is:
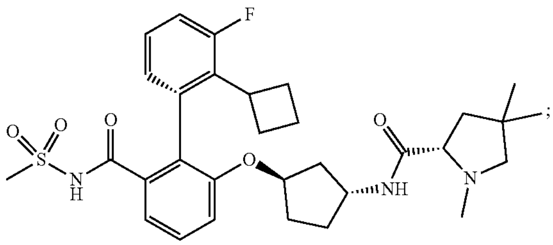
;
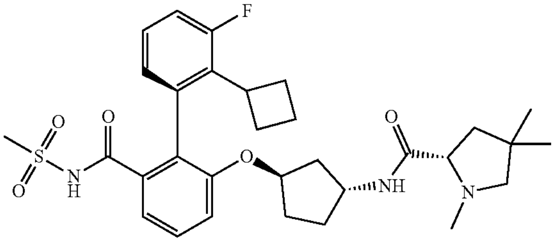
;
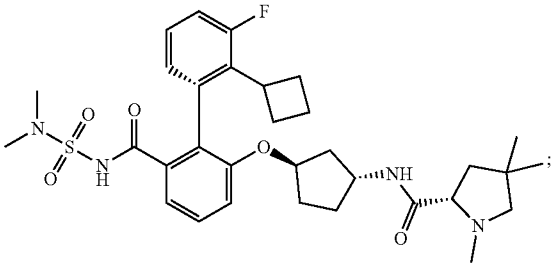
;
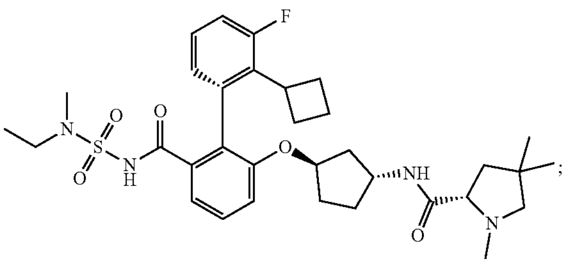
;
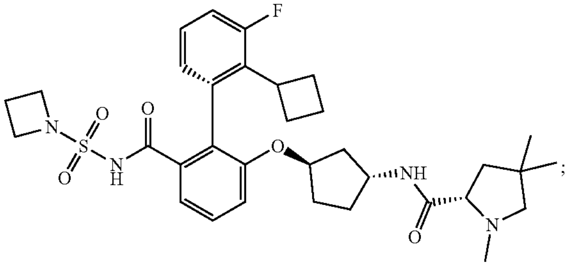
;
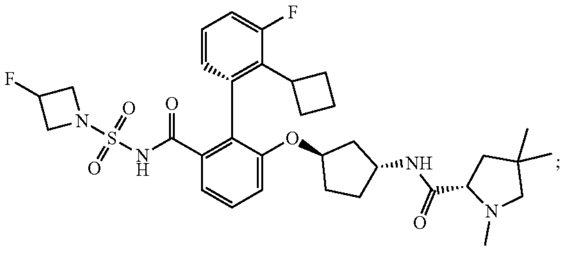
;
-continued
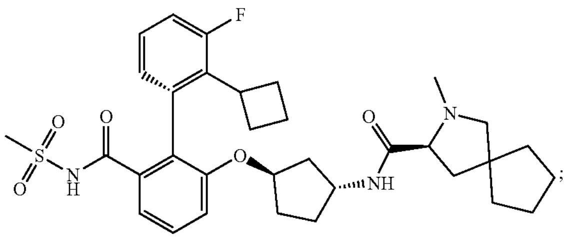
;
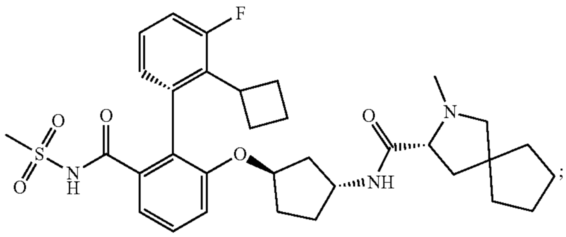
;
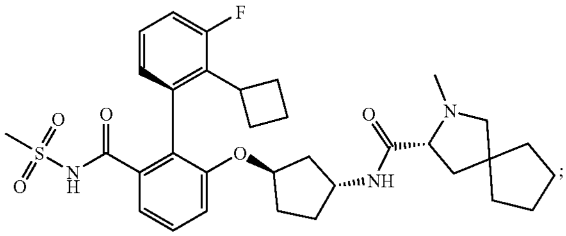
;
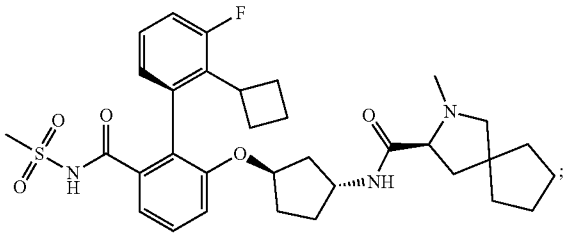
;
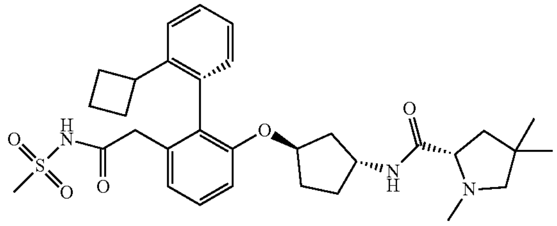
;
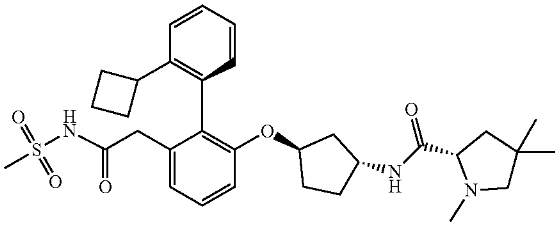
;
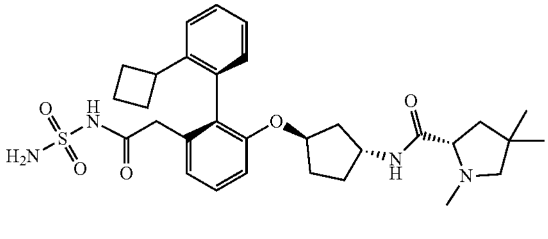
;

-continued

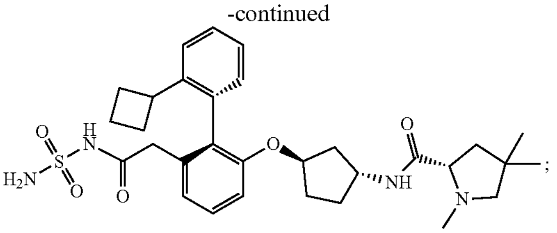

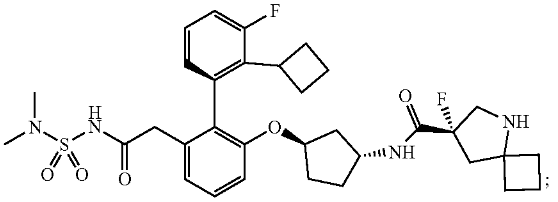

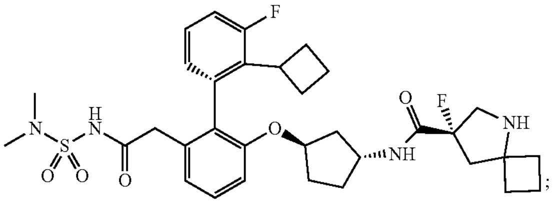

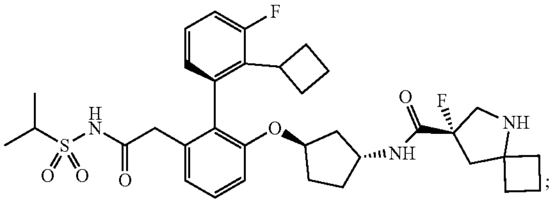

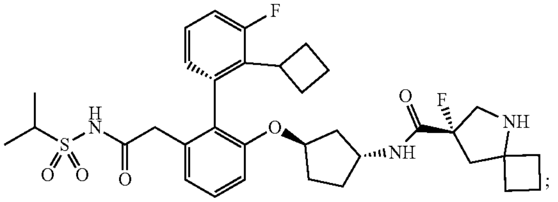

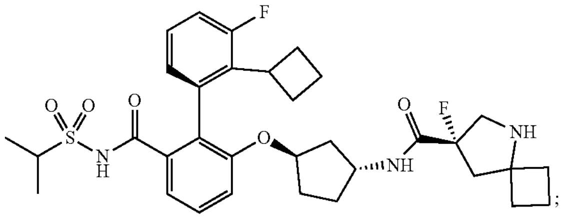

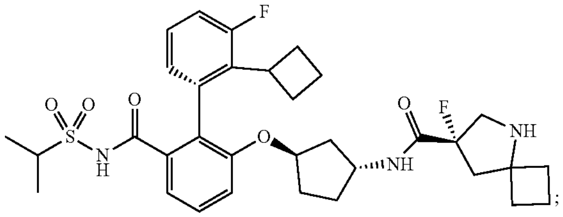

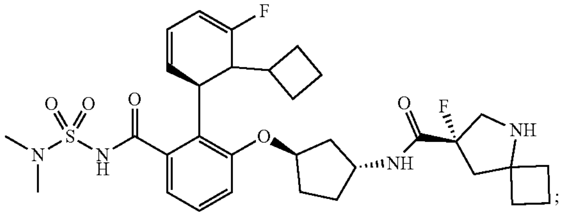

or

-continued

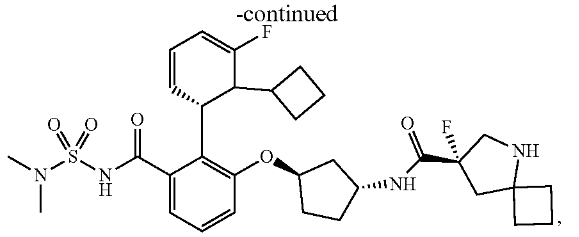

or a pharmaceutically acceptable salt thereof.

E48 A compound according to embodiment E24, or a pharmaceutically acceptable salt thereof, having formula (IA-4):

(IA-4)

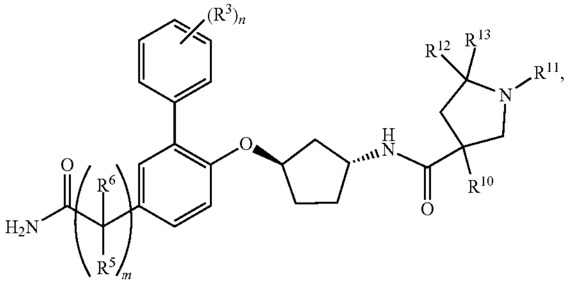

wherein:

m is 0 or 1;

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, or $C_1$-$C_3$ alkyl optionally substituted with 1 to 3 halogens;

$R^{10}$ is H or halogen;

$R^{11}$ is H or $C_1$-$C_3$ alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E49 A compound according to embodiment E48, or a pharmaceutically acceptable salt thereof, having formula (IA-4a) or (IA-4b):

(IA-4a)

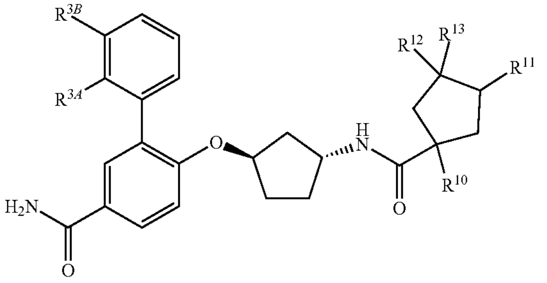

-continued (IA-4b)

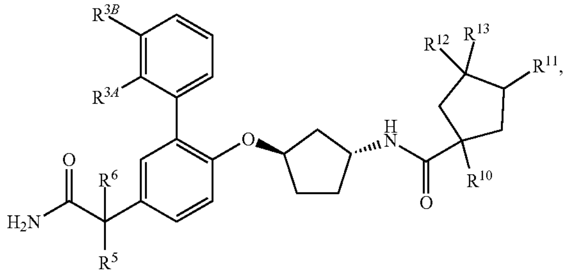

wherein:

$R^{3A}$ is $C_1$-$C_6$ alkyl or $C_3$-$C_4$ cycloalkyl, preferably $R^{3A}$ is —$CH_2CH_3$, —$CH(CH_3)_2$, or $C_3$-$C_4$ cycloalkyl;

$R^{3B}$ is halogen, preferably $R^{3B}$ is F;

$R^5$ and $R^6$ are each independently H or $C_1$-$C_3$ alkyl, preferably $R^5$ and $R^6$ are each independently H, —$CH_3$, or —$CH_2CH_3$;

$R^{10}$ is H or halogen, preferably $R^{10}$ is H or F;

$R^{11}$ is $C_1$-$C_3$ alkyl; and $R^{12}$ and $R^{13}$ are each $C_1$-$C_3$ alkyl or $R^{12}$ and $R^{13}$ together form a $C_3$-$C_6$ cycloalkyl optionally substituted with 1 to 3 halogens.

E50 A compound according to embodiment E49, or a pharmaceutically acceptable salt thereof, wherein $R^{3A}$ is cyclobutyl and $R^{3B}$ is F.

E51 A compound according to embodiment E49, or a pharmaceutically acceptable salt thereof, having formula (IA-4b), wherein $R^5$ and $R^6$ are each —$CH_3$.

E52 A compound according to any one of embodiments E48 to E51, or a pharmaceutically acceptable salt thereof, wherein $R^{10}$ is F and $R^{11}$ is H.

E53 A compound according to any one of embodiments E48 to E52, or a pharmaceutically acceptable salt thereof, wherein $R^{12}$ and $R^{13}$ together form a cyclobutyl.

E54 A compound according to embodiment E48, which is:

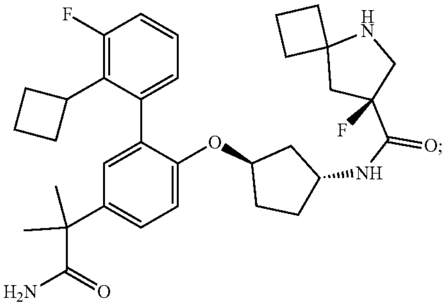

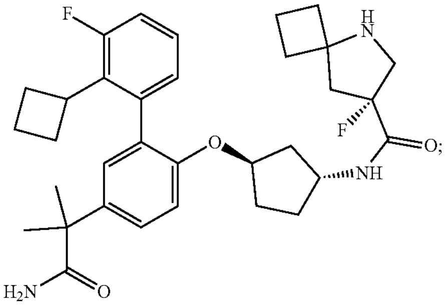

or a pharmaceutically acceptable salt thereof.

E55 A compound according to embodiment E24, or a pharmaceutically acceptable salt thereof, having formula (IA-5):

(IA-5)

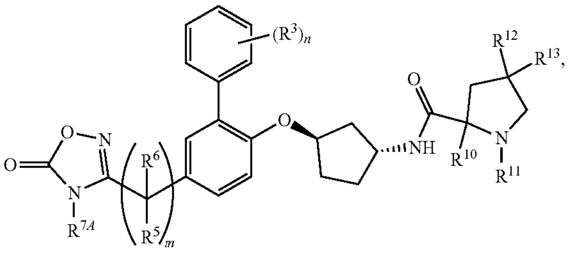

wherein:

m is 0 or 1;

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, or $C_1$-$C_3$ alkyl optionally substituted with 1 to 3 halogens;

$R^{7A}$ is H, $C_1$-$C_3$ alkyl optionally substituted with 1 to 3 halogens, or $C_3$-$C_4$ cycloalkyl;

$R^{10}$ is H or $C_1$-$C_3$ alkyl;

$R^{11}$ is H or $C_1$-$C_3$ alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E56 A compound according to embodiment E55, or a pharmaceutically acceptable salt thereof, having formula (IA-5a) or (IA-5b):

(IA-5a)

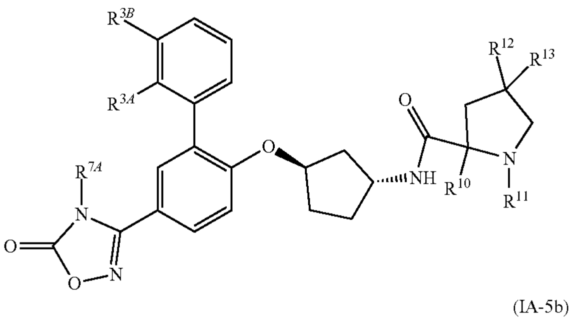

(IA-5b)

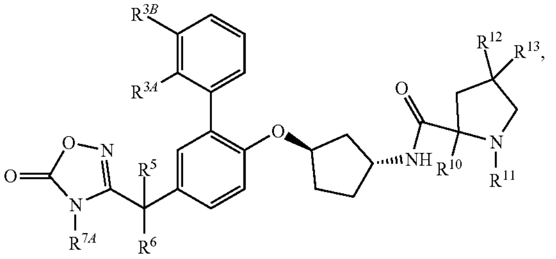

wherein:

$R^{3A}$ is $C_1$-$C_6$ alkyl or $C_3$-$C_4$ cycloalkyl, preferably $R^{3A}$ is —$CH_2CH_3$, —$CH(CH_3)_2$, or $C_3$-$C_4$ cycloalkyl;

$R^{3B}$ is halogen, preferably $R^{3B}$ is F;

$R^5$ and $R^6$ are each independently H or $C_1$-$C_3$ alkyl, preferably $R^5$ and $R^6$ are each independently H, —$CH_3$, or —$CH_2CH_3$;

$R^{7A}$ is H, $C_1$-$C_3$ alkyl, or $C_3$-$C_4$ cycloalkyl, preferably $R^{7A}$ is H, —$CH_3$, —$CH_2CH_3$, —$CH(CH_3)_2$, or cyclopropyl, more preferably $R^{7A}$ is H or —$CH_3$;

$R^{10}$ is H or $C_1$-$C_3$ alkyl, preferably $R^{10}$ is H;

$R^{11}$ is H or $C_1$-$C_3$ alkyl; and $R^{12}$ and $R^{13}$ each $C_1$-$C_3$ alkyl or together form a $C_3$-$C_6$ cycloalkyl optionally substituted with 1 to 3 halogens.

E57 A compound according to embodiment E56, or a pharmaceutically acceptable salt thereof, wherein $R^{3A}$ is cyclobutyl and $R^{3B}$ is F.

E58 A compound according to embodiment E56, or a pharmaceutically acceptable salt thereof, having formula (IA-5b), wherein $R^5$ and $R^6$ are each —$CH_3$.

E59 A compound according to any one of embodiments E55 to E58, or a pharmaceutically acceptable salt thereof, wherein $R^{10}$ is H and $R^{11}$ is —$CH_3$.

E60 A compound according to any one of embodiments E55 to E59, or a pharmaceutically acceptable salt thereof, wherein $R^{12}$ and $R^{13}$ are each —$CH_3$.

E61 A compound according to embodiment E51, which is:

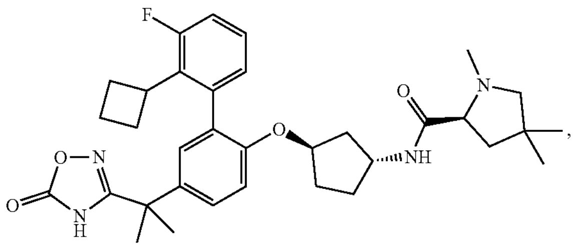 [SMILES: CN1CC(C)(C)C[C@H]1C(=O)N[C@@H]1CC[C@@H](Oc2ccc(C(C)(C)c3noc(=O)[nH]3)cc2-c2cccc(F)c2C2CCC2)C1]

or a pharmaceutically acceptable salt thereof.

E62 A compound according to embodiment E24, or a pharmaceutically acceptable salt thereof, having formula (IA-6):

(IA-6)

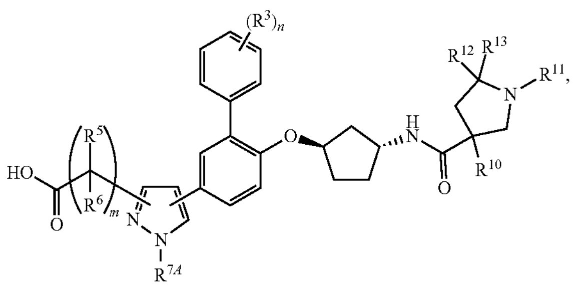

wherein:

m is 0 or 1;

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, or $C_1$-$C_3$ alkyl optionally substituted with 1 to 3 halogens;

$R^{7A}$ is H, $C_1$-$C_3$ alkyl optionally substituted with 1 to 3 halogens, or $C_3$-$C_4$ cycloalkyl;

$R^{10}$ is H or halogen;

$R^{11}$ is H or $C_1$-$C_3$ alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E63 A compound according to embodiment E62, or a pharmaceutically acceptable salt thereof, having formula (IA-6a) or (IA-6b):

(IA-6a)

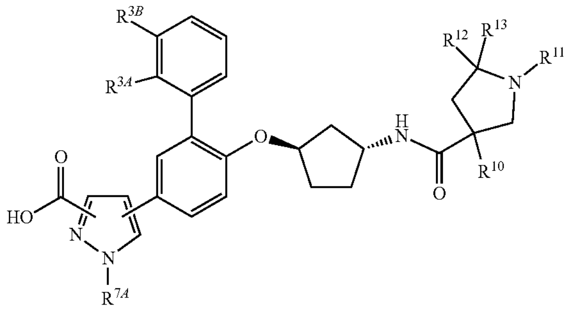

(IA-6b)

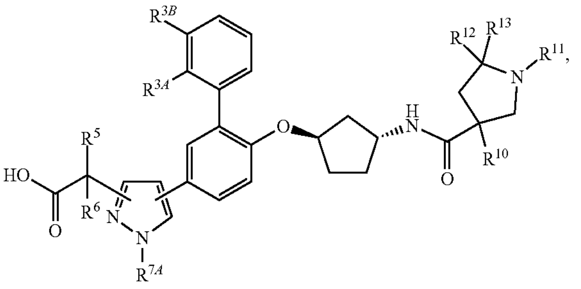

wherein:

$R^{3A}$ is $C_1$-$C_6$ alkyl or $C_3$-$C_4$ cycloalkyl, preferably $R^{3A}$ is —$CH_2CH_3$, —$CH(CH_3)_2$, or $C_3$-$C_4$ cycloalkyl;

$R^{3B}$ is halogen, preferably $R^{3B}$ is F;

$R^5$ and $R^6$ are each independently H or $C_1$-$C_3$ alkyl, preferably $R^5$ and $R^6$ are each independently H, —$CH_3$, or —$CH_2CH_3$;

$R^{7A}$ is H, $C_1$-$C_3$ alkyl, or $C_3$-$C_4$ cycloalkyl, preferably H, —$CH_3$, —$CH_2CH_3$, —$CH(CH_3)_2$, or cyclopropyl;

$R^{10}$ is H or halogen, preferably $R^{10}$ is H or F;

$R^{11}$ is $C_1$-$C_3$ alkyl; and $R^{12}$ and $R^{13}$ together form a $C_3$-$C_6$ cycloalkyl optionally substituted with 1 to 3 halogens.

E64 A compound according to embodiment E63, or a pharmaceutically acceptable salt thereof, wherein $R^{3A}$ is cyclobutyl and $R^{3B}$ is F.

E65 A compound according to embodiment E63 or E64, or a pharmaceutically acceptable salt thereof, having formula (IA-6b), wherein $R^5$ and $R^6$ are each —$CH_3$.

E66 A compound according to embodiment E63 or E64, or a pharmaceutically acceptable salt thereof, having formula (IA-6b), wherein one of $R^5$ and $R^6$ is —$CH_3$ and the other of $R^5$ and $R^6$ is H.

E67 A compound according to any one of embodiments E62 to E64, or a pharmaceutically acceptable salt thereof, wherein $R^{10}$ is F and $R^{11}$ is H.

E68 A compound according to any one of embodiments E62 to E67, or a pharmaceutically acceptable salt thereof, wherein and $R^{12}$ and $R^{13}$ together form cyclobutyl.

E69 A compound according to embodiment E62, which is:

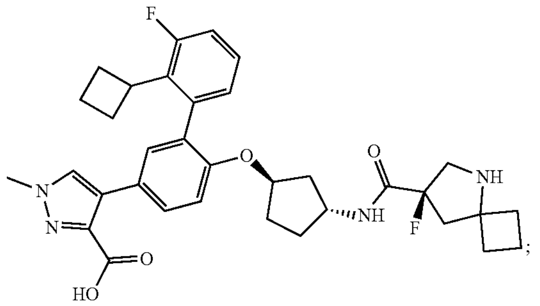

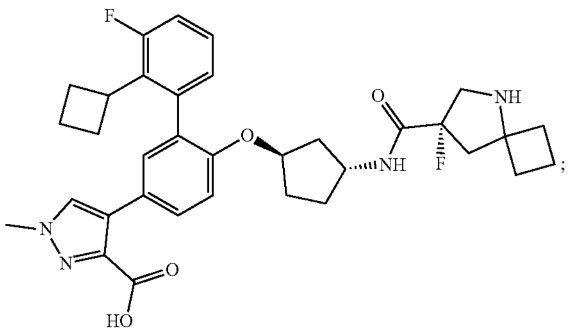

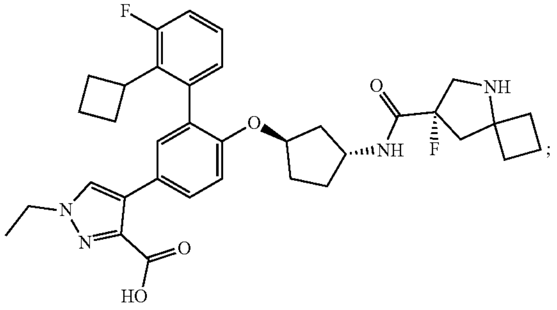

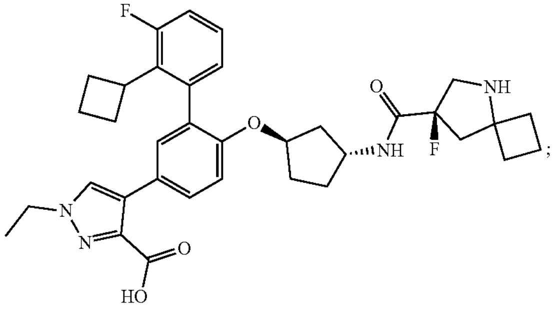

-continued

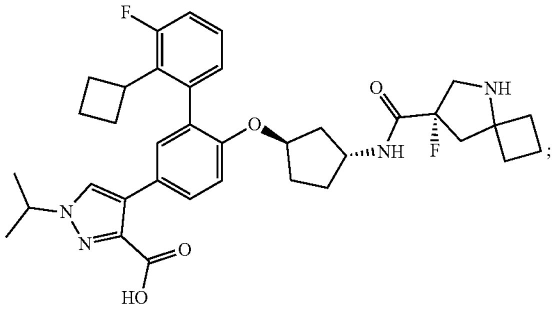

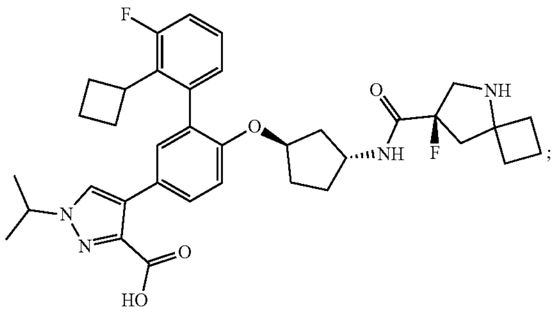

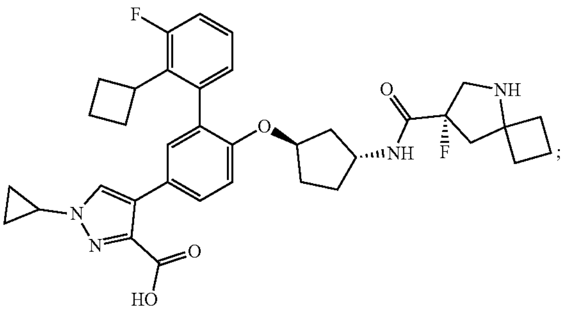

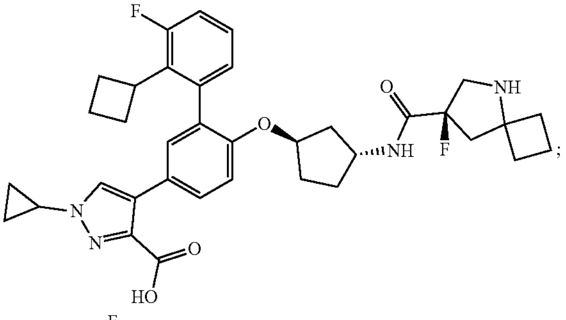

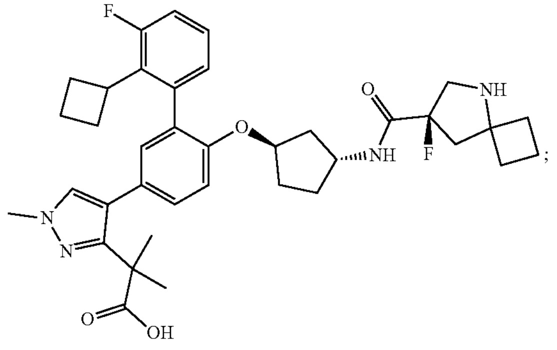

-continued

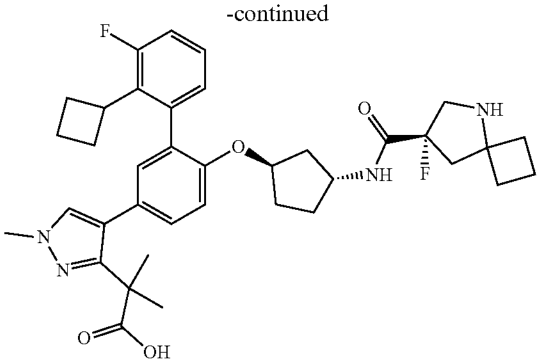

;

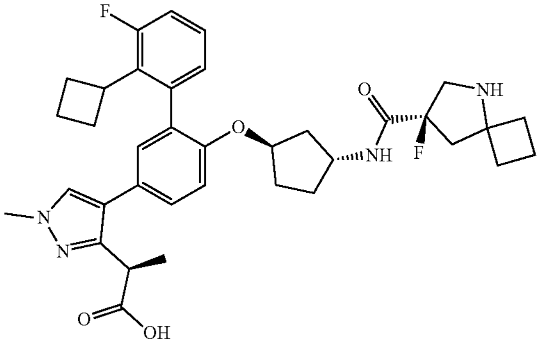

;

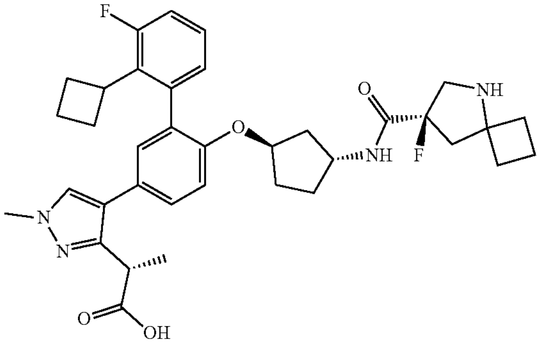

;

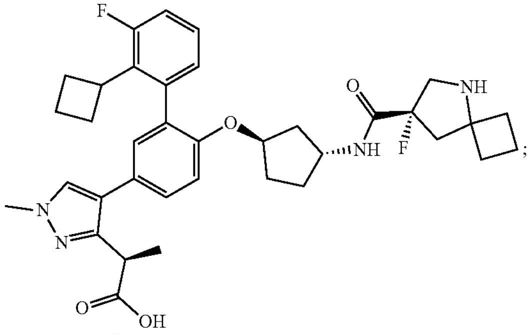

; or

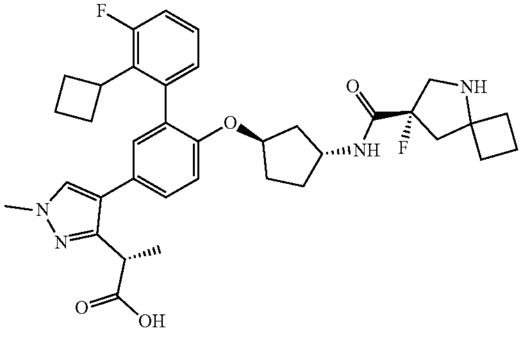

, or a pharmaceutically acceptable salt thereof.

E70 A compound according to embodiment E24, or a pharmaceutically acceptable salt thereof, having formula (IA-7):

(IA-7)

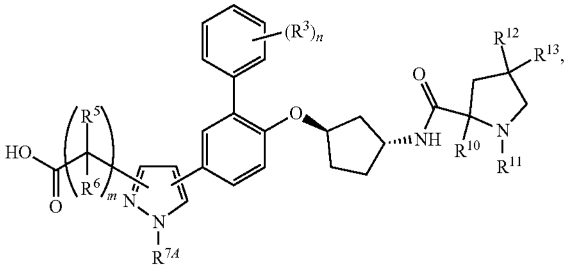

wherein:

m is 0 or 1;

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, or $C_1$-$C_3$ alkyl optionally substituted with 1 to 3 halogens;

$R^{7A}$ is H, $C_1$-$C_3$ alkyl optionally substituted with 1 to 3 halogens, or $C_3$-$C_4$ cycloalkyl;

$R^{10}$ is H or $C_1$-$C_3$ alkyl;

$R^{11}$ is H or $C_1$-$C_3$ alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E71 A compound according to embodiment E70, or a pharmaceutically acceptable salt thereof, having formula (IA-7a) or (IA-7b):

(IA-7a)

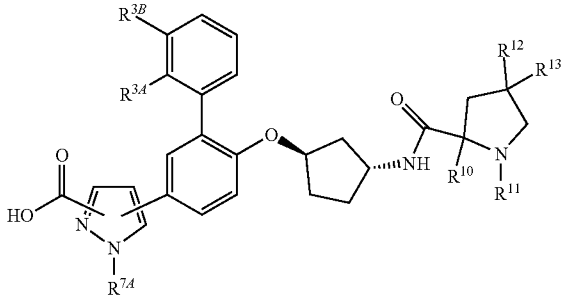

-continued (IA-7b)

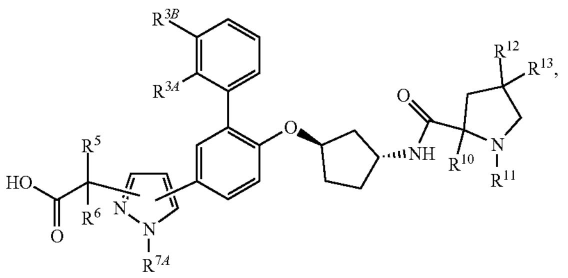

wherein:

$R^{3A}$ is $C_1$-$C_6$ alkyl or $C_3$-$C_4$ cycloalkyl, preferably $R^{3A}$ is —$CH_2CH_3$, —$CH(CH_3)_2$, or $C_3$-$C_4$ cycloalkyl;

$R^{3B}$ is halogen, preferably $R^{3B}$ is F;

$R^5$ and $R^6$ are each independently H or $C_1$-$C_3$ alkyl, preferably H, —$CH_3$, or —$CH_2CH_3$;

$R^{7A}$ is H, $C_1$-$C_3$ alkyl, or $C_3$-$C_4$ cycloalkyl, preferably H, —$CH_3$, —$CH_2CH_3$, —$CH(CH_3)_2$, or cyclopropyl;

$R^{10}$ is H or $C_1$-$C_3$ alkyl, preferably $R^{10}$ is H; and $R^{11}$, $R^{12}$, and $R^{13}$ are each $C_1$-$C_3$ alkyl.

E72 A compound according to embodiment E71, or a pharmaceutically acceptable salt thereof, wherein $R^{3A}$ is cyclobutyl and $R^{3B}$ is F.

E73 A compound according to embodiment E71, or a pharmaceutically acceptable salt thereof, having formula (IA-7b), wherein $R^5$ and $R^6$ are each H.

E74 A compound according to any one of embodiments E70 to E73, or a pharmaceutically acceptable salt thereof, wherein $R^{10}$ is H and $R^{11}$ is —$CH_3$.

E75 A compound according to any one of embodiments E70 to E74, or a pharmaceutically acceptable salt thereof, wherein $R^{12}$ and $R^{13}$ are each —$CH_3$.

E76 A compound according to embodiment E70, which is:

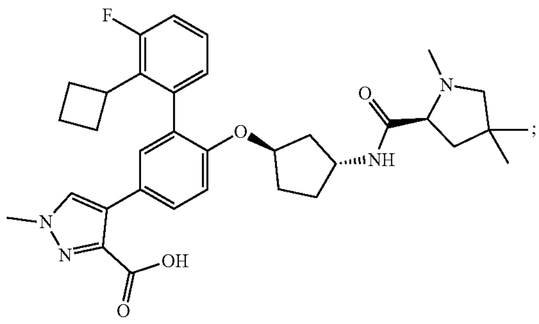

; or

-continued

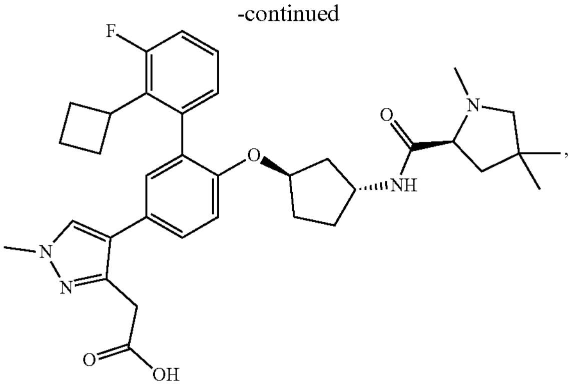

or a pharmaceutically acceptable salt thereof.

E77 A compound according to embodiment E24, or a pharmaceutically acceptable salt thereof, having formula (IA-8) or (IA-8'):

(IA-8)

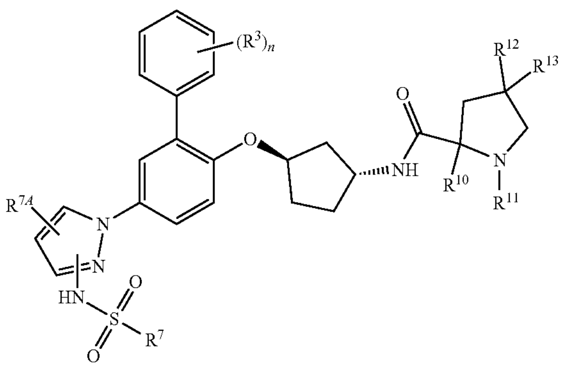

(IA-8')

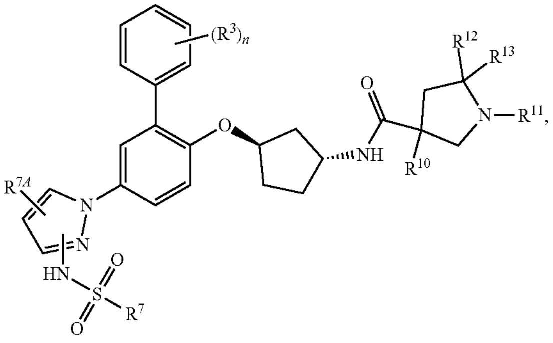

wherein:

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^7$ is selected from the group consisting of $C_1$-$C_3$ alkyl, $C_3$-$C_4$ cycloalkyl optionally substituted with 1 to 4 halogens or a $C_1$-$C_3$ alkyl optionally substituted with 1 to 3 halogens, and —$NR^8R^9$, wherein $R^3$ and $R^9$ are each independently H or $C_1$-$C_3$ alkyl or $R^3$ and $R^9$ together form a 4-5 membered N-containing heterocycloalkyl ring optionally substituted with 1 to 4 halogens;

$R^{7A}$ is H, $C_1$-$C_3$ alkyl optionally substituted with 1 to 3 halogens, or $C_3$-$C_4$ cycloalkyl;

$R^{10}$ in formula (IA-8) is H or $C_1$-$C_3$ alkyl, preferably H, and $R^{10}$ in formula (IA-8') is H or halogen;

$R^{11}$ is H or $C_1$-$C_3$ alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E78 A compound according to embodiment E77, or a pharmaceutically acceptable salt thereof, having formula (IA-8a) or (IA-8a'):

(IA-8a)

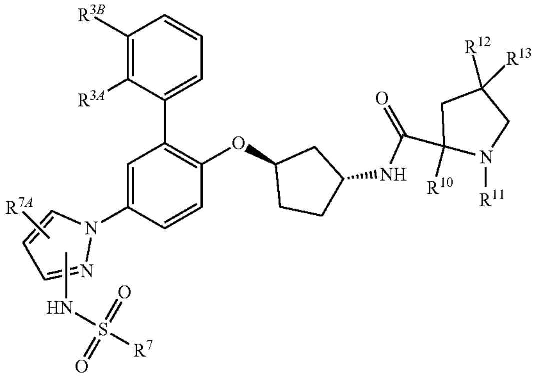

(IA-8a')

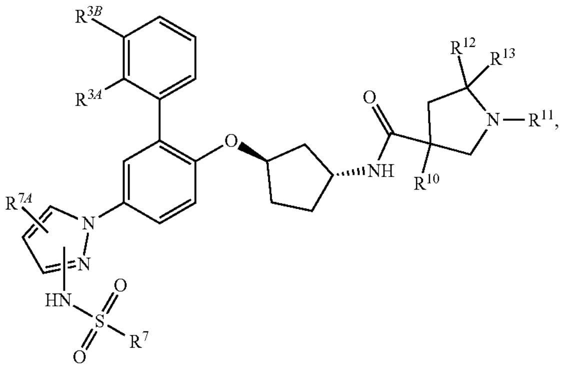

wherein:

$R^{3A}$ is $C_1$-$C_6$ alkyl or $C_3$-$C_4$ cycloalkyl, preferably $R^{3A}$ is —$CH_2CH_3$, —$CH(CH_3)_2$, or $C_3$-$C_4$ cycloalkyl;

$R^{3B}$ is halogen, preferably $R^{3B}$ is F;

$R^7$ is selected from the group consisting of $C_1$-$C_3$ alkyl, $C_3$-$C_4$ cycloalkyl optionally substituted with 1 to 4 halogens or a $C_1$-$C_3$ alkyl, and —$NR_3R^9$, preferably $R^7$ is —$CH_3$, —$CH_2CH_3$, —$CH(CH_3)_2$, cyclopropyl, cyclopropyl substituted with —$CH_3$, —$NH_2$, —$N((CH)_3)_2$, —$N(CH_3)(CH_2CH_3)$, or azetidine optionally substituted with 1, 2, or 3 F;

$R^{7A}$ is H, $C_1$-$C_3$ alkyl, or $C_3$-$C_4$ cycloalkyl, preferably $R^{7A}$ is H, —$CH_3$, —$CH_2CH_3$, —$CH(CH_3)_2$, or cyclopropyl;

$R^{10}$ is H, halogen, or $C_1$-$C_3$ alkyl, preferably $R^{10}$ is H or halogen;

$R^{11}$ is H or $C_1$-$C_3$ alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E79 A compound according to embodiment E78, or a pharmaceutically acceptable salt thereof, wherein $R^{3A}$ is cyclobutyl and $R^{3B}$ is F.

E80 A compound according to any one of embodiments E77 to E79, or a pharmaceutically acceptable salt thereof, wherein $R^{10}$ is H and $R^{11}$ is —$CH_3$ or wherein $R^{10}$ is F and $R^{11}$ is H.

E81 A compound according to any one of embodiments E77 to E80, or a pharmaceutically acceptable salt thereof, wherein $R^{12}$ and $R^{13}$ are each —$CH_3$ or $R^{12}$ and $R^{13}$ together form a $C_3$-$C_6$ cycloalkyl.

E82 A compound according to any one of embodiments E77 to E81, or a pharmaceutically acceptable salt thereof, wherein $R^7$ and $R^{7A}$ are each —$CH_3$.

E83 A compound according to embodiment E77, which is:

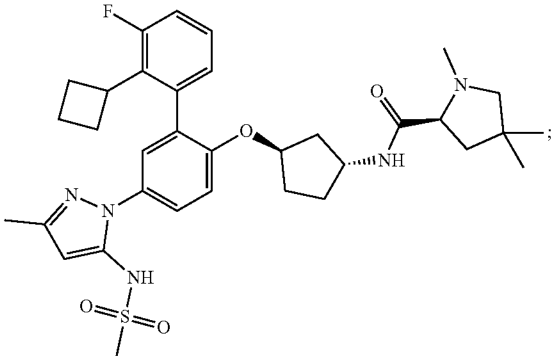

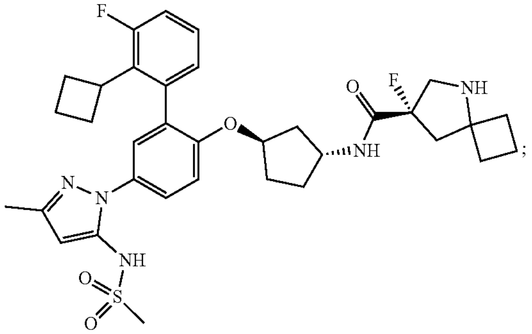

or

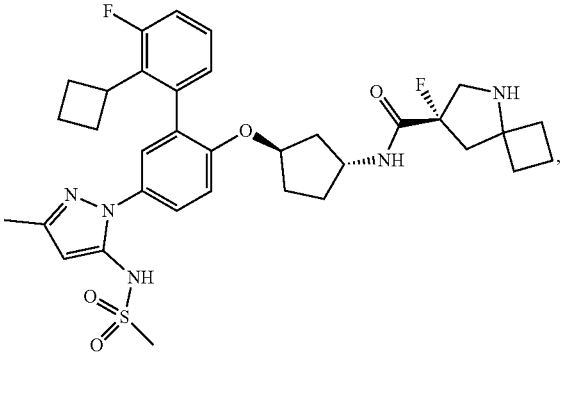

or a pharmaceutically acceptable salt thereof.

E84 A compound according to embodiment E24, or a pharmaceutically acceptable salt thereof, having formula (IA-9):

(IA-9)

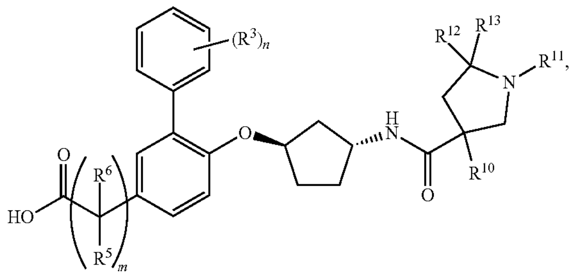

wherein:

m is 0 or 1;

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, $C_1$-$C_3$ deuterated alkyl, or $C_1$-$C_3$ alkyl optionally substituted with 1 to 3 halogens;

$R^{10}$ is H or halogen;

$R^{11}$ is H or $C_1$-$C_3$ alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E85 A compound according to embodiment E84, or a pharmaceutically acceptable salt thereof, having formula (IA-9a) or (IA-9b):

(IA-9a)

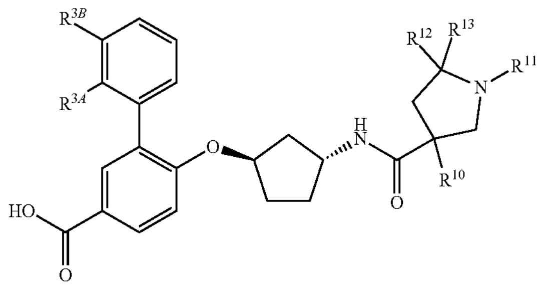

(IA-9b)

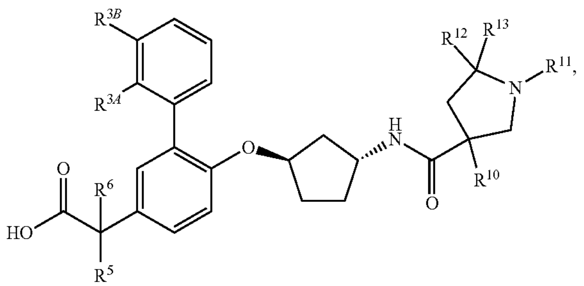

wherein:

$R^{3A}$ is $C_1$-$C_6$ alkyl or $C_3$-$C_4$ cycloalkyl, preferably $R^{3A}$ is —$CH_2CH_3$, —$CH(CH_3)_2$, or $C_3$-$C_4$ cycloalkyl;

$R^{3B}$ is halogen, preferably $R^{3B}$ is F;

$R^5$ and $R^6$ are each independently H or $C_1$-$C_3$ alkyl, preferably $R^5$ and $R^6$ are each independently H, —$CH_3$, or —$CH_2CH_3$;

$R^{10}$ is H or halogen, preferably $R^{10}$ is H or F;

$R^{11}$ is H or $C_1$-$C_3$ alkyl; and $R^{12}$ and $R^{13}$ are each $C_1$-$C_3$ alkyl or $R^{12}$ and $R^{13}$ together form a $C_3$-$C_6$ cycloalkyl optionally substituted with 1 to 3 halogens.

E86 A compound according to embodiment E85, or a pharmaceutically acceptable salt thereof, wherein $R^{3A}$ is cyclobutyl and $R^{3B}$ is F.

E87 A compound according to embodiment E85, or a pharmaceutically acceptable salt thereof, having formula (IA-9b), wherein $R^5$ and $R^6$ are each H.

E88 A compound according to embodiment E85, or a pharmaceutically acceptable salt thereof, having formula (IA-9b), wherein $R^5$ and $R^6$ are each —$CH_3$.

E89 A compound according to any one of embodiments E84 to E88, or a pharmaceutically acceptable salt thereof, wherein $R^{10}$ is F, $R^{11}$ is H, and $R^{12}$ and $R^{13}$ are each —$CH_3$.

E90 A compound according to any one of embodiments E84 to E88, or a pharmaceutically acceptable salt thereof, wherein $R^{10}$ is F, $R^{11}$ is H, and $R^{12}$ and $R^{13}$ together form cyclobutyl or cyclopentyl, preferably cyclobutyl.

E91 A compound according to any one of embodiments E84 to E88, or a pharmaceutically acceptable salt thereof, wherein $R^{10}$ is H and $R^{11}$, $R^{12}$, and $R^{13}$ are each —$CH_3$.

E92 A compound according to embodiment E84, which is:

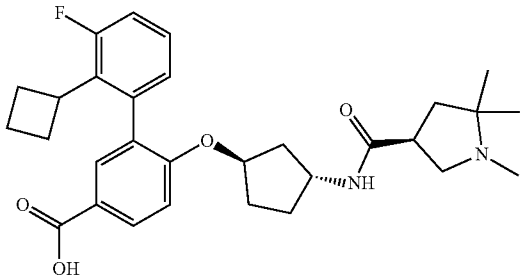

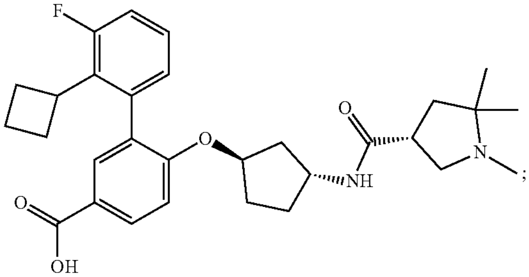

;

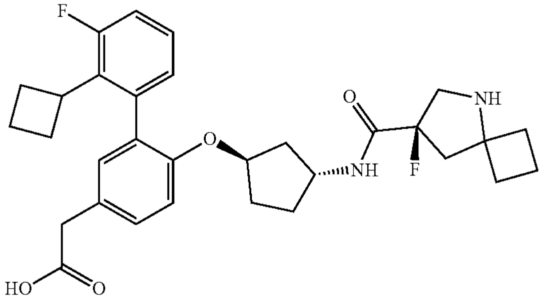

;

-continued
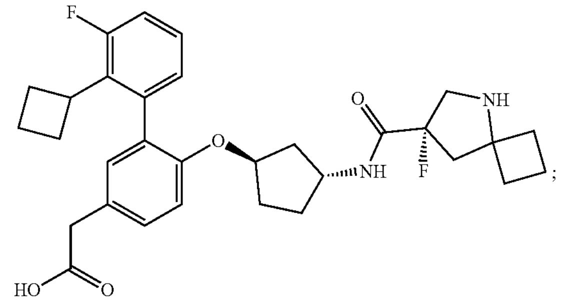
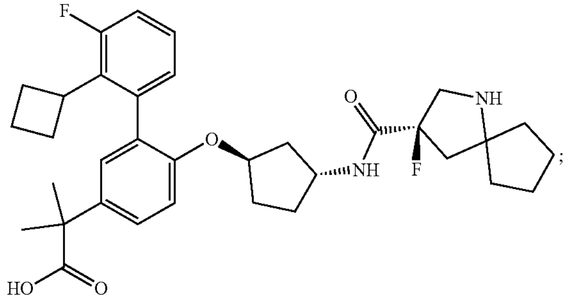
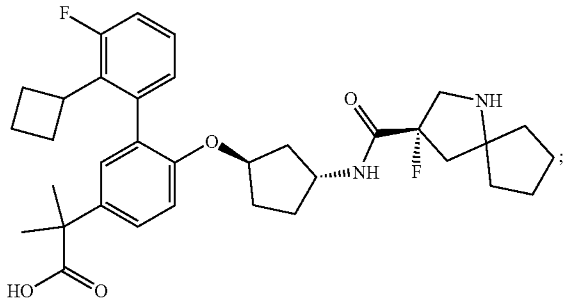
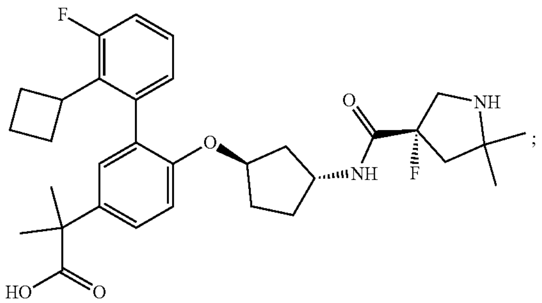
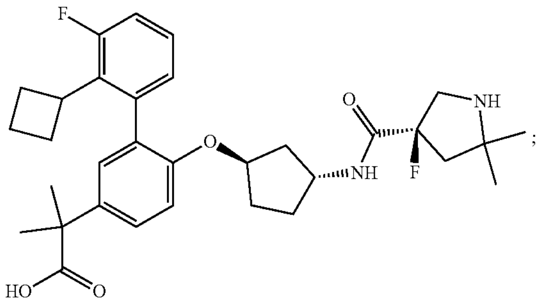
-continued
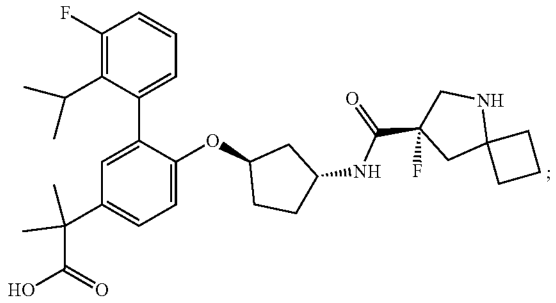
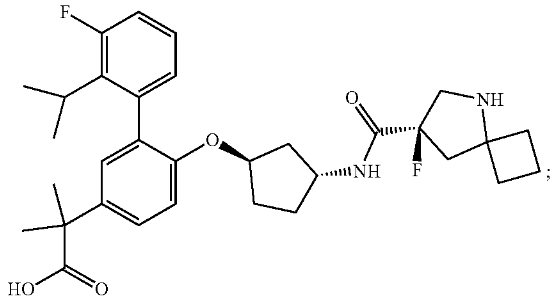
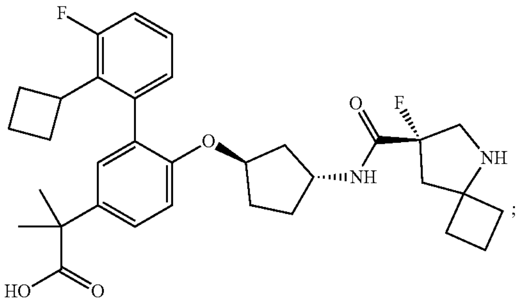
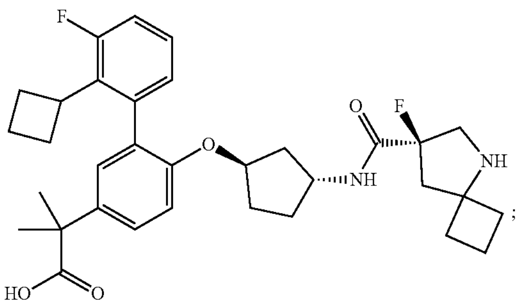
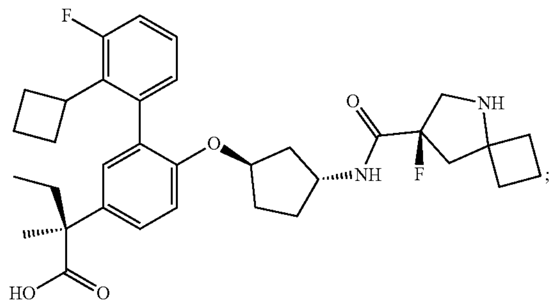

-continued
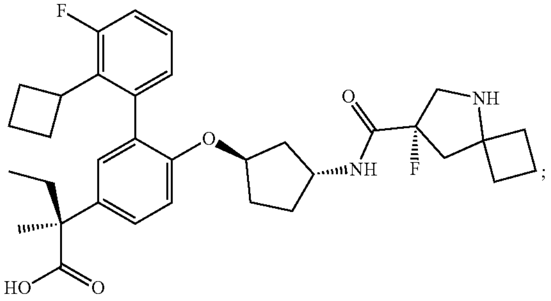
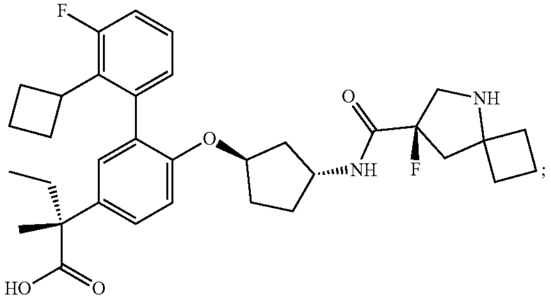
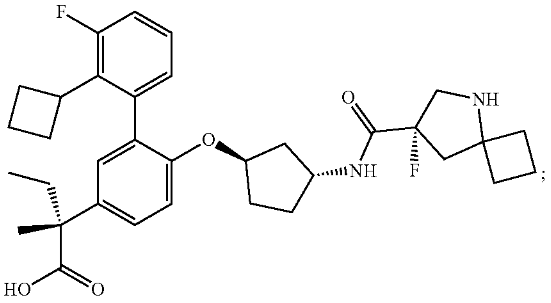
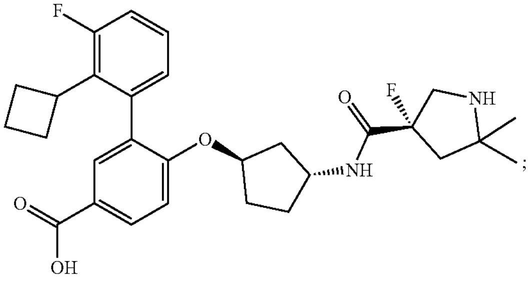
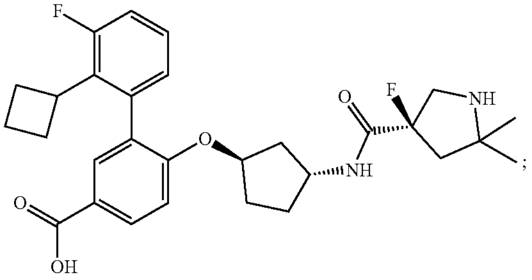
-continued
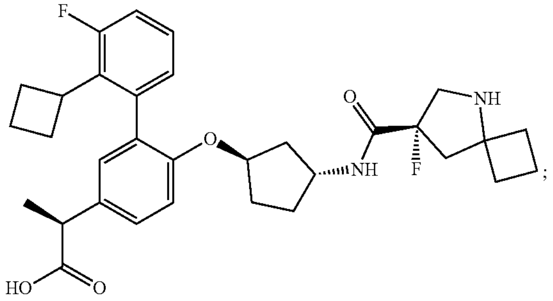
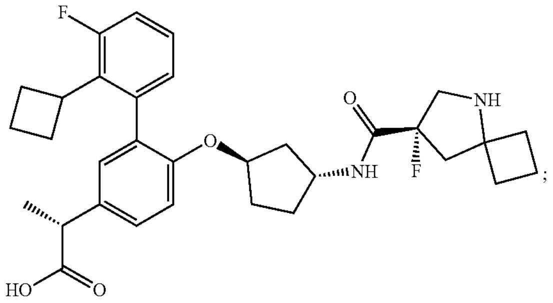
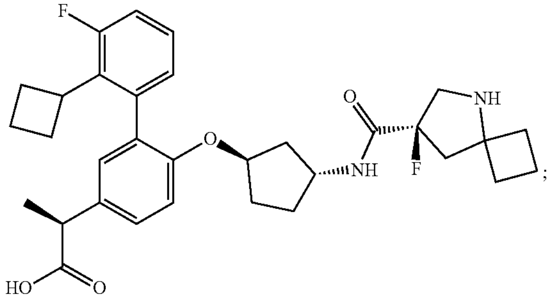
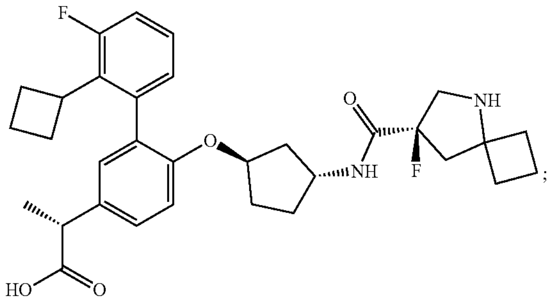
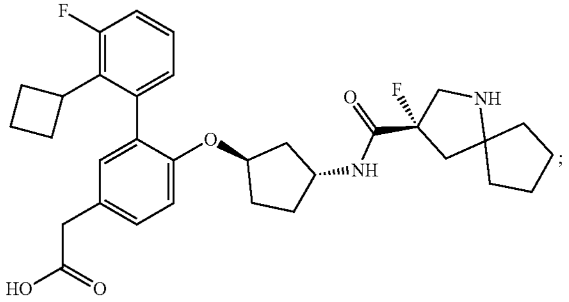

-continued
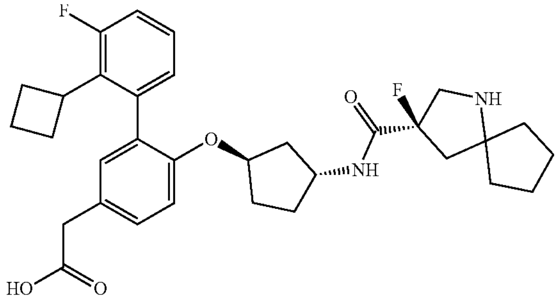;
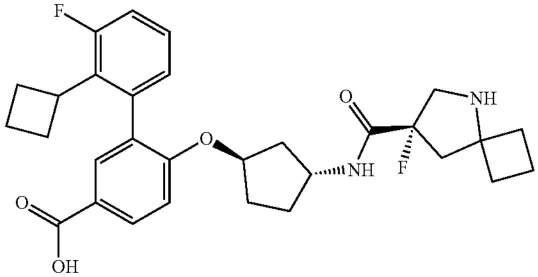;
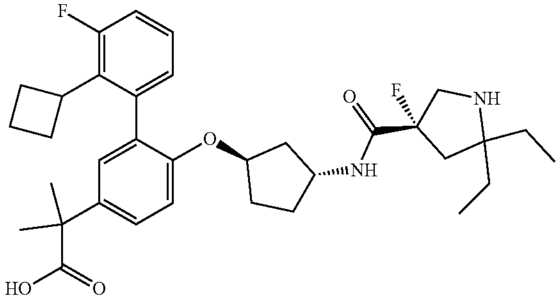;
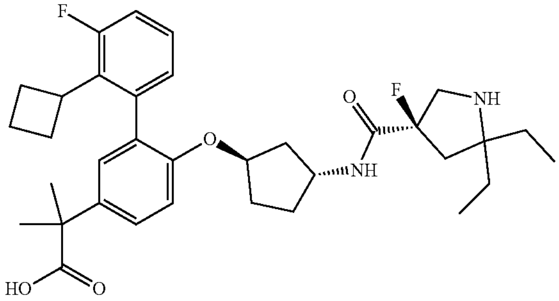;
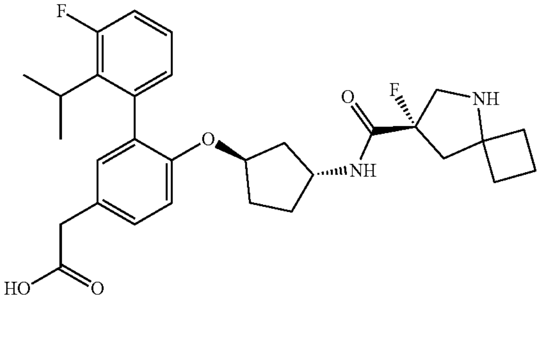;
-continued
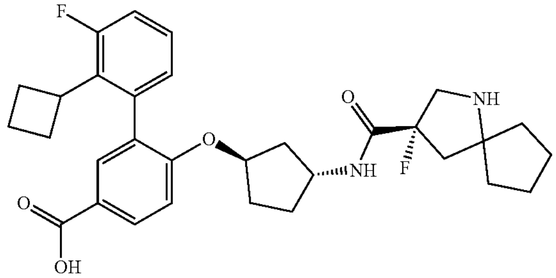;
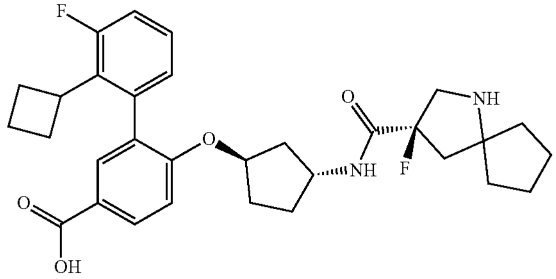;
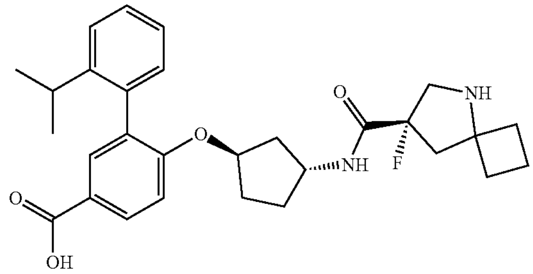;
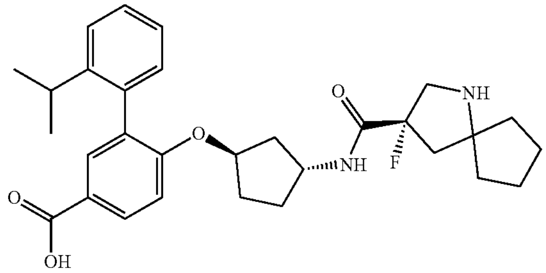;
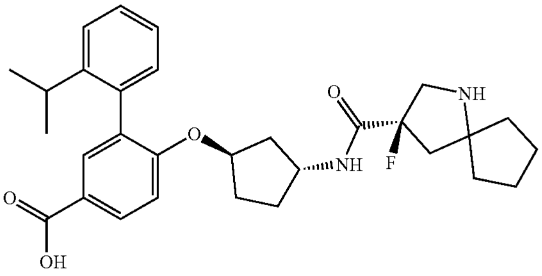;
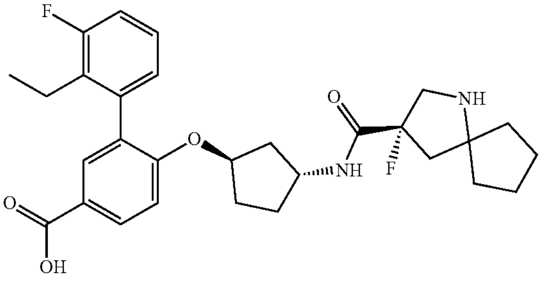;

-continued

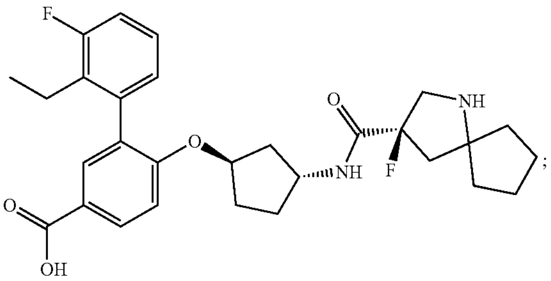

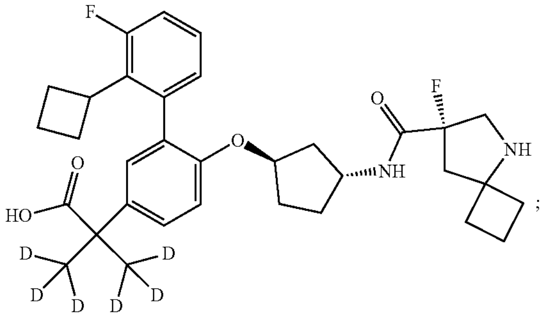

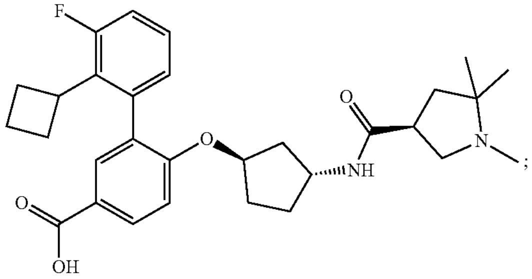

or

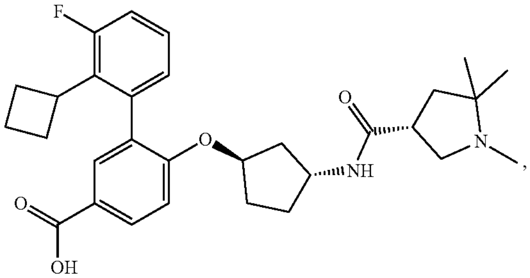

or a pharmaceutically acceptable salt thereof.

E93 A compound according to embodiment E84, which is:

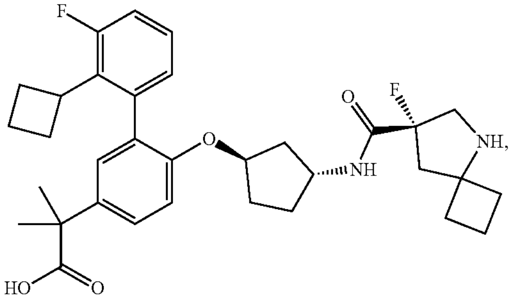 [SMILES: CC(C)(C(=O)O)c1ccc(O[C@@H]2CC[C@@H](NC(=O)[C@@]3(F)CNC4(CCC4)C3)C2)c(-c2cccc(F)c2C2CCC2)c1]

or a pharmaceutically acceptable salt thereof.

E94 A compound according to embodiment E84, which is:

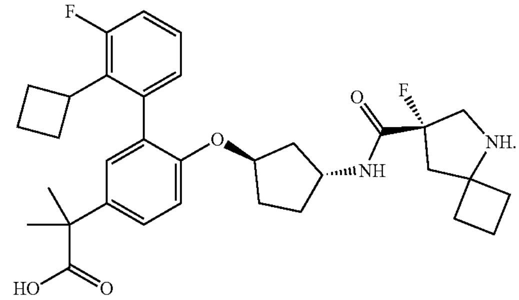 [SMILES: CC(C)(C(=O)O)c1ccc(O[C@@H]2CC[C@@H](NC(=O)[C@@]3(F)CNC4(CCC4)C3)C2)c(-c2cccc(F)c2C2CCC2)c1]

E95 A compound according to embodiment E84, which is:

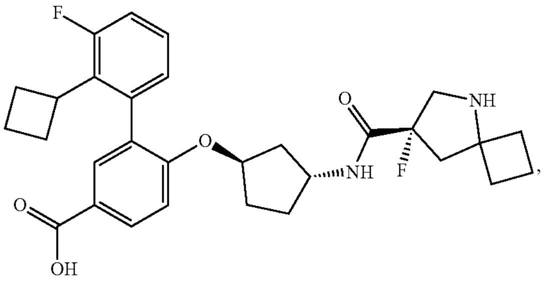 [SMILES: O=C(O)c1ccc(O[C@@H]2CC[C@@H](NC(=O)[C@@]3(F)CNC4(CCC4)C3)C2)c(-c2cccc(F)c2C2CCC2)c1]

or a pharmaceutically acceptable salt thereof.

E96 A compound according to embodiment E84, which is:

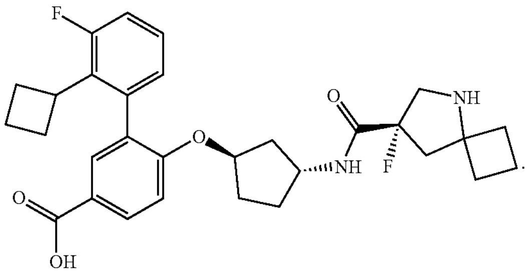 [SMILES: O=C(O)c1ccc(O[C@@H]2CC[C@@H](NC(=O)[C@@]3(F)CNC4(CCC4)C3)C2)c(-c2cccc(F)c2C2CCC2)c1]

E97 A compound according to embodiment E84, which is:

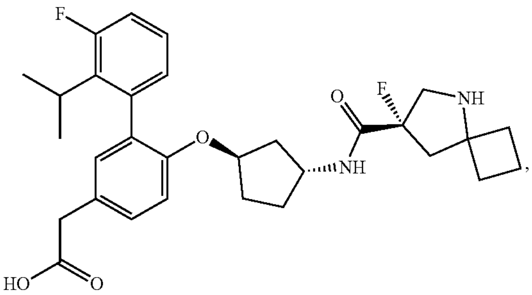 [SMILES: CC(C)c1c(F)cccc1-c1cc(CC(=O)O)ccc1O[C@@H]1CC[C@@H](NC(=O)[C@@]2(F)CNC3(CCC3)C2)C1]

or a pharmaceutically acceptable salt thereof.

E98 A compound according to embodiment E84, which is:

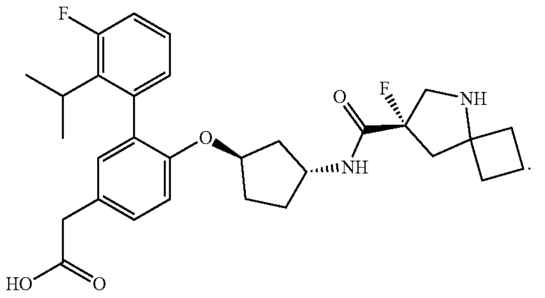 [SMILES: CC(C)c1c(F)cccc1-c1cc(CC(=O)O)ccc1O[C@@H]1CC[C@@H](NC(=O)[C@@]2(F)CNC3(CCC3)C2)C1]

E99 A compound according to embodiment E84, which is:

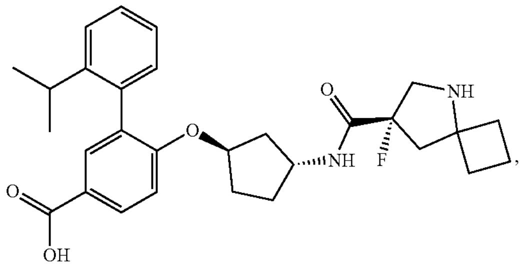 [SMILES: CC(C)c1ccccc1-c1cc(C(=O)O)ccc1O[C@@H]1CC[C@@H](NC(=O)[C@@]2(F)CNC3(CCC3)C2)C1]

or a pharmaceutically acceptable salt thereof.

E100 A compound according to embodiment E84, which is:

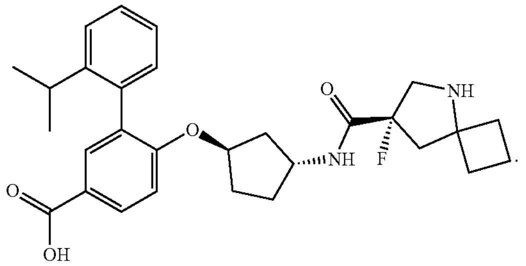 [SMILES: CC(C)c1ccccc1-c1cc(C(=O)O)ccc1O[C@@H]1CC[C@@H](NC(=O)[C@@]2(F)CNC3(CCC3)C2)C1]

E101 A compound according to embodiment E24, or a pharmaceutically acceptable salt thereof, having formula (IA-10):

(IA-10)

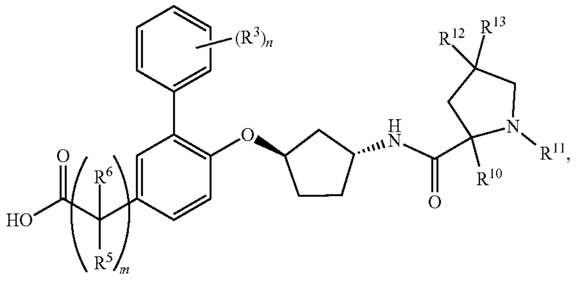

wherein:

m is 0 or 1;

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, or $C_1$-$C_3$ alkyl optionally substituted with 1 to 3 halogens;

$R^{10}$ is H or $C_1$-$C_3$ alkyl;

$R^{11}$ is H, $C_1$-$C_3$ alkyl, or $C_1$-$C_3$ deuterated alkyl; and $R^{12}$ and $R^{13}$ are each independently H or $C_1$-$C_3$ alkyl, or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens, or $R^{12}$ and $R^{13}$ together form a 3-6 membered heterocycloalkyl comprising at least one heteroatom selected from the group consisting of N, O, and S, and optionally substituted with (i) 1 to 3 halogens or (ii) $C_1$-$C_3$ alkyl optionally substituted with 1 to 3 halogens.

E102 A compound according to embodiment 101, or a pharmaceutically acceptable salt thereof, having formula (IA-10a), (IA-10b), (IA-10c), or (IA-10d):

(IA-10a)

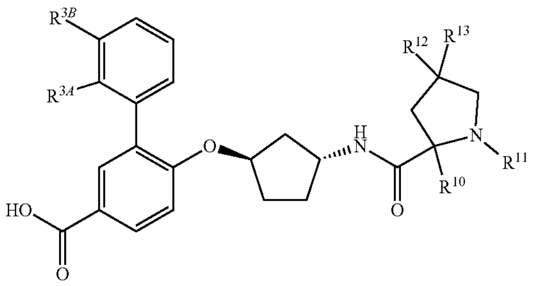

(IA-10b)

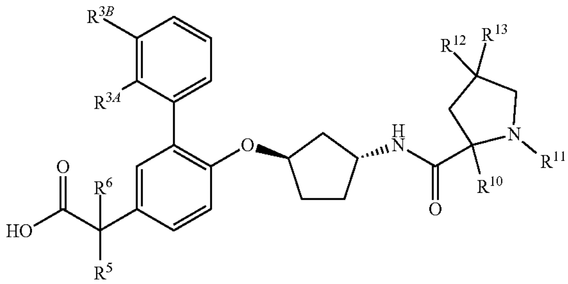

(IA-10c)

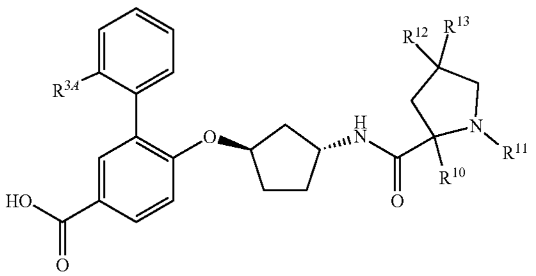

-continued (IA-10d)

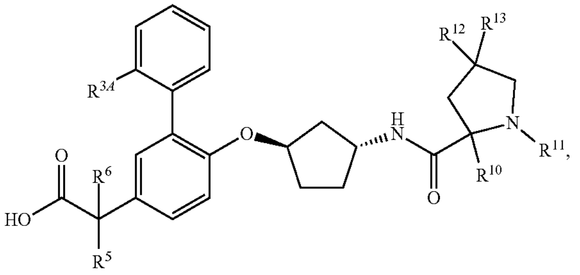

wherein:

$R^{3A}$ is $C_1$-$C_6$ alkyl or $C_3$-$C_4$ cycloalkyl, preferably $R^{3A}$ is —$CH_2CH_3$, —$CH(CH_3)_2$, or $C_3$-$C_4$ cycloalkyl;

$R^{3B}$ is halogen, preferably $R^{3B}$ is F;

$R^5$ and $R^6$ are each independently H or $C_1$-$C_3$ alkyl, preferably $R^5$ and $R^6$ are each independently H, —$CH_3$ or —$CH_2CH_3$;

$R^{10}$ is H or $C_1$-$C_3$ alkyl, preferably $R^{10}$ is H;

$R^{11}$ is $C_1$-$C_3$ alkyl or $C_1$-$C_3$ deuterated alkyl; and $R^{12}$ and $R^{13}$ are each $C_1$-$C_3$ alkyl, or $R^{12}$ and $R^{13}$ together form a $C_3$-$C_6$ cycloalkyl optionally substituted with 1 to 3 halogens, or $R^{12}$ and $R^{13}$ together form a 4-6 membered heterocycloalkyl comprising at least one heteroatom selected from the group consisting of N, O, and S, and optionally substituted with 1 to 3 halogens.

E103 A compound according to embodiment E102, or a pharmaceutically acceptable salt thereof, wherein $R^{3A}$ is cyclobutyl and $R^{3B}$ is F.

E104 A compound according to embodiment E102, or a pharmaceutically acceptable salt thereof, wherein $R^{3A}$ is —$CH(CH_3)_2$ and $R^{3B}$ is F.

E105 A compound according to embodiment E102, or a pharmaceutically acceptable salt thereof, having formula (IA-10b) or (IA-10d), wherein $R^5$ and $R^6$ are each H.

E106 A compound according to embodiment E102, or a pharmaceutically acceptable salt thereof, having formula (IA-10b) or (IA-10d), wherein $R^5$ and $R^6$ are each —$CH_3$.

E107 A compound according to embodiment E102, or a pharmaceutically acceptable salt thereof, having formula (IA-10b) or (IA-10d), wherein one of $R^5$ and $R^6$ is H and the other of $R^5$ and $R^6$ is —$CH_3$.

E108 A compound according to any one of embodiments E101 to E107, or a pharmaceutically acceptable salt thereof, wherein $R^{10}$ is H and $R^{11}$ is —$CH_3$.

E109 A compound according to any one of embodiments E101 to E108, or a pharmaceutically acceptable salt thereof, wherein $R^{12}$ and $R^{13}$ are each —$CH_3$.

E110 A compound according to any one of embodiments E101 to E108, or a pharmaceutically acceptable salt thereof, wherein $R^{12}$ and $R^{13}$ together form cyclobutyl or cyclopentyl, preferably cyclopentyl.

E111 A compound according to any one of embodiments E101 to E108, or a pharmaceutically acceptable salt thereof, wherein $R^{12}$ and $R^{13}$ together form a 6-membered heterocycloalkyl comprising at least one heteroatom selected from the group consisting of N, O, and S, preferably $R^{12}$ and $R^{13}$ together form tetrahydropyran.

E112 A compound according to embodiment E101, which is:

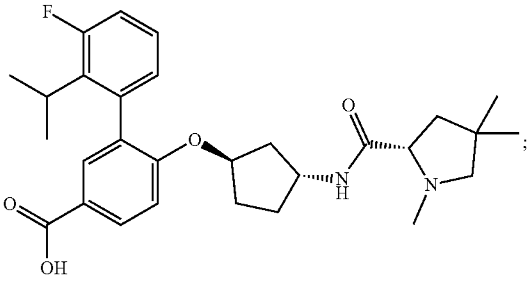

;

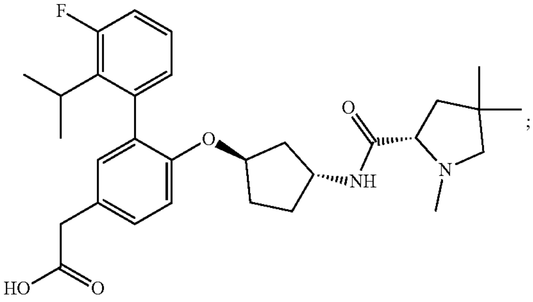

;

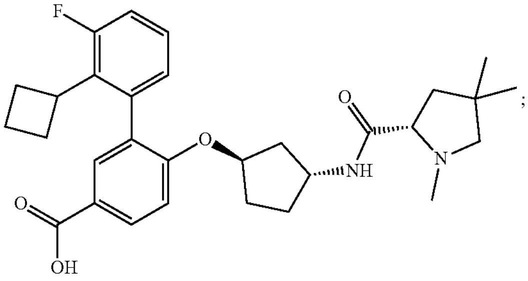

;

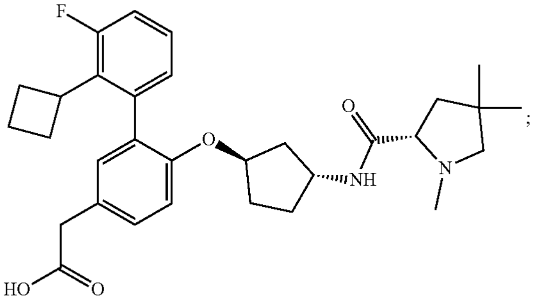

;

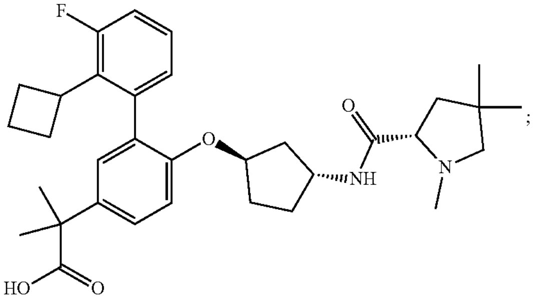

;

-continued
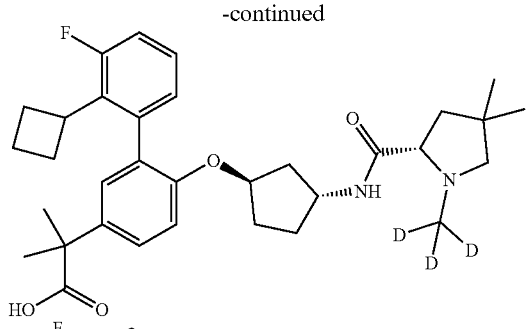
;
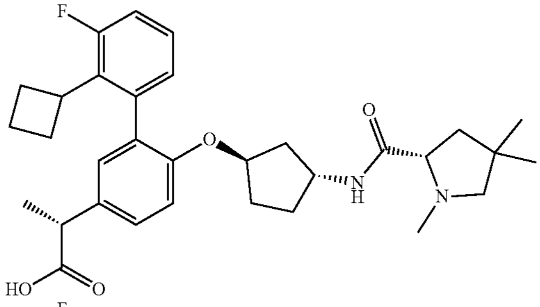
;
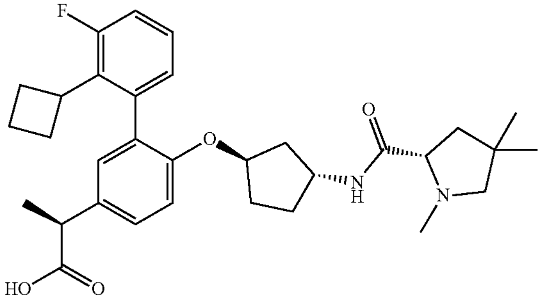
;
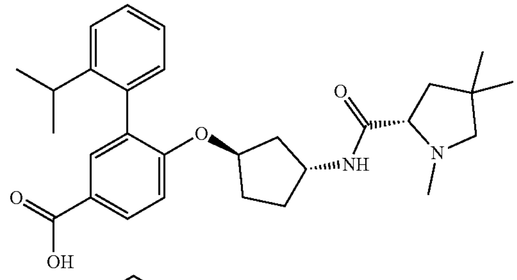
;
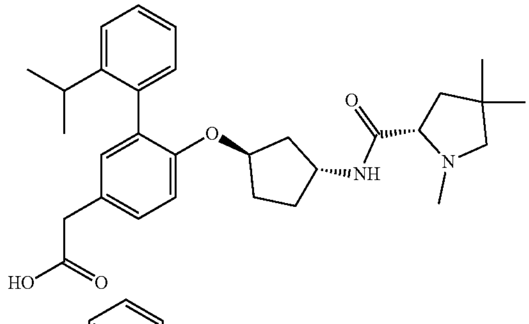
;
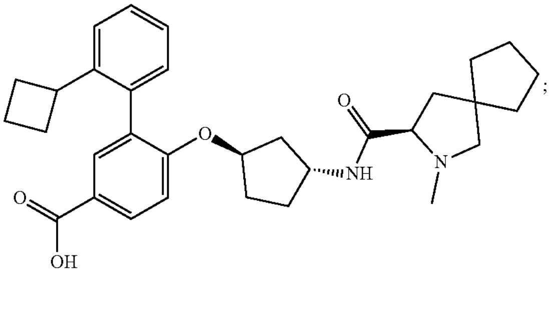
;
-continued
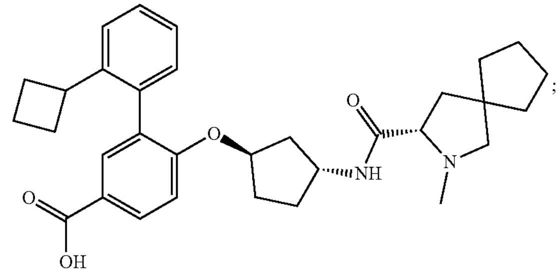
;
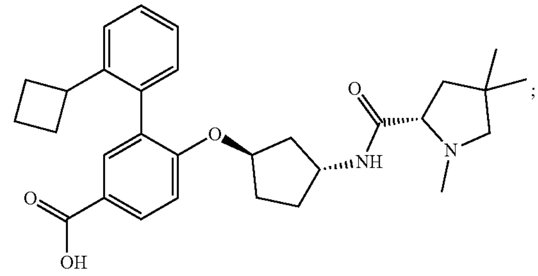
;
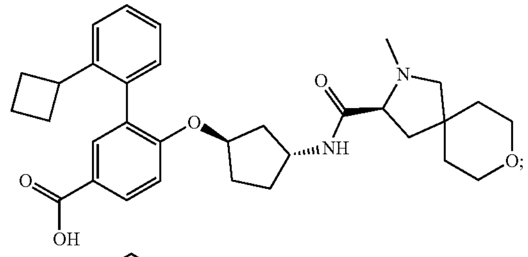
; or
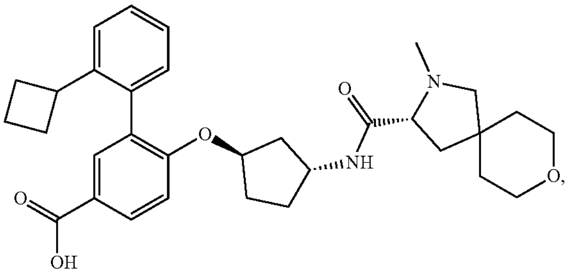
,
or a pharmaceutically acceptable salt thereof.
E113 A compound according to embodiment E101, which is:
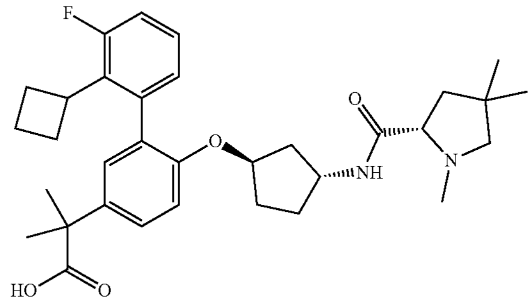
,
or a pharmaceutically acceptable salt thereof.

E114 A compound according to embodiment E101, which is:

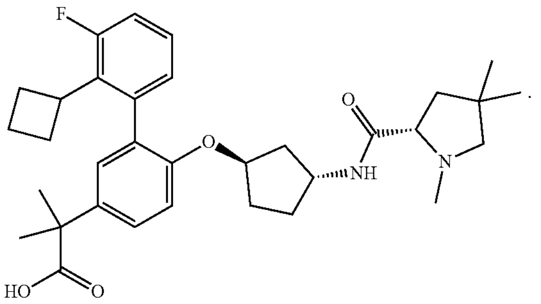 [SMILES: CN1CC(C)(C)C[C@H]1C(=O)N[C@@H]1CC[C@@H](Oc2ccc(C(C)(C)C(=O)O)cc2-c2cccc(F)c2C2CCC2)C1]

E115 A compound according to embodiment E101, which is:

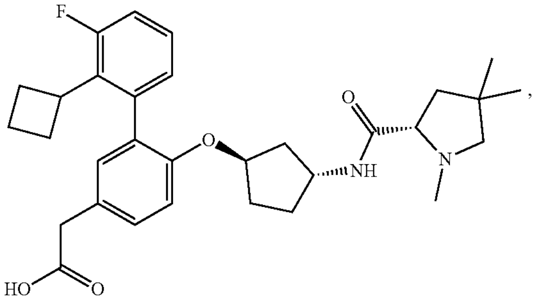 [SMILES: CN1CC(C)(C)C[C@H]1C(=O)N[C@@H]1CC[C@@H](Oc2ccc(CC(=O)O)cc2-c2cccc(F)c2C2CCC2)C1]

or a pharmaceutically acceptable salt thereof.

E116 A compound according to embodiment E101, which is:

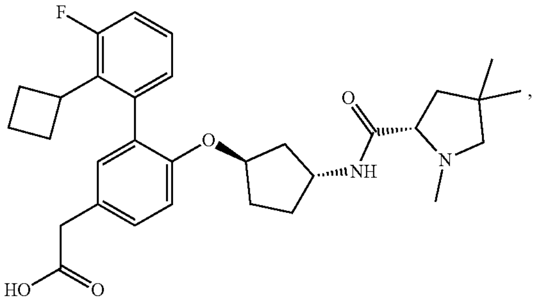 [SMILES: CN1CC(C)(C)C[C@H]1C(=O)N[C@@H]1CC[C@@H](Oc2ccc(CC(=O)O)cc2-c2cccc(F)c2C2CCC2)C1]

E117 A compound according to embodiment E24, or a pharmaceutically acceptable salt thereof, having formula (IA-11):

(IA-11)

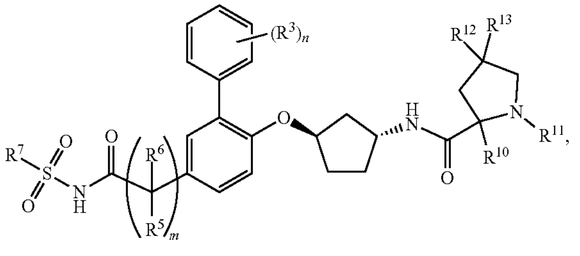

wherein:

m is 0 or 1;

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, or $C_1$-$C_3$ alkyl optionally substituted with 1 to 3 halogens;

$R^7$ is selected from the group consisting of $C_1$-$C_3$ alkyl, $C_3$-$C_4$ cycloalkyl optionally substituted with 1 to 4 halogens or a $C_1$-$C_3$ alkyl optionally substituted with 1 to 3 halogens, and —$NR^8R^9$, wherein $R^3$ and $R^9$ are each independently H or $C_1$-$C_3$ alkyl or $R^3$ and $R^9$ together form a 4-5 membered N-containing heterocycloalkyl ring optionally substituted with 1 to 4 halogens;

$R^{10}$ is H or $C_1$-$C_3$ alkyl;

$R^{11}$ is H, $C_1$-$C_3$ alkyl, or $C_1$-$C_3$ deuterated alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E118 A compound according to embodiment E111, or a pharmaceutically acceptable salt thereof, having formula (IA-11a), (IA-11b), or (IA-11c):

(IA-11a)

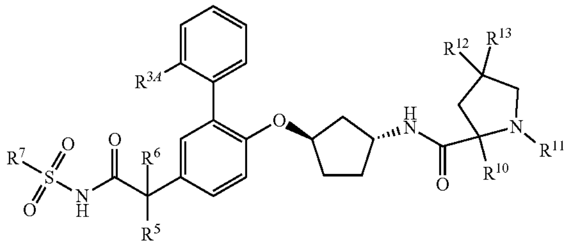

(IA-11b)

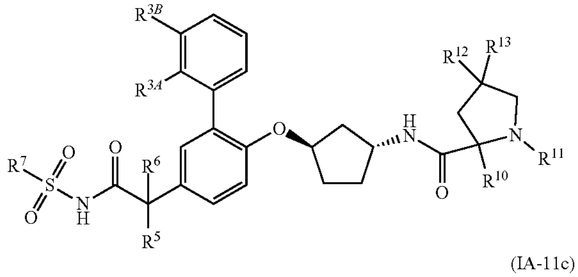

(IA-11c)

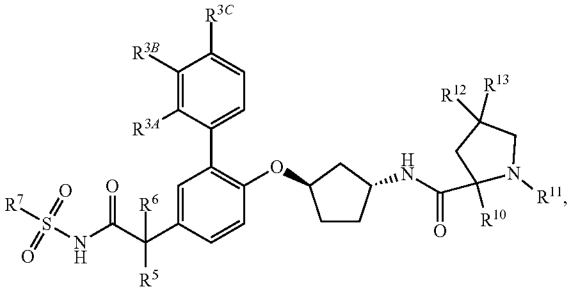

wherein:

$R^{3A}$ is $C_1$-$C_3$ alkyl optionally substituted with 1 to 3 halogens or $C_3$-$C_4$ cycloalkyl, preferably $R^{3A}$ is —$CH_2CH_3$, —$CH_2CF_3$, —$CH(CH_3)_2$, or $C_3$-$C_4$ cycloalkyl;

$R^{3B}$ is halogen, preferably $R^{3B}$ is F;

$R^{3C}$ is halogen, preferably $R^{3C}$ is F;

$R^5$ and $R^6$ are each independently H or $C_1$-$C_3$ alkyl, preferably H, —$CH_3$, or —$CH_2CH_3$;

$R^7$ is selected from the group consisting of $C_1$-$C_3$ alkyl, $C_3$-$C_4$ cycloalkyl optionally substituted with 1 to 4 halogens or a $C_1$-$C_3$ alkyl, and —$NR^8R^9$, preferably $R^7$ is —$CH_3$, —$CH_2CH_3$, —$CH(CH_3)_2$, cyclopropyl, cyclopropyl substituted with —$CH_3$, —$NH_2$, —$N((CH)_3)_2$, —$N(CH_3)(CH_2CH_3)$, or azetidine optionally substituted with 1, 2, or 3 F;

$R^{10}$ is H or $C_1$-$C_3$ alkyl, preferably $R^{10}$ is H;

$R^{11}$ is $C_1$-$C_3$ alkyl or $C_1$-$C_3$ deuterated alkyl; and $R^{12}$ and $R^{13}$ are each $C_1$-$C_3$ alkyl.

E119 A compound according to embodiment E118, or a pharmaceutically acceptable salt thereof, having formula (IA-11a), wherein $R^{3A}$ is —$CH_2CF_3$, preferably $CH_2CF_3$.

E120 A compound according to embodiment E118, or a pharmaceutically acceptable salt thereof, having formula (IA-11b) or (IA-11c), wherein $R^{3A}$ is —$CH_2CH_3$, cyclopropyl, or cyclobutyl, $R^{3B}$ is F, and $R^{3C}$ is F.

E121 A compound according to any one of embodiments E117 to E120, or a pharmaceutically acceptable salt thereof, wherein $R^5$ and $R^6$ are each H.

E122 A compound according to any one of embodiments E117 to E120, or a pharmaceutically acceptable salt thereof, wherein $R^5$ and $R^6$ are each —$CH_3$.

E123 A compound according to any one of embodiments E117 to E120, or a pharmaceutically acceptable salt thereof, wherein one of $R^5$ and $R^6$ is H and the other of $R^5$ and $R^6$ is —$CH_3$.

E124 A compound according to any one of embodiments E117 to E123, or a pharmaceutically acceptable salt thereof, wherein $R^{10}$ is H.

E125 A compound according to any one of embodiments E117 to E124, or a pharmaceutically acceptable salt thereof, wherein $R^{11}$, $R^{12}$, and $R^{13}$ are each —$CH_3$.

E126 A compound according to any one of embodiments E117 to E124, or a pharmaceutically acceptable salt thereof, wherein $R^{11}$ is —$CD_3$ and $R^{12}$ and $R^{13}$ are each —$CH_3$.

E127 A compound according to any one of embodiments E117 to E126, or a pharmaceutically acceptable salt thereof, wherein $R^7$ is —$CH_3$ or —$N((CH)_3)_2$.

E128 A compound according to embodiment E117, which is:

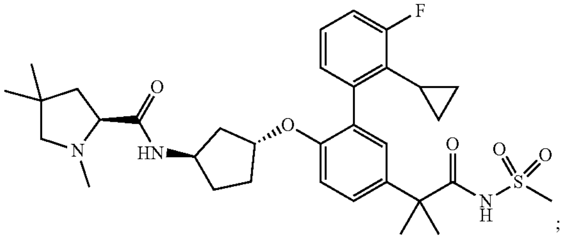

;

-continued

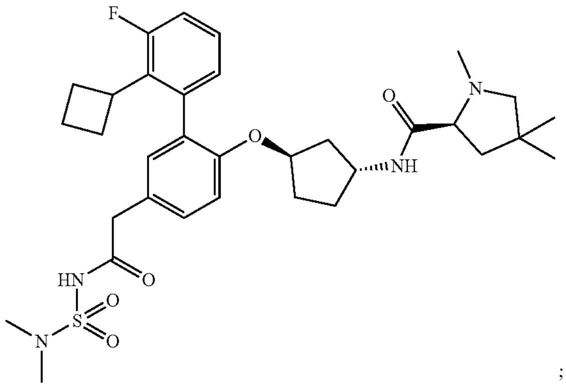

;

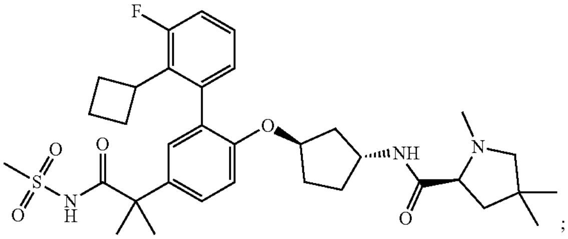

;

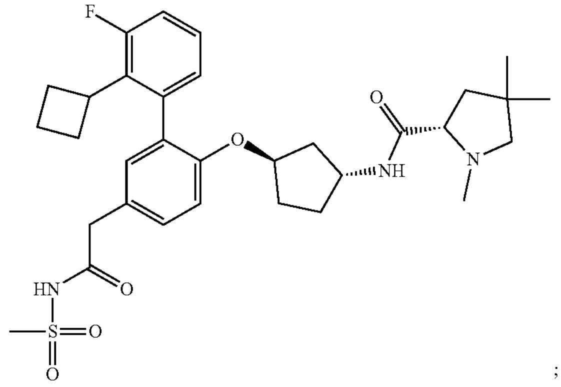

;

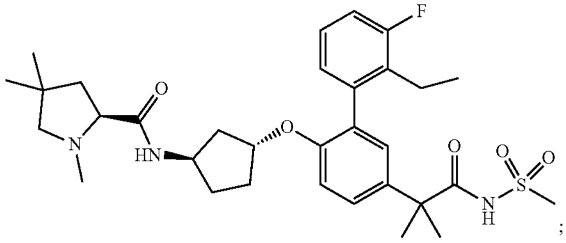

;

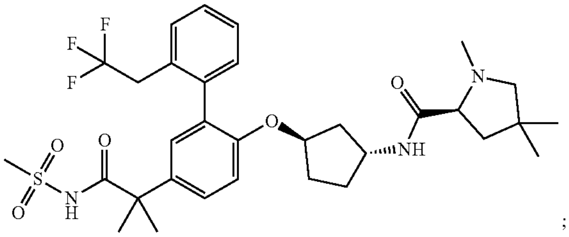

;

-continued

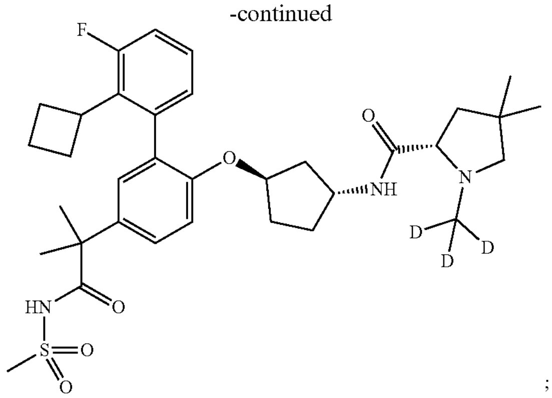

;

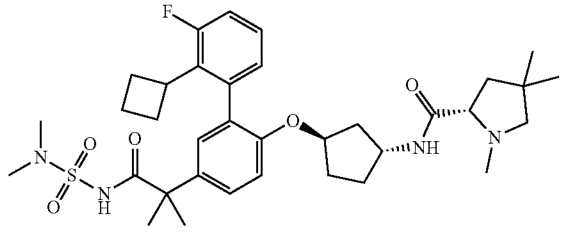

;

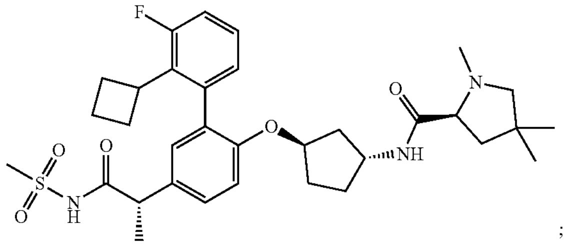

;

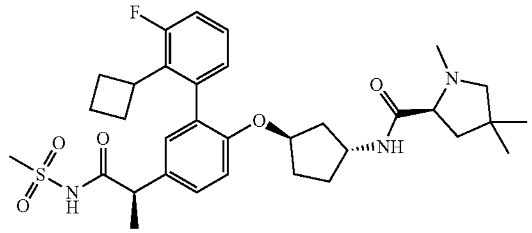

or

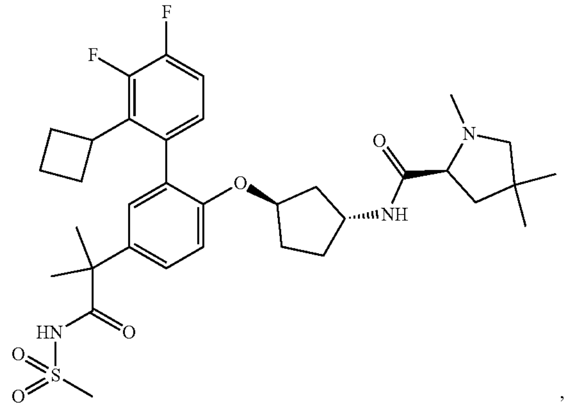

, or a pharmaceutically acceptable salt thereof.

E129 A compound according to embodiment E117, which is:

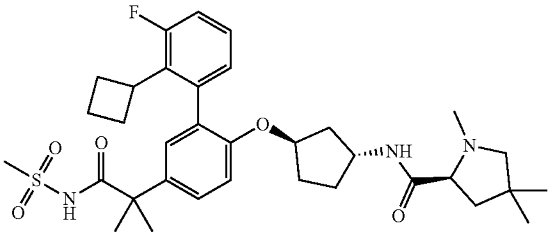

, or a pharmaceutically acceptable salt thereof.

E130 A compound according to embodiment E17, which is

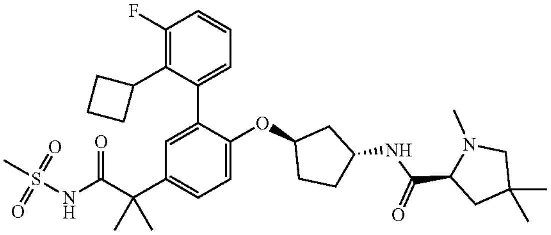

.

E130 A compound according to embodiment E24, or a pharmaceutically acceptable salt thereof, having formula (IA-12):

(IA-12)

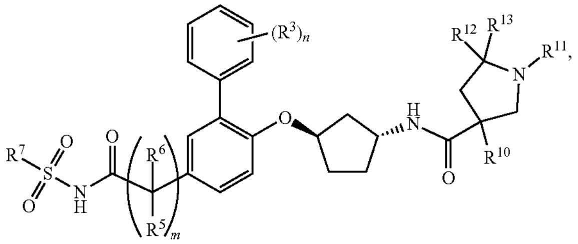

wherein:

m is 0 or 1;

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, or $C_1$-$C_3$ alkyl optionally substituted with 1 to 3 halogens;

$R^7$ is selected from the group consisting of $C_1$-$C_3$ alkyl, $C_3$-$C_4$ cycloalkyl optionally substituted with 1 to 4 halogens or a $C_1$-$C_3$ alkyl optionally substituted with 1 to 3 halogens, and —$NR^8R^9$, wherein $R^3$ and $R^9$ are each independently H or $C_1$-$C_3$ alkyl or $R^3$ and $R^9$ together form a 4-5 membered N-containing heterocycloalkyl ring optionally substituted with 1 to 4 halogens;

$R^{10}$ is H or halogen;

$R^{11}$ is H, $C_1$-$C_3$ alkyl, or $C_1$-$C_3$ deuterated alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E132 A compound according to embodiment E131, or a pharmaceutically acceptable salt thereof, having formula (IA-12a) or (IA-12b):

(IA-12a)

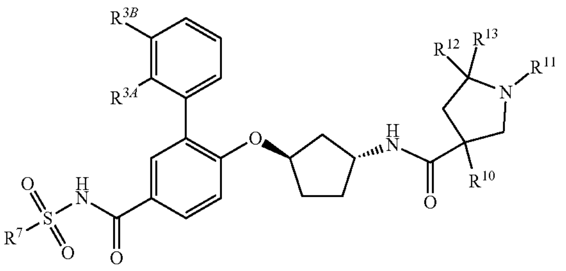

(IA-12b)

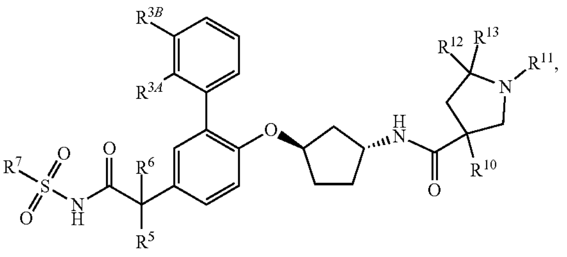

wherein:

$R^{3A}$ is $C_1$-$C_3$ alkyl or $C_3$-$C_4$ cycloalkyl, preferably $R^{3A}$ is —$CH_2CH_3$, —$CH(CH_3)_2$, or $C_3$-$C_4$ cycloalkyl;

$R^{3B}$ is halogen, preferably $R^{3B}$ is F;

$R^5$ and $R^6$ are each independently H or $C_1$-$C_3$ alkyl, preferably $R^5$ and $R^6$ are each independently H, —$CH_3$, or —$CH_2CH_3$;

$R^7$ is selected from the group consisting of $C_1$-$C_3$ alkyl, $C_3$-$C_4$ cycloalkyl optionally substituted with 1 to 4 halogens or a $C_1$-$C_3$ alkyl, and

—$NR^8R^9$, preferably $R^7$ is —$CH_3$, —$CH_2CH_3$, —$CH(CH_3)_2$, cyclopropyl substituted with —$CH_3$, —$NH_2$, —$N((CH)_3)_2$, —$N(CH_3)(CH_2CH_3)$, or azetidine optionally substituted with 1, 2, or 3 F;

$R^{10}$ is H or halogen, preferably $R^{10}$ is H or F;

$R^{11}$ is H or $C_1$-$C_3$ alkyl; and $R^{12}$ and $R^{13}$ are each $C_1$-$C_3$ alkyl or $R^{12}$ and $R^{13}$ together form a $C_3$-$C_6$ cycloalkyl optionally substituted with 1 to 3 halogens.

E133 A compound according to embodiment E132, or a pharmaceutically acceptable salt thereof, wherein $R^{3A}$ is —$CH_2CH_3$ and $R^{3B}$ is F.

E134 A compound according to embodiment E132, or a pharmaceutically acceptable salt thereof, wherein $R^{3A}$ is cyclopropyl or cyclobutyl, preferably $R^{3A}$ is cyclobutyl, and $R^{3B}$ is F.

E135 A compound according to any one of embodiments E131 to E134, or a pharmaceutically acceptable salt thereof, wherein $R^5$ and $R^6$ are each —$CH_3$.

E136 A compound according to any one of embodiments E131 to E135, or a pharmaceutically acceptable salt thereof, wherein $R^{10}$ is F.

E137 A compound according to any one of embodiments E131 to E136, or a pharmaceutically acceptable salt thereof, wherein $R^{11}$ is H.

E138 A compound according to any one of embodiments E131 to E137, or a pharmaceutically acceptable salt thereof, wherein $R^{12}$ and $R^{13}$ are each —$CH_3$.

E139 A compound according to any one of embodiments E131 to E137, or a pharmaceutically acceptable salt thereof, wherein $R^{12}$ and $R^{13}$ together form cyclobutyl.

E140 A compound according to any one of embodiments E131 to E137, or a pharmaceutically acceptable salt thereof, wherein $R^{12}$ and $R^{13}$ together form cyclopentyl.

E141 A compound according to embodiment E131 or E140, or a pharmaceutically acceptable salt thereof, wherein $R^7$ is —$CH_3$, —$CH_2CH_3$, —$CH(CH_3)_2$, cyclopropyl, cyclopropyl substituted with —$CH_3$, —$N((CH)_3)_2$, —$N(CH_3)(CH_2CH_3)$, or azetidine optionally substituted with 1, 2, or 3 F.

E142 A compound according to embodiment E131, which is:

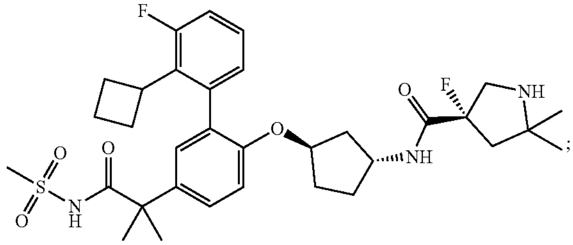
;

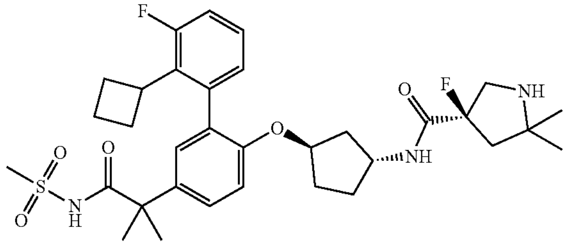
;

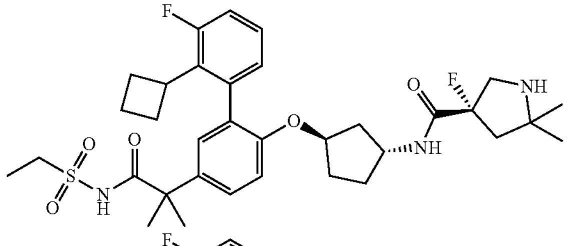
;

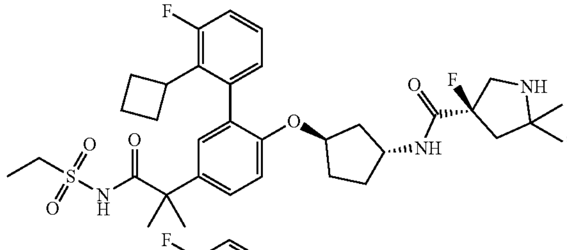
;

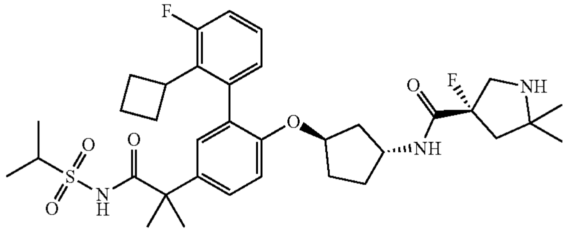
;

-continued
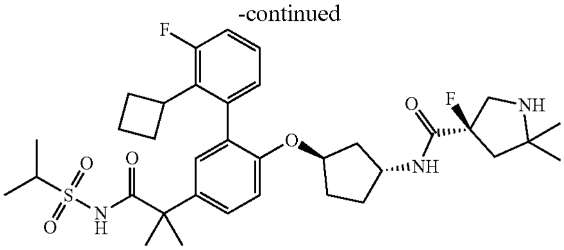
;
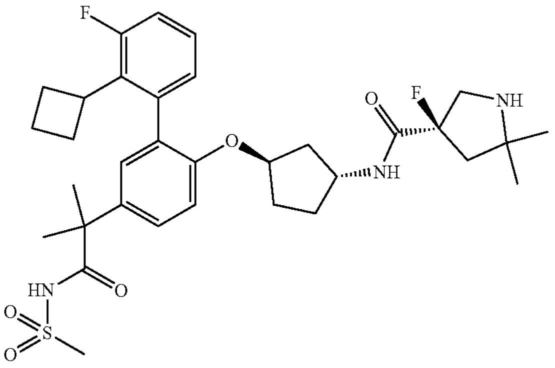
;
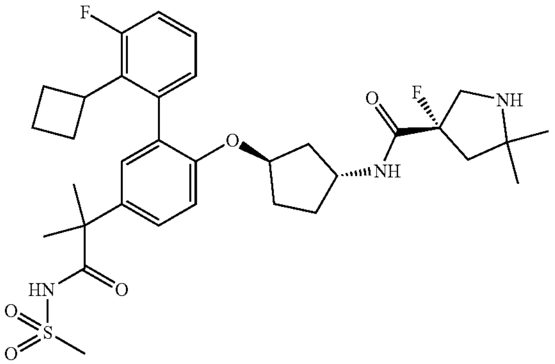
;
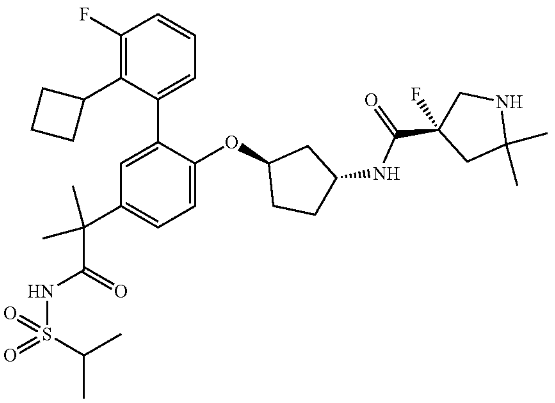
;
-continued
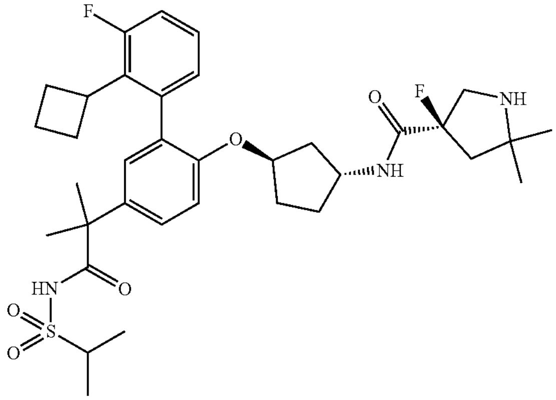
;
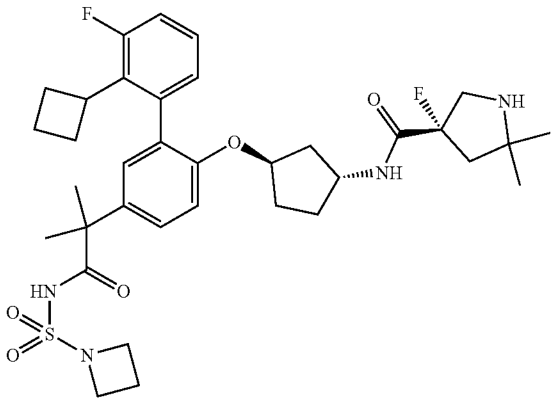
;
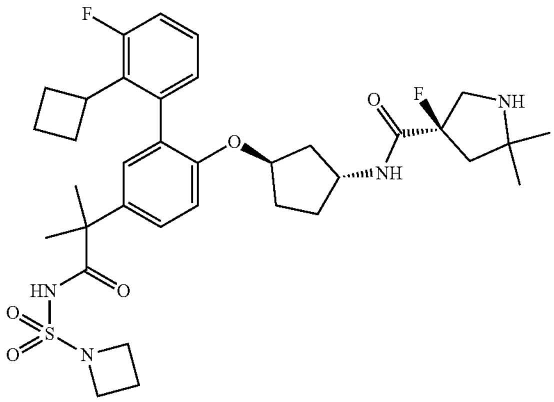
;
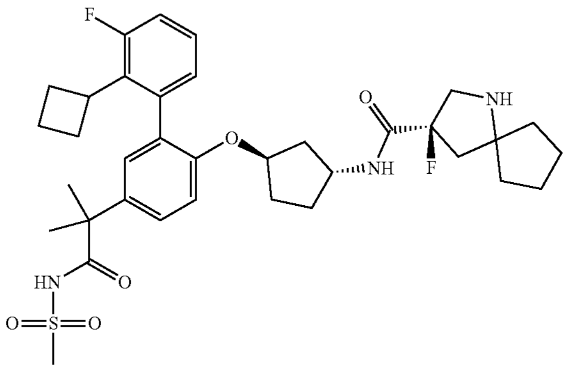
;

-continued
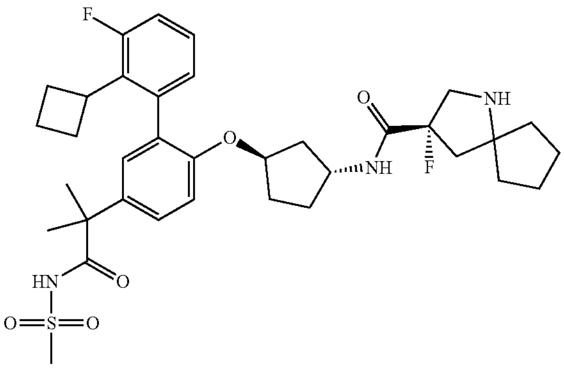
;
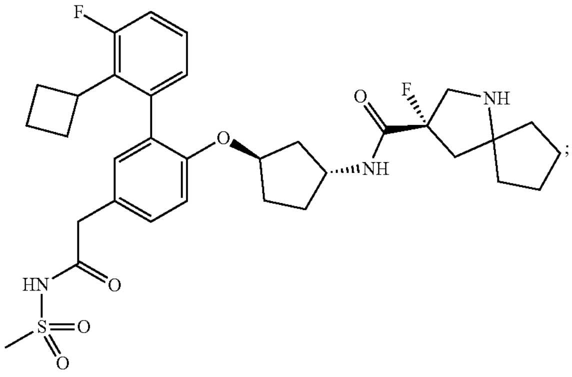
;
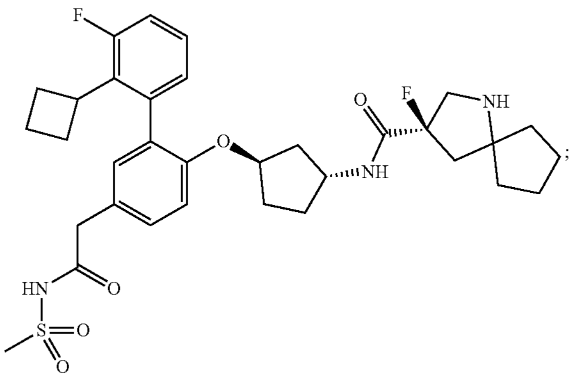
;
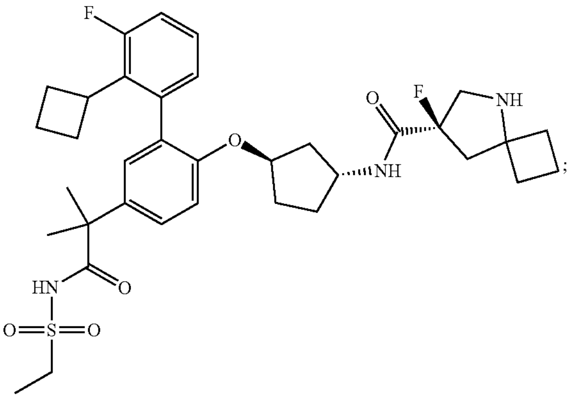
;
-continued
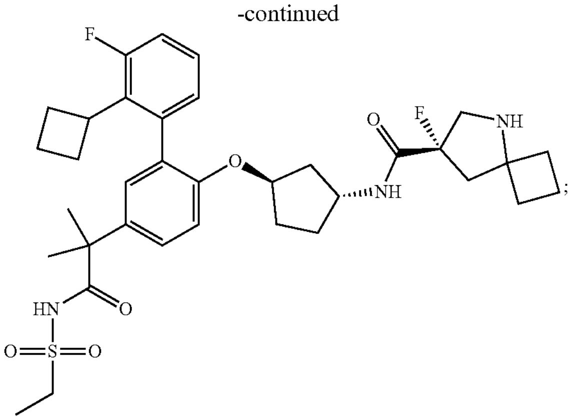
;
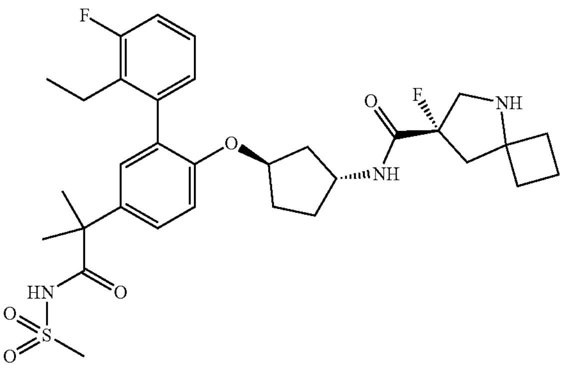
;
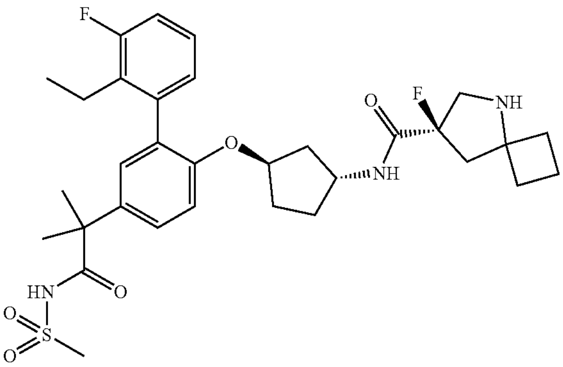
;
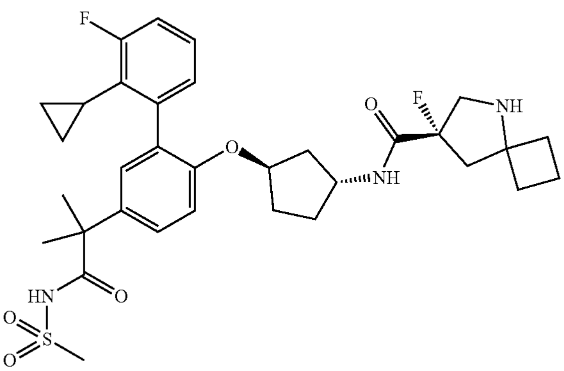
;

-continued
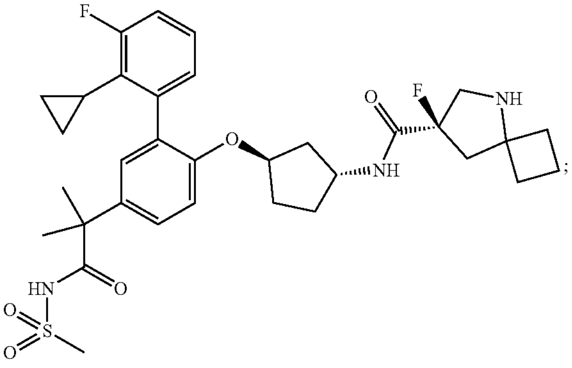
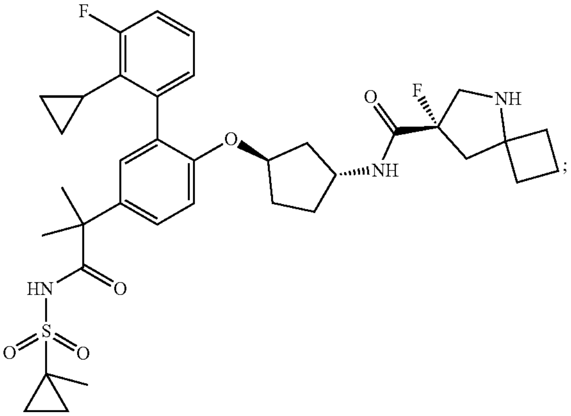
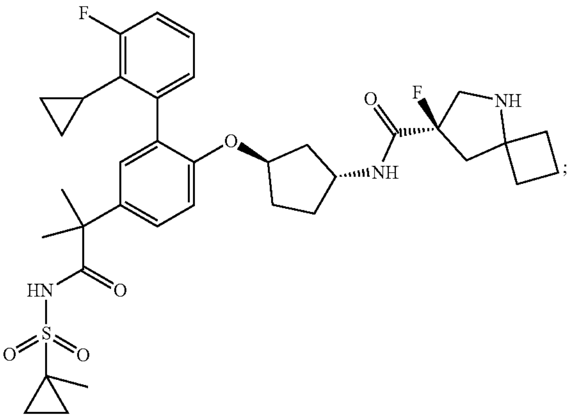
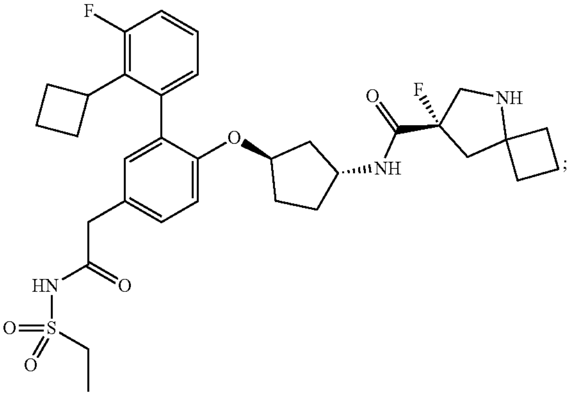
-continued
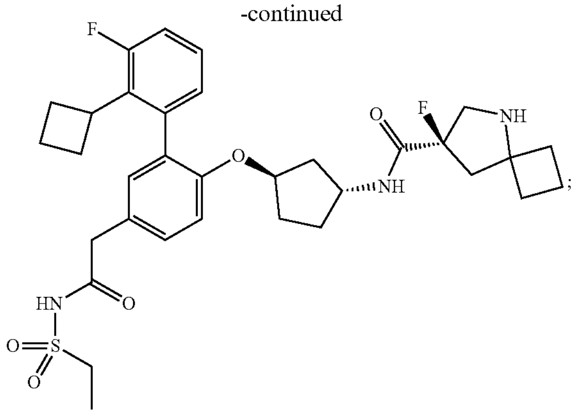
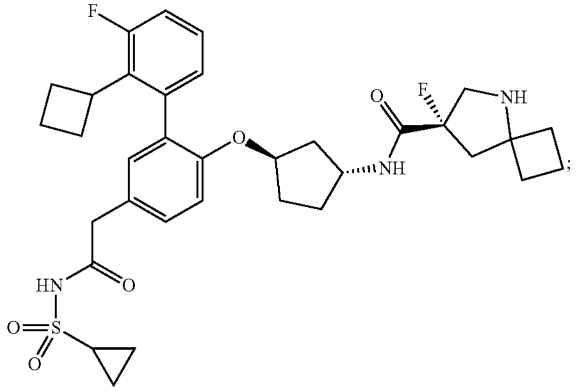
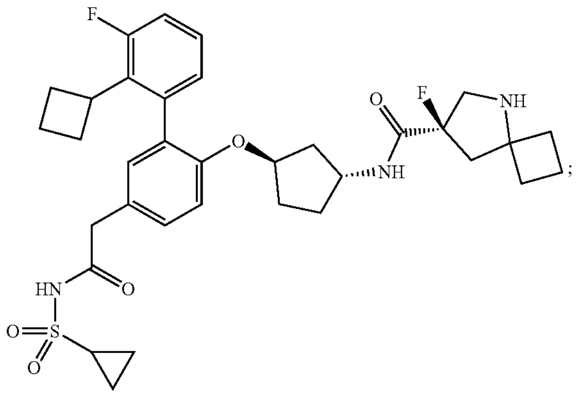
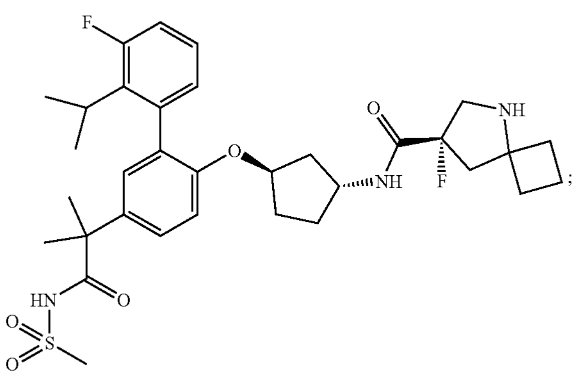

-continued
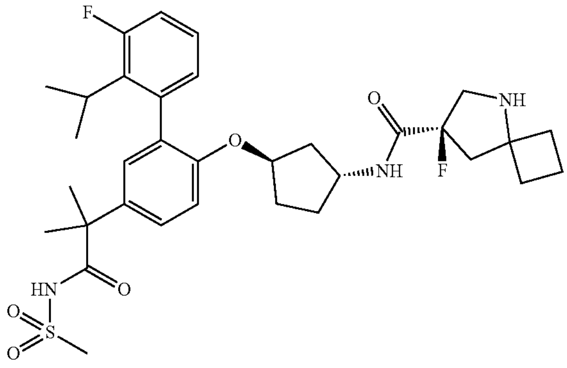
;
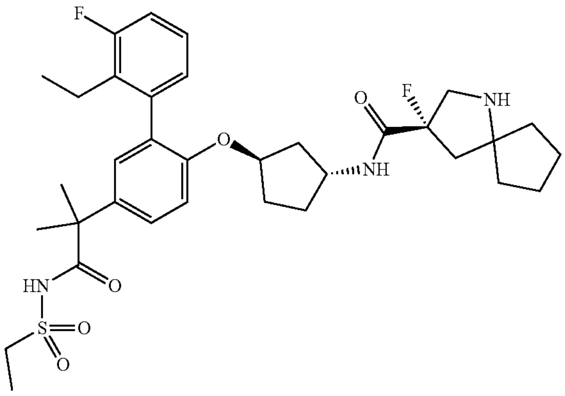
;
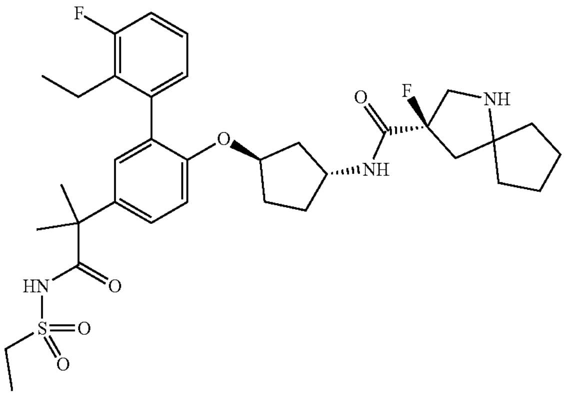
;
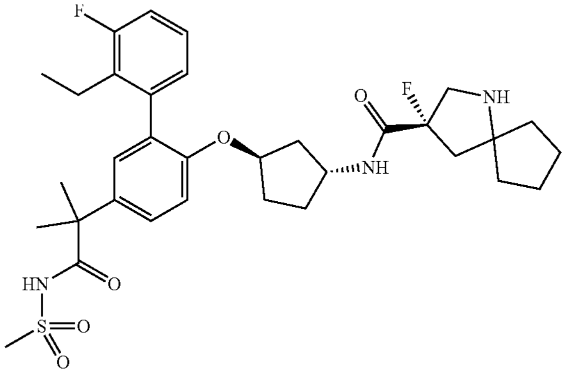
;
-continued
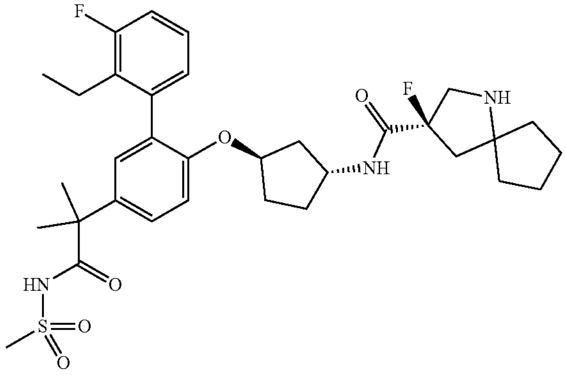
;
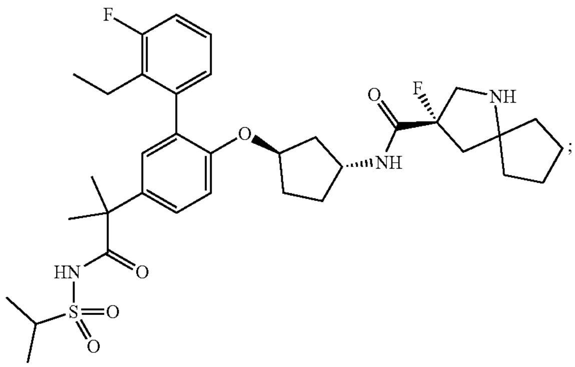
;
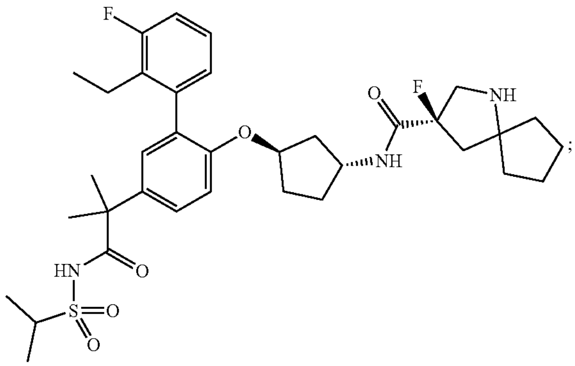
;
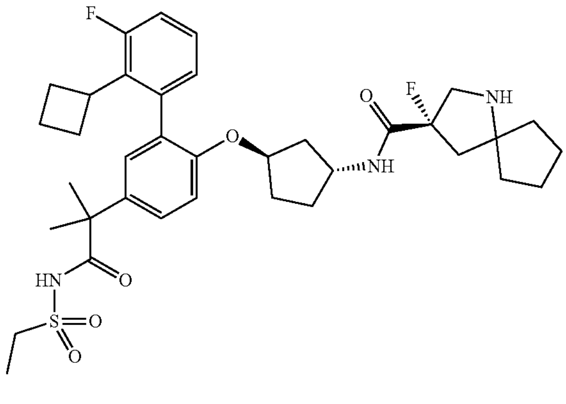
;

-continued
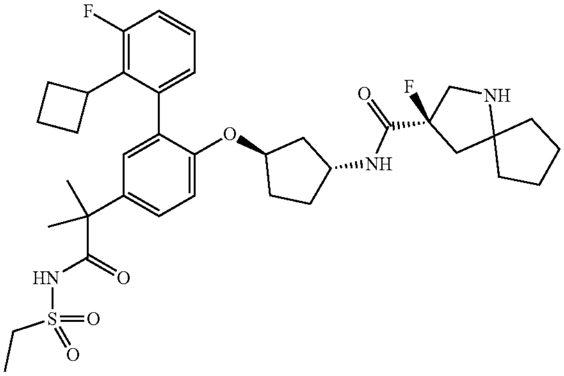
;
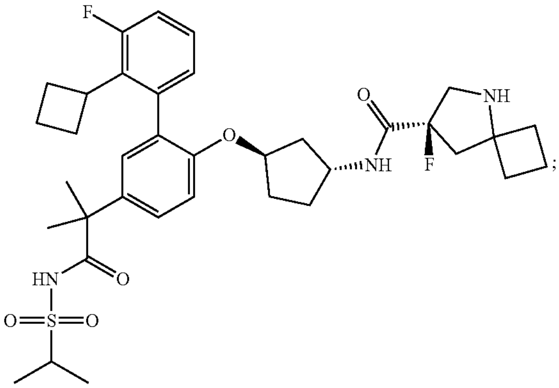
;
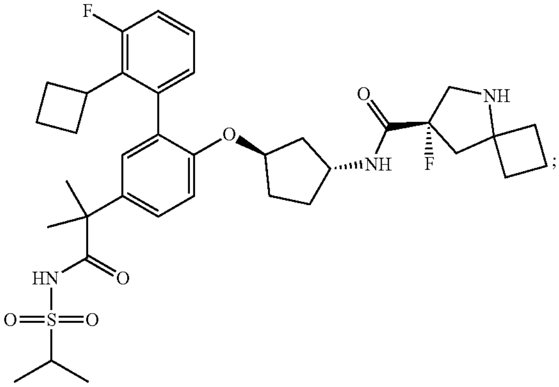
;
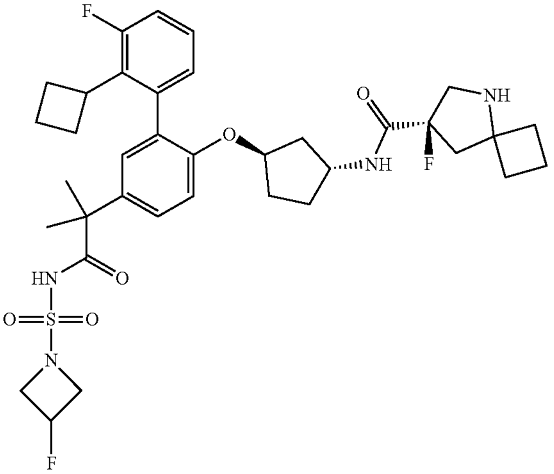
;
-continued
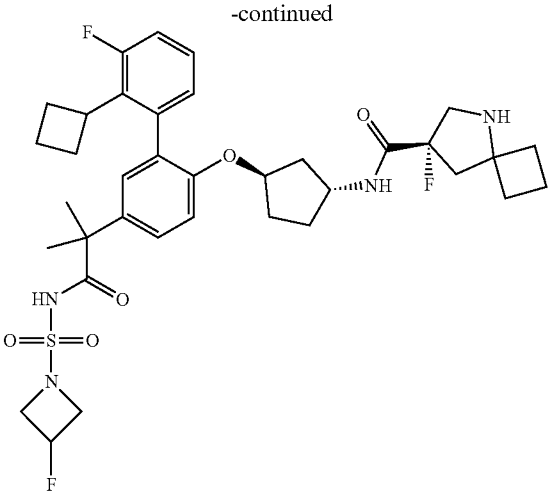
;
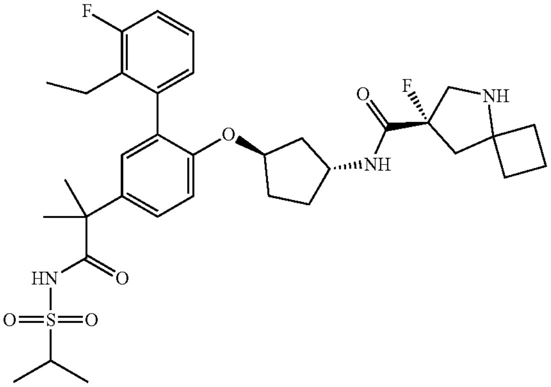
;
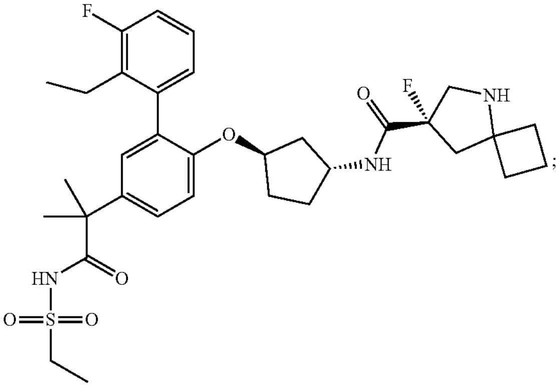
;
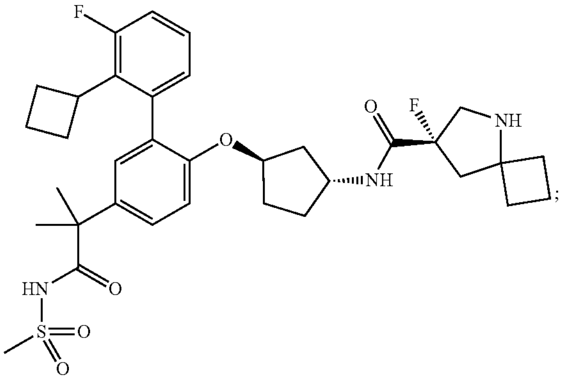
;

-continued
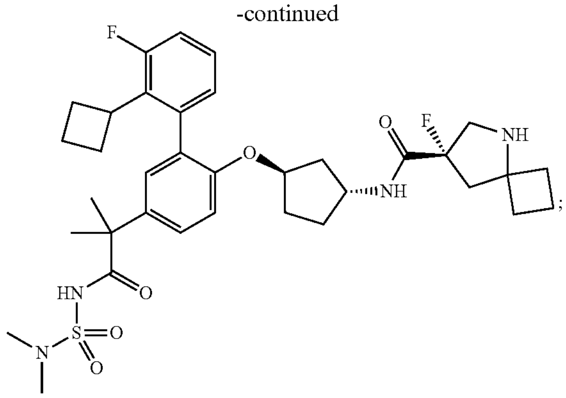
;
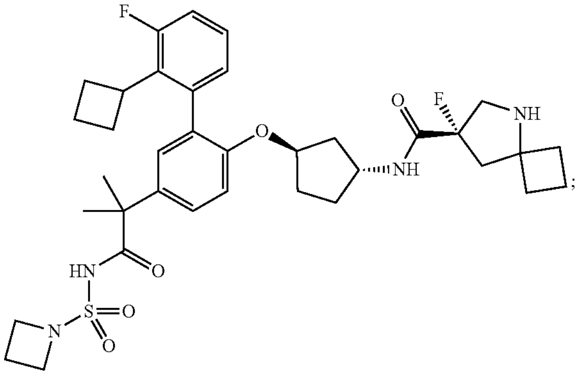
;
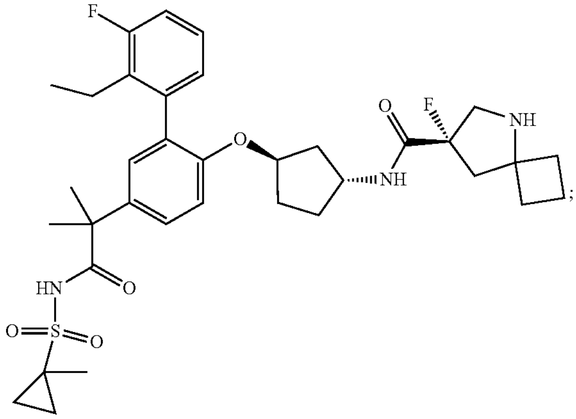
;
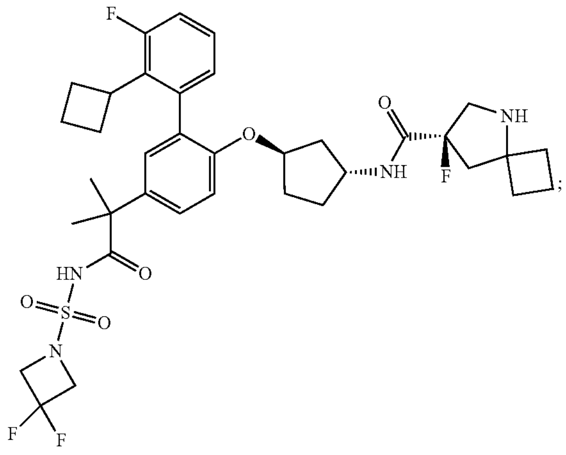
;
-continued
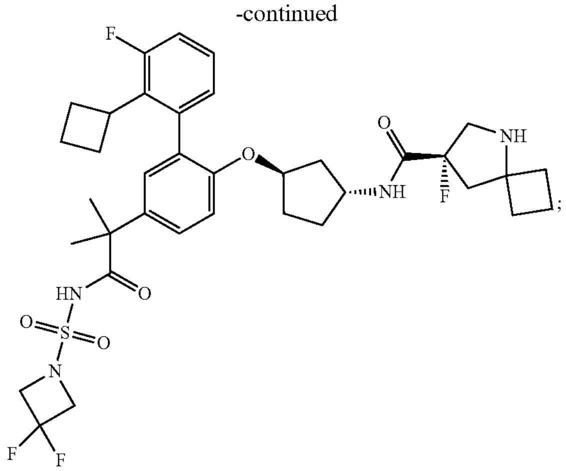
;
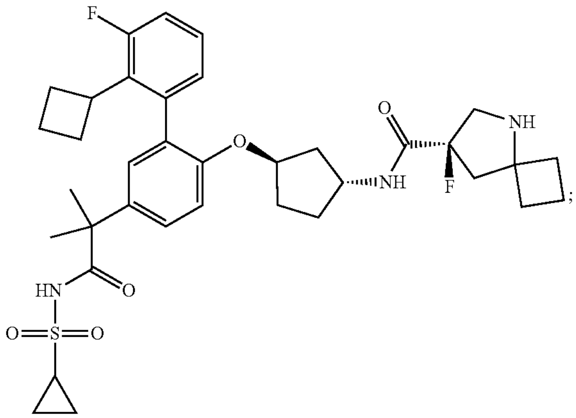
;
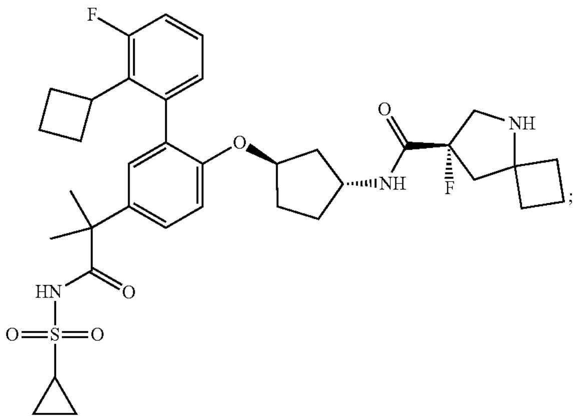
;
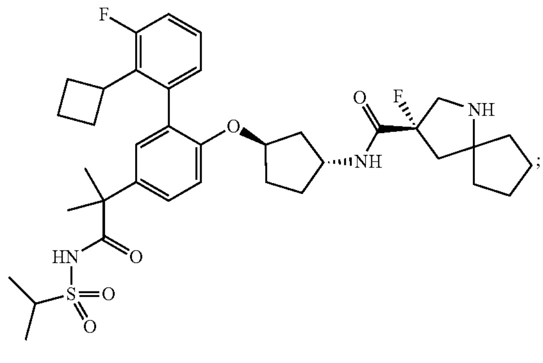
;

-continued
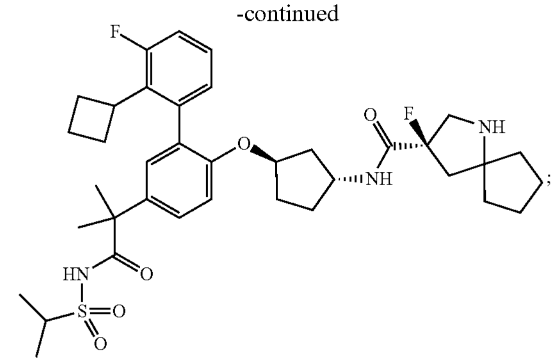
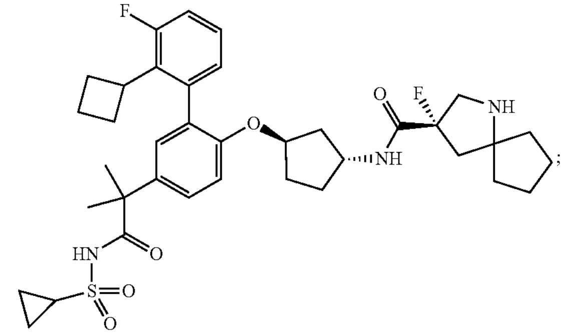
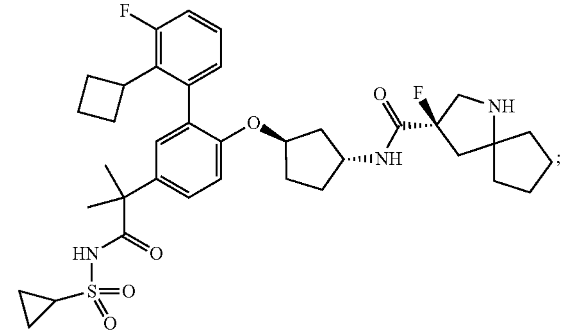
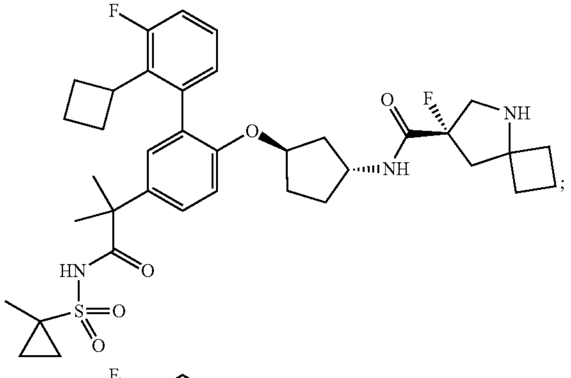
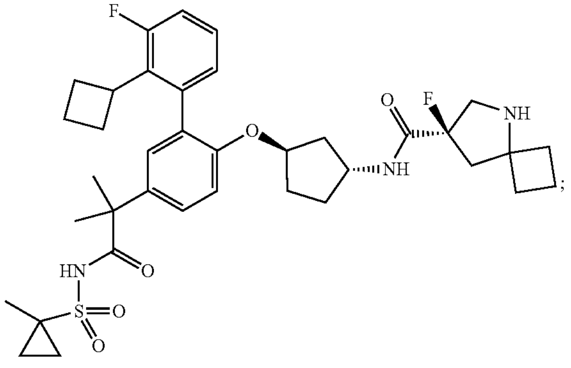
-continued
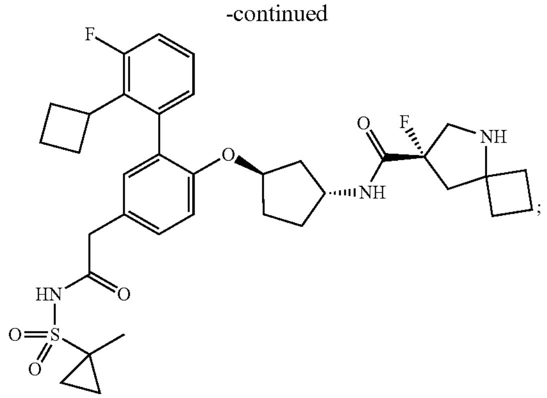
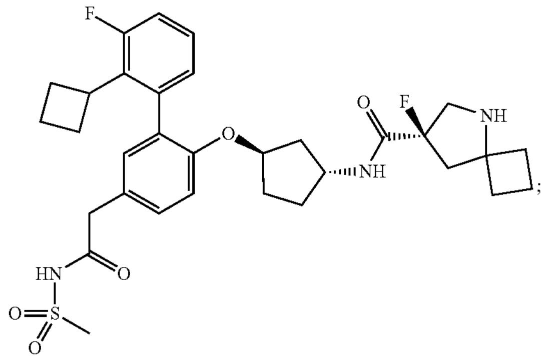
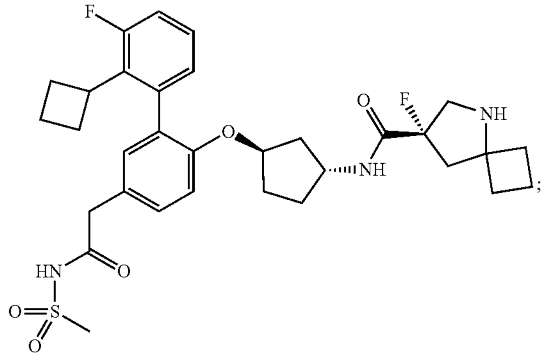
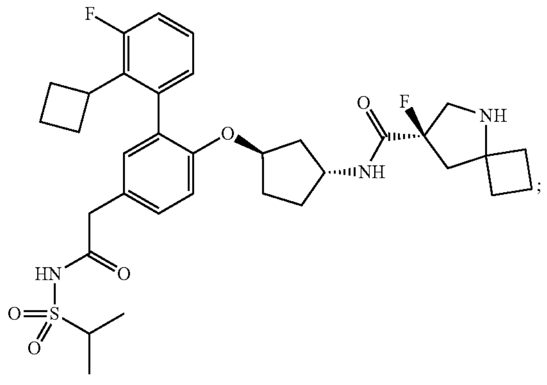

-continued
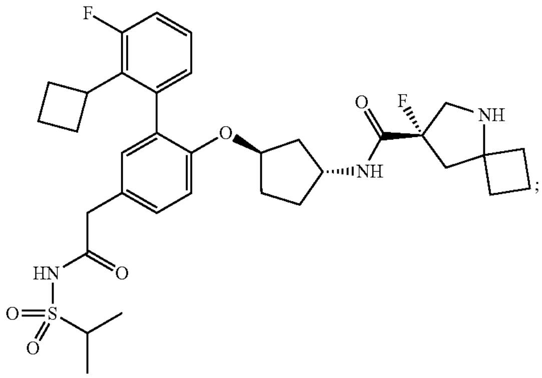
;
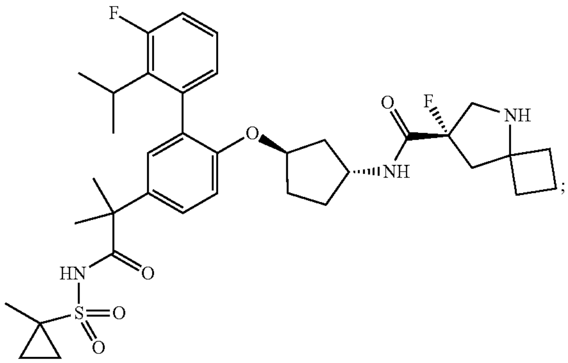
;
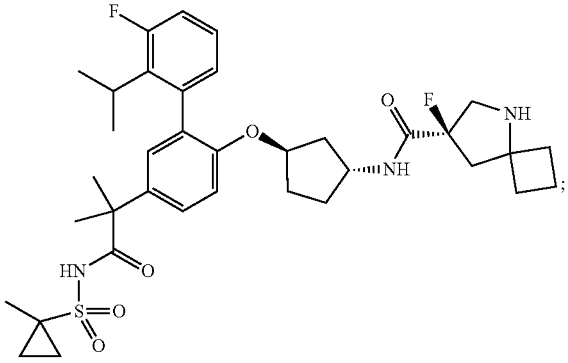
;
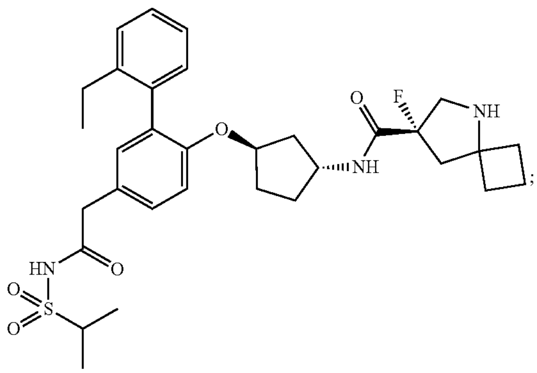
;
-continued
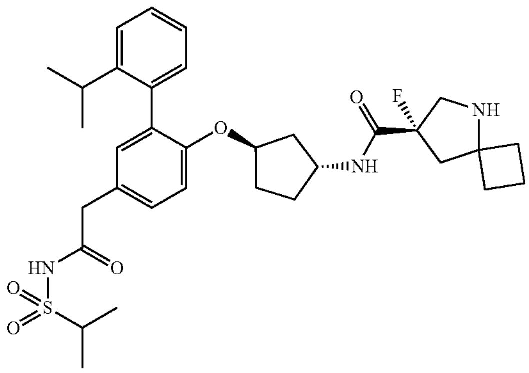
;
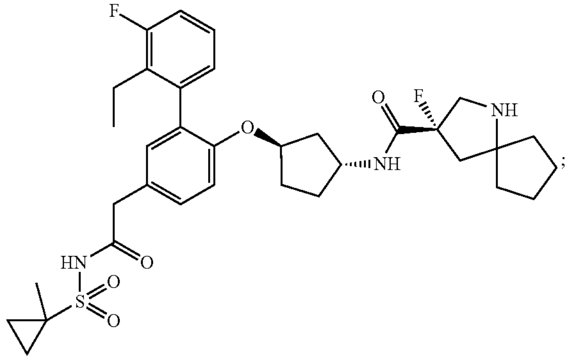
;
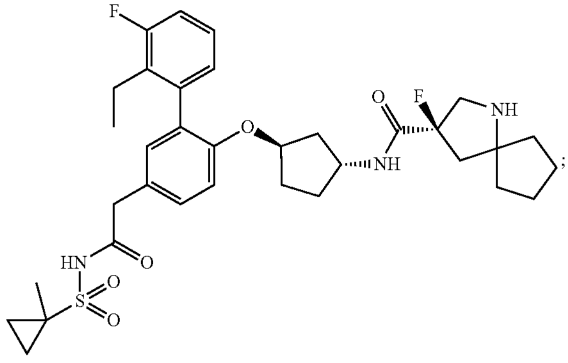
;
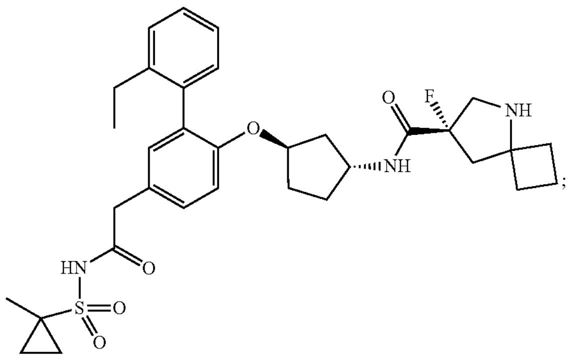
;

-continued
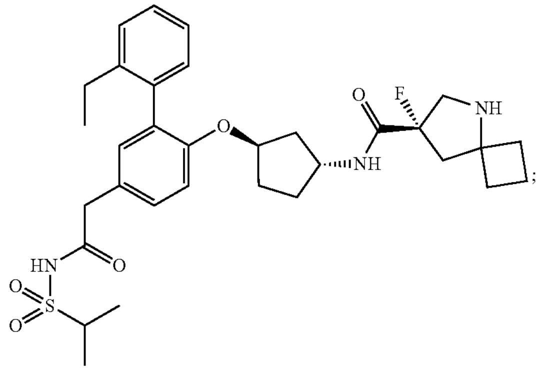
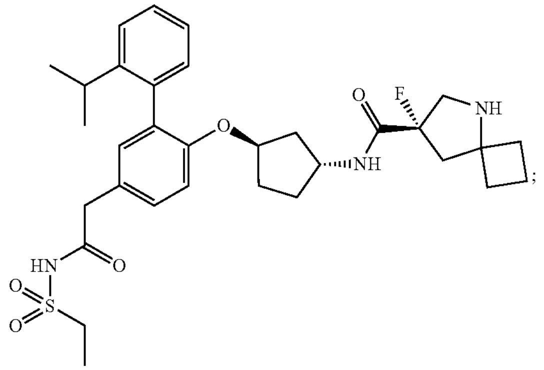
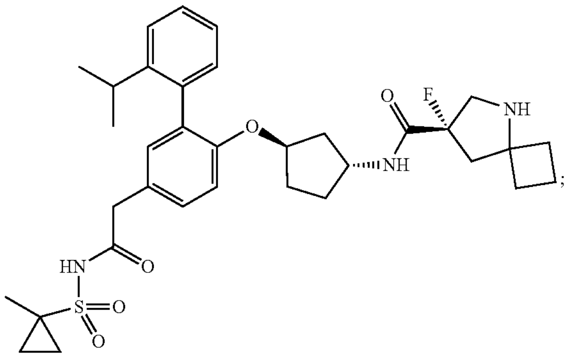
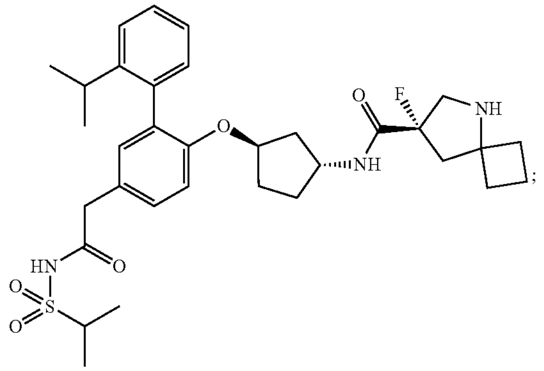
-continued
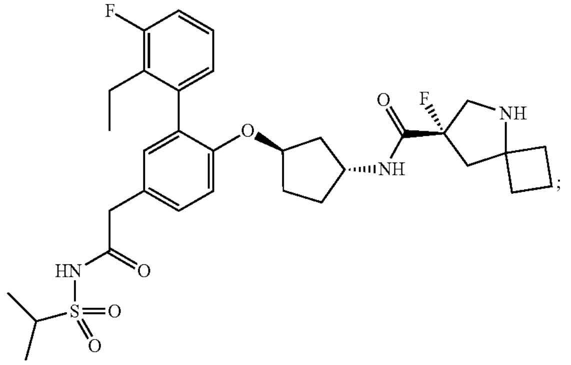
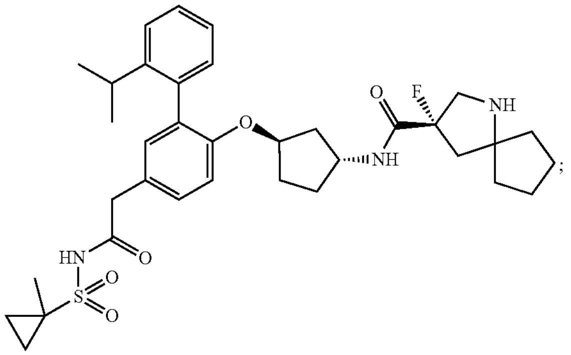
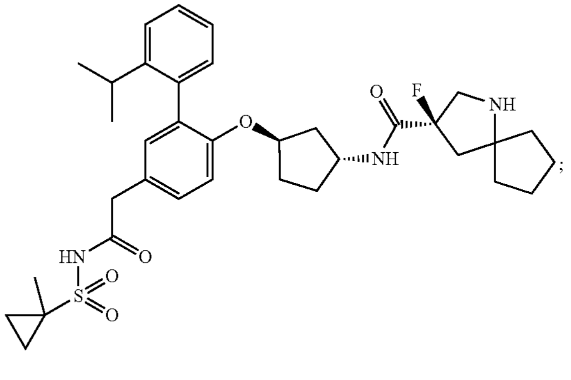
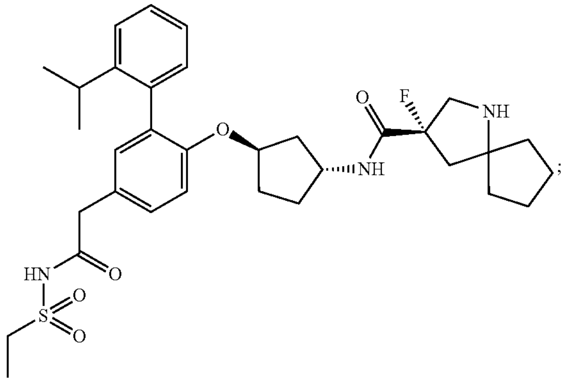

-continued
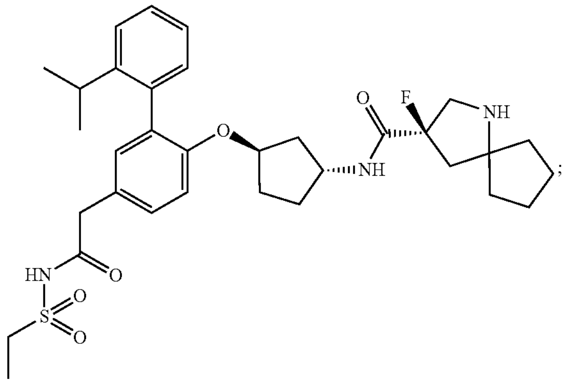
;
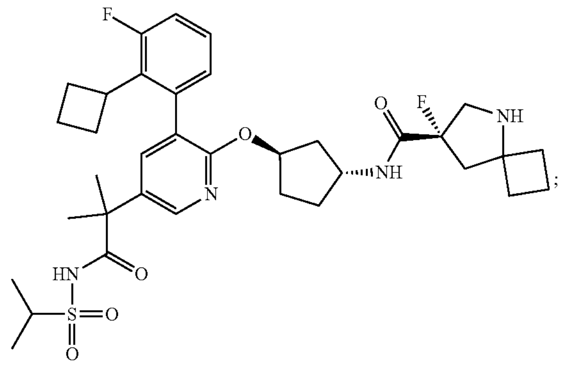
;
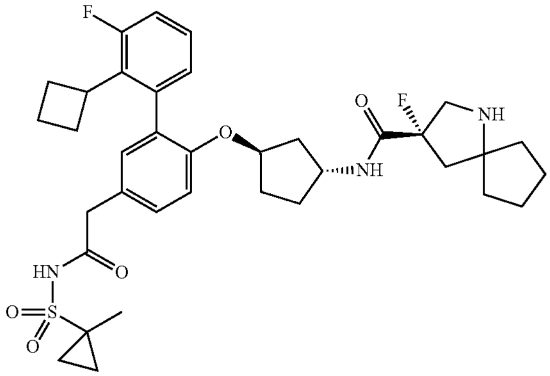
;
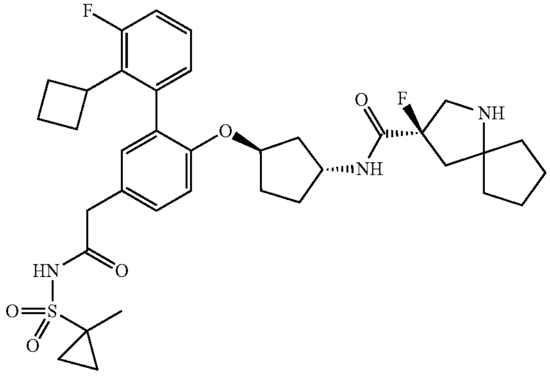
;
-continued
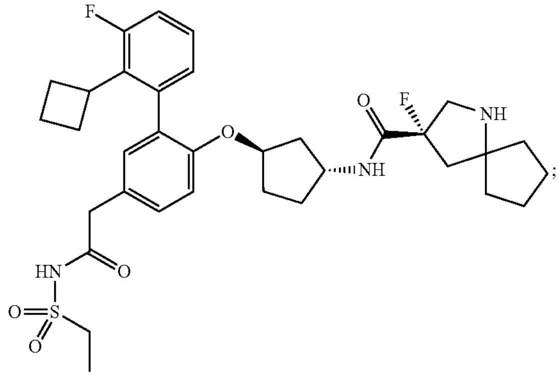
;
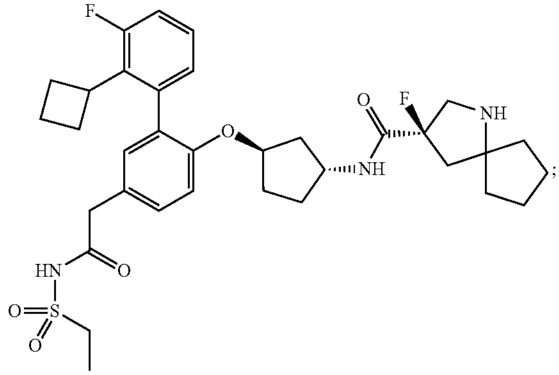
;
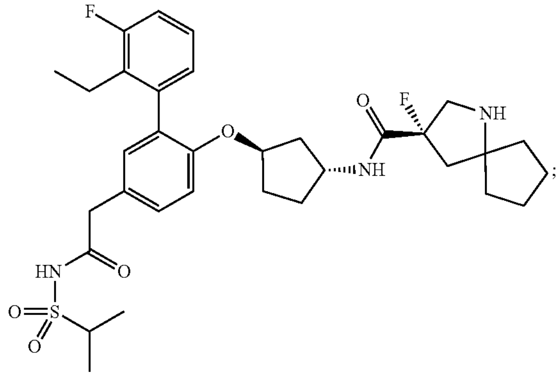
;
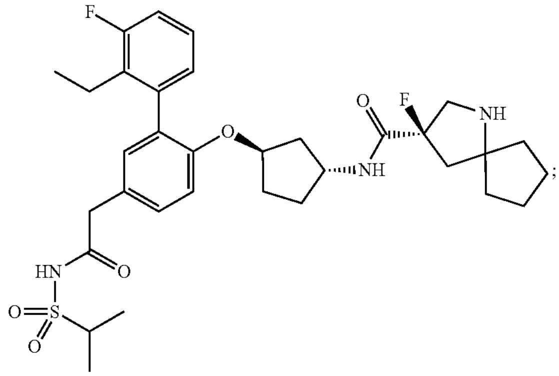
;

-continued
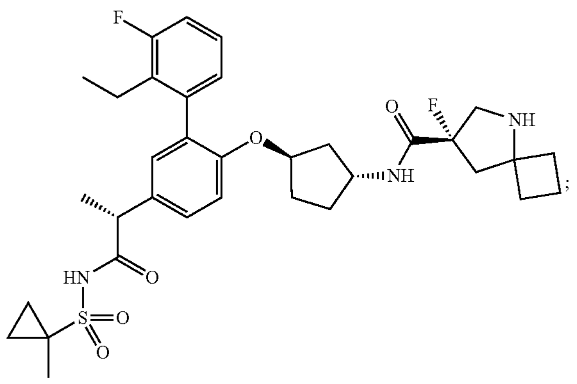
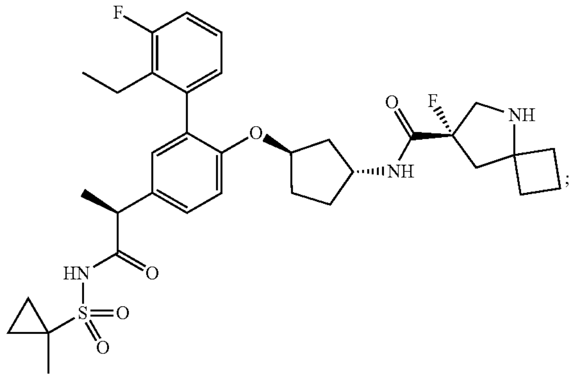
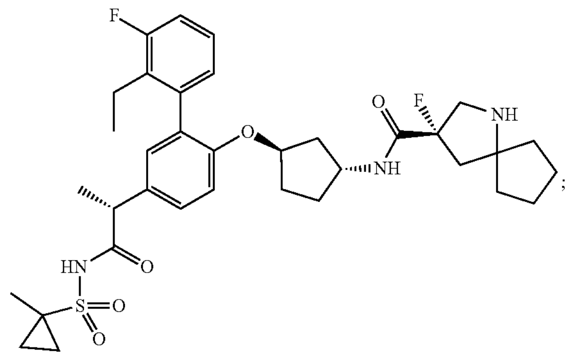
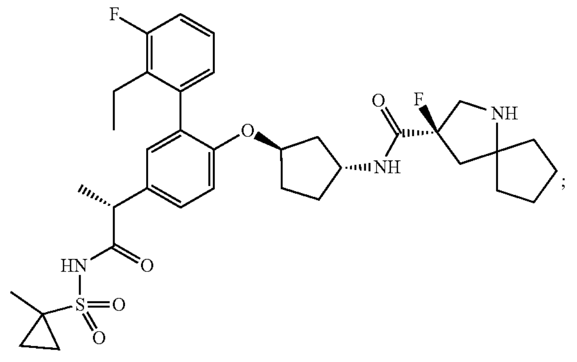
-continued
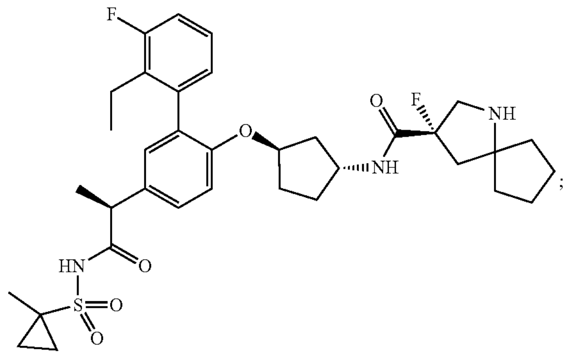
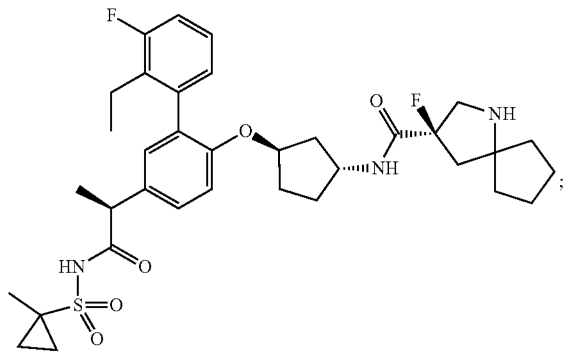
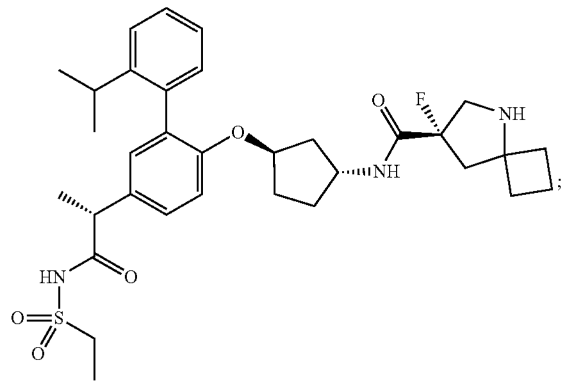
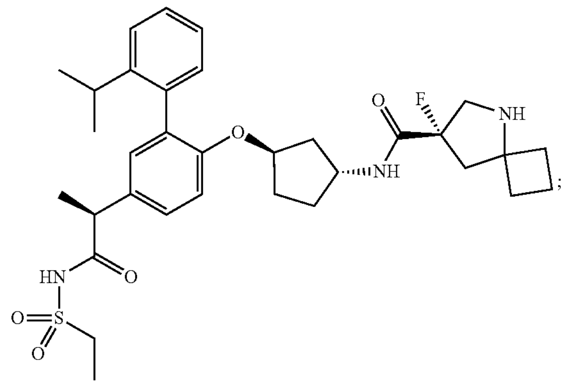

-continued
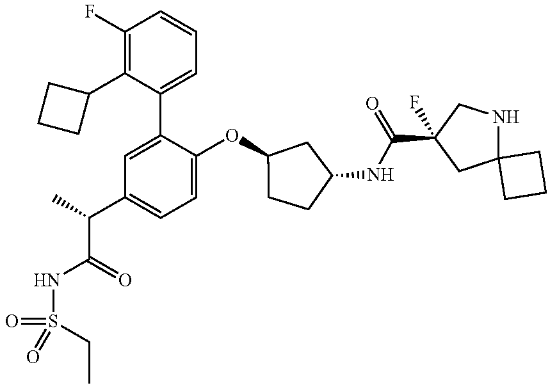
;
or
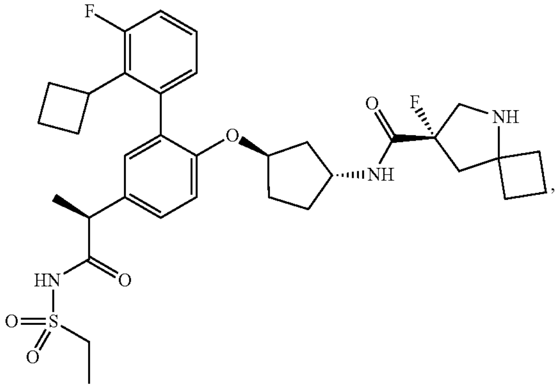 [SMILES: CCS(=O)(=O)NC(=O)[C@@H](C)c1ccc(O[C@@H]2CC[C@@H](NC(=O)[C@@]3(F)CNC4(CCC4)C3)C2)c(-c2cccc(F)c2C2CCC2)c1]
,
or a pharmaceutically acceptable salt thereof.
E143 A compound according to embodiment E131, which is:
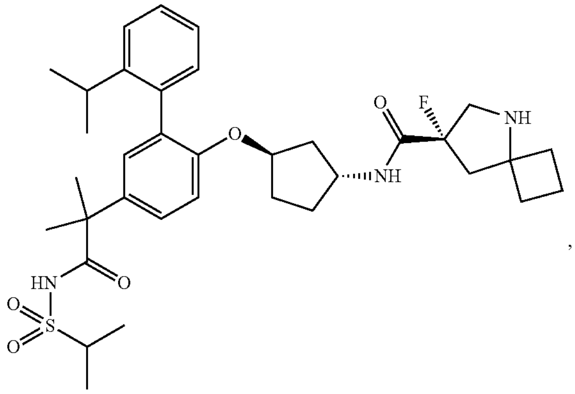 [SMILES: CC(C)c1ccccc1-c1cc(C(C)(C)C(=O)NS(=O)(=O)C(C)C)ccc1O[C@@H]1CC[C@@H](NC(=O)[C@@]2(F)CNC3(CCC3)C2)C1]
,
or a pharmaceutically acceptable salt thereof.
E144 A compound according to embodiment E131, which is:
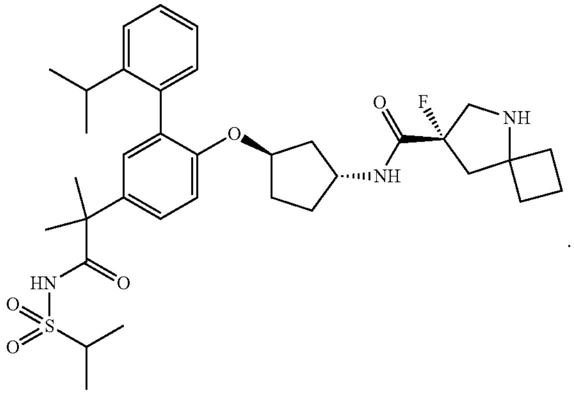 [SMILES: CC(C)c1ccccc1-c1cc(C(C)(C)C(=O)NS(=O)(=O)C(C)C)ccc1O[C@@H]1CC[C@@H](NC(=O)[C@@]2(F)CNC3(CCC3)C2)C1]
.
E145 A compound according to embodiment E24, or a pharmaceutically acceptable salt thereof, having formula (IA-13), (IA-14), (A-15), (A-16), or (IA-17):
(IA-13)
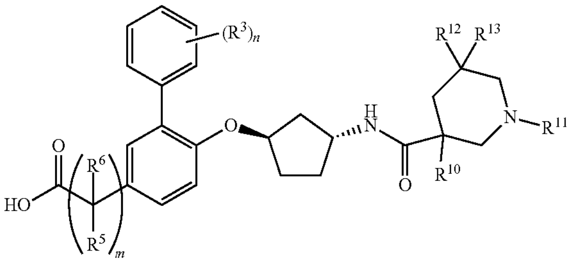
(IA-14)
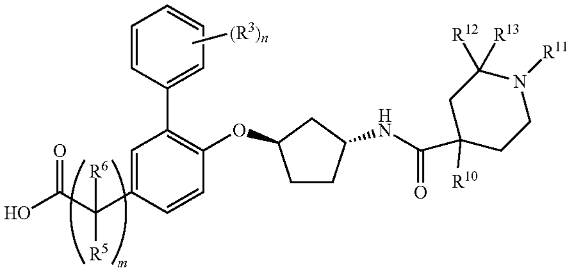
(IA-15)
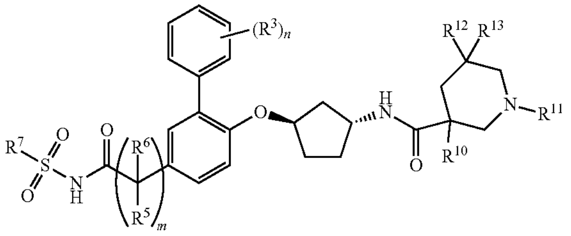

-continued (IA-16)

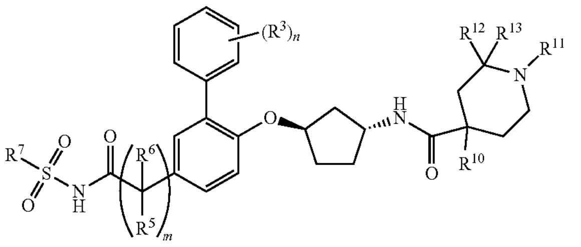

(IA-17)

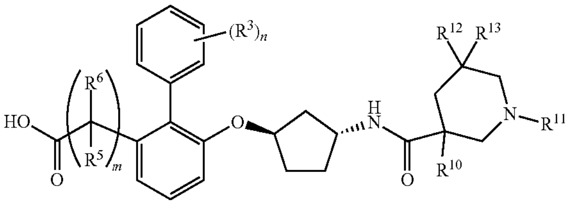

wherein:

m is 0 or 1;

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, or $C_1$-$C_3$ alkyl optionally substituted with 1 to 3 halogens;

$R^7$ is selected from the group consisting of $C_1$-$C_3$ alkyl, $C_3$-$C_4$ cycloalkyl optionally substituted with 1 to 4 halogens or a $C_1$-$C_3$ alkyl optionally substituted with 1 to 3 halogens, and —$NR^8R^9$, wherein $R^3$ and $R^9$ are each independently H or $C_1$-$C_3$ alkyl or $R^3$ and $R^9$ together form a 4-5 membered N-containing heterocycloalkyl ring optionally substituted with 1 to 4 halogens;

$R^{10}$ is H or halogen;

$R^{11}$ is H, $C_1$-$C_3$ alkyl, or $C_1$-$C_3$ deuterated alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E146 A compound according to embodiment E145, or a pharmaceutically acceptable salt thereof, having formula (IA-13a), (IA-14a), (IA-15a), (IA-16a), or (IA-17a):

(IA-13a)

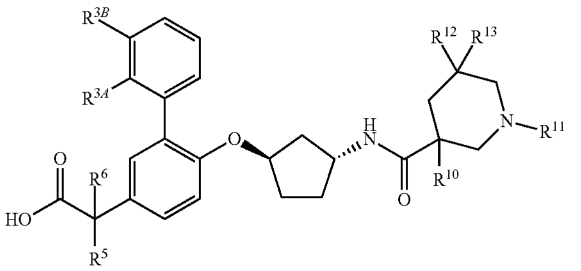

-continued (IA-14a)

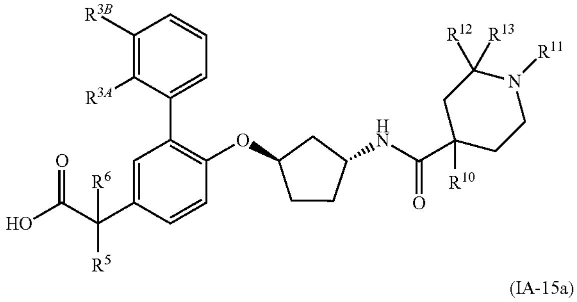

(IA-15a)

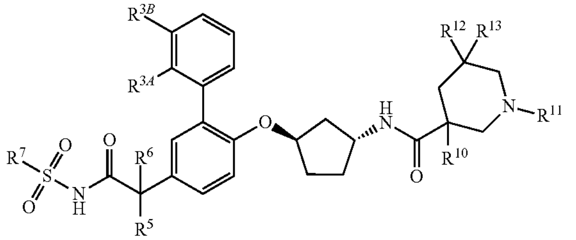

(IA-16a)

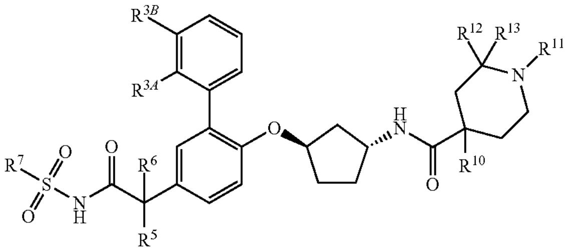

(IA-17a)

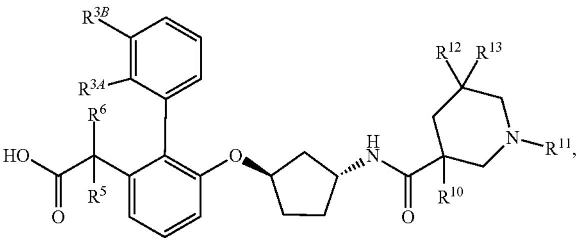

wherein:

$R^{3A}$ is $C_1$-$C_3$ alkyl or $C_3$-$C_4$ cycloalkyl, preferably $R^{3A}$ is —$CH_2CH_3$, —$CH(CH_3)_2$, or $C_3$-$C_4$ cycloalkyl;

$R^{3B}$ is halogen, preferably $R^{3B}$ is F;

$R^5$ and $R^6$ are each independently H or $C_1$-$C_3$ alkyl, preferably $R^5$ and $R^6$ are each independently H, —$CH_3$, or —$CH_2CH_3$;

$R^7$ is selected from the group consisting of $C_1$-$C_3$ alkyl, $C_3$-$C_4$ cycloalkyl optionally substituted with 1 to 4 halogens or a $C_1$-$C_3$ alkyl, and —$NR^8R^9$, preferably $R^7$ is —$CH_3$, —$CH_2CH_3$, —$CH(CH_3)_2$, cyclopropyl, cyclopropyl substituted with —$CH_3$, —$NH_2$, —$N((CH)_3)_2$, —$N(CH_3)(CH_2CH_3)$, or azetidine optionally substituted with 1, 2, or 3 F;

$R^{10}$ is H or halogen, preferably $R^{10}$ is H or F;

$R^{11}$ is H or $C_1$-$C_3$ alkyl; and $R^{12}$ and $R^{13}$ are each H or $C_1$-$C_3$ alkyl, or $R^{12}$ and $R^{13}$ together form a $C_3$-$C_6$ cycloalkyl optionally substituted with 1 to 3 halogens.

E147 A compound according to embodiment E146, or a pharmaceutically acceptable salt thereof, wherein $R^{3A}$ is cyclobutyl and $R^{3B}$ is F.

E148 A compound according to any one of embodiments E145 to E147, or a pharmaceutically acceptable salt thereof, wherein $R^5$ and $R^6$ are each —$CH_3$.

E149 A compound according to any one of embodiments E145 to E148, or a pharmaceutically acceptable salt thereof, wherein $R^{10}$ is H.

E150 A compound according to any one of embodiments E145 to E148, or a pharmaceutically acceptable salt thereof, wherein $R^{10}$ is F.

E151 A compound according to any one of embodiments E145 to E150, or a pharmaceutically acceptable salt thereof, wherein $R^{11}$ is H.

E152 A compound according to any one of embodiments E145 to E151, or a pharmaceutically acceptable salt thereof, wherein $R^{12}$ and $R^{13}$ are each —$CH_3$.

E153 A compound according to any one of embodiments E145 to E151, or a pharmaceutically acceptable salt thereof, wherein $R^{12}$ and $R^{13}$ are each H.

E154 A compound according to embodiment E145, which is:

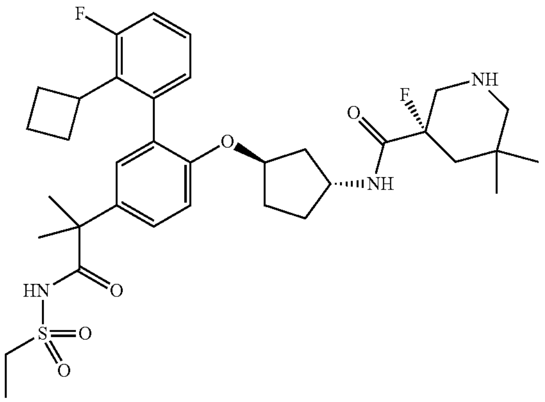
;

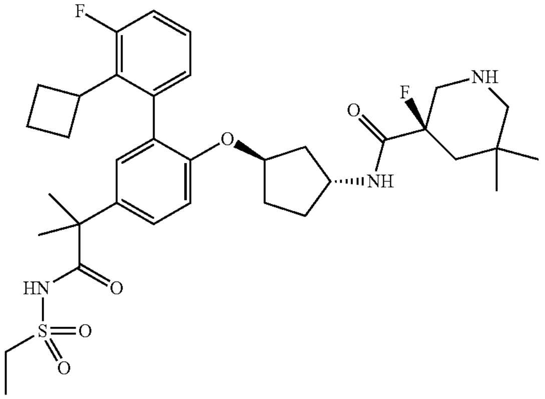
;

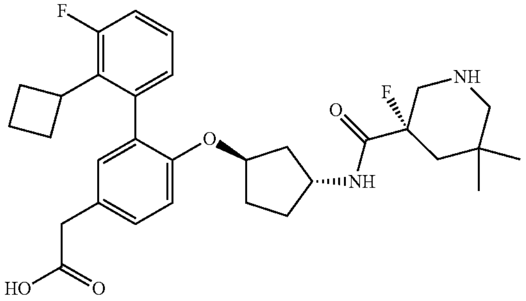
;

-continued

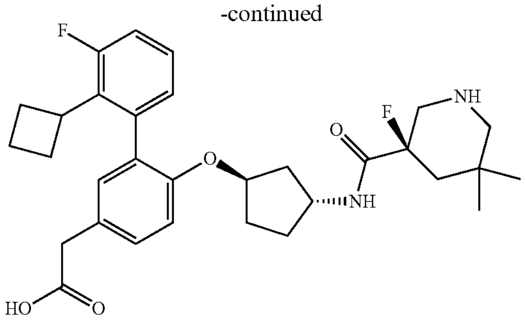
;

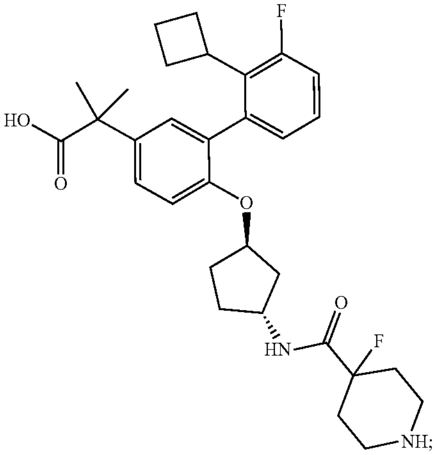
;

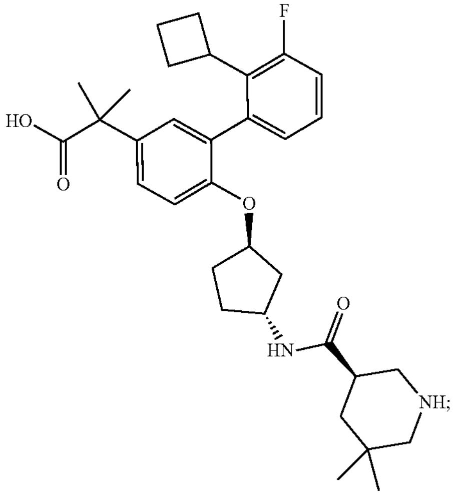
;

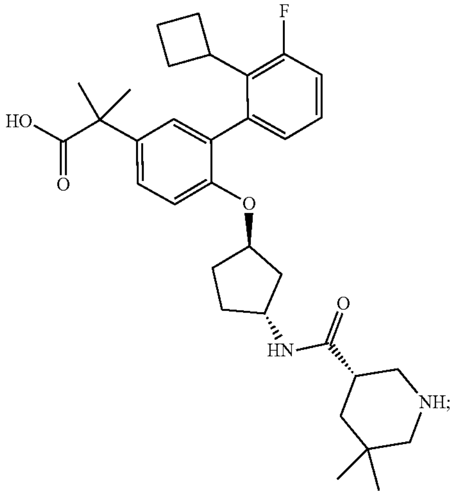
;

-continued
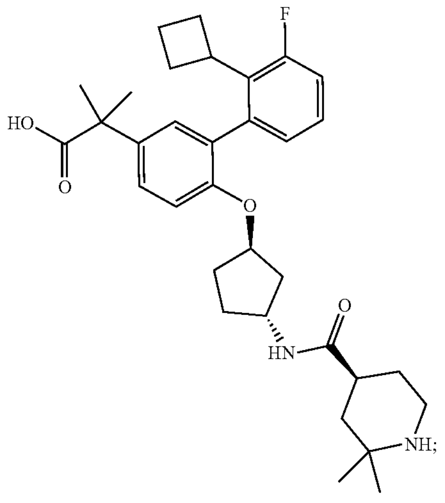
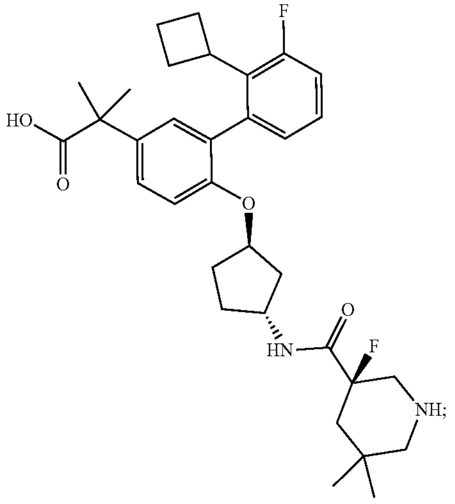
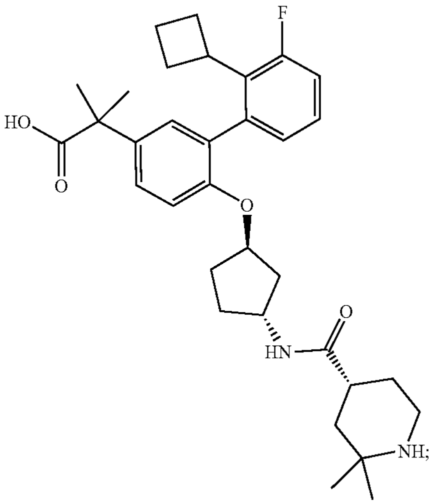
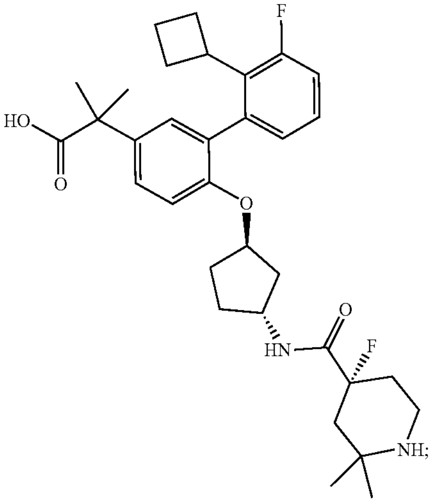
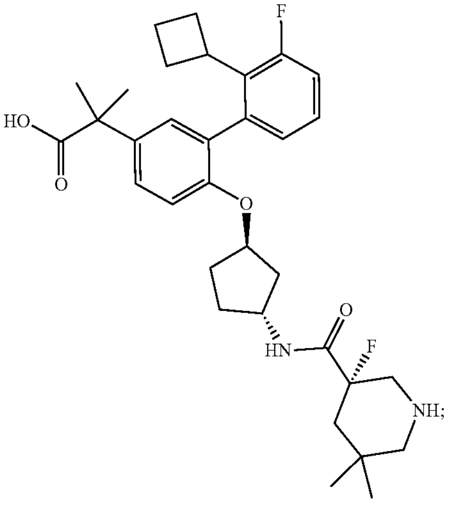
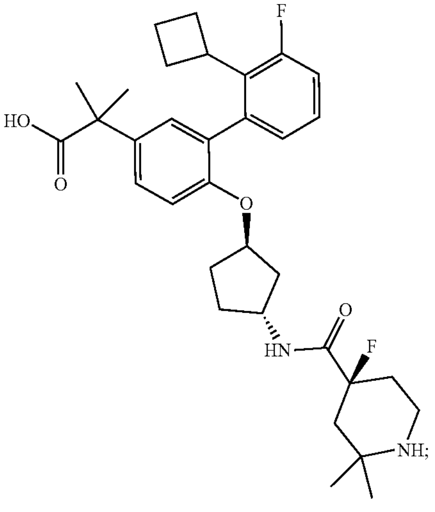

-continued
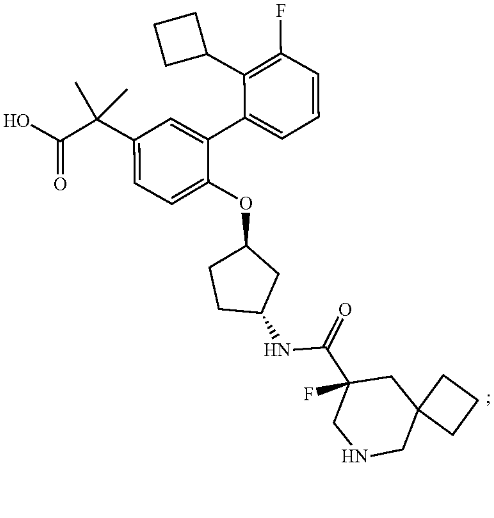
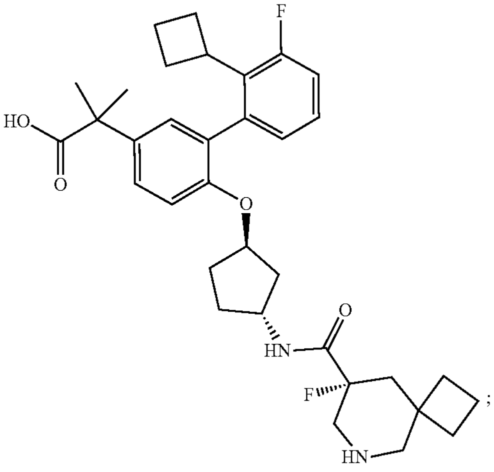
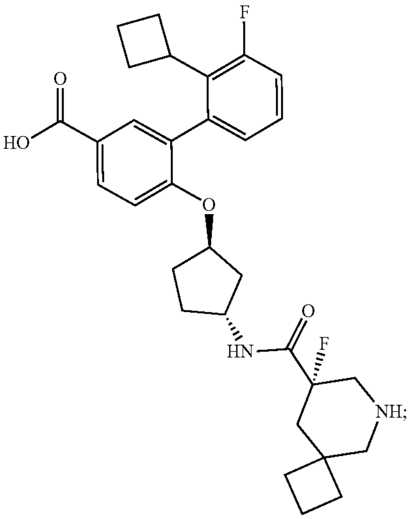
-continued
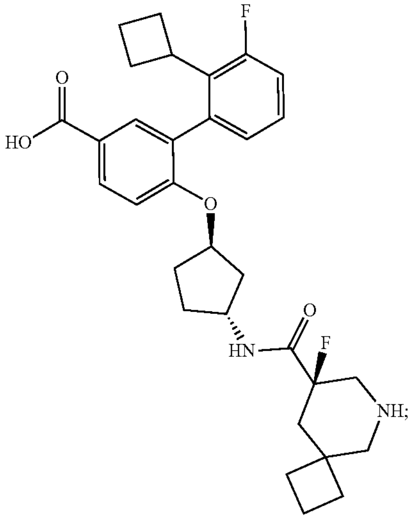
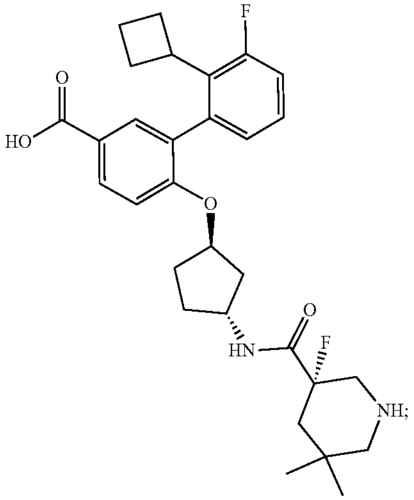
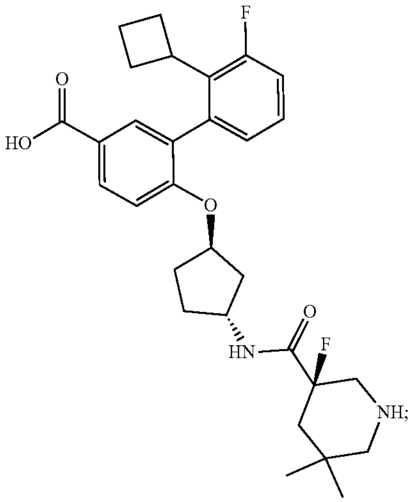

-continued
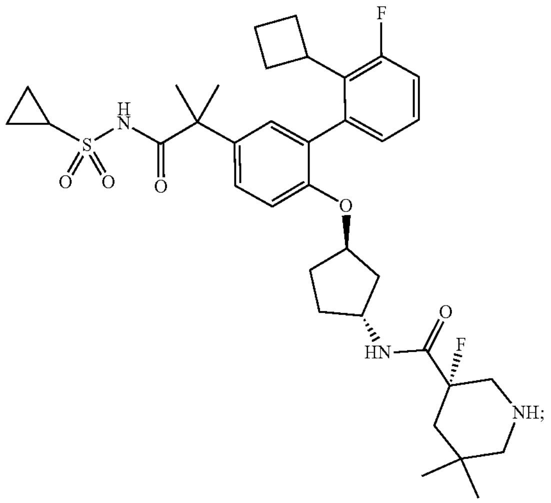
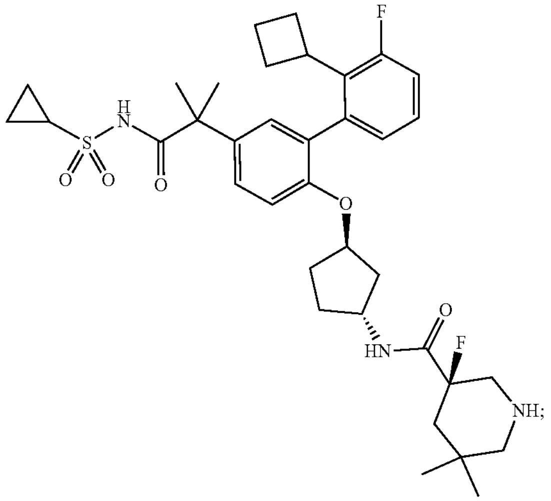
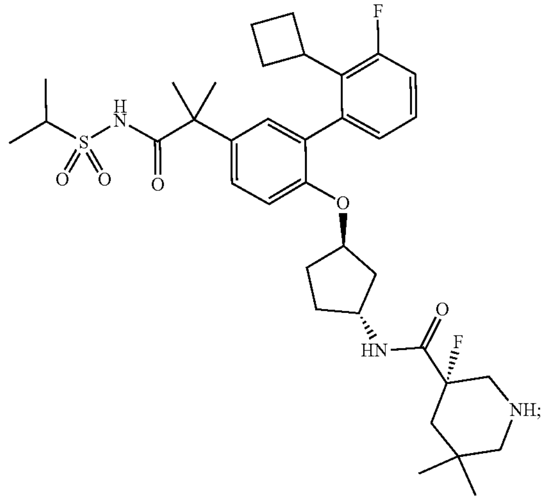
-continued
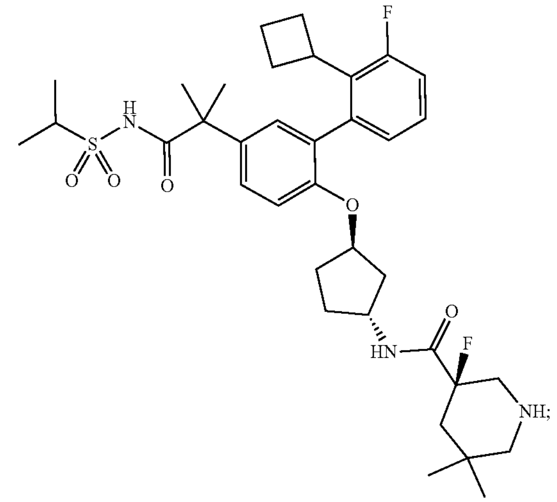
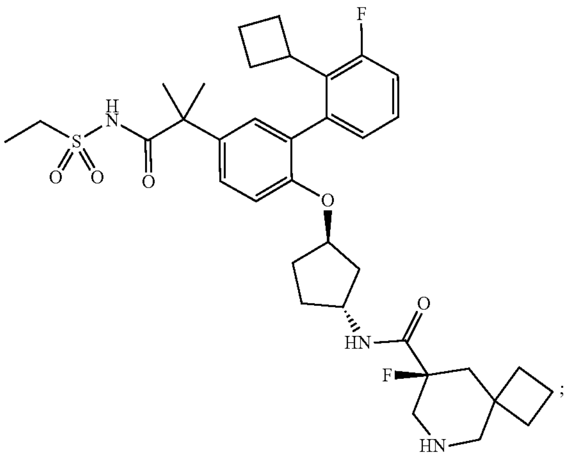
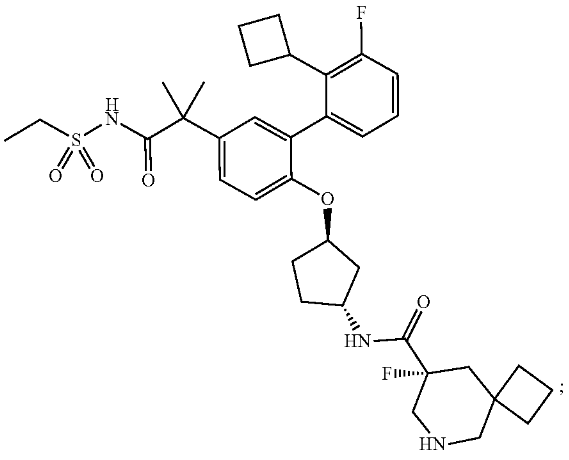

-continued
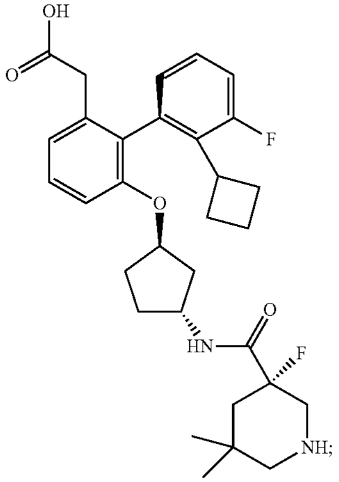
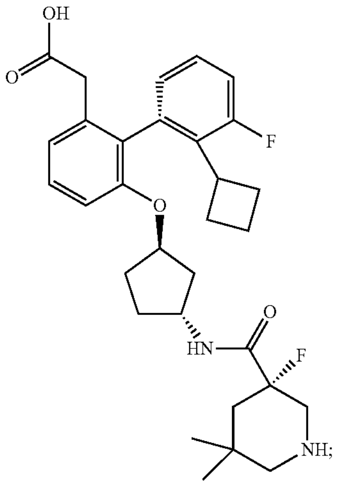
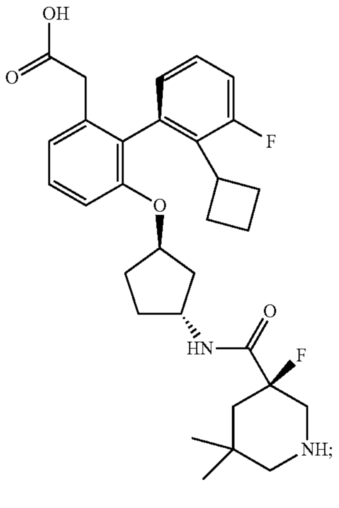
-continued
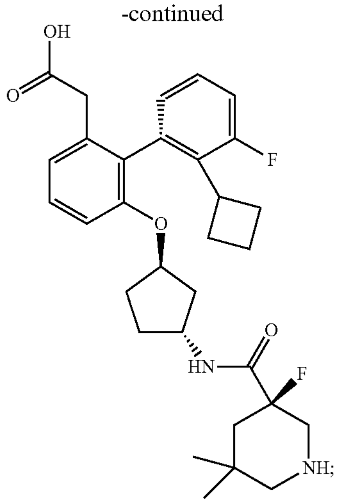
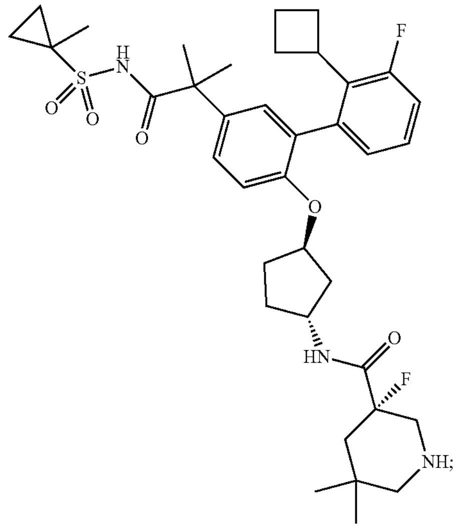
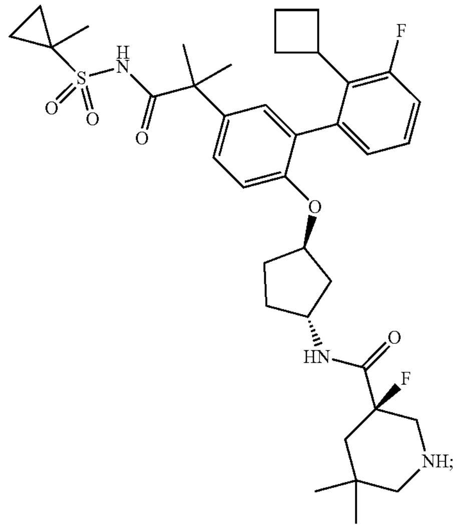

-continued
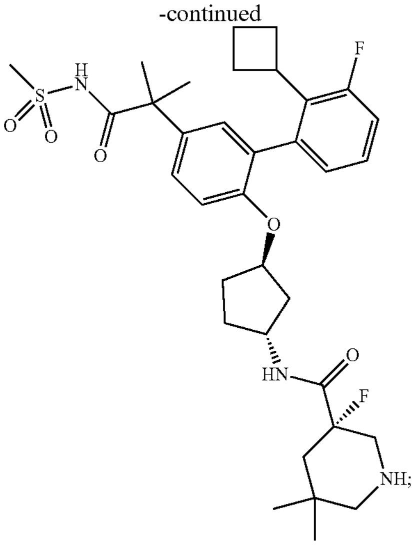
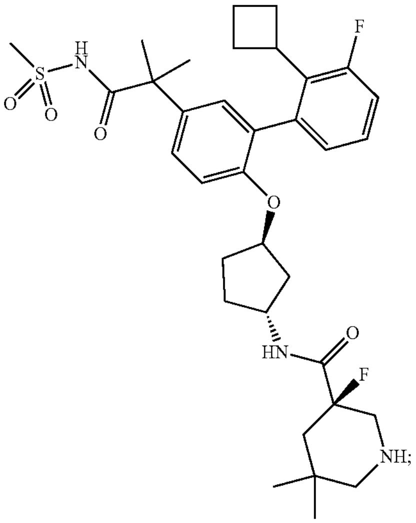
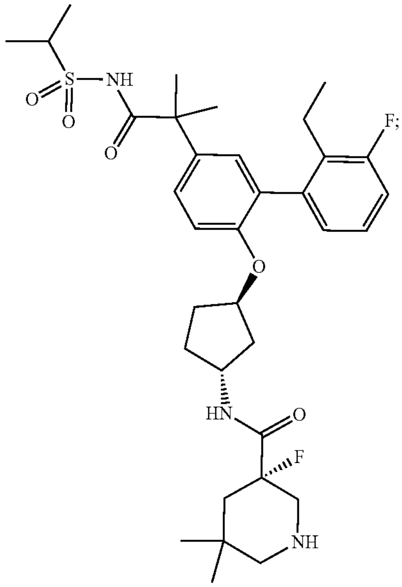
-continued
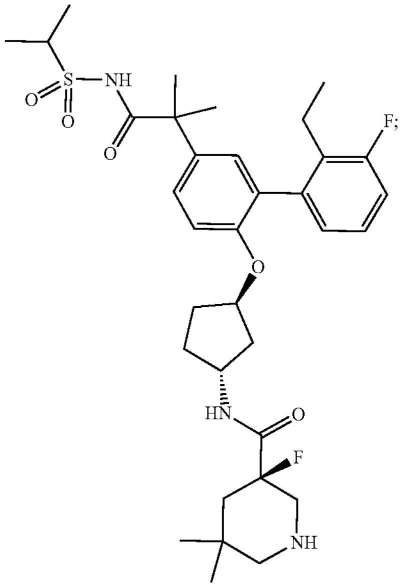
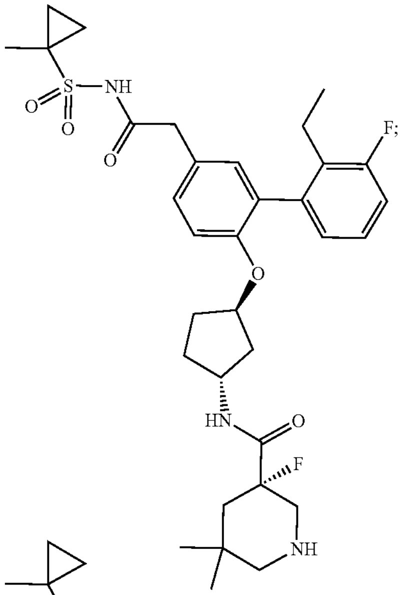
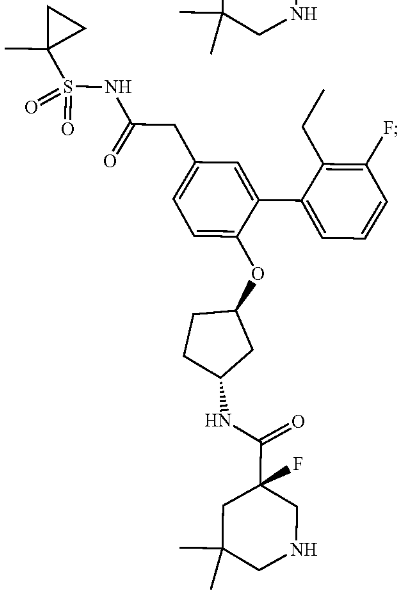

-continued
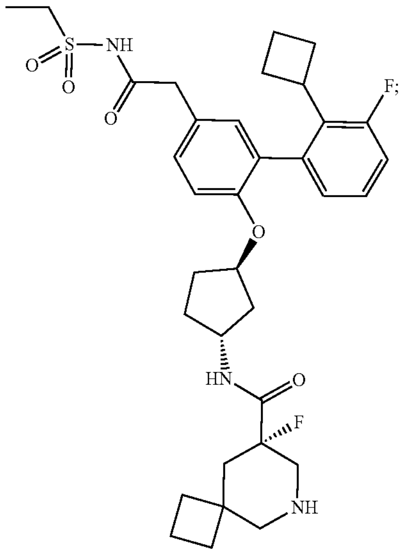
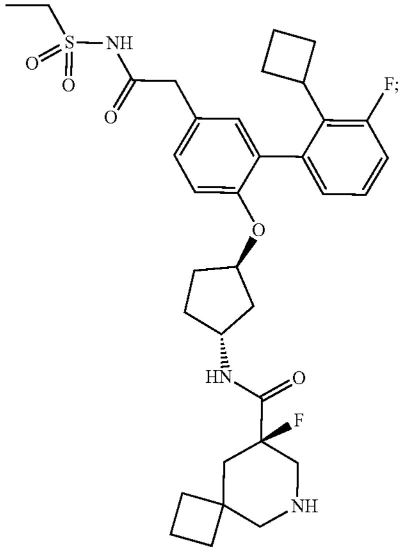
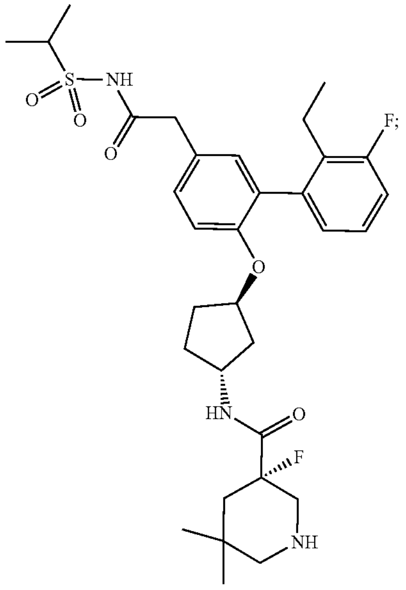
-continued
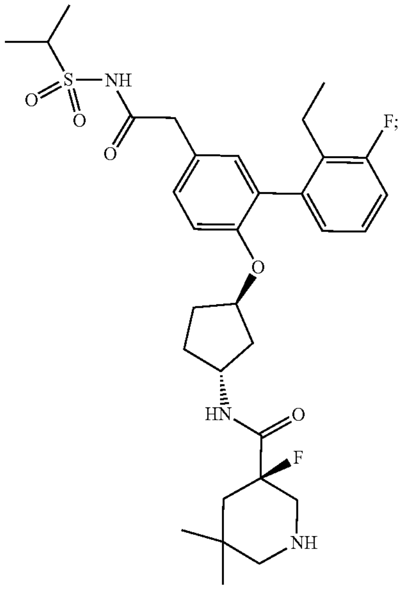
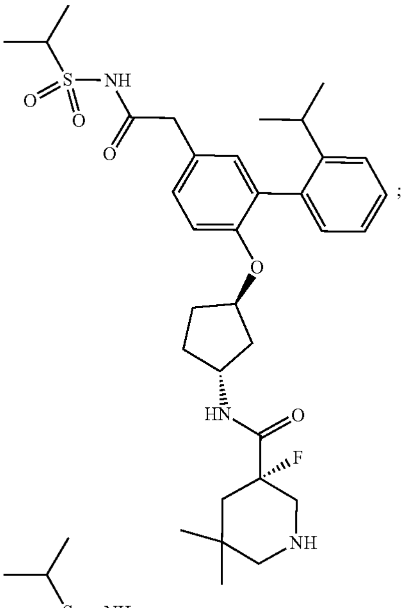
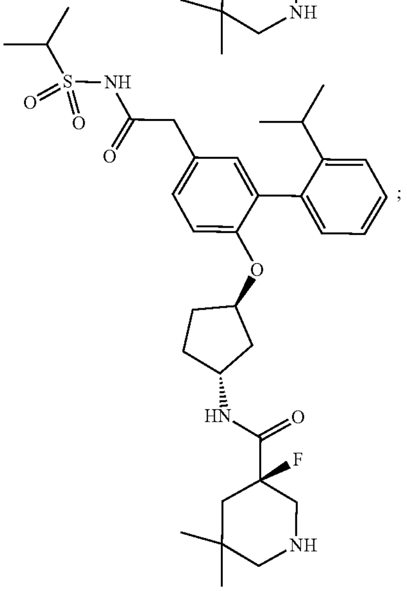

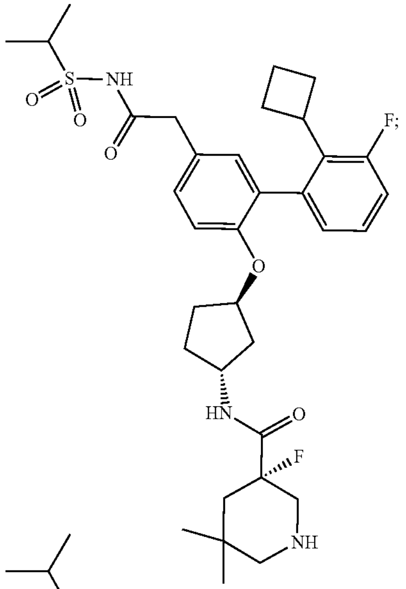
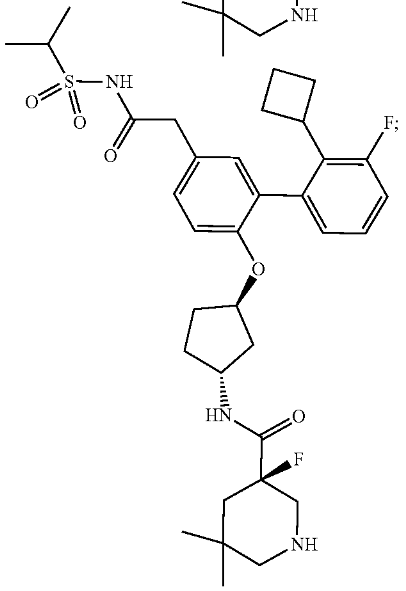
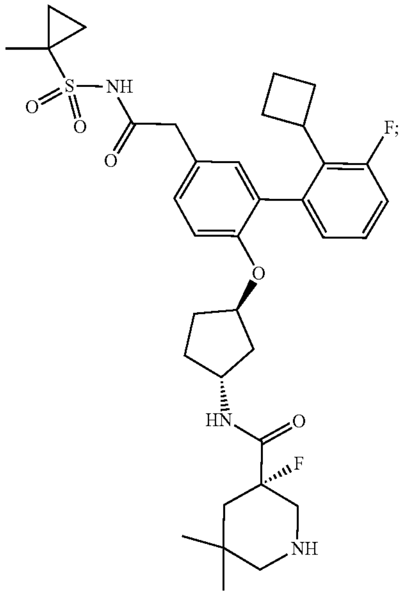
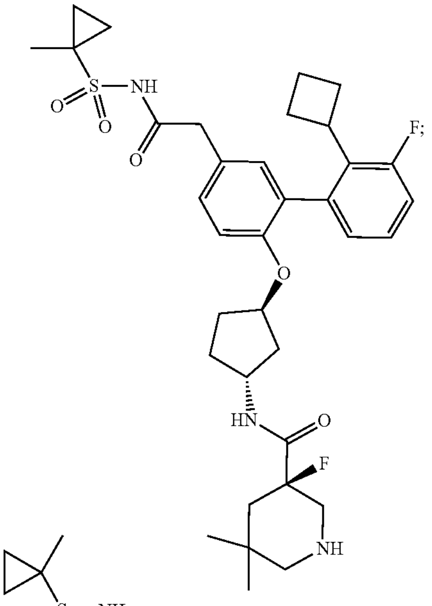
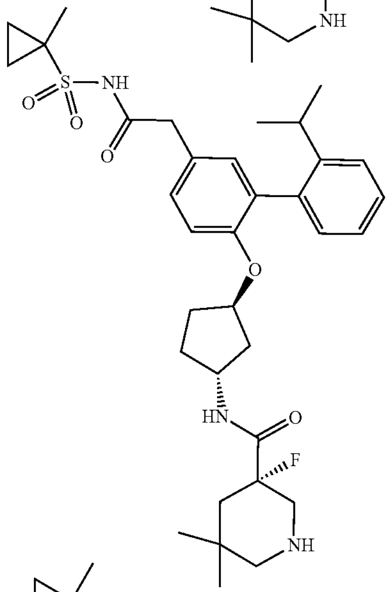
; or
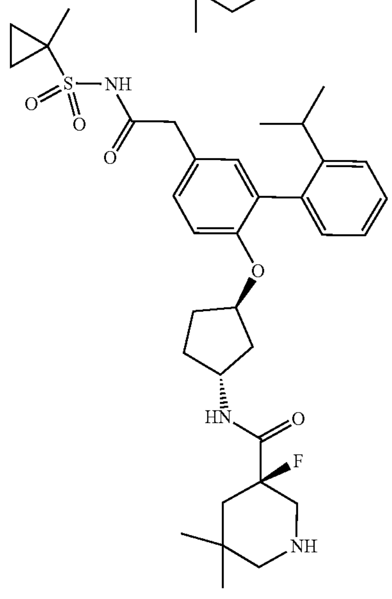
,
or a pharmaceutically acceptable salt thereof.

E155 A compound according to embodiment E1 or E2, or a pharmaceutically acceptable salt thereof, having formula (IB):

(IB)

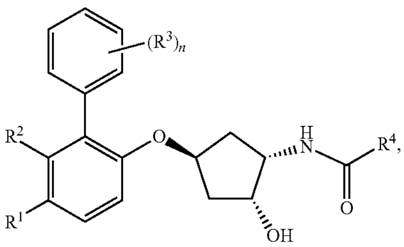

wherein:

one of $R^1$ and $R^2$ is H and the other one of $R^1$ and $R^2$ is a group of formula (E1-1) or (E2-1); and $R^4$ is a group of formula (E4-1), (E4-2), (E4-3), (E4-4), (E4-5), or (E-4-6):

(E4-1)

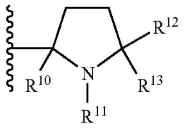

(E4-2)

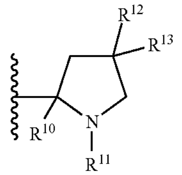

(E4-3)

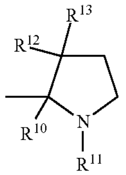

(E4-4)

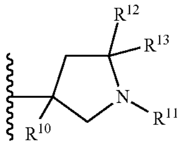

(E4-5)

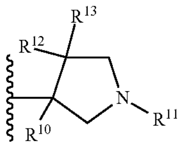

(E4-6)

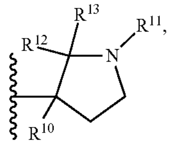

where the wave line represents the point of attachment to linking group L, $R^{10}$ is H, halogen, —OH, —CN, or $C_1$-$C_3$ alkyl optionally substituted with 1 to 3 halogens, with the proviso that when $R^{10}$ is adjacent to the ring N of $R^4$, $R^{10}$ is not OH or halogen, $R^{11}$ is H, $C_1$-$C_3$ alkyl optionally substituted with 1 to 3 halogens, $C_2$-$C_3$ hydroxyalkyl, or $C_1$-$C_3$ deuterated alkyl, and $R^{12}$ and $R^{13}$ are each independently H, halogen, or $C_1$-$C_3$ alkyl optionally substituted with 1 to 3 halogens, with the proviso that when $R^{12}$ and $R^{13}$ are adjacent to the ring N of $R^4$, $R^{12}$ and $R^{13}$ are not halogen, or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens, or $R^{12}$ and $R^{13}$ together form a 3-6 membered heterocycloalkyl comprising at least one heteroatom selected from the group consisting of N, O, and S, and optionally substituted with (i) 1 to 3 halogens or (ii) $C_1$-$C_3$ alkyl optionally substituted with 1 to 3 halogens, with the proviso that when $R^{12}$ and $R^{13}$ are adjacent to the ring N of $R^4$ and form a 3-6 membered heterocycloalkyl, said 3-6 membered heterocycloalkyl is not attached to the $R^4$ ring by a heteroatom.

E156 A compound according to embodiment E155, or a pharmaceutically acceptable salt thereof, having formula (IB-1) or (IB-2):

(IB-1)

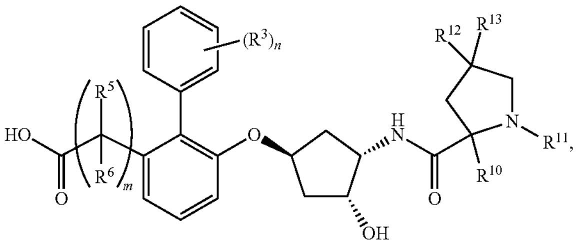

(IB-2)

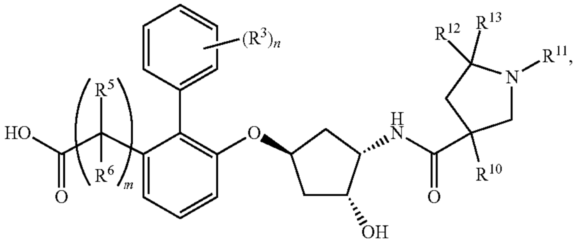

wherein:

m is 0 or 1;

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, or $C_1$-$C_3$ alkyl optionally substituted with 1 to 3 halogens;

$R^{10}$ in formula (IB-1) is H or $C_1$-$C_3$ alkyl and in formula (IB-2) $R^{10}$ is H or halogen;

$R^{11}$ is H or $C_1$-$C_3$ alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E157 A compound according to embodiment E156, or a pharmaceutically acceptable salt thereof, having formula (lB-1a) or (IB-2a):

(IB-1a)

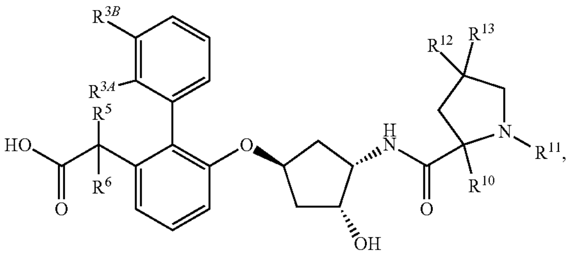

(IB-2a)

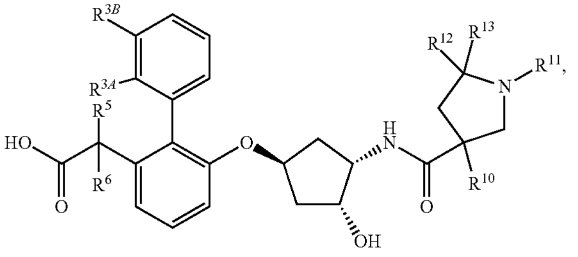

wherein:

$R^{3A}$ is $C_1$-$C_6$ alkyl or $C_3$-$C_4$ cycloalkyl, preferably $R^{3A}$ is —$CH_2CH_3$, —$CH(CH_3)_2$, or $C_3$-$C_4$ cycloalkyl;

$R^{3B}$ is halogen, preferably $R^{3B}$ is F;

$R^5$ and $R^6$ are each independently H or $C_1$-$C_3$ alkyl, preferably $R^5$ and $R^6$ are each independently H, —$CH_3$, or —$CH_2CH_3$;

in formula (IB-1a), $R^{10}$ is H or $C_1$-$C_3$ alkyl, preferably $R^{10}$ is H; and $R^{11}$, $R^{12}$, and $R^{13}$ are each $C_1$-$C_3$ alkyl, and in formula (IB-2a), $R^{10}$ is H or halogen, preferably $R^{10}$ is H or F;

$R^{11}$ is H or $C_1$-$C_3$ alkyl; and $R^{12}$ and $R^{13}$ are each $C_1$-$C_3$ alkyl or $R^{12}$ and $R^{13}$ together form a $C_3$-$C_6$ cycloalkyl optionally substituted with 1 to 3 halogens.

E158 A compound according to E157, or a pharmaceutically acceptable salt thereof, wherein $R^{3A}$ is cyclobutyl and $R^{3B}$ is F.

E159 A compound according to any one of embodiments E156 to E158, or a pharmaceutically acceptable salt thereof, wherein $R^5$ and $R^6$ are each H.

E160 A compound according to any one of embodiments E156 to E159, or a pharmaceutically acceptable salt thereof, wherein $R^{10}$ is H and $R^{11}$ is —$CH_3$.

E161 A compound according to any one of embodiments E156 to E160, or a pharmaceutically acceptable salt thereof, wherein $R^{12}$ and $R^{13}$ are each —$CH_3$.

E162 A compound according to any one of embodiments E156 to E159, or a pharmaceutically acceptable salt thereof, having formula (IB-2a), wherein $R^{10}$ is F, $R^{11}$ is H, and $R^{12}$ and $R^{13}$ are each —$CH_3$.

E163 A compound according to any one of embodiments E156 to E159, or a pharmaceutically acceptable salt thereof, having formula (IB-2a), wherein $R^{10}$ is F, $R^{11}$ is H, and $R^{12}$ and $R^{13}$ together form cyclobutyl or cyclopentyl.

E164 A compound according to embodiment E156, which is:

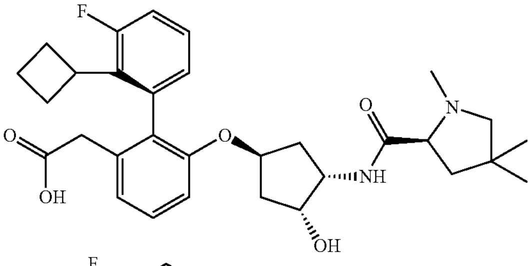

; or

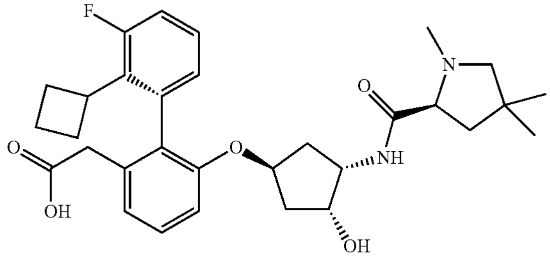

, or a pharmaceutically acceptable salt thereof.

E165 A compound according to embodiment E155, or a pharmaceutically acceptable salt thereof, having formula (IB-3) or (IB-4):

(IB-3)

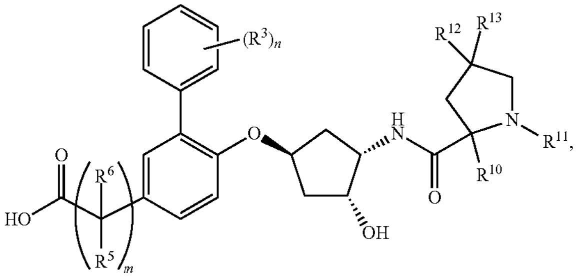

(IB-4)

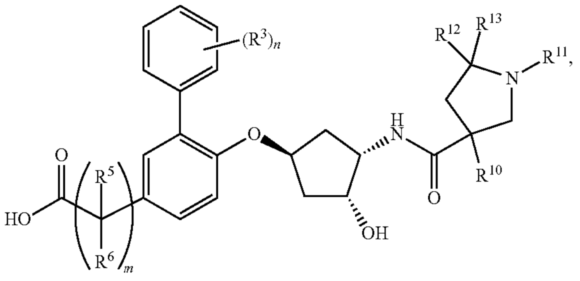

wherein:

m is 0 or 1;

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, or $C_1$-$C_3$ alkyl optionally substituted with 1 to 3 halogens;

$R^{10}$ in formula (IB-3) is H or $C_1$-$C_3$ alkyl and in formula (IB-4) $R^{10}$ is H or halogen;

$R^{11}$ is H or $C_1$-$C_3$ alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E166 A compound according to embodiment E165, or a pharmaceutically acceptable salt thereof, having formula (IB-3a), (IB-3b), (IB-3c), or (IB-4a):

(IB-3a)

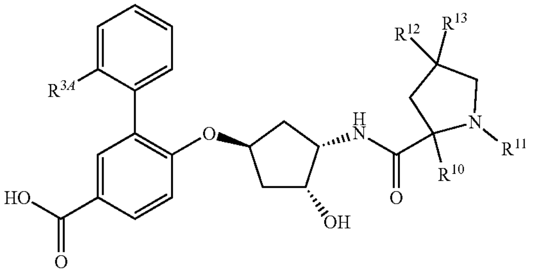

(IB-3b)

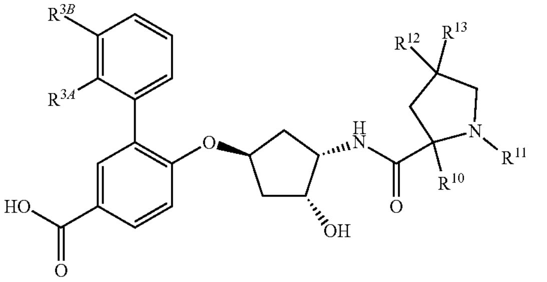

(IB-3c)

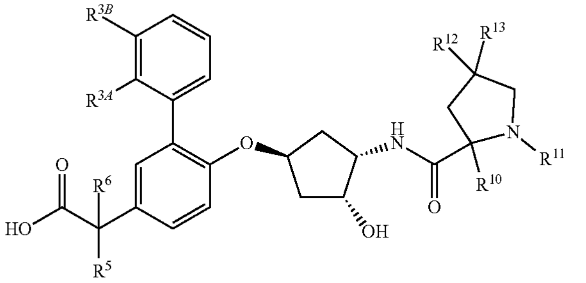

(IB-4a)

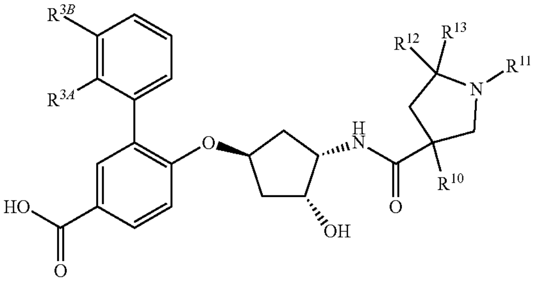

-continued (IB-4b)

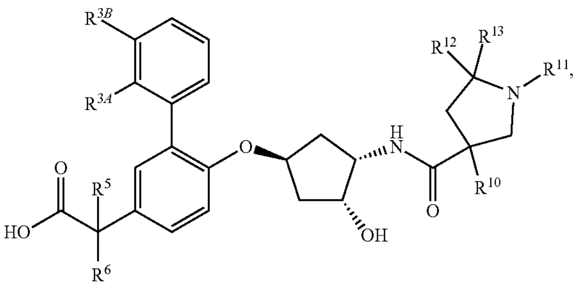

wherein:

$R^{3A}$ is $C_1$-$C_6$ alkyl or $C_3$-$C_4$ cycloalkyl, preferably $R^{3A}$ is —$CH_2CH_3$, —$CH(CH_3)_2$, or $C_3$-$C_4$ cycloalkyl;

$R^{3B}$ is halogen, preferably $R^{3B}$ is F;

$R^5$ and $R^6$ are each independently H or $C_1$-$C_3$ alkyl, preferably $R^5$ and $R^6$ are each independently H, —$CH_3$, or —$CH_2CH_3$;

in formulae (IB-3a), (IB-3b), and (IB-3c), $R^{10}$ is H or $C_1$-$C_3$ alkyl, preferably H; and $R^{11}$, $R^{12}$, and $R^{13}$ are each $C_1$-$C_3$ alkyl, and in formulae (IB-4a) and (IB-4b), $R^{10}$ is H or halogen, preferably $R^{10}$ is H or F;

$R^{11}$ is H or $C_1$-$C_3$ alkyl; and $R^{12}$ and $R^{13}$ are each $C_1$-$C_3$ alkyl or $R^{12}$ and $R^{13}$ together form a $C_3$-$C_6$ cycloalkyl optionally substituted with 1 to 3 halogens.

E167 A compound according to E166, or a pharmaceutically acceptable salt thereof, wherein $R^{3A}$ is cyclobutyl and $R^{3B}$ is F.

E168 A compound according to any one of embodiments E165 to E167, or a pharmaceutically acceptable salt thereof, wherein $R^5$ and $R^6$ are each H.

E169 A compound according to any one of embodiments E165 to E167, or a pharmaceutically acceptable salt thereof, wherein $R^5$ and $R^6$ are each —$CH_3$.

E170 A compound according to any one of embodiments E165 to E169, or a pharmaceutically acceptable salt thereof, wherein $R^{10}$ is H and $R^{11}$ is —$CH_3$.

E171 A compound according to any one of embodiments E165 to E170, or a pharmaceutically acceptable salt thereof, wherein $R^{12}$ and $R^{13}$ are each —$CH_3$.

E172 A compound according to any one of embodiments E165 to E169, or a pharmaceutically acceptable salt thereof, having formula (IB-4a) or (IB-4b), wherein $R^{10}$ is F, $R^{11}$ is H, and $R^{12}$ and $R^{13}$ are each —$CH_3$.

E173 A compound according to any one of embodiments E165 to E169, or a pharmaceutically acceptable salt thereof, having formula (IB-4a) or (IB-4b), wherein $R^{10}$ is F, $R^{11}$ is H, and $R^{12}$ and $R^{13}$ together form cyclobutyl or cyclopentyl, preferably cyclobutyl.

E174 A compound according to embodiment E165, which is:

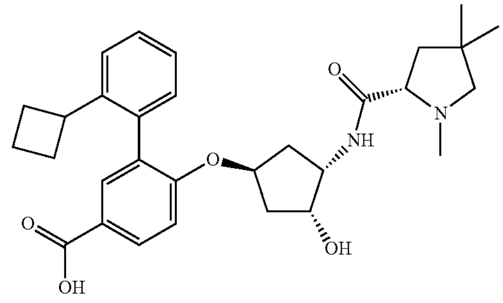
;
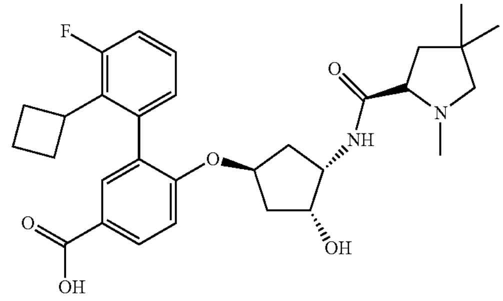
;
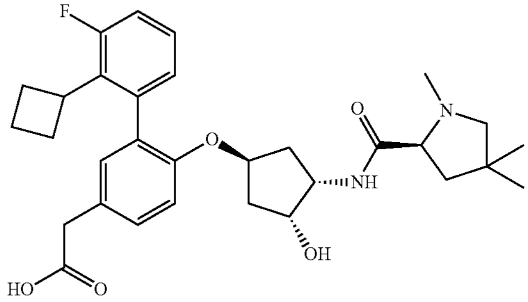
;
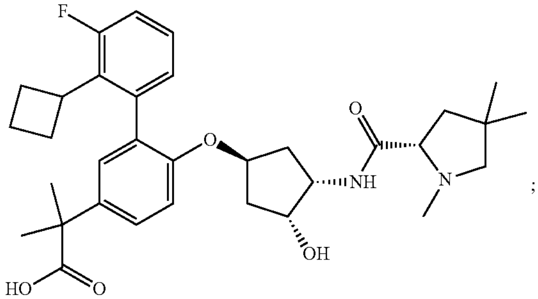
;
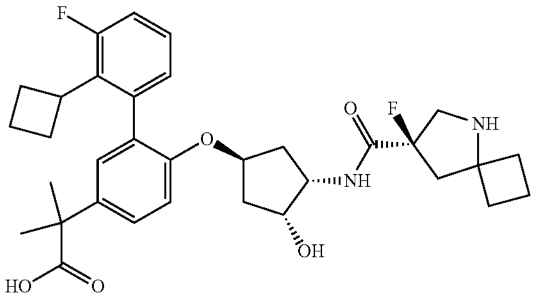
; or
-continued
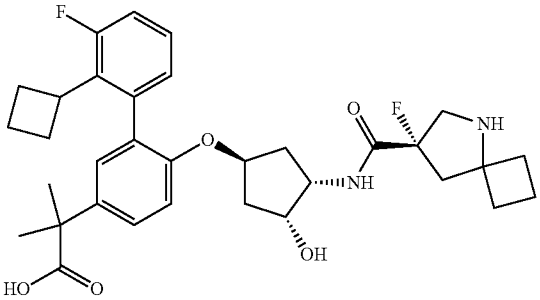
,
or a pharmaceutically acceptable salt thereof.
E175 A compound according to embodiment E1 or E2, or a pharmaceutically acceptable salt thereof, having formula (IC):
(IC)
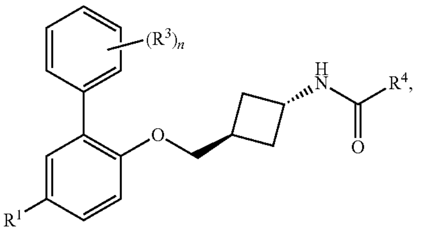
wherein:
$R^1$ is a group of formula (E1-1) or (E2-1); and
$R^4$ is a group of formula (E4-1), (E4-2), (E4-3), (E4-4), (E4-5), or (E-4-6):
(E4-1)
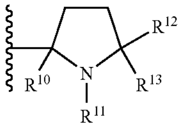
(E4-2)
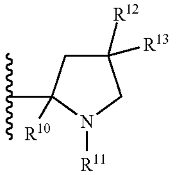
(E4-3)
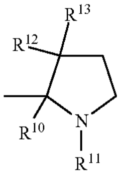
(E4-4)
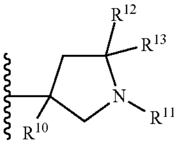

-continued (E4-5)

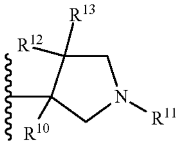

(E4-6)

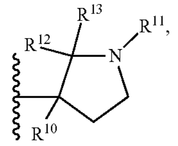

where the wave line ~~~~ represents the point of attachment to linking group L, $R^{10}$ is H, halogen, —OH, —CN, or $C_1$-$C_3$ alkyl optionally substituted with 1 to 3 halogens, with the proviso that when $R^{10}$ is adjacent to the ring N of $R^4$, $R^{10}$ is not —OH or halogen;

$R^{11}$ is H, $C_1$-$C_3$ alkyl optionally substituted with 1 to 3 halogens, $C_2$-$C_3$ hydroxyalkyl, or $C_1$-$C_3$ deuterated alkyl, and $R^{12}$ and $R^{13}$ are each independently H, halogen, or $C_1$-$C_3$ alkyl optionally substituted with 1 to 3 halogens, with the proviso that when $R^{12}$ and $R^{13}$ are adjacent to the ring N of $R^4$, $R^{12}$ and $R^{13}$ are not halogen, or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens, or $R^{12}$ and $R^{13}$ together form a 3-6 membered heterocycloalkyl comprising at least one heteroatom selected from the group consisting of N, O, and S, and optionally substituted with (i) 1 to 3 halogens or (ii) $C_1$-$C_3$ alkyl optionally substituted with 1 to 3 halogens, with the proviso that when $R^{12}$ and $R^{13}$ are adjacent to the ring N of $R^4$ and form a 3-6 membered heterocycloalkyl, said 3-6 membered heterocycloalkyl is not attached to the $R^4$ ring by a heteroatom.

E176 A compound according to embodiment E175, or a pharmaceutically acceptable salt thereof, having formula (IC-1) or formula (IC-2):

(IC-1)

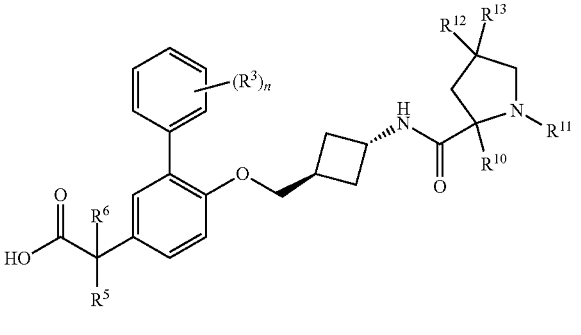

-continued (IC-2)

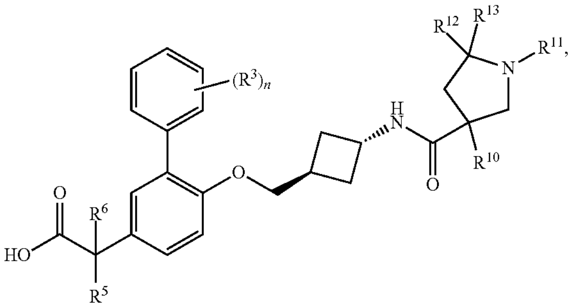

wherein:

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, or $C_1$-$C_3$ alkyl optionally substituted with 1 to 3 halogens;

$R^{10}$ in formula (IC-1) is H or $C_1$-$C_3$ alkyl and $R^{10}$ in formula (IC-2) is H or halogen;

$R^{11}$ is H or $C_1$-$C_3$ alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E177 A compound according to embodiment E176, or a pharmaceutically acceptable salt thereof, having formula (IC-1a) of formula (IC-2a):

(IC-1a)

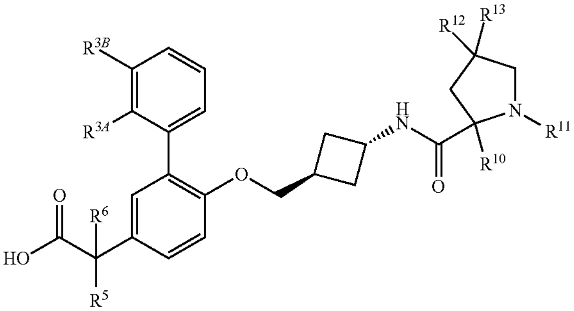

(IC-2a)

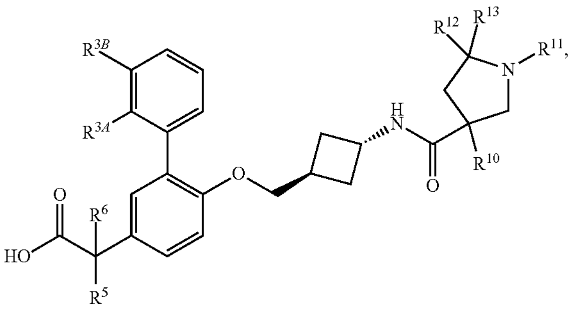

wherein:

$R^{3A}$ is $C_1$-$C_6$ alkyl or $C_3$-$C_4$ cycloalkyl, preferably $R^{3A}$ is —$CH_2CH_3$, —$CH(CH_3)_2$, or $C_3$-$C_4$ cycloalkyl;

$R^{3B}$ is halogen, preferably $R^{3B}$ is F;

$R^5$ and $R^6$ are each independently H or $C_1$-$C_3$ alkyl, preferably $R^5$ and $R^6$ are each independently H, —$CH_3$, or —$CH_2CH_3$;

$R^{10}$ in formula (IC-1a) is H or $C_1$-$C_3$ alkyl, preferably $R^{10}$ in formula (IC-1a) is H, and $R^{10}$ in formula (IC-2a) is H or halogen, preferably $R^{10}$ in formula (IC-2a) is F;

$R^{11}$ is$_1$-$C_3$ alkyl; and $R^{12}$ and $R^{13}$ are each $C_1$-$C_3$ alkyl or $R^{12}$ and $R^{13}$ together form a $C_3$-$C_6$ cycloalkyl.

E178 A compound according to embodiment E177, or a pharmaceutically acceptable salt thereof, wherein $R^{3A}$ is cyclobutyl and $R^{3B}$ is F.

E179 A compound according to any one of embodiments E176 to E178, or a pharmaceutically acceptable salt thereof, wherein $R^5$ and $R^6$ are each H.

E180 A compound according to any one of embodiments E176 to E178, or a pharmaceutically acceptable salt thereof, wherein $R^5$ and $R^6$ are each —$CH_3$.

E181 A compound according to any one of embodiments E176 to E180, or a pharmaceutically acceptable salt thereof, wherein, in formula (IC-1a), $R^{10}$ is H and $R^{11}$ is —$CH_3$, and wherein, in formula (IC-2a), $R^{10}$ is F and $R^{11}$ is H.

E182 A compound according to any one of embodiments E176 to E181, or a pharmaceutically acceptable salt thereof, wherein $R^{12}$ and $R^{13}$ are each —$CH_3$.

E183 A compound according to embodiment E176, which is:

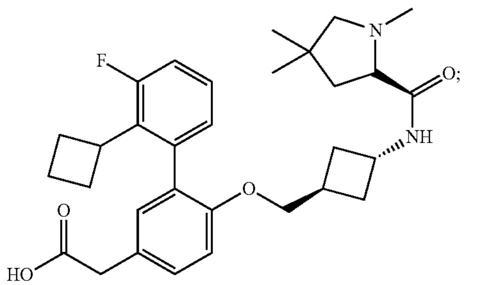

;

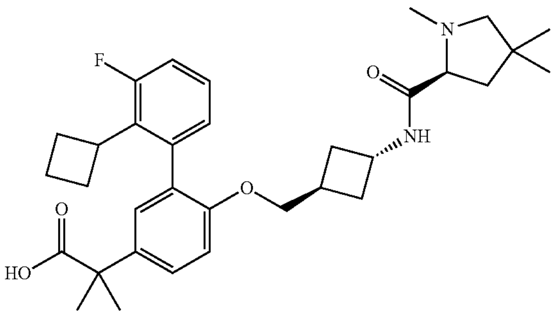

;

-continued

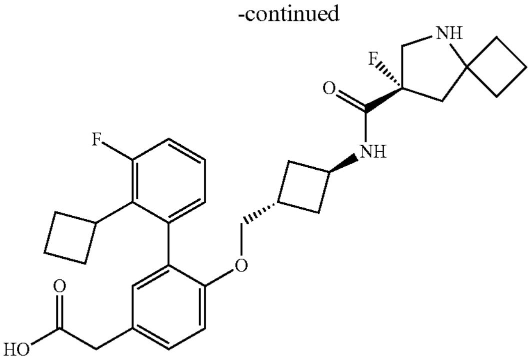

; or

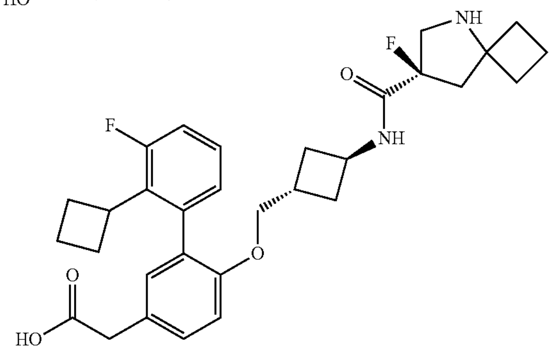

, or a pharmaceutically acceptable salt thereof.

E184 A compound according to embodiment E175, or a pharmaceutically acceptable salt thereof, having formula (IC-3) or formula (IC-4):

(IC-3)

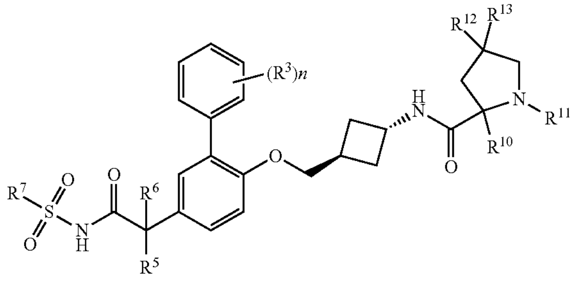

(IC-4)

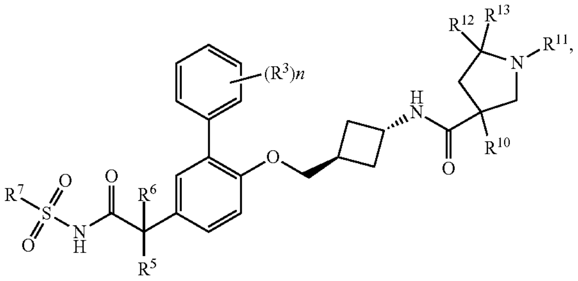

wherein:

n is 1 or 2;

each $R^3$ is independently selected from the group consisting of halogen, $C_1$-$C_6$ alkyl optionally substituted with 1 to 3 halogens, and $C_3$-$C_4$ cycloalkyl optionally substituted with 1 to 4 halogens;

$R^5$ and $R^6$ are each independently H, halogen, or $C_1$-$C_3$ alkyl optionally substituted with 1 to 3 halogens;

$R^7$ is selected from the group consisting of $C_1$-$C_3$ alkyl, $C_3$-$C_4$ cycloalkyl optionally substituted with 1 to 4 halogens or a $C_1$-$C_3$ alkyl optionally substituted with 1 to 3 halogens, and —$NR^8R^9$, wherein $R^3$ and $R^9$ are each independently H or $C_1$-$C_3$ alkyl or $R^3$ and $R^9$ together form a 4-5 membered N-containing heterocycloalkyl ring optionally substituted with 1 to 4 halogens;

$R^{10}$ in formula (IC-3) is H or $C_1$-$C_3$ alkyl and $R^{10}$ in formula (IC-4) is H or halogen;

$R^{11}$ is H or $C_1$-$C_3$ alkyl; and $R^{12}$ and $R^{13}$ are each independently H or $C_1$-$C_3$ alkyl or $R^{12}$ and $R^{13}$ together form a $C_3$-$C_6$ cycloalkyl optionally substituted with (i) 1 to 3 halogens or (ii) $C_1$-$C_3$ alkyl optionally substituted with 1 to 3 halogens.

E185 A compound according to embodiment E184, or a pharmaceutically acceptable salt thereof, having formula (IC-3a) or (IC-4a):

(IC-3a)

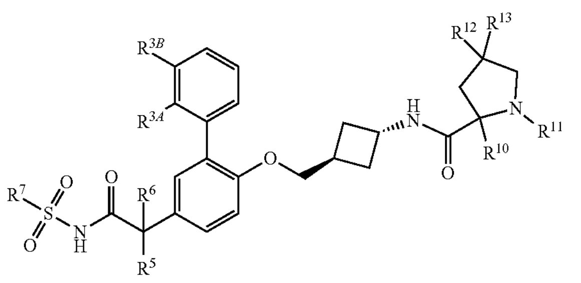

(IC-4a)

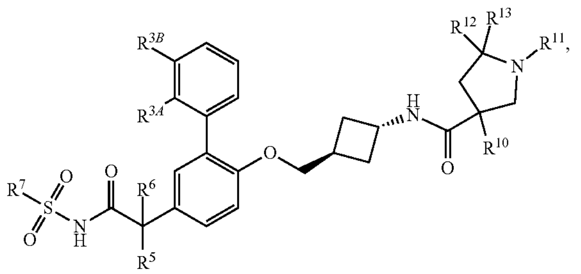

wherein:

$R^{3A}$ is $C_1$-$C_6$ alkyl or $C_3$-$C_4$cycloalkyl, preferably $R^{3A}$ is —$CH_2CH_3$, —$CH(CH_3)_2$, or $C_3$—C cycloalkyl;

$R^{3B}$ is halogen, preferably $R^{3B}$ is F;

$R^5$ and $R^6$ are each independently H or $C_1$-$C_3$ alkyl, preferably $R^5$ and $R^6$ are each independently H, —$CH_3$, or —$CH_2CH_3$;

$R^7$ is selected from the group consisting of $C_1$-$C_3$ alkyl, $C_3$-$C_4$ cycloalkyl optionally substituted with to 4 halogens or a $C_1$-$C_3$ alkyl, and —$NR^8R^9$, preferably $R^7$ is —$CH_3$, —$CH_2CH_3$, —$CH(CH_3)_2$, cyclopropyl, cyclopropyl substituted with —$CH_3$, —$NH_2$, —$N((CH)_3)_2$, —$N(CH_3)(CH_2CH_3)$, or azetidine optionally substituted with 1, 2, or 3 F;

$R^{10}$ in formula (IC-3a) is H or $C_1$-$C_3$ alkyl, preferably $R^{10}$ in formula (IC-3a) is H, and $R^{10}$ in formula (IC-4a) is H or halogen, preferably $R^{10}$ in formula (IC-4a) is F;

$R^{11}$ is H or $C_1$-$C_3$ alkyl; and $R^{12}$ and $R^{13}$ are each $C_1$-$C_3$ alkyl or $R^{12}$ and $R^{13}$ together form a $C_3$-$C_6$ cycloalkyl.

E186 A compound according to embodiment E185, or a pharmaceutically acceptable salt thereof, wherein $R^{3A}$ is cyclobutyl and $R^{3B}$ is F.

E187 A compound according to any one of embodiments E184 to E178, or a pharmaceutically acceptable salt thereof, wherein $R^5$ and $R^6$ are each H.

E188 A compound according to any one of embodiments E184 to E178, or a pharmaceutically acceptable salt thereof, wherein $R^5$ and $R^6$ are each —$CH_3$.

E189 A compound according to any one of embodiments E184 to E178, or a pharmaceutically acceptable salt thereof, wherein one of $R^5$ and $R^6$ is H and the other of $R^5$ and $R^6$ is —$CH_3$.

E190 A compound according to any one of embodiments E184 to E181, or a pharmaceutically acceptable salt thereof, wherein, in formula (IC-3a), $R^{10}$ is H and $R^{11}$ is —$CH_3$, and wherein, in formula (IC-4a), $R^{10}$ is F and $R^{11}$ is H.

E191 A compound according to any one of embodiments E184 to E182, or a pharmaceutically acceptable salt thereof, wherein $R^{12}$ and $R^{13}$ are each —$CH_3$.

E192 A compound according to any one of embodiments E184 to E183, or a pharmaceutically acceptable salt thereof, wherein $R^7$ is —$CH_3$.

E193 A compound according to embodiment E184, which is:

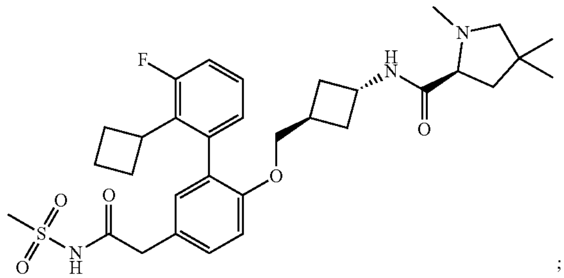

;

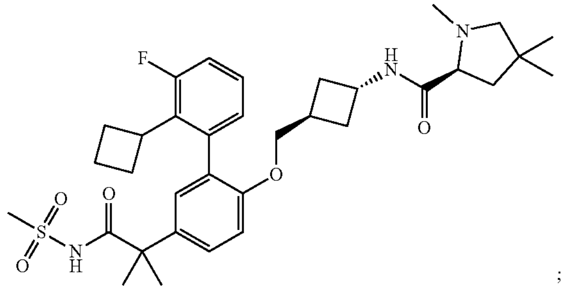

;

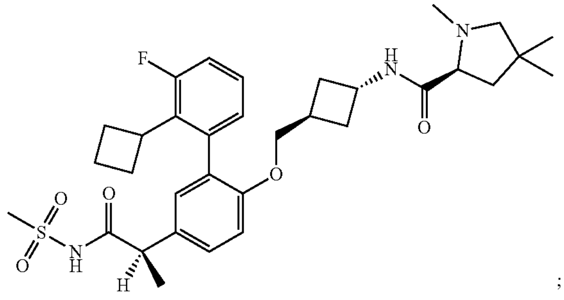

;

-continued

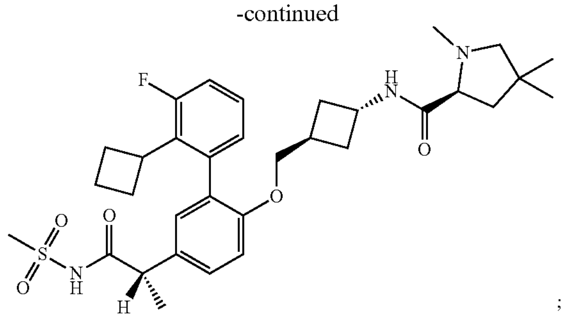

;

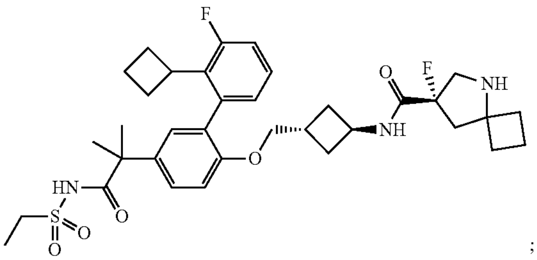

; or

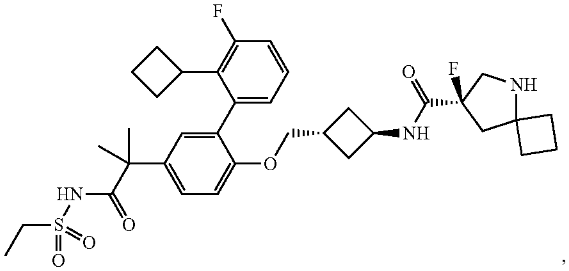

, or a pharmaceutically acceptable salt thereof.

E194 A compound of Formula (I'):

(I')

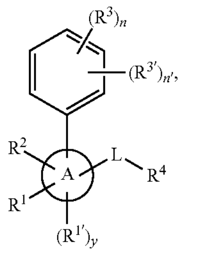

or a pharmaceutically acceptable salt thereof, wherein:

Ring A is phenyl or a 5-6 membered N-containing heteroaryl consisting of one or two N atoms and carbon atoms as ring members;

y is 0 when Ring A is the 5 or 6 membered N-containing heteroaryl consisting of two N atoms and carbon atoms as ring members; y is 1 when Ring A is the 5 or 6 membered N-containing heteroaryl consisting of one N atom and carbon atoms as ring members; and y is 2 when Ring A is phenyl;

L is a linking group of formula:

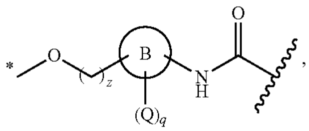

, where:

the asterisk * represents the point of attachment to Ring A and the wave line ∿∿∿ represents the point of attachment to $R^4$, z is 0 or 1, q is 0, 1, or 2, each Q is independently -D, —OH, —$CH_3$, or halogen, and Ring B is a $C_3$-$C_6$ cycloalkyl;

each $R^{1'}$ is independently H or D, one of $R^1$ and $R^2$ is H, D, or halogen and the other one of $R^1$ and $R^2$ is a group of formula (E1-1), (E1-2), (E1-3), (E2-1), (E2-2), or (E3-1):

(E1-1)

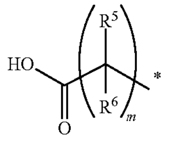

(E1-2)

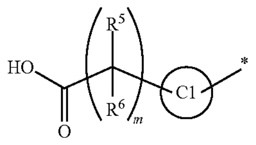

(E1-3)

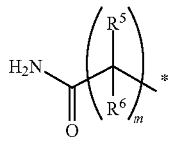

(E2-1)

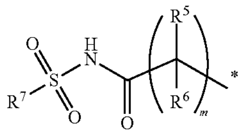

(E2-2)

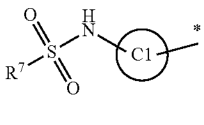

(E3-1)

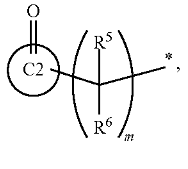

, where each asterisk * represents the point of connection to Ring A, m is 0 or 1, $R^5$ and $R^6$ are each independently (i) H, (ii) halogen, (iii) $C_1$-$C_6$ alkyl optionally substituted with 1 to 3 halogens and 1 to 3 —OH, (iv) $C_1$-$C_6$ deuterated alkyl, (v) $C_2$-$C_6$ alkenyl, or (iii) $C_2$-$C_6$ alkynyl, or $R^5$ and $R^6$ are each D, or $R^5$ and $R^6$ together form a $C_3$-$C_6$ cycloalkyl or a 4-6 membered heterocycloalkyl comprising at least one heteroatom selected from the group consisting of N, O, and S, $R^7$ is selected from the group consisting of $C_1$-$C_6$ alkyl optionally substituted with 1 to 3 halogens, $C_1$-$C_6$ deuterated alkyl optionally substituted with 1 to 3 halogens, $C_3$-$C_5$ cycloalkyl optionally deuterated and optionally substituted with (i) 1 to 4 halogens, (ii) $C_1$-$C_3$ alkyl optionally substituted with 1 to 3 halogens, or (iii) $C_1$-$C_3$ deuterated alkyl optionally substituted with 1 to 3 halogens; and —$NR^8R^9$, wherein $R^3$ and $R^9$ are each independently H, $C_1$-$C_6$ alkyl, or $C_1$-$C_6$ deuterated alkyl, or $R^3$ and $R^9$ together form a 4-6 membered N-containing heterocycloalkyl ring optionally substituted with 1 to 4 halogens, Ring C1 is 5-6 membered N-containing heteroaryl optionally substituted with one group selected from (i) $C_1$-$C_3$ alkyl optionally substituted with 1 to 4 halogens, (ii) $C_2$-$C_3$ hydroxyalkyl, and (iii) $C_3$-$C_4$ cycloalkyl, wherein said optional substituent of Ring C1 is optionally deuterated, and Ring C2 is 5-6 membered N-containing heterocyclic ring optionally substituted with one group selected from (i) $C_1$-$C_3$ alkyl optionally substituted with 1 to 4 halogens, (ii) $C_2$-$C_3$ hydroxyalkyl, and (iii) $C_3$-$C_4$ cycloalkyl, wherein said optional substituent of Ring C2 is optionally deuterated;

n is 0, 1, or 2 and n' is 3, 4, or 5, with the proviso that n+n' is 5;

each $R^3$ is independently selected from the group consisting of (i) halogen, (ii) $C_1$-$C_6$ alkyl optionally substituted with 1 to 3 halogens, (iii) $C_1$-$C_6$ deuterated alkyl optionally substituted with 1 to 3 halogens, (iv) $C_2$-$C_6$ alkenyl, (v) $C_2$-$C_6$ alkynyl, and (vi) $C_3$-$C_6$ cycloalkyl optionally deuterated and optionally substituted with 1 to 4 halogens;

each $R^{3'}$ is independently H or D; and $R^4$ is a 3-6 membered N-containing heterocycloalkyl optionally substituted with 1 to 4 substituents independently selected from the group consisting of:

-D, halogen,

—OH,

—CN, $C_1$-$C_3$ alkyl optionally substituted with 1 to 3 halogens, $C_1$-$C_3$ deuterated alkyl optionally substituted with 1 to 3 halogens, a spirocyclic $C_3$-$C_6$ cycloalkyl optionally deuterated and optionally substituted with (i) 1 to 3 halogens, (ii) $C_1$-$C_3$ alkyl optionally substituted with 1 to 3 halogens, or (iii) $C_1$-$C_3$ deuterated alkyl, and a spirocyclic 3-6 membered heterocycloalkyl comprising at least one heteroatom selected from the group consisting of N, O, and S, wherein said spirocyclic 3-6 membered heterocycloalkyl is optionally deuterated and optionally substituted with (i) 1 to 3 halogens, (ii) $C_1$-$C_3$ alkyl optionally substituted with 1 to 3 halogens, or (iii) $C_1$-$C_3$ deuterated alkyl, wherein the point of attachment to linking group L is at a carbon atom.

E195 A compound of embodiment E194 or a pharmaceutically acceptable salt thereof, having formula (II'):

(II')

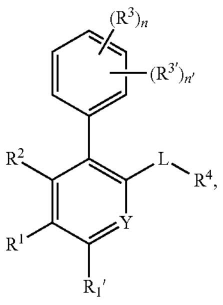

wherein:

Y is N or C—$R^1$, preferably Y is C—$R^{1'}$;

L is a linking group selected from the group consisting of L1', L2', and L3', preferably L is linking group L1':

(L1')

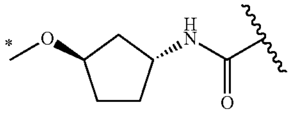

(L2')

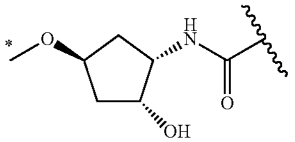

(L3')

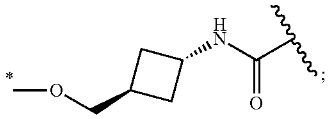

where the asterisk * represents the point of attachment to Ring A and the wave line represents the point of attachment to $R^4$; and $R^4$ is a group of formula (E4-1), (E4-2), (E4-3), (E4-4), (E4-5), (E4-6), (E5-1), (E5-2), (E5-3), (E5-4), (E5-5), (E5-6), (E5-7), (E5-8), or (E5-9):

(E4-1)

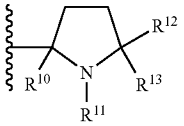

(E4-2)

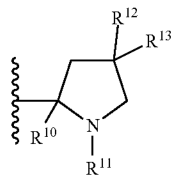

-continued (E4-3)

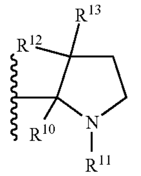

(E4-4)

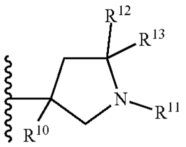

(E4-5)

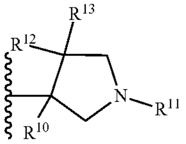

(E4-6)

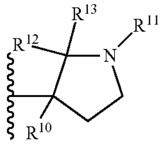

(E5-1)

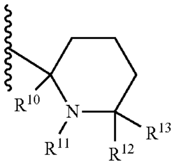

(E5-2)

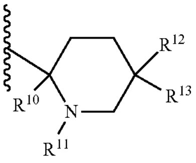

(E5-3)

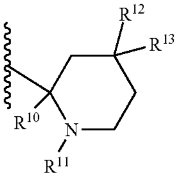

(E5-4)

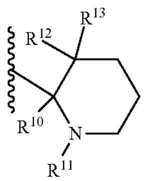

(E5-5)

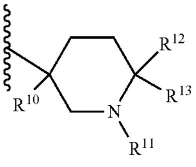

-continued (E5-6)

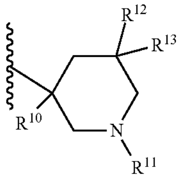

(E5-7)

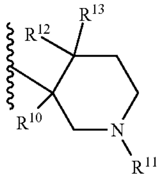

(E5-8)

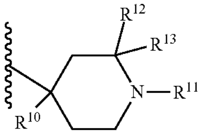

(E5-9)

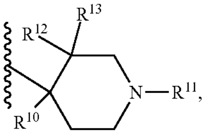

wherein:

the wave line represents the point of attachment to linking group L;

$R^{10}$ is (i) H, (ii) D, (iii) halogen, (iv) —OH, (v) —CN, (vi) $C_1$-$C_3$ alkyl optionally substituted with 1 to 3 halogens, (vii) $C_1$-$C_3$ deuterated alkyl, optionally substituted with 1 to 3 halogens, with the proviso that when $R^{10}$ is adjacent to the ring N of $R^4$, $R^{10}$ is not OH or halogen;

$R^{11}$ is (i) H, (ii) $C_1$-$C_3$ alkyl optionally substituted with 1 to 3 halogens, (iii) $C_1$-$C_3$ deuterated alkyl, or (iv) $C_2$-$C_3$ hydroxyalkyl; and $R^{12}$ and $R^{13}$ are each independently (i) H, (ii) halogen, (iii) $C_1$-$C_3$ alkyl optionally substituted with 1 to 3 halogens, or (iv) $C_1$-$C_3$ deuterated alkyl, with the proviso that when $R^{12}$ and $R^{13}$ are adjacent to the ring N of $R^4$, $R^{12}$ and $R^{13}$ are not halogen, or $R^{12}$ and $R^{13}$ are each D, or $R^{12}$ and $R^{13}$ together form a $C_3$-$C_6$ cycloalkyl optionally deuterated and optionally substituted with (i) 1 to 3 halogens, (ii) $C_1$-$C_3$ alkyl optionally substituted with 1 to 3 halogens, or (iii) $C_1$-$C_3$ deuterated alkyl;

or $R^{12}$ and $R^{13}$ together form a 3-6 membered heterocycloalkyl comprising at least one heteroatom selected from the group consisting of N, O, and S, and optionally deuterated and optionally substituted with (i) 1 to 3 halogens, (ii) $C_1$-$C_3$ alkyl optionally substituted with 1 to 3 halogens, or (iii) $C_1$-$C_3$ deuterated alkyl, with the proviso that when $R^{12}$ and $R^{13}$ are adjacent to the ring N of $R^4$ and form a 3-6 membered heterocycloalkyl, said 3-6 membered heterocycloalkyl is not attached to the $R^4$ ring by a heteroatom.

E196 A compound according to embodiment E194 or E195, or a pharmaceutically acceptable salt thereof, wherein:

one of $R^1$ and $R^2$ is H, D, or halogen and the other one of $R^1$ and $R^2$ is a group of formula (E1-1), (E1-2a), (E1-2b), (E1-3), (E2-1), (E2-2a), (E2-2b), or (E3-1a):

(E1-1)

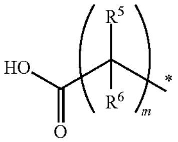

(E1-2a)

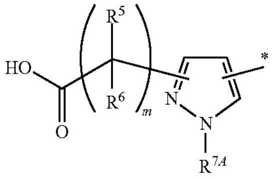

(E1-2b)

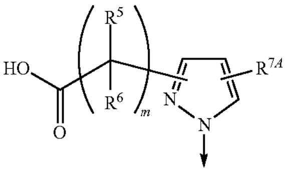

(E1-3)

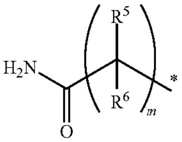

(E2-1)

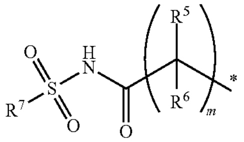

(E2-2a)

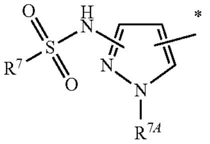

(E2-2b)

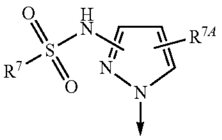

(E3-1a)

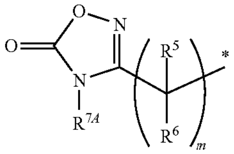

wherein:

each asterisk * represents the point of connection of the other one of $R^1$ and $R^2$ to the Ring A;

m is 0 or 1;

$R^5$ and $R^6$ are each independently (i) H, (ii) halogen, (iii) $C_1$-$C_6$ alkyl optionally substituted with 1 to 3 halogens and 1 to 3 —OH, (iv) $C_1$-$C_3$ deuterated alkyl, (v) $C_2$-$C_6$ alkenyl, (vi) $C_{2-e}$ alkynyl, or $R^7$ and $R^6$ are both 0, or $R^5$ and $R^6$ together form a $C_3$-$C_6$cycloalkyl or a 4-6 membered heterocycloalkyl comprising at least one heteroatom selected from the group consisting of N, O, and S;

$R^7$ is selected from the group consisting of $C_1$-$C_3$ alkyl optionally substituted with 1 to 3 halogens, $C_1$-$C_3$ deuterated alkyl optionally substituted with 1 to 3 halogens, $C_3$-$C_4$ cycloalkyl optionally deuterated and optionally substituted with (i) 1 to 4 halogens, (ii) a $C_1$-$C_3$ alkyl optionally substituted with 1 to 3 halogens, or (iii) a $C_1$-$C_3$ deuterated alkyl optionally substituted with 1 to 3 halogens, and —$NR^8R^9$, wherein $R^3$ and $R^9$ are each independently H, $C_1$-$C_6$ alkyl, or $C_1$-$C_6$ deuterated alkyl, or $R^3$ and $R^9$ together form a 4-6 membered N-containing heterocycloalkyl ring optionally substituted with 1 to 4 halogens; and $R^{7A}$ is (i) H, (ii) $C_1$-$C_3$ alkyl optionally substituted with 1 to 3 halogens, (iii) $C_1$-$C_3$ deuterated alkyl, (iv) $C_2$-$C_3$ hydroxyalkyl, or (v) $C_3$-$C_4$ cycloalkyl, wherein said $C_3$-$C_4$ cycloalkyl is optionally deuterated.

E197 A compound according to any one of embodiments E194 to E196, or a pharmaceutically acceptable salt thereof, wherein:

at least one $R^3$ is present and is selected from (i) $C_1$-$C_6$ alkyl, (ii) $C_1$-$C_6$ deuterated alkyl optionally substituted with 1 to 3 halogens, (iii) $C_3$-$C_6$ cycloalkyl optionally deuterated and optionally substituted with 1 to 4 halogens, preferably at least one $R^3$ is present and selected from (i) $C_1$-$C_3$ alkyl, (ii) $C_1$-$C_3$ deuterated alkyl optionally substituted with 1 to 3 halogens, and (iii) $C_3$-$C_4$ cycloalkyl optionally deuterated and optionally substituted with 1 to 4 halogens.

Any of the compounds described in any one of embodiments E31, E38, E47, E54, E61, E69, E76, E83, E92-E100, E112-E116, E128-E130, E142-E144, E154, E164, E174, E183, and E193, or pharmaceutically acceptable salts thereof, may be claimed individually or grouped together with one or more other compounds of embodiments E31, E38, E47, E54, E61, E69, E76, E83, E92-E100, E112-E116, E128-E130, E142-E144, E154, E164, E174, E183, and E193, or pharmaceutically acceptable salts thereof.

E198 A pharmaceutical composition comprising a compound of any one of embodiments E1 to E197, or a pharmaceutically acceptable salt thereof, and at least one pharmaceutically acceptable excipient.

E199 A method for treating cancer, the method comprising: administering to a subject in need thereof a therapeutically effective amount of a compound of any one of embodiments E1 to E197, or a pharmaceutically acceptable salt thereof.

E200 A method for treating cancer, the method comprising:

administering to a subject in need thereof a therapeutically effective amount of a compound of any one of embodiments E1 to E197, or a pharmaceutically acceptable salt thereof, as a single agent.

E201 A method for treating cancer, the method comprising: administering to a subject in need thereof a therapeutically effective amount of a compound of any one of embodiments E1 to E197, or a pharmaceutically acceptable salt thereof, and further comprising administering a therapeutically effective amount of an additional anticancer therapeutic agent.

E202 A method for treating cancer of any one of embodiments E199 to E201, wherein the cancer is multiple myeloma, lung cancer, breast cancer, prostate cancer, acute myeloid leukemia.

E203 A compound of any one of embodiments E1 to E197, or a pharmaceutically acceptable salt thereof, for use as a medicament.

E204 A compound of any one embodiments E1 to E197, or a pharmaceutically acceptable salt thereof, for use in the treatment of cancer.

E205 A compound for use in the treatment of cancer according to embodiment E204, wherein said cancer is multiple myeloma, lung cancer, breast cancer, prostate cancer, or acute myeloid leukemia.

E206 Use of a compound of any one of embodiments E1 to E197, or a pharmaceutically acceptable salt thereof, for the manufacture of a medicament for the treatment of cancer.

E207 Use of a compound, or a pharmaceutically acceptable salt thereof, according to embodiment E206, wherein the cancer is multiple myeloma, lung cancer, breast cancer, prostate cancer, acute myeloid leukemia.

E208 A method for the treatment of a disorder mediated by inhibition of KAT2A or KAT2B in a subject, the method comprising:

administering to the subject in need thereof a compound of any one of embodiments E1 to E197, or a pharmaceutically acceptable salt thereof, in an amount that is effective for treating the disorder.

E209 A pharmaceutical combination comprising a compound of any one of embodiments E1 to E197 or a pharmaceutically acceptable salt thereof, and at least one additional therapeutic agent or a pharmaceutically acceptable salt thereof.

E210 A pharmaceutical composition comprising the pharmaceutical combination of embodiment E209 and at least one excipient.

The references to the methods of treatment of this description are to be interpreted as also being references to the compound(s), pharmaceutical compositions, and medicaments of the present invention for use in those methods. For example, the method treating a disorder mediated by inhibition of KAT2A or KAT2B, such as small cell lung cancer (SCLC), neuroendocrine prostate cancer (NEPC), acute myeloid leukemia (AML), and multiple myeloma, in a subject by administering a therapeutically effective amount of a compound of any one of embodiments E1 to E179, or a pharmaceutically acceptable salt thereof, to the subject, may be interpreted as: (1) a KAT2A or KAT2B inhibiting compound, or a pharmaceutically acceptable salt thereof, for use as a medicament; (2) a KAT2A or KAT2B inhibiting compound, or a pharmaceutically acceptable salt thereof, for use in treating a disorder mediated by inhibition of KAT2A or KAT2B in a subject; (3) use of a KAT2A or KAT2B inhibiting compound, or a pharmaceutically acceptable salt thereof, for treating a disorder mediated by inhibition of KAT2A or KAT2B in a subject; and/or (4) use of a KAT2A or KAT2B inhibiting compound inhibiting compound, or a pharmaceutically acceptable salt thereof, in the manufacture of a medicament for treating a disorder mediated by inhibition of KAT2A or KAT2B in a subject.

Each of the embodiments described herein may be combined with any other embodiment(s) described herein not inconsistent with the embodiment(s) with which it is combined. In addition, any of the compounds described in the Examples, or pharmaceutically acceptable salts thereof, may be claimed individually or grouped together with one or more other compounds of the Examples, or pharmaceutically acceptable salts thereof, for any of the embodiment(s) described herein.

Furthermore, each of the embodiments described herein envisions within its scope pharmaceutically acceptable salts of the compounds described herein.

Definitions

Unless otherwise defined herein, scientific and technical terms used in connection with the present invention have the meanings that are commonly understood by those of ordinary skill in the art.

The invention described herein suitably may be practiced in the absence of any element(s) not specifically disclosed herein.

"Compounds of the invention" include compounds of Formula I. One of ordinary skill in the art will appreciate that compounds of the invention include conformational isomers (e.g., cis and trans isomers) and all optical isomers (e.g., enantiomers and diastereomers), racemic, diastereomeric and other mixtures of such isomers, tautomers thereof, where they may exist.

One of ordinary skill in the art will also appreciate that compounds of the invention include solvates, hydrates, isomorphs, polymorphs, esters, salt forms, prodrugs, and isotopically labelled versions thereof (including deuterium substitutions), where they may be formed.

As used herein, the singular form "a", "an", and "the" include plural references unless indicated otherwise. For example, "a" substituent includes one or more substituents.

As used herein, the term "about" when used to modify a numerically defined parameter (e.g., the dose of 5 mg) means that the parameter may vary by as much as 10% below or above the stated numerical value for that parameter. For example, a dose of about 5 mg means 5%+10%, i.e., it may vary between 4.5 mg and 5.5 mg.

If substituents are described as being "independently selected" from a group, each substituent is selected independent of the other. Each substituent therefore may be identical to or different from the other substituent(s).

"Optional" or "optionally" means that the subsequently described event or circumstance may, but need not occur, and the description includes instances where the event or circumstance occurs and instances in which it does not.

The terms "optionally substituted" and "substituted or unsubstituted" are used interchangeably to indicate that the particular group being described may have no non-hydrogen substituents (i.e., unsubstituted), or the group may have one or more non-hydrogen substituents (i.e., substituted). If not otherwise specified, the total number of substituents that may be present is equal to the number of H atoms present on the unsubstituted form of the group being described. Where an optional substituent is attached via a double bond, such as an oxo (=O) substituent, the group occupies two available valences, so the total number of other substituents that are included is reduced by two. In the case where optional substituents are selected independently from a list of alternatives, the selected groups may be the same or different.

Throughout the disclosure, it will be understood that the number and nature of optional substituent groups will be limited to the extent that such substitutions make chemical sense to one of ordinary skill in the art.

"D" refers to deuterium.

"Halogen" or "halo" refers to fluoro, chloro, bromo, and iodo (F, Cl, Br, I).

"Cyano" refers to a substituent having a carbon atom joined to a nitrogen atom by a triple bond, i.e., —C≡N, also referred to herewith as —CN.

"Hydroxy" refers to an —OH group.

"Oxo" refers to a double bonded oxygen (═O).

"Alkyl" refers to a saturated, monovalent aliphatic hydrocarbon radical that has a specified number of carbon atoms, including straight chain or branched chain groups. Alkyl groups may contain, but are not limited to, 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$ alkyl"), 1 to 3 carbon atoms ("$C_1$-$C_3$ alkyl"), or 1 to 2 carbon atoms ("$C_1$-$C_2$ alkyl"). Examples include, but are not limited to, methyl ($-CH_3$), ethyl ($-CH_2CH_3$), n-propyl ($-CH_2CH_2CH_3$), isopropyl ($-CH(CH_3)_2$), n-butyl ($-CH_2CH_2CH_2CH_3$), and the like.

"Deuterated alkyl" refers to the foregoing alkyl groups in which hydrogen atoms are partially or completely replaced with its isotope deuterium. Examples include, but are not limited to, $-CD_3$ (deuterated methyl), $-CD_2CD_3$ (deuterated ethyl), and $-CD_2CD_2CD_3$ (deuterated propyl).

"Haloalkyl" refers to an alkyl group as defined above containing the specified number of carbon atoms wherein at least one hydrogen atom has been replaced by halogen. Haloalkyl groups man contain, but are not limited to, 1-6 carbon atoms ("$C_1$-$C_6$ haloalkyl"), 1-4 carbon atoms ("$C_1$-$C_4$ haloalkyl"), or 1-2 carbon atoms ("$C_1$-$C_2$ haloalkyl").

"Fluoroalkyl" refers to an alkyl group, as defined herein, wherein from one to all of the hydrogen atoms of the alkyl group are replaced by fluoro atoms. Examples include, but are not limited to, fluoromethyl, difluoromethyl, fluoroethyl, difluoroethyl, trifluoroethyl, and tetrafluoroethyl. Examples of fully substituted fluoroalkyl groups (also referred to as perfluoroalkyl groups) include trifluoromethyl ($-CF_3$) and pentafluoroethyl ($-C_2F_5$).

"Hydroxyalkyl" refers to an alkyl group, as defined above, that is substituted with 1, 2, or 3 hydroxy (—OH) groups.

"Alkoxy" refers to an alkyl group, as defined herein, that is single bonded to an oxygen atom. The attachment point of an alkoxy radical to a molecule is through the oxygen atom. An alkoxy radical may be depicted as alkyl-O—. Alkoxy groups may contain, but are not limited to, 1 to 6 carbon atoms ("$C_1$-$C_6$ alkoxy"), 1 to 4 carbon atoms ("$C_1$-$C_4$ alkoxy"), or 1 to 3 carbon atoms ("$C_1$-$C_3$ alkoxy"). Alkoxy groups include, but are not limited to, methoxy, ethoxy, n-propoxy, isobutoxy, and the like.

"Haloalkoxy" refers to an alkoxyl group as defined above containing the specified number of carbon atoms wherein at least one hydrogen atom has been replaced by halogen. Haloalkoxy groups may contain, but are not limited to, 1-6 carbon atoms, ("$C_1$-$C_6$ haloalkoxy"), 1-4 carbon atoms ("$C_1$-$C_4$ haloalkoxy"), or 1-2 carbon atoms ("$C_1$-$C_2$ haloalkoxy"). More specifically, fluorinated alkoxyl groups may be specifically referred to as "fluoroalkoxy."

"Alkenyl" refers to an alkyl group, as defined herein, consisting of at least two carbon atoms and at least one carbon-carbon double bond. For example, as used herein, the term "$C_2$-$C_6$ alkenyl" means straight or branched chain unsaturated radicals of 2 to 6 carbon atoms, including, but not limited to, ethenyl, 1-propenyl, 2-propenyl, 1-, 2-, or 3-butenyl, and the like.

"Alkynyl" refers to an alkyl group, as defined herein, consisting of at least two carbon atoms and at least one carbon-carbon triple bond. Examples include, but are not limited to, ethynyl, 1-propynyl, 2-propynyl, 1-, 2-, or 3-butynyl, and the like.

"Cycloalkyl" refers to a fully saturated hydrocarbon ring system that has the specified number of carbon atoms, which may be a monocyclic, bridged or fused bicyclic or polycyclic ring system that is connected to the base molecule through a carbon atom of the cycloalkyl ring. Cycloalkyl groups may contain, but are not limited to, 3 to 6 carbon atoms ("$C_3$-$C_6$ cycloalkyl"), 3 to 5 carbon atoms ("$C_3$-$C_5$ cycloalkyl") or 3 to 4 carbon atoms ("$C_3$-$C_4$ cycloalkyl"). Examples include, but are not limited to, cyclopropyl, cyclobutyl, cyclopentyl, and cyclohexyl. Cycloalkyl groups may be optionally substituted, unsubstituted or substituted, as further defined herein.

"Heterocycloalkyl" refers to a fully saturated ring system containing the specified number of ring atoms and containing at least one heteroatom selected from N, O and S as a ring member, where ring S atoms are optionally substituted with one or two oxo groups (i.e., $S(O)_q$, where q is 0, 1 or 2) and where the heterocycloalkyl ring is connected to the base molecule via a ring atom, which may be C or N. Heterocycloalkyl rings may contain 1 to 3 heteroatoms selected from N, O, and $S(O)_q$ as ring members, or 1 to 2 ring heteroatoms, provided that such heterocycloalkyl rings do not contain two contiguous oxygen or sulfur atoms. Heterocycloalkyl rings may be optionally substituted, unsubstituted or substituted, as further defined herein. Such substituents may be present on the heterocyclic ring attached to the base molecule, or on a spirocyclic, bridged or fused ring attached thereto.

Heterocycloalkyl rings may include, but are not limited to, 3-6 membered heterocyclyl groups, for example 3-6 membered heterocycloalkyl groups, in accordance with the definition herein. Illustrative examples of heterocycloalkyl rings include, but are not limited to a monovalent radical of:

oxirane (oxiranyl)

thiarane (thiaranyl)

aziridine (aziridinyl)

oxetane (oxetanyl)

thiatane (thiatanyl)

azetidine (azetidinyl)

tetrahydrofuran (tetrahydrofuranyl)

tetrahydrothiophene (tetrahydrothiophenyl)

pyrrolidine (pyrrolidinyl)

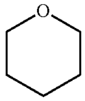
tetrahydropyran (tetrahydropyranyl)

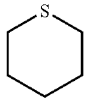
tetrahydrothiopyran (tetrahydrothiopyranyl)

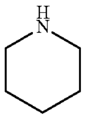
piperidine (piperidinyl)

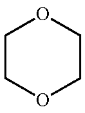
1,4-dioxane (1,4-dioxanyl)

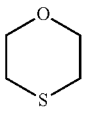
1,4-oxthiarane (1,4-oxathiaranyl)

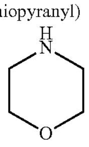
morpholine (morpholinyl)

-continued

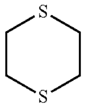 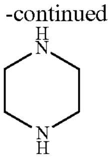 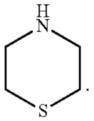

1,4-dithiane (1,4-dithianyl) piperazine (piperazinyl) thiomorpholine (thiamorpholinyl)

"N-containing heterocycloalkyl" as used herein, refers to a fully saturated cycloalkyl ring system in which one or more of the ring methylene groups ($-CH_2-$) has been replaced with $-NR^{11}-$ and optionally a further ring methylene group is replaced with a heteroatom selected from oxygen and sulfur.

Non-limiting examples of N-containing heterocycloalkyl include pyrazolidinyl, pyrrolidinyl, imidazolidinyl, piperidinyl, piperazinyl, or morpholinyl, wherein the N of the heterocycloalkyl is substituted with $R^{11}$ as defined herein. Non-limiting examples of such N-containing heterocycloalkyl include:

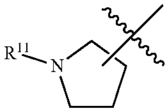, 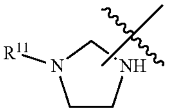,

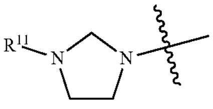, 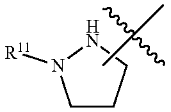,

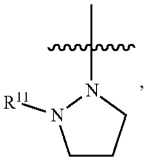, 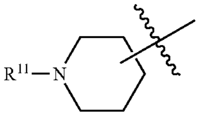,

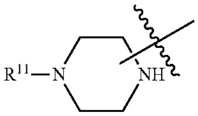, and 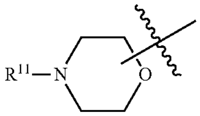

where the ∿∿ can attach to the heterocycloalkyl at any atom of sufficient valency and provides the point of attachment within $R^4$ to linking group L. Such rings N-containing heterocycloalkyl may be unsubstituted or substituted, as further defined herein. Such substituents may be present on the heterocyclic ring attached to the base molecule, or on a spirocyclic, bridged or fused ring attached thereto.

"5-6 membered N-containing heteroaryl" refers to a monocyclic ring system containing 5 to 6 ring atoms with at least one nitrogen as a ring member, and optionally further containing nitrogen, oxygen, and sulfur as a ring member in a ring in which all carbon atoms in the ring are of $sp^2$ hybridization and in which the pi electrons are in conjugation. Such a heteroaryl group may be attached through a ring carbon atom or, where valency permits, through a ring heteroatom atom. Such heteroaryl groups may be unsubstituted or substituted, as further defined herein.

Illustrative examples of monocyclic heteroaryl groups include, but are not limited to a monovalent radical of:

  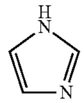 

pyrrole (pyrrolyl) pyrazole (pyrazolyl) imidazole (imidazolyl) isoxazole (isoxazolyl)

   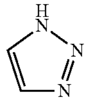

oxazole (oxazolyl) isothiazole (isothiazolyl) thiazolyl (thiazolyl) 1,2,3-triazole (1,2,3-triazolyl)

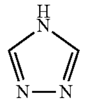  

1,3,4-triazole (1,3,4-triazolyl) 1-oxa-2,3-diazole (1-oxa-2,3-diazolyl) 1-oxa-2,4-diazole (1-oxa-2,4-diazolyl)

  

1-oxa-2,5-diazole (1-oxa-2,5-diazolyl) 1-oxa-3,4-diazole (1-oxa-3,4-diazolyl) 1-thia-2,3-diazole (1-thia-2,3-diazolyl)

  

1-thia-2,4-diazole (1-thia-2,4-diazolyl) 1-thia-2,5-diazole (1-thia-2,5-diazolyl) 1-thia-3,4-diazole (1-thia-3,4-diazolyl)

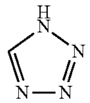 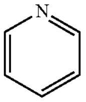 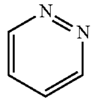

tetrazole (tetrazolyl) pyridine (pyridinyl) pyridazine (pyridazinyl)

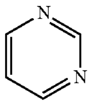 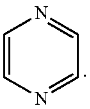.

pyrimidine (pyrimidinyl) pyrazine (pyrazinyl)

In the case of Ring C1, non-limiting examples include imidazolyl, pyrazolyl, or pyrrolyl, wherein a ring carbon or ring N is substituted with $R^{7A}$ as defined herein and illustrated below:

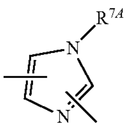, 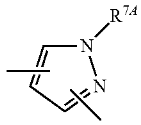, 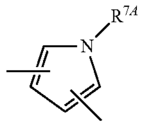,

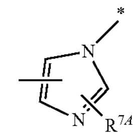, 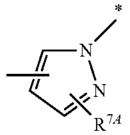, 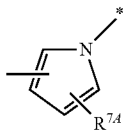, where the asterisk * can attach to the heteroaryl at any atom of sufficient valency and provides the point of attachment from Ring C1 to Ring A and $R^{7A}$ is as defined herein.

"5-6 membered N-containing heterocyclic ring" refers to carbocyclic group in which at least one of the ring carbon atoms has been replaced by a nitrogen and further ring carbons are optionally replaced by nitrogen, oxygen, or sulfur, where the ring may be saturated (i.e., 5-6 membered N-containing heterocycloalkyl), partially unsaturated, or aromatic (i.e., a 5-6 membered N-containing heteroaryl), and where a substituent can occur on any atom of sufficient valency.

"Amino" refers to a group —$NH_2$, which is unsubstituted. Where the amino is described as substituted or optionally substituted, the term includes groups of the form —NRxRy, where each of Rx and Ry is defined as further described herein. For example, "alkylamino" refers to a group —NRxRy, wherein one of Rx and Ry is an alkyl moiety and the other is H, and "dialkylamino" refers to —NRxRy wherein both of Rx and Ry are alkyl moieties, where the alkyl moieties have the specified number of carbon atoms (e.g., —NH($C_1$-$C_4$ alkyl) or —N($C_1$-$C_4$ alkyl)$_2$).

A wavy line "∿∿∿" or an asterisk "*" used in a chemical structure in the present disclosure refers to the point of the attachment of a substituent.

"Deuterium enrichment factor" as used herein means the ratio between the deuterium abundance and the natural abundance of deuterium, each relative to hydrogen abundance. An atomic position designated as having deuterium typically has a deuterium enrichment factor of, in particular embodiments, at least 1000 (15% deuterium incorporation), at least 2000 (30% deuterium incorporation), at least 3000 (45% deuterium incorporation), at least 3500 (52.5% deuterium incorporation), at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

A "pharmaceutical composition" refers to a mixture of one or more of the compounds of the invention, or a pharmaceutically acceptable salt, solvate, hydrate or prodrug thereof as an active ingredient, and at least one pharmaceutically acceptable excipient.

The term "pharmaceutically acceptable" means the substance (e.g., the compounds described herein) and any salt thereof, or composition containing the substance or salt of the invention is suitable for administration to a subject or patient.

"Excipient" as used herein describes any ingredient other than the compound(s) of the invention. The choice of excipient will to a large extent depend on factors such as the mode of administration, the effect of the excipient on solubility and stability, and the nature of the dosage form.

As used herein, "excipient" includes any and all solvents, dispersion media, coatings, antibacterial and antifungal agents, isotonic and absorption delaying agents, carriers, diluents and the like that are physiologically compatible. Examples of excipients include one or more of water, saline, phosphate buffered saline, dextrose, glycerol, ethanol and the like, as well as combinations thereof, and may include isotonic agents, for example, sugar, sodium chloride, or polyalcohol such as mannitol, or sorbitol in the composition. Examples of excipients also include various organic solvents (such as hydrates and solvates). The pharmaceutical compositions may, if desired, contain additional excipients such as flavorings, binders/binding agents, lubricating agents, disintegrants, sweetening or flavoring agents, coloring matters or dyes, and the like. For example, for oral administration, tablets containing various excipients, such as citric acid may be employed together with various disintegrants such as starch, alginic acid and certain complex silicates and with binding agents such as sucrose, gelatin and acacia.

Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of excipients, therefore, also include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with additional excipients such as water, ethanol, propylene glycol, glycerin, or combinations thereof.

Examples of excipients also include pharmaceutically acceptable substances such as wetting agents or minor amounts of auxiliary substances such as wetting or emulsifying agents, preservatives, or buffers, which enhance the shelf life or effectiveness of the compound.

The term "treating", "treat" or "treatment" as used herein embraces both preventative, i.e., prophylactic, and palliative treatment, i.e., relieve, alleviate, or slow the progression of the patient's disease (or condition) or any tissue damage associated with the disease.

The term "treat" or "treating" a cancer as used herein means to administer a compound of the present invention to a subject having cancer, or diagnosed with cancer, to achieve at least one positive therapeutic effect, such as, for example, reduced number of cancer cells, reduced tumor size, reduced rate of cancer cell infiltration into peripheral organs, or reduced rate of tumor metastases or tumor growth, reversing, alleviating, or inhibiting the progress of, the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

The term "tumor size" refers to the total size of the tumor which can be measured as the length and width of a tumor. Tumor size may be determined by a variety of methods known in the art, such as, e.g., by measuring the dimensions of tumor(s) upon removal from the subject, e.g., using callipers, or while in the body using imaging techniques, e.g., bone scan, ultrasound, CR or MRI scans.

As used herein, the term, "subject, "individual" or "patient," used interchangeably, refers to any animal, including mammals. Mammals according to the invention include canine, feline, bovine, caprine, equine, ovine, porcine, rodents, lagomorphs, primates, humans and the like, and encompass mammals in utero. In an embodiment, humans are suitable subjects. Human subjects may be of any gender and at any stage of development.

As used herein, an "effective dosage" or "effective amount" of drug, compound or pharmaceutical composition is an amount sufficient to affect any one or more beneficial or desired, including biochemical, histological and/or behavioral symptoms, of the disease, its complications and intermediate pathological phenotypes presenting during development of the disease.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which may include one or more of the following:

(1) preventing the disease; for example, preventing a disease, condition or disorder in an individual that may be predisposed to the disease, condition or disorder but does not yet experience or display the pathology or symptomatology of the disease;

(2) inhibiting the disease; for example, inhibiting a disease, condition or disorder in an individual that is experiencing or displaying the pathology or symptomatology of the disease, condition or disorder (i.e., arresting (or slowing) further development of the pathology or symptomatology or both); and (3) ameliorating the disease; for example, ameliorating a disease, condition or disorder in an individual that is experiencing or displaying the pathology or symptomatology of the disease, condition or disorder (i.e., reversing the pathology or symptomatology or both).

In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, (4) relieving to some extent (or, preferably, eliminating) one or more signs or symptoms associated with the cancer, (5) decreasing the dose of other medications required to treat the disease, and/or (6) enhancing the effect of another medication, and/or (7) delaying the progression of the disease in a patient.

Salts

Salts encompassed within the term "pharmaceutically acceptable salts" refer to the compounds of this invention which are generally prepared by reacting the free base or free acid with a suitable organic or inorganic acid, or a suitable organic or inorganic base, respectively, to provide a salt of the compound of the invention that is suitable for administration to a subject or patient.

In addition, the compounds of Formula (I) may also include other salts of such compounds which are not necessarily pharmaceutically acceptable salts, which may be useful as intermediates for one or more of the following: 1) preparing compounds of Formula (I); 2) purifying compounds of Formula (I); 3) separating enantiomers of compounds of Formula I; or 4) separating diastereomers of compounds of Formula (I).

Suitable acid addition salts are formed from acids which form non-toxic salts. Examples include, but are not limited to, acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, 1,5-naphathalenedisulfonic acid and xinofoate salts.

Suitable base salts are formed from bases which form non-toxic salts. Examples include, but are not limited to aluminum, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts.

For a review on suitable salts, see PAULEKUHN, G. S., et al., "Trends in Active Pharmaceutical Ingredient Salt Selection Based on Analysis of the Orange Book Database," Journal of Medicinal Chemistry, 2007, 50(26):6665-6672.

Pharmaceutically acceptable salts of compounds of the invention may be prepared by methods well known to one skilled in the art, including but not limited to the following procedures (i) by reacting a compound of the invention with the desired acid or base;

(ii) by removing an acid- or base-labile protecting group from a suitable precursor of a compound of the invention or by ring-opening a suitable cyclic precursor, for example, a lactone or lactam, using the desired acid or base; or (iii) by converting one salt of a compound of the invention to another. This may be accomplished by reaction with an appropriate acid or base or by means of a suitable ion exchange procedure.

These procedures are typically carried out in solution. The resulting salt may precipitate out and be collected by filtration or may be recovered by evaporation of the solvent.

Solvates

The compounds of the invention, and pharmaceutically acceptable salts thereof, may exist in unsolvated and solvated forms. The term 'solvate' is used herein to describe a molecular complex comprising the compound of the invention, or a pharmaceutically acceptable salt thereof, and one or more pharmaceutically acceptable solvent molecules, for example, ethanol. The term 'hydrate' is employed when said solvent is water.

In addition, the compounds of Formula I may also include other solvates of such compounds which are not necessarily pharmaceutically acceptable solvates, which may be useful as intermediates for one or more of the following: 1) preparing compounds of Formula I; 2) purifying compounds of Formula I; 3) separating enantiomers of compounds of Formula I; or 4) separating diastereomers of compounds of Formula I.

A currently accepted classification system for organic hydrates is one that defines isolated site, channel, or metal-ion coordinated hydrates—see BRITTAIN, H. G. Polymorphism in Pharmaceutical Solids. $2^{nd}$ Ed. CRC Press, 2009. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Solid Form

The compounds of the invention may exist in a continuum of solid states ranging from amorphous to crystalline. The term 'amorphous' refers to a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may also exist in a mesomorphic state (mesophase or liquid crystal) when subjected to suitable conditions. The mesomorphic state is intermediate between the true crystalline state and the true liquid state (either melt or solution) and consists of two dimensional order on the molecular level. Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $—COO^{-}Na^{+}$, $—COO^{-}K^{+}$, or $—SO_3^{-}Na^{+}$) or non-ionic (such as $—N^{-}N^{+}(CH_3)_3$) polar head group. For more information, see HARTSHORNE, N. H. and STUART, A., Crystals and the Polarizing Microscope. 4th Ed. London, Edward Arnold, 1970.

Stereoisomers

Compounds of the invention may exist as two or more stereoisomers. Stereoisomers of the compounds may include cis and trans isomers (geometric isomers), optical isomers such as R and S enantiomers, diastereomers, rotational isomers, atropisomers, and conformational isomers. For example, compounds of the invention containing one or more asymmetric carbon atoms may exist as two or more stereoisomers. Where a compound of the invention contains an alkenyl group, geometric cis/trans (or Z/E) isomers are possible. Cis/trans isomers may also exist for saturated rings.

chiral high pressure liquid chromatography (HPLC). Alternatively, the racemate (or a racemic precursor) may be reacted with a suitable optically active compound, for example, an alcohol, or, in the case where a compound of the invention contains an acidic or basic moiety, a base or acid such as 1-phenylethylamine or tartaric acid. The resulting diastereomeric mixture may be separated by chromatography, fractional crystallization, or by using both of said techniques, and one or both of the diastereoisomers converted to the corresponding pure enantiomer(s) by means well known to a skilled person. Chiral compounds of the invention (and chiral precursors thereof) may be obtained in enantiomerically-enriched form using chromatography, typically HPLC Concentration of the eluate affords the enriched mixture. Chiral chromatography using sub- and supercritical fluids may be employed. Methods for chiral chromatography useful in some embodiments of the present invention are known in the art (see, for example, SMITH, R. M., Supercritical Fluid Chromatography with Packed Columns. 1st Ed. RSC Chromatography Monographs, 1988).

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two crystal forms are produced in equimolar amounts each comprising a single enantiomer. While both of the crystal forms present in a racemic mixture have identical physical properties, they may have different physical properties compared to the true racemate. Racemic mixtures may be separated by conventional techniques known to those skilled in the art—see, for example, ELIEL, E. L. and WILEN, S. H., Stereochemistry of Organic Compounds. 1st Ed. New York, Wiley, 1994.

Tautomerism

Where structural isomers are interconvertible via a low energy barrier, tautomeric isomerism ('tautomerism') may occur. This may take the form of proton tautomerism in compounds of the invention containing, for example, an imidic acid/amide tautomer such as:

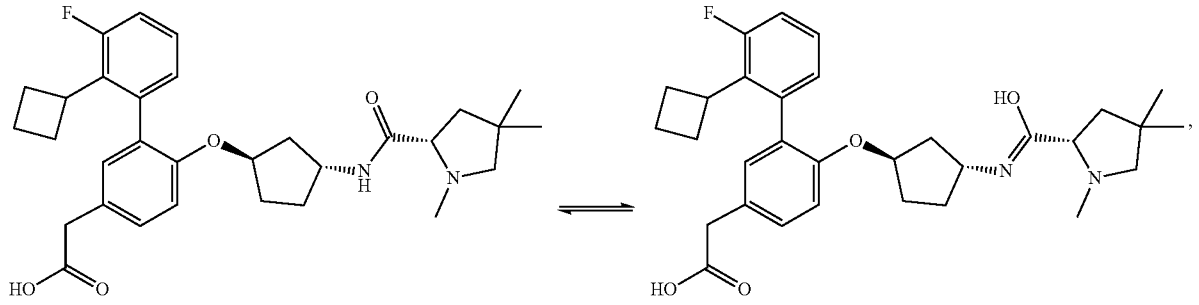

amide form imidic amide form

The pharmaceutically acceptable salts of compounds of the invention may also contain a counterion which is optically active (e.g., d-lactate or I-lysine) or racemic (e.g., dl-tartrate or dl-arginine).

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, or so-called valence tautomerism in compounds which contain an aromatic moiety. It follows that a single compound may exhibit more than one type of isomerism.

It must be emphasized that while, for conciseness, the compounds of the invention have been drawn herein in a single tautomeric form, all possible tautomeric forms are included within the scope of the invention.

Isotopes

The present invention includes all pharmaceutically acceptable isotopically-labeled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention may include isotopes of hydrogen, such as $^2H$ (D, deuterium) and $^3H$ (T, tritium), carbon, such as $^{11}C$ $^{13}C$ and $^{14}C$, chlorine, such as $^{36}Cl$, fluorine, such as $^{18}F$, iodine, such as 1231 and 1251 nitrogen, such as $^{13}N$ and $^{15}N$, oxygen, such as $^{15}O$, $^{17}O$ and $^{18}O$, and sulfur, such as $^{35}S$ Certain isotopically-labelled compounds of the invention, for example those incorporating a radioactive isotope, are useful in one or both of drug or substrate tissue distribution studies. The radioactive isotopes, such as, tritium and $^{14}C$ are particularly useful for this purpose in view of their ease of incorporation and ready means of detection.

Substitution with positron emitting isotopes, such as, $^{11}C$, $^{18}F$, $^{15}O$ and $^{13}N$, may be useful in Positron Emission Topography (PET) studies for examining substrate receptor occupancy. Substitution with deuterium ($^2H$) may afford certain therapeutic advantages resulting from greater metabolic stability, for example increased in vivo half-life, reduced dosage requirements, reduced CYP450 inhibition (competitive or time dependent), or an improvement in therapeutic index or tolerability.

In some embodiments, the disclosure provides deuterium-labeled (or deuterated) compounds and salts, where the formula and variables of such compounds and salts are each and independently as described herein. "Deuterated" means that at least one of the atoms in the compound is deuterium in an abundance that is greater than the natural abundance of deuterium (typically approximately 0.015%). A skilled artisan recognized that in chemical compounds with a hydrogen atom, the hydrogen atom actually represents a mixture of H and D, with about 0.015% being D. The concentration of the deuterium incorporated into the deuterium-labeled compounds and salt of the invention may be defined by the deuterium enrichment factor. It is understood that one or more deuterium may exchange with hydrogen under physiological conditions.

In some embodiments, one or more hydrogen atoms on certain metabolic sites on the compounds of the invention are deuterated.

Isotopically-labeled compounds of the invention may generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g., $D_2O$, $d_6$-acetone, $d_6$-DMSO.

Prodrugs

A compound of the invention may be administered in the form of a prodrug. Thus, certain derivatives of a compound of the invention which may have little or no pharmacological activity themselves may, when administered into or onto the body, be converted into a compound of the invention having the desired activity, for example by hydrolytic cleavage, particularly hydrolytic cleavage promoted by an esterase or peptidase enzyme. Such derivatives are referred to as 'prodrugs'. Further information on the use of prodrugs may be found in RAUTIO, J., et al., "The expanding role of prodrugs in contemporary drug design and development," Nature Reviews Drug Discovery, 2018, 17(8):559-587.

Prodrugs in accordance with the invention may, for example, be produced by replacing appropriate functionalities present in compounds of the invention with certain moieties known to those skilled in the art as 'pro-moieties' as described, for example, in BUNDGAARD, H., Design of Prodrugs. New York, Elsevier, 1985.

Thus, a prodrug in accordance with the invention may be (a) an ester or amide derivative of a carboxylic acid when present in a compound of the invention; (b) an ester, carbonate, carbamate, phosphate or ether derivative of a hydroxyl group when present in a compound of the invention; (c) an amide, imine, carbamate or amine derivative of an amino group when present in a compound of the invention; (d) a thioester, thiocarbonate, thiocarbamate or sulfide derivatives of a thiol group when present in a compound of the invention; or (e) an oxime or imine derivative of a carbonyl group when present in a compound of the invention.

Some specific examples of prodrugs in accordance with the invention include:

(i) when a compound of the invention contains a carboxylic acid functionality (—COOH), an ester thereof, such as a compound wherein the hydrogen of the carboxylic acid functionality of the compound is replaced by $C_1$-$C_3$ alkyl (e.g., ethyl) or ($C_1$-$C_3$ alkyl)C(═O)$OCH_2$-(e.g., $^t$BuC(═O)$OCH_2$—), for instance:

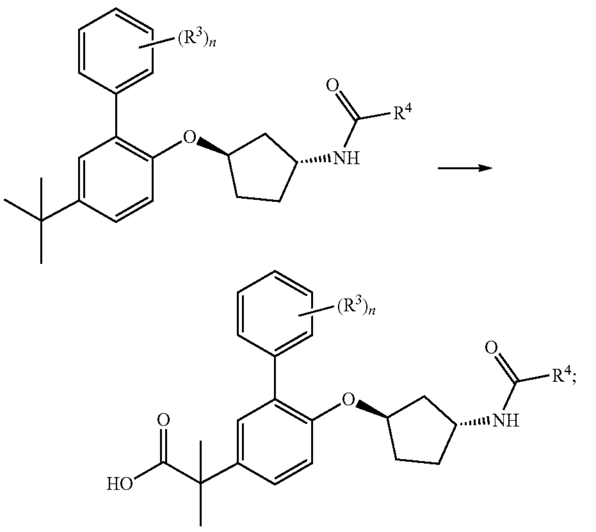

(ii) when a compound of the invention contains an alcohol functionality (—OH), an ester thereof, such as a compound wherein the hydrogen of the alcohol functionality of the compound is replaced by —CO($C_1$-$C_3$ alkyl) (e.g., methylcarbonyl) or the alcohol is esterified with an amino acid;

(iii) when a compound of the invention contains an alcohol functionality (—OH), an ether thereof, such as a compound wherein the hydrogen of the alcohol functionality of the compound is replaced by ($C_1$-$C_3$ alkyl)C(═O)$OCH_2$— or —$CH_2OP$(═O)$(OH)_2$;

(iv) when a compound of the invention contains an alcohol functionality (—OH), a phosphate thereof, such as a compound wherein the hydrogen of the alcohol functionality of the compound is replaced by —P(═O)$(OH)_2$ or —P(═O)$(O^-Na^+)_2$ or —P(═O)$(O^-)_2Ca^{2+}$;

(v) when a compound of the invention contains a primary or secondary amino functionality (—$NH_2$ or —NHR where R≠H), an amide thereof, for example, a compound wherein, as the case may be, one or both hydrogens of the amino functionality of the compound is/are replaced by ($C_1$-$C_{10}$)alkanoyl, —$COCH_2NH_2$ or the amino group is derivatized with an amino acid;

(vi) when a compound of the invention contains a primary or secondary amino functionality (—$NH_2$ or —NHR where R≠H), an amine thereof, for example, a compound wherein, as the case may be, one or both hydrogens of the amino functionality of the compound is/are replaced by —$CH_2OP(=O)(OH)_2$.

Certain compounds of the invention may themselves act as prodrugs of other compounds the invention It is also possible for two compounds of the invention to be joined together in the form of a prodrug. In certain circumstances, a prodrug of a compound of the invention may be created by internally linking two functional groups in a compound of the invention, for instance by forming a lactone.

Metabolites

Also included within the scope of the invention are active metabolites of compounds of the invention, that is, compounds formed in vivo upon administration of the drug, often by oxidation or dealkylation. Some examples of metabolites in accordance with the invention include, but are not limited to, (i) where the compound of the invention contains an alkyl group, a hydroxyalkyl derivative thereof (—CH→—COH):

(ii) where the compound of the invention contains an alkoxy group, a hydroxy derivative thereof (—OR→—OH);

(iii) where the compound of the invention contains a tertiary amino group, a secondary amino derivative thereof (—NRR'→—NHR or —NHR');

(iv) where the compound of the invention contains a secondary amino group, a primary derivative thereof (—NHR→—$NH_2$);

(v) where the compound of the invention contains a phenyl moiety, a phenol derivative thereof (-Ph→-PhOH);

(vi) where the compound of the invention contains an amide group, a carboxylic acid derivative thereof (—$CONH_2$→COOH); and (vii) where the compound contains a hydroxy or carboxylic acid group, the compound may be metabolized by conjugation, for example with glucuronic acid to form a glucuronide. Other routes of conjugative metabolism exist. These pathways are frequently known as Phase 2 metabolism and include, for example, sulfation or acetylation. Other functional groups, such as NH groups, may also be subject to conjugation.

Protein Degraders

Disclosed herein are bifunctional compounds comprising a targeting ligand (i.e., compound of the disclosure) linked to an E3 ligase ligand or a ligand known to interact with the ubiquitin proteasome system (UPS) through a linker. The bifunctional compounds of the disclosure have the general structure: [Degron]-[Linker]-[Targeting Ligand], wherein the linker is covalently bound to at least one degron and covalently bound to at least one targeting ligand, wherein the degron is a compound capable of binding to a ubiquitin ligase such as an E3 Ubiquitin Ligase (e.g., cereblon (CRBN), von Hippel-Lindau (VHL), etc.), and the targeting ligand or compound of the disclosure is capable of binding at the histone acetyltransferase domain of KAT2A and/or KAT2B. The bifunctional compounds of the disclosure can be used as therapeutics to treat a condition disclosed herein.

In one embodiment, a bifunctional compound of the disclosure has the formula:

[Degron]–[Linker]- [Compound of Formula (I)].

Deqron: The degron is a compound that is highly effective in recruiting a targeted protein to a ubiquitin ligase for proteosomal degradation. The degron recruits the targeted protein through the linker and the targeting ligand (i.e., compound of the disclosure). In some embodiments, the degron is a compound that can bind to a ubiquitin ligase. In one embodiment, the degron can bind to an E3 ubiquitin ligase, such as cereblon, wherein the degron is thalidomide, lenalidomide, pomalidomide, or iberdomide, or newer IMiDs CRBN ligands, or analogues thereof (e.g., WO2019/060693, WO2019/140387, WO2019/236483). In one embodiment, the degron can bind to an E3 ubiquitin ligase, such as von Hippel-Lindau ligand (e.g., WO2020/092907; WO2013106643; BUCKLEY, D. L., et al., "Targeting the von Hippel-Lindau E3 Ubiquitin Ligase Using Small Molecules to Disrupt the VHL/HIF-1a Interaction," Journal of the American Chemical Society, 2012, 134(10):4465-4468; SOARES, P., et al., "Group-Based Optimization of Potent and Cell-Active Inhibitors of the von Hippel-Lindau (VHL) E3 Ubiquitin Ligase: Structure-Activity Relationships Leading to the Chemical Probe (2S,4R)-1-((S)-2-(1-Cyanocyclopropanecarboxamido)-3,3-dimethylbutanoyl)-4-hydroxy-N-(4-(4-methylthiazol-5-yl)benzyl)pyrrolidine-2-carboxamide (VH298)," Journal of Medicinal Chemistry, 2018, 61(2): 599-618). In a further embodiment, the degron can bind to an E3 ubiquitin ligase, such as an inhibitor of apoptosis protein ligases (IAP1, IAP2, XIAP) (e.g., ITOH, Y., et al., "Protein knockdown using methyl bestatin-ligand hybrid molecules: design and synthesis of inducers of ubiquitination-mediated degradation of cellular retinoic acid-binding proteins," Journal of the American Chemical Society, 2010, 132(16):5820-5826; MARES, A., et al., "Extended pharmacodynamic responses observed upon PROTAC-mediated degradation of RIPK2," Communications Biology, 2020, 3:1-13; TINWORTH, C., et al., "PROTAC-Mediated Degradation of Bruton's Tyrosine Kinase Is Inhibited by Covalent Binding," ACS Chemical Biology, 2019, 14(3):342-347). In a further embodiment, the degron binds a ubiquitin proteasome protein that induces degradation, such as the Hsp70/90 chaperone complex (e.g., WO2020/207395), Usp14 (e.g., WO2019/238886), UchL5 (e.g., WO2019238816), and Rpn11 (e.g., WO2019/238817). In some embodiments, the degron is an amino acid moiety (e.g., ZHANG, J., et al., "Single amino acid-based PROTACs trigger degradation of the oncogenic kinase BCR-ABL in chronic myeloid leukemia (CML)," Journal of Biological Chemistry, 2023, 299(8):104994).

Linker: The Linker ("L") provides a covalent attachment between the Targeting Ligand and the Degron. The Linker has two terminating groups, wherein one terminating group attaches to the Degron and the other terminating group attaches to the Targeting Ligand, which is a compound of Formula (I). The structure of the Linker may not be critical, provided it does not substantially interfere with the activity of the Targeting Ligand or the Degron. The optimal Linker length and composition may vary by target and may be estimated based upon, for example, 1) X-ray structures of the original Targeting Ligand bound to its target; and/or 2) computational modeling of the protein target and the UPS protein. Linker length and composition can be also modified to modulate metabolic stability and pharmacokinetic (PK)

and pharmacodynamics (PD) parameters. In some embodiments, the Linker is designed and optimized based on SAR (structure-activity relationship) and X-ray crystallography of the Targeting Ligand with regard to the location of attachment for the Linker. In some embodiments, a target ligand can bind multiple protein targets, and selectivity of the bifunctional compounds disclosed herein can be achieved by varying the linker length such that the ligand can target a different binding pocket, e.g., deeper or shallower binding pockets than others.

In some embodiments, the Linker is a $C_{2-20}$ alkylene or a polyethylene glycol (PEG) chain. In other embodiments, the Linker may be an alkylene chain, a PEG chain, or a bivalent alkylene chain, each of which may be interrupted by or terminate with at least one of —O—, —S—, —$N(R^L)$—, —C=C—, —C(O)—, —C(O)O—, —OC(O)—, —OC(O)O—, — $C(NOR^L)$—, —$C(O)N(R^L)$—, —$C(O)N(R^L)C(O)$—, —$C(O)N(R^L)C(O)N(R^L)$—, —$N(R^L)C(O)$—, —$N(R^L)C(O)N(R^L)$—, —$N(R^L)C(O)O$—, —$OC(O)N(R^L)$—, —$C(NR^L)$—, —$N(R^L)C(NR^L)$—, —$C(NR^L)N(R^L)$—, —$N(R^L)C(NR^L)N(R^L)$—, —$OB(CH_3)O$—, —$S(O)_2$—, —OS(O)—, —S(O)O—, —S(O)—, —$OS(O)_2$—, —$S(O)_2O$—, —$N(R^L)S(O)_2$—, —$S(O)_2N(R^L)$—, —$N(R^L)S(O)$—, —$S(O)N(R^L)$—, —$N(R^L)S(O)_2N(R^L)$—, —$N(R^L)S(O)N(R^L)$—, $C_{3-12}$ carbocyclene, 3- to 12-membered heterocyclene, 5- to 12-membered heteroarylene, or arylene, or any combination thereof, wherein $R^L$ is H or $C_{1-6}$ alkyl. In one embodiment, In some embodiments, the Linker is $C_{1-10}$ alkylene-NH—, wherein the nitrogen is bound to the degron. In one embodiment, the Linker is $C_{1-10}$ alkylene or 1-8 PEG units that are interrupted by or terminate in —$(CH_2)_{n'}$—C(O)—NH—, where n' is 0, 1, 2, 3, 4, or 5.

Nonlimiting examples of a Linker include —$(CH_2CH_2$—$O)_n$—$(CH_2)_{n'}$—C(O)—, $(CH_2)_{n'}$—C(O)—$N(R^L)$—$(CH_2CH_2$—$O)_{n'}$—$(CH_2)_{n'}$—C(O)—, —$(CH_2CH_2$—$O)_{n'}$—$(CH_2)_{n'}$—$N(R^L)$—C(O)—, —$(CH_2CH_2$—$O)_{n'}$—$(CH_2)_{n'}$—C(O)—$N(R^L)$—, —$(CH_2)_{n'}$-phenylene-$N(R^L)$—C(O)—$(CH_2)_{n'}$—, —$N(R^L)$—$(CH_2)_{n'}$—O-phenylene-$(CH_2)_n$—$N(R^L)$—$(CH_2)_{n'}$—, —$(CH_2)_{n'}$—C(O)—$N(R^L)$-phenylene-C(O)—, —$N(R^L)$—$(CH_2)_{n'}$-phenylene-$(CH_2)_{n'}$-heterocyclylene-, —$(CH_2)_{n'}$-phenylene-$N(R^L)$—C(O)—$(CH_2CH_2$—$O)_n$—$(CH_2)_{n'}$—, —$(CH_2)_{n'}$-phenylene-$(CH_2)_n$-heterocyclylene-$(CH_2)_n$—C(O)—$N(R^L)$—$(CH_2)_{n'}$—, —$(CH_2)_{n'}$-phenylene-O—$(CH_2)_{n'}$-heterocyclylene-$(CH_2)_{n'}$—, —$(CH_2)_{n'}$-phenylene-$(CH_2)_{n'}$-heterocyclylene-$(CH_2)_{n'}$—O—, —$(CH_2)_{n'}$-heterocyclylene-$(CH_2)_{n'}$ wherein $R^L$ is H or $C_{1-6}$ alkyl; n' is 0, 1, 2, 3, 4, 5, 6, 7, 8, 9, or 10; and n" is 1, 2, 3, 4, 5, 6, 7, 8, 9, or 10.

Pharmaceutical Compositions

In another embodiment, the invention comprises pharmaceutical compositions. For pharmaceutical composition purposes, the compound per se or pharmaceutically acceptable salt thereof will simply be referred to as the compounds of the invention.

The compositions of this invention may be in a variety of forms. These include, for example, liquid, semi-solid and solid dosage forms, such as liquid solutions (e.g., injectable and infusible solutions), dispersions or suspensions, tablets, capsules, pills, powders, liposomes and suppositories. The form depends on the intended mode of administration and therapeutic application.

Typical compositions are in the form of injectable or infusible solutions, such as compositions similar to those used for passive immunization of humans with antibodies in general. One mode of administration is parenteral (e.g., intravenous, subcutaneous, intraperitoneal, intramuscular). In another embodiment, the compound is administered by intravenous infusion or injection. In yet another embodiment, the compound is administered by intramuscular or subcutaneous injection.

Oral administration of a solid dosage form may be, for example, presented in discrete units, such as hard or soft capsules, pills, cachets, lozenges, or tablets, each containing a predetermined amount of at least one compound of the invention. In another embodiment, the oral administration may be in a powder or granule form. In another embodiment, the oral dosage form is sub-lingual, such as, for example, a lozenge. In such solid dosage forms, the compounds of the invention are ordinarily combined with one or more adjuvants. Such capsules or tablets may comprise a controlled release formulation. In the case of capsules, tablets, and pills, the dosage forms also may comprise buffering agents or may be prepared with enteric coatings.

In another embodiment, oral administration may be in a liquid dosage form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as one or more of wetting, emulsifying, suspending, flavoring (e.g., sweetening), or perfuming agents.

In another embodiment, the invention comprises a parenteral dosage form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using one or more of suitable dispersing, wetting agents, or suspending agents.

In another embodiment, the invention comprises a topical dosage form. "Topical administration" includes, for example, dermal and transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical excipients include alcohol, water, mineral oil, liquid petrolatum, white petrolatum, glycerin, polyethylene glycol and propylene glycol. Penetration enhancers may be incorporated—see, for example, FINNIN, B. C. and MORGAN, T. M., "Transdermal penetration enhancers: Applications, limitations, and potential," Journal of Pharmaceutical Sciences, 1999, 88(10):955-958.

Formulations suitable for topical administration to the eye include, for example, eye drops wherein the compound of this invention is dissolved or suspended in a suitable excipient. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration, the compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the invention comprises a rectal dosage form. Such rectal dosage form may be in the form of, for example, a suppository. Cocoa butter is a traditional suppository base, but various alternatives may be used as appropriate.

Other excipients and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, ALLEN, L. V. and ANSEL, H. C. Ansel's Pharmaceutical Dosage Forms and Drug Delivery Systems. $10^{th}$ Ed. Philadelphia, Lippincott Williams & Wilkins, 2014; ADEJARE, A. Remington: The Science and Practice of Pharmacy. $23^{rd}$ Ed. Philadelphia, Lippincott Williams & Wilkins, 2000; ROWE, R. C., et al., Handbook of Pharmaceutical Excipients. $5^{th}$ Ed. Chicago, Pharmaceutical Press, 2006; STAHL, P. H. and WERMUTH, C. G., Pharmaceutical Salts: Properties, Selection, and Use. $2^{nd}$ Revised Ed. New York, Wiley-VCH, 2011; and BRITTAIN, H. G. Polymorphism in Pharmaceutical Solids. $2^{nd}$ Ed. CRC Press, 2009.

Acceptable excipients are nontoxic to subjects at the dosages and concentrations employed, and may comprise one or more of the following: 1) buffers such as phosphate, citrate, or other organic acids; 2) salts such as sodium chloride; 3) antioxidants such as ascorbic acid or methionine; 4) preservatives such as octadecyldimethylbenzyl ammonium chloride, hexamethonium chloride, benzalkonium chloride, benzethonium chloride, phenol, butyl or benzyl alcohol; 5) alkyl parabens such as methyl or propyl paraben, catechol, resorcinol, cyclohexanol, 3-pentanol, or m-cresol; 6) low molecular weight (less than about 10 residues) polypeptides; 7) proteins such as serum albumin, gelatin, or immunoglobulins; 8) hydrophilic polymers such as polyvinylpyrrolidone; 9) amino acids such as glycine, glutamine, asparagine, histidine, arginine, or lysine; 10) monosaccharides, disaccharides, or other carbohydrates including glucose, mannose, or dextrins; 11) chelating agents such as EDTA; 12) sugars such as sucrose, mannitol, trehalose or sorbitol; 13) salt-forming counter-ions such as sodium, metal complexes (e.g., Zn-protein complexes), or 14) non-ionic surfactants such as polysorbates (e.g., polysorbate 20 or polysorbate 80), poloxamers or polyethylene glycol (PEG).

For oral administration, the compositions may be provided in the form of tablets or capsules containing 0.01, 0.05, 0.1, 0.5, 1.0, 2.5, 5.0, 10.0, 15.0, 25.0, 50.0, 75.0, 100, 125, 150, 175, 200, 250 or 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Dosing regimens may depend on the route of administration, dose scheduling, and use of flat-dose, body surface area or weight-based dosing. For example, for weight-based dosing, intravenously doses may range from about 0.01 to about 10 mg/kg/minute during a constant rate infusion.

Liposome containing compounds of the invention may be prepared by methods known in the art (See, for example, CHANG, H. I. and YEH, M. K., "Clinical development of liposome-based drugs: formulation, characterization, and therapeutic efficacy," International Journal of Nanomedicine, 2012, 7:49-60). Particularly useful liposomes may be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

Compounds of the invention may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in ADEJARE, A. Remington: The Science and Practice of Pharmacy. $23^{rd}$ Ed. Philadelphia, Lippincott Williams & Wilkins, 2000.

Sustained-release preparations may be used. Suitable examples of sustained-release preparations include semipermeable matrices of solid hydrophobic polymers containing a compound of the invention, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides, copolymers of L-glutamic acid and 7 ethyl-L-glutamate, non-degradable ethylene-vinyl acetate, degradable lactic acid-glycolic acid copolymers such as those used in leuprolide acetate for depot suspension (injectable microspheres composed of lactic acid-glycolic acid copolymer and leuprolide acetate), sucrose acetate isobutyrate, and poly-D-(−)-3-hydroxybutyric acid.

The formulations to be used for intravenous administration must be sterile. This is readily accomplished by, for example, filtration through sterile filtration membranes. Compounds of the invention are generally placed into a container having a sterile access port, for example, an intravenous solution bag or vial having a stopper pierceable by a hypodermic injection needle.

Suitable emulsions may be prepared using commercially available fat emulsions, such as a lipid emulsions comprising soybean oil, a fat emulsion for intravenous administration (e.g., comprising safflower oil, soybean oil, egg phosphatides and glycerin in water), emulsions containing soya bean oil and medium-chain triglycerides, and lipid emulsions of cottonseed oil. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion may comprise fat droplets between 0.1 and 1.0 μm, particularly 0.1 and 0.5 μm, and have a pH in the range of 5.5 to 8.0.

For example, the emulsion compositions may be those prepared by mixing a compound of the invention with a lipid emulsions comprising soybean oil or the components thereof (soybean oil, egg phospholipids, glycerol and water).

Compositions for inhalation or insufflation include solutions and suspensions in pharmaceutically acceptable aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

A drug product intermediate (DPI) is a partly processed material that must undergo further processing steps before it becomes bulk drug product. Compounds of the invention may be formulated into drug product intermediate DPI containing the active ingredient in a higher free energy form than the crystalline form. One reason to use a DPI is to improve oral absorption characteristics due to low solubility, slow dissolution, improved mass transport through the mucus layer adjacent to the epithelial cells, and in some cases, limitations due to biological barriers such as metabolism and transporters. Other reasons may include improved solid state stability and downstream manufacturability. In one embodiment, the drug product intermediate contains a compound of the invention isolated and stabilized in the amorphous state (for example, amorphous solid dispersions (ASDs)). There are many techniques known in the art to manufacture ASD's that produce material suitable for integration into a bulk drug product, for example, spray dried dispersions (SDD's), melt extrudates (often referred to as HME's), co-precipitates, amorphous drug nanoparticles, and nano-adsorbates. In one embodiment amorphous solid dispersions comprise a compound of the invention and a polymer excipient. Other excipients as well as concentrations of said excipients and the compound of the invention are well known in the art and are described in standard textbooks. See, for example, SHAH, N., et al., Amorphous Solid Dispersions: Theory and Practice. New York, Springer, 2014.

Administration and Dosing

Typically, a compound of the invention is administered in an amount effective to treat a condition as described herein. The compounds of the invention may be administered as compound per se, or alternatively, as a pharmaceutically acceptable salt. For administration and dosing purposes, the compound per se or pharmaceutically acceptable salt thereof will simply be referred to as the compounds of the invention.

The compounds of the invention are administered by any suitable route in the form of a pharmaceutical composition adapted to such a route, and in a dose effective for the treatment intended. The compounds of the invention may be administered orally, rectally, vaginally, parenterally, topically, intranasally, or by inhalation.

The compounds of the invention may be administered orally. Oral administration may involve swallowing, so that the compound enters the gastrointestinal tract, or buccal or sublingual administration may be employed by which the compound enters the bloodstream directly from the mouth.

In another embodiment, the compounds of the invention may also be administered parenterally, for example directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors, and infusion techniques.

In another embodiment, the compounds of the invention may also be administered topically to the skin or mucosa, that is, dermally or transdermally. In another embodiment, the compounds of the invention may also be administered intranasally or by inhalation. In another embodiment, the compounds of the invention may be administered rectally or vaginally. In another embodiment, the compounds of the invention may also be administered directly to the eye or ear.

The dosage regimen for the compounds of the invention or compositions containing said compounds is based on a variety of factors, including the type, age, weight, sex and medical condition of the patient; the severity of the condition; the route of administration; and the activity of the particular compound employed. Thus, the dosage regimen may vary widely. In one embodiment, the total daily dose of a compound of the invention is typically from about 0.01 to about 100 mg/kg (i.e., mg compound of the invention per kg body weight) for the treatment of the indicated conditions discussed herein. In another embodiment, total daily dose of the compound of the invention is from about 0.1 to about 50 mg/kg, and in another embodiment, from about 0.5 to about 30 mg/kg. It is not uncommon that the administration of the compounds of the invention will be repeated a plurality of times in a day (typically no greater than 4 times). Multiple doses per day typically may be used to increase the total daily dose, if desired.

Therapeutic Methods and Uses

The compounds of the invention act as inhibitors of KAT2A and/or KAT2B, and may be useful in the treatment, prevention, suppression, and amelioration of diseases such as cancers, disorders and conditions mediated by KAT2A and KAT2B, or a combination thereof.

"Cancer" as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; (5) benign and malignant cells of other proliferative diseases in which aberrant serine/threonine kinase activation occurs; (6) any tumors that proliferate by aberrant signaling, metabolic, epigenetic and transcriptional mechanism; and (7) benign and malignant cells of other proliferative diseases in which aberrant signaling, metabolic, epigenetic and transcriptional mechanism occur.

For convenience, certain well-known abbreviations, may be used herein, including: estrogen receptor positive (ER+), human epidermal growth factor receptor 2 negative (HER2-), non-small cell lung cancer (NSCLC), small cell lung cancer (SCLC), and castration resistant prostate cancer (CRPC).

Additional embodiments relate to methods of treating cancer in a subject in need thereof comprising administering to the subject an amount of a compound described herein that is effective in treating cancer.

In another embodiment, the cancer is selected from the group consisting of lung cancer, mesothelioma, bone cancer, pancreatic cancer, skin cancer, cancer of the head or neck, cutaneous or intraocular melanoma, uterine cancer, ovarian cancer, rectal cancer, cancer of the anal region, stomach cancer, hepatic carcinoma, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, hematology malignancy, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, glioblastoma, brain stem glioma, and pituitary adenoma, or a combination of two or more of the foregoing cancers.

In another embodiment, the cancer is breast, lung, colon, brain, prostate, stomach, pancreatic, ovarian, melanoma, endocrine, uterine, testicular, or bladder.

In another embodiment, the cancer is breast, lung, prostate, pancreatic, or ovarian.

In another embodiment, the cancer is breast cancer.

In another embodiment, the breast cancer is ER+ breast cancer.

In another embodiment, the breast cancer is ER+ HER2− breast cancer.

In another embodiment, the breast cancer is locally advanced or metastatic ER+ HER2− breast cancer.

In another embodiment, the lung cancer is non-small cell lung cancer (NSCLC). In certain embodiments, the lung cancer is small cell lung cancer (SCLC).

In another embodiment, the lung cancer is locally advanced or metastatic NSCLC or locally advanced or metastatic SCLC.

In another embodiment, the prostate cancer is castration resistant prostate cancer. In certain embodiments the prostate cancer is neuroendocrine prostate cancer (NEPC).

In another embodiment, the prostate cancer is locally advanced or metastatic castration resistant prostate cancer.

In another embodiment, the cancer is colon cancer.

Additional embodiments relate to methods of treating hematologic tumors in a subject.

Some embodiments relate to the treatment of hematologic tumors in a subject in need thereof comprising administering to the subject an amount of a compound described herein that is effective in treating the hematologic tumor.

In another embodiment, the hematologic tumor is leukemia, lymphoma or multiple myeloma. In certain embodiments, the hematologic tumor is acute myeloid leukemia.

In another embodiment, the hematologic tumor is multiple myeloma.

In another embodiment, the cancer is multiple myeloma, breast cancer, or prostate cancer. In another embodiment, the cancer is multiple myeloma.

Further embodiments relate to methods of treating cancer in a patient which comprises administering to the patient an amount of a compound described herein that is effective in treating cancer in combination with an anti-tumor agent selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

More embodiments relate to pharmaceutical compositions for treating cancer in a patient comprising an amount of a compound described herein that is effective in treating cancer, and a pharmaceutically acceptable carrier.

Yet more embodiments relate to a method of treating a disorder associated with angiogenesis in a patient, including a human, comprising administering to said patient an amount of a compound described herein, as defined above, or a pharmaceutically acceptable salt, solvate, hydrate or prodrug thereof, that is effective in treating said disorder in combination with one or more anti-tumor agents listed above. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi, Yersinia* spp., *Bordetella pertussis*, and group A *Streptococcus.*

Some embodiments relate to a method of (and to a pharmaceutical composition for) treating cancer in a patient which comprise an amount of a compound described herein, or a pharmaceutically acceptable salt, solvate, or hydrate thereof, in combination with an amount of one or more substances selected from anti-angiogenesis agents, signal transduction inhibitors (e.g., inhibiting the means by which regulatory molecules that govern the fundamental processes of cell growth, differentiation, and survival communicated within the cell), and antiproliferative agents, which amounts are together effective in treating said abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound described herein in the methods and pharmaceutical compositions described herein.

Tyrosine kinase inhibitors can also be combined with a compound described herein.

VEGF inhibitors, for example, sutent and axitinib, can also be combined with a compound described herein.

ErbB2 receptor inhibitors may be administered in combination with a compound described herein. Various other compounds, such as styrene derivatives, have also been shown to possess tyrosine kinase inhibitory properties, and some of tyrosine kinase inhibitors have been identified as erbB2 receptor inhibitors.

Epidermal growth factor receptor (EGFR) inhibitors may be administered in combination with a compound of the present invention.

PI3K inhibitors, such as PI3K alpha or PI3K beta inhibitors, may be administered in combination with a compound of the present invention.

Mammalian target of rapamycin (mTOR) inhibitors may be administered in combination with a compound of the present invention.

c-Met inhibitors may be administered in combination with a compound of the present invention.

CDK inhibitors may be administered in combination with a compound of the present invention.

MEK inhibitors may be administered in combination with a compound of the present invention.

PARP inhibitors may be administered in combination with a compound of the present invention.

JAK inhibitors may be administered in combination with a compound of the present invention.

An antagonist of a Programmed Death 1 protein (PD-1) may be administered in combination with a compound of the present invention.

An antagonist of Programmed Death-Ligand 1 (PD-L1) may be administered in combination with a compound of the present invention.

Other antiproliferative agents that may be used with the compounds described herein include inhibitors of the enzyme farnesyl protein transferase and inhibitors of the receptor tyrosine kinase PDGFr.

A compound described herein may also be used with other agents useful in treating abnormal cell growth or cancer, including, but not limited to, agents capable of enhancing antitumor immune responses, such as CTLA4 (cytotoxic lymphocyte antigen 4) antibodies and other agents capable of blocking CTLA4, and bispecific antibodies capable of binding to CD3 on T-cells and to B-cell maturation antigen (BCMA) on the surface of myeloma cells (e.g., Elranatamab); and anti-proliferative agents such as other farnesyl protein transferase inhibitors, for example the farnesyl protein transferase.

A compound described herein may be applied as a sole therapy or may involve one or more other anti-tumor substances, for example those selected from, for example, mitotic inhibitors, alkylating agents, anti-metabolites, growth factor inhibitors, cell cycle inhibitors, intercalating antibiotics, enzymes, and anti-hormones.

The compounds described herein may be used alone or in combination with one or more of a variety of anti-cancer agents or supportive care agents. For example, the compounds described herein may be used with cytotoxic agents. Some embodiments also contemplate the use of the compounds described herein together with hormonal therapy. Further, some embodiments provide a compound described herein alone or in combination with one or more supportive care products, e.g., a product selected from the group consisting of Filgrastim (Neupogen), ondansetron (Zofran), Fragmin, Procrit, Aloxi, Emend, or combinations thereof. Such conjoint treatment may be achieved by way of the simultaneous, sequential or separate dosing of the individual components of the treatment.

The compounds described herein may be used with antitumor agents, alkylating agents, antimetabolites, antibiotics, plant-derived antitumor agents, camptothecin derivatives, tyrosine kinase inhibitors, antibodies, interferons, and/or biological response modifiers. In this regard, the following is a non-limiting list of examples of secondary agents that may be used with the compounds described herein.

Co-Administration

The compounds of the invention may be used alone, or in combination with one or more other therapeutic agents. The invention provides any of the uses, methods or compositions as defined herein wherein the compound of the invention, or pharmaceutically acceptable salt thereof, is used in combination with one or more other therapeutic agent discussed herein.

The administration of two or more compounds "in combination" means that all of the compounds are administered closely enough in time to affect treatment of the subject. The two or more compounds may be administered simultaneously or sequentially, via the same or different routes of administration, on same or different administration schedules and with or without specific time limits depending on the treatment regimen. Additionally, simultaneous administration may be carried out by mixing the compounds prior to administration or by administering the compounds at the same point in time but as separate dosage forms at the same or different site of administration. Examples of "in combination" include, but are not limited to, "concurrent administration," "co-administration," "simultaneous administration," "sequential administration" and "administered simultaneously".

A compound of the invention and the one or more other therapeutic agents may be administered as a fixed or non-fixed combination of the active ingredients. The term "fixed combination" means a compound of the invention, or a pharmaceutically acceptable salt thereof, and the one or more therapeutic agents, are both administered to a subject simultaneously in a single composition or dosage. The term "non-fixed combination" means that a compound of the invention, or a pharmaceutically acceptable salt thereof, and the one or more therapeutic agents are formulated as separate compositions or dosages such that they may be administered to a subject in need thereof simultaneously or at different times with variable intervening time limits, wherein such administration provides effective levels of the two or more compounds in the body of the subject.

These agents and compounds of the invention may be combined with pharmaceutically acceptable vehicles such as saline, Ringer's solution, dextrose solution, and the like. The particular dosage regimen, i.e., dose, timing and repetition, will depend on the particular individual and that individual's medical history.

Kits

Another aspect of the invention provides kits comprising the compound of the invention or pharmaceutical compositions comprising the compound of the invention. A kit may include, in addition to the compound of the invention or pharmaceutical composition thereof, diagnostic or therapeutic agents. A kit may also include instructions for use in a diagnostic or therapeutic method. In some embodiments, the kit includes the compound or a pharmaceutical composition thereof and a diagnostic agent. In other embodiments, the kit includes the compound or a pharmaceutical composition thereof and one or more therapeutic agents, such as anticancer therapeutic agents.

In yet another embodiment, the invention comprises kits that are suitable for use in performing the methods of treatment described herein. In one embodiment, the kit contains a first dosage form comprising one or more of the compounds of the invention in quantities sufficient to carry out the methods of the invention. In another embodiment, the kit comprises one or more compounds of the invention in quantities sufficient to carry out the methods of the invention and a container for the dosage and a container for the dosage.

Synthetic Methods

Compounds of the present disclosure may be synthesized by routes that include processes analogous to those well-known in the chemical arts, particularly in light of the description contained herein. The starting materials are generally available from commercial sources or may be prepared using methods well known to those skilled in the art. Many of the compounds used herein, are related to, or may be derived from, compounds in which one or more of the scientific interest or commercial need has occurred. Accordingly, such compounds may be one or more of 1) commercially available; 2) reported in the literature or 3) prepared from other commonly available substances by one skilled in the art using materials which have been reported in the literature.

For illustrative purposes, the reaction schemes depicted below provide potential routes for synthesizing the compounds of the present disclosure as well as key intermediates. For a more detailed description of the individual reaction steps, see the Examples section below. Those skilled in the art will appreciate that other synthetic routes may be used to synthesize the inventive compounds. Although specific starting materials and reagents are discussed below, other starting materials and reagents may be substituted to provide one or more of a variety of derivatives or reaction conditions. In addition, many of the compounds prepared by the methods described below may be further modified in light of this disclosure using conventional chemistry well known to those skilled in the art.

The skilled person will appreciate that the experimental conditions set forth in the schemes that follow are illustrative of suitable conditions for effecting the transformations shown, and that it may be necessary or desirable to vary the precise conditions employed for the preparation of compounds of the disclosure. It will be further appreciated that it may be necessary or desirable to carry out the transformations in a different order from that described in the schemes, or to modify one or more of the transformations to provide the desired compound of the disclosure.

In the preparation of compounds of the disclosure it is noted that some of the preparation methods useful for the preparation of the compounds described herein may require protection of remote functionality (e.g., a primary amine, secondary amine, carboxyl, etc. in a precursor of a compound of the disclosure). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see SMITH, M. B., March's Advanced Organic Chemistry: Reactions, Mechanisms, and Structure. $8^{th}$ Ed. New Jersey, Wiley, 2019.

For example, if a compound contains an amine or carboxylic acid functionality, such functionality may interfere with reactions at other sites of the molecule if left unprotected. Accordingly, such functionalities may be protected by an appropriate protecting group (PG) which may be removed in a subsequent step. Suitable protecting groups for amine and carboxylic acid protection include those protecting groups commonly used in peptide synthesis (such as N-t-butoxycarbonyl (Boc), benzyloxycarbonyl (Cbz), and 9-fluorenylmethylenoxycarbonyl (Fmoc) for amines and lower alkyl or benzyl esters for carboxylic acids) which are generally not chemically reactive under the reaction conditions described and may typically be removed without chemically altering other functionality in a compound of the disclosure.

General Experimental Details $^{1}H$ and $^{19}F$ Nuclear Magnetic Resonance (NMR) spectra were recorded on Bruker XWIN-NMR (400 or 700 MHz) spectrometer. $^{1}H$ and $^{19}F$ resonances are reported in parts per million (ppm) downfield from tetramethylsilane. $^{1}H$ NMR data are reported as multiplicity (e.g., s, singlet; d, doublet; t, triplet; q, quartet; quint, quintuplet; dd, doublet of doublets; dt, doublet of triplets; br s, broad singlet; m, multiplet). For spectra obtained in $CDCl_3$, DMSO-$d_6$, and $CD_3OD$, the residual protons (7.27, 2.50, and 3.31 ppm, respectively) were used as the internal reference. All observed coupling constants, J, are reported in Hertz (Hz). "δ" means chemical shift. Exchangeable protons are not always observed.

Optical rotations were determined on a Jasco P-2000 or a Rudolph Autopol IV polarimeter. All final compounds were purified to ≥95% purity, unless otherwise specified. When absolute stereochemistry is known, (R,S) labels are used. When absolute stereochemistry is not known, the software-generated names are modified to include the symbol (ξ) indicating one single isomer with unknown stereochemistry, and the chemical structures are modified to include "or 1" at the chiral center where the stereochemistry is not known. In cases where there are atropisomers and absolute stereochemistry is not known, the software-generated names are modified to include the symbol (ψ) indicating one single isomer with unknown stereochemistry.

Mass spectra, MS (m/z), were recorded using either electrospray ionization (ESI) or atmospheric pressure chemical ionization (APCI). Where relevant and unless otherwise stated, the m/z data provided are for isotopes $^{19}F$, $^{35}Cl$, $^{79}Br$ and $^{127}I$.

The compounds and intermediates described below were named using the naming convention provided with ACD/Labs 2022.2.0, File Version N25E41, Build 131856, 30 Jan. 2025, and ACD/Labs 2023.2.0, File Version C45H41, Build 137017, 18 Jan. 2024 (Advanced Chemistry Development, 8 King Street East, Suite 107, Toronto, Ontario, M5C 1B5, Canada). The naming convention provided with ACD/Labs 2022.2.0 and ACD/Labs 2023.2.0 is well known by those skilled in the art and it is believed that the naming convention provided with ACD/Labs 2022.2.0 and ACD/Labs 2023.2.0 generally comports with the IUPAC (International Union for Pure and Applied Chemistry) recommendations on Nomenclature of Organic Chemistry and the CAS Index rules. Unless noted otherwise, all reactants were obtained commercially without further purifications or were prepared using methods known in the literature.

Abbreviations

In the non-limiting Examples and Preparations that illustrate the invention and that are set out in the description, and in the following Schemes, the following the abbreviations, definitions and analytical procedures may be referred to: "ACN" means acetonitrile, "AIBN" means azobisisbutyronitrile, "APCI" means atmospheric pressure chemical ionization, "aq" means aqueous, "atm" means atmosphere(s), "$BBr_3$" means boranetribromide "BOC", "Boc," or "boc" means N-tert-butoxycarbonyl, "$Boc_2O$" means di-tert-butyl dicarbonate, "B(pin)" means pinacolato boron ($(CH_3)_4C_2O_2B$—), "$B_2Pin_2$" means Bis(pinacolato) diborane, "br" means broad signal, "Bn" means benzyl, "Bu" means butyl, "nBu" means normal-butyl, "tBu" means tert-butyl, "KO$^t$Bu" means potassium tert-butoxide, "c"

means concentration, "° C." means degrees Celsius, "$CDCl_3$" means deuterated chloroform, "$CO_2$" means carbon dioxide, "$Cs_2CO_3$" means cesium carbonate, "d" means doublet, "DBU" means 1,8-diazabicyclo 5.4.0 undec-7-ene, "DCE" means dichloroethane, "DCM" ($CH_2Cl_2$) means methylene chloride, "dd" means doublet of doublets", "de" means diastereomeric excess, "DEA" means diethylamine, "DIAD" means diisopropyl azodicarboxylate, "DIPEA" and "DIEA" means diisopropyl ethyl amine, "DMAP" means 4-(dimethylamino)pyridine, "DME" means 1,2-dimethoxyethane, "DMSO-$d_6$" means deuterated dimethylsulfoxide, "DMF" means N,N-dimethyl formamide, "DMSO" means dimethylsulfoxide, "dt" means doublet of triplets, "EA" or "EtOAc" means ethyl acetate, "EDCI" means 1-ethyl-3-(3-dimethylaminopropyl)carbodiimide, "ESI" means electrospray ionization, "ee" means enantiomeric excess, "equiv" means equivalent, "Et" means ethyl, "EtOH" means ethanol, "g" means gram, "h" means hour, "HATU" means 1-[Bis(dimethylamino)methylene]-1H-1,2,3-triazolo[4,5-b]pyridinium 3-oxid hexafluorophosphate, "HCl" means hydrochloric acid, "HOAc" or "AcOH" means acetic acid, "$^1H$ NMR[11] means proton nuclear magnetic resonance, "$H_2O$" means water, "HPLC" means high pressure liquid chromatography, "i-Pr" or "$^i$Pr" means isopropyl, "IPA" means isopropyl alcohol, "$K_2CO_3$" means potassium carbonate, "KOAc" means potassium acetate, "KOH" means potassium hydroxide, "L" means liter, "LAH" means lithium aluminium hydride, "LCMS" means liquid chromatography mass spectrometry, "LDA" means lithium diisopropylamide, "LiHMDS" means lithium hexamethyldisilazide (lithium bis(trimethylsilyl)amide), "LiOH" means lithium hydroxide, "m" means multiplet, "M" means molar, "Me" means methyl, "MeCN" means acetonitrile, "MeOH" means methanol, "mg" means milligram, "$MgSO_4$" means magnesium sulfate, "MHz" means mega Hertz, "mL" means milliliter, "min" means minute, "mm" means millimeter, "mmol" means millimole, "MS" means mass spectrometry, "MTBE" means methyl tert-butyl ether, "N" means normal, "$NaHCO_3$" means sodium bicarbonate, "$Na_2SO_4$" means sodium sulfate, "NBS" means N-bromosuccinimide, "N/D" means not determined, "$NH_3$" means ammonia, "$NH_4Cl$" means ammonium chloride, "NIS" means N-iodosuccinimde, "NMI" means 1-methylimidazole, "$PdCl_2$(dppf)" means [1,1'-Bis(diphenylphosphino)ferrocene]dichloropalladium(II), "PE" means petroleum ether, "Ph" means phenyl, "ppm" means parts per million, "PTSA" means p-toluenesulfonic acid monohydrate, "q" means quartet, "quint" means quintet, "RT" means room temperature "s" means singlet, "sat." means saturated, "$SiO_2$" means silica, "sxt" means sextuplet, "t" means triplet, "TBAF" means tetrabutylammonium fluoride, TBME" means tert-Butyl methyl ether, "TCFH" means chloro-N,N,N',N'-tetramethylformamidinium hexafluorophosphate, "td" means triplet of doublets, "TEA" means triethyl amine, "TFA" means trifluoroacetic acid, "THF" means tetrahydrofuran, "TMSCN" means trimethylsilyl cyanide, "SFC" means supercritical fluid chromatography, "TLC" means thin layer chromatography, "Rf" means retention factor, "~" means approximately, "rt" means retention time, "uL" means microliter, "um" means micrometer.

The schemes described below are intended to provide a general description of the methodology employed in the preparation of the compounds of the present disclosure. Some of the compounds of the present disclosure contain a single chiral center. In the following schemes, the general methods for the preparation of the compounds are shown either in racemic or enantioenriched form. It will be apparent to one skilled in the art that each of the synthetic transformations may be conducted in a precisely similar manner whether the materials are enantioenriched or racemic. Moreover, the resolution to the desired optically active material may take place at any desired point in the sequence using well known methods such as described herein and in the chemistry literature.

General Methods:

Unless stated otherwise, the variables in Schemes I-XII have the same meanings as defined herein.

Scheme 1: General Method A

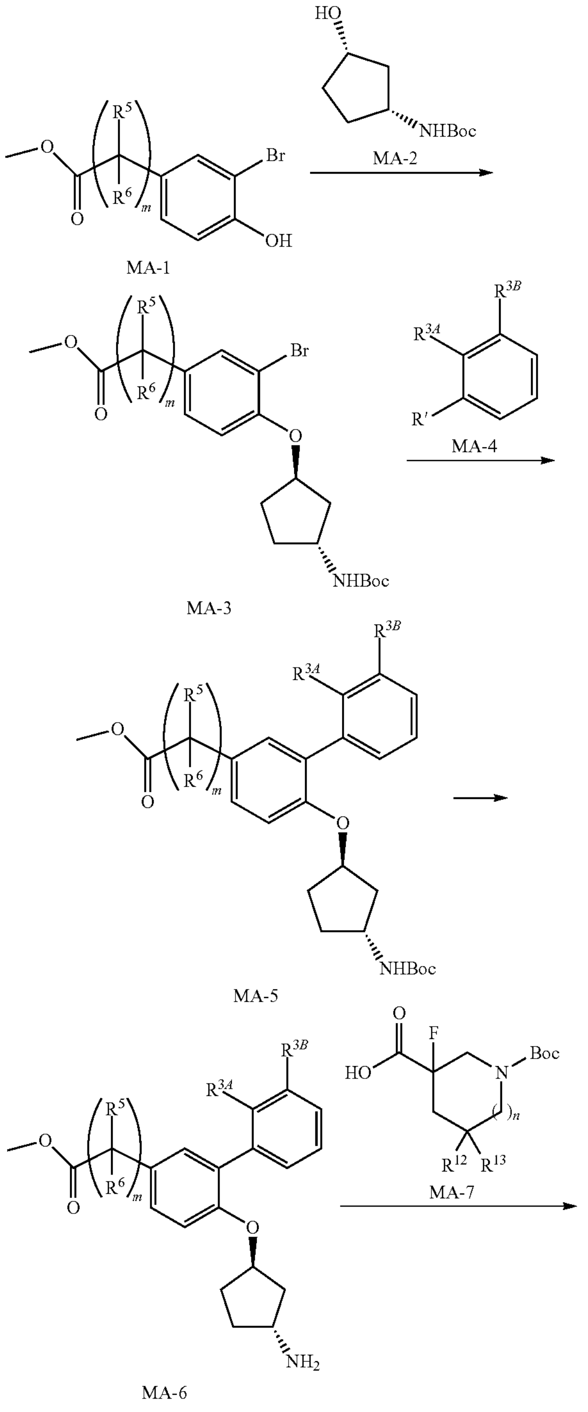

MA-1

MA-2

MA-3

MA-4

MA-5

MA-6

MA-7

-continued

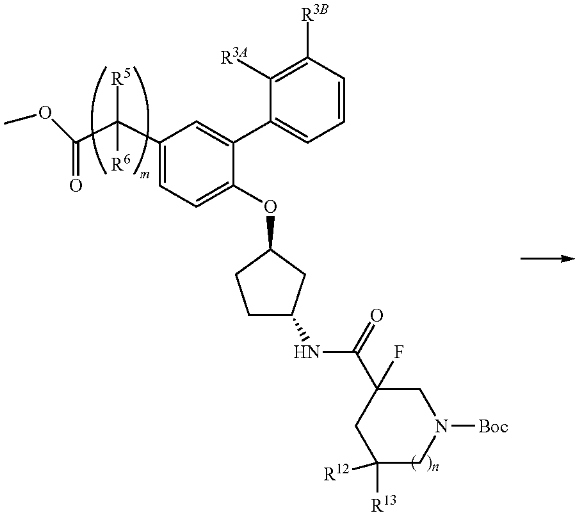

MA-8

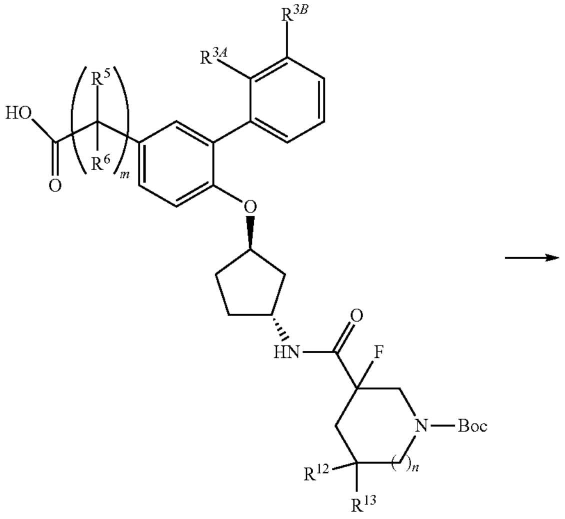

MA-9

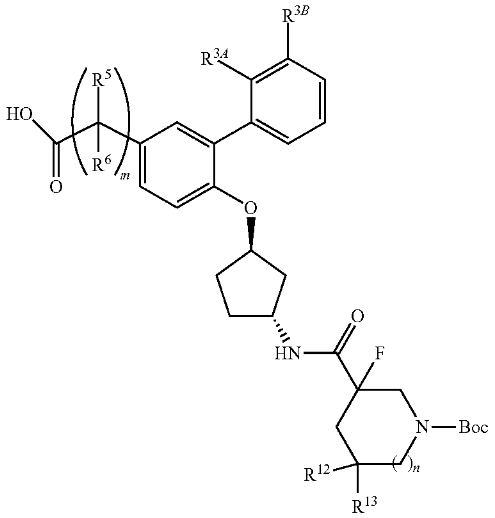

Formula A

-continued

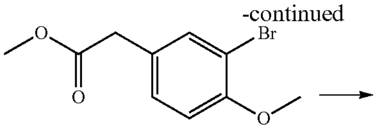

MA-10

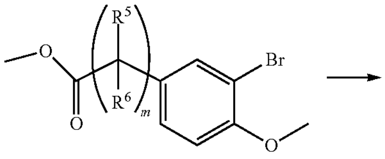

MA-11

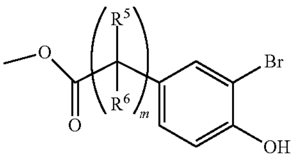

MA-1

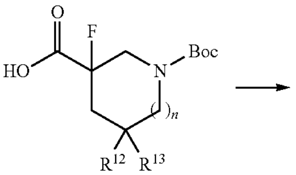

MA-12

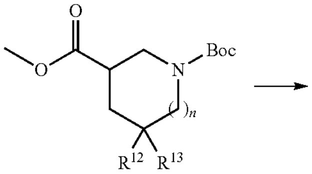

MA-13

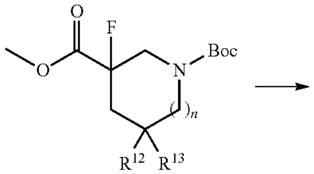

MA-14

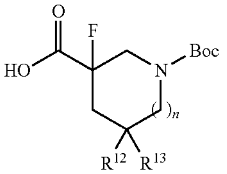

MA-7

General Method A refers to a synthetic sequence for preparing compounds of Formula A, as depicted above. Mitsunobu reaction between phenol MA-1 and commercially available amino alcohol MA-2 provides ether MA-3. Suzuki coupling with boronate or boronic ester MA-4 (where R' is $(HO)_2B$— or $(CH_3)_4C_2O_2B$— (i.e., pinacolato boron "B(pin)")) under standard cross-coupling conditions gives MA-5. Deprotection of the amine under acidic conditions gives amine MA-6. Amide coupling between amine MA-6 and acid MA-7 (n=0 or 1) affords amide MA-8. Ester hydrolysis of the ester group to give MA-9 followed by deprotection of protecting groups (Boc) using conditions known in the art provides acid Formula A.

In cases where MA-1 is not commercially available ($R^5$ and $R^6$ are not H and m is not 0), MA-1 is synthesized via a two-step procedure from bromide MA-10 involving alkylation and demethylation to give MA-1.

Acid MA-7 (n=0 or 1) is formed via a 3-step procedure depicted above. Acid MA-12 is converted to ester MA-13 following standard esterification conditions. α-Deprotonation followed by fluorination installs the fluoro-group on MA-14. Finally, hydrolysis of ester MA-14 gives acid MA-7.

Scheme II: General Method B

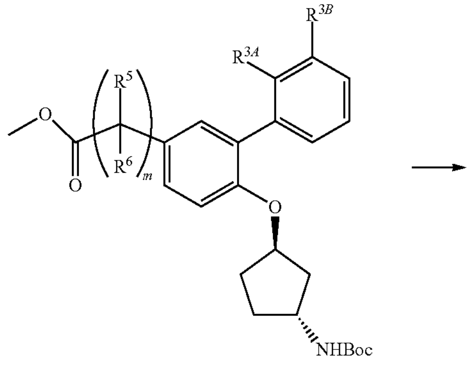

MA-5

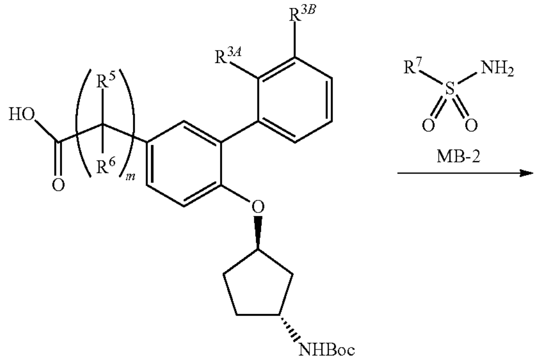

MB-1

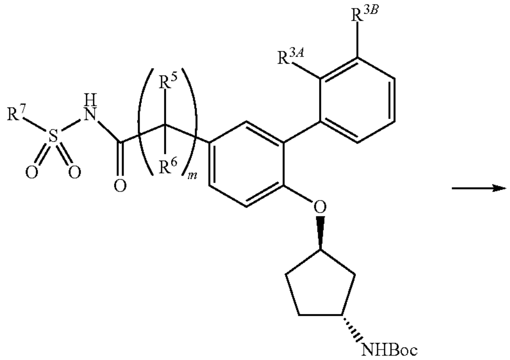

MB-3

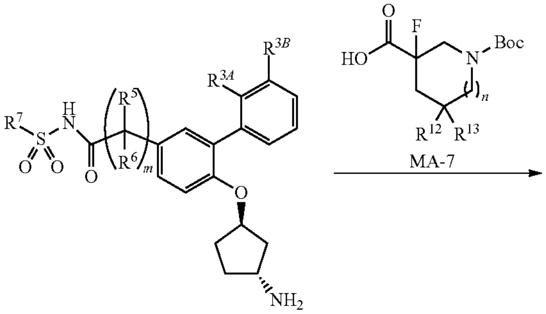

MB-4

-continued

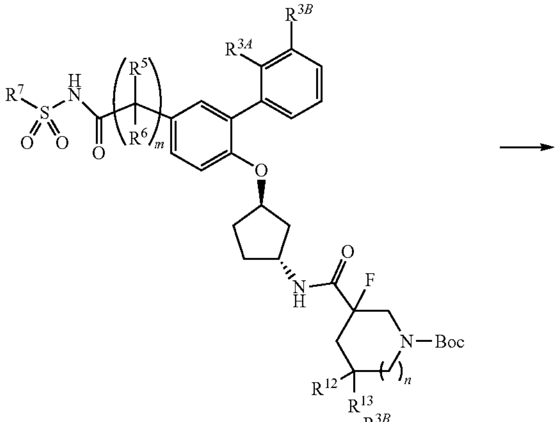

MB-5

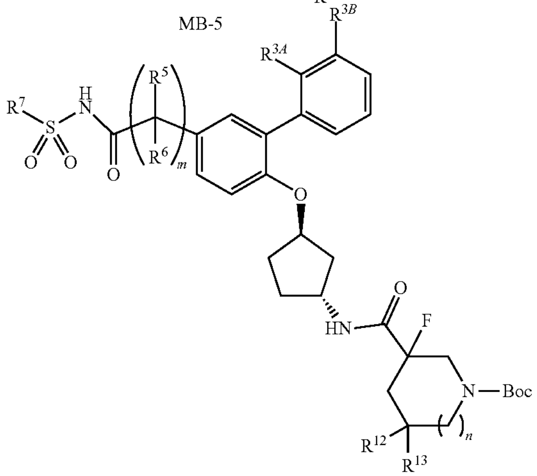

Formula B

General Method B refers to a synthetic sequence for preparing compounds of Formula B, as depicted above. Hydrolysis of ester MA-5 yields acid MB-1. Coupling of acid MB-1 with MB-2 under standard conditions gives MB-3. Deprotection of the amine under acidic conditions gives amine MB-4. Amide coupling between amine MB-4 and acid MA-7 affords amide MB-5. Deprotection of protecting groups (Boc) using conditions known in the art provides Formula B.

Scheme III: General Method C

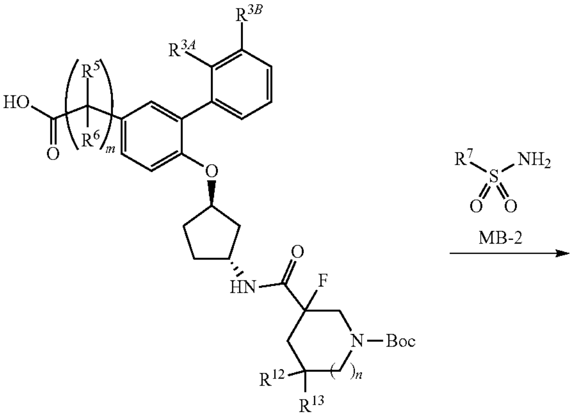

MA-9

-continued

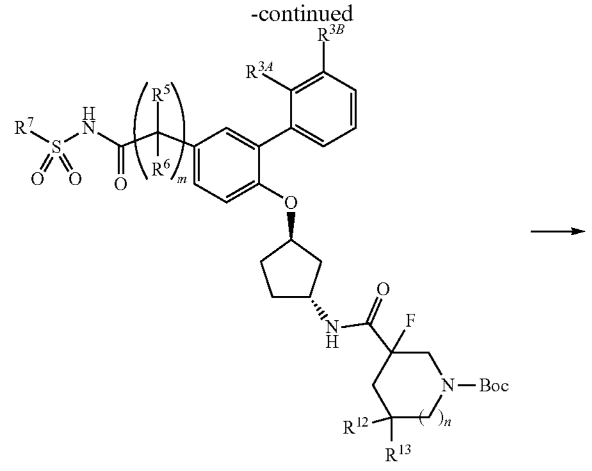

MB-5

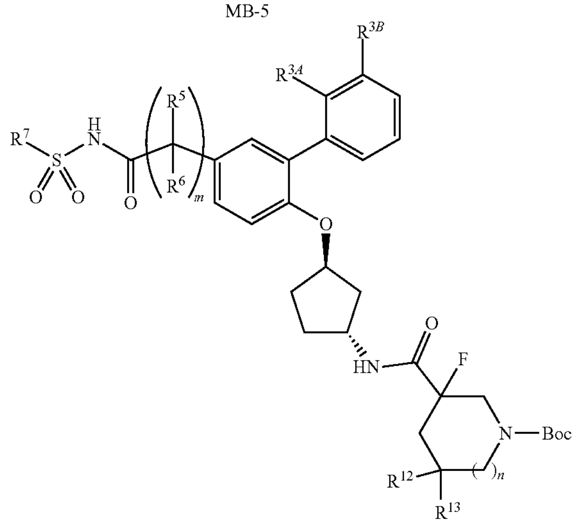

Formula C

General Method C refers to a synthetic sequence for preparing compounds of Formula C, as depicted above. Coupling of acid MA-9 with MB-2 under standard conditions gives MB-5. Deprotection of protecting groups (Boc) using conditions known in the art provides Formula C.

Scheme IV: General Method D

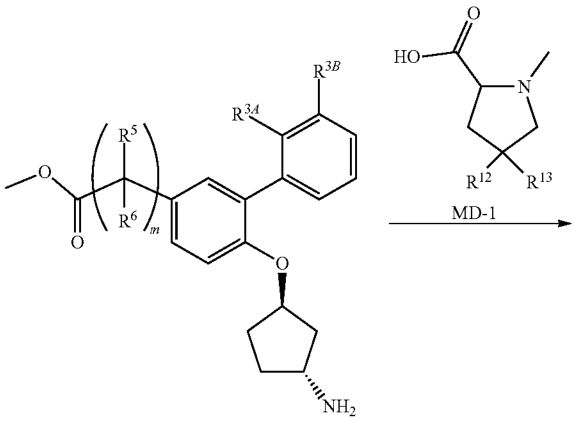

MA-6

-continued

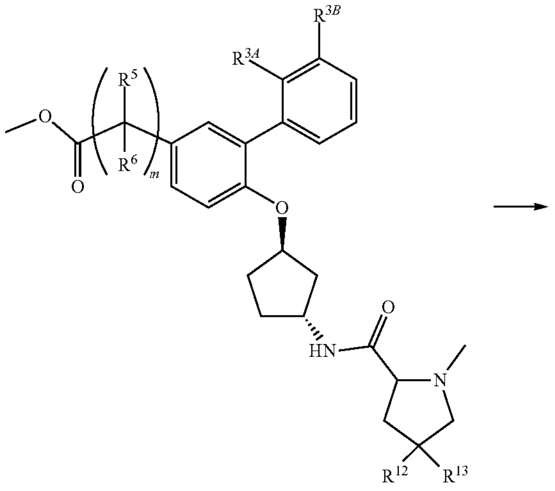

MA-2

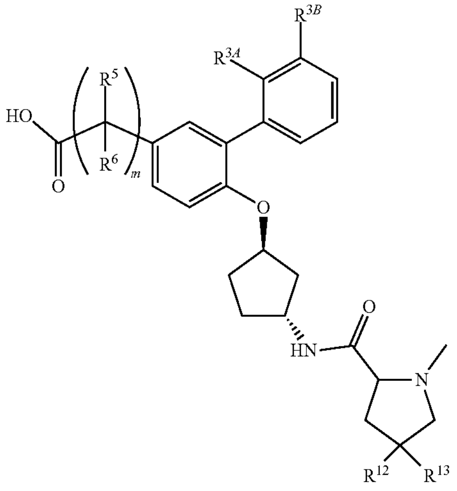

Formula D

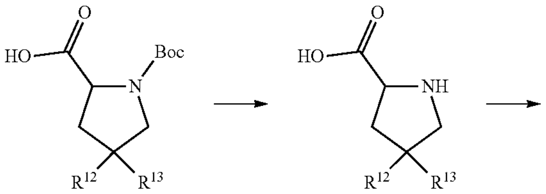

MD-3 MD-4

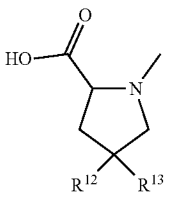

MD-1

General Method D refers to a synthetic sequence for preparing compounds of Formula D, as depicted above. Amide coupling between amine MA-6 and acid MD-1 affords amide MD-2. Ester hydrolysis of the ester group provides acid Formula D.

In cases where MD-1 is not commercially available ($R^{12}$ and $R^{13}$ are not methyl), MD-1 is synthesized via a two-step procedure from acid MD-3 involving Boc removal under acidic conditions followed by Eschweiler-Clarke methylation to give MD-1.

Scheme V: General Method E

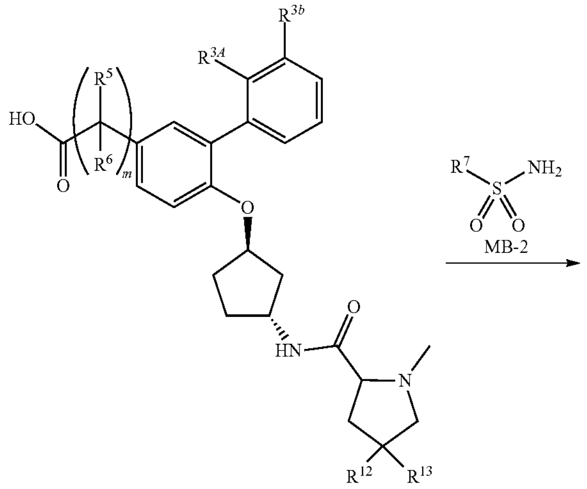

Formula D

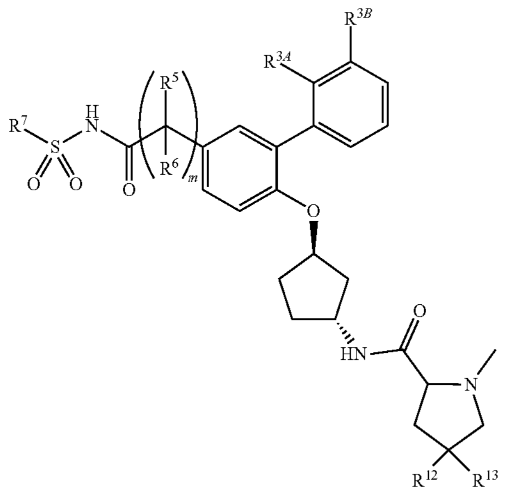

Formula E

General Method E refers to a synthetic sequence for preparing compounds of Formula E, as depicted above. Coupling of acid Formula D with MB-2 under standard conditions gives Formula E.

Scheme VI: General Method F

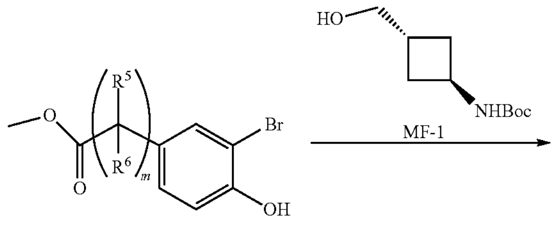

MA-1

-continued

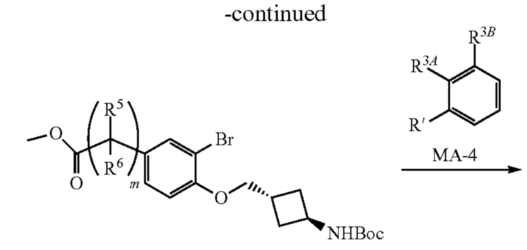

MF-2

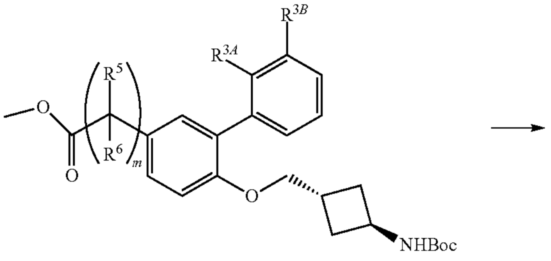

MF-3

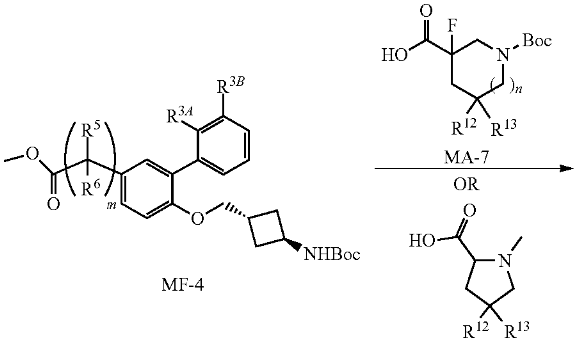

MF-4

MD-1

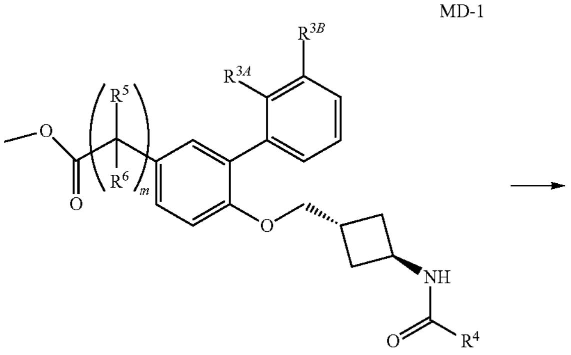

MF-5

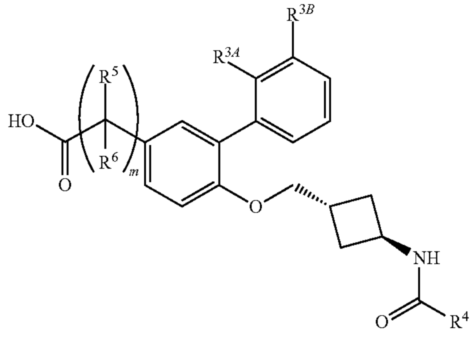

Formula F

General Method F refers to a synthetic sequence for preparing compounds of Formula F, as depicted above.

Mitsunobu reaction between phenol MA-1 and commercially available amino alcohol MF-1 provides ether MF-2. Suzuki coupling with boronate or boronic ester MA-4 (where R' is $(HO)_2B$— or B(pin) defined above) under standard cross-coupling conditions gives MF-3. Deprotection of the amine under acidic conditions gives amine MF-4. Amide coupling between amine MF-4 and either acid MA-7 or acid MD-1 affords amide MF-5. Ester hydrolysis of the ester group and in cases where $R_4$ contains a protecting group, deprotection of protecting groups (Boc) using conditions known in the art provides acid Formula F.

Scheme VII: General Method G

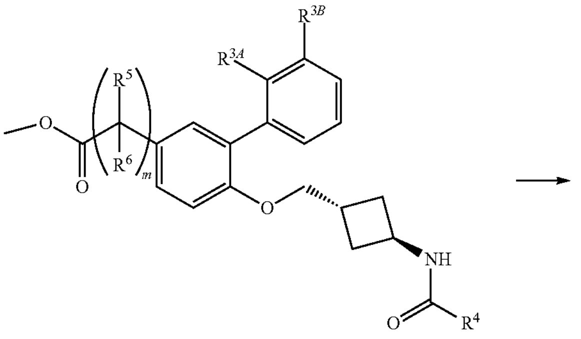

MF-5

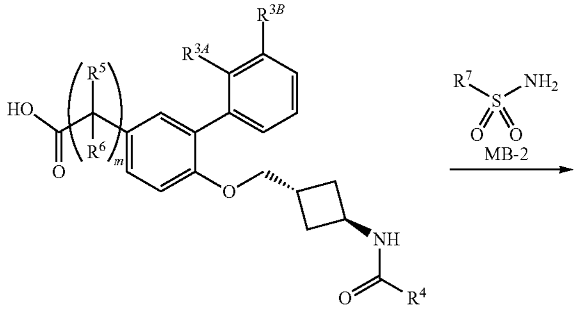

MG-1

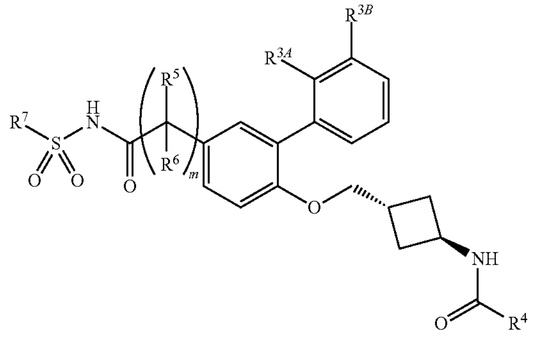

Formula G

General Method G refers to a synthetic sequence for preparing compounds of Formula G, as depicted above. Ester hydrolysis of ester MF-5 affords acid MG-1. Coupling of acid MG-1 with MB-2 under standard conditions and in cases where $R_4$ contains a protecting group, deprotection of protecting groups (Boc) using conditions known in the art gives Formula G.

Scheme VIII: General Method H

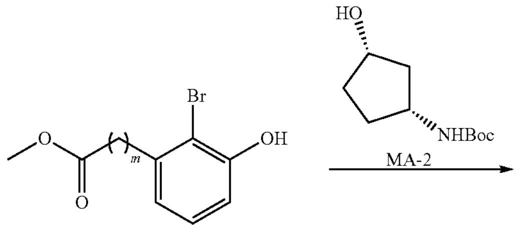

MH-1

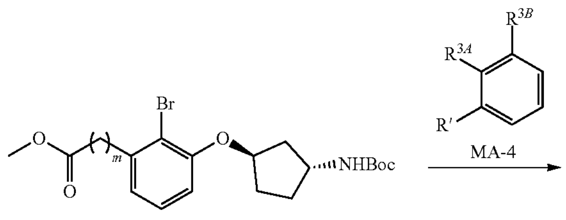

MH-2

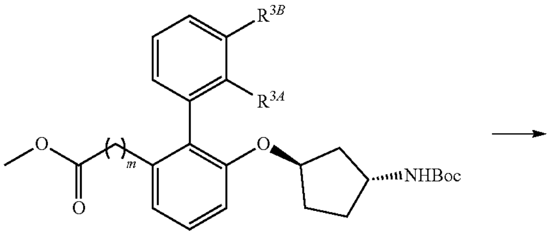

MH-3

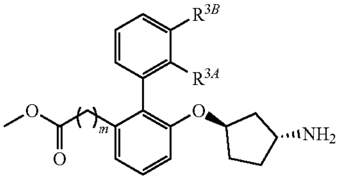

MH-4

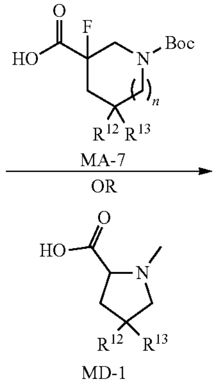

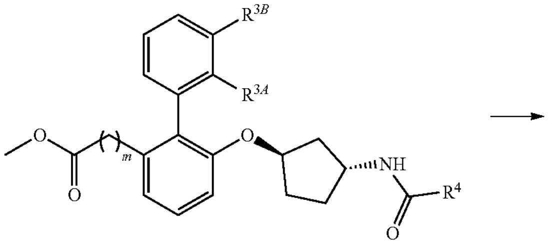

MH-5

-continued

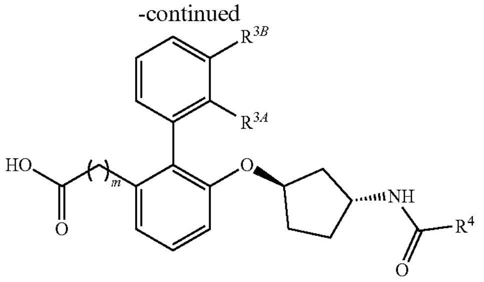

Formula H

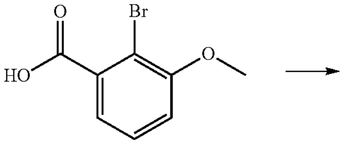

MH-6

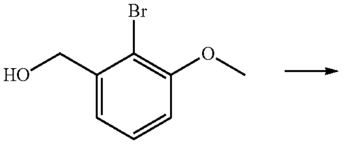

MH-7

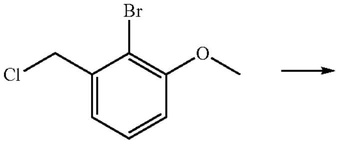

MH-8

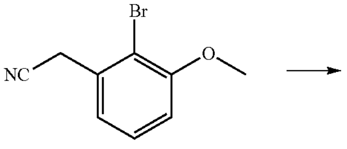

MH-9

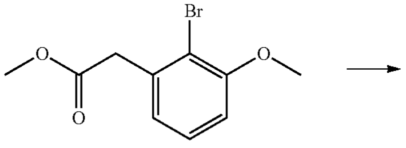

MH-10

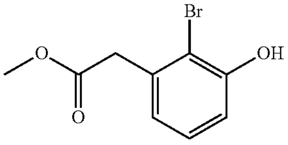

MH-1

General Method H refers to a synthetic sequence for preparing compounds of Formula H, as depicted above. Mitsunobu reaction between phenol MH-1 and commercially available amino alcohol MA-2 provides ether MH-2. Suzuki coupling with boronate or boronic ester MA-4 (where R' is $(HO)_2B$— or B(pin) defined above) under standard cross-coupling conditions gives MH-3. Deprotection of the amine under acidic conditions gives amine MH-4. Amide coupling between amine MH-4 and either acid MA-7 or acid MD-1 affords amide MH-5. Ester hydrolysis of the ester group and in cases where $R_4$ contains a protecting group, deprotection of protecting groups (Boc) using conditions known in the art provides acid Formula H.

In cases where MH-1 is not commercially available (m is not 0), MH-1 is synthesized from MH-6. Reduction of acid MH-6 provides alcohol MH-7 which can be subsequently converted to chloride MH-8 using thionyl chloride. Chloride MH-8 is transformed to cyano MH-9 via displacement. Hydrolysis of cyano MH-9 under acidic conditions afford ester MH-10. Finally, demethylation of ester MH-10 provides phenol MH-1.

Scheme IX: General Method I

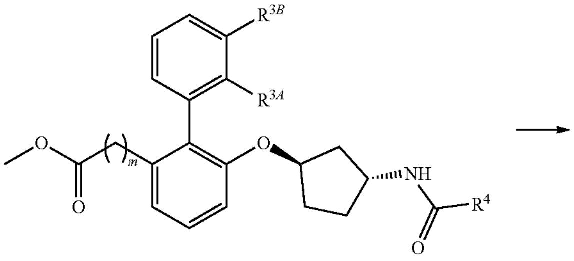

MH-5

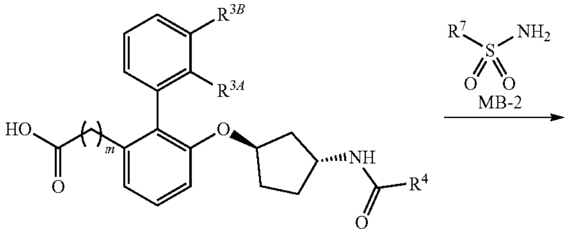

MI-1

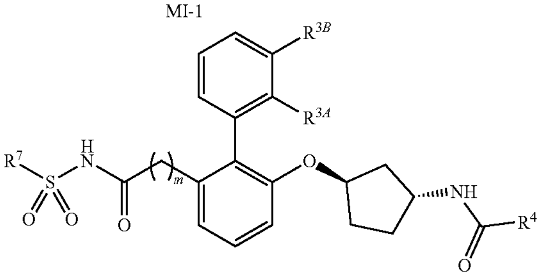

Formula I

General Method I refers to a synthetic sequence for preparing compounds of Formula I, as depicted above. Ester hydrolysis of ester MH-5 affords acid MI-1. Coupling of acid MI-1 with MB-2 under standard conditions and in cases where $R_4$ contains a protecting group, deprotection of protecting groups (Boc) using conditions known in the art gives Formula I.

Scheme X: General Method J

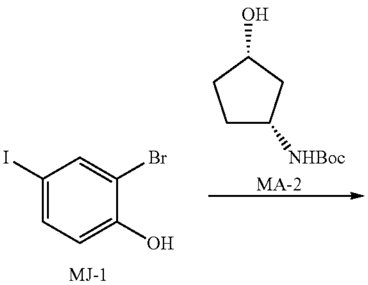

MJ-1

-continued
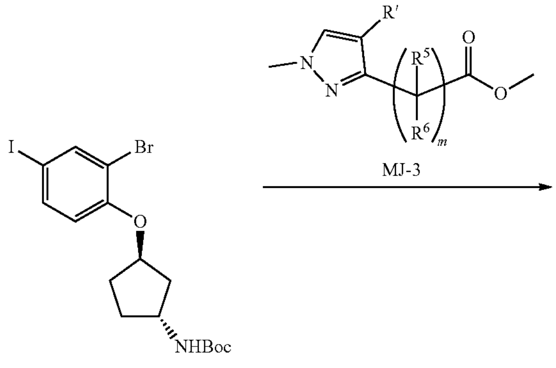
MJ-2
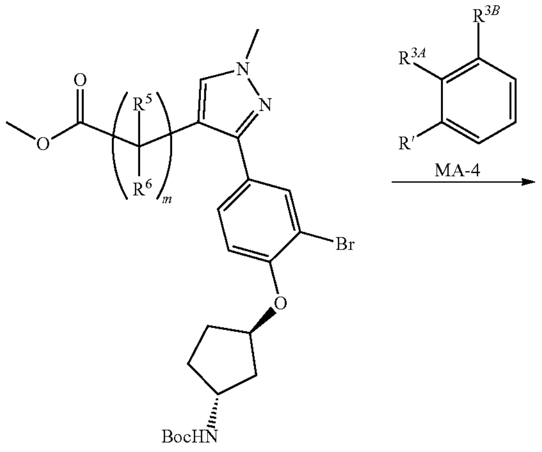
MJ-4
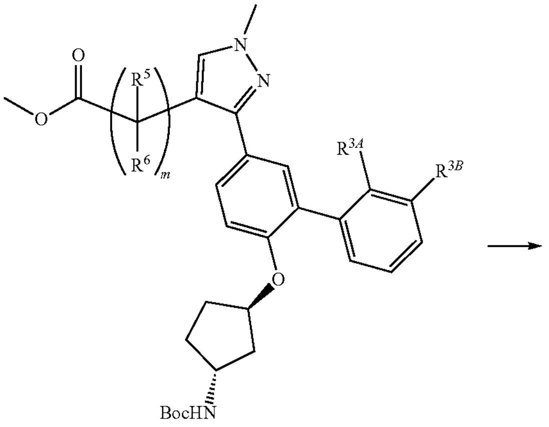
MJ-5
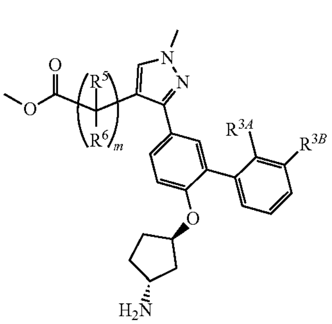
MJ-6
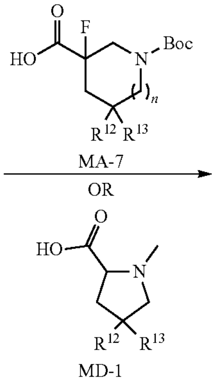
-continued
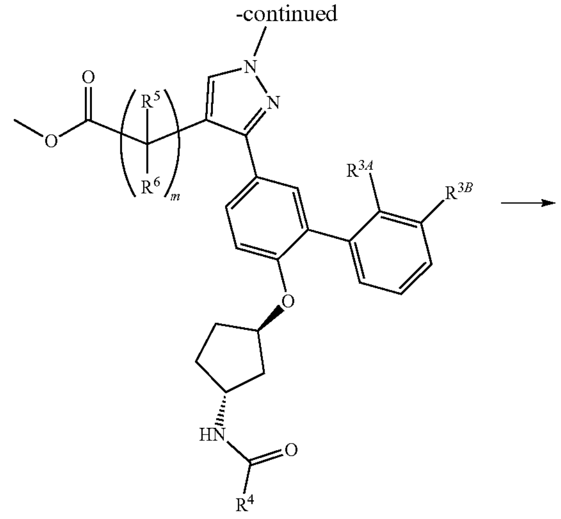
MJ-7
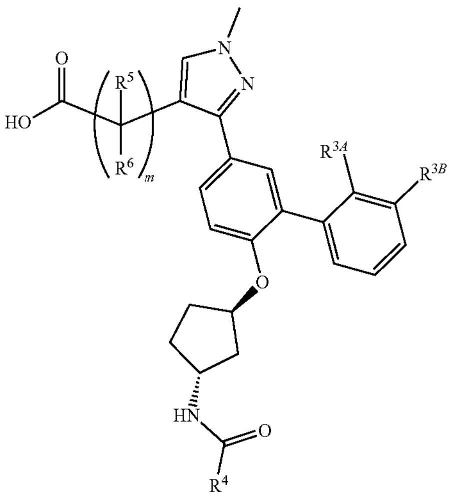
Formula J
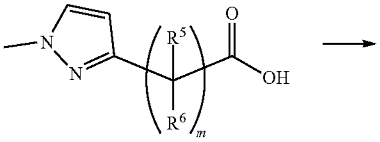
MJ-8
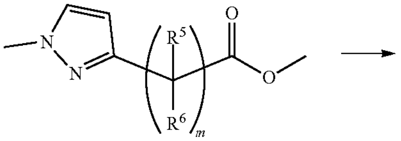
MJ-9
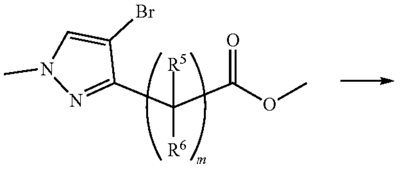
MJ-10

-continued

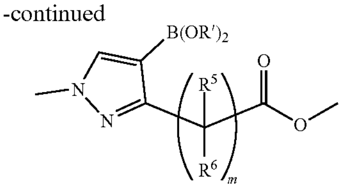

MJ-3

General Method J refers to a synthetic sequence for preparing compounds of Formula J, as depicted above. Mitsunobu reaction between phenol MJ-1 and commercially available amino alcohol MA-2 provides ether MJ-2. Suzuki coupling of iodide MJ-2 with boronate or boronic ester MJ-3 (where R' is $(HO)_2B$— or B(pin) defined above) under standard cross-coupling conditions gives MJ-4. Suzuki coupling of bromide MJ-4 with boronate or boronic ester MA-4 (where R' is $(HO)_2B$— or B(pin) defined above) under standard cross-coupling conditions gives MJ-5. Deprotection of the amine under acidic conditions gives amine MJ-6. Amide coupling between amine MJ-6 and either acid MA-7 or acid MD-1 affords amide MJ-7. Ester hydrolysis of the ester group and in cases where $R_4$ contains a protecting group, deprotection of protecting groups (Boc) using conditions known in the art provides acid Formula J.

Boronic ester MJ-3 is formed in the 3-4 step sequence starting with acid MJ-8. Acid MJ-8 is converted to ester MJ-9. Alkylation is done in some cases to install $R^5$ and/or $R^6$. Bromination of pyrrole MJ-9 affords bromide MJ-10 which can then be converted to boronic ester MJ-3 following standard Miyaura borylation conditions.

Scheme XI: General Method K

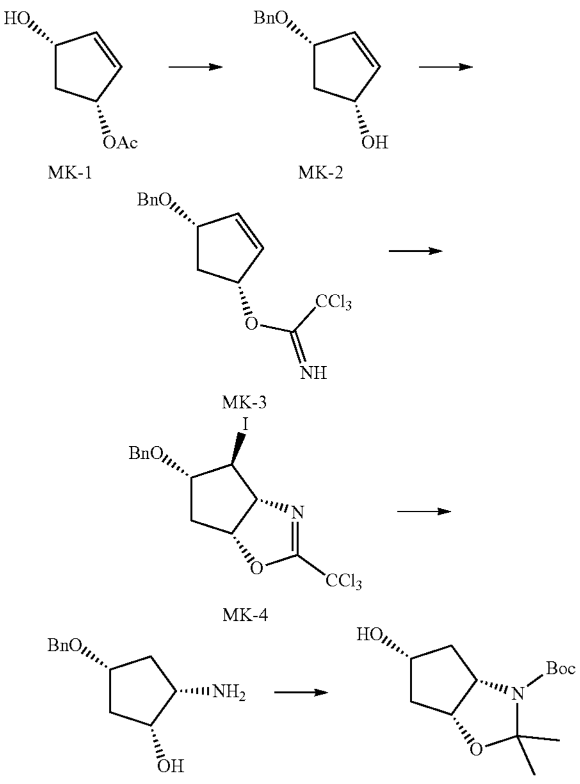

MK-1 MK-2 MK-3 MK-4 MK-5 MK-6

-continued

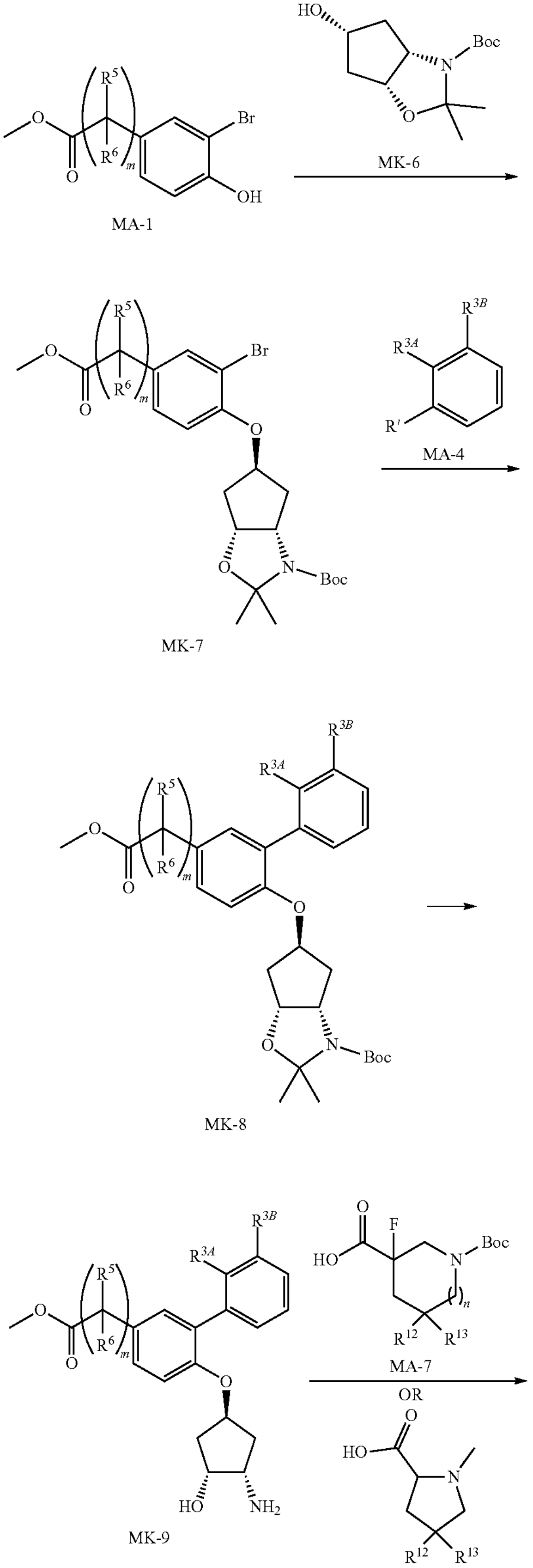

MA-1 MK-6 MK-7 MA-4 MK-8 MK-9 MA-7 OR MD-1

-continued

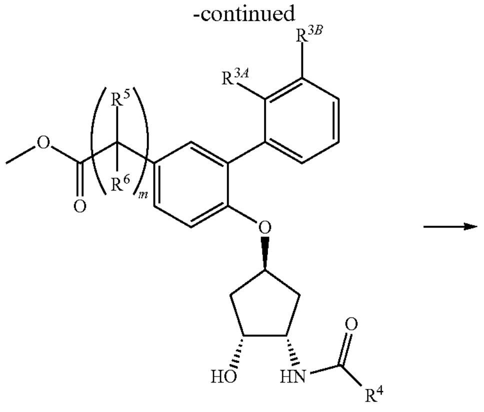

MK-10

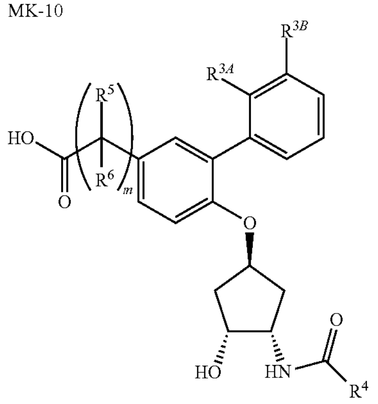

Formula K

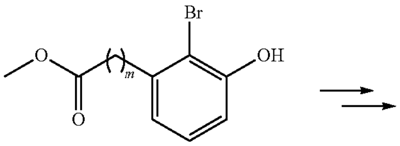

MH-1

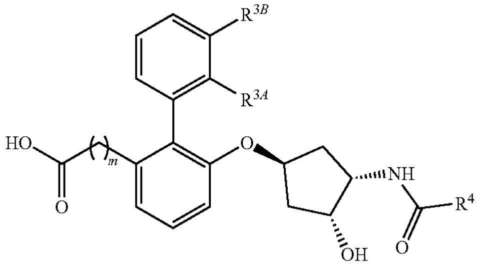

Formula K

General Method K refers to a synthetic sequence for preparing compounds of Formula K, as depicted above. Benzyl protection of alcohol MK-1 via benzylation followed by hydrolysis provides alcohol MK-2. Imidate formation from alcohol MK-2 provides MK-3. Iodo-cyclization affords MK-4. Deprotection of aminoalcohol followed by radical mediated deiodination affords MK-5. Protection of MK-5 first with a Boc group on the nitrogen followed by hemiaminal formation and debenzylation following standard conditions provides alcohol MK-6.

Mitsunobu reaction between phenol MA-1 and alcohol MK-6 provides ether MK-7. Suzuki coupling of bromide MK-7 with boronate or boronic ester MA-4 (where R' is $(HO)_2B$— or B(pin) defined above) under standard cross-coupling conditions gives MK-8. Acid mediated deprotection provides amine MK-9. Amide coupling between amine MK-9 and either acid MA-7 or acid MD-1 affords amide MK-10. Ester hydrolysis of the ester group and in cases where $R_4$ contains a protecting group, deprotection of protecting groups (Boc) using conditions known in the art provides acid Formula K. Additionally, phenol MH-1 can be used in place of phenol MA-1 to provide compounds Formula K.

Scheme XII: General Method L

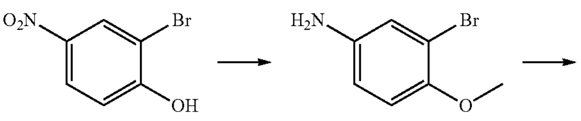

ML-1 ML-2

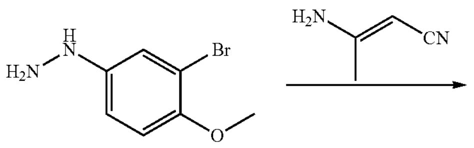

ML-3

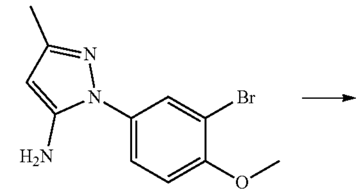

ML-4

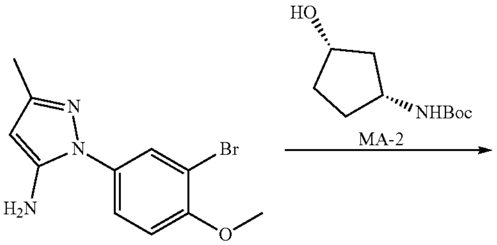

ML-5

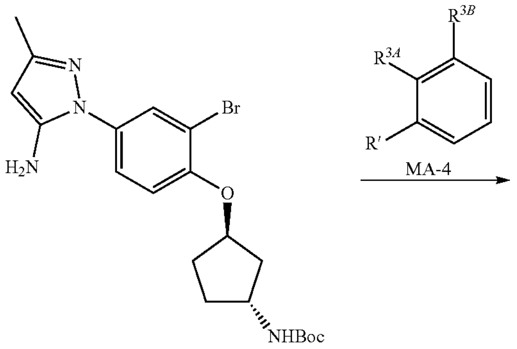

ML-6

-continued

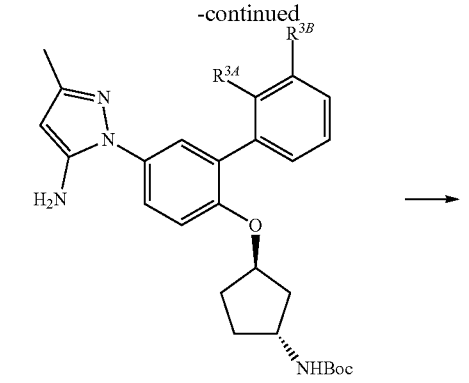

ML-7

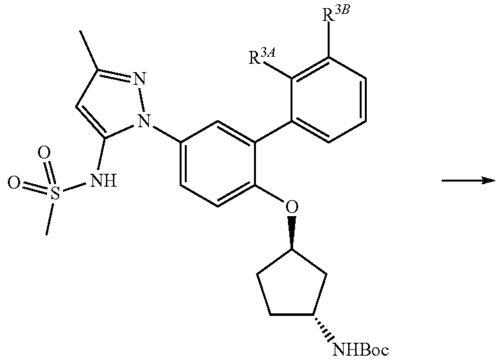

ML-8

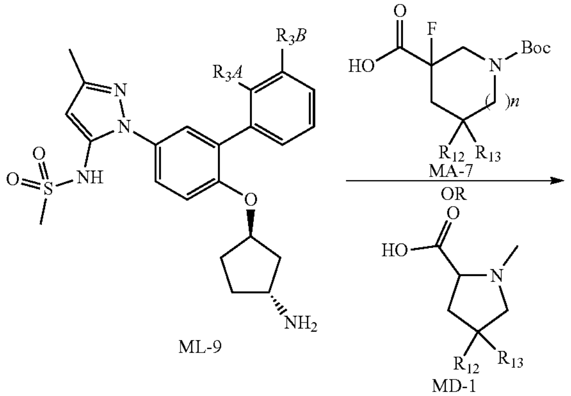

ML-9

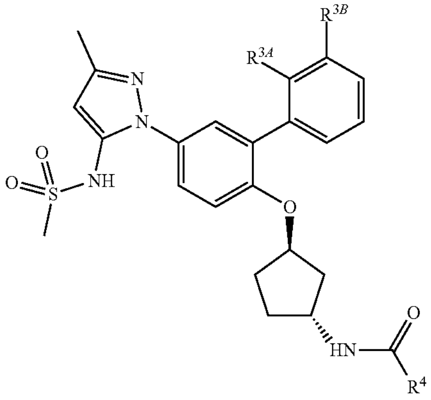

Formula L

General Method L refers to a synthetic sequence for preparing compounds of Formula L, as depicted above. Phenol ML-1 is converted to aniline ML-2 in a two-step procedure involving methylation and nitro reduction under standard conditions. Diazotization and reduction of aniline ML-2 gives hydrazine ML-3 then cyclization with amino acrylonitrile provides amino pyrazole ML-4. Demethylation reveals phenol ML-5. Mitsunobu reaction between phenol ML-5 and commercially available amino alcohol MA-2 provides ether ML-6. Suzuki coupling of bromide ML-6 with boronate or boronic ester MA-4 (where R' is $(HO)_2B$— or B(pin) defined above) under standard cross-coupling conditions gives ML-7. Sulfonamide formation from amine ML-7 affords sulfonamide ML-8. Deprotection of the Boc-protected amine under acidic conditions gives amine ML-9. Amide coupling between amine ML-9 and either acid MA-7 or acid MD-1 and in cases where $R_4$ contains a protecting group, deprotection of protecting groups (Boc) using conditions known in the art provides affords sulfonamide Formula L.

Preparation of Intermediates

Preparation of Intermediate 1: methyl 2-(3-bromo-4-hydroxyphenyl)-2-methylpropanoate Step 1: Methyl (3-bromo-4-methoxyphenyl)acetate (1a)

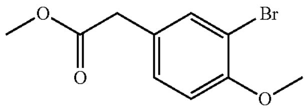

To a solution of methyl (4-methoxyphenyl)acetate (200 g, 1.11 mol) in ACN (1.8 L), NBS (207.4 g, 1.17 mol) was added slowly at 25° C. The mixture was stirred for 15 h and then concentrated under reduced pressure. The residue was dissolved in EtOAc (1.5 L), washed with saturated $NaHCO_3$ (2×) and brine (2×), dried over $Na_2SO_4$, filtered, and concentrated under reduced pressure to give methyl (3-bromo-4-methoxyphenyl)acetate (1a) (280 g, 97%) as an orange oil. LCMS ESI (+) 259.0, 261.0 (M+H). $^1$H NMR (400 MHz, DMSO-$d_6$) δ 7.48 (d, J=2.0 Hz, 1H), 7.23 (dd, J=8.4, 2.4 Hz, 1H), 7.04 (d, J=8.4 Hz, 1H), 3.83 (s, 3H), 3.63 (s, 2H), 3.61 (s, 3H).

Step 2: Methyl 2-(3-bromo-4-methoxyphenyl)-2-methylpropanoate (1b)

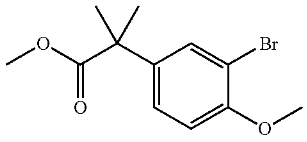

To a solution of methyl (3-bromo-4-methoxyphenyl)acetate (1a) (180 g, 0.695 mol) in THF (2.5 L), iodomethane (247 g, 1.74 mol) was added slowly at −50° C. KO$^t$Bu (195 g, 1.74 mol) was then added portion-wise, maintaining the internal temperature below −40° C. Removed cooling bath and stirred for 4 h. The mixture was quenched with ice-water and then extracted with EtOAc. The organic layer was washed with brine (2×), dried over $Na_2SO_4$, filtered, and concentrated under reduced pressure. The residue was purified by silica gel chromatography (THF/PE=1/10) to give methyl 2-(3-bromo-4-methoxyphenyl)-2-methylpropanoate (1b) (160 g, 80%) as a yellow oil. LCMS ESI (+) 287.0, 289.0 (M+H). $^1$H NMR (400 MHz, DMSO-$d_6$) δ 7.45 (d, J=2.4 Hz, 1H), 7.27 (dd, J=8.4, 2.4 Hz, 1H), 7.06 (d, J=8.8 Hz, 1H), 3.83 (s, 3H), 3.58 (s, 3H), 1.48 (s, 6H).

Step 3: Methyl 2-(3-bromo-4-hydroxyphenyl)-2-methylpropanoate (Intermediate 1)

Intermediate 1

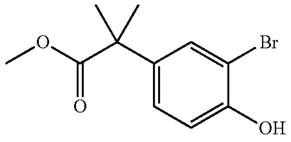

To a solution of methyl 2-(3-bromo-4-methoxyphenyl)-2-methylpropanoate (1b) (150 g, 0.522 mol) in DCM (1.5 L), $BBr_3$ (97 mL, 1.05 mol) was added slowly at 0° C. Removed cooling bath and stirred for 12 h. The mixture was cooled back down to 0° C., quenched with MeOH drop-wise, and then neutralized with saturated $NaHCO_3$. The solution was extracted with DCM (2×) and the combined organics were dried over $Na_2SO_4$, filtered, and concentrated under reduced pressure. The residue was purified by silica gel chromatography (THF/PE=1/8) to give methyl 2-(3-bromo-4-hydroxyphenyl)-2-methylpropanoate (Intermediate 1) (130 g, 91%) as a yellow solid. LCMS ESI (+) 273.0, 275.0 (M+H). $^1$H NMR (400 MHz, DMSO-$d_6$) δ 10.20 (s, 1H), 7.35 (d, J=2.4 Hz, 1H), 7.11 (dd, J=8.8, 2.4 Hz, 1H), 6.90 (d, J=8.8 Hz, 1H), 3.57 (s, 3H), 1.45 (s, 6H).

Preparation of Intermediate 2: 2-(2-cyclobutyl-3-fluorophenyl)-4,4,5,5-tetramethyl-1,3,2-dioxaborolane Step 1: 1-(2-fluoro-6-methoxyphenyl)cyclobutan-1-ol (2a)

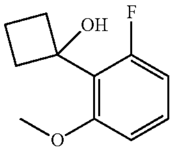

To a solution of 1-fluoro-3-methoxybenzene (50.5 g, 0.396 mol) in THF (600 mL), LDA (2.0 M, 0.516 mol) was added drop-wise at −65° C. Stirred for 1 h at −65° C., then added cyclobutanone (33.4 g, 0.476 mol) drop-wise. After 1 h, the reaction was quenched with saturated $NH_4Cl$ and water at 0° C. then extracted with EtOAc (3×). The combined organics were washed with brine (2×), dried over $Na_2SO_4$, filtered, and concentrated under reduced pressure. The residue was purified by silica gel chromatography (0-17% EtOAc/PE) to give 1-(2-fluoro-6-methoxyphenyl) cyclobutan-1-ol (2a) (45 g, 56%) as a light yellow oil. $^1$H NMR (400 MHz, CHLOROFORM-d) δ=7.19 (dt, J=6.4, 8.3 Hz, 1H), 6.73-6.62 (m, 2H), 3.86 (s, 3H), 2.78-2.65 (m, 3H), 2.51-2.28 (m, 3H), 1.94-1.79 (m, 1H)

Step 2: 2-cyclobutyl-1-fluoro-3-methoxybenzene (2b)

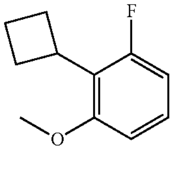

To a solution of 1-(2-fluoro-6-methoxyphenyl)cyclobutan-1-ol (2a) (45.0 g, 0.229 mol) in DCM (650 mL), triethylsilane (80.0 g, 0.688 mol, 110 mL) was added at 0° C. After 30 min, TFA (105 g, 0.917 mol, 68.1 mL) and the mixture were stirred at 25° C. for 16 h. The reaction mixture was concentrated under reduced pressure and the residue was purified by column chromatography (0-10% EtOAc/PE) to give 2-cyclobutyl-1-fluoro-3-methoxybenzene (2b) (23.7 g, 57% yield) as a yellow oil. $^1$H NMR (400 MHz, CHLOROFORM-d) δ=7.00 (dt, J=6.6, 8.3 Hz, 1H), 6.60-6.50 (m, 2H), 3.85-3.68 (m, 4H), 2.47-2.36 (m, 2H), 2.27-2.15 (m, 2H), 1.97-1.76 (m, 2H)

Step 3: 2-cyclobutyl-3-fluorophenol (2c)

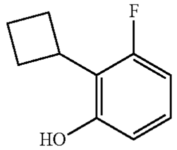 [SMILES: Oc1cccc(F)c1C1CCC1]

To a solution of 2-cyclobutyl-1-fluoro-3-methoxybenzene (2b) (41.2 g, 0.229 mol) in DCM (700 mL), $BBr_3$ (172 g, 66.1 mL, 0.686 mol) was added dropwise at −65° C. The reaction was stirred at 0° C. for 2 h, and then quenched with ice-water and extracted with DCM (3×). The combined organics were washed with brine (3×), dried over $Na_2SO_4$, and filtered. The filtrate was concentrated under reduced pressure and the residue was purified by silica gel chromatography (0-10% EtOAc/PE) to give 2-cyclobutyl-3-fluorophenol (2c) (31.5 g, 83%) as a brown oil. $^1$H NMR (400 MHz, CHLOROFORM-d) δ=7.01 (dt, J=6.3, 8.2 Hz, 1H), 6.62 (t, J=9.4 Hz, 1H), 6.55 (d, J=8.1 Hz, 1H), 4.96 (br s, 1H), 3.83-3.73 (m, 1H), 2.59-2.48 (m, 2H), 2.44-2.34 (m, 2H), 2.07-1.90 (m, 2H)

Step 4: 2-cyclobutyl-3-fluorophenyl trifluoromethanesulfonate (2d)

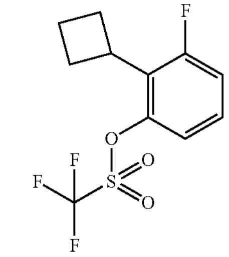 [SMILES: O=S(=O)(Oc1cccc(F)c1C1CCC1)C(F)(F)F]

To a solution of 2-cyclobutyl-3-fluorophenol (2c) (31.0 g, 0.187 mol) in pyridine (350 mL), trifluoromethanesulfonic anhydride (63.2 g, 37.7 mL, 0.224 mol) was added dropwise at 0° C. The reaction was stirred at room temperature for 2 h then quenched with EtOAc. The reaction was concentrated under reduced pressure and the residue was purified by silica gel chromatography (0-10% EtOAc/PE) to give 2-cyclobutyl-3-fluorophenyl trifluoromethanesulfonate (2d) (38.4 g, 69%) as a light-yellow oil. $^1$H NMR (400 MHz, $CDCl_3$) δ ppm 7.25 (td, J=8.36, 5.94 Hz, 1H) 7.08 (td, J=10.12, 8.80 Hz, 2H) 3.81 (quin, J=9.19 Hz, 1H) 2.40-2.57 (m, 4H) 1.90-2.16 (m, 2H).

-

Step 5: 2-(2-cyclobutyl-3-fluorophenyl)-4,4,5,5-tetramethyl-1,3,2-dioxaborolane (Intermediate 2)

Intermediate 2

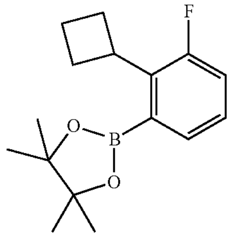

A mixture of 2-cyclobutyl-3-fluorophenyl trifluoromethanesulfonate (2d) (19.2 g, 0.064 mol), bis(pinacolato)diborane (22.9 g, 0.090 mol), and KOAc (19.0 g, 0.193 mol) in dioxane (400 mL) was degassed and purged with $N_2$ (3×). [1,1'-Bis(diphenylphosphino)ferrocene]dichloropalladium (4.71 g, 6.44 mmol) was added to the mixture, and the mixture was stirred at 110° C. for 24 h. The reaction mixture was concentrated under reduced pressure then PE was added to the residue and the mixture was stirred for 2 h. The solids were filtered out and the filtrate was concentrated under reduced pressure. The residue was purified by silica gel chromatography (0-10% EtOAc/PE) to give 2-(2-cyclobutyl-3-fluorophenyl)-4,4,5,5-tetramethyl-1,3,2-dioxaborolane (Intermediate 2) (85%) as a light-yellow oil. $^1$H NMR (400 MHz, $CDCl_3$) δ ppm 7.42 (dd, J=7.26, 1.10 Hz, 1H) 7.15 (td, J=7.70, 4.84 Hz, 1H) 7.03-7.10 (m, 1H) 4.15 (quin, J=9.19 Hz, 1H) 2.31-2.55 (m, 4H) 1.87-2.11 (m, 2H) 1.37-1.41 (m, 12H).

Preparation of Intermediate 3: 5-(tert-butoxycarbonyl)-7-fluoro-5-azaspiro[3.4]octane-7-carboxylic acid Step 1: 5-tert-butyl 7-methyl 5-azaspiro[3.4]octane-5,7-dicarboxylate (3a)

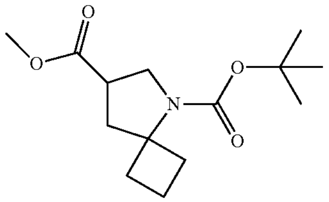 [SMILES: COC(=O)C1CN(C(=O)OC(C)(C)C)C2(CCC2)C1]

To a solution of 5-(tert-butoxycarbonyl)-5-azaspiro[3.4]octane-7-carboxylic acid (7.0 g, 27 mmol) in DMF (91 mL), $K_2CO_3$ (9.5 g, 69 mmol) was added, followed by iodomethane (4.9 g, 2.1 mL, 34 mmol). The reaction mixture was stirred at room temperature for 4 h then concentrated under reduced pressure. The residue was partitioned between EtOAc and water. The organics were separated, washed again with water and brine, dried over $MgSO_4$, filtered and concentrated under reduced pressure to give 5-tert-butyl 7-methyl 5-azaspiro[3.4]octane-5,7-dicarboxylate (3a) (7.0 g, 95%) as an orange oil. LCMS APCI (+) 170.1 (M-Boc). $^1$H NMR (400 MHz, DMSO-$d_6$, 80° C.) δ ppm 3.65 (s, 3H) 3.49-3.57 (m, 1H) 3.38-3.47 (m, 1H) 2.93-3.02 (m, 2H) 2.75-2.83 (m, 1H) 2.39 (dd, J=12.57, 6.82 Hz, 1H) 2.19 (dd, J=12.38, 9.01 Hz, 1H) 1.77-1.89 (m, 2H) 1.58-1.74 (m, 2H) 1.46 (s, 9H).

Step 2: 5-tert-butyl 7-methyl 7-fluoro-5-azaspiro[3.4]octane-5,7-dicarboxylate (3b)

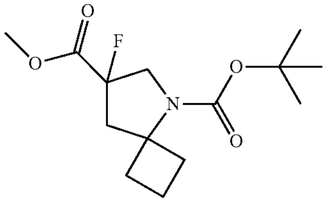 [SMILES: COC(=O)C1(F)CN(C(=O)OC(C)(C)C)C2(CCC2)C1]

To a −78° C. solution of LDA (2.0 M, 6.4 mL, 12.8 mmol) in THF (26 mL), a solution of 5-tert-butyl 7-methyl 5-azaspiro[3.4]octane-5,7-dicarboxylate (3a) (1.38 g, 5.12 mmol) in THF (13 mL) was added via syringe pump at a rate of 0.4 mL/min. After 1 h at −78° C., this solution was cannulated into a −78° C. solution of N-fluorobenzenesulfonimide (1.04 g, 12.8 mmol) in THF (26 mL) drop-wise. After 1 h at −78° C., the reaction was quenched with saturated $NH_4Cl$ while cold then allowed to warm to RT. The reaction was partitioned between EtOAc and water. The organics were separated, washed with brine, dried over $MgSO_4$, filtered, and concentrated under reduced pressure. The residue was purified by silica gel chromatography (0-20% EtOAc/heptanes) to give 5-tert-butyl 7-methyl 7-fluoro-5-azaspiro[3.4]octane-5,7-dicarboxylate (3b) (950 mg, 65%) as a clear oil. LCMS APCI (+) 188.1 (M-Boc). $^1$H NMR (400 MHz, DMSO-$d_6$, 80° C.) δ ppm 3.78 (s, 4H) 3.68-3.72 (m, 1H) 3.17 (q, J=10.13 Hz, 1H) 2.67-2.83 (m, 2H) 2.44 (d, J=14.38 Hz, 1H) 1.89-2.07 (m, 2H) 1.56-1.78 (m, 2H) 1.47 (s, 9H).

Step 3: 5-(tert-butoxycarbonyl)-7-fluoro-5-azaspiro[3.4]octane-7-carboxylic acid (Intermediate 3)

Intermediate 3

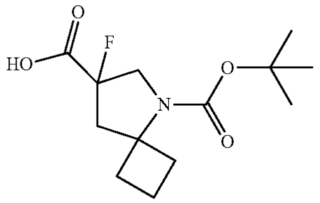

To a solution of 5-tert-butyl 7-methyl 7-fluoro-5-azaspiro[3.4]octane-5,7-dicarboxylate (3b) (798 mg, 2.78 mmol) in MeOH (13.9 mL), LiOH (1 M, 5.55 mL, 5.55 mmol) was added. After stirring for 2 h at RT, the reaction was diluted with EtOAc, washed with 1 N HCl and brine, dried over $MgSO_4$, filtered, and concentrated under reduced pressure to give 5-(tert-butoxycarbonyl)-7-fluoro-5-azaspiro[3.4]octane-7-carboxylic acid (Intermediate 3) (736 mg, 97%) as a light brown waxy solid. LCMS APCI (−) 272.1 (M-H). $^1$H NMR (400 MHz, DMSO-$d_6$, 80° C.) δ ppm 3.75 (s, 1H) 3.68 (s, 1H) 3.12-3.24 (m, 1H) 2.66-2.83 (m, 2H) 2.42 (d, J=14.26 Hz, 1H) 1.90-2.06 (m, 2H) 1.59-1.77 (m, 2H) 1.47 (s, 9H).

Intermediate 3'

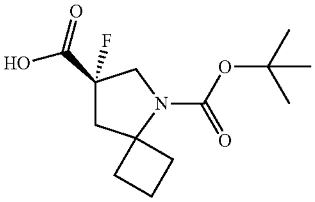

-continued

Intermediate 3''

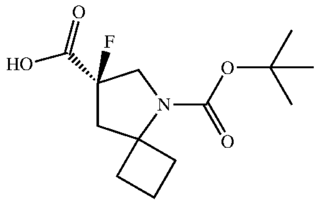

The racemic compound could be purified into its enantiomers via preparative SFC (Column: Chiralpak IC SFC, 250×21 mm, 5 um; Temperature: 25° C.; Pressure: 120 bar; Flow rate: 70 mL/min; 10% MeOH+10 mm $NH_3$ in $CO_2$). Peak 1: (7S)-5-(tert-butoxycarbonyl)-7-fluoro-5-azaspiro[3.4]octane-7-carboxylic acid (Intermediate 3') was isolated as a white solid (>99% ee).

$$[\alpha]_D^{22} = +6.1°(c0.1, \text{MeOH}).$$

Absolute stereochemistry of Intermediate 3' was determined by small molecule x-ray crystallography. Peak 2: (7R)-5-(tert-butoxycarbonyl)-7-fluoro-5-azaspiro[3.4]octane-7-carboxylic acid. (Intermediate 3") was isolated as a white solid (93% ee).

$$[\alpha]_D^{22} = -11.8°(c0.1, \text{MeOH}).$$

Procedure for single crystal x-ray diffraction: crystals of the (3aS,4R,5R,6S,7R,7aR)-4,6,7-trihydroxyhexahydro-2H-1,3-benzodioxol-5-aminium salt of Intermediate 3' were grown from Acetonitrile/$H_2O$ and the structure and stereochemistry of Intermediate 3' was confirmed with small molecule x-ray crystallography using a Bruker SMART Pt135 CCD diffractometer equipped with Cu $K_\alpha$ radiation ($\lambda$=1.54178 Å).

Preparation of Intermediate 4: 1-(tert-butoxycarbonyl)-3-fluoro-5,5-dimethylpyrrolidine-3-carboxylic acid Intermediate 4

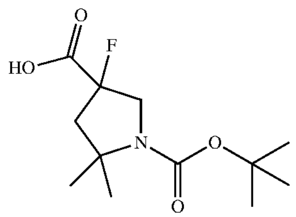

Intermediate 4 was made in a similar manner as Intermediate 3 starting from 1-(tert-butoxycarbonyl)-5,5-dimethylpyrrolidine-3-carboxylic acid. LCMS APCI (+) 162.1 (M-Boc). $^1$H NMR (400 MHz, DMSO-$d_6$) δ=3.86-3.77 (m, 1H), 3.75 (s, 1H), 2.48-2.23 (m, 2H), 1.45-1.41 (m, 15H)

Preparation of Intermediate 5: 1-(tert-butoxycarbonyl)-3-fluoro-1-azaspiro[4.4]nonane-3-carboxylic acid Intermediate 5

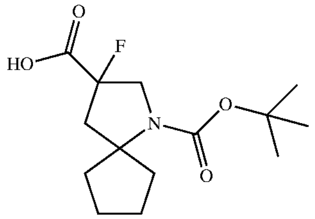

Intermediate 5 was made in a similar manner as Intermediate 3 starting from 1-(tert-butoxycarbonyl)-1-azaspiro[4.4]nonane-3-carboxylic acid. LCMS APCI (+) 188.1 (M-Boc). $^1$H NMR (400 MHz, DMSO-d6) δ 3.84-3.71 (m, 2H), 2.50-2.25 (m, 3H), 2.20-2.05 (m, 1H), 1.84-1.66 (m, 3H), 1.59-1.47 (m, 3H), 1.44 (s, 9H).

Preparation of Intermediate 6: methyl (2-bromo-3-hydroxyphenyl)acetate

Step 1: (2-bromo-3-methoxyphenyl)methanol (6a)

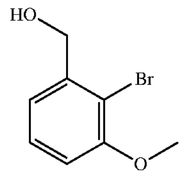

A solution of 2-bromo-3-methoxybenzoic acid (200 g, 866 mmol) in THF (3000 mL) was cooled in an ice-water bath, and then borane THF (89.3 g, 1040 mmol) was added slowly. After 30 min, the ice-bath was removed, and the reaction mixture was stirred for 12 h. The mixture was quenched with MeOH (100 mL) until no gas formed. The mixture was concentrated under reduced pressure to give (2-bromo-3-methoxyphenyl)methanol (6a) (182 g, 96.9%) as white solid. $^1$H NMR (400 MHz, DMSO-$d_6$) δ=7.39-7.32 (m, 1H), 7.14 (d, J=7.5 Hz, 1H), 7.00 (d, J=8.1 Hz, 1H), 5.41 (t, J=5.7 Hz, 1H), 4.51 (d, J=5.5 Hz, 2H), 3.84 (s, 3H).

Step 2: 2-bromo-1-(chloromethyl)-3-methoxybenzene (6b)

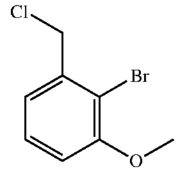

To a solution of (2-bromo-3-methoxyphenyl)methanol (6a) (180 g, 829 mmol) in DCM (300 mL), thionyl chloride (592 g, 4980 mmol) was added slowly. The reaction was stirred for 1 h, then concentrated under reduced pressure. The residue was basified with saturated $Na_2CO_3$ to pH=8-9. Added water then extracted with DCM (3×). The combined organics were washed with brine and concentrated under reduced pressure to give 2-bromo-1-(chloromethyl)-3-methoxybenzene (6b) (180 g, 92.2%) as a yellow solid. $^1$H NMR (400 MHz, DMSO-$d_6$) δ=7.41-7.34 (m, 1H), 7.22-7.18 (m, 1H), 7.12 (dd, J=1.1, 8.4 Hz, 1H), 4.83 (s, 2H), 3.87 (s, 3H).

Step 3: (2-bromo-3-methoxyphenyl)acetonitrile (6c)

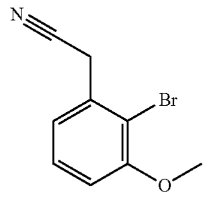

A solution of 2-bromo-1-(chloromethyl)-3-methoxybenzene (6b) (180 g, 764 mmol) and TMSCN (152 g, 1530 mmol) in ACN (2000 mL) was cooled in an ice-water bath, and then TBAF (400 g, 1530 mmol) was added. The ice bath was removed, and the reaction was stirred for 18 h, then concentrated under reduced pressure. The residue was purified by silica gel chromatography (0-30% EtOAc/PE) to give (2-bromo-3-methoxyphenyl)acetonitrile (6c) (160 g, 92.6%) as a white solid. $^1$H NMR (400 MHz, DMSO-$d_6$) δ=7.44-7.37 (m, 1H), 7.13 (t, J=8.3 Hz, 2H), 4.08 (s, 2H), 3.87 (s, 3H).

Step 4: methyl (2-bromo-3-methoxyphenyl)acetate (6d)

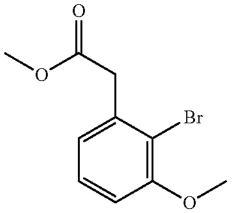

To a solution of (2-bromo-3-methoxyphenyl)acetonitrile (6c) (160 g, 708 mmol) in MeOH (2000 mL), saturated HCl in MeOH (51.6 g, 1420 mmol) was added. After 16 h, the reaction was concentrated under reduced pressure. The residue was dissolved in DCM, washed with water, concentrated and purified by silica gel chromatography (0-15% EtOAc/PE) to give methyl (2-bromo-3-methoxyphenyl)acetate (6d), 81.8%) as a yellow oil. $^1$H NMR (400 MHz, DMSO-$d_6$) δ=7.35-7.27 (m, 1H), 7.06-6.97 (m, 2H), 3.86-3.82 (m, 5H), 3.62 (s, 3H).

Step 5: methyl (2-bromo-3-hydroxyphenyl)acetate (Intermediate 6)

Intermediate 6

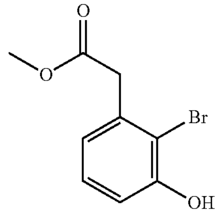

A solution of methyl (2-bromo-3-methoxyphenyl)acetate (6d) (150 g, 579 mmol) in DCM (2000 mL) was cooled in an ice-water bath, and then borane tribromide (290 g, 1160 mmol) was added slowly. The ice bath was removed after 30 min, then the reaction was stirred for 16 h. The mixture was quenched by adding MeOH slowly. Added water then extracted with DCM (2×). The combined organics were concentrated under reduced pressure and the residue was purified by silica gel chromatography (0-50% EtOAc/PE) to give methyl (2-bromo-3-hydroxyphenyl)acetate (Intermediate 6) (100 gm 70.5%) as a yellow solid. $^1$H NMR (400 MHz, DMSO-$d_6$) δ=10.21 (s, 1H), 7.16-7.08 (m, 1H), 6.88 (dd, J=1.5, 8.1 Hz, 1H), 6.82 (dd, J=1.5, 7.5 Hz, 1H), 3.78 (s, 2H), 3.62 (s, 3H).

Preparation of Intermediate 7: 2-[3-fluoro-2-(propan-2-yl)phenyl]-4,4,5,5-tetramethyl-1,3,2-dioxaborolane Step 1: 3-fluoro-2-(prop-1-en-2-yl)phenol (7a)

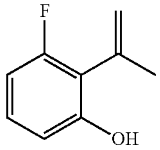

A solution of 2-bromo-3-fluorophenol (50 g, 262 mmol) and 4,4,5,5-tetramethyl-2-(prop-1-en-2-yl)-1,3,2-dioxaborolane (66.0 g, 393 mmol), $K_2CO_3$ (72.4 g, 524 mmol) and [1,1'-Bis(diphenylphosphino)ferrocene]dichloropalladium (13.4 g, 18.3 mmol) in dioxane (500 mL) and water (100 mL) was degassed and purged with $N_2$ (5×). The reaction was heated to 90° C. for 18 h, then filtered and concentrated under reduced pressure. The residue was purified (2×) by silica gel chromatography (0-10% EtOAc/PE) to give 3-fluoro-2-(prop-1-en-2-yl)phenol (7a) (32.2 g, 80.8%) as a yellow oil. $^1$H NMR (400 MHz, DMSO-$d_6$) δ=9.71 (s, 1H), 7.06 (dt, J=6.8, 8.2 Hz, 1H), 6.66 (d, J=8.3 Hz, 1H), 6.59 (dt, J=1.0, 8.9 Hz, 1H), 5.35-5.21 (m, 1H), 4.97-4.81 (m, 1H), 1.99-1.94 (m, 3H).

Step 2: 3-fluoro-2-(propan-2-yl)phenol (7b)

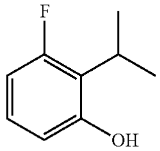

To a solution of 3-fluoro-2-(prop-1-en-2-yl)phenol (7a) (32.2 g, 211.3 mmol) in THF (500 mL), 10% palladium on carbon (33.8 g, 31.7 mmol) was added. The reaction mixture was stirred under hydrogen (25 psi) for 20 h. The reaction mixture was filtered and the filtrate was concentrated under reduced pressure to give 3-fluoro-2-(propan-2-yl)phenol (7b) (29.1 g, 89.2%) as a yellow oil. $^1$H NMR (400 MHz, DMSO-$d_6$) δ=9.68 (s, 1H), 7.02-6.91 (m, 1H), 6.61 (d, J=8.1 Hz, 1H), 6.52 (dd, J=8.7, 10.7 Hz, 1H), 3.41-3.34 (m, 1H), 1.24 (dd, J=0.7, 7.0 Hz, 6H).

Step 3: 3-fluoro-2-(propan-2-yl)phenyl trifluoromethanesulfonate (7c)

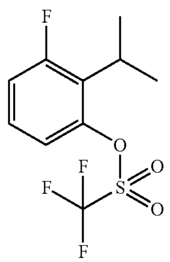 [SMILES: CC(C)c1c(F)cccc1OS(=O)(=O)C(F)(F)F]

A solution of 3-fluoro-2-(propan-2-yl)phenol (7b) (29.1 g, 189 mmol) and TEA (28.6 g, 39.5 mL, 283 mmol) in DCM (450 mL) was cooled in an ice-water bath, and then trifluoromethanesulfonic anhydride (79.9 g, 47.6 mL, 283 mmol) was added drop-wise. After stirring for 2 h at 0° C. the reaction was poured into a mixture of saturated $NaHCO_3$ and ice. The aqueous was extracted with DCM (3×) and the combined organics were washed with brine, dried over $Na_2SO_4$, filtered, and concentrated. The residue was purified by silica gel chromatography (0-2% EtOAc/PE) to give 3-fluoro-2-(propan-2-yl)phenyl trifluoromethanesulfonate (7c) (40.0 g, 74.0%) as a yellow oil. $^1$H NMR (400 MHz, DMSO-$d_6$) δ=7.54-7.42 (m, 1H), 7.41-7.32 (m, 1H), 7.26 (d, J=8.4 Hz, 1H), 3.26-3.17 (m, 1H), 1.32 (dd, J=1.3, 7.0 Hz, 6H).

Step 4: 2-[3-fluoro-2-(propan-2-yl)phenyl]-4,4,5,5-tetramethyl-1,3,2-dioxaborolane (Intermediate 7)

Intermediate 7

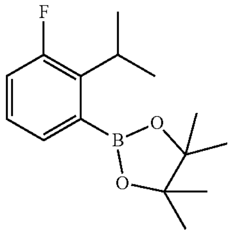

A mixture of -fluoro-2-(propan-2-yl)phenyl trifluoromethanesulfonate (7c) (40.0 g, 140 mmol), bis(pinacolato) diborane (53.2 g, 210 mmol), KOAc (27.4 g, 279 mmol) and bis(diphenylphosphino)ferrocene]dichloropalladium (5.11 g, 6.99 mmol) in dioxane (500 mL) was heated to 80° C. for 12 h. The reaction mixture was filtered, the filtrate was concentrated under reduced pressure, and the residue was purified by silica gel chromatography (0-10% EtOAc/PE) to give 2-[3-fluoro-2-(propan-2-yl)phenyl]-4,4,5,5-tetramethyl-1,3,2-dioxaborolane (Intermediate 7) (20.9 g, 56.8%) as a light-yellow oil. 1H NMR (400 MHz, DMSO-$d_6$) δ=7.36 (dd, J=1.8, 6.8 Hz, 1H), 7.26-7.14 (m, 2H), 3.60 (td, J=7.0, 13.6 Hz, 1H), 1.30 (s, 12H), 1.27 (d, J=1.5 Hz, 3H), 1.25 (d, J=1.5 Hz, 3H).

Preparation of Intermediate 8: 2-methyl-8-oxa-2-azaspiro[4.5]decane-3-carboxylic acid Intermediate 8

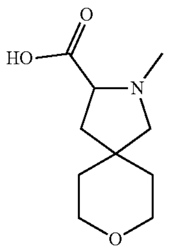

To a solution of 2-(tert-butoxycarbonyl)-8-oxa-2-azaspiro[4.5]decane-3-carboxylic acid (100 mg, 0.35 mmol) in DCM (3.5 mL), HCl (4 N in dioxane, 0.876 mL, 3.5 mmol) was added. After 4 h, the reaction was concentrated in vacuo. The residue was dissolved in 1:1 formic acid: formaldehyde (37% in water) and heated to 100° C. overnight. The reaction was concentrated and then the residue was dissolved in 1:1 MeOH:DCM and loaded onto a SCX-2 cartridge. Next, the cartridge was rinsed with 1:1 MeOH:DCM followed by 7N $NH_3$ in MeOH to give 2-methyl-8-oxa-2-azaspiro[4.5]decane-3-carboxylic acid (Intermediate 8) (69 mg, 99%). LCMS APCI (+) 200.1 (M+H).

Preparation of Intermediate 9: 2-methyl-2-azaspiro[4.4]nonane-3-carboxylic acid

Intermediate 9

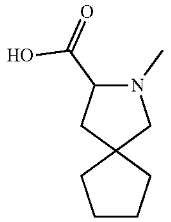

Intermediate 9 was made in a similar manner as Intermediate 8 without Boc deprotection starting from 2-azaspiro[4.4]nonane-3-carboxylic acid. LCMS APCI (+) 184.1 (M+H). $^1$H NMR (400 MHz, MeOD) δ=4.38 (dd, J=7.5, 9.8 Hz, 1H), 3.58 (d, J=11.5 Hz, 1H), 3.19 (d, J=11.5 Hz, 1H), 3.07-2.97 (m, 3H), 2.53 (dd, J=9.8, 13.4 Hz, 1H), 2.14 (dd, J=7.4, 13.4 Hz, 1H), 1.83-1.64 (m, 8H)

Preparation of Intermediate 10: 4,4-dimethyl-1-($^2H_3$)methylproline

Step 1: 2-benzyl 1-(tert-butyl) (2S)-4,4-dimethylpyrrolidine-1,2-dicarboxylate (10a)

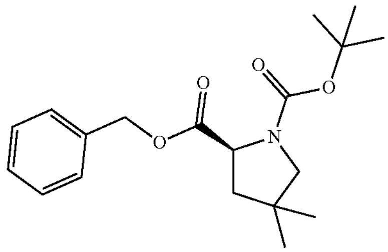 [SMILES: CC1(C)C[C@@H](C(=O)OCc2ccccc2)N(C(=O)OC(C)(C)C)C1]

To a mixture of 1-(tert-butoxycarbonyl)-4,4-dimethyl-L-proline (1.02 g, 4.18 mmol) and potassium carbonate (637 mg, 4.61 mmol) in acetonitrile (14 ml) at 23° C., benzyl bromide (497 μl, 4.19 mmol) was added. The mixture was stirred for 23 hours at 23° C., and then the reaction mixture was diluted with EtOAc and water. The EtOAc layer was washed with brine, dried over $Na_2SO_4$, filtered, and concentrated under reduced pressure and the residue was purified by column chromatography (0-100% EtOAc/Heptane) to give 2-benzyl 1-(tert-butyl) (2S)-4,4-dimethylpyrrolidine-1,2-dicarboxylate (10a) as a colorless oil (1.17 g, 84%). LCMS ESI (+) 356.1 (M+Na). $^1$H NMR (400 MHz, $CDCl_3$) δ ppm 7.29-7.41 (m, 5H) 5.05-5.32 (m, 2H) 4.27-4.44 (m, 1H) 3.15-3.42 (m, 2H) 1.99-2.10 (m, 1H) 1.68-1.81 (m, 1H) 1.33-1.49 (m, 9H) 1.03-1.14 (m, 6H)

Step 2: benzyl 4,4-dimethyl-L-prolinate (10b)

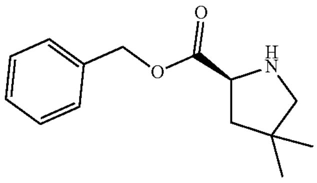 [SMILES: CC1(C)CN[C@H](C(=O)OCc2ccccc2)C1]

A mixture of 2-benzyl 1-(tert-butyl) (2S)-4,4-dimethylpyrrolidine-1,2-dicarboxylate (10a) (1.17 g, 3.52 mmol) in DCM (9 ml) and 4 N HCl in 1,4-dioxane (8.81 ml, 35.2 mmol) was stirred at 23° C. for 1.5 hours. The reaction mixture was concentrated to an oil under reduced pressure then EtOAc and saturated $NaHCO_3$ (aq) were added. The EtOAc layer was washed with brine, dried over $Na_2SO_4$, filtered, and concentrated under reduced pressure to give benzyl 4,4-dimethyl-L-prolinate (10c) as a light amber liquid (825 mg, 100%). LCMS ESI (+) 234.1 (M+H). $^1H$ NMR (400 MHz, $CDCl_3$) δ ppm 7.29-7.46 (m, 5H) 5.09-5.25 (m, 2H) 3.94 (t, J=8.01 Hz, 1 H) 3.61-3.81 (m, 1H) 2.63-2.88 (m, 2H) 2.47 (br s, 2H) 1.96 (dd, J=12.72, 8.80 Hz, 1H) 1.67 (dd, J=12.72, 7.21 Hz, 1H) 1.08 (s, 3H) 1.04 (s, 3H).

Step 3: benzyl 4,4-dimethyl-1-($^2H_3$)methyl-L-prolinate (10d)

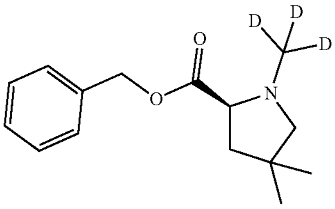 [SMILES: [2H]C([2H])([2H])N1CC(C)(C)C[C@H]1C(=O)OCc1ccccc1]

A mixture of benzyl 4,4-dimethyl-L-prolinate (10c) (241 mg, 1.03 mmol) and potassium carbonate (286 mg, 2.07 mmol) in $CD_3CN$ (3.44 ml) was sparged with dry nitrogen for 5 minutes. The mixture was cooled in an ice-water bath, and then iodomethane-$d_3$ (51.4 μl, 0.826 mmol) was added. After 3 hours, the reaction mixture was diluted with EtOAc and water. The EtOAc layer was washed with brine, dried over $Na_2SO_4$, filtered, and concentrated under reduced pressure, and the residue was purified by column chromatography (0-100% EtOAc/Heptane) to give benzyl 4,4-dimethyl-1-($^2H_3$)methyl-L-prolinate (10d) as a colorless liquid (77 mg, 30%). LCMS ESI (+) 251.2 (M+H). $^1H$ NMR (400 MHz, $CDCl_3$) δ ppm 7.29-7.42 (m, 5H) 5.10-5.27 (m, 2H) 3.16 (t, J=8.38 Hz, 1H) 2.92 (d, J=9.05 Hz, 1H) 2.20 (d, J=9.05 Hz, 1H) 1.96 (dd, J=12.72, 8.93 Hz, 1H) 1.81 (dd, J=12.72, 7.83 Hz, 1H) 1.17 (s, 3H) 1.07 (s, 3H).

Step 4: 4,4-dimethyl-1-($^2H_3$)methyl-L-proline (Intermediate 10)

Intermediate 10

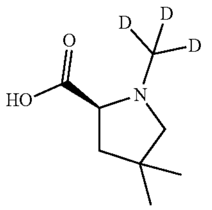

A mixture of benzyl 4,4-dimethyl-1-($^2H_3$)methyl-L-prolinate (77 mg, 0.31 mmol) and 10% Palladium on Carbon (8 mg) in ethanol (1.0 ml) was hydrogenated at 1 atm (balloon) and RT for 17 hours. The reaction mixture was diluted with methanol and then filtered through celite. The filtrate was concentrated under reduced pressure to give 4,4-dimethyl-1-($^2H_3$)methyl-L-proline as a white solid (Intermediate 10) (48 mg, 97%). $^1H$ NMR (400 MHz, $CDCl_3$) δ ppm 3.75-3.96 (m, 2H) 2.71 (br d, J=10.88 Hz, 1H) 2.29 (dd, J=13.39, 9.23 Hz, 1H) 2.13 (dd, J=13.45, 7.82 Hz, 1H) 1.21 (d, J=4.03 Hz, 6H)

Preparation of Intermediate 11: methyl 2-(3-bromo-4-hydroxyphenyl)propanoate

Step 1: methyl-2-(3-bromo-4-methoxyphenyl)propanoate (11a)

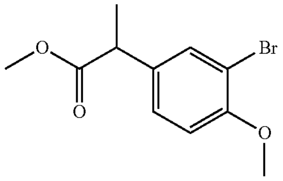

To a solution of methyl 2-(3-bromo-4-methoxyphenyl) acetate (in THF (50 mL), sodium hydride (60% in oil) (810 mg, 20.3 mmol) was added at 15° C. After 30 min, the reaction was cooled to 0° C., and methyl iodide (2.79 g, 19.7 mmol) was added. Removed ice-bath and stirred for 16 h. The reaction mixture was added to saturated aq.$NH_4Cl$ (100 mL) at 0° C. and extracted with EtOAc (3×). The combined organics were washed with brine, dried over $Na_2SO_4$ and concentrated under reduced pressure. The crude product was purified by flash column chromatography (0-10% EtOAc/PE) to give methyl -2-(3-bromo-4-methoxyphenyl)propanoate (11a) (3.2 g, 60.7%) as colorless oil. $^1H$ NMR (400 MHz, DMSO-d6) δ ppm 7.49 (d, J=2.1 Hz, 1H) 7.26 (dd, J=2.2, 8.4 Hz, 1H) 7.07 (d, J=8.5 Hz, 1H) 3.83 (s, 3H) 3.81-3.74 (m, 1H) 3.59 (s, 3H) 1.38 (d, J=8.0 Hz, 3H).

Step 2: 2-(3-bromo-4-hydroxyphenyl)propanoic acid (11 b)

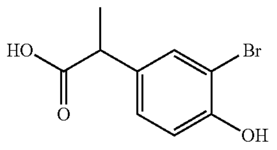

To a solution of methyl-2-(3-bromo-4-methoxyphenyl) propanoate in acetic acid (24.0 mL), HBr (12.0 mL) was added. The resulting solution was heated at 110° C. for 24 h. The reaction mixture was cooled to rt, then extracted with EtOAc (2×30 mL). The combined organic layers were washed with brine (30 mL), dried over $Na_2SO_4$, and concentrated. The crude product was purified by flash column chromatography (0-40% EtOAc/PE) to give 2-(3-bromo-4-hydroxyphenyl)propanoic acid (11b) (1.6 g, 66% yield) as a colorless oil. $^1H$ NMR (400 MHz, DMSO-d6) δ ppm 12.29 (br s, 1H) 10.15 (s, 1H) 7.37 (d, J=2.0 Hz, 1H) 7.09 (dd, J=2.2, 8.4 Hz, 1H) 6.90 (d, J=8.4 Hz, 1H) 3.58 (q, J=7.0 Hz, 1H) 1.31 (d, J=7.3 Hz, 3H).

Intermediate 11

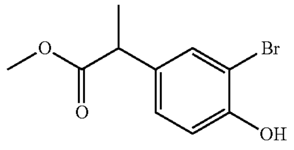

A solution of 2-(3-bromo-4-hydroxyphenyl)propanoic acid (11b) (1.95 g, 7.95 mmol) in MeOH (25.0 mL) was cooled to 0° C. then thionyl chloride was added slowly. The ice bath was removed, and the reaction was stirred at rt for 16 h. The reaction mixture was concentrated under reduced pressure and the residue was dissolved in EtOAc (30 mL), washed with saturated $NaHCO_3$ (10 mL), brine (10 mL), dried over $Na_2SO_4$, filtered, and concentrated under reduced pressure to give methyl 2-(3-bromo-4-hydroxyphenyl)propanoate (Intermediate 11) (1.67 g, 81.0% yield) as a yellow oil. $^1H$ NMR (400 MHz, DMSO-d6) δ ppm 10.20 (s, 1H) 7.38 (s, 1H) 7.10 (d, J=8.0 Hz, 1H) 6.91 (d, J=8.0 Hz, 1H) 3.71 (q, J=6.7 Hz, 1H) 3.58 (d, J=1.4 Hz, 3H) 1.35 (d, J=8.8 Hz, 3H) 1.34 (br d, J=7.1 Hz, 3H)

Preparation of Intermediate 12: 2-(2-ethyl-3-fluorophenyl)-4,4,5,5-tetramethyl-1,3,2-dioxaborolane Step 1: 1-(2-bromo-6-fluorophenyl)ethan-1-ol (12a)

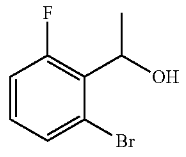

To a solution of 2-fluoro-6-bromobenzaldehyde (3.0 g, 1.8 mL, 14.78 mmol) at 0° C., $CH_3MgBr$ (8.69 mL, 3.4 M, 29.56 mmol) was added dropwise. The resulting mixture was stirred at 0° C. for 40 min. The reaction was quenched with saturated $NH_4Cl$ (100 mL) and extracted with EtOAc (2×100 mL). The combined organic layers were dried over $Na_2SO_4$, filtered and concentrated. The crude product was purified by flash column chromatography (0-20% EtOAc/heptane) to give 1-(2-bromo-6-fluorophenyl)ethan-1-ol (12a) (2.91 g, 13.3 mmol, 89.9%) as a colorless oil. $^1H$ NMR (400 MHz, $CDCl_3$) δ 7.25 (td, J=1.1, 7.9 Hz, 1H), 7.01 (dt, J=6.1, 8.1 Hz, 1H), 6.97-6.89 (m, 1H), 5.30-5.21 (m, 1H), 1.52 (dd, J=1.1, 6.7 Hz, 3H)

Step 2: 1-Bromo-2-ethyl-3-fluorobenzene (12b)

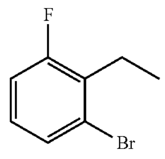

To a suspension of $InCl_3$ (0.26 g, 1.2 mmol) in 1,2-dichloroethane (50 mL), chlorodimethylsilane (2.6 mL, 24 mmol) was added followed by 1-(2-bromo-6-fluorophenyl) ethan-1-01 (12a) (2.6 g, 12 mmol) in 1,2-dichloroethane (10 mL). The resulting mixture was stirred at RT for 1 hr, and then heated at 80° C. for 3 hr. The mixture was cooled to RT, filtered, and washed with heptane. The filtrate was concentrated under reduced pressure. The crude product was purified by flash column chromatography (heptane) to give 1-bromo-2-ethyl-3-fluorobenzene as a colorless oil (12b) (1.75 g, 73%). $^1H$ NMR (400 MHz, $CDCl_3$) δ 7.45-7.31 (m, 1H), 7.12-6.91 (m, 2H), 2.85 (dq, J=2.2, 7.5 Hz, 2H), 1.20 (t, J=7.5 Hz, 3H)

Step 3: 2-(2-ethyl-3-fluorophenyl)-4,4,5,5-tetramethyl-1,3,2-dioxaborolane (Intermediate 12)

Intermediate 12

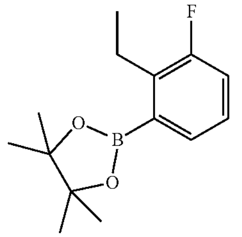

A mixture of 1-bromo-2-ethyl-3-fluorobenzene (12b) (586 mg, 2.89 mmol), KOAc (850 mg, 8.66 mmol), and $B_2Pin_2$ (879 mg, 3.46 mmol) in 1,4-dioxane (14.4 mL) was degassed three times, then Pd(dppf)$Cl_2$-DCM (189 mg, 0.231 mmol) was added. The mixture was heated at 100° C. for 18 hr. The reaction mixture was cooled to RT and the volatile was removed under reduced pressure. The crude mixture was purified by flash column chromatography (0-20% EtOAc/heptane) to give 2-(2-ethyl-3-fluorophenyl)-4,4,5,5-tetramethyl-1,3,2-dioxaborolane (Intermediate 12) as colorless oil (541 mg, 75%). $^1H$ NMR (400 MHz, $CDCl_3$) δ 7.64-7.47 (m, 1H), 7.19-7.11 (m, 1H), 7.10-7.02 (m, 1H), 2.96 (dq, J=2.0, 7.5 Hz, 2H), 1.36 (s, 12H), 1.17 (t, J=7.4 Hz, 3H).

Preparation of Intermediate 13: 2-(2-cyclopropyl-3-fluorophenyl)-4,4,5,5-tetramethyl-1,3,2-dioxaborolane Intermediate 13

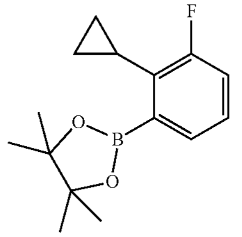

A mixture of 1-bromo-2-cyclopropyl-3-fluorobenzene (430 mg, 2.00 mmol), 4,4,4',4',5,5,5',5'-octamethyl-2,2'-bi(1,3,2-dioxaborolane) (609 mg, 2.40 mmol), $PdCl_2$(dppf).DCM (81.7 mg, 0.1 mmol), and potassium acetate (589 mg, 6.00 mmol) in toluene (5 ml) was sparged with dry nitrogen for 5 minutes then heated to 95° C. for 20 hours. The reaction mixture was diluted with EtOAc and water, and then filtered through a sintered glass funnel containing celite. The clear amber EtOAc layer was washed with brine, dried over $Na_2SO_4$, filtered, and concentrated under reduced pressure. The residue was purified by silica gel chromatography (0-100% EtOAc/Heptane) to give 2-(2-cyclopropyl-3-fluorophenyl)-4,4,5,5-tetramethyl-1,3,2-dioxaborolane (Intermediate 13) (406 mg, 77%) as an amber liquid. $^1H$ NMR (400 MHz, $CDCl_3$) b ppm 7.42 (d, J=7.21 Hz, 1H) 7.13 (td, J=7.67, 4.95 Hz, 1H) 7.00 (dd, J=11.43, 8.25 Hz, 1H) 2.20 (tt, J=8.67, 5.58 Hz, 1H) 1.38 (s, 12H) 0.89-0.99 (m, 2H) 0.77-0.87 (m, 2H).

Preparation of Intermediate 14: 2-(2-cyclobutyl-3,4-difluorophenyl)-4,4,5,5-tetramethyl-1,3,2-dioxaborolane Step 1: 1-(2,3-difluoro-6-methoxyphenyl)cyclobutan-1-ol (14a)

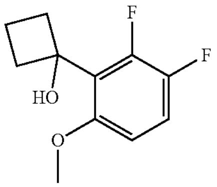

To a solution of 1,2-difluoro-4-methoxybenzene (721 mg, 5 mmol) in THF (5.00 ml) cooled in a dry-ice acetone bath, 1 M LDA (5.50 ml, 5.50 mmol) was added. After 1-hour, cyclobutanone (747 μl, 10.0 mmol) was added neat. The reaction mixture was allowed to warm to 23° C. for 18 hours then quenched with saturated $NH_4Cl$(aq) and diluted with water and EtOAc. The EtOAc layer was washed with brine, dried over $Na_2SO_4$, filtered, and concentrated under reduced pressure. The residue was purified by column chromatography (0-100% EtOAc/heptane) to give 1-(2,3-difluoro-6-methoxyphenyl)cyclobutan-1-ol (14a) (463 mg, 39%) as a light amber oil. LCMS ESI (+) 197.1 (MH-$H_2O$). 1H NMR (400 MHz, CHLOROFORM-d) b ppm 7.00 (q, J=9.17 Hz, 1H) 6.49-6.61 (m, 1H) 3.82 (s, 3H) 2.64-2.79 (m, 2H) 2.39-2.51 (m, 2H) 2.25-2.38 (m, 1H) 1.81-1.95 (m, 1H).

Step 2: 2-cyclobutyl-3,4-difluoro-1-methoxybenzene (14b)

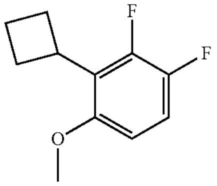

To a solution of 1-(2,3-difluoro-6-methoxyphenyl)cyclobutan-1-ol (14a) (460 mg, 2.15 mmol) in DCM (7 ml) cooled in an ice-water bath, triethyl silane (1.03 ml, 6.44 mmol) was added followed by TFA (622 μl, 8.59 mmol). After 1 hour, the reaction mixture was concentrated under reduced pressure, and then the residue was purified by column chromatography (0-100% EtOAc/heptane) to give 2-cyclobutyl-3,4-difluoro-1-methoxybenzene (14b) (413 mg, 64%) as an oil. $^1$H NMR (400 MHz, $CDCl_3$) δ ppm 6.91 (q, J=9.17 Hz, 1H) 6.50 (ddd, J=9.11, 3.73, 2.08 Hz, 1H) 3.80-3.93 (m, 1H) 3.79 (s, 3H) 2.42-2.59 (m, 2H) 2.23-2.39 (m, 2H) 1.83-2.12 (m, 2H) 0.95 (t, J=7.95 Hz, 3H) 0.53 (q, J=7.99 Hz, 2H).

Step 3: 2-cyclobutyl-3,4-difluorophenol (14c)

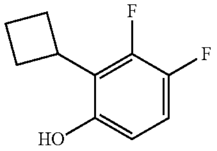 [SMILES: Oc1ccc(F)c(F)c1C1CCC1]

To a solution of 2-cyclobutyl-3,4-difluoro-1-methoxybenzene (14b) (389 mg, 1.96 mmol), AcOH (4 ml, 70 mmol) was added followed by 48 wt % HBr (1.6 ml, 14 mmol). The mixture was heated to 100° C. for 48 hours. The reaction mixture was diluted with EtOAc, washed with water, saturated $NaHCO_3$ (aq) and brine, dried over $MgSO_4$, filtered, and concentrated under reduced pressure. Next, the residue was purified by column chromatography (0-10% EtOAc/Heptane) to give 2-cyclobutyl-3,4-difluorophenol (14c) (234 mg, 64%) as an orange oil. $^1$H NMR (400 MHz, $CDCl_3$) δ ppm 6.84 (q, J=9.05 Hz, 1H) 6.44 (ddd, J=9.02, 3.88, 2.14 Hz, 1H) 4.66 (br s, 1H) 3.70-3.82 (m, 1H) 2.46-2.58 (m, 2H) 2.34-2.43 (m, 2H) 2.06 (s, 1H) 1.89-1.99 (m, 1H)

Step 4: 2-cyclobutyl-3,4-difluorophenyl trifluoromethanesulfonate (14d)

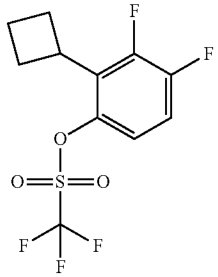 [SMILES: O=S(=O)(Oc1ccc(F)c(F)c1C1CCC1)C(F)(F)F]

To a flask containing 2-cyclobutyl-3,4-difluorophenol (14c) (234 mg, 1.27 mmol), pyridine (6.35 ml) was added. The solution was cooled in an ice water bath, and then a 1 M solution of triflicanhydride (2.54 ml, 2.54 mmol) in DCM was added dropwise. After 1.5 hrs, the reaction mixture was concentrated under reduced pressure, and then the residue was dissolved in EtOAc and washed with 1 N HCl (aq) and 1 N NaOH (aq). The EtOAc solution was dried over $MgSO_4$, filtered, and concentrated under reduced pressure to give 2-cyclobutyl-3,4-difluorophenyl trifluoromethanesulfonate (14d) (318 mg, 79%) as an orange oil. $^1$H NMR (400 MHz, $CDCl_3$) δ ppm 7.08 (q, J=8.88 Hz, 1H) 6.96-7.02 (m, 1H) 3.73-3.86 (m, 1H) 2.40-2.54 (m, 4H) 2.03-2.16 (m, 1H) 1.91-2.01 (m, 1H).

Step 5: 2-(2-cyclobutyl-3,4-difluorophenyl)-4,4,5,5-tetramethyl-1,3,2-dioxaborolane (Intermediate 14)

Intermediate 14

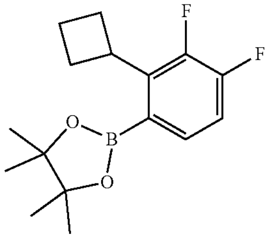

To a flask containing 2-cyclobutyl-3,4-difluorophenyl trifluoromethanesulfonate (14d) (318 mg, 1.01 mmol), 1,4-Dioxane (6.7 ml) was added followed by Bis(pinacolato) diborane (511 mg, 2.01 mmol) and potassium acetate (296 mg, 3.02 mmol). The mixture was sparged with dry nitrogen then $PdCl_2$(dppf).DCM (82.1 mg, 0.1 mmol) was added. The resulting mixture was heated to 100° C. for 20 hours. The reaction mixture was diluted with EtOAc, water, and brine. The mixture was filtered through celite and the EtOAc layer was dried over $MgSO_4$, filtered, and concentrated under reduced pressure. The residue was purified by silica gel chromatography (0-50% EtOAc/Heptanes) to give 2-(2- cyclobutyl-3,4-difluorophenyl)-4,4,5,5-tetramethyl-1,3,2-dioxaborolane (Intermediate 14) (260 mg, 88%) as an oil. $^1$H NMR (400 MHz, $CDCl_3$) δ ppm 9.31-9.39 (m, 1H) 8.87-8.95 (m, 1H) 6.16 (quin, J=9.19 Hz, 1H) 4.38-4.52 (m, 2H) 4.27-4.37 (m, 2H) 3.84-4.05 (m, 2H) 3.32 (s, 12H).

Preparation of Intermediate 15: tert-butyl [(1R,3R)-3-(2-bromo-4-iodophenoxy)cyclopentyl]carbamate Intermediate 15

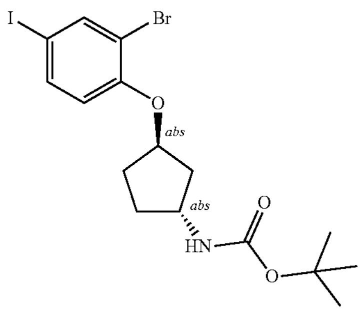

A solution of 2-bromo-4-iodophenol (800 mg, , and PPh in THF (24.0 mL) was cooled in an ice-water bath. was slowly added. The ice-water bath was removed and the reaction was stirred overnight. The reaction was concentrated under reduced pressure and the residue was purified by silica gel chromatography (0-20% EtOAc/PE) to give tert-butyl ((1R,3R)-3-(2-bromo-4-iodophenoxy)cyclopentyl)carbamate (15a) (0.97 g, 75.2% yield) as white solid. $^1$H NMR (400 MHz, $CDCl_3$) δ ppm 7.82 (d, J=2.0 Hz, 1H) 7.50 (dd, J=1.8, 8.7 Hz, 1H) 6.60 (d, J=8.6 Hz, 1H) 4.85-4.78 (m, 1H) 4.50 (br s, 1H) 4.30-4.17 (m, 1H) 2.41-2.20 (m, 2H) 2.19-2.08 (m, 1H) 1.99-1.86 (m, 1H) 1.84-1.73 (m, 1H) 1.46 (s, 10H).

Preparation of Intermediate 16: methyl [1-methyl-4-(4,4,5,5-tetramethyl-1,3,2-dioxaborolan-2-yl)-1H-pyrazol-3-yl]acetate Step 1: methyl 2-(1-methyl-1H-pyrazol-3-yl)acetate (16a)

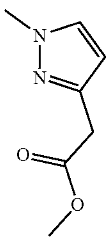

A solution of 2-(1-methyl-1H-pyrazol-3-yl)acetic acid (900 mg, 6.42 mmol) in MeOH (20.0 mL) was cooled in an ice-water bath, and then thionyl chloride (1.15 g, 9.63 mmol) was added drop-wise. Next, the ice-water bath was removed and the reaction was stirred overnight. The reaction was concentrated under reduced pressure and the residue was dissolved with DCM, then washed with saturated $NaHCO_3$ and brine. The organics were concentrated under reduced pressure to give methyl 2-(1-methyl-1H-pyrazol-3-yl)acetate (16a) (1.06 g, >99% crude yield) as light yellow oil. $^1$H NMR (400 MHz, $CDCl_3$) δ ppm 7.30 (d, J=2.1 Hz, 1H) 6.20 (d, J=2.2 Hz, 1H) 3.87 (s, 3H) 3.74 (s, 3H) 3.68 (s, 2H).

Step 2: methyl 2-(4-bromo-1-methyl-1 H-pyrazol-3-yl)acetate (16b)

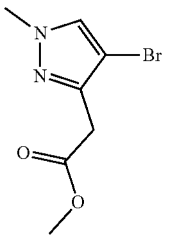

To a solution of methyl 2-(1-methyl-1 H-pyrazol-3-yl) acetate in ACN (65.0 mL), NBS (1.28 g, 7.22 mmol) was added. The reaction was stirred overnight then concentrated under reduced pressure. The residue was dissolved in EtOAc and then washed with saturated $Na_2CO_3$ and brine. The organics were dried over $Na_2SO_4$, filtered, and concentrated to give methyl 2-(4-bromo-1-methyl-1H-pyrazol-3-yl)acetate (16b) (1.22 g, 76.1% yield) as brown yellow oil. LCMS APCI (+) 233.1 (M+H). $^1$H NMR (400 MHz, $CDCl_3$) δ ppm 7.37 (s, 1H) 3.87 (s, 3H) 3.74 (s, 3H) 3.71 (s, 2H).

Step 3: methyl 2-(1-methyl-4-(4,4,5,5-tetramethyl-1,3,2-dioxaborolan-2-yl)-1H-pyrazol-3-yl)acetate (Intermediate 16)

Intermediate 16

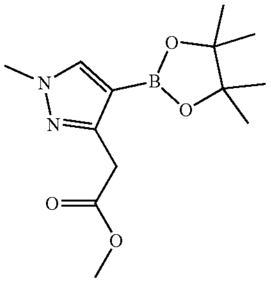

To a solution of methyl 2-(4-bromo-1-methyl-1 H-pyrazol-3-yl)acetate bispinacolatodiborane (981 mg, 3.86 mmol) and cesium fluoride (587 mg, 3.86 mmol) in dioxane, di(1-adamantyl)-n-butylphosphine (46.2 mg, 0.13 mmol) and palladium(II) acetate (14.4 mg, 0.06 mmol) were added. The reaction was heated at 100° C. for 16 hours under $N_2$. The reaction was concentrated and the residue was purified by silica gel chromatography (0-100% EtOAc/PE) to give methyl 2-(1-methyl-4-(4,4,5,5-tetramethyl-1,3,2-dioxaborolan-2-yl)-1H-pyrazol-3-yl)acetate (Intermediate 16) (340 mg, 94.3% yield) as yellow oil. LCMS APCI (+) 281.1 (M+H). $^1$H NMR (400 MHz, $CDCl_3$) δ ppm 7.60 (s, 1H) 3.87 (s, 5H) 3.72 (s, 3H) 1.28 (s, 12H).

Preparation of Intermediate 17: methyl 2-[1-methyl-4-(4,4,5,5-tetramethyl-1,3,2-dioxaborolan-2-yl)-1H-pyrazol-3-yl] propanoate Step 1: methyl 2-(4-bromo-1-methyl-1 H-pyrazol-3-yl)propanoate (17a)

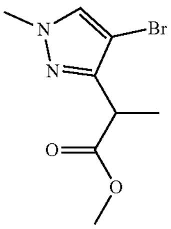

A solution of methyl 2-(4-bromo-1-methyl-1H-pyrazol-3-yl)acetate in THF (15 mL) was cooled in an ice-water bath then sodium hydride (60% on mineral oil, 126 mg, 3.15 mmol ) was added. After 30 min, methyl iodide (435 mg, 3.06 mmol) was added. The ice-bath was removed, and the reaction was stirred for 2 h. Quenched with saturated $NH_4Cl$ then extracted with EtOAc (2×). The combined organics were washed with brine, dried over $Na_2SO_4$, and concentrated under reduced pressure. The crude product was purified by silica gel chromatography (10-35% EtOAc/PE) to give methyl 2-(4-bromo-1-methyl-1 H-pyrazol-3-yl)propanoate (17a) (420 mg, 56.6%) as yellow oil. LCMS APCI (+) 247.1 (M+H). $^1H$ NMR (400 MHz, $CDCl_3$) δ ppm 7.34 (s, 1H) 3.91-3.88 (m, 1H) 3.86 (s, 3H) 3.72 (s, 3H) 1.55 (d, J=7.5 Hz, 3H).

Step 2: methyl 2-(1-methyl-4-(4,4,5,5-tetramethyl-1,3,2-dioxaborolan-2-yl)-1 H-pyrazol-3-yl)propanoate (Intermediate 17)

Intermediate 17

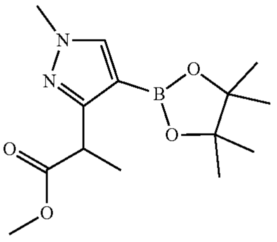

A mixture of methyl 2-(4-bromo-1-methyl-1H-pyrazol-3-yl)propanoate , 4,4,5,5-tetramethyl-1,3,2-dioxaborolane (829 mg, triethylamine (491 mg, and in dioxane (10 mL) was stirred at 100° C. under $N_2$ protection for 15 hours. The reaction was diluted with ice-water (15 mL) and extracted with EtOAc (2×). The combined organics were washed with brine, dried over $Na_2SO_4$, then filtered, and concentrated. The residue was purified by silica gel chromatography (15-35% EtOAc/PE) to give methyl 2-(1-methyl-4-(4,4,5,5-tetramethyl-1,3,2-dioxaborolan-2-yl)-1H-pyrazol-3-yl)propanoate (Intermediate 17) (350 mg, 73.5% yield) as yellow oil. LCMS APCI (+) 295.3 (M+H). $^1H$ NMR (400 MHz, $CDCl_3$) δ ppm 7.59 (s, 1H) 4.18-4.16 (m, 1H) 3.85 (s, 3H) 3.68 (s, 3H) 1.55 (d, J=7.3 Hz, 3H) 1.25 (s, 12H).

Preparation of Intermediate 18: methyl 2-methyl-2-[1-methyl-4-(4,4,5,5-tetramethyl-1,3,2-dioxaborolan-2-yl)-1H-pyrazol-3-yl]propanoate Step 1: methyl 2-(4-bromo-1-methyl-1H-pyrazol-3-yl)-2-methylpropanoate (18a)

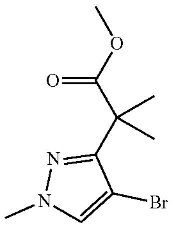

A solution of methyl 2-(4-bromo-1-methyl-1H-pyrazol-3-yl)propanoate in THF (10.0 mL) was cooled in an ice-water bath, then was added. After 1.5 h, then methyl iodide (494 mg, 3.48 mmol) was added, the ice-bath was removed, and the reaction was stirred for 2 hours. The reaction mixture was quenched with cold saturated $NH_4Cl$ (25 mL) and extracted with EtOAc (2×). The combined organics were washed with brine, dried over $Na_2SO_4$, filtered, and concentrated under reduced pressure. The crude product was redissolved in THF (10.0 mL) and cooled in an ice-water bath. Added LiHMDS (1.50 mL, 1.0 M THF solution) then after 1.5 h added methyl iodide (200 mg). Removed ice-bath and stirred for 2 h. The reaction mixture was quenched with cold saturated $NH_4Cl$ (25 mL) and extracted with EtOAc (2×). The combined organics were washed with brine, dried over $Na_2SO_4$, filtered, and concentrated under reduced pressure to give methyl 2-(4-bromo-1-methyl-1H-pyrazol-3-yl)-2-methylpropanoate (18a) (400 mg, 88% yield) as yellow oil. LCMS APCI (+) 261.2 (M+H). $^1H$ NMR (400 MHz, $CDCl_3$) δ ppm 7.35 (s, 1H) 3.86 (s, 3H) 3.71 (s, 3H) 1.62 (s, 6H).

Step 2: methyl 2-methyl-2-(1-methyl-4-(4,4,5,5-tetramethyl-1,3,2-dioxaborolan-2-yl)-1H-pyrazol-3-yl)propanoate (Intermediate 18)

Intermediate 18

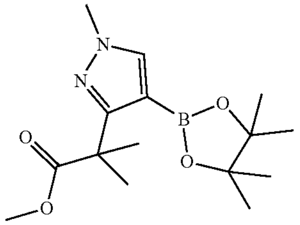

A mixture of methyl 2-(4-bromo-1-methyl-1H-pyrazol-3-yl)-2-methylpropanoate (, bispinacolatodiborane (686 mg, 5.36 mmol), triethylamine (407 mg, 4.02 mmol), and Pd(dppf)Cl in dioxane (5.0 mL) was degassed with $N_2$ then heated at 100° C. for 15 hours. Additional bispinacolatodiborane (686 mg, 5.36 mmol), triethylamine (407 mg, 4.02 mmol), and Pd(dppf)Cl in dioxane (5.0 mL), was degassed with $N_2$ and heated at 100° C. for another 15 hours. The reaction was diluted with ice-water and extracted with EtOAc (2×). The combined organics were washed with brine, dried over $Na_2SO_4$, filtered, and concentrated under reduced pressure. The residue was purified by silica gel chromatography (10-25% EtOAc/PE) to give methyl 2-methyl-2-(1-methyl-4-(4,4,5,5-tetramethyl-1,3,2-dioxaborolan-2-yl)-1H-pyrazol-3-yl) propanoate (Intermediate 18) (300 mg, 72.6% yield) as yellow oil. LCMS APCI (+) 309.3 (M+H). $^1H$ NMR (400 MHz, $CDCl_3$) δ ppm 7.63 (s, 1H) 3.84 (s, 3H) 3.66 (s, 3H) 1.62 (s, 6H) 1.28 (s, 12H).

Preparation of Intermediate 19: methyl 1-methyl-4-(4,4,5,5-tetramethyl-1,3,2-dioxaborolan-2-yl)-1H-pyrazole-3-carboxylate Intermediate 19

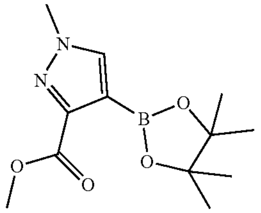

A mixture of methyl 4-bromo-1-methyl-1 H-pyrazole-3-carboxylate (1,4,4,5,5-tetramethyl-1,3,2-dioxaborolane (2.34 g, 18.3 mmol), Et, and Pd(dppf)CI in dioxane (15.0 mL) was stirred at 100° C. under $N_2$ protection for 15 hours. The reaction was poured into water (35 mL) and extracted with EtOAc (2×40 mL). The combined organic layers were washed with brine (30 mL), dried over $Na_2SO_4$, filtered, and concentrated. The residue was purified by silica gel chromatography (30-50% EtOAc/heptanes) to give methyl 1-methyl-4-(4,4,5,5-tetramethyl-1,3,2-dioxaborolan-2-yl)-1H-pyrazole-3-carboxylate (Intermediate 19) (200 mg, 16.5% yield) as a yellow solid. LCMS APCI (+) 267.3 (M+H). $^1$H NMR (400 MHz, $CDCl_3$) δ ppm 7.62 (s, 1H) 3.96 (s, 3H) 3.93 (s, 3H), 1.36 (s, 12H).

Preparation of Intermediate 20: 1-(tert-butoxycarbonyl)-3-fluoro-5,5-dimethylpiperidine-3-carboxylic acid Intermediate 20

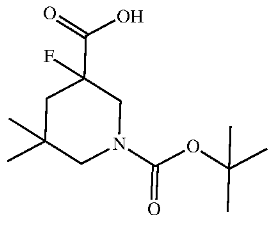

Intermediate 20 was made in a similar manner as Intermediate 3 starting from 1-(tert-butoxycarbonyl)-5,5-dimethylpiperidine-3-carboxylic acid. LCMS APCI (+) 220.1 (M+H-56). $^1$H NMR (400 MHz, $CDCl_3$) δ ppm 4.64-4.36 (m, 1H) 4.04-3.70 (m, 1H) 3.31-2.94 (m, 1H) 2.75-2.57 (m, 2H) 1.96-1.88 (m, 1H) 1.48 (s, 9H) 1.08 (s, 3H) 0.97 (s, 3H).

Preparation of Intermediate 21: 6-(tert-butoxycarbonyl)-8-fluoro-6-azaspiro[3.5]nonane-8-carboxylic acid Intermediate 21

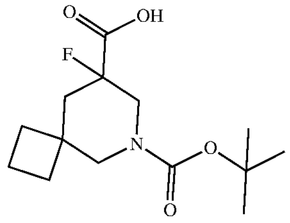

Intermediate 21 was made in a similar manner as Intermediate 3 starting from 6-(tert-butoxycarbonyl)-6-azaspiro[3.5]nonane-8-carboxylic acid. LCMS APCI (+) 188.2 (M+H-Boc). $^1$H NMR (400 MHz, DMSO-d6) δ=4.23-4.12 (m, 2H), 3.25-3.06 (m, 1H), 2.81-2.71 (m, 1H), 2.21-2.08 (m, 1H), 1.95-1.66 (m, 8H), 1.44-1.42 (m, 9H)

Preparation of Intermediate 22: tert-butyl (3aS,5R,6aR)-5-hydroxy-2,2-dimethyltetrahydro-2H-cyclopenta[d][1,3]oxazole-3(3aH)-carboxylate Step 1: (1R,4S)-4-(benzyloxy)cyclopent-2-en-1-yl acetate (22a)

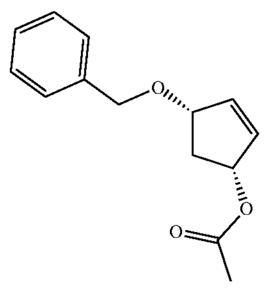 [SMILES: CC(=O)O[C@H]1C=C[C@@H](OCc2ccccc2)C1]

A mixture of (1R,4S)-4-hydroxycyclopent-2-en-1-yl acetate (2.78 g, 19.6 mmol), benzylbromide (4.01 g, 23.5 mmol) and silver(I)oxide (4.99 g, 21.5 mmol) in DCM (39.1 ml) was stirred at 23° C. for 19 hours. The reaction mixture was filtered through celite then concentrated under reduced pressure. The residue was purified by silica gel chromatography (0-100% EtOAc/Heptane) to give tert-butyl (3aS,5R,6aR)-5-hydroxy-2,2-dimethyltetrahydro-2H-cyclopenta[d]oxazole-3(3aH)-carboxylate (22a) (1.95 g, 43%) as a colorless oil. LCMS-ESI(+)=255.1 (M+Na), $^1$H NMR (400 MHz, $CDCl_3$) δ ppm 7.27-7.42 (m, 5H) 6.15 (dt, J=5.69, 1.56 Hz, 1H) 6.01 (dt, J=5.62, 1.59 Hz, 1H) 5.52 (ddt, J=6.02, 4.00, 0.98, 0.98 Hz, 1H) 4.54-4.63 (m, 2H) 4.52 (dddd, J=5.09, 4.20, 2.20, 0.86 Hz, 1H) 2.79 (dt, J=14.40, 7.29 Hz, 1H) 2.06 (s, 3H) 1.78 (dt, J=14.21, 4.39 Hz, 1H).

Step 2: (1R,4S)-4-(benzyloxy)cyclopent-2-en-1-ol (22b)

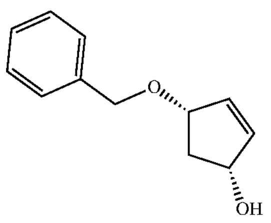 [SMILES: O[C@H]1C=C[C@@H](OCc2ccccc2)C1]

A mixture of (1R,4S)-4-(benzyloxy)cyclopent-2-en-1-yl acetate (22a) (1.95 g, 8.395 mmol) and potassium carbonate (1.39 g, 10.1 mmol) in methanol (28.0 ml) was stirred in an ice-water bath for 75 minutes. The reaction mixture was quenched with saturated $NH_4Cl$ (aq) then concentrated under reduced pressure. The mixture was diluted with EtOAc and water. The EtOAc layer was washed with brine, dried over $Na_2SO_4$, filtered, and concentrated under reduced pressure. The residue was purified by silica gel chromatography (0-100% EtOAc/Heptane) to give (1R,4S)-4-(benzyloxy)cyclopent-2-en-1-ol (22b) (1.488 g, 93%) as a colorless oil. LCMS-ESI(+)=208.1 (M+$H_2O$), $^1$H NMR (400 MHz, $CDCl_3$) δ ppm 7.29-7.41 (m, 5H) 6.05-6.10 (m, 2H) 4.64-4.70 (m, 1H) 4.54-4.64 (m, 2H) 4.47 (ddd, J=6.88, 4.13, 0.73 Hz, 1H) 2.69 (dt, J=14.06, 7.03 Hz, 1H) 1.70 (dt, J=14.03, 4.05 Hz, 1H), $$[\alpha]_D^{22} = -20.1°(c0.5, MeOH).$$

Step 3: (1R,4S)-4-(benzyloxy)cyclopent-2-en-1-yl 2,2,2-trichloroacetimidate (22c)

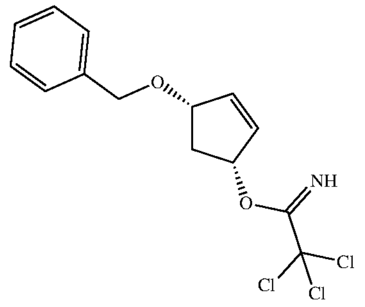 [SMILES: N=C(O[C@H]1C=C[C@@H](OCc2ccccc2)C1)C(Cl)(Cl)Cl]

To a solution of (1R,4S)-4-(benzyloxy)cyclopent-2-en-1-ol (22b) (1.48 g, 7.80 mmol) and 2,2,2-trichloroacetonitrile (861 ul, 8.59 mmol) in DCM (39.0 ml) at 23° C., DBU (117 ul, 0.781 mmol) was added. The mixture was stirred for 90 minutes then quenched with saturated $NH_4Cl$(aq) and diluted with DCM and water. The DCM layer was washed with brine, dried over $Na_2SO_4$, filtered, and concentrated under reduced pressure. The residue was purified by silica gel chromatography (0-100% EtOAc/Heptane) to give (1R,4S)-4-(benzyloxy)cyclopent-2-en-1-yl 2,2,2-trichloroacetimidate (22c) (2.22 g, 85%) as a colorless liquid. $^1$H NMR (400 MHz, $CDCl_3$) b ppm 8.31 (br s, 1H) 7.28-7.41 (m, 5H) 6.19-6.24 (m, 1H) 6.14-6.18 (m, 1H) 5.64-5.71 (m, 1H) 4.53-4.64 (m, 3H) 2.90 (dt, J=14.31, 7.27 Hz, 1H) 1.94 (dt, J=14.31, 4.52 Hz, 1H).

Step 4: (3aR,4S,5S,6aR)-5-(benzyloxy)-4-iodo-2-(trichloromethyl)-3a,5,6,6a-tetrahydro-4H-cyclopenta[d]oxazole (22d)

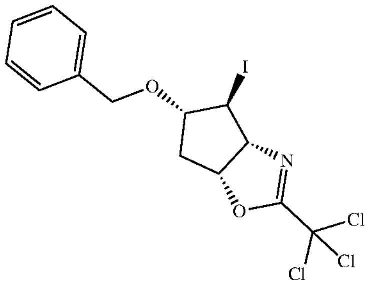 [SMILES: ClC(Cl)(Cl)C1=N[C@H]2[C@H](I)[C@@H](OCc3ccccc3)C[C@H]2O1]

To a solution of (1R,4S)-4-(benzyloxy)cyclopent-2-en-1-yl 2,2,2-trichloroacetimidate (22c) (2.22 g, 6.658 mmol) in DCM (22.2 ml) at 23° C., NIS (1.89 g, 7.99 mmol) was added. The reaction mixture was stirred for 3.5 hours and then quenched with 10% aqueous $Na_2S2O_3$. The layers were separated and then the aqueous layer was washed with DCM. The combined DCM extracts were washed with brine, dried over $Na_2SO_4$, filtered, and concentrated under reduced pressure.

The residue was purified by silica gel chromatography (0-100% EtOAc/Heptane) to give (3aR,4S,5S,6aR)-5-(benzyloxy)-4-iodo-2-(trichloromethyl)-3a,5,6,6a-tetrahydro-4H-cyclopenta[d]oxazole (22d) (2.15 g, 70%) as a white solid. LCMS-ESI(+)=459.9/461.9 (M+H), $^1$H NMR (400 MHz, $CDCl_3$) δ ppm 7.28-7.39 (m, 5H) 5.48 (t, J=7.15 Hz, 1H) 5.19 (d, J=7.70 Hz, 1H) 4.68 (d, J=1.96 Hz, 1H) 4.41-4.59 (m, 2H) 4.34 (d, J=4.40 Hz, 1H) 2.75 (ddd, J=15.89, 6.48, 4.52 Hz, 1H) 2.52 (dd, J=15.96, 1.90 Hz, 1H).

$$[\alpha]_D^{21} = +13.4°(C0.6, CHCl3).$$

Step 5: (1R,2R,3S,4S)-2-amino-4-(benzyloxy)-3-iodocyclopentan-1-ol hydrochloride (22e)

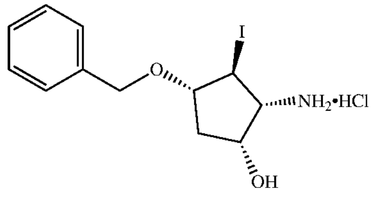

A mixture of (3aR,4S,5S,6aR)-5-(benzyloxy)-4-iodo-2-(trichloromethyl)-3a,5,6,6a-tetrahydro-4H-cyclopenta[d]oxazole (22d) (2.15 g, 4.67 mmol) and 2M HCl(aq) (6 ml, 10 mmol) in methanol (23.3 ml) was stirred at 23° C. for 20 hours. The reaction mixture was concentrated to a solid then suspended in MTBE. The solid was filtered and then dried at 70° C. under reduced pressure to give (1R,2R,3S,4S)-2-amino-4-(benzyloxy)-3-iodocyclopentan-1-ol hydrochloride (22e) (1.38 g, 81%) as a white solid. LCMS-ESI(+)=334.0 (M+H), $^1$H NMR (400 MHz, DMSO-d6) δ ppm 8.25 (br s, 3H) 7.25-7.41 (m, 5H) 4.50-4.65 (m, 2H) 4.12-4.22 (m, 2H) 4.09 (br s, 1H) 3.48-3.62 (m, 1H) 2.26-2.39 (m, 1H) 1.64-1.75 (m, 1H)

Step 6: (1R,2S,4R)-2-amino-4-(benzyloxy)cyclopentan-1-ol hydrochloride (22f)

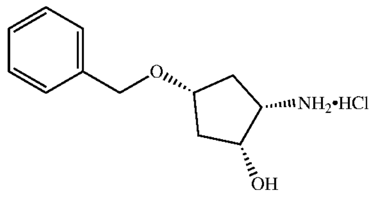

A suspension of (1R,2R,3S,4S)-2-amino-4-(benzyloxy)-3-iodocyclopentan-1-ol hydrochloride (22e) (1.35 g, 3.65 mmol) and AIBN (59.9 mg, 0.365 mmol) in a mixture of toluene (12.2 ml) and methanol (360 ul) was heated to 70° C. and then $(TMS)_3SiH$ (5.63 ml, 18.2 mmol) was added. The temperature was increased to 90° C. for 1 hour. The reaction mixture was concentrated to remove methanol and then the residue was diluted with EtOAc and 1 N HCl (5 ml). The layers were separated and the EtOAc layer was extracted with water. The water and HCl(aq) layer were pooled, then frozen and lyophilized to give (1R,2S,4R)-2-amino-4-(benzyloxy)cyclopentan-1-ol hydrochloride salt (22f) (1.26 g) as a light amber foam. LCMS-ESI (+)=208.1 (M+H), $^1$H NMR (400 MHz, $CD_3OD$) δ ppm 7.20-7.43 (m, 5H) 4.45-4.59 (m, 2H) 4.24-4.33 (m, 1H) 4.05-4.15 (m, 1H) 3.51 (td, J=7.06, 5.44 Hz, 1H) 2.23-2.40 (m, 2H) 1.87-2.02 (m, 2H).

Step 7: tert-butyl ((1 S,2R,4R)-4-(benzyloxy)-2-hydroxycyclopentyl)carbamate (22 g)

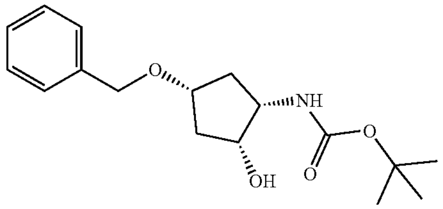 [SMILES: CC(C)(C)OC(=O)N[C@H]1C[C@@H](OCc2ccccc2)C[C@H]1O]

To a mixture of (1R,2S,4R)-2-amino-4-(benzyloxy)cyclopentan-1-ol (22f) (890 mg, 3.65 mmol) and Boc anhydride (956 mg, 4.38 mmol) in DCM (12.2 ml) cooled in an ice-water bath, TEA (1.02 ml, 7.3 mmol) was added. The mixture was allowed to warm to 23° C. over 17 hours and then purified by silica gel chromatography (0-100% EtOAc/Heptane) to give tert-butyl ((1S,2R,4R)-4-(benzyloxy)-2-hydroxycyclopentyl)carbamate (22 g) (837 mg, 75%) as a colorless oil. LCMS-ESI(+)=330.1 (M+Na), $^1$H NMR (400 MHz, $CDCl_3$) δ ppm 7.28-7.41 (m, 5H) 5.22-5.44 (m, 1H) 4.39-4.58 (m, 2H) 4.03-4.19 (m, 2H) 3.94 (br d, J=2.45 Hz, 1H) 2.50-2.91 (m, 1H) 2.40 (ddd, J=14.67, 8.50, 6.54 Hz, 1H) 2.02-2.12 (m, 2H) 1.87-2.00 (m, 1H) 1.76 (ddt, J=14.52, 7.18, 2.29, 2.29 Hz, 1H) 1.46 (s, 9H).

Step 8: tert-butyl (3aS,5R,6aR)-5-(benzyloxy)-2,2-dimethyltetrahydro-2H-cyclopenta[d]oxazole-3(3aH)-carboxylate (23h)

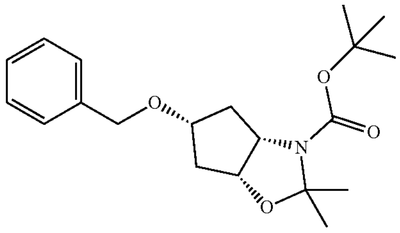 [SMILES: CC(C)(C)OC(=O)N1[C@H]2C[C@@H](OCc3ccccc3)C[C@H]2OC1(C)C]

A mixture of tert-butyl ((1S,2R,4R)-4-(benzyloxy)-2-hydroxycyclopentyl)carbamate (22 g) (834 mg, 2.71 mmol), 2,2-dimethoxypropane (667 ul, 5.43 mmol), and PTSA (46.7 mg, 0.271 mmol) in acetone (9.0 ml) was stirred at 23° C. for 17.5 hours. The reaction mixture was quenched with saturated $NaHCO_3$(aq), and then diluted with EtOAc and water. The EtOAc layer was washed with brine, dried over $Na_2SO_4$, filtered, and concentrated to an oil. The residue was purified by silica gel chromatography (EtOAc/Heptane 0-100%) to give tert-butyl (3aS,5R,6aR)-5-(benzyloxy)-2,2-dimethyltetrahydro-2H-cyclopenta[d]oxazole-3(3aH)-carboxylate (22h) (810 mg, 85%) as a colorless oil. LCMS-ESI(+)=248.2 (M-Boc+H). $^1$H NMR (400 MHz, $CDCl_3$) δ ppm 7.28-7.39 (m, 5H) 4.44-4.61 (m, 3H) 3.96-4.28 (m, 2H) 2.20-2.38 (m, 1H) 2.10-2.20 (m, 1H) 1.86-2.10 (m, 2H) 1.59-1.71 (m, 3H) 1.49 (br d, J=9.29 Hz, 9H) 1.44 (br d, J=9.78 Hz, 3H).

Step 9: tert-butyl (3aS,5R,6aR)-5-hydroxy-2,2-dimethyltetrahydro-2H-cyclopenta[d]oxazole-3(3aH)-carboxylate (Intermediate 22)

Intermediate 22

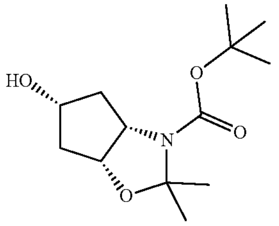

A mixture of tert-butyl (3aS,5R,6aR)-5-(benzyloxy)-2,2-dimethyltetrahydro-2H-cyclopenta[d]oxazole-3(3aH)-carboxylate (22h) (810 mg, 2.33 mmol) and 10% Pd/C (80 mg) in ethanol (7.77 ml) was hydrogenated (1 atm, balloon) at 23° C. for 1 hour. The reaction mixture was filtered through celite then concentrated under reduced pressure to give tert-butyl (3aS,5R,6aR)-5-hydroxy-2,2-dimethyltetrahydro-2H-cyclopenta[d]oxazole-3(3aH)-carboxylate (Intermediate 22) (592 mg, 99%) as a light tan solid. LCMS-ESI(+)=158.2 (M-Boc+H), $^1$H NMR (400 MHz, $CDCl_3$) δ ppm 4.67 (t, J=4.89 Hz, 1H) 4.28 (br s, 2H) 2.86 (br dd, J=5.69, 2.14 Hz, 1H) 2.20 (br d, J=14.92 Hz, 1H) 2.00-2.17 (m, 2H) 1.81 (dt, J=14.95, 4.63 Hz, 1H) 1.67 (br s, 3H) 1.49 (s, 9H) 1.43-1.47 (m, 3H).

Preparation of Intermediate 23: tert-butyl {(1R,3R)-3-[4-(5-amino-3-methyl-1H-pyrazol-1-yl)-2-bromophenoxy]cyclopentyl}carbamate Step 1: (2E)-3-aminobut-2-enenitrile (23a)

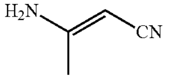

To a solution of acetonitrile (500 mg in dimethoxyethane (18.0 mL), LiHMDS (1.02 g was added. The mixture was heated to 90° C. for 18 h and then concentrated under reduced pressure. The residue was diluted with water then extracted with EtOAc (3×). The combined organics were dried over $Na_2SO_4$, filtered, and concentrated. The crude product which was purified by silica gel chromatography (0-60% EtOAc/PE) to give (2E)-aminobut-2-enenitrile (400 mg, 80% yield) (23a) as yellow oil. $^1$H NMR (400 MHz, DMSO-$d_6$) δ ppm 6.47 (br s, 4H) 3.89 (s, 1H) 3.61 (s, 3H) 1.93 (s, 3H) 1.76 (s, 3H).

Step 2: 2-bromo-1-methoxy-4-nitrobenzene (23b)

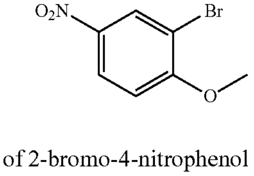

To a mixture of 2-bromo-4-nitrophenol (1.0 g, 4.59 mmol) and K in DMF (20 mL), methyl iodide (1.95 g, 13.8 mmol) was added. The reaction was stirred at RT for 16 hours. The reaction suspension was poured into ice-water then the solid was collected by filtration to give 2-bromo-1-methoxy-4-nitrobenzene (1.32 g, >99% crude yield) (23b) as white solid. $^1$H NMR (400 MHz, DMSO-$d_6$) δ ppm 8.43 (d, J=2.7 Hz, 1H) 8.29 (dd, J=2.8, 9.2 Hz, 1H) 7.34 (d, J=9.2 Hz, 1H) 4.01 (s, 3H).

Step 3: 3-bromo-4-methoxyaniline (23c)

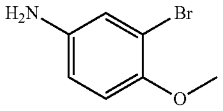

To a solution of 2-bromo-1-methoxy-4-nitrobenzene and NH in MeOH (20.0 mL), iron (1.59 g, 28.4 mmol) was added. The mixture was heated at 80° C. for 2 hours. The suspension was filtered. The filtrate was extracted with EtOAc (2×) and the combined organics were concentrated under reduced pressure to give 3-bromo-4-methoxyaniline (23c) (870 mg, 75.5% yield) as a brown solid. LCMS APCI (+) 202.1 (M+H). $^1$H NMR (400 MHz, $CDCl_3$) δ ppm 6.96 (d, J=2.7 Hz, 1H) 6.77 (d, J=8.6, Hz, 1H) 6.63 (dd, J=2.8, 8.6 Hz, 1H) 3.84 (s, 3H).

Step 4: (3-bromo-4-methoxyphenyl)hydrazine (23d)

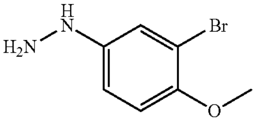

A solution of 3-bromo-4-methoxyaniline in H and concentrated HCl (11 mL) was cooled in an ice-water bath and then sodium nitrite (449 mg, 6.50 mmol) was added to the solution portion-wise. After 30 mins tin (II) chloride (1.96 g, 10.3 mmol) was added followed by drop-wase addition of concentrated HCl (11 mL). After 2 hrs, the solid was collected by filtration and washed with ethyl acetate to give (3-bromo-4-methoxyphenyl)hydrazine hydrochloride (23d) (670 mg, 71.7% yield) as light red solid. LCMS APCI (+) 218.1 (M+H). $^1$H NMR (400 MHz, DMSO-$d_6$) δ ppm 10.18 (br s, 3H) 7.30 (d, J=2.6, Hz, 1H) 7.09-7.00 (m, 2H) 3.80 (s, 3H).

Step 5: 1-(3-bromo-4-methoxyphenyl)-3-methyl-1H-pyrazol-5-amine (23e)

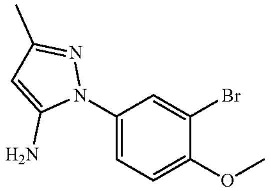 [SMILES: COc1ccc(-n2nc(C)cc2N)cc1Br]

A solution of (3-bromo-4-methoxyphenyl)hydrazine and 3-aminobut-2-enenitrile in concentrated HCl (5.00 mL) and H was stirred at 100° C. for 1 hour. The solution was cooled and then saturated aqueous lithium chloride (25 mL) was added. The solid was collected by filtration to give 1-(3-bromo-4-methoxyphenyl)-3-methyl-1H-pyrazol-5-amine (23d) (600 mg, 83.9% yield) as a yellow solid. LCMSAPCI (+) 282.0 (M+H). $^1$H NMR (400 MHz, DMSO-$d_6$) δ ppm 7.72 (d, J=2.4 Hz, 1H) 7.53 (dd, J=2.4, 8.8 Hz, 1H) 7.18 (d, J=8.9 Hz, 1H) 5.30 (s, 1H) 5.19 (br s, 2H) 3.88 (s, 3H) 2.05 (s, 3H).

Step 6: 4-(5-amino-3-methyl-1 H-pyrazol-1-yl)-2-bromophenol (23f)

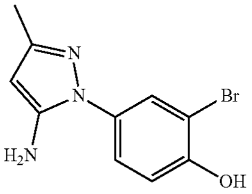

To a solution of 1-(3-bromo-4-methoxyphenyl)-3-methyl-1 H-pyrazol-5-amine in DCM (20.0 mL) was added BBr at −20° C. The resulting reaction mixture was stirred at 30° C. for 3 hours. The solution was poured into $H_2O$ (40 mL), and the pH was adjusted to pH ~7 with saturated $NaHCO_3$. Extracted with DCM (30×) and EtOAc (2×). The combined organics were concentrated under reduced pressure to give 4-(5-amino-3-methyl-1 H-pyrazol-1-yl)-2-bromophenol (23f) (425 mg, 89.4% yield) as a brownish yellow solid. LCMS APCI (+) 267.8 (M+H). $^1$H NMR (400 MHz, DMSO-$d_6$) δ ppm 10.37 (s, 1H) 7.59 (d, J=2.4 Hz, 1H) 7.33 (dd, J=2.5, 8.7 Hz, 1H) 6.99 (d, J=8.8 Hz, 1H) 5.27 (s, 1H) 5.15 (s, 2H) 2.03 (s, 3H).

Step 7: tert-butyl {(1R,3R)-3-[4-(5-amino-3-methyl-1H-pyrazol-1-yl)-2-bromophenoxy]cyclopentyl}carbamate (Intermediate 23)

Intermediate 23

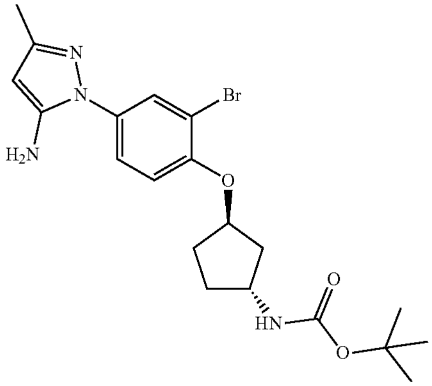

To a solution of 4-(5-amino-3-methyl-1H-pyrazol-1-yl)-2-bromophenol, tert-butyl ((1R,3S)-3-hydroxycyclopentyl) carbamate (479 mg, 2.38 mmol), and triphenylphosphine (832 mg, 3.17 mmol) in THF (15.0 mL), DIAD (641 mg, 3.17 mmol) was added drop-wise. After stirring overnight, the solution was concentrated under reduced pressure and the residue was purified by silica gel chromatography (0-50% EtOAc/PE) to give tert-butyl ((1R,3R)-3-(4-(5-amino-3-methyl-1H-pyrazol-1-yl)-2-bromophenoxy)cyclopentyl)carbamate Intermediate 23 (1.26 g, >99% crude yield) as a yellow solid. LCMS APCI (+) 472.9 (M+Na).

Preparation of Intermediate 24: methyl 2-(3-bromo-4-hydroxyphenyl)-2-methylbutanoate Step 1: methyl 2-(3-bromo-4-methoxyphenyl)butanoate (24a)

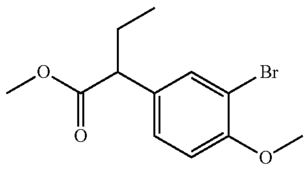

To a solution of methyl 2-(3-bromo-4-methoxyphenyl) acetate (5 g, 19.3 mmol) in THF (50.0 mL), NaH (60% in oil) (810 mg, 20.3 mmol) was added at 0° C. The mixture was stirred at 25° C. for 0.5 h, then ethyl iodide (3.07 g, 19.7 mmol) was added at 0° C. After addition, the mixture was stirred at 25° C. for 16 h. The solution was quenched with ice water, then extracted with EtOAc (3×). The combined organics were washed with brine, dried over $Na_2SO_4$, filtered, and concentrated. The residue was purified by silica gel chromatography (0-10% EtOAc/PE) to give methyl 2-(3-bromo-4-hydroxyphenyl)-2-methylbutanoate (24a) (3.4 g, 61.4% yield) as a yellow oil. $^1$H NMR (400 MHz, DMSO-$d_6$) δ ppm 7.48 (d, J=2.1 Hz, 1H) 7.26 (dd, J=2.1, 8.5 Hz, 1H) 7.07 (d, J=8.5 Hz, 1H) 3.82 (s, 3H) 3.58 (s, 3H) 3.55-3.48 (m, 1H) 1.98-1.87 (m, 1H) 1.74-1.58 (m, 1H) 0.89-0.71 (m, 3H).

Step 2: methyl 2-(3-bromo-4-methoxyphenyl)-2-methylbutanoate (24b)

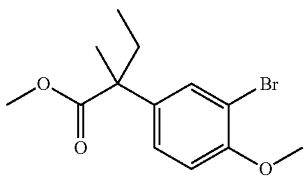

To a solution of methyl 2-(3-bromo-4-hydroxyphenyl)-2-methylbutanoate (24a) (2.0 g, 6.97 mmol) in THF (20.0 mL), LiHMDS (2.33 g, 13.9 mmol, 13.9 mL, 1.0 M THF solution) was added at 0° C. The resulting solution was stirred for 0.5 h, and then methyl iodide (1.98 g, 13.9 mmol) was added at −10° C. The reaction mixture was stirred at 25° C. for 3 h. The reaction was quenched with saturated $NH_4Cl$ then extracted with EtOAc (3×). The combined organics were washed with brine, dried over $Na_2SO_4$, filtered, and concentrated. The residue was purified by silica gel chromatography (0-10% EtOAc/PE) to give methyl 2-(3-bromo-4-methoxyphenyl)-2-methylbutanoate (24b) (1.6 g, 76.3% yield) as a colorless oil.

Step 3: 2-(3-bromo-4-hydroxyphenyl)-2-methylbutanoic acid (24c)

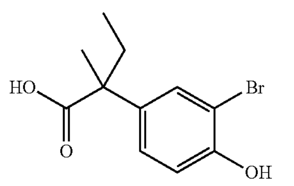

To a solution of in acetic acid (10.0 mL), hydrobromic acid (5.00 mL) was added. The reaction was heated at 110° C. for 16 h and then poured into $H_2O$ and extracted with EtOAc (3×). The combined organics were washed with brine, dried over $Na_2SO_4$, and concentrated. The residue was purified by silica gel chromatography (0-20% EtOAc/PE) to give 2-(3-bromo-4-hydroxyphenyl)-2-methylbutanoic acid (24c) (1.24 g, 92% yield) as a colorless oil. $^1$H NMR (400 MHz, DMSO-$d_6$) δ ppm 12.28 (br s, 1H) 10.15 (br s, 1H) 7.34 (d, J=2.4 Hz, 1H) 7.12 (dd, J=2.3, 8.5 Hz, 1H) 6.90 (d, J=8.5 Hz, 1H) 1.94-1.87 (m, 1H) 1.85-1.74 (m, 1H) 1.36 (s, 3H) 0.75 (t, J=7.3 Hz, 3H).

Step 4: methyl 2-(3-bromo-4-hydroxyphenyl)-2-methylbutanoate (Intermediate 24)

Intermediate 24

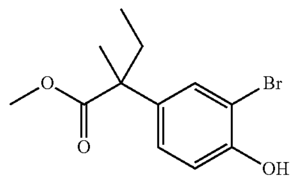

To a solution of 2-(3-bromo-4-hydroxyphenyl)-2-methylbutanoic acid (24c) (1.33 g, 4.87 mmol) in MeOH (15 mL), was added $H_2SO_4$ (1.5 mL). The reaction was refluxed at 80° C. for 16 hours and then concentrated. The residue was extracted with EtOAc (3×) and the combined organics were washed with saturated $NaHCO_3$, and brine, dried over $Na_2SO_4$, and concentrated to give methyl 2-(3-bromo-4-hydroxyphenyl)-2-methylbutanoate (Intermediate 24) (1.08 g 77.2% yield) as a light yellow oil. $^1$H NMR (400 MHz, DMSO-$d_6$) δ ppm 10.19 (s, 1H) 7.30 (d, J=2.3 Hz, 1H) 7.07 (dd, J=2.3, 8.6 Hz, 1H) 6.90 (d, J=8.6 Hz, 1H) 3.57 (s, 3H) 1.97-1.78 (m, 2H), 1.39 (s, 3H) 0.73 (t, J=7.4 Hz, 3H).

Preparation of Intermediate 25: methyl 1-ethyl-4-(4,4,5,5-tetramethyl-1,3,2-dioxaborolan-2-yl)-1H-pyrazole-3-carboxylate Step 1: methyl 4-bromo-1-ethyl-1 H-pyrazole-3-carboxylate (25a)

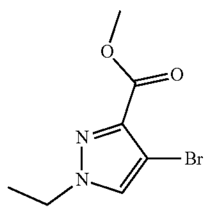

To a mixture of and K in ACN (20.0 mL), iodoethane (2.28 g, 14.6 mmol) was added dropwise. The reaction was heated at 60° C. for 16 hrs. The reaction was filtered and the filtrate was concentrated and purified by silica gel chromatography (0-50% EtOAc/PE) to provide methyl 4-bromo-1-ethyl-1H-pyrazole-3-carboxylate (25a) (1.5 g, 66% yield) as a light yellow solid. LCMS APCI (+) 233.0 (M+H). $^1$H NMR (400 MHz, $CDCl_3$) δ ppm 7.52 (s, 1H) 4.25 (q, J=7.3 Hz, 2H) 3.95 (s, 3H) 1.52 (t, J=7.3 Hz, 3H).

Step 2: methyl 1-ethyl-4-(4,4,5,5-tetramethyl-1,3,2-dioxaborolan-2-yl)-1H-pyrazole-3-carboxylate (Intermediate 25)

Intermediate 25

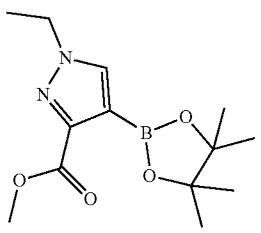

A mixture of methyl 4-bromo-1-ethyl-1H-pyrazole-3-carboxylate, bispinacolatodiborane (2.16 g, 8.50 mmol), and Pd(dppf)CI in dioxane (15.0 mL) was stirred at 100° C. for 16 hours. The reaction mixture was concentrated, and the residue was purified by silica gel chromatography (0-50% EtOAc/PE) to give methyl 1-ethyl-4-(4,4,5,5-tetramethyl-1,3,2-dioxaborolan-2-yl)-1H-pyrazole-3-carboxylate (Intermediate 25) (1.3 g, 82% yield) as a yellow oil. LCMSAPCI (+) 281.1 (M+H). $^1$H NMR (400 MHz, $CDCl_3$) δ ppm 7.63 (s, 1H) 4.25-4.20 (m, 2H) 3.89 (s, 3H) 1.50-1.43 (t, J=7.3 Hz, 3H) 1.33 (s, 12H).

Preparation of Intermediate 26: methyl 1-(propan-2-yl)-4-(4,4,5,5-tetramethyl-1,3,2-dioxaborolan-2-yl)-1H-pyrazole-3-carboxylate

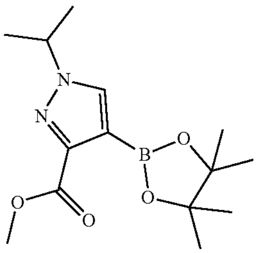 [SMILES: COC(=O)c1nn(C(C)C)cc1B1OC(C)(C)C(C)(C)O1]

Intermediate 26 was made in a similar fashion as Intermediate 25 using isopropyl iodide in place of ethyl iodide. LCMS APCI (+) 295.1 (M+H). $^1$H NMR (400 MHz, $CDCl_3$) b ppm 7.70 (s, 1H) 4.69-4.59 (m, 1H) 3.94 (s, 3H) 1.56-1.52 (m, 6H) 1.39 (s, 12H).

Preparation of Intermediate 27: methyl 1-cyclopropyl-4-(4,4,5,5-tetramethyl-1,3,2-dioxaborolan-2-yl)-1H-pyrazole-3-carboxylate Step 1: methyl 4-bromo-1-cyclopropyl-1 H-pyrazole-3-carboxylate (27a)

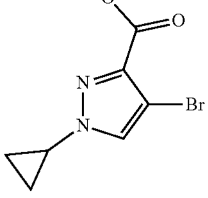

A mixture of 2,2-bipyridine (1.68 g, 10.7 mmol) and $Cu(OAc)_2$ (1.95 g, 10.7 mmol) in DCE (20 mL) was heated at 75° C. for 25 min then cooled to RT. Next, a solution of methyl 4-bromo-1H-pyrazole-3-carboxylate (2.0 g, 10 mmol) in DCE (20 mL), cyclopropylboronic acid (1.68 g, 19.5 mmol) and $Na_2CO_3$ (2.07 g, 19.5 mmol) was added to the mixture. The mixture was heated at 75° C. under 02 balloon for 4 h. The reaction mixture was filtered, and the filtrate was concentrated and purified by silica gel chromatography (0-30% EtOAc/PE) to give methyl 4-bromo-1-cyclopropyl-1H-pyrazole-3-carboxylate (27a) (1.16 g, 50% yield) as an oil. LCMS APCI (+) 244.9 (M+H). $^1$H NMR (400 MHz, DMSO-$d_6$) δ ppm 8.22 (s, 1H) 3.88-3.81 (m, 1H) 3.79 (s, 3H) 1.14-1.06 (m, 2H) 1.05-0.97 (m, 2H).

Step 2: methyl 1-cyclopropyl-4-(4,4,5,5-tetramethyl-1,3,2-dioxaborolan-2-yl)-1H-pyrazole-3-carboxylate (Intermediate 27)

(Intermediate 27)

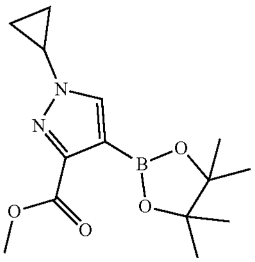

A mixture of methyl 4-bromo-1-cyclopropyl-1 H-pyrazole-3-carboxylate, methyl 4-bromo-1-cyclopropyl-1H-pyrazole-3-carboxylate (27a) (1.06 g, 4.309 mmol), bispinacolatodiborane (1.64 g, 6.46 mmol), KOAc (1.27 g, 12.9 mmol) and Pd(dppf)CI in dioxane (20 mL) was stirred at 100° C. for 16 hours. The mixture was concentrated and purified by silica gel chromatography (0-40% EtOAc/PE) to give methyl 1-cyclopropyl-4-(4,4,5,5-tetramethyl-1,3,2-dioxaborolan-2-yl)-1H-pyrazole-3-carboxylate (Intermediate 27) (690 mg, 54.8% yield) as a yellow oil. LCMS APCI (+) 293.1 (M+H).

Preparation of Intermediate 28: 1-(tert-butoxycarbonyl)-5,5-diethyl-3-fluoropyrrolidine-3-carboxylic acid Step 1: 1-tert-butyl 3-methyl 5,5-diethylpyrrolidine-1,3-dicarboxylate (28a)

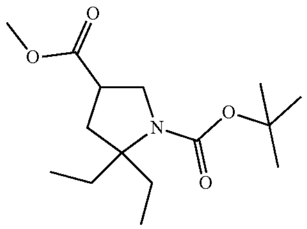 [SMILES: CCC1(CC)CC(C(=O)OC)CN1C(=O)OC(C)(C)C]

A solution of 5,5-diethylpyrrolidine-3-carboxylic acid (620 mg, 3.6 mmol, prepared according to Org. Lett, 2019, 21, 9296-9299) in MeOH (7.70 mL) was cooled in an ice-water bath, and then thionyl chloride (4.31 g, 36.2 mmol) was added drop-wise. After 2 h, the reaction was concentrated and the residue was dissolved in THF (50 mL), then concentrated again (3×) to give a brown oil. The brown oil was dissolved in DCM (15.7 mL) then TEA (733 mg, 7.24 mmol) was added followed by $Boc_2O$ (949 mg, 4.35 mmol). The reaction was stirred overnight and then more TEA (733 mg, 7.24 mmol) and $Boc_2O$ (949 mg, 4.35 mmol) were added. After 4 h, the reaction was concentrated and the residue was purified by silica gel chromatography (0-40% EtOAc/PE) to give 1-tert-butyl 3-methyl 5,5-diethylpyrrolidine-1,3-dicarboxylate (28a) (920 mg, 89.0%) as colorless oil. $^{1}H$ NMR (400 MHz, CHLOROFORM-d) δ 3.92-3.75 (m, 1H), 3.70 (s, 3H), 3.50-3.36 (m, 1H), 3.05-2.92 (m, 1H), 2.20-1.80 (m, 4H), 1.79-1.53 (m, 2H), 1.45 (br d, J=7.8 Hz, 9H), 0.90-0.77 (m, 6H).

Step 2: 1-tert-butyl 3-methyl 5,5-diethyl-3-fluoropyrrolidine-1,3-dicarboxylate (28b)

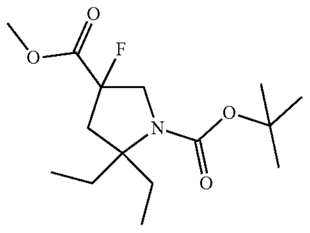 [SMILES: CCC1(CC)CC(F)(C(=O)OC)CN1C(=O)OC(C)(C)C]

To a −78° C. solution of LDA (2.0 M, 863 mmol, 8.06 mmol) in THF (16 mL) was added a solution of 1-tert-butyl 3-methyl 5,5-diethylpyrrolidine-1,3-dicarboxylate (28a) (920 mg, 3.22 mmol) in THF (8.2 mL) slowly. After 1 h at −78° C., this solution was cannulated into a −78° C. solution of N-fluorobenzenesulfonimide (2.54 g, 8.06 mmol) in THF (16 mL) dropwise. After 1 h at −78° C., the reaction was quenched with saturated $NH_4Cl$ while cold then allowed to warm to RT. The reaction was partitioned between EtOAc and water. The organics were separated, and the aqueous was extracted again with EtOAc. The organics were combined and concentrated. The residue was dissolved in DCM, washed with saturated citric acid aqueous, water, and brine. The organics were dried over $Na_2SO_4$, filtered, and concentrated. The residue was purified by silica gel chromatography (0-30% EtOAc/heptanes) to give 1-tert-butyl 3-methyl 5,5-diethyl-3-fluoropyrrolidine-1,3-dicarboxylate (28b) (630 mg, 64%) as a yellow oil. $^{1}H$ NMR (400 MHz, CHLOROFORM-d) δ 4.14-3.63 (m, 5H), 2.54-1.79 (m, 5H), 1.62-1.39 (m, 10H), 0.91-0.81 (m, 6H).

Step 3: 1-(tert-butoxycarbonyl)-5,5-diethyl-3-fluoropyrrolidine-3-carboxylic acid (Intermediate 28)

(Intermediate 28)

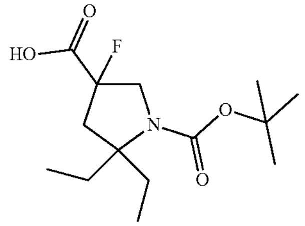

To a solution of 1-tert-butyl 3-methyl 5,5-diethyl-3-fluoropyrrolidine-1,3-dicarboxylate (28b) (430 mg, 1.42 mmol) in MeOH (4.0 mL) and water (1.5 mL), $LiOH \cdot H_2O$ (102 mg, 4.25 mmol) was added. After 3 h, the reaction solution was concentrated to remove MeOH and the resulting aqueous solution was acidified to pH=4-5 with 1 M HCl. The aqueous phase was extracted with DCM (3×). The combined organic layers were washed with brine, dried over $Na_2SO_4$, and concentrated to give 1-(tert-butoxycarbonyl)-5,5-diethyl-3-fluoropyrrolidine-3-carboxylic acid (Intermediate 28) (264 mg, 64.4%) as a white solid. $^{1}H$ NMR (400 MHz, DMSO-$d_6$) δ 3.96-3.60 (m, 3H), 2.53-2.27 (m, 2H), 2.12-1.80 (m, 3H), 1.46 (d, J=7.3 Hz, 9H), 0.93-0.76 (m, 6H)

Preparation of Intermediate 29: methyl 2-(5-bromo-6-methoxypyridin-3-yl)-2-methylpropanoate Step 1: methyl (5-bromo-6-methoxypyridin-3-yl)acetate (29a)

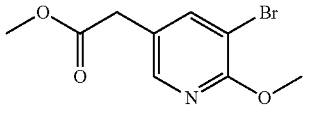

A suspension of (5-bromo-6-methoxypyridin-3-yl)acetonitrile (488 mg, 2.15 mmol) in methanol (2.15 mL) was cooled in an ice-water bath then thionyl chloride (639 mg, 392 μL, 2.50 Eq, 5.37 mmol) was added. The ice-bath was removed, and the reaction was stirred for 19 hours. The reaction mixture was concentrated to a white solid and then the solid was suspended in EtOAc and neutralized with saturated $NaHCO_3$ (aq). The organics were separated and washed with brine, dried over $Na_2SO_4$, filtered and concentrated under reduced pressure. The residue was purified by silica gel chromatography (0-50% EtOAc/heptanes) to give methyl (5-bromo-6-methoxypyridin-3-yl)acetate (29a) (432 mg, 77%) as a colorless oil. LCMS ESI (+) 260.0/262.0 (M+H). $^{1}H$ NMR (400 MHz, $CDCl_3$) δ ppm 7.98 (d, J=1.96 Hz, 1H) 7.79 (d, J=2.08 Hz, 1H) 4.00 (s, 3H) 3.72 (s, 3H) 3.54 (s, 2H).

Step 2: methyl 2-(5-bromo-6-methoxypyridin-3-yl)-2-methylpropanoate (29b)

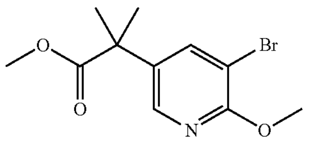

A solution of methyl (5-bromo-6-methoxypyridin-3-yl) acetate (29a) (430 mg, 1.65 mmol) in THF (5.5 mL) was cooled in an ice-water bath then methyl iodide (516 mg, 227 μL, 3.64 mmol) was added followed by potassium tert-butoxide (390 mg, 1.74 mL, 2 molar, 3.47 mmol). After 3 hours the reaction mixture was quenched with saturated $NH_4Cl$(aq) then diluted with EtOAc and water. The organic layer was separated, washed with brine, dried over $Na_2SO_4$, filtered and concentrated under reduced pressure. The residue was purified by silica gel chromatography (0-50% EtOAc/heptanes) to give methyl 2-(5-bromo-6-methoxypyridin-3-yl)-2-methylpropanoate (29b) (410 mg, 86%) as a colorless oil. LCMS ESI (+) 288.0/290.0 (M+H). $^{1}H$ NMR (400 MHz, $CDCl_3$) δ ppm 8.10 (d, J=2.32 Hz, 1H) 7.81 (d, J=2.32 Hz, 1H) 4.01 (s, 3H) 3.68 (s, 3H) 1.59 (s, 6H).

Step 3: methyl 2-(5-bromo-6-methoxypyridin-3-yl)-2-methylpropanoate (Intermediate 29)

Intermediate 29

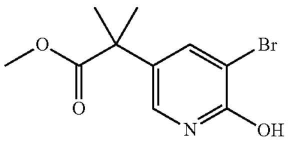

To a mixture of methyl 2-(5-bromo-6-methoxypyridin-3-yl)-2-methylpropanoate (29b) (408 mg, 1.42 mmol) and sodium iodide (531 mg, 3.54 mmol) in ACN (4.72 mL) was added TMS-CI (385 mg, 449 μL, 3.54 mmol). The reaction mixture was stirred at RT for 6 hours then quenched with saturated $NaHCO_3$(aq). The mixture was diluted with EtOAc and water. The organic layer separated. washed with brine, dried over $Na_2SO_4$, filtered and concentrated under reduced pressure. The residue was purified by silica gel chromatography (0-100% EtOAc/heptanes) to give methyl 2-(5-bromo-6-hydroxypyridin-3-yl)-2-methylpropanoate (Intermediate 29) (340 mg, 87%) as a white solid. LCMS ESI(+) 274/276 (M+H). $^1$H NMR (400 MHz, $CDCl_3$) δ=13.69-12.68 (m, 1H), 7.93 (br s, 1H), 7.45 (br s, 1H), 3.70 (br s, 3H), 1.52 (br s, 6H).

Preparation of Intermediate 30: methyl 2-(3-bromo-4-hydroxyphenyl)-2-($^2H_3$)methyl($^2H_3$)propanoate

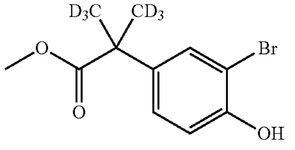 [SMILES: [2H]C([2H])([2H])C(C(=O)OC)(c1ccc(O)c(Br)c1)C([2H])([2H])[2H]]

Intermediate 30 was made in a similar manner as Intermediate I using iodo($^2H_3$)methane in place of methyl iodide. $^1$H NMR (400 MHz, DMSO-$d_6$) δ 10.18 (s, 1H), 7.36 (d, J=2.4 Hz, 1H), 7.12 (dd, J=2.4, 8.5 Hz, 1H), 6.91 (d, J=8.5 Hz, 1H), 3.58 (s, 3H).

EXAMPLES

In order that this disclosure may be better understood, the following examples are set forth. These examples are for purposes of illustration only and are not to be construed as limiting the scope of the disclosure in any manner.

Preparation of Examples

Example A1: 2-(2'-cyclobutyl-3'-fluoro-6-{[(1R,3R)-3-{[(7S)-7-fluoro-5-azaspiro[3.4]octane-7-carbonyl]amino}cyclopentyl]oxy}[1,1'-biphenyl]-3-yl)-2-methylpropanoic acid

A1

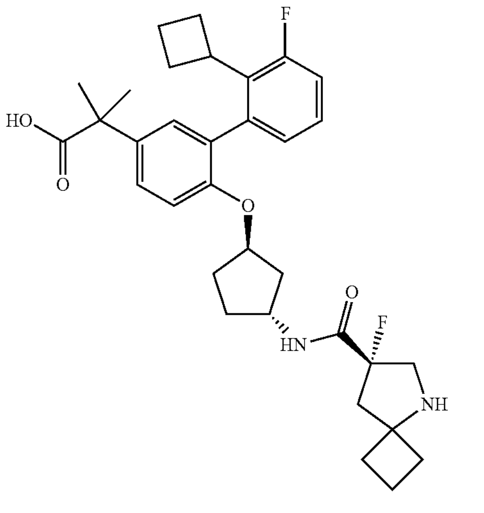

Example A1 was prepared according to General Method A.

Step 1: methyl 2-[3-bromo-4-({(1R,3R)-3-[(tert-butoxycarbonyl)amino]cyclopentyl}oxy)phenyl]-2-methylpropanoate (Ala)

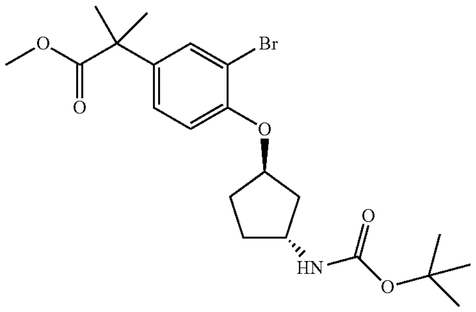 [SMILES: COC(=O)C(C)(C)c1ccc(O[C@@H]2CC[C@@H](NC(=O)OC(C)(C)C)C2)c(Br)c1]

A solution of methyl 2-(3-bromo-4-hydroxyphenyl)-2-methylpropanoate (Intermediate 1) (2.05 g, 7.506 mmol), tert-butyl ((1R,3S)-3-hydroxycyclopentyl)carbamate (1.813 g, 9.007 mmol) and triphenylphosphine (3.937 g, 15.01 mmol) was cooled in an ice-water bath, and then diisopropyl azodicarboxylate (3.035 g, 2.919 mL, 15.01 mmol) was added drop-wise to the solution. After 2 h, the reaction was concentrated under reduced pressure and purified by silica gel chromatography (0-50% EtOAc/heptanes) to give methyl 2-[3-bromo-4-({(1R,3R)-3-[(tert-butoxycarbonyl)amino]cyclopentyl}oxy)phenyl]-2-methylpropanoate (Ala) (3.14 g, 92%) as a clear gum. LCMS APCI (+) 356.1, 358.1 (M-Boc). $^1$H NMR (400 MHz, $CDCl_3$) δ ppm 7.50 (d, J=2.50 Hz, 1H) 7.19 (dd, J=8.63, 2.38 Hz, 1H) 6.78 (d, J=8.63 Hz, 1H) 4.79-4.86 (m, 1H) 4.49 (br s, 1H) 4.24 (br d, J=6.00 Hz, 1H) 3.66 (s, 3H) 2.35 (br dd, J=14.26, 7.38 Hz, 1H) 2.22-2.30 (m, 1H) 2.07-2.17 (m, 1H) 1.88-1.99 (m, 1H) 1.76 (dt, J=13.91, 6.86 Hz, 1H) 1.55 (s, 6H) 1.48-1.53 (m, 1H) 1.45 (s, 9H)

Step 2: methyl 2-[6-({(1R,3R)-3-[(tert-butoxycarbonyl)amino]cyclopentyl}oxy)-2'-cyclobutyl-3'-fluoro[1,1'-biphenyl]-3-yl]-2-methylpropanoate (A1b)

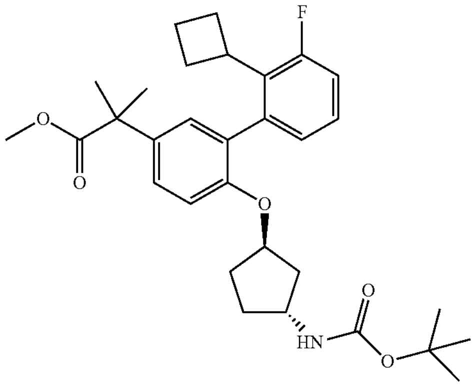 [SMILES: COC(=O)C(C)(C)c1ccc(O[C@@H]2CC[C@@H](NC(=O)OC(C)(C)C)C2)c(-c2cccc(F)c2C2CCC2)c1]

A solution of methyl 2-[3-bromo-4-({(1R,3R)-3-[(tert-butoxycarbonyl)amino]cyclopentyl}oxy)phenyl]-2-methylpropanoate (Ala) (3.14 g, 6.88 mmol), 2-(2-cyclobutyl-3-fluorophenyl)-4,4,5,5-tetramethyl-1,3,2-dioxaborolane (Intermediate 2) (2.19 g, 7.91 mol) and $Cs_2CO_3$ (6.73 g, 20.6 mmol) in 5:1 dioxane:water (41.4 mL) was sparged with $N_2$ for 15 minutes. 1,1'-Bis(di-t-butylphosphino)ferrocene palladium dichloride (0.224 g, 0.344 mmol) was added and the reaction was heated to 90° C. for 4 h. The reaction was concentrated under reduced pressure and the residue was dissolved in EtOAc, washed with brine, dried over $MgSO_4$, filtered, and concentrated under reduced pressure. The residue was purified by silica gel chromatography (0-50% EtOAc/heptanes) to give methyl 2-[6-({(1R,3R)-3-[(tert-butoxycarbonyl)amino]cyclopentyl}oxy)-2'-cyclobutyl-3'-fluoro[1,1'-biphenyl]-3-yl]-2-methylpropanoate (A1b) (3.35 g, 92.6%) as an orange gum. LCMS APCI (+) 426.3 (M-Boc). $^1$H NMR (400 MHz, $CDCl_3$) δ ppm 7.23-7.26 (m, 1H) 7.10-7.17 (m, 1H) 7.06 (t, J=2.31 Hz, 1H) 6.98 (ddd, J=11.57, 8.19, 1.13 Hz, 1H) 6.89 (td, J=7.41, 1.19 Hz, 1H) 6.82 (d, J=8.25 Hz, 1H) 4.68 (qt, J=6.03, 2.89 Hz, 1H) 4.29-4.48 (m, 1H) 3.85-4.03 (m, 1H) 3.66 (s, 3H) 3.39-3.52 (m, 1H) 2.24-2.36 (m, 1H) 2.07-2.23 (m, 2H) 1.85-2.06 (m, 4H) 1.64-1.83 (m, 4H) 1.57 (d, J=5.50 Hz, 6H) 1.43 (d, J=3.00 Hz, 9H) 1.33-1.41 (m, 1H).

Step 3: methyl 2-(6-{[(1R,3R)-3-aminocyclopentyl]oxy}-2'-cyclobutyl-3'-fluoro[1,1'-biphenyl]-3-yl)-2-methylpropanoate (A1c)

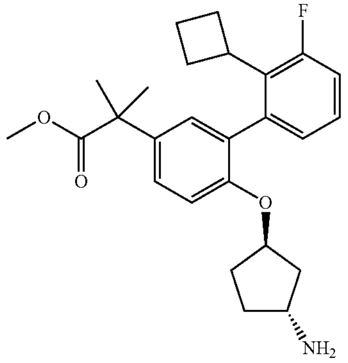 [SMILES: COC(=O)C(C)(C)c1ccc(O[C@@H]2CC[C@@H](N)C2)c(-c2cccc(F)c2C2CCC2)c1]

To a solution of methyl 2-[6-({(1R,3R)-3-[(tert-butoxycarbonyl)amino]cyclopentyl}oxy)-2'-cyclobutyl-3'-fluoro [1,1'-biphenyl]-3-yl]-2-methylpropanoate (A1b) (3.35 g, 6.37 mmol) in DCM (31.9 mL), HCl (4 N in dioxane, 15.9 mL, 63.7 mmol) was added. After 4 h, the reaction was concentrated under reduced pressure and the residue was dissolved in EtOAc, washed with 1 N NaOH and brine, dried over $MgSO_4$, filtered, and concentrated under reduced pressure to give methyl 2-(6-{[(1R,3R)-3-aminocyclopentyl]oxy}-2'-cyclobutyl-3'-fluoro[1,1'-biphenyl]-3-yl)-2-methylpropanoate (A1c) (2.66 g, 98%) as an orange gum. LCMSAPCI (+) 426.1 (M+H). $^1$H NMR (400 MHz, $CDCl_3$) δ ppm 7.25 (br d, J=2.57 Hz, 1H) 7.09-7.16 (m, 1H) 7.06 (d, J=2.08 Hz, 1H) 6.98 (dd, J=11.13, 8.19 Hz, 1H) 6.85-6.90 (m, 1H) 6.80-6.85 (m, 1H) 4.75 (dt, J=5.78, 3.04 Hz, 1H) 3.66 (s, 3H) 3.39-3.53 (m, 2H) 2.24-2.36 (m, 2H) 2.12-2.23 (m, 2H) 1.97-2.05 (m, 2H) 1.84-1.93 (m, 2H) 1.69-1.81 (m, 3H) 1.58 (d, J=5.38 Hz, 6H) 1.30-1.40 (m, 1 H).

Step 4: tert-butyl (7S)-7-{[(1R,3R)-3-{[2'-cyclobutyl-3'-fluoro-5-(1-methoxy-2-methyl-1-oxopropan-2-yl)[1,1'-biphenyl]-2-yl]oxy}cyclopentyl]carbamoyl}-7-fluoro-5-azaspiro[3.4]octane-5-carboxylate (A1d)

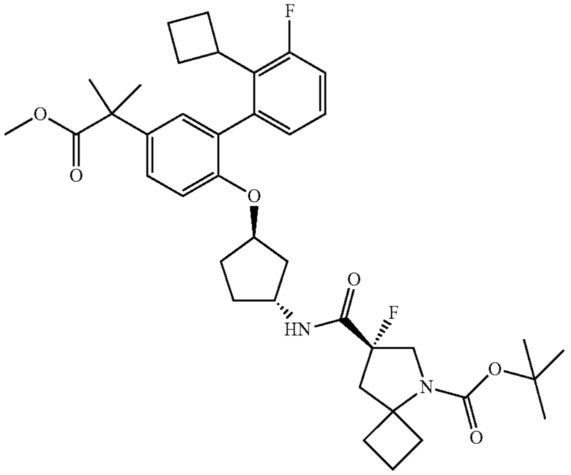 [SMILES: COC(=O)C(C)(C)c1ccc(O[C@@H]2CC[C@@H](NC(=O)[C@@]3(F)CN(C(=O)OC(C)(C)C)C4(CCC4)C3)C2)c(-c2cccc(F)c2C2CCC2)c1]

A solution of methyl 2-(6-{[(1R,3R)-3-aminocyclopentyl]oxy}-2'-cyclobutyl-3'-fluoro[1,1'-biphenyl]-3-yl)-2-methylpropanoate (A1c) (356 mg, 0.837 mmol), (7S)-5-(tert-butoxycarbonyl)-7-fluoro-5-azaspiro[3.4]octane-7-carboxylic acid (Intermediate 3') (208 mg, 0.761 mmol) and 1-methylimidazole (219 mg, 0.211 mL, 2.66 mmol) was cooled in an ice-water batch. Chloro-N,N,N',N'-tetramethylformamidinium hexafluorophosphate (256 mg, 0.913 mmol) was added, and the ice bath was removed. After 3 h, the reaction was concentrated under reduced pressure and residue was dissolved in EtOAc, washed with water and brine, dried over $MgSO_4$, filtered, and concentrated under reduced pressure. The crude product was purified by silica gel chromatography (0-50% EtOAc/heptanes) to give tert-butyl (7S)-7-{[(1R,3R)-3-{[2'-cyclobutyl-3'-fluoro-5-(1-methoxy-2-methyl-1-oxopropan-2-yl)[1,1'-biphenyl]-2-yl]oxy}cyclopentyl]carbamoyl}-7-fluoro-5-azaspiro[3.4]octane-5-carboxylate (A1d) (411 mg, 79.3%) as a foamy white solid. LCMS APCI (+) 581.2 (M-Boc). $^1$H NMR (400 MHz, DMSO-d6) δ ppm 8.24-8.41 (m, 1H) 7.27 (dd, J=8.69, 2.56 Hz, 1H) 7.18-7.24 (m, 1H) 7.10 (dd, J=11.82, 7.32 Hz, 1H) 6.99 (d, J=8.76 Hz, 1H) 6.95 (dd, J=2.38, 1.50 Hz, 1H) 6.88 (ddd, J=7.57, 3.38, 1.19 Hz, 1H) 4.82 (br d, J=2.63 Hz, 1H) 3.98-4.16 (m, 1H) 3.62-3.72 (m, 1H) 3.59 (s, 4H) 3.36-3.50 (m, 1H) 2.59-3.11 (m, 3H) 1.58-2.22 (m, 15H) 1.38-1.56 (m, 17H)

Step 5: 2-(6-{[(1R,3R)-3-{[(7S)-5-(tert-butoxycarbonyl)-7-fluoro-5-azaspiro[3.4]octane-7-carbonyl]amino}cyclopentyl]oxy}-2'-cyclobutyl-3'-fluoro[1,1'-biphenyl]-3-yl)-2-methylpropanoic acid (A1e)

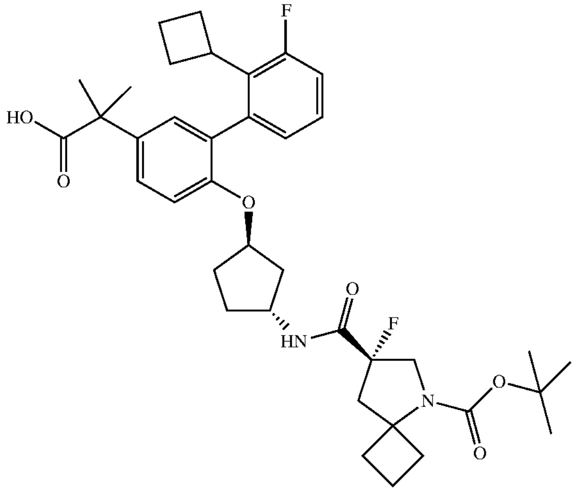 [SMILES: CC(C)(C)OC(=O)N1C[C@](F)(C(=O)N[C@@H]2CC[C@@H](Oc3ccc(C(C)(C)C(=O)O)cc3-c3cccc(F)c3C3CCC3)C2)CC12CCC2]

To solution of tert-butyl (7S)-7-{[(1R,3R)-3-{[2'-cyclobutyl-3'-fluoro-5-(1-methoxy-2-methyl-1-oxopropan-2-yl)[1,1'-biphenyl]-2-yl]oxy}cyclopentyl]carbamoyl}-7-fluoro-5-azaspiro[3.4]octane-5-carboxylate (A1d) (240 mg, 0.353 mmol) in 1:1 THF:MeOH (6 mL), LiOH (1 N, 5.29 mL, 5.29 mmol) was added. The mixture was heated to 70° C. overnight. The reaction was cooled to RT, acidified with 1 N HCl then extracted with DCM (2×). The organics were combined, dried over $Na_2SO_4$, filtered, and concentrated under reduced pressure to give 2-(6-{[(1R,3R)-3-{[(7S)-5-(tert-butoxycarbonyl)-7-fluoro-5-azaspiro[3.4]octane-7-carbonyl]amino}cyclopentyl]oxy}-2'-cyclobutyl-3'-fluoro[1,1'-biphenyl]-3-yl)-2-methylpropanoic acid (A1e) (250 mg, 93%) as a foamy white solid. LCMS APCI (+) 567.3 (M-Boc). $^1$H NMR (400 MHz, DMSO-d6) δ ppm 8.08-7.93 (m, 1H), 7.32 (dd, J=2.4, 8.6 Hz, 1H), 7.21 (dt, J=5.6, 7.8 Hz, 1H), 7.07 (dd, J=8.2, 11.9 Hz, 1H), 7.03-6.95 (m, 2H), 6.88 (dd, J=2.1, 7.1 Hz, 1H), 4.84-4.75 (m, 1H), 4.15-4.01 (m, 1H), 3.65-3.57 (m, 3H), 3.52-3.36 (m, 1H), 3.26-3.11 (m, 1H), 2.84-2.73 (m, 1H), 2.69-2.56 (m, 1H), 2.28-2.14 (m, 1H), 2.13-2.06 (m, 1H), 2.00 (br d, J=6.3 Hz, 2H), 1.95-1.87 (m, 3H), 1.86-1.78 (m, 3H), 1.75-1.57 (m, 4H), 1.50-1.43 (m, 17H).

Step 6: 2-(2'-cyclobutyl-3'-fluoro-6-{[(1R,3R)-3-{[(7S)-7-fluoro-5-azaspiro[3.4]octane-7-carbonyl]amino}cyclopentyl]oxy}[1,1'-biphenyl]-3-yl)-2-methylpropanoic acid (Example A1)

A1

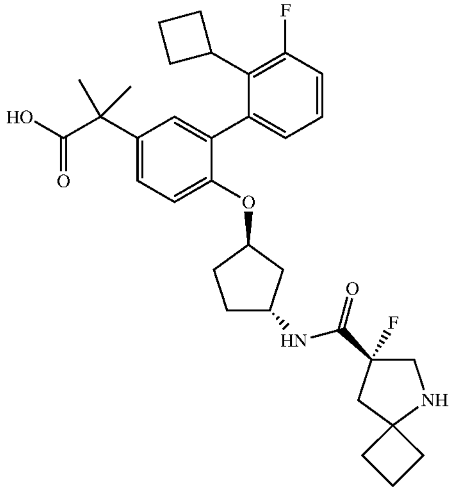

To a solution of 2-(6-{[(1R,3R)-3-{[(7S)-5-(tert-butoxycarbonyl)-7-fluoro-5-azaspiro[3.4]octane-7-carbonyl]amino}cyclopentyl]oxy}-2'-cyclobutyl-3'-fluoro[1,1'-biphenyl]-3-yl)-2-methylpropanoic acid (A1e) (203 mg, 0.304 mmol) in DCM (1.52 mL) was added HCl (4 N in dioxane 1.52 mL, 6.09 mmol). After stirring for 2 h at RT, the reaction was concentrated under reduced pressure and the residue was purified by Prep HPLC (Phenomenex Gemini NX C18 150×21.2 mm, 5 um, AXIA Pack column, Mobile phase A: Water+10 mM Ammonium Acetate, Mobile phase B: Acetonitrile, 20-60% B in 8.0 minutes, 40 mL/min) to give 2-(2'-cyclobutyl-3'-fluoro-6-{[(1R,3R)-3-{[(7S)-7-fluoro-5-azaspiro[3.4]octane-7-carbonyl]amino}cyclopentyl]oxy}[1,1'-biphenyl]-3-yl)-2-methylpropanoic acid (Example A1) (99 mg, 57%). LCMS APCI (+) 567.3 (M+H). $^1$H NMR (400 MHz, DMSO-d6) δ ppm 7.82 (br s, 1H), 7.32 (dd, J=2.5, 8.6 Hz, 1H), 7.21 (dt, J=5.6, 7.9 Hz, 1H), 7.08 (ddd, J=1.1, 8.3, 11.9 Hz, 1H), 7.03-6.96 (m, 2H), 6.92-6.81 (m, 1H), 4.84-4.75 (m, 1H), 4.18-3.98 (m, 1H), 3.54-3.40 (m, 1H), 3.30-3.12 (m, 3H), 2.38-1.96 (m, 10H), 1.91-1.58 (m, 7H), 1.50 (d, J=2.4 Hz, 7H).

$$[\alpha]_D^{22} = -12.1°(c0.1, \text{MeOH}).$$

Examples A2-A44 reported in Table 1 were synthesized with non-critical changes or substitutions to the exemplified procedures for Example A1 that one skilled in the art would be able to realize.

TABLE 1

| Ex. | Structure and Name | Characterization Data ($^1H$ NMR, optical rotation, and/or LCMS) |
|---|---|---|
| A2 | 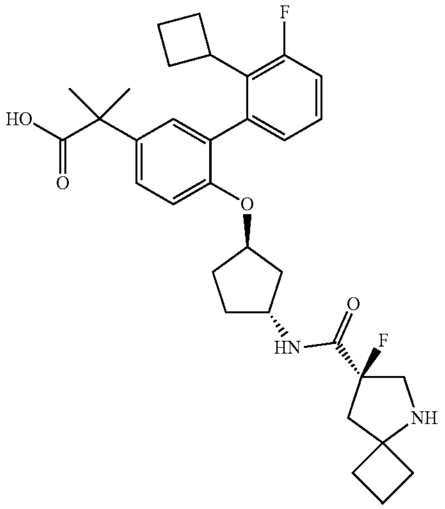 [SMILES: CC(C)(C(=O)O)c1ccc(O[C@@H]2CC[C@@H](NC(=O)[C@]3(F)CNC4(CCC4)C3)C2)c(-c2cccc(F)c2C2CCC2)c1] 2-(2'-cyclobutyl-3'-fluoro-6-{[(1R,3R)-3-({[(7R)-7-fluoro-5-azaspiro[3.4]oct-7-yl]carbonyl}amino)cyclopentyl]oxy}biphenyl-3-yl)-2-methylpropanoic acid | $^1H$ NMR (400 MHz, DMSO-$d_6$) δ 7.76 (br s, 1H), 7.32 (dd, J = 1.5, 8.5 Hz, 1H), 7.20 (dt, J = 5.7, 7.8 Hz, 1H), 7.07 (ddd, J = 1.0, 8.2, 11.9 Hz, 1H), 7.03-6.96 (m, 2H), 6.88 (dd, J = 4.0, 7.3 Hz, 1H), 4.88-4.69 (m, 1H), 4.23-3.96 (m, 1H), 3.57-3.37 (m, 1H), 3.23-2.95 (m, 2H), 1.63-1.61 (m, 1H), 2.36-1.59 (m, 17H), 1.49 (br s, 8H). $[\alpha]_D^{22}$ = −19.96° (c 0.1, MeOH). LCMS (m/z) $(M + H)^+$: 567.3 |
| A3 | 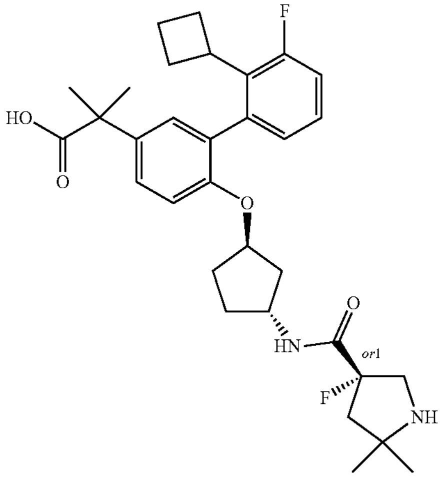 [SMILES: CC1(C)C[C@@](F)(C(=O)N[C@@H]2CC[C@@H](Oc3ccc(C(C)(C)C(=O)O)cc3-c3cccc(F)c3C3CCC3)C2)CN1] 2-(2'-cyclobutyl-3'-fluoro-6-{[(1R,3R)-3-{[(3ξ)-3-fluoro-5,5-dimethylpyrrolidine-3-carbonyl]amino}cyclopentyl]oxy}[1,1'-biphenyl]-3-yl)-2-methylpropanoic acid | $^1H$ NMR (400 MHz, DMSO-$d_6$) δ 12.27 (br s, 1H), 9.79-9.52 (m, 2H), 8.53 (br t, J = 5.3 Hz, 1H), 7.30 (dd, J = 2.4, 8.6 Hz, 1H), 7.25-7.16 (m, 1H), 7.10 (dd, J = 7.9, 11.9 Hz, 1H), 7.03-6.94 (m, 2H), 6.87 (br d, J = 7.7 Hz, 1H), 4.82 (br s, 1H), 4.08 (br dd, J = 7.7, 15.6 Hz, 1H), 3.84-3.60 (m, 2H), 3.49-3.39 (m, 3H), 2.41-2.30 (m, 1H), 2.30-2.24 (m, 1H), 2.23-1.93 (m, 4H), 1.91-1.59 (m, 6H), 1.48-1.40 (m, 12H). LCMS (m/z) $(M + H)^+$: 555.5 |

TABLE 1-continued

| Ex. | Structure and Name | Characterization Data ($^1$H NMR, optical rotation, and/or LCMS) |
|---|---|---|
| A4 | 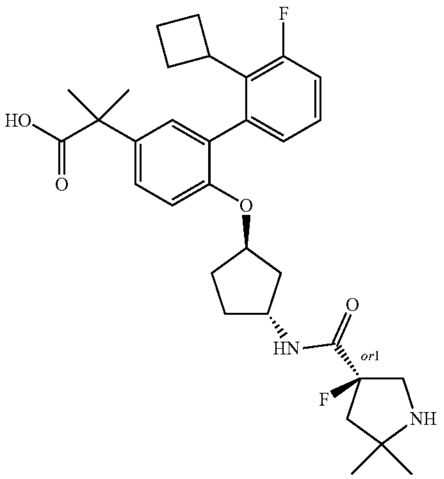 [SMILES: CC1(C)C[C@](F)(C(=O)N[C@@H]2CC[C@@H](Oc3ccc(C(C)(C)C(=O)O)cc3-c3cccc(F)c3C3CCC3)C2)CN1] 2-(2'-cyclobutyl-3'-fluoro-6-{[(1R,3R)-3-{[(3ξ)-3-fluoro-5,5-dimethylpyrrolidine-3-carbonyl]amino}cyclopentyl]oxy}[1,1'-biphenyl]-3-yl)-2-methylpropanoic acid | $^1$H NMR (400 MHz, DMSO-$d_6$) δ 12.27 (br s, 1H), 9.70 (br s, 2H), 8.52 (br t, J = 5.7 Hz, 1H), 7.30 (dd, J = 2.4, 8.6 Hz, 1H), 7.25-7.17 (m, 1H), 7.10 (dd, J = 8.3, 11.6 Hz, 1H), 7.03-6.95 (m, 2H), 6.88 (br d, J = 7.7 Hz, 1H), 4.82 (br s, 1H), 4.08 (qd, J = 7.4, 14.9 Hz, 1H), 3.83-3.58 (m, 2H), 3.49-3.37 (m, 3H), 2.35 (br d, J = 15.8 Hz, 1H), 2.30-2.25 (m, 1H), 2.21-1.92 (m, 4H), 1.91-1.62 (m, 6H), 1.49-1.42 (m, 12H). LCMS (m/z) $(M + H)^+$: 555.5 |
| A5 | 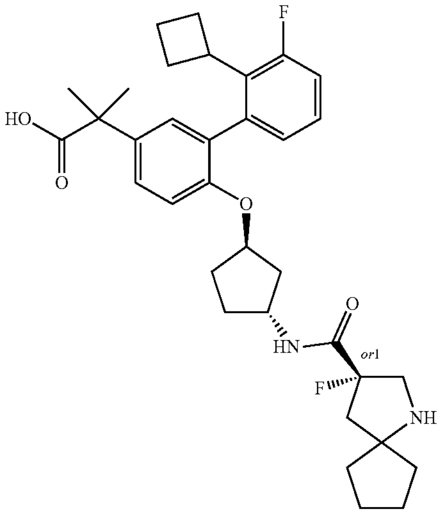 [SMILES: CC(C)(C(=O)O)c1ccc(O[C@@H]2CC[C@@H](NC(=O)[C@@]3(F)CNC4(CCCC4)C3)C2)c(-c2cccc(F)c2C2CCC2)c1] 2-(2'-cyclobutyl-3'-fluoro-6-{[(1R,3R)-3-{[(3ξ)-3-fluoro-1-azaspiro[4.4]nonane-3-carbonyl]amino}cyclopentyl]oxy}[1,1'-biphenyl]-3-yl)-2-methylpropanoic acid | $^1$H NMR (400 MHz, DMSO-$d_6$) δ 8.12 (br dd, J = 2.3, 6.1 Hz, 1H), 7.29 (dd, J = 2.0, 8.6 Hz, 1H), 7.25-7.18 (m, 1H), 7.15-7.06 (m, 1H), 7.02-6.95 (m, 2H), 6.88 (dd, J = 3.7, 7.0 Hz, 1H), 4.84-4.74 (m, 1H), 4.18-3.99 (m, 1H), 3.48-3.41 (m, 2H), 3.18-3.07 (m, 1H), 3.04-2.92 (m, 1H), 2.24-1.93 (m, 6H), 1.91-1.82 (m, 3H), 1.81-1.69 (m, 3H), 1.67-1.50 (m, 9H), 1.45 (br d, J = 4.6 Hz, 7H). $[\alpha]_D^{22}$ = −21.6° (c 0.04, MeOH). LCMS (m/z) $(M + H)^+$: 581.4 |

TABLE 1-continued

| Ex. | Structure and Name | Characterization Data ($^1$H NMR, optical rotation, and/or LCMS) |
|---|---|---|
| A6 | 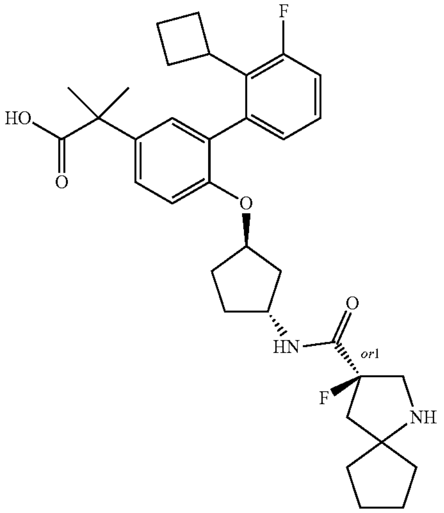 [SMILES: CC(C)(C(=O)O)c1ccc(O[C@@H]2CC[C@@H](NC(=O)[C@]3(F)CNC4(CCCC4)C3)C2)c(-c2cccc(F)c2C2CCC2)c1] 2-(2'-cyclobutyl-3'-fluoro-6-{[(1R,3R)-3-{[(3ξ)-3-fluoro-1-azaspiro[4.4]nonane-3-carbonyl]amino}cyclopentyl]oxy}[1,1'-biphenyl]-3-yl)-2-methylpropanoic acid | $^1$H NMR (400 MHz, DMSO-$d_6$) δ 8.12 (br dd, J = 3.3, 6.8 Hz, 1H), 7.34-7.26 (m, 1H), 7.26-7.17 (m, 1H), 7.14-7.07 (m, 1H), 7.04-6.93 (m, 2H), 6.91-6.86 (m, 1H), 4.85-4.72 (m, 1H), 4.15-3.98 (m, 1H), 3.45-3.41 (m, 2H), 3.16-3.05 (m, 1H), 3.04-2.88 (m, 1H), 1.94 (br s, 6H), 1.91-1.69 (m, 6H), 1.68-1.51 (m, 9H), 1.44 (br d, J = 3.7 Hz, 7H). 22 $[\alpha]_D^{22}$ = +40.0° (c 0.01, MeOH). LCMS (m/z) $(M + H)^+$: 581.4 |
| A7 | 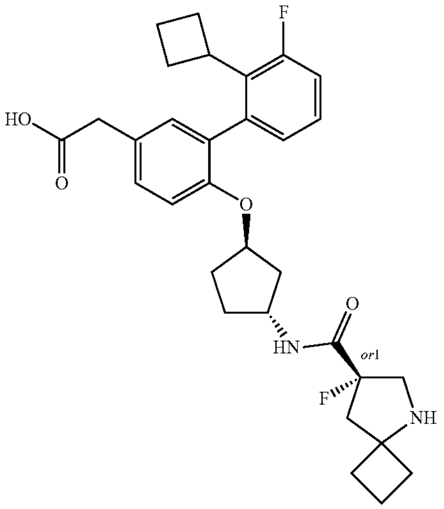 [SMILES: O=C(O)Cc1ccc(O[C@@H]2CC[C@@H](NC(=O)[C@@]3(F)CNC4(CCC4)C3)C2)c(-c2cccc(F)c2C2CCC2)c1] (2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)acetic acid | $^1$H NMR (400 MHz, DMSO-$d_6$) δ 8.08 (dt, J = 2.5, 8.1 Hz, 1H), 7.26-7.17 (m, 2H), 7.14-7.05 (m, 1H), 7.01-6.93 (m, 2H), 6.90-6.82 (m, 1H), 4.78 (br s, 1H), 4.08 (br s, 1H), 3.52 (s, 2H), 3.47-3.42 (m, 1H), 3.17-2.92 (m, 2H), 2.30-2.00 (m, 7H), 1.96 (br d, J = 2.4 Hz, 1H), 1.90-1.37 (m, 11H). $[\alpha]_D^{22}$ = −40.0° (c 0.1, MeOH). LCMS (m/z) $(M + H)^+$: 539.0 |

TABLE 1-continued

| Ex. | Structure and Name | Characterization Data ($^1$H NMR, optical rotation, and/or LCMS) |
|---|---|---|
| A8 | 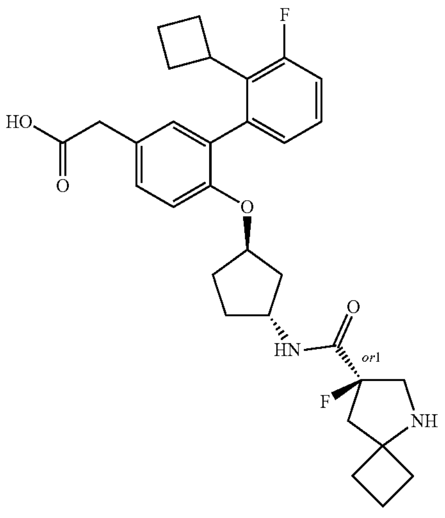 [SMILES: O=C(O)Cc1ccc(O[C@@H]2CC[C@@H](NC(=O)[C@]3(F)CNC4(CCC4)C3)C2)c(-c2cccc(F)c2C2CCC2)c1] (2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)acetic acid | $^1$H NMR (400 MHz, DMSO-$d_6$, 80° C.) δ 7.76 (br s, 1H), 7.27-7.16 (m, 2H), 7.11-7.02 (m, 1H), 7.01-6.93 (m, 2H), 6.88 (br s, 1H), 4.82-4.73 (m, 1H), 4.16-3.98 (m, 1H), 3.61-3.41 (m, 3H), 3.15-3.06 (m, 2H), 2.31-1.33 (m, 20H). $[\alpha]_D^{22}$ = −15.0° (c 0.05, MeOH). LCMS (m/z) $(M + H)^+$: 539.0 |
| A9 | 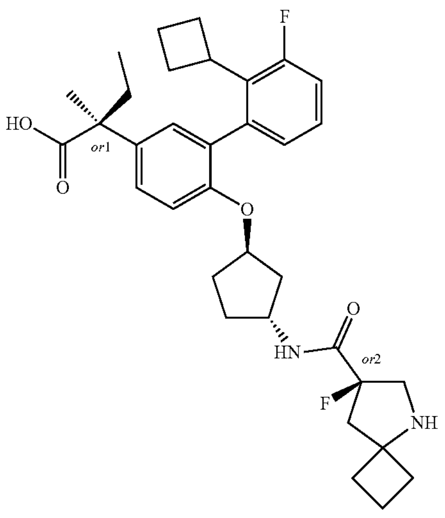 [SMILES: CC[C@](C)(C(=O)O)c1ccc(O[C@@H]2CC[C@@H](NC(=O)[C@]3(F)CNC4(CCC4)C3)C2)c(-c2cccc(F)c2C2CCC2)c1] (2ξ)-2-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-2-methylbutanoic acid | $^1$H NMR (400 MHz, DMSO-$d_6$) δ 12.55-11.96 (m, 1H), 10.18-9.50 (m, 2H), 8.57-8.45 (m, 1H), 7.26 (ddd, J = 2.6, 6.3, 8.7 Hz, 1H), 7.20 (dd, J = 5.7, 7.7 Hz, 1H), 7.10 (dd, J = 8.1, 11.7 Hz, 1H), 6.99 (d, J = 8.6 Hz, 1H), 6.95 (d, J = 2.0 Hz, 1H), 6.87 (t, J = 6.7 Hz, 1H), 4.83 (br s, 1H), 4.09 (br dd, J = 7.4, 14.4 Hz, 1H), 3.72-3.53 (m, 2H), 3.46-3.39 (m, 1H), 2.70-2.52 (m, 3H), 2.48-2.38 (m, 1H), 2.25-2.13 (m, 3H), 2.13-1.99 (m, 2H), 1.99-1.62 (m, 11H), 1.58-1.43 (m, 2H), 1.40 (s, 3H), 0.77 (q, J = 7.5 Hz, 3H). $[\alpha]_D^{22}$ = −18.0° (c 0.1, MeOH). LCMS (m/z) $(M + H)^+$: 581.4 |

TABLE 1-continued

| Ex. | Structure and Name | Characterization Data ($^1$H NMR, optical rotation, and/or LCMS) |
|---|---|---|
| A10 | 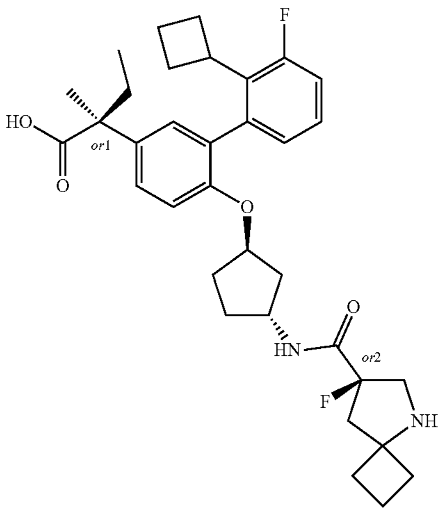 [SMILES: CC[C@](C)(C(=O)O)c1ccc(O[C@@H]2CC[C@@H](NC(=O)[C@]3(F)CNC4(CCC4)C3)C2)c(-c2cccc(F)c2C2CCC2)c1] (2ξ)-2-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-2-methylbutanoic acid | $^1$H NMR (400 MHz, DMSO-$d_6$) δ 12.70-11.91 (m, 1H), 10.21-9.60 (m, 2H), 8.65-8.43 (m, 1H), 7.30-7.18 (m, 2H), 7.14-7.07 (m, 1H), 7.03-6.94 (m, 2H), 6.91-6.85 (m, 1H), 4.83 (br d, J = 2.6 Hz, 1H), 4.20-4.02 (m, 1H), 3.72-3.53 (m, 2H), 3.50-3.39 (m, 1H), 2.68-2.53 (m, 3H), 2.48-2.37 (m, 1H), 2.26-2.13 (m, 3H), 2.12-2.00 (m, 2H), 1.99-1.63 (m, 11H), 1.47 (br d, J = 4.8 Hz, 2H), 1.41 (s, 3H), 0.84-0.73 (m, 3H). $[\alpha]_D^{22}$ = −37.3° (c 0.1, MeOH). LCMS (m/z) $(M + H)^+$: 581.4 |
| A11 | 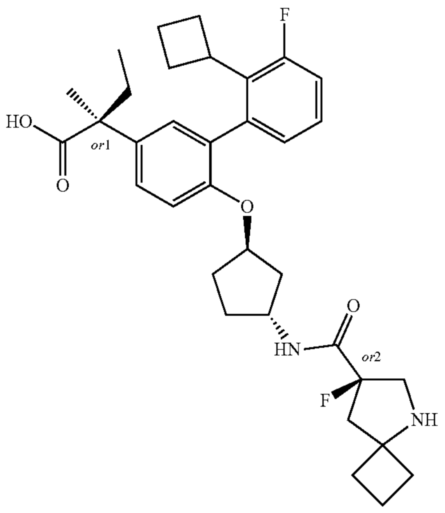 [SMILES: CC[C@](C)(C(=O)O)c1ccc(O[C@@H]2CC[C@@H](NC(=O)[C@]3(F)CNC4(CCC4)C3)C2)c(-c2cccc(F)c2C2CCC2)c1] (2ξ)-2-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-2-methylbutanoic acid | $^1$H NMR (400 MHz, DMSO-$d_6$) δ 12.70-11.55 (m, 1H), 10.52-9.47 (m, 2H), 8.50 (br t, J = 6.5 Hz, 1H), 7.30-7.24 (m, 1H), 7.24-7.17 (m, 1H), 7.10 (dd, J = 8.3, 11.7 Hz, 1H), 7.00 (d, J = 8.7 Hz, 1H), 6.96 (t, J = 2.9 Hz, 1H), 6.87 (d, J = 7.6 Hz, 1H), 4.83 (br s, 1H), 4.15-4.03 (m, 1H), 3.72-3.54 (m, 2H), 3.48-3.39 (m, 1H), 2.68-2.53 (m, 3H), 2.43 (br d, J = 2.8 Hz, 1H), 2.25-2.14 (m, 3H), 2.11-2.00 (m, 2H), 1.97-1.64 (m, 11H), 1.58-1.45 (m, 2H), 1.41 (s, 3H), 0.77 (q, J = 7.5 Hz, 3H). $[\alpha]_D^{22}$ = 3.43° (c 0.05, MeOH). LCMS (m/z) $(M + H)^+$: 581.4 |

TABLE 1-continued

| Ex. | Structure and Name | Characterization Data ($^1H$ NMR, optical rotation, and/or LCMS) |
|---|---|---|
| A12 | 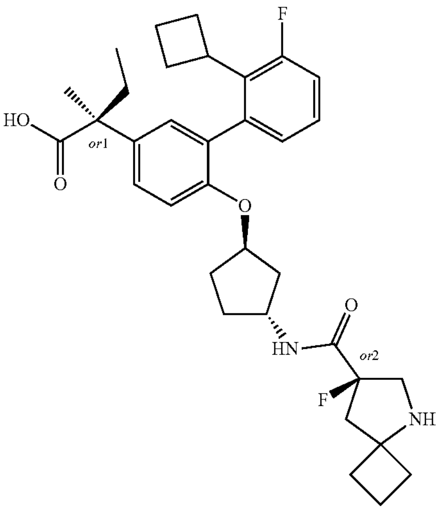 [SMILES: CC[C@](C)(C(=O)O)c1ccc(O[C@@H]2CC[C@@H](NC(=O)[C@]3(F)CNC4(CCC4)C3)C2)c(-c2cccc(F)c2C2CCC2)c1] (2ξ)-2-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-2-methylbutanoic acid | $^1H$ NMR (400 MHz, DMSO-$d_6$) δ 12.70-11.95 (m, 1H), 10.04-9.57 (m, 2H), 8.51 (br t, J = 6.0 Hz, 1H), 7.29-7.24 (m, 1H), 7.24-7.17 (m, 1H), 7.13-7.06 (m, 1H), 7.02-6.94 (m, 2H), 6.91-6.84 (m, 1H), 4.82 (br s, 1H), 4.15-4.04 (m, 1H), 3.71-3.54 (m, 2H), 3.46-3.38 (m, 1H), 2.69-2.53 (m, 3H), 2.47-2.38 (m, 1H), 2.26-2.14 (m, 3H), 2.11-1.99 (m, 2H), 1.96-1.63 (m, 11H), 1.57-1.44 (m, 2H), 1.43-1.38 (m, 3H), 0.77 (q, J = 7.4 Hz, 3H). $[\alpha]_D^{22}$ = 16.5° (c 0.05, MeOH). LCMS (m/z) $(M + H)^+$: 581.4 |
| A13 | 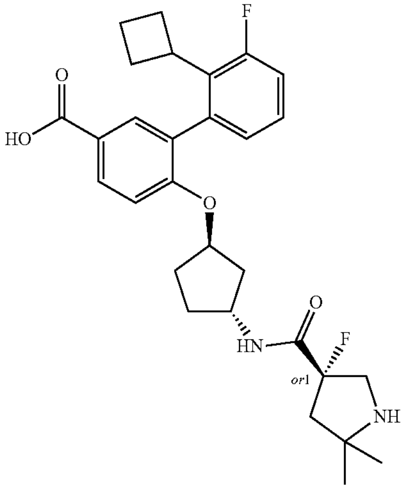 [SMILES: CC1(C)C[C@@](F)(C(=O)N[C@@H]2CC[C@@H](Oc3ccc(C(=O)O)cc3-c3cccc(F)c3C3CCC3)C2)CN1] 2'-cyclobutyl-3'-fluoro-6-{[(1R,3R)-3-{[(3ξ)-3-fluoro-5,5-dimethylpyrrolidine-3-carbonyl]amino}cyclopentyl]oxy}[1,1'-biphenyl]-3-carboxylic acid | $^1H$ NMR (600 MHz, DMSO-$d_6$) δ 7.94 (dd, J = 2.0, 8.5 Hz, 1H), 7.87 (br dd, J = 7.6, 11.1 Hz, 1H), 7.62 (s, 1H), 7.23 (dt, J = 5.7, 7.8 Hz, 1H), 7.16-7.07 (m, 2H), 6.88 (dd, J = 3.6, 7.3 Hz, 1H), 4.95 (br s, 1H), 4.16-4.03 (m, 1H), 3.44 (br d, J = 7.3 Hz, 1H), 3.21 (br d, J = 3.8 Hz, 3H), 2.28-2.01 (m, 6H), 1.95-1.67 (m, 7H), 1.63-1.46 (m, 2H), 1.21 (s, 6H). $[\alpha]_D^{22}$ = −17.4° (c 0.1, MeOH). LCMS (m/z) $(M + H)^+$: 513.1 |

TABLE 1-continued

| Ex. | Structure and Name | Characterization Data ($^1H$ NMR, optical rotation, and/or LCMS) |
|---|---|---|
| A14 | 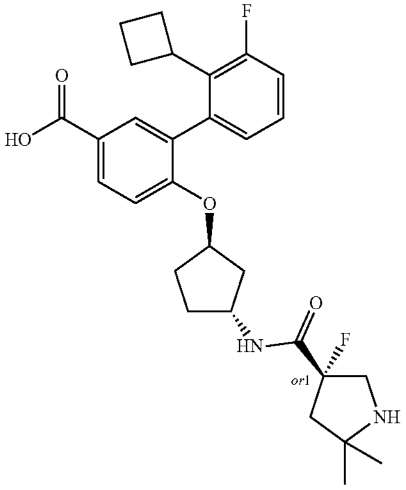 [SMILES: CC1(C)C[C@@](F)(C(=O)N[C@@H]2CC[C@@H](Oc3ccc(C(=O)O)cc3-c3cccc(F)c3C3CCC3)C2)CN1] 2'-cyclobutyl-3'-fluoro-6-{[(1R,3R)-3-{[(3ξ)-3-fluoro-5,5-dimethylpyrrolidine-3-carbonyl]amino}cyclopentyl]oxy}[1,1'-biphenyl]-3-carboxylic acid | $^1H$ NMR (600 MHz, DMSO-$d_6$) δ 7.98-7.92 (m, 1H), 7.86-7.78 (m, 1H), 7.62 (s, 1H), 7.27-7.19 (m, 1H), 7.15-7.07 (m, 2H), 6.91-6.84 (m, 1H), 4.95 (br d, J = 2.4 Hz, 1H), 4.15-4.02 (m, 1H), 3.46-3.41 (m, 2H), 2.27-2.14 (m, 2H), 2.14-2.02 (m, 4H), 1.89-1.68 (m, 6H), 1.61-1.45 (m, 2H), 1.20 (s, 3H), 1.13 (s, 3H). $[\alpha]_D^{22}$ = −19.4° (c 0.1, MeOH). LCMS (m/z) $(M + H)^+$: 513.2 |
| A15 | 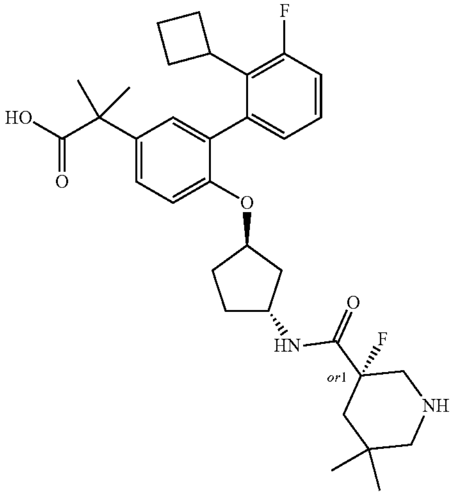 [SMILES: CC1(C)CNC[C@](F)(C(=O)N[C@@H]2CC[C@@H](Oc3ccc(C(C)(C)C(=O)O)cc3-c3cccc(F)c3C3CCC3)C2)C1] 2-(2'-cyclobutyl-3'-fluoro-6-{[(1R,3R)-3-{[(3ξ)-3-fluoro-5,5-dimethylpiperidine-3-carbonyl]amino}cyclopentyl]oxy}[1,1'-biphenyl]-3-yl)-2-methylpropanoic acid | $^1H$ NMR (400 MHz, MeOD) δ 8.32-8.23 (m, 1H), 7.35 (dd, J = 2.5, 8.6 Hz, 1H), 7.16 (dt, J = 5.5, 7.8 Hz, 1H), 7.06 (t, J = 2.2 Hz, 1H), 7.03-6.94 (m, 2H), 6.87 (t, J = 7.3 Hz, 1H), 4.22-4.04 (m, 1H), 3.56-3.39 (m, 3H), 3.15 (br d, J = 13.0 Hz, 1H), 2.96 (d, J = 13.0 Hz, 1H), 2.30 (br t, J = 10.0 Hz, 1H), 2.20-1.60 (m, 13H), 1.55 (d, J = 5.7 Hz, 6H), 1.51-1.38 (m, 1H), 1.23 (s, 3H), 1.07 (d, J = 1.6 Hz, 3H). $[\alpha]_D^{22}$ = −34.6° (c 0.2, MeOH). LCMS (m/z) $(M + H)^+$: 569.3 |

TABLE 1-continued

| Ex. | Structure and Name | Characterization Data ($^1$H NMR, optical rotation, and/or LCMS) |
|---|---|---|
| A16 | 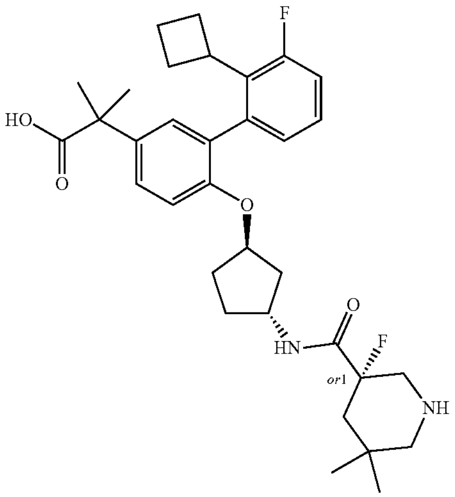 [SMILES: CC1(C)CNC[C@](F)(C(=O)N[C@@H]2CC[C@@H](Oc3ccc(C(C)(C)C(=O)O)cc3-c3cccc(F)c3C3CCC3)C2)C1] 2-(2'-cyclobutyl-3'-fluoro-6-{[(1R,3R)-3-{[(3ξ)-3-fluoro-5,5-dimethylpiperidine-3-carbonyl]amino}cyclopentyl]oxy}[1,1'-biphenyl]-3-yl)-2-methylpropanoic acid | $^1$H NMR (400 MHz, MeOD) δ 8.35-8.23 (m, 1H), 7.35 (dd, J = 2.6, 8.7 Hz, 1H), 7.16 (ddt, J = 1.8, 5.6, 7.8 Hz, 1H), 7.06 (t, J = 2.4 Hz, 1H), 7.02-6.94 (m, 2H), 6.87 (ddd, J = 1.2, 4.8, 7.5 Hz, 1H), 4.19-4.05 (m, 1H), 3.57-3.38 (m, 3H), 3.15 (br d, J = 13.0 Hz, 1H), 2.96 (d, J = 13.0 Hz, 1H), 2.41-2.23 (m, 1H), 2.22-1.56 (m, 13H), 1.55 (d, J = 5.7 Hz, 6H), 1.51-1.40 (m, 1H), 1.23 (s, 3H), 1.07 (s, 3H). [α]$_D^{22}$ = −12.8° (c 0.2, MeOH). LCMS (m/z) (M + H)$^+$: 569.4 |
| A17 | 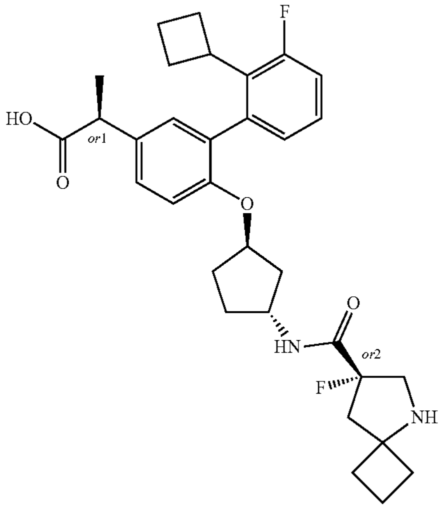 [SMILES: C[C@H](C(=O)O)c1ccc(O[C@@H]2CC[C@@H](NC(=O)[C@@]3(F)CNC4(CCC4)C3)C2)c(-c2cccc(F)c2C2CCC2)c1] (2ξ)-2-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)propanoic acid | $^1$H NMR (400 MHz, MeOD) δ 7.30 (dd, J = 2.3, 8.5 Hz, 1H), 7.16 (dt, J = 5.5, 7.8 Hz, 1H), 7.06 (s, 1H), 7.01-6.85 (m, 3H), 4.80-4.75 (m, 1H), 4.22-4.08 (m, 1H), 3.62 (q, J = 7.2 Hz, 1H), 3.55-3.37 (m, 2H), 3.28-3.15 (m, 1H), 2.49-1.66 (m, 20H), 1.43 (dd, J = 1.4, 7.2 Hz, 3H). [α]$_D^{22}$ = −17.6° (c 0.1, MeOH). LCMS (m/z) (M + H)$^+$: 553.3 |

TABLE 1-continued

| Ex. | Structure and Name | Characterization Data ($^1$H NMR, optical rotation, and/or LCMS) |
|---|---|---|
| A18 | 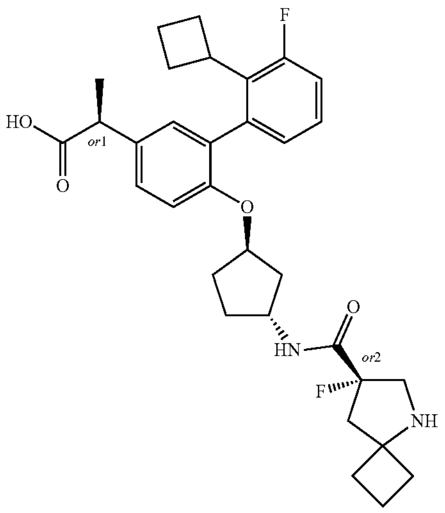 [SMILES: C[C@H](C(=O)O)c1ccc(O[C@@H]2CC[C@@H](NC(=O)[C@@]3(F)CNC4(CCC4)C3)C2)c(-c2cccc(F)c2C2CCC2)c1] (2ξ)-2-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)propanoic acid | $^1$H NMR (400 MHz, MeOD) δ 7.32 (br dd, J = 2.5, 8.5 Hz, 1H), 7.19-7.06 (m, 2H), 7.01-6.85 (m, 3H), 4.70-4.51 (m, 1H), 4.26-4.03 (m, 1H), 3.59-3.37 (m, 3H), 3.20-3.01 (m, 1H), 2.46-1.55 (m, 20H), 1.40 (d, J = 7.0 Hz, 3H). $[\alpha]_D^{22}$ = −17.0° (c 0.1, MeOH). LCMS (m/z) (M + H)$^+$: 553.2 |
| A19 | 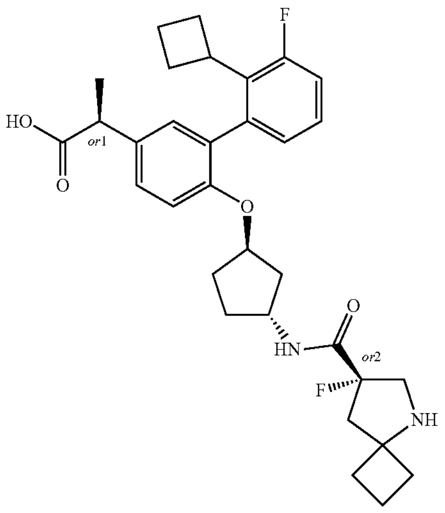 [SMILES: C[C@H](C(=O)O)c1ccc(O[C@@H]2CC[C@@H](NC(=O)[C@@]3(F)CNC4(CCC4)C3)C2)c(-c2cccc(F)c2C2CCC2)c1] (2ξ)-2-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)propanoic acid | $^1$H NMR (400 MHz, MeOD) δ 7.29 (dd, J = 2.3, 8.5 Hz, 1H), 7.16 (ddt, J = 2.3, 5.6, 7.8 Hz, 1H), 7.05 (d, J = 2.2 Hz, 1H), 7.02-6.81 (m, 3H), 4.80-4.71 (m, 1H), 4.25-4.04 (m, 1H), 3.63 (q, J = 7.2 Hz, 1H), 3.54-3.37 (m, 2H), 3.30-3.23 (m, 1H), 2.51-1.64 (m, 20H), 1.45-1.41 (m, 3H). $[\alpha]_D^{22}$ = −21.4° (c 0.1, MeOH). LCMS (m/z) (M + H)$^+$: 553.2 |

TABLE 1-continued

| Ex. | Structure and Name | Characterization Data ($^1$H NMR, optical rotation, and/or LCMS) |
|---|---|---|
| A20 | 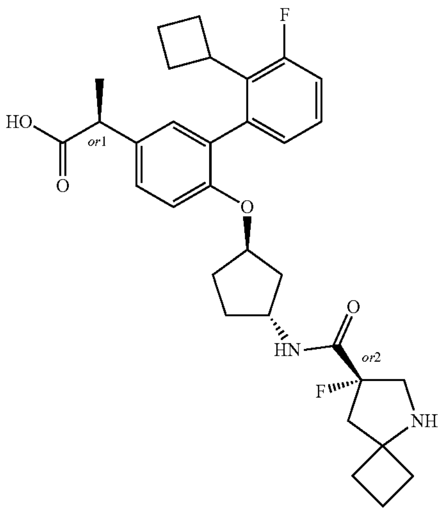 [SMILES: C[C@H](C(=O)O)c1ccc(O[C@@H]2CC[C@@H](NC(=O)[C@@]3(F)CNC4(CCC4)C3)C2)c(-c2cccc(F)c2C2CCC2)c1] (2ξ)-2-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)propanoic acid | $^1$H NMR (400 MHz, MeOD) δ 7.29 (dd, J = 2.2, 8.4 Hz, 1H), 7.20-7.12 (m, 1H), 7.05 (dd, J = 2.3, 5.6 Hz, 1H), 7.01-6.82 (m, 3H), 4.80-4.74 (m, 1H), 4.24-4.03 (m, 1H), 3.63 (q, J = 7.1 Hz, 1H), 3.56-3.36 (m, 2H), 3.30-3.21 (m, 1H), 2.51-1.60 (m, 20H), 1.46-1.41 (m, 3H). $[\alpha]_D^{22}$ = −9.1° (c 0.1, MeOH). LCMS (m/z) $(M + H)^+$: 553.3 |
| A21 | 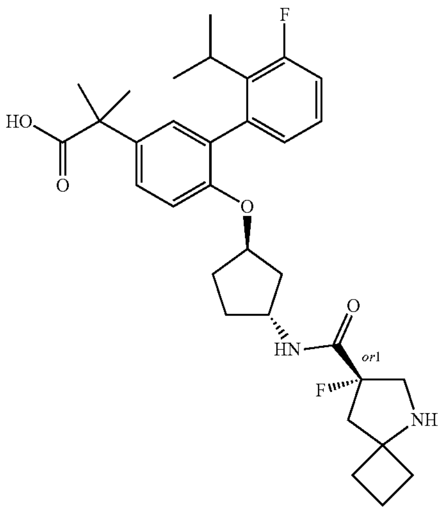 [SMILES: CC(C)c1c(F)cccc1-c1cc(C(C)(C)C(=O)O)ccc1O[C@@H]1CC[C@@H](NC(=O)[C@@]2(F)CNC3(CCC3)C2)C1] 2-[3'-fluoro-6-{[(1R,3R)-3-{[(7ξ)-7-fluoro-5-azaspiro[3.4]octane-7-carbonyl]amino}cyclopentyl]oxy}-2'-(propan-2-yl)[1,1'-biphenyl]-3-yl]-2-methylpropanoic acid | $^1$H NMR (400 MHz, DMSO-$d_6$) δ 11.05-9.50 (m, 1H), 8.56-8.43 (m, 1H), 7.33-7.28 (m, 1H), 7.24-7.18 (m, 1H), 7.13-7.06 (m, 1H), 7.02 (dd, J = 1.8, 8.8 Hz, 1H), 6.99-6.96 (m, 1H), 6.88-6.83 (m, 1H), 4.91-4.77 (m, 1H), 4.17-3.99 (m, 1H), 3.69-3.46 (m, 3H), 2.70-2.60 (m, 1H), 2.60-2.54 (m, 2H), 2.48-2.37 (m, 1H), 2.24-1.97 (m, 3H), 1.94-1.71 (m, 5H), 1.54-1.43 (m, 8H), 1.26-1.21 (m, 3H), 1.15-1.02 (m, 3H). $[\alpha]_D^{22}$ = −19.3° (c 0.1, MeOH). LCMS (m/z) $(M + H)^+$: 555.4 |

TABLE 1-continued

| Ex. | Structure and Name | Characterization Data ($^1H$ NMR, optical rotation, and/or LCMS) |
|---|---|---|
| A22 | 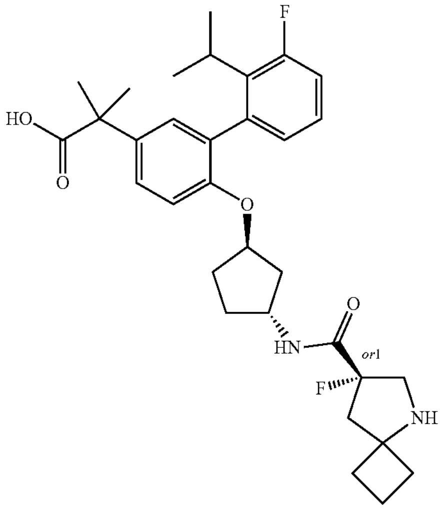 [SMILES: CC(C)c1c(F)cccc1-c1cc(C(C)(C)C(=O)O)ccc1O[C@@H]1CC[C@@H](NC(=O)[C@@]2(F)CNC3(CCC3)C2)C1] 2-[3'-fluoro-6-{[(1R,3R)-3-{[(7ξ)-7-fluoro-5-azaspiro[3.4]octane-7-carbonyl]amino}cyclopentyl]oxy}-2'-(propan-2-yl)[1,1'-biphenyl]-3-yl]-2-methylpropanoic acid | $^1H$ NMR (400 MHz, DMSO-$d_6$) δ 10.87-9.36 (m, 1H), 8.59-8.32 (m, 1H), 7.38-7.26 (m, 1H), 7.25-7.15 (m, 1H), 7.15-7.05 (m, 1H), 7.05-6.93 (m, 2H), 6.89-6.81 (m, 1H), 4.90-4.75 (m, 1H), 4.18-3.98 (m, 1H), 3.72-3.44 (m, 3H), 2.70-2.61 (m, 1H), 2.59 (br d, J = 5.6 Hz, 2H), 2.44-2.32 (m, 1H), 2.23-1.99 (m, 3H), 1.95-1.72 (m, 5H), 1.45 (br s, 8H), 1.24 (br s, 3H), 1.10 (br d, J = 6.7 Hz, 3H). $[\alpha]_D^{22}$ = −16.0° (c 0.1, MeOH). LCMS (m/z) $(M + H)^+$: 555.4 |
| A23 | 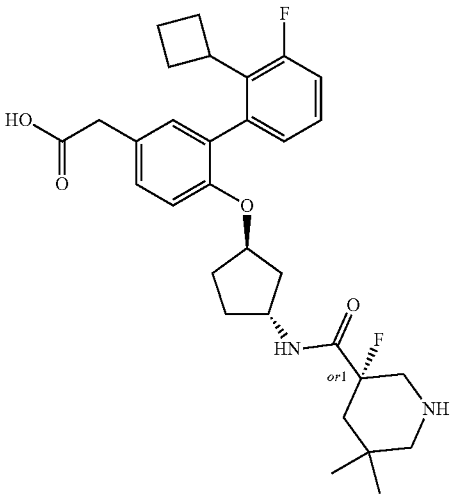 [SMILES: CC1(C)CNC[C@](F)(C(=O)N[C@@H]2CC[C@@H](Oc3ccc(CC(=O)O)cc3-c3cccc(F)c3C3CCC3)C2)C1] (2'-cyclobutyl-3'-fluoro-6-{[(1R,3R)-3-{[(3ξ)-3-fluoro-5,5-dimethylpiperidine-3-carbonyl]amino}cyclopentyl]oxy}[1,1'-biphenyl]-3-yl)acetic acid | $^1H$ NMR (400 MHz, MeOD) δ 8.26 (br s, 1H), 7.33 (dd, J = 2.5, 8.6 Hz, 1H), 7.17 (dt, J = 5.7, 7.7 Hz, 1H), 7.06-6.96 (m, 3H), 6.87 (t, J = 6.9 Hz, 1H), 4.21-3.95 (m, 1H), 3.57-3.47 (m, 2H), 3.45-3.33 (m, 3H), 3.19-3.11 (m, 1H), 3.00-2.91 (m, 1H), 2.38-1.67 (m, 14H), 1.55 (d, J = 9.8 Hz, 6H), 1.51-1.43 (m, 1H), 1.27-1.19 (m, 6H), 1.07 (d, J = 2.4 Hz, 3H). LCMS (m/z) $(M + H)^+$: 541.3 |

TABLE 1-continued

| Ex. | Structure and Name | Characterization Data ($^1H$ NMR, optical rotation, and/or LCMS) |
|---|---|---|
| A24 | 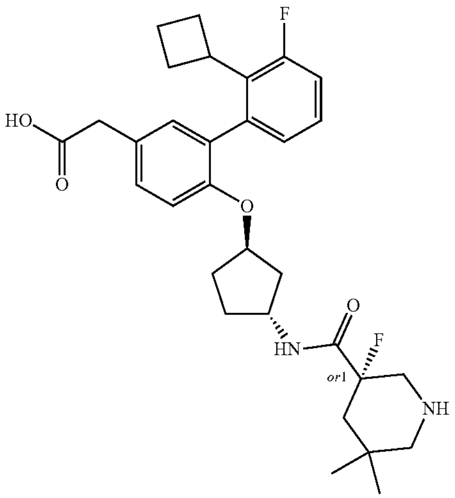 [SMILES: CC1(C)CNC[C@](F)(C(=O)N[C@@H]2CC[C@@H](Oc3ccc(CC(=O)O)cc3-c3cccc(F)c3C3CCC3)C2)C1] (2'-cyclobutyl-3'-fluoro-6-{[(1R,3R)-3-{[(3ξ)-3-fluoro-5,5-dimethylpiperidine-3-carbonyl]amino}cyclopentyl]oxy}[1,1'-biphenyl]-3-yl)acetic acid | $^1H$ NMR (400 MHz, MeOD) δ 7.2-7.3 (m, 1H), 7.1-7.2 (m, 1H), 6.9-7.0 (m, 3H), 6.8-6.9 (m, 1H), 4.81 (br d, 1H, J = 2.2 Hz), 4.0-4.2 (m, 1H), 3.56 (s, 2H), 3.4-3.5 (m, 2H), 3.16 (br d, 1H, J = 12.8 Hz), 2.96 (br d, 1H, J = 12.8 Hz), 1.4-2.4 (m, 15H), 1.2-1.2 (m, 3H), 1.0-1.1 (m, 3H). LCMS (m/z) $(M + H)^+$: 541.3 |
| A25 | 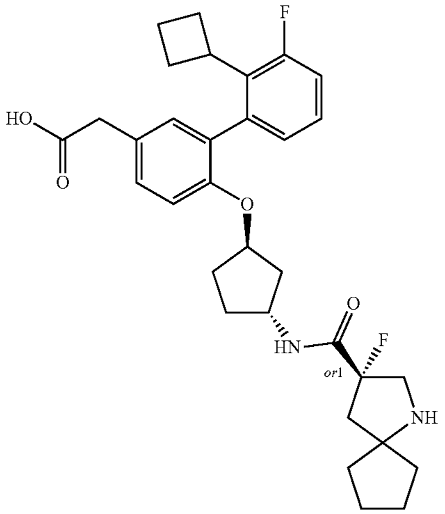 [SMILES: O=C(O)Cc1ccc(O[C@@H]2CC[C@@H](NC(=O)[C@@]3(F)CNC4(CCCC4)C3)C2)c(-c2cccc(F)c2C2CCC2)c1] (2'-cyclobutyl-3'-fluoro-6-{[(1R,3R)-3-{[(3ξ)-3-fluoro-1-azaspiro[4.4]nonane-3-carbonyl]amino}cyclopentyl]oxy}[1,1'-biphenyl]-3-yl)acetic acid | $^1H$ NMR (600 MHz, DMSO-$d_6$) δ 8.15-8.02 (m, 1H), 7.25-7.17 (m, 2H), 7.10 (dd, J = 8.2, 11.8 Hz, 1H), 6.96 (br d, J = 6.5 Hz, 2H), 6.87 (s, 1H), 4.90-4.61 (m, 1H), 4.10 (br dd, J = 7.3, 14.9 Hz, 3H), 3.47-3.43 (m, 4H), 3.18 (td, J = 1.4, 3.1 Hz, 1H), 3.05-2.89 (m, 1H), 2.26-2.14 (m, 2H), 2.13-2.02 (m, 3H), 2.01-1.84 (m, 4H), 1.81-1.75 (m, 1H), 1.73-1.62 (m, 5H), 1.60-1.51 (m, 1H), 1.49-1.36 (m, 2H). LCMS (m/z) $(M + H)^+$: 553.4 |

TABLE 1-continued

| Ex. | Structure and Name | Characterization Data ($^1$H NMR, optical rotation, and/or LCMS) |
|---|---|---|
| A26 | 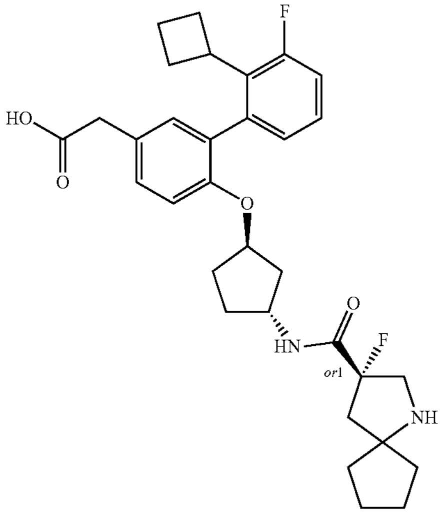 [SMILES: O=C(O)Cc1ccc(O[C@@H]2CC[C@@H](NC(=O)[C@@]3(F)CNC4(CCCC4)C3)C2)c(-c2cccc(F)c2C2CCC2)c1] (2'-cyclobutyl-3'-fluoro-6-{[(1R,3R)-3-{[(3ξ)-3-fluoro-1-azaspiro[4.4]nonane-3-carbonyl]amino}cyclopentyl]oxy}[1,1'-biphenyl]-3-yl)acetic acid | LCMS (m/z) $(M + H)^+$: 553.0 |
| A27 | 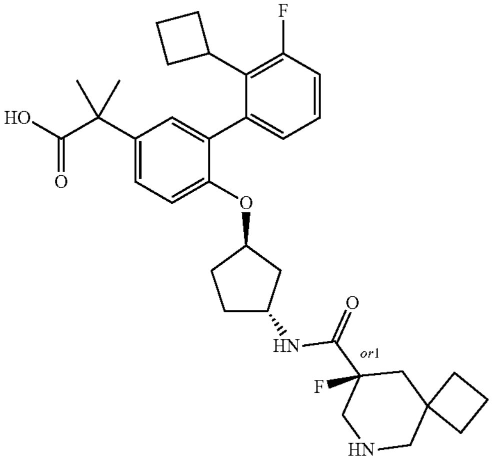 [SMILES: CC(C)(C(=O)O)c1ccc(O[C@@H]2CC[C@@H](NC(=O)[C@@]3(F)CNCC4(CCC4)C3)C2)c(-c2cccc(F)c2C2CCC2)c1] 2-(2'-cyclobutyl-3'-fluoro-6-{[(1R,3R)-3-{[(8ξ)-8-fluoro-6-azaspiro[3.5]nonane-8-carbonyl]amino} cyclopentyl]oxy}[1,1'-biphenyl]-3-yl)-2-methylpropanoic acid | First to elute<br>$^1$H NMR (600 MHz, DMSO-$d_6$) δ = 8.00 (br d, J = 5.4 Hz, 1H), 7.32-7.27 (m, 1H), 7.24-7.18 (m, 1H), 7.13-7.06 (m, 1H), 6.99 (br dd, J = 2.2, 4.4 Hz, 2H), 6.90-6.85 (m, 1H), 4.80 (br s, 1H), 4.10-3.97 (m, 2H), 3.47-3.39 (m, 1H), 3.19-3.16 (m, 2H), 2.93 (br d, J = 12.4 Hz, 1H), 2.81-2.72 (m, 1H), 2.50 (br d, J = 1.8 Hz, 1H), 2.21-2.02 (m, 3H), 1.93-1.62 (m, 14H), 1.57-1.42 (m, 9H).<br>$[\alpha]_D^{22}$ = −11.3° (c 0.1, MeOH)<br>LCMS (m/z) $(M + H)^+$: 582.0 |

TABLE 1-continued

| Ex. | Structure and Name | Characterization Data ($^1H$ NMR, optical rotation, and/or LCMS) |
|---|---|---|
| A28 | 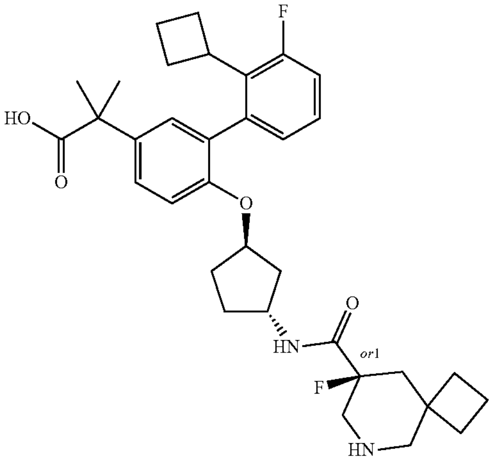 [SMILES: CC(C)(C(=O)O)c1ccc(O[C@@H]2CC[C@@H](NC(=O)[C@@]3(F)CNCC4(CCC4)C3)C2)c(-c2cccc(F)c2C2CCC2)c1] 2-(2'-cyclobutyl-3'-fluoro-6-{[(1R,3R)-3-{[(8ξ)-8-fluoro-6-azaspiro[3.5]nonane-8-carbonyl]amino}cyclopentyl]oxy}[1,1'-biphenyl]-3-yl)-2-methylpropanoic acid | Second to elute $^1H$ NMR (600 MHz, DMSO-$d_6$, 40 of 42 observed) δ = 8.00 (br s, 1H), 7.30 (br d, J = 8.4 Hz, 1H), 7.24-7.18 (m, 1H), 7.12-7.06 (m, 1H), 7.01-6.96 (m, 2H), 6.88 (br t, J = 7.1 Hz, 1H), 4.80 (br s, 1H), 4.09-3.97 (m, 1H), 3.48-3.39 (m, 1H), 3.00-2.89 (m, 1H), 2.86-2.72 (m, 1H), 2.44-2.29 (m, 1H), 2.23-2.03 (m, 3H), 2.02-1.61 (m, 16H), 1.58-1.36 (m, 8H). $[\alpha]_D^{22}$ = −36.7° (c 0.1, MeOH) LCMS (m/z) $(M + H)^+$: 582.0 |
| A29 | 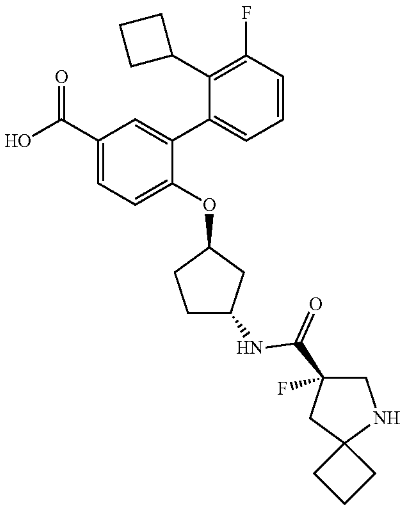 [SMILES: O=C(O)c1ccc(O[C@@H]2CC[C@@H](NC(=O)[C@@]3(F)CNC4(CCC4)C3)C2)c(-c2cccc(F)c2C2CCC2)c1] 2'-cyclobutyl-3'-fluoro-6-{[(1R,3R)-3-{[(7S)-7-fluoro-5-azaspiro[3.4]octane-7-carbonyl]amino}cyclopentyl]oxy}[1,1'-biphenyl]-3-carboxylic acid | $^1H$ NMR (400 MHz, DMSO-$d_6$) δ 8.23-8.15 (m, 1H), 7.94 (dd, J = 2.2, 8.6 Hz, 1H), 7.62 (t, J = 2.1 Hz, 1H), 7.28-7.21 (m, 1H), 7.18-7.08 (m, 2H), 6.89 (d, J = 7.5 Hz, 1H), 4.96 (br. s, 1H), 4.18-4.02 (m, 1H), 3.47-3.35 (m, 1H), 3.20-2.97 (m, 2H), 2.25-2.17 (m, 2H), 2.12-1.93 (m, 8H), 1.86-1.41 (m, 10H) LCMS (m/z) $(M + H)^+$: 525.3 |

TABLE 1-continued

| Ex. | Structure and Name | Characterization Data ($^1$H NMR, optical rotation, and/or LCMS) |
|---|---|---|
| A30 | 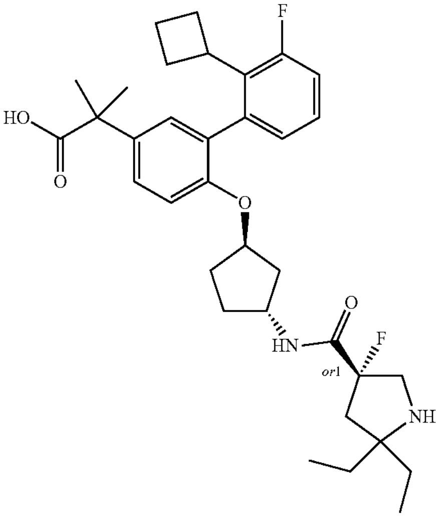 [SMILES: CCC1(CC)C[C@@](F)(C(=O)N[C@@H]2CC[C@@H](Oc3ccc(C(C)(C)C(=O)O)cc3-c3cccc(F)c3C3CCC3)C2)CN1]<br>2-(2'-cyclobutyl-6-{[(1R,3R)-3-{[(3ξ)-5,5-diethyl-3-fluoropyrrolidine-3-carbonyl]amino}cyclopentyl]oxy}-3'-fluoro[1,1'-biphenyl]-3-yl)-2-methylpropanoic acid | $^1$H NMR (400 MHz, DMSO-$d_6$) δ 8.30-7.96 (m, 1H), 7.38-7.28 (m, 1H), 7.27-7.17 (m, 1H), 7.16-7.05 (m, 1H), 7.03-6.94 (m, 2H), 6.88 (dd, J = 3.3, 7.0 Hz, 1H), 5.11-4.65 (m, 1H), 4.22-3.93 (m, 1H), 3.51-3.39 (m, 1H), 3.17-2.95 (m, 2H), 2.28-1.63 (m, 12H), 1.59-1.38 (m, 11H), 1.35-1.27 (m, 1H), 0.87-0.72 (m, 6H).<br>LCMS (m/z) $(M + H)^+$: 583.6 |
| A31 | 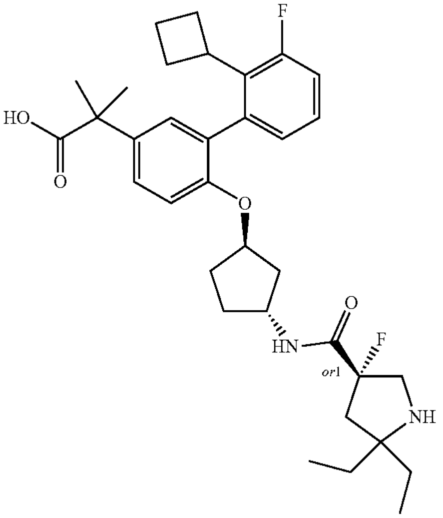 [SMILES: CCC1(CC)C[C@@](F)(C(=O)N[C@@H]2CC[C@@H](Oc3ccc(C(C)(C)C(=O)O)cc3-c3cccc(F)c3C3CCC3)C2)CN1]<br>2-(2'-cyclobutyl-6-{[(1R,3R)-3-{[(3ξ)-5,5-diethyl-3-fluoropyrrolidine-3-carbonyl]amino}cyclopentyl]oxy}-3'-fluoro[1,1'-biphenyl]-3-yl)-2-methylpropanoic acid | $^1$H NMR (400 MHz, DMSO-$d_6$) δ 8.15-8.09 (m, 1H), 7.30 (d, J = 8.7 Hz, 1H), 7.25-7.18 (m, 1H), 7.14-7.08 (m, 1H), 6.99 (td, J = 2.1, 4.6 Hz, 2H), 6.88 (ddd, J = 0.9, 3.4, 7.6 Hz, 1H), 4.83-4.79 (m, 1H), 4.08 (br. dd, J = 7.8, 15.3 Hz, 1H), 3.48-3.41 (m, 1H), 3.14-2.97 (m, 2H), 2.23-1.68 (m, 12H), 1.57-1.40 (m, 11H), 1.35-1.29 (m, 1H), 0.80 (q, J = 6.9 Hz, 6H).<br>LCMS (m/z) $(M + H)^+$: 583.3 |

TABLE 1-continued

| Ex. | Structure and Name | Characterization Data ($^1$H NMR, optical rotation, and/or LCMS) |
| --- | --- | --- |
| A32 | 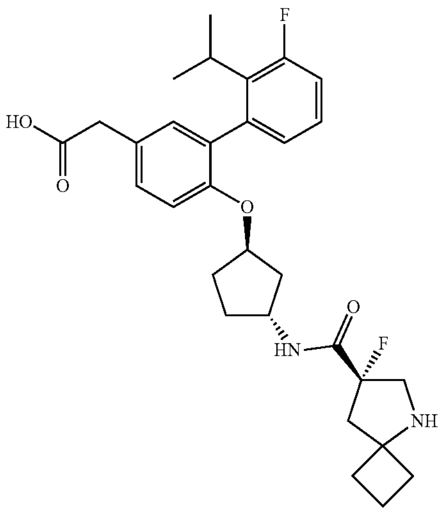 [SMILES: CC(C)c1c(F)cccc1-c1cc(CC(=O)O)ccc1O[C@@H]1CC[C@@H](NC(=O)[C@@]2(F)CNC3(CCC3)C2)C1] [3'-fluoro-6-{[(1R,3R)-3-{[(7S)-7-fluoro-5-azaspiro[3.4]octane-7-carbonyl]amino}cyclopentyl]oxy}-2'-(propan-2-yl)[1,1'-biphenyl]-3-yl]acetic acid | $^1$H NMR (400 MHz, DMSO-$d_6$) δ 9.91 (br. s, 1H) 8.43-8.57 (m, 1H) 7.16-7.26 (m, 2H) 7.10 (dd, J = 11.94, 7.82 Hz, 1H) 7.00 (d, J = 7.75 Hz, 1H) 6.95 (t, J = 2.13 Hz, 1H) 6.84 (d, J = 7.50 Hz, 1H) 4.72-4.90 (m, 1H) 4.00-4.15 (m, 1H) 3.46-3.71 (m, 4H) 2.54-2.75 (m, 2H) 2.30-2.46 (m, 1H) 1.64-2.26 (m, 8H) 1.38-1.59 (m, 2H) 1.04-1.32 (m, 8H). LCMS (m/z) (M + H)$^+$: 527.3 |
| A33 | 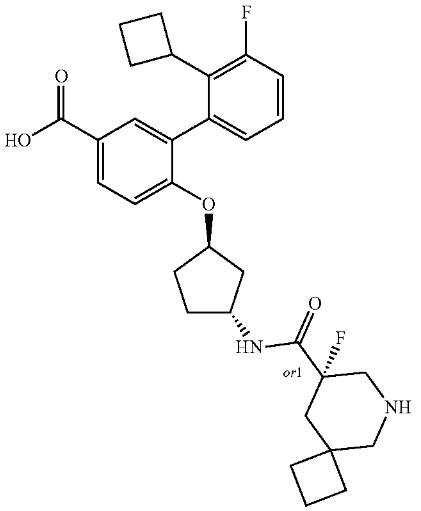 [SMILES: O=C(O)c1ccc(O[C@@H]2CC[C@@H](NC(=O)[C@@]3(F)CNCC4(CCC4)C3)C2)c(-c2cccc(F)c2C2CCC2)c1] 2'-cyclobutyl-3'-fluoro-6-{[(1R,3R)-3-{[(8ξ)-8-fluoro-6-azaspiro[3.5]nonane-8-carbonyl]amino}cyclopentyl]oxy}[1,1'-biphenyl]-3-carboxylic acid | $^1$H NMR (400 MHz, DMSO-$d_6$) δ 13.33-11.81 (m, 1H), 9.93-8.65 (m, 1H), 8.45 (br. t, J = 8.3 Hz, 1H), 7.95 (dd, J = 1.8, 8.6 Hz, 1H), 7.62 (t, J = 2.2 Hz, 1H), 7.29-7.20 (m, 1H), 7.18-7.09 (m, 2H), 6.89 (d, J = 7.6 Hz, 1H), 4.98 (br. s, 1H), 4.07 (td, J = 7.5, 14.9 Hz, 1H), 2.94 ( dd, J = 5.7, 12.7 Hz, 1H), 2.25-1.46 (m, 20H). LCMS (m/z) (M + H)$^+$: 539.3 $[\alpha]_D^{22}$ = −46.9° (c 0.1, MeOH) |

TABLE 1-continued

| Ex. | Structure and Name | Characterization Data ($^1H$ NMR, optical rotation, and/or LCMS) |
|---|---|---|
| A34 | 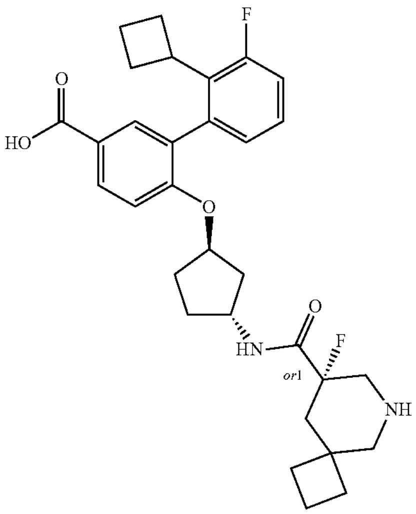 [SMILES: O=C(O)c1ccc(O[C@@H]2CC[C@@H](NC(=O)[C@@]3(F)CNCC4(CCC4)C3)C2)c(-c2cccc(F)c2C2CCC2)c1]<br>2'-cyclobutyl-3'-fluoro-6-{[(1R,3R)-3-{[(8ξ)-8-fluoro-6-azaspiro[3.5]nonane-8-carbonyl]amino}cyclopentyl]oxy}[1,1'-biphenyl]-3-carboxylic acid | $^1H$ NMR (400 MHz, DMSO-$d_6$) δ 13.09-11.48 (m, 1H), 10.21-8.65 (m, 1H), 8.45 (br. t, J = 8.1 Hz, 1H), 7.96 (dd, J = 1.9, 8.6 Hz, 1H), 7.62 (t, J = 2.3 Hz, 1H), 7.29-7.21 (m, 1H), 7.18-7.09 (m, 2H), 6.89 (d, J = 7.5 Hz, 1H), 4.98 (br. s, 1H), 4.06 (br. s, 1H), 3.43 (br. s, 2H), 3.29-3.19 (m, 2H), 2.95 (br. dd, J = 4.5, 12.7 Hz, 1H), 1.50 (br. d, J = 4.9 Hz, 20H). LCMS (m/z) $(M + H)^+$: 539.4 $[\alpha]_D^{22}$ = −13.3° (c 0.1, MeOH) |
| A35 | 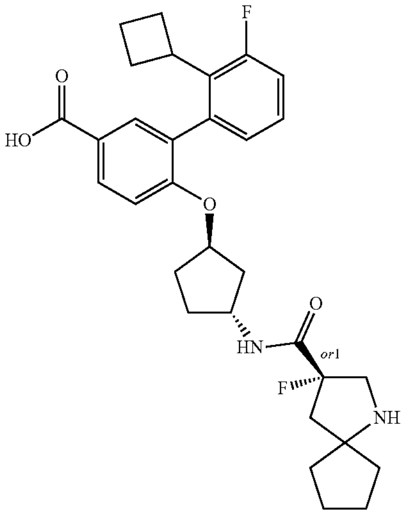 [SMILES: O=C(O)c1ccc(O[C@@H]2CC[C@@H](NC(=O)[C@@]3(F)CNC4(CCCC4)C3)C2)c(-c2cccc(F)c2C2CCC2)c1]<br>2'-cyclobutyl-3'-fluoro-6-{[(1R,3R)-3-{[(3ξ)-3-fluoro-1-azaspiro[4.4]nonane-3-carbonyl]amino}cyclopentyl]oxy}[1,1'-biphenyl]-3-carboxylic acid | $^1H$ NMR (400 MHz, DMSO-$d_6$) δ 10.40-9.31 (m, 1H), 8.58 (br. t, J = 9.7 Hz, 1H), 7.95 (dd, J = 2.0, 8.6 Hz, 1H), 7.62 (t, J = 2.1 Hz, 1H), 7.31-7.21 (m, 1H), 7.20-7.10 (m, 2H), 6.94-6.85 (m, 1H), 4.98 (br. s, 1H), 4.19-4.04 (m, 1H), 3.77-3.51 (m, 3H), 2.44-2.31 (m, 1H), 2.26-1.91 (m, 8H), 1.90-1.60 (m, 12H), 1.60-1.38 (m, 2H). LCMS (m/z) $(M + H)^+$: 539.4 $[\alpha]_D^{22}$ = −115.2° (c 0.1, MeOH) |

TABLE 1-continued

| Ex. | Structure and Name | Characterization Data ($^1$H NMR, optical rotation, and/or LCMS) |
|---|---|---|
| A36 | 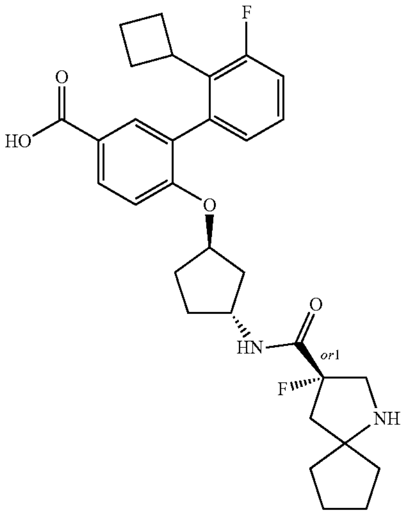 [SMILES: O=C(O)c1ccc(O[C@@H]2CC[C@@H](NC(=O)[C@@]3(F)CNC4(CCCC4)C3)C2)c(-c2cccc(F)c2C2CCC2)c1] 2'-cyclobutyl-3'-fluoro-6-{[(1R,3R)-3-{[(3ξ)-3-fluoro-1-azaspiro[4.4]nonane-3-carbonyl]amino}cyclopentyl]oxy}[1,1'-biphenyl]-3-carboxylic acid | $^1$H NMR (400 MHz, DMSO-$d_6$) δ 9.90-9.34 (m, 1H), 8.57 (br. s, 1H), 7.96 (dd, J = 2.0, 8.6 Hz, 1H), 7.62 (t, J = 2.3 Hz, 1H), 7.24 (dd, J = 5.8, 7.8 Hz, 1H), 7.19-7.10 (m, 2H), 6.90 (d, J = 7.5 Hz, 1H), 4.99 (br. d, J = 3.3 Hz, 1H), 4.22-4.03 (m, 1H), 3.79-3.54 (m, 2H), 3.41 (br. d, J = 8.6 Hz, 1H), 2.44-2.35 (m, 1H), 2.29-2.12 (m, 2H), 2.11-1.90 (m, 6H), 1.89-1.58 (m, 12H), 1.57-1.40 (m, 2H). LCMS (m/z) $(M + H)^+$: 539.4 |
| A37 | 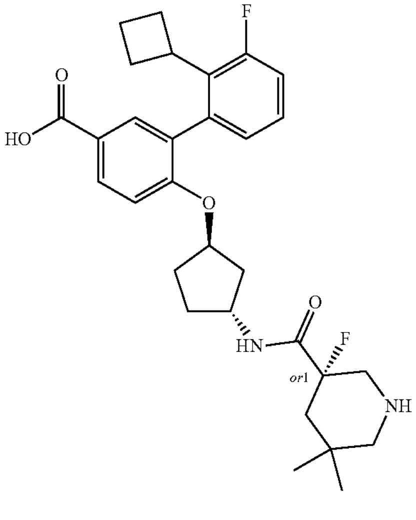 [SMILES: CC1(C)CNC[C@](F)(C(=O)N[C@@H]2CC[C@@H](Oc3ccc(C(=O)O)cc3-c3cccc(F)c3C3CCC3)C2)C1] 2'-cyclobutyl-3'-fluoro-6-{[(1R,3R)-3-{[(3ξ)-3-fluoro-5,5-dimethylpiperidine-3-carbonyl]amino}cyclopentyl]oxy}[1,1'-biphenyl]-3-carboxylic acid | $^1$H NMR (400 MHz, DMSO-$d_6$) δ 8.52-8.42 (m, 1H), 7.98-7.91 (m, 1H), 7.64-7.59 (m, 1H), 7.28-7.20 (m, 1H), 7.18-7.07 (m, 2H), 6.88 (d, J = 7.6 Hz, 1H), 5.07-4.86 (m, 1H), 4.17-3.96 (m, 1H), 3.30-3.16 (m, 3H), 3.02-2.94 (m, 1H), 2.91-2.81 (m, 1H), 2.29-1.69 (m, 12H), 1.69-1.38 (m, 3H), 1.16-1.08 (m, 3H), 0.99-0.91 (m, 3H). LCMS (m/z) $(M + H)^+$: 527.4 $[\alpha]_D^{22}$ = −45.3 ° (c 0.1, MeOH) |

TABLE 1-continued

| Ex. | Structure and Name | Characterization Data ($^1$H NMR, optical rotation, and/or LCMS) |
|---|---|---|
| A38 | 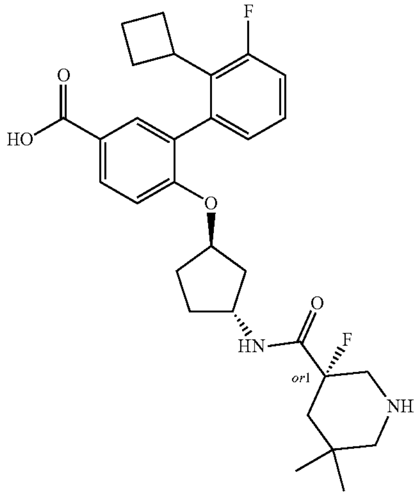 [SMILES: CC1(C)CNC[C@](F)(C(=O)N[C@@H]2CC[C@@H](Oc3ccc(C(=O)O)cc3-c3cccc(F)c3C3CCC3)C2)C1] 2'-cyclobutyl-3'-fluoro-6-{[(1R,3R)-3-{[(3ξ)-3-fluoro-5,5-dimethylpiperidine-3-carbonyl]amino}cyclopentyl]oxy}[1,1'-biphenyl]-3-carboxylic acid | $^1$H NMR (400 MHz, DMSO-$d_6$) δ 8.54-8.41 (m, 1H), 8.00-7.89 (m, 1H), 7.66-7.59 (m, 1H), 7.29-7.20 (m, 1H), 7.18-7.07 (m, 2H), 6.93-6.83 (m, 1H), 5.04-4.89 (m, 1H), 4.17-3.97 (m, 1H), 3.32-3.21 (m, 3H), 3.02-2.93 (m, 1H), 2.92-2.84 (m, 1H), 2.30-1.69 (m, 12H), 1.68-1.42 (m, 3H), 1.16-1.08 (m, 3H), 1.01-0.92 (m, 3H). LCMS (m/z) (M + H)$^+$: 527.2 |
| A39 | 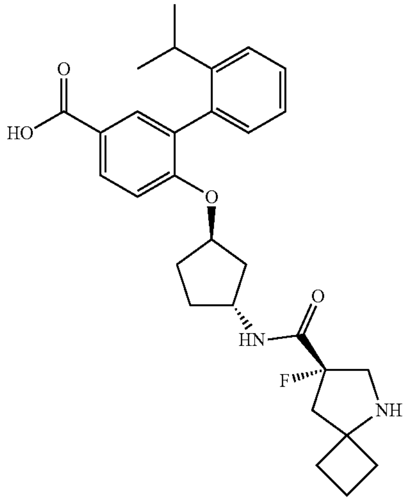 [SMILES: CC(C)c1ccccc1-c1cc(C(=O)O)ccc1O[C@@H]1CC[C@@H](NC(=O)[C@@]2(F)CNC3(CCC3)C2)C1] 6-{[(1R,3R)-3-{[(7S)-7-fluoro-5-azaspiro[3.4]octane-7-carbonyl]amino} cyclopentyl]oxy}-2'-(propan-2-yl)[1,1'-biphenyl]-3-carboxylic acid | $^1$H NMR (400 MHz, DMSO-$d_6$) δ 0.96 (dd, J =6.82, 3.52 Hz, 3H), 1.16 (d, J = 6.82 Hz, 3H), 1.39-1.54 (m, 2H), 1.57-1.65 (m, 1H), 1.65-1.72 (m, 1H), 1.74-1.80 (m, 1H), 1.85 (br. dd, J = 13.97, 6.49 Hz, 1H), 1.93-2.03 (m, 4H), 2.06-2.27 (m, 3H), 2.57-2.70 (m, 1H), 2.89-3.19 (m, 3H), 3.97-4.14 (m, 2H), 4.95 (br. d, J = 2.86 Hz, 1H), 7.01 (d, J = 7.48 Hz, 1H), 7.13 (d, J = 8.80 Hz, 1H), 7.19 (td, J = 7.26, 1.54 Hz, 1H), 7.29-7.40 (m, 2H), 7.60 (t, J = 2.09 Hz, 1H), 7.93 (dd, J = 8.58, 2.20 Hz, 1H), 8.16 (td, J = 7.37, 2.64 Hz, 1H). LCMS (m/z) (M + H)$^+$: 495.3 |

TABLE 1-continued

| Ex. | Structure and Name | Characterization Data ($^1$H NMR, optical rotation, and/or LCMS) |
| --- | --- | --- |
| A40 | 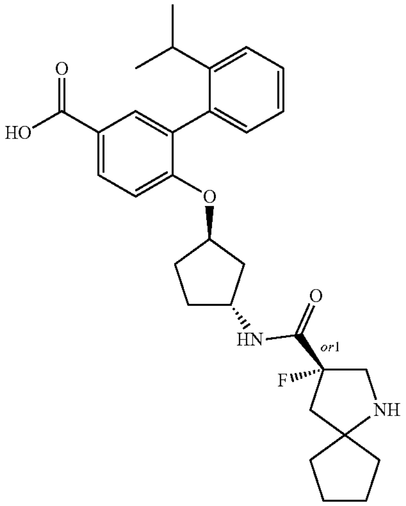 [SMILES: CC(C)c1ccccc1-c1cc(C(=O)O)ccc1O[C@@H]1CC[C@@H](NC(=O)[C@@]2(F)CNC3(CCCC3)C2)C1] 6-{[(1R,3R)-3-{[(3ξ)-3-fluoro-1-azaspiro[4.4]nonane-3-carbonyl]amino}cyclopentyl]oxy}-2'-(propan-2-yl)[1,1'-biphenyl]-3-carboxylic acid | $^1$H NMR (400 MHz, DMSO-$d_6$) δ 0.96 (dd, J = 6.69, 4.69 Hz, 3 H) 1.16 (d, J = 6.88 Hz, 3 H) 1.40-1.70 (m, 10 H) 1.70-2.02 (m, 4 H) 2.03-2.25 (m, 2H) 2.59-2.74 (m, 1 H) 2.93-3.24 (m, 3 H) 4.04-4.14 (m, 1 H) 4.95 (br. d, J = 2.50 Hz, 1 H) 7.01 (br. d, J = 7.63 Hz, 1 H) 7.13 (d, J = 8.76 Hz, 1 H) 7.19 (t, J = 7.00 Hz, 1 H) 7.30-7.40 (m, 2 H) 7.60 (t, J = 2.00 Hz, 1 H) 7.93 (dd, J = 8.69, 2.06 Hz, 1 H) 8.16 (td, J = 7.29, 2.44 Hz, 1 H). LCMS (m/z) (M + H)$^+$: 509.3 |
| A41 | 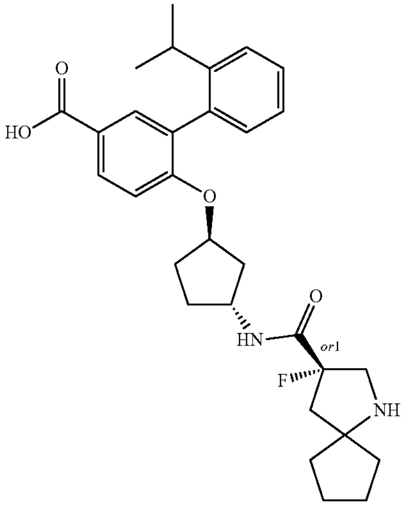 [SMILES: CC(C)c1ccccc1-c1cc(C(=O)O)ccc1O[C@@H]1CC[C@@H](NC(=O)[C@@]2(F)CNC3(CCCC3)C2)C1] 6-{[(1R,3R)-3-{[(3ξ)-3-fluoro-1-azaspiro[4.4]nonane-3-carbonyl]amino}cyclopentyl]oxy}-2'-(propan-2-yl)[1,1'-biphenyl]-3-carboxylic acid | $^1$H NMR (400 MHz, DMSO-$d_6$) δ 0.96 (dd, J = 6.63, 4.50 Hz, 3H) 1.16 (d, J = 6.88 Hz, 3H) 1.43-1.67 (m, 10H) 1.73-2.00 (m, 4H) 2.03-2.27 (m, 2H) 2.66 (quind, J = 6.80, 6.80, 6.80, 6.80, 2.81 Hz, 1H) 2.90-3.25 (m, 3H) 4.03-4.14 (m, 1H) 4.95 (br. d, J = 2.50 Hz, 1H) 7.01 (br. d, J = 7.63 Hz, 1H) 7.13(d, J = 8.76 Hz, 1H) 7.19 (t, J = 7.19 Hz, 1H) 7.30-7.40 (m, 2H) 7.60 (t, J = 2.06 Hz, 1 H) 7.93 (dd, J = 8.63, 2.13 Hz, 1H) 8.16 (td, J = 7.38, 2.50 Hz, 1H). LCMS (m/z) (M + H)$^+$: 509.2 |

TABLE 1-continued

| Ex. | Structure and Name | Characterization Data ($^1$H NMR, optical rotation, and/or LCMS) |
|---|---|---|
| A42 | 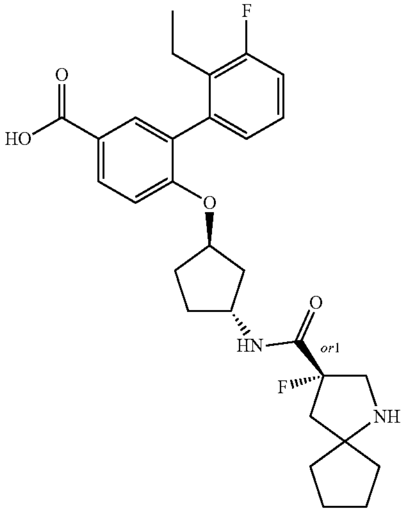 [SMILES: CCc1c(F)cccc1-c1cc(C(=O)O)ccc1O[C@@H]1CC[C@@H](NC(=O)[C@@]2(F)CNC3(CCCC3)C2)C1] 2'-ethyl-3'-fluoro-6-{[(1R,3R)-3-{[(3ξ)-3-fluoro-1-azaspiro[4.4]nonane-3-carbonyl]amino}cyclopentyl]oxy}[1,1'-biphenyl]-3-carboxylic acid | $^1$H NMR (400 MHz, DMSO-$d_6$) δ 8.21 (br. s, 1H), 7.96 (dd, J = 2.1, 8.7 Hz, 1H), 7.64 (d, J = 2.1 Hz, 1H), 7.29-7.21 (m, 1H), 7.19-7.11 (m, 2H), 6.92 (d, J = 7.4 Hz, 1H), 4.97 (br. s, 1H), 4.12-4.03 (m, 1H), 3.18-2.97 (m, 3H), 2.35-2.22 (m, 2H), 2.21-2.03 (m, 2H), 2.02-1.93 (m, 1H), 1.91-1.74 (m, 3H), 1.72-1.43 (m, 10H), 0.91 (t, J = 7.4 Hz, 3H). LCMS (m/z) $(M + H)^+$: 513.4 |
| A43 | 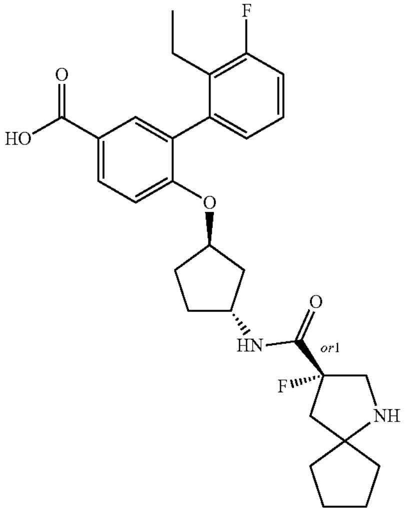 [SMILES: CCc1c(F)cccc1-c1cc(C(=O)O)ccc1O[C@@H]1CC[C@@H](NC(=O)[C@@]2(F)CNC3(CCCC3)C2)C1] 2'-ethyl-3'-fluoro-6-{[(1R,3R)-3-{[(3ξ)-3-fluoro-1-azaspiro[4.4]nonane-3-carbonyl]amino}cyclopentyl]oxy}[1,1'-biphenyl]-3-carboxylic acid | $^1$H NMR (400 MHz, DMSO-$d_6$) δ 8.20 (br. d, J = 3.0 Hz, 1H), 7.96 (br. d, J = 7.9 Hz, 1H), 7.64 (br. s, 1H), 7.26 (br. d, J = 6.9 Hz, 1H), 7.19-7.10 (m, 2H), 6.92 (br. d, J = 7.3 Hz, 1H), 4.97 (br. s, 1H), 4.09 (br. d, J = 6.8 Hz, 1H), 3.16-2.94 (m, 3H), 2.24 (br. d, J = 14.1 Hz, 2H), 1.95 (br. s, 2H), 1.93-1.76 (m, 3H), 1.72-1.41 (m, 11H), 0.91 (br. t, J = 7.1 Hz, 3H). LCMS (m/z) $(M + H)^+$: 513.4 |

TABLE 1-continued

| Ex. | Structure and Name | Characterization Data ($^1$H NMR, optical rotation, and/or LCMS) |
|---|---|---|
| A44 | 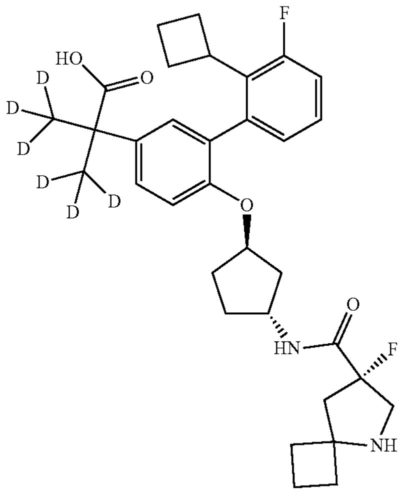 [SMILES: [2H]C([2H])([2H])C(C(=O)O)(c1ccc(O[C@@H]2CC[C@@H](NC(=O)[C@@]3(F)CNC4(CCC4)C3)C2)c(-c2cccc(F)c2C2CCC2)c1)C([2H])([2H])[2H]] 2-(2'-cyclobutyl-3'-fluoro-6-{[(1R,3R)-3-{[(7S)-7-fluoro-5-azaspiro[3.4]octane-7-carbonyl]amino} cyclopentyl]oxy}[1,1'-biphenyl]-3-yl)-2-(2H3)methyl(2H3)propanoic acid | $^1$H NMR (400 MHz, DMSO-d6) δ 8.23-8.10 (m, 1H), 7.30 (dd, J = 2.5, 8.6 Hz, 1H), 7.22 (dt, J = 5.8, 7.7 Hz, 1H), 7.15-7.07 (m, 1H), 7.02-6.95 (m, 2H), 6.88 (ddd, J = 1.1, 3.1, 7.5 Hz, 1H), 4.81 (br s, 1H), 4.08 (dt, J = 7.6, 15.4 Hz, 1H), 3.49-3.37 (m, 1H), 3.21-2.92 (m, 2H), 2.30-1.93 (m, 10H), 1.86 (br dd, J = 3.7, 7.1 Hz, 2H), 1.82-1.60 (m, 6H), 1.57-1.37 (m, 2H). LCMS (m/z) (M + H)$^+$: 573.8 |

Example 1B1: (7ξ)-N-{(1R,3R)-3-[(2'-cyclobutyl-5-{1-[(ethanesulfonyl)amino]-2-methyl-1-oxopropan-2-yl}-3'-fluoro[1,1'-biphenyl]-2-yl)oxy]cyclopentyl}-7-fluoro-5-azaspiro[3.4]octane-7-carboxamide; and Example B32: (7ξ)-N-{(1R,3R)-3-[(2'-cyclobutyl-5-{1-[(ethanesulfonyl)amino]-2-methyl-1-oxopropan-2-yl}-3'-fluoro[1,1I'-biphenyl]-2-yl)oxy]cyclopentyl}-7-fluoro-5-azaspiro[3.4]octane-7-carboxamide

B1

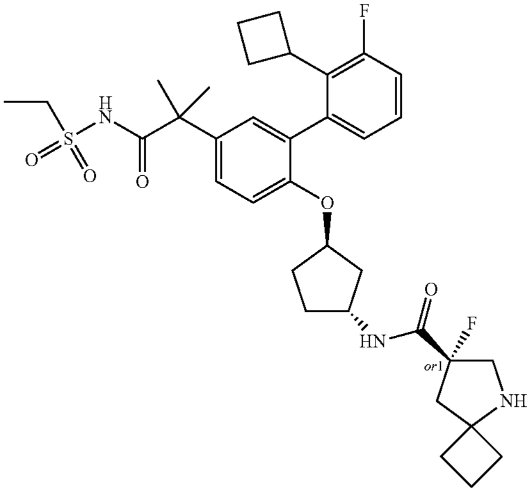

-continued

B2

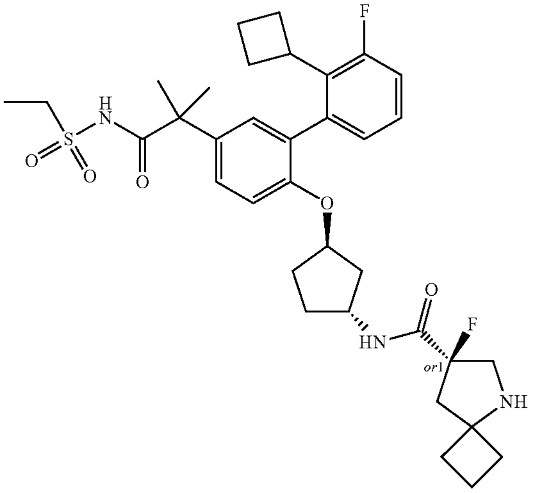

Examples B1 and B2 were prepared according to General Method B. Step 1: 2-[6-({(1R,3R)-3-[(tert-butoxycarbonyl)amino]cyclopentyl}oxy)-2'-cyclobutyl-3'-fluoro[1,1'-biphenyl]-3-yl]-2-methylpropanoic acid (B1a)

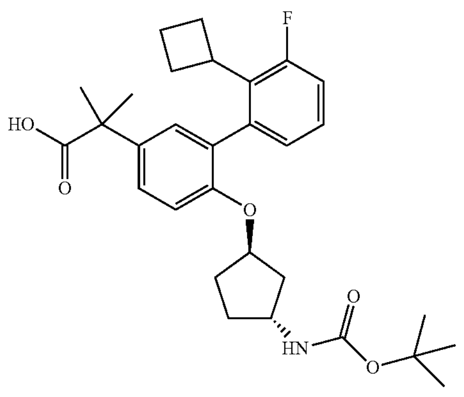 [SMILES: CC(C)(C)OC(=O)N[C@@H]1CC[C@@H](Oc2ccc(C(C)(C)C(=O)O)cc2-c2cccc(F)c2C2CCC2)C1]

To a solution of methyl 2-[6-({(1R,3R)-3-[(tert-butoxycarbonyl)amino]cyclopentyl}oxy)-2'-cyclobutyl-3'-fluoro[1,1-biphenyl]-3-yl]-2-methylpropanoate (A1b) (3.93 g, 7.48 mmol) in MeOH (50.0 mL), LiOH (1.5 N, 10.0 mL, 5.29 mmol) was added. The reaction was stirred at RT overnight but was not complete. LiOH·$H_2O$ (941 mg, 22.4 mg) was added and heated to 40° C. overnight. The MeOH was removed under reduced pressure and then the residue was partitioned between EtOAc and 1 N HCl. The aqueous layer was extracted with EtOAc (3×), then the combined organics were washed with brine, dried over $Na_2SO_4$, filtered, and concentrated under reduced pressure to a light yellow gum. A minimum amount of EtOAc was added, diluted with PE, and sonicated until a white precipitate formed which was collected by filtration to give 2-[6-({(1R,3R)-3-[(tert-butoxycarbonyl)amino]cyclopentyl}oxy)-2'-cyclobutyl-3'-fluoro[1,1'-biphenyl]-3-yl]-2-methylpropanoic acid (B1a) (3.7 g, 97%). LCMS (+) ESI 534.3 (M+Na). $^1$H NMR (400 MHz, DMSO-d6) δ ppm 12.46-12.14 (m, 1H), 7.29 (dd, J=2.4, 8.7 Hz, 1H), 7.25-7.17 (m, 1H), 7.14-7.06 (m, 1H), 7.01-6.94 (m, 2H), 6.91-6.81 (m, 2H), 4.83-4.70 (m, 1H), 3.84-3.65 (m, 1H), 3.48-3.39 (m, 1H), 2.24-2.12 (m, 1H), 2.11-1.92 (m, 3H), 1.89-1.61 (m, 6H), 1.46 (d, J=5.3 Hz, 7H), 1.35 (d, J=1.5 Hz, 10H).

Step 2: tert-butyl {(1R,3R)-3-[(2'-cyclobutyl-5-{1-[(ethanesulfonyl)amino]-2-methyl-1-oxopropan-2-yl}-3'-fluoro[1,1'-biphenyl]-2-yl)oxy]cyclopentyl}carbamate (Bib)

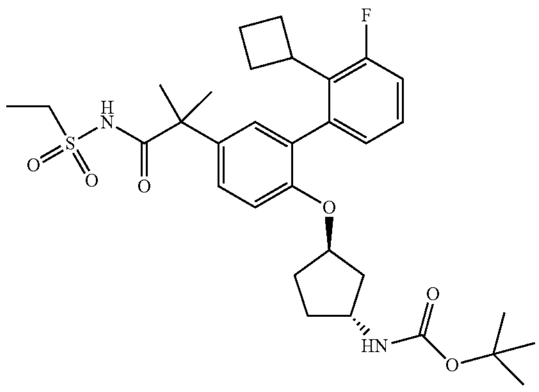 [SMILES: CCS(=O)(=O)NC(=O)C(C)(C)c1ccc(O[C@@H]2CC[C@@H](NC(=O)OC(C)(C)C)C2)c(-c2cccc(F)c2C2CCC2)c1]

To a solution of 2-[6-({(1R,3R)-3-[(tert-butoxycarbonyl)amino]cyclopentyl}oxy)-2'-cyclobutyl-3'-fluoro[1,1'-biphenyl]-3-yl]-2-methylpropanoic acid (B1a) (300 mg, 0.586 mmol) in DCM (8.0 mL), carbonyldiimidazole (143 mg, 0.880 mmol) was added. The reaction was stirred at 25-30° C. for 1 h, then ethanesulfonamide (160 mg, 1.47 mmol) and 1,8-diazabicyclo[5.4.0]undec-7-ene (357 mg, 2.35 mmol) were added. After 3 h, the reaction was concentrated under reduced pressure and the residue was purified by silica gel chromatography (0-10% MeOH/EtOAc) to give tert-butyl {(1R,3R)-3-[(2'-cyclobutyl-5-{1-[(ethanesulfonyl)amino]-2-methyl-1-oxopropan-2-yl}-3'-fluoro[1,1'-biphenyl]-2-yl)oxy]cyclopentyl}carbamate (Bib) as an impure yellow gum which was used directly in the next step. LCMS (+) ESI 625.3 (M+Na).

Step 3: 2-(6-{[(1R,3R)-3-aminocyclopentyl]oxy}-2'-cyclobutyl-3'-fluoro[1,1'-biphenyl]-3-yl)-N-(ethanesulfonyl)-2-methylpropanamide (Bic)

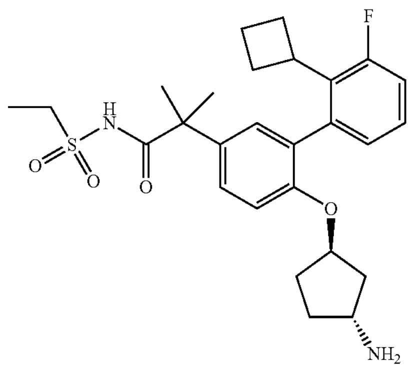 [SMILES: CCS(=O)(=O)NC(=O)C(C)(C)c1ccc(O[C@@H]2CC[C@@H](N)C2)c(-c2cccc(F)c2C2CCC2)c1]

A solution of 2-(6-{[(1R,3R)-3-aminocyclopentyl]oxy}-2'-cyclobutyl-3'-fluoro[1,1'-biphenyl]-3-yl)-N-(ethanesulfonyl)-2-methylpropanamide (Bic) from the previous step in DCM (5.0 mL) was cooled in an ice-water bath. HCl (2 N in dioxane, 4.0 mL, 8.0 mmol) was added and then the ice-bath was removed. The reaction was stirred for 3 h and then concentrated under reduced pressure to give 2-(6-{[(1R,3R)-3-aminocyclopentyl]oxy}-2'-cyclobutyl-3'-fluoro[1,1'-biphenyl]-3-yl)-N-(ethanesulfonyl)-2-methylpropanamide hydrochloride (Bic) as a white solid which was used directly in the next step. LCMS (+) APCI 503.2 (M+H).

Step 4: tert-butyl (7ξ)-7-({(1R,3R)-3-[(2'-cyclobutyl-5-{1-[(ethanesulfonyl)amino]-2-methyl-1-oxopropan-2-yl}-3'-fluoro[1,1'-biphenyl]-2-yl)oxy]cyclopentyl}carbamoyl)-7-fluoro-5-azaspiro[3.4]octane-5-carboxylate (B1d); and tert-butyl (7ξ)-7-({(1R,3R)-3-[(2'-cyclobutyl-5-{1-[(ethanesulfonyl)amino]-2-methyl-1-oxopropan-2-yl}-3'-fluoro[1,1'-biphenyl]-2-yl)oxy]cyclopentyl}carbamoyl)-7-fluoro-5-azaspiro[3.4]octane-5-carboxylate (Be)

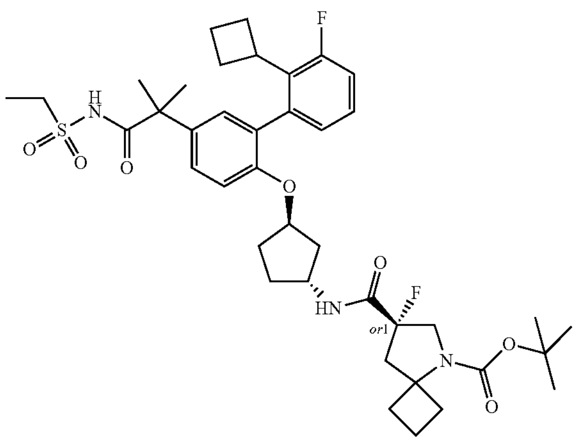

-continued

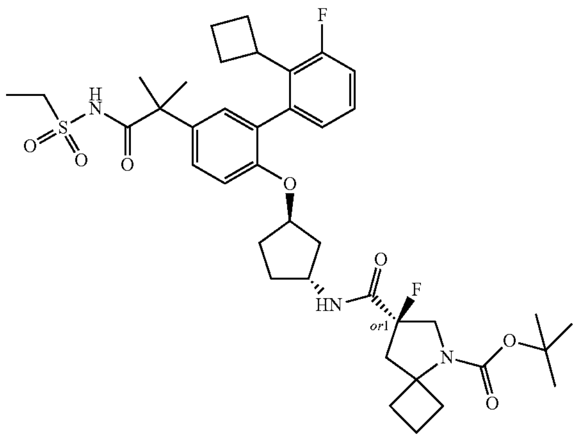

To a solution of 2-(6-{[(1R,3R)-3-aminocyclopentyl]oxy}-2'-cyclobutyl-3'-fluoro[1,1'-biphenyl]-3-yl)-N-(ethanesulfonyl)-2-methylpropanamide hydrochloride (B1c) (80 mg, 0.16 mmol) and 5-(tert-butoxycarbonyl)-7-fluoro-5-azaspiro[3.4]octane-7-carboxylic acid (Intermediate 3) (52.2 mg, 0.191 mmol) in ACN (5.0 mL), 1-methylimidazole (45.7 mg, 0.557 mmol), chloro-N,N,N',N'-tetramethylformamidinium hexafluorophosphate (51.4 mg, 0.183 mmol), and N,N-diisopropylethylamine (61.7 mg, 0.0832 mL, 0.477 mmol) were added. The reaction was stirred at RT for 16 h and then more 1-methylimidazole (19.6 mg, 0.239 mmol), chloro-N,N,N',N'-tetramethylformamidinium hexafluorophosphate (22.3 mg, 0.0796 mmol), and N,N-diisopropylethylamine (30.9 mg, 0.0416 mL, 0.239 mmol) were added. The reaction was stirred at RT for 16 h then combined with a previous 15 mg scale reaction and concentrated under reduced pressure. The residue was purified by silica gel chromatography (0-50% EtOAc/PE) to give a mixture of diastereomers LCMS (+) APCI 780.5 (M+Na) which were separated by preparative SFC (DAICEL CHIRALPAK AD column (250×30 mm, 10 μm particle size), Temperature: 40° C., Pressure: 100.0 bar, Flow Rate: 70 mL/min, eluting with 25% $^{i}$PrOH+0.1% $NH_4OH$ in $CO_2$) to give tert-butyl (7ξ)-7-({(1R,3R)-3-[(2'-cyclobutyl-5-{1-[(ethanesulfonyl)amino]-2-methyl-1-oxopropan-2-yl}-3'-fluoro[1,1'-biphenyl]-2-yl)oxy]cyclopentyl}carbamoyl)-7-fluoro-5-azaspiro[3.4]octane-5-carboxylate (B1d) (15 mg) as peak 1; and tert-butyl (7ξ)-7-({(1R,3R)-3-[(2'-cyclobutyl-5-{1-[(ethanesulfonyl)amino]-2-methyl-1-oxopropan-2-yl}-3'-fluoro[1,1'-biphenyl]-2-yl)oxy]cyclopentyl}carbamoyl)-7-fluoro-5-azaspiro[3.4]octane-5-carboxylate (B1e) (15 mg) as peak 2.

Step 5: (7ξ)-N-{(1R,3R)-3-[(2'-cyclobutyl-5-{1-[(ethanesulfonyl)amino]-2-methyl-1-oxopropan-2-yl}-3'-fluoro[1,1'-biphenyl]-2-yl)oxy]cyclopentyl}-7-fluoro-5-azaspiro[3.4]octane-7-carboxamide (Example B1); and (7ξ)-N-{(1R,3R)-3-[(2'-cyclobutyl-5-{1-[(ethanesulfonyl)amino]-2-methyl-1-oxopropan-2-yl}-3'-fluoro[1,1'-biphenyl]-2-yl)oxy]cyclopentyl}-7-fluoro-5-azaspiro[3.4]octane-7-carboxamide (Example B2)

B1

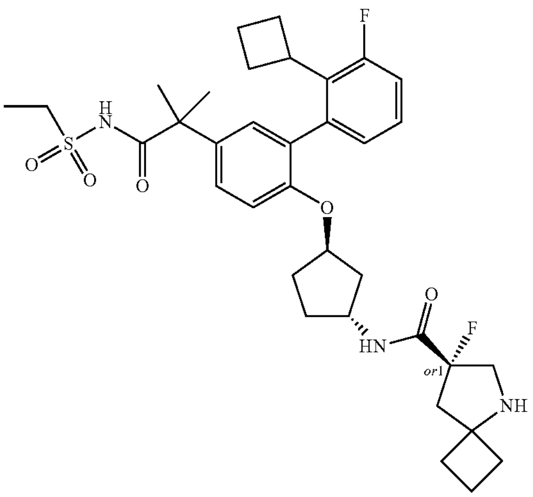

B2

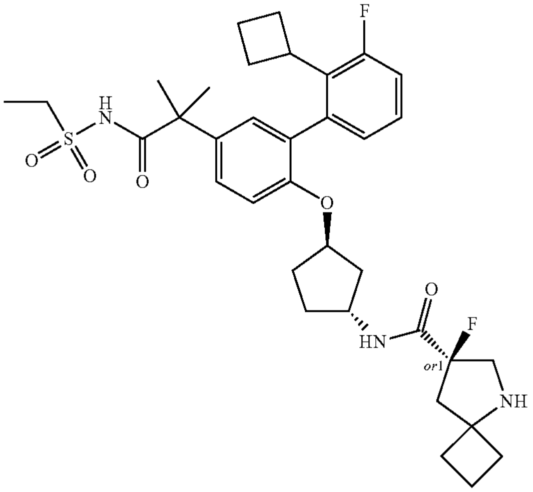

A solution of tert-butyl (7ξ)-7-({(1R,3R)-3-[(2'-cyclobutyl-5-{1-[(ethanesulfonyl)amino]-2-methyl-1-oxopropan-2-yl}-3'-fluoro[1,1'-biphenyl]-2-yl)oxy]cyclopentyl}carbamoyl)-7-fluoro-5-azaspiro[3.4]octane-5-carboxylate (B1d) (15 mg) in DCM (5.0 mL) was cooled in an ice-water bath. HCl (2 N in dioxane, 4.0 mL, 8.0 mmol) was added and then the ice-bath was removed. The reaction was stirred for 16 h and then concentrated under reduced pressure and lyophilized to give (7ξ)-N-{(1R,3R)-3-[(2'-cyclobutyl-5-{1-[(ethanesulfonyl)amino]-2-methyl-1-oxo-propan-2-yl}-3'-fluoro[1,1'-biphenyl]-2-yl)oxy]cyclopentyl}-7-fluoro-5-azaspiro[3.4]octane-7-carboxamide (Example B1) (8.77 mg, 64%) as a brown solid. LCMS (+) ESI 658.3 (M+H). $^1$H NMR (400 MHz, DMSO-d6) δ ppm 11.53-9.36 (m, 2H), 8.56-8.48 (m, 1H), 7.29-7.19 (m, 2H), 7.15-7.07 (m, 1H), 7.06-7.01 (m, 1H), 6.99-6.94 (m, 1H), 6.92-6.85 (m, 1H), 4.87-4.79 (m, 1H), 4.21-4.00 (m, 2H), 3.71-3.54 (m, 4H), 2.62-2.52 (m, 2H), 2.47-2.36 (m, 1H), 2.24-2.11 (m, 3H), 2.10-1.95 (m, 3H), 1.94-1.61 (m, 8H), 1.55-1.44 (m, 8H), 1.30-1.25 (m, 1H), 1.06 (t, J=7.3 Hz, $$3H)\cdot[\alpha]_D^{22} = -28.1^\circ$$

(c 0.1, MeOH). Example B2 was made in a similar manner starting from B1e. LCMS (+) ESI 658.3 (M+H). $^1$H NMR (400 MHz, DMSO-d6) δ ppm 11.24-9.60 (m, 2H), 8.72-8.38 (m, 1H), 7.28-7.19 (m, 2H), 7.14-7.07 (m, 1H), 7.05-7.00 (m, 1H), 6.98-6.95 (m, 1H), 6.90-6.85 (m, 1H), 4.88-4.78 (m, 1H), 4.15-4.01 (m, 1H), 3.71-3.52 (m, 4H), 3.29 (br s, 1H), 2.62-2.54 (m, 2H), 2.47 (br s, 1H), 2.23-2.13 (m, 3H), 2.10-1.96 (m, 3H), 1.93-1.77 (m, 6H), 1.75-1.63 (m, 2H), 1.53-1.44 (m, 8H), 1.30-1.25 (m, 1H), 1.06 (t, J=7.4 Hz, $$3H\cdot[\alpha]_D^{22} = -10.5^\circ$$

(c 0.1, MeOH).

Examples B3-B35 reported in Table 2 were synthesized with non-critical changes or substitutions to the exemplified procedures for Examples 1B1 and B32 that one skilled in the art would be able to realize. In Examples B7 and B8, proline was methylated after Boc deprotection using formic acid and formaldehyde.

TABLE 2

| Ex. | Structure and Name | Characterization Data ($^1$H NMR, optical rotation, and/or LCMS) |
|---|---|---|
| B3 | 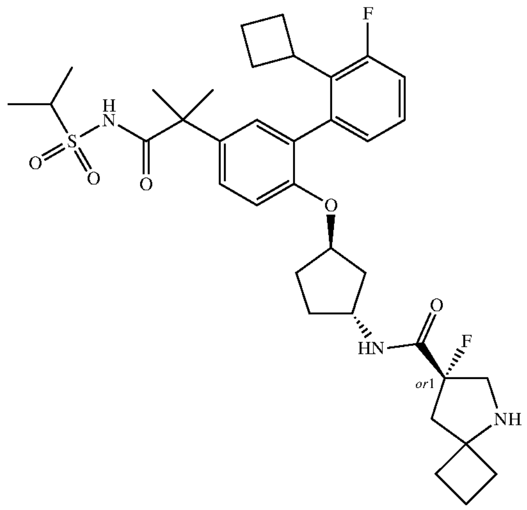 [SMILES: CC(C)S(=O)(=O)NC(=O)C(C)(C)c1ccc(O[C@@H]2CC[C@@H](NC(=O)[C@@]3(F)CNC4(CCC4)C3)C2)c(-c2cccc(F)c2C2CCC2)c1] (7ξ)-N-{(1R,3R)-3-[(2'-cyclobutyl-3'-fluoro-5-{2-methyl-1-oxo-1-[(propan-2-ylsulfonyl)amino]propan-2-yl}biphenyl-2-yl)oxy]cyclopentyl}-7-fluoro-5-azaspiro[3.4]octane-7-carboxamide | $^1$H NMR (400 MHz, DMSO-$d_6$) δ 11.10-9.58 (m, 2H), 8.56-8.48 (m, 1H), 7.29-7.19 (m, 2H), 7.15-7.08 (m, 1H), 7.03 (d, J = 8.8 Hz, 1H), 6.98-6.95 (m, 1H), 6.87 (dd, J = 1.9, 7.6 Hz, 1H), 4.87-4.80 (m, 1H), 4.16-4.00 (m, 1H), 3.67-3.55 (m, 3H), 3.31-3.27 (m, 2H), 2.69-2.55 (m, 1H), 2.47-2.41 (m, 1H), 2.24-2.12 (m, 3H), 2.08-1.96 (m, 3H), 1.93-1.63 (m, 8H), 1.50 (br d, J = 17.8 Hz, 7H), 1.15 (dd, J = 5.1, 6.8 Hz, 6H). $[\alpha]_D^{22}$ = −17.81° (c 0.1, MeOH). LCMS (m/z) $(M + H)^+$: 672.2 |

TABLE 2-continued

| Ex. | Structure and Name | Characterization Data ($^1$H NMR, optical rotation, and/or LCMS) |
|---|---|---|
| B4 | 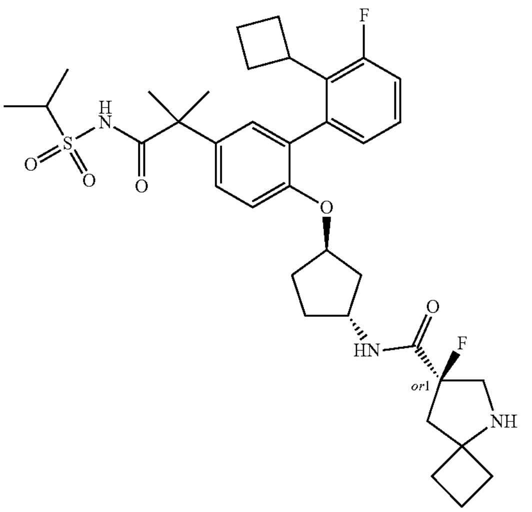 [SMILES: CC(C)S(=O)(=O)NC(=O)C(C)(C)c1ccc(O[C@@H]2CC[C@@H](NC(=O)[C@]3(F)CNC4(CCC4)C3)C2)c(-c2cccc(F)c2C2CCC2)c1]<br>(7ξ)-N-{(1R,3R)-3-[(2'-cyclobutyl-3'-fluoro-5-{2-methyl-1-oxo-1-[(propan-2-ylsulfonyl)amino]propan-2-yl}biphenyl-2-yl)oxy]cyclopentyl}-7-fluoro-5-azaspiro[3.4]octane-7-carboxamide | $^1$H NMR (400 MHz, DMSO-$d_6$) δ 11.50-9.15 (m, 2H), 8.55-8.48 (m, 1H), 7.29-7.19 (m, 2H), 7.15-7.08 (m, 1H), 7.05-7.01 (m, 1H), 6.99-6.95 (m, 1H), 6.89-6.86 (m, 1H), 4.87-4.80 (m, 1H), 4.02 (s, 2H), 3.69-3.57 (m, 4H), 2.65 (br s, 2H), 2.48-2.45 (m, 1H), 2.23-2.14 (m, 3H), 2.11-1.97 (m, 3H), 1.94-1.66 (m, 8H), 1.55-1.44 (m, 8H), 1.16 (dd, J = 5.1, 6.8 Hz, 6H). $[\alpha]_D^{22}$ = −5.79° (c 0.1, MeOH). LCMS (m/z) (M + H)$^+$: 672.5 |
| B5 | 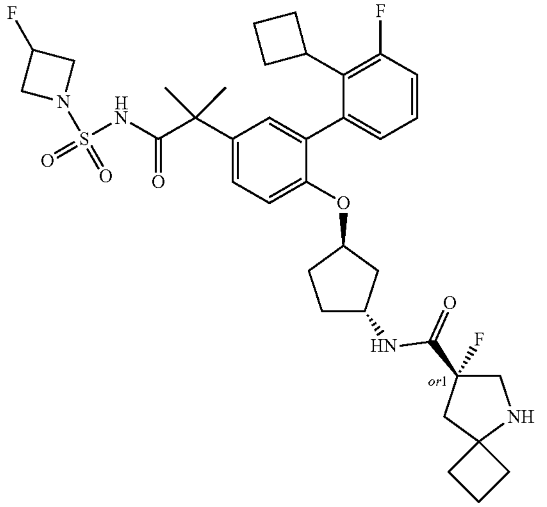 [SMILES: CC(C)(C(=O)NS(=O)(=O)N1CC(F)C1)c1ccc(O[C@@H]2CC[C@@H](NC(=O)[C@@]3(F)CNC4(CCC4)C3)C2)c(-c2cccc(F)c2C2CCC2)c1]<br>(7ξ)-N-[(1R,3R)-3-{[2'-cyclobutyl-3'-fluoro-5-(1-{[(3-fluoroazetidin-1-yl)sulfonyl]amino}-2-methyl-1-oxopropan-2-yl)biphenyl-2-yl]oxy}cyclopentyl]-7-fluoro-5-azaspiro[3.4]octane-7-carboxamide | $^1$H NMR (400 MHz, DMSO-$d_6$) δ 8.37 (br t, J = 6.9 Hz, 1H), 7.30 (dd, J = 2.3, 8.5 Hz, 1H), 7.23-7.18 (m, 1H), 7.09 (dd, J = 8.3, 11.6 Hz, 1H), 7.02 (t, J = 2.8 Hz, 1H), 6.96 (d, J = 8.8 Hz, 1H), 6.88 (br d, J = 8.4 Hz, 1H), 5.24-5.00 (m, 1H), 4.80 (br s, 1H), 4.16-4.02 (m, 1H), 4.02-3.76 (m, 4H), 3.53-3.45 (m, 3H), 2.73-2.54 (m, 2H), 2.46-2.22 (m, 4H), 2.22-1.92 (m, 6H), 1.92-1.59 (m, 8H), 1.59-1.48 (m, 1H), 1.44 (br d, J = 8.4 Hz, 6H). $[\alpha]_D^{22}$ = −19.38° (c 0.1, MeOH). LCMS (m/z) (M + H)$^+$: 703.4 |

TABLE 2-continued

| Ex. | Structure and Name | Characterization Data ($^1$H NMR, optical rotation, and/or LCMS) |
|---|---|---|
| B6 | 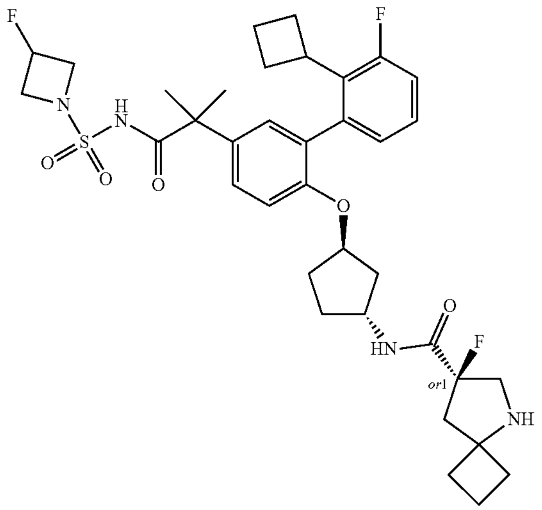 [SMILES: CC(C)(C(=O)NS(=O)(=O)N1CC(F)C1)c1ccc(O[C@@H]2CC[C@@H](NC(=O)[C@]3(F)CNC4(CCC4)C3)C2)c(-c2cccc(F)c2C2CCC2)c1] (7ξ)-N-[(1R,3R)-3-{[2'-cyclobutyl-3'-fluoro-5-(1-{[(3-fluoroazetidin-1-yl)sulfonyl]amino}-2-methyl-1-oxopropan-2-yl)biphenyl-2-yl]oxy}cyclopentyl]-7-fluoro-5-azaspiro[3.4]octane-7-carboxamide | $^1$H NMR (400 MHz, DMSO-$d_6$) δ 8.44-8.28 (m, 1H), 7.31 (dd, J = 2.4, 8.6 Hz, 1H), 7.25-7.17 (m, 1H), 7.13-6.94 (m, 3H), 6.88 (t, J = 5.6 Hz, 1H), 5.23-5.01 (m, 1H), 4.80 (br s, 1H), 4.15-4.01 (m, 1H), 4.01-3.75 (m, 4H), 3.56-3.38 (m, 4H), 2.44-2.33 (m, 2H), 2.32-2.17 (m, 3H), 2.16-1.96 (m, 5H), 1.94-1.62 (m, 8H), 1.62-1.49 (m, 1H), 1.44 (br d, J = 7.9 Hz, 7H). $[\alpha]_D^{22}$ = −224.15° (c 0.1, MeOH). LCMS (m/z) $(M + H)^+$: 703.3 |
| B7 | 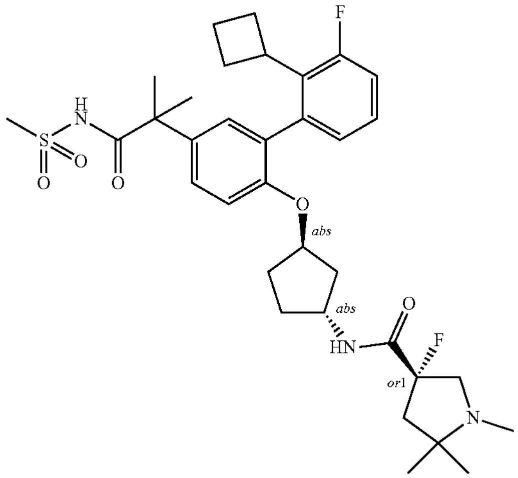 (3ξ)-N-{(1R,3R)-3-[(2'-cyclobutyl-3'-fluoro-5-{1-[(methanesulfonyl)amino]-2-methyl-1-oxopropan-2-yl}[1,1'-biphenyl]-2-yl)oxy]cyclopentyl}-3-fluoro-1,5,5-trimethylpyrrolidine-3-carboxamide | $^1$H NMR (600 MHz, DMSO-$d_6$) δ 11.34-11.04 (m, 1H), 8.31-7.98 (m, 1H), 7.27-7.19 (m, 2H), 7.12-7.06 (m, 1H), 7.00 (br d, J = 8.6 Hz, 1H), 6.95 (t, J = 2.9 Hz, 1H), 6.87 (ddd, J = 1.1, 6.1, 7.4 Hz, 1H), 4.80 (br dd, J = 2.7, 5.4 Hz, 1H), 3.51-3.42 (m, 1H), 3.15-3.05 (m, 3H), 2.23-1.96 (m, 8H), 1.90-1.63 (m, 6H), 1.57-1.40 (m, 9H), 1.23 (br s, 3H), 1.16-0.89 (m, 6H). $[\alpha]_D^{22}$ = −16.8° (c 0.2, MeOH + 1 drop $CHCl_3$). LCMS (m/z) $(M + H)^+$: 646.9 |

TABLE 2-continued

| Ex. | Structure and Name | Characterization Data ($^1$H NMR, optical rotation, and/or LCMS) |
|---|---|---|
| B8 | 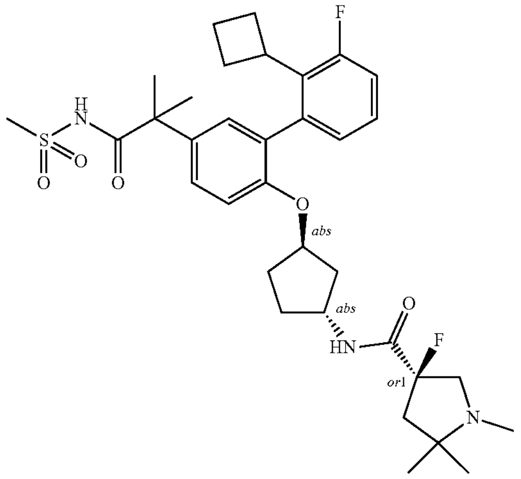 (3ξ)-N-{(1R,3R)-3-[(2'-cyclobutyl-3'-fluoro-5-{1-[(methanesulfonyl)amino]-2-methyl-1-oxopropan-2-yl}[1,1'-biphenyl]-2-yl)oxy]cyclopentyl}-3-fluoro-1,5,5-trimethylpyrrolidine-3-carboxamide | 1H NMR (600 MHz, DMSO-$d_6$) δ 8.18-8.01 (m, 1H), 7.27-7.17 (m, 2H), 7.08 (dd, J = 8.2, 11.2 Hz, 1H), 7.00-6.91 (m, 2H), 6.89-6.84 (m, 1H), 4.81-4.74 (m, 1H), 4.03 (br d, J = 7.4 Hz, 1H), 3.46 (br d, J = 6.4 Hz, 1H), 3.16-3.16 (m, 3H), 3.06-2.99 (m, 1H), 2.92-2.84 (m, 1H), 2.24-1.94 (m, 8H), 1.91-1.82 (m, 3H), 1.81-1.60 (m, 4H), 1.54-1.39 (m, 6H), 1.07 (br s, 3H). $[\alpha]_D^{22}$ = −20.0° (c 0.1, MeOH + 1 drop $CHCl_3$). LCMS (m/z) $(M + H)^+$: 646.9 |
| B9 | 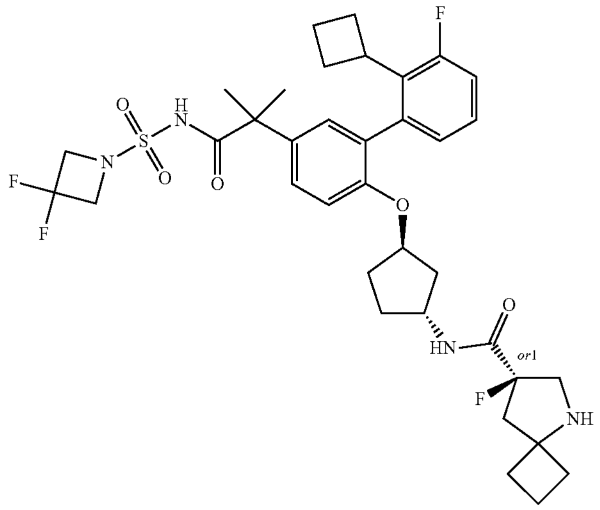 [SMILES: CC(C)(C(=O)NS(=O)(=O)N1CC(F)(F)C1)c1ccc(O[C@@H]2CC[C@@H](NC(=O)[C@]3(F)CNC4(CCC4)C3)C2)c(-c2cccc(F)c2C2CCC2)c1] (7ξ)-N-[(1R,3R)-3-({2'-cyclobutyl-5-[1-(3,3-difluoroazetidine-1-sulfonamido)-2-methyl-1-oxopropan-2-yl]-3'-fluoro[1,1'-biphenyl]-2-yl}oxy)cyclopentyl]-7-fluoro-5-azaspiro[3.4]octane-7-carboxamide | $^1$H NMR (400 MHz, DMSO-$d_6$) δ 8.48-8.41 (m, 1H), 7.30 (dd, J = 2.4, 8.6 Hz, 1H), 7.23-7.17 (m, 1H), 7.11-7.02 (m, 2H), 6.93 (d, J = 8.8 Hz, 1H), 6.87 (dd, J = 3.7, 6.6 Hz, 1H), 4.78 (br s, 1H), 4.15-3.96 (m, 5H), 3.64-3.52 (m, 3H), 2.45-2.32 (m, 3H), 2.25-1.95 (m, 7H), 1.94-1.62 (m, 9H), 1.54-1.42 (m, 2H), 1.39 (s, 6H). $[\alpha]_D^{22}$ = −69.1° (c 0.1, MeOH). LCMS (m/z) $(M + H)^+$: 721.3 |

TABLE 2-continued

| Ex. | Structure and Name | Characterization Data ($^1$H NMR, optical rotation, and/or LCMS) |
|---|---|---|
| B10 | 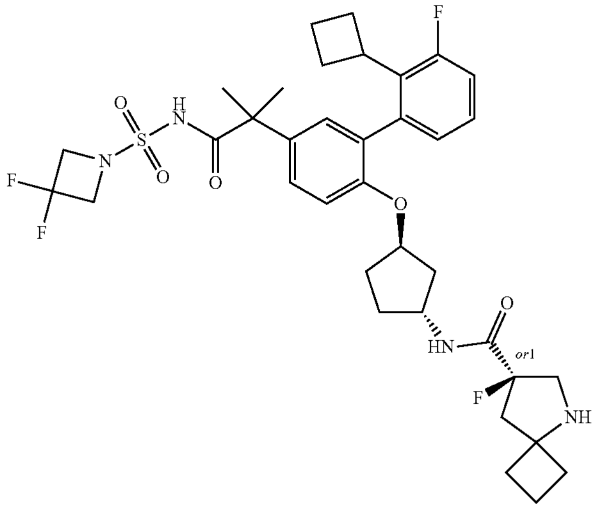 [SMILES: CC(C)(C(=O)NS(=O)(=O)N1CC(F)(F)C1)c1ccc(O[C@@H]2CC[C@@H](NC(=O)[C@]3(F)CNC4(CCC4)C3)C2)c(-c2cccc(F)c2C2CCC2)c1] (7ξ)-N-[(1R,3R)-3-({2'-cyclobutyl-5-[1-(3,3-difluoroazetidine-1-sulfonamido)-2-methyl-1-oxopropan-2-yl]-3'-fluoro[1,1'-biphenyl]-2-yl}oxy)cyclopentyl]-7-fluoro-5-azaspiro[3.4]octane-7-carboxamide | $^1$H NMR (400 MHz, DMSO-$d_6$) δ 8.46-8.38 (m, 1H), 7.30 (dd, J = 2.4, 8.6 Hz, 1H), 7.23-7.16 (m, 1H), 7.08 (dd, J = 8.3, 11.7 Hz, 1H), 7.03 (t, J = 2.4 Hz, 1H), 6.92 (d, J = 8.7 Hz, 1H), 6.87 (ddd, J = 1.1, 2.3, 7.5 Hz, 1H), 4.78 (br s, 1H), 4.15-3.93 (m, 5H), 3.64-3.49 (m, 3H), 2.42-2.30 (m, 3H), 2.24-1.96 (m, 7H), 1.93-1.66 (m, 9H), 1.57-1.43 (m, 2H), 1.39 (s, 6H). $[\alpha]_D^{22}$ = −218° (c 0.01, MeOH). LCMS (m/z) (M + H)$^+$: 721.3 |
| B11 | 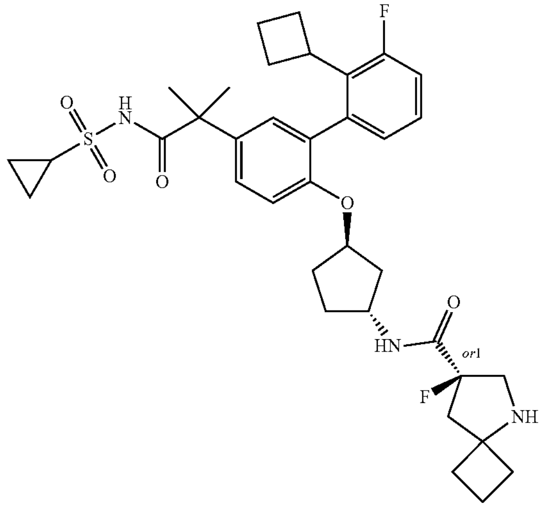 [SMILES: CC(C)(C(=O)NS(=O)(=O)C1CC1)c1ccc(O[C@@H]2CC[C@@H](NC(=O)[C@]3(F)CNC4(CCC4)C3)C2)c(-c2cccc(F)c2C2CCC2)c1] (7ξ)-N-[(1R,3R)-3-({2'-cyclobutyl-5-[1-(cyclopropanesulfonamido)-2-methyl-1-oxopropan-2-yl]-3'-fluoro[1,1'-biphenyl]-2-yl}oxy)cyclopentyl]-7-fluoro-5-azaspiro[3.4]octane-7-carboxamide | $^1$H NMR (400 MHz, DMSO-d6) δ = 8.26-8.18 (m, 1H), 7.29-7.17 (m, 2H), 7.13-7.05 (m, 1H), 7.00-6.95 (m, 2H), 6.90-6.84 (m, 1H), 4.84 (s, 1H), 4.15-3.99 (m, 1H), 3.23-3.09 (m, 3H), 2.93-2.81 (m, 1H), 2.34-2.15 (m, 3H), 2.13-1.96 (m, 7H), 1.92-1.82 (m, 2H), 1.81-1.61 (m, 6H), 1.55-1.39 (m, 8H), 0.88-0.73 (m, 4H). LCMS (m/z) (M + H)$^+$: 670.1 |

TABLE 2-continued

| Ex. | Structure and Name | Characterization Data ($^1$H NMR, optical rotation, and/or LCMS) |
|---|---|---|
| B12 | 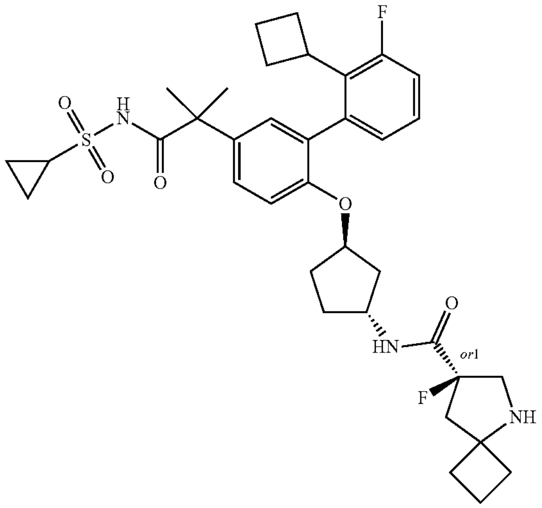 [SMILES: CC(C)(C(=O)NS(=O)(=O)C1CC1)c1ccc(O[C@@H]2CC[C@@H](NC(=O)[C@]3(F)CNC4(CCC4)C3)C2)c(-c2cccc(F)c2C2CCC2)c1] (7ξ)-N-[(1R,3R)-3-({2'-cyclobutyl-5-[1-(cyclopropanesulfonamido)-2-methyl-1-oxopropan-2-yl]-3'-fluoro[1,1'-biphenyl]-2-yl}oxy)cyclopentyl]-7-fluoro-5-azaspiro[3.4]octane-7-carboxamide | $^1$H NMR (400 MHz, DMSO-$d_6$) δ 7.85 (br s, 1H), 7.29 (dd, J = 2.5, 8.6 Hz, 1H), 7.22 (dt, J = 5.6, 7.9 Hz, 1H), 7.08 (ddd, J = 1.1, 8.3, 11.9 Hz, 1H), 7.00 (d, J = 8.8 Hz, 2H), 6.93-6.81 (m, 1H), 4.80 (br s, 1H), 4.17-4.00 (m, 1H), 3.50 (quin, J = 9.1 Hz, 1H), 3.34-3.03 (m, 3H), 2.91 (tt, J = 4.9, 8.0 Hz, 1H), 2.38-2.16 (m, 3H), 2.16-1.98 (m, 7H), 1.97-1.63 (m, 8H), 1.51 (d, J = 7.3 Hz, 7H), 1.07-0.95 (m, 2H), 0.94-0.83 (m, 2H). LCMS (m/z) $(M + H)^+$: 670.9 |
| B13 | 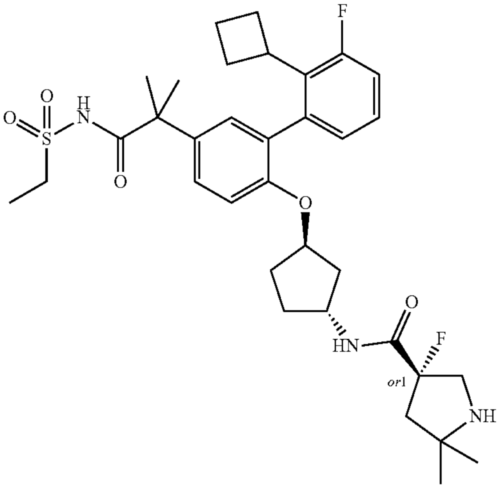 [SMILES: CCS(=O)(=O)NC(=O)C(C)(C)c1ccc(O[C@@H]2CC[C@@H](NC(=O)[C@@]3(F)CNC(C)(C)C3)C2)c(-c2cccc(F)c2C2CCC2)c1] (3ξ)-N-[(1R,3R)-3-({2'-cyclobutyl-5-[1-(ethanesulfonamido)-2-methyl-1-oxopropan-2-yl]-3'-fluoro[1,1'-biphenyl]-2-yl}oxy)cyclopentyl]-3-fluoro-5,5-dimethylpyrrolidine-3-carboxamide | $^1$H NMR (600 MHz, DMSO-$d_6$) δ 8.23 (br t, J = 8.5 Hz, 1H), 7.27 (dd, J = 2.5, 8.6 Hz, 1H), 7.23-7.17 (m, 1H), 7.09 (dd, J = 8.1, 11.7 Hz, 1H), 7.03-6.93 (m, 2H), 6.86 (ddd, J = 1.0, 4.4, 7.5 Hz, 1H), 4.79 (br d, J = 2.0 Hz, 1H), 4.04 (br d, J = 7.5 Hz, 1H), 3.46 (br s, 1H), 3.15-3.08 (m, 2H), 2.23-1.94 (m, 6H), 1.92-1.62 (m, 6H), 1.58-1.38 (m, 8H), 1.28 (s, 3H), 1.23 (d, J = 2.7 Hz, 3H), 1.00 (t, J = 7.3 Hz, 3H). $[\alpha]_D^{22}$ = −10.0° (c 0.3, MeOH). LCMS (m/z) $(M + H)^+$: 646.3 |

TABLE 2-continued

| Ex. | Structure and Name | Characterization Data ($^1H$ NMR, optical rotation, and/or LCMS) |
| --- | --- | --- |
| B14 | 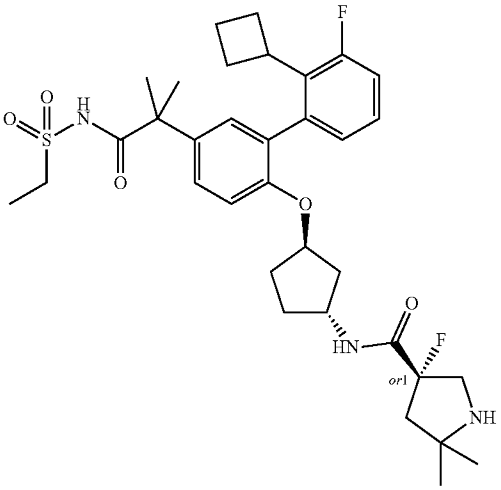 [SMILES: CCS(=O)(=O)NC(=O)C(C)(C)c1ccc(O[C@@H]2CC[C@@H](NC(=O)[C@@]3(F)CNC(C)(C)C3)C2)c(-c2cccc(F)c2C2CCC2)c1]<br>(3ξ)-N-[(1R,3R)-3-({2'-cyclobutyl-5-[1-(ethanesulfonamido)-2-methyl-1-oxopropan-2-yl]-3'-fluoro[1,1'-biphenyl]-2-yl}oxy)cyclopentyl]-3-fluoro-5,5-dimethylpyrrolidine-3-carboxamide | $^1H$ NMR (600 MHz, DMSO-$d_6$) δ 8.23 (br t, J = 8.9 Hz, 1H), 7.27 (dd, J = 2.5, 8.6 Hz, 1H), 7.21 (dt, J = 5.7, 7.8 Hz, 1H), 7.12-7.05 (m, 1H), 7.02-6.93 (m, 2H), 6.87 (ddd, J = 1.1, 5.0, 7.5 Hz, 1H), 4.79 (br d, J = 2.5 Hz, 1H), 4.05-3.99 (m, 1H), 3.48-3.43 (m, 2H), 3.26 (br s, 1H), 3.14-3.05 (m, 2H), 2.24-1.94 (m, 6H), 1.93-1.82 (m, 2H), 1.82-1.62 (m, 4H), 1.57-1.39 (m, 8H), 1.28 (br s, 6H), 1.00 (s, 3H). $[\alpha]_D^{22}$ = −17.5° (c 0.1, MeOH). LCMS (m/z) $(M + H)^+$: 646.3 |
| B15 | 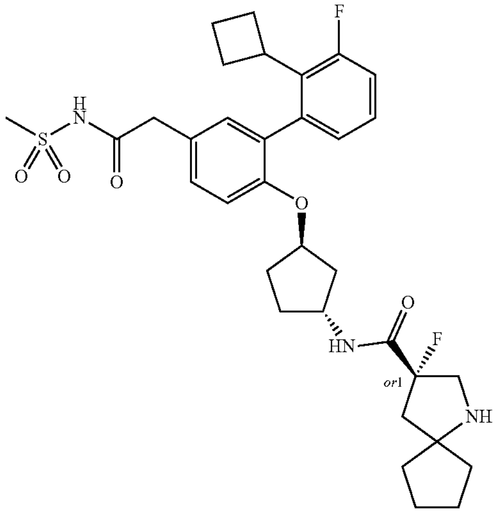 [SMILES: CS(=O)(=O)NC(=O)Cc1ccc(O[C@@H]2CC[C@@H](NC(=O)[C@@]3(F)CNC4(CCCC4)C3)C2)c(-c2cccc(F)c2C2CCC2)c1]<br>(3ξ)-N-[(1R,3R)-3-({2'-cyclobutyl-3'-fluoro-5-[2-(methanesulfonamido)-2-oxoethyl][1,1'-biphenyl]-2-yl}oxy)cyclopentyl]-3-fluoro-1-azaspiro[4.4]nonane-3-carboxamide | $^1H$ NMR (400 MHz, DMSO-$d_6$) δ 10.53-9.15 (m, 1H), 8.53 (br t, J = 7.8 Hz, 1H), 7.27-7.18 (m, 2H), 7.11 (br dd, J = 8.7, 11.3 Hz, 1H), 7.04-6.95 (m, 2H), 6.87 (br d, J = 7.0 Hz, 1H), 4.82 (br s, 1H), 4.18-4.00 (m, 1H), 3.80-3.61 (m, 2H), 3.56 (s, 2H), 3.49-3.42 (m, 1H), 3.22 (s, 3H), 2.54 (br s, 1H), 2.44-2.31 (m, 1H), 2.26-2.15 (m, 1H), 2.13-1.97 (m, 5H), 1.95-1.54 (m, 13H), 1.51-1.40 (m, 1H). $[\alpha]_D^{22}$ = −53.1° (c 0.05, MeOH). LCMS (m/z) $(M + H)^+$: 630.5 |

TABLE 2-continued

| Ex. | Structure and Name | Characterization Data ($^{1}H$ NMR, optical rotation, and/or LCMS) |
|---|---|---|
| B16 | 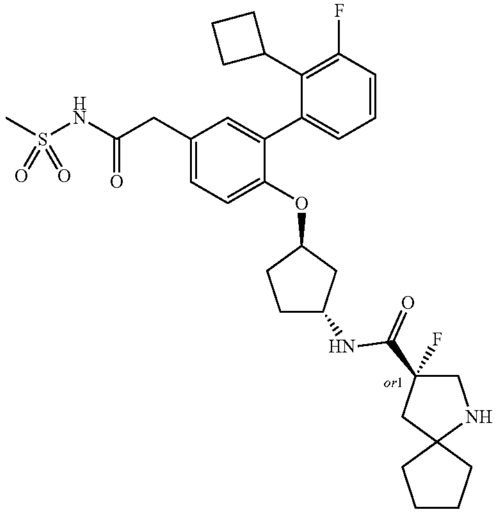 [SMILES: CS(=O)(=O)NC(=O)Cc1ccc(O[C@@H]2CC[C@@H](NC(=O)[C@@]3(F)CNC4(CCCC4)C3)C2)c(-c2cccc(F)c2C2CCC2)c1] (3ξ)-N-[(1R,3R)-3-({2'-cyclobutyl-3'-fluoro-5-[2-(methanesulfonamido)-2-oxoethyl][1,1'-biphenyl]-2-yl}oxy)cyclopentyl]-3-fluoro-1-azaspiro[4.4]nonane-3-carboxamide | $^{1}H$ NMR (400 MHz, DMSO-$d_6$) δ 10.31-9.01 (m, 1H), 8.53 (br t, J = 7.6 Hz, 1H), 7.26-7.19 (m, 2H), 7.11 (dd, J = 8.3, 11.6 Hz, 1H), 7.04-6.96 (m, 2H), 6.87 (d, J = 7.6 Hz, 1H), 4.86-4.77 (m, 1H), 4.17-4.00 (m, 1H), 3.83-3.60 (m, 2H), 3.56 (s, 2H), 3.47-3.40 (m, 1H), 3.22 (s, 3H), 2.56-2.52 (m, 1H), 2.44-2.35 (m, 1H), 2.27-2.14 (m, 1H), 2.13-1.97 (m, 5H), 1.92-1.53 (m, 13H), 1.49-1.40 (m, 1H). $[\alpha]_D^{22}$ = −18.4° (c 0.05, MeOH). LCMS (m/z) $(M + H)^+$: 630.5 |
| B17 | 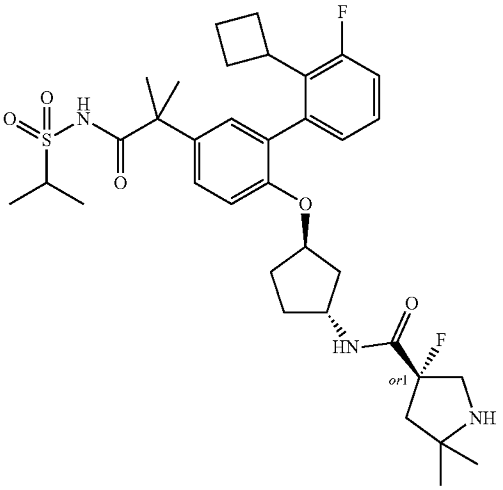 [SMILES: CC(C)S(=O)(=O)NC(=O)C(C)(C)c1ccc(O[C@@H]2CC[C@@H](NC(=O)[C@@]3(F)CNC(C)(C)C3)C2)c(-c2cccc(F)c2C2CCC2)c1] (3ξ)-N-[(1R,3R)-3-({2'-cyclobutyl-3'-fluoro-5-[2-methyl-1-oxo-1-(propane-2-sulfonamido)propan-2-yl][1,1'-biphenyl]-2-yl}oxy)cyclopentyl]-3-fluoro-5,5-dimethylpyrrolidine-3-carboxamide | $^{1}H$ NMR (600 MHz, DMSO-$d_6$) δ 7.89 (br t, J = 8.1 Hz, 1H), 7.29 (dd, J = 2.5, 8.5 Hz, 1H), 7.21 (dt, J = 5.5, 7.9 Hz, 1H), 7.07 (ddd, J = 1.0, 8.2, 11.9 Hz, 1H), 7.02-6.95 (m, 2H), 6.87 (t, J = 6.4 Hz, 1H), 4.78 (td, J = 2.8, 5.5 Hz, 1H), 4.15-4.00 (m, 1H), 3.58 (spt, J = 6.8 Hz, 1H), 3.52-3.43 (m, 1H), 3.37-3.28 (m, 2H), 3.21 (br s, 1H), 2.25-1.64 (m, 12H), 1.59-1.40 (m, 8H), 1.25 (s, 3H), 1.21-1.17 (m, 3H), 1.15 (dd, J = 3.5, 6.9 Hz, 6H). $[\alpha]_D^{22}$ = −13.7° (c 0.1, MeOH). LCMS (m/z) $(M + H)^+$: 660.1 |

TABLE 2-continued

| Ex. | Structure and Name | Characterization Data ($^1$H NMR, optical rotation, and/or LCMS) |
|---|---|---|
| B18 | 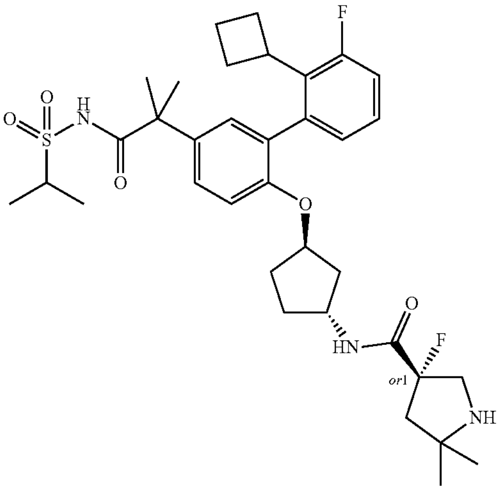 [SMILES: CC(C)S(=O)(=O)NC(=O)C(C)(C)c1ccc(O[C@@H]2CC[C@@H](NC(=O)[C@@]3(F)CNC(C)(C)C3)C2)c(-c2cccc(F)c2C2CCC2)c1] (3ξ)-N-[(1R,3R)-3-({2'-cyclobutyl-3'-fluoro-5-[2-methyl-1-oxo-1-(propane-2-sulfonamido)propan-2-yl][1,1'-biphenyl]-2-yl}oxy)cyclopentyl]-3-fluoro-5,5-dimethylpyrrolidine-3-carboxamide | $^1$H NMR (600 MHz, DMSO-$d_6$) δ 7.88 (br t, J = 8.2 Hz, 1H), 7.32-7.26 (m, 1H), 7.20 (dt, J = 5.6, 7.9 Hz, 1H), 7.07 (ddd, J = 1.0, 8.2, 11.9 Hz, 1H), 7.02-6.96 (m, 2H), 6.87 (t, J = 6.6 Hz, 1H), 4.78 (td, J = 2.9, 5.5 Hz, 1H), 4.14-4.00 (m, 1H), 3.85 (br d, J = 4.2 Hz, 1H), 3.61-3.54 (m, 1H), 3.51-3.44 (m, 1H), 3.37-3.28 (m, 2H), 3.20 (br s, 2H), 2.26-1.64 (m, 12H), 1.49 (d, J = 12.2 Hz, 6H), 1.25 (d, J = 2.4 Hz, 3H), 1.19 (d, J = 3.6 Hz, 3H), 1.15 (dd, J = 3.5, 6.7 Hz, 6H). $[\alpha]_D^{22}$ = −17.2° (c 0.1, MeOH). LCMS (m/z) $(M + H)^+$: 660.1 |
| B19 | 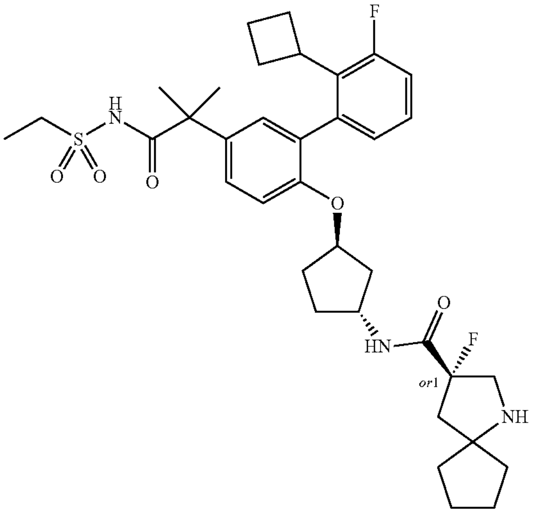 [SMILES: CCS(=O)(=O)NC(=O)C(C)(C)c1ccc(O[C@@H]2CC[C@@H](NC(=O)[C@@]3(F)CNC4(CCCC4)C3)C2)c(-c2cccc(F)c2C2CCC2)c1] (3ξ)-N-[(1R,3R)-3-({2'-cyclobutyl-5-[1-(ethanesulfonamido)-2-methyl-1-oxopropan-2-yl]-3'-fluoro[1,1'-biphenyl]-2-yl}oxy)cyclopentyl]-3-fluoro-1-azaspiro[4.4]nonane-3-carboxamide | $^1$H NMR (400 MHz, DMSO-$d_6$) δ 11.58-10.55 (m, 1H), 10.11-9.27 (m, 2H), 8.54 (br t, J = 7.1 Hz, 1H), 7.29-7.16 (m, 2H), 7.11 (dd, J = 8.1, 11.4 Hz, 1H), 7.03 (d, J = 8.8 Hz, 1H), 6.96 (dd, J = 2.7, 3.7 Hz, 1H), 6.91-6.85 (m, 1H), 4.84 (br s, 1H), 4.15-4.00 (m, 1H), 3.80-3.56 (m, 2H), 3.53-3.41 (m, 1H), 3.33-3.27 (m, 2H), 2.48-2.28 (m, 2H), 2.20-1.96 (m, 6H), 1.94-1.61 (m, 12H), 1.59-1.41 (m, 8H), 1.06 (t, J = 7.4 Hz, 3H). $[\alpha]_D^{22}$ = −32.9° (c 0.1, MeOH). LCMS (m/z) $(M + H)^+$: 672.3 |

TABLE 2-continued

| Ex. | Structure and Name | Characterization Data ($^1$H NMR, optical rotation, and/or LCMS) |
|---|---|---|
| B20 | 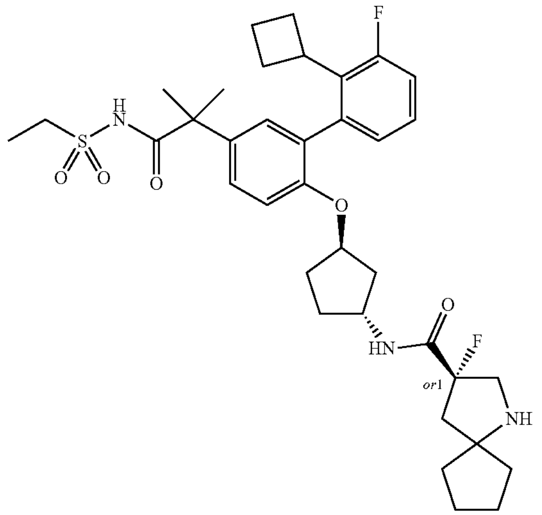 [SMILES: CCS(=O)(=O)NC(=O)C(C)(C)c1ccc(O[C@@H]2CC[C@@H](NC(=O)[C@@]3(F)CNC4(CCCC4)C3)C2)c(-c2cccc(F)c2C2CCC2)c1] (3ξ)-N-[(1R,3R)-3-({2'-cyclobutyl-5-[1-(ethanesulfonamido)-2-methyl-1-oxopropan-2-yl]-3'-fluoro[1,1'-biphenyl]-2-yl}oxy)cyclopentyl]-3-fluoro-1-azaspiro[4.4]nonane-3-carboxamide | $^1$H NMR (400 MHz, DMSO-$d_6$) δ 11.55-10.75 (m, 1H), 10.03-9.20 (m, 2H), 8.54 (s, 1H), 7.31-7.17 (m, 2H), 7.11 (dd, J = 8.2, 11.7 Hz, 1H), 7.03 (d, J = 8.6 Hz, 1H), 6.97 (dd, J = 2.5, 4.9 Hz, 1H), 6.88 (d, J = 7.5 Hz, 1H), 4.84 (br s, 1H), 4.16-4.01 (m, 1H), 3.66 (br d, J = 5.6 Hz, 2H), 3.50-3.42 (m, 1H), 3.32-3.24 (m, 2H), 2.48-2.29 (m, 2H), 2.22-1.97 (m, 6H), 1.94-1.62 (m, 12H), 1.60-1.38 (m, 8H), 1.06 (t, J = 7.4 Hz, 3H). $[\alpha]_D^{22}$ = −21.8° (c 0.1, MeOH). LCMS (m/z) $(M + H)^+$: 672.3 |
| B21 | 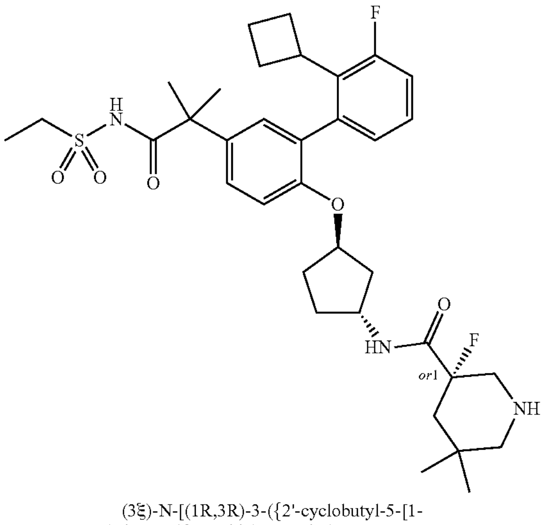 (3ξ)-N-[(1R,3R)-3-({2'-cyclobutyl-5-[1-(ethanesulfonamido)-2-methyl-1-oxopropan-2-yl]-3'-fluoro[1,1'-biphenyl]-2-yl}oxy)cyclopentyl]-3-fluoro-5,5-dimethylpiperidine-3-carboxamide | $^1$H NMR (400 MHz, MeOD) δ 8.26 (br s, 1H), 7.33 (dd, J = 2.5, 8.6 Hz, 1H), 7.17 (dt, J = 5.7, 7.7 Hz, 1H), 7.06-6.96 (m, 3H), 6.87 (t, J = 6.9 Hz, 1H), 4.21-3.95 (m, 1H), 3.57-3.47 (m, 2H), 3.45-3.33 (m, 3H), 3.19-3.11 (m, 1H), 3.00-2.91 (m, 1H), 2.38-1.67 (m, 14H), 1.55 (d, J = 9.8 Hz, 6H), 1.51-1.43 (m, 1H), 1.27-1.19 (m, 6H), 1.07 (d, J = 2.4 Hz, 3H). $[\alpha]_D^{22}$ = −42.6° (c 0.2, MeOH). LCMS (m/z) $(M + H)^+$: 660.5 |

TABLE 2-continued

| Ex. | Structure and Name | Characterization Data ($^1$H NMR, optical rotation, and/or LCMS) |
|---|---|---|
| B22 | 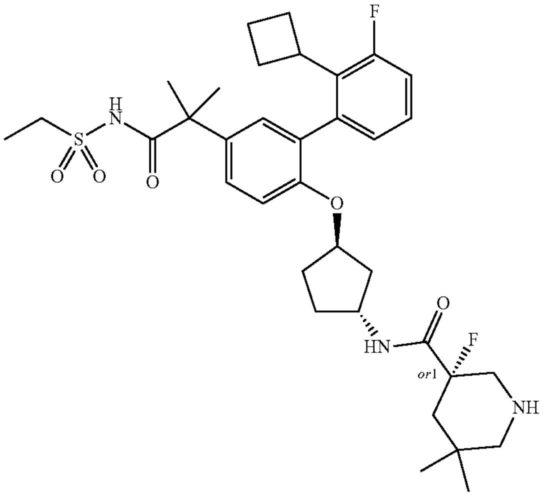 [SMILES: CCS(=O)(=O)NC(=O)C(C)(C)c1ccc(O[C@@H]2CC[C@@H](NC(=O)[C@@]3(F)CNCC(C)(C)C3)C2)c(-c2cccc(F)c2C2CCC2)c1] (3ξ)-N-[(1R,3R)-3-({2'-cyclobutyl-5-[1-(ethanesulfonamido)-2-methyl-1-oxopropan-2-yl]-3'-fluoro[1,1'-biphenyl]-2-yl}oxy)cyclopentyl]-3-fluoro-5,5-dimethylpiperidine-3-carboxamide | $^1$H NMR (400 MHz, MeOD) δ 8.26 (br d, J = 4.2 Hz, 1H), 7.33 (dd, J = 2.4, 8.6 Hz, 1H), 7.23-7.14 (m, 1H), 7.05-6.94 (m, 3H), 6.86 (dd, J = 4.8, 6.8 Hz, 1H), 4.21-3.99 (m, 1H), 3.53-3.46 (m, 2H), 3.44-3.35 (m, 3H), 3.15 (br d, J = 12.8 Hz, 1H), 3.00-2.91 (m, 1H), 2.38-1.66 (m, 14H), 1.55 (d, J = 9.9 Hz, 6H), 1.51-1.43 (m, 1H), 1.28-1.18 (m, 6H), 1.07 (s, 3H). $[\alpha]_D^{22}$ = −15.7° (c 0.2, MeOH). LCMS (m/z) (M + H)$^+$: 660.5 |
| B23 | 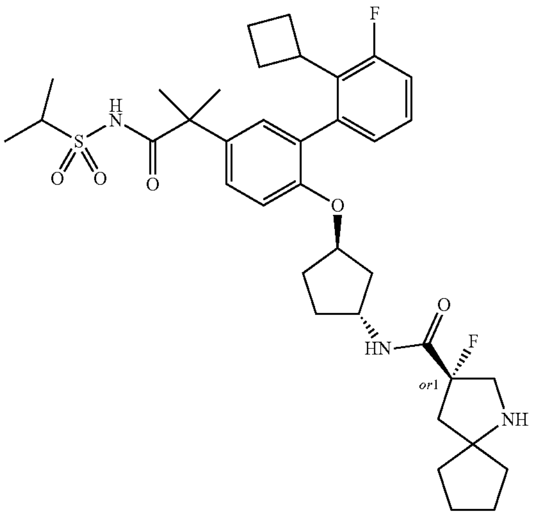 [SMILES: CC(C)S(=O)(=O)NC(=O)C(C)(C)c1ccc(O[C@@H]2CC[C@@H](NC(=O)[C@@]3(F)CNC4(CCCC4)C3)C2)c(-c2cccc(F)c2C2CCC2)c1] (3ξ)-N-[(1R,3R)-3-({2'-cyclobutyl-3'-fluoro-5-[2-methyl-1-oxo-1-(propane-2-sulfonamido)propan-2-yl][1,1'-biphenyl]-2-yl}oxy)cyclopentyl]-3-fluoro-1-azaspiro[4.4]nonane-3-carboxamide | $^1$H NMR (400 MHz, DMSO-$d_6$) δ 8.29-8.20 (m, 1H), 7.27 (dd, J = 2.6, 8.6 Hz, 1H), 7.25-7.18 (m, 1H), 7.13-7.05 (m, 1H), 7.02-6.94 (m, 2H), 6.89-6.84 (m, 1H), 4.80 (br. d, J = 2.4 Hz, 1H), 3.99 (s, 1H), 3.59-3.50 (m, 1H), 3.48-3.40 (m, 2H), 3.24-3.16 (m, 1H), 2.58-2.53 (m, 2H), 2.21 (br. s, 1H), 2.17-1.96 (m, 4H), 1.91-1.83 (m, 2H), 1.81-1.53 (m, 13H), 1.44 (br. d, J = 10.1 Hz, 7H), 1.08 (dd, J = 2.6, 6.8 Hz, 6H). $[\alpha]_D^{22}$ = −25.4° (c 0.1, MeOH) LCMS (m/z) (M + H)$^+$: 686.4 |

TABLE 2-continued

| Ex. | Structure and Name | Characterization Data ($^1$H NMR, optical rotation, and/or LCMS) |
|---|---|---|
| B24 | 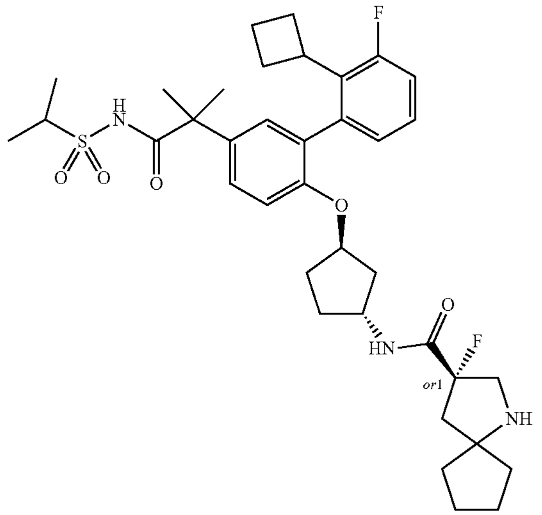 [SMILES: CC(C)S(=O)(=O)NC(=O)C(C)(C)c1ccc(O[C@@H]2CC[C@@H](NC(=O)[C@@]3(F)CNC4(CCCC4)C3)C2)c(-c2cccc(F)c2C2CCC2)c1] (3ξ)-N-[(1R,3R)-3-({2'-cyclobutyl-3'-fluoro-5-[2-methyl-1-oxo-1-(propane-2-sulfonamido)propan-2-yl][1,1'-biphenyl]-2-yl}oxy)cyclopentyl]-3-fluoro-1-azaspiro[4.4]nonane-3-carboxamide | $^1$H NMR (400 MHz, DMSO-$d_6$) δ 8.33-8.13 (m, 1H), 7.32-7.24 (m, 1H), 7.24-7.17 (m, 1H), 7.14-7.05 (m, 1H), 7.02-6.93 (m, 2H), 6.90-6.82 (m, 1H), 4.87-4.71 (m, 1H), 4.19-3.97 (m, 1H), 3.57-3.51 (m, 1H), 3.49-3.44 (m, 2H), 3.23-3.15 (m, 1H), 2.36-2.29 (m, 1H), 2.28-2.13 (m, 2H), 2.13-1.95 (m, 4H), 1.91-1.85 (m, 2H), 1.84-1.51 (m, 13H), 1.49-1.37 (m, 7H), 1.13-0.98 (m, 6H). LCMS (m/z) (M + H)$^+$: 686.4 |
| B25 | 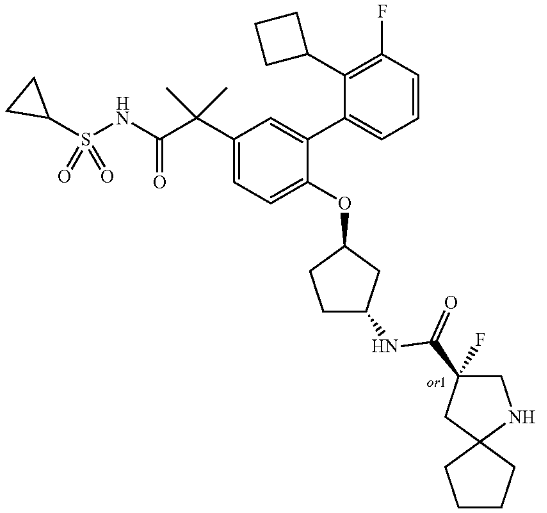 [SMILES: CC(C)(C(=O)NS(=O)(=O)C1CC1)c1ccc(O[C@@H]2CC[C@@H](NC(=O)[C@@]3(F)CNC4(CCCC4)C3)C2)c(-c2cccc(F)c2C2CCC2)c1] (3ξ)-N-[(1R,3R)-3-({2'-cyclobutyl-5-[1-(cyclopropanesulfonamido)-2-methyl-1-oxopropan-2-yl]-3'-fluoro[1,1'-biphenyl]-2-yl}oxy)cyclopentyl]-3-fluoro-1-azaspiro[4.4]nonane-3-carboxamide | $^1$H NMR (400 MHz, DMSO-$d_6$) δ 11.53-10.82 (m, 1H), 9.89-9.27 (m, 2H), 8.76-8.39 (m, 1H), 7.31-7.19 (m, 2H), 7.16-7.08 (m, 1H), 7.07-7.01 (m, 1H), 6.97-6.92 (m, 1H), 6.91-6.85 (m, 1H), 4.95-4.76 (m, 1H), 4.21-3.97 (m, 1H), 3.85-3.56 (m, 2H), 3.52-3.44 (m, 1H), 3.05-2.89 (m, 1H), 2.42-2.30 (m, 1H), 2.23-1.98 (m, 6H), 1.94-1.62 (m, 13H), 1.49 (br. d, J = 15.0 Hz, 8H), 1.06-0.87 (m, 4H). $[\alpha]_D^{22}$ = −213.4° (c 0.1, MeOH) LCMS (m/z) (M + H)$^+$: 684.3 |

TABLE 2-continued

| Ex. | Structure and Name | Characterization Data ($^1$H NMR, optical rotation, and/or LCMS) |
|---|---|---|
| B26 | 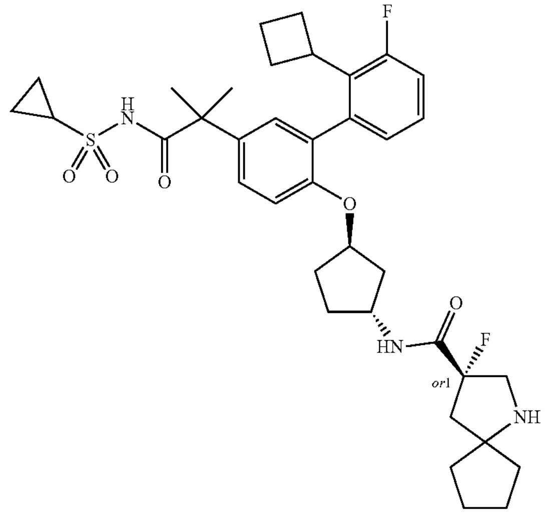 [SMILES: CC(C)(C(=O)NS(=O)(=O)C1CC1)c1ccc(O[C@@H]2CC[C@@H](NC(=O)[C@@]3(F)CNC4(CCCC4)C3)C2)c(-c2cccc(F)c2C2CCC2)c1] (3ξ)-N-[(1R,3R)-3-({2'-cyclobutyl-5-[1-(cyclopropanesulfonamido)-2-methyl-1-oxopropan-2-yl]-3'-fluoro[1,1'-biphenyl]-2-yl}oxy)cyclopentyl]-3-fluoro-1-azaspiro[4.4]nonane-3-carboxamide | $^1$H NMR (400 MHz, DMSO-$d_6$) δ 7.33 (dd, J = 2.4, 8.6 Hz, 1H), 7.23-7.13 (m, 1H), 7.07-6.95 (m, 3H), 6.92-6.82 (m, 1H), 4.86-4.82 (m, 1H), 4.27-4.08 (m, 1H), 3.99-3.79 (m, 1H), 3.78-3.64 (m, 1H), 3.57-3.44 (m, 1H), 3.04-2.92 (m, 1H), 2.73-2.41 (m, 2H), 2.38-2.26 (m, 1H), 2.23-1.92 (m, 9H), 1.90-1.69 (m, 8H), 1.67-1.41 (m, 8H), 1.19-1.05 (m, 2H), 1.03-0.90 (m, 2H). $[\alpha]_D^{21}$ = −77.9° (c 0.1, MeOH) LCMS (m/z) $(M + H)^+$: 684.3 |
| B27 | 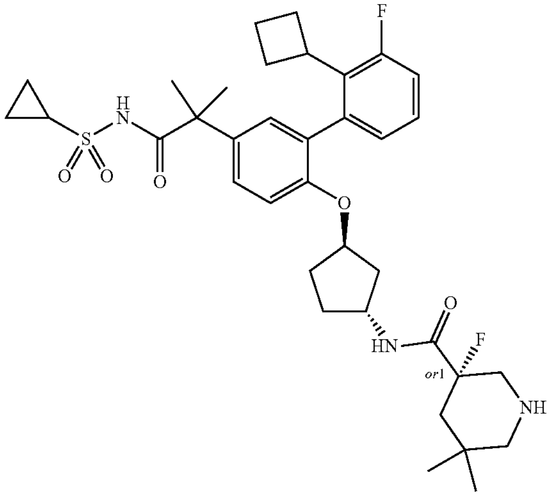 [SMILES: CC1(C)CNC[C@](F)(C(=O)N[C@@H]2CC[C@@H](Oc3ccc(C(C)(C)C(=O)NS(=O)(=O)C4CC4)cc3-c3cccc(F)c3C3CCC3)C2)C1] (3ξ)-N-[(1R,3R)-3-({2'-cyclobutyl-5-[1-(cyclopropanesulfonamido)-2-methyl-1-oxopropan-2-yl]-3'-fluoro[1,1'-biphenyl]-2-yl}oxy)cyclopentyl]-3-fluoro-5,5-dimethylpiperidine-3-carboxamide | $^1$H NMR (400 MHz, $CD_3OD$) δ 8.26 (dt, J = 3.3, 6.1 Hz, 1H), 7.33 (dd, J = 2.5, 8.6 Hz, 1H), 7.23-7.12 (m, 1H), 7.06-6.95 (m, 3H), 6.87 (t, J = 7.5 Hz, 1H), 4.23-3.99 (m, 1H), 3.70-3.41 (m, 3H), 3.20-3.11 (m, 1H), 3.04-2.92 (m, 2H), 2.40-1.58 (m, 14H), 1.55 (d, J = 7.6 Hz, 6H), 1.51-1.44 (m, 1H), 1.23 (s, 3H), 1.14 (br. t, J = 4.6 Hz, 2H), 1.07 (d, J = 2.3 Hz, 3H), 1.00-0.92 (m, 2H). $[\alpha]_D^{25}$ = −46.3° (c 0.16, MeOH) LCMS (m/z) $(M + H)^+$: 672.4 |

TABLE 2-continued

| Ex. | Structure and Name | Characterization Data ($^1$H NMR, optical rotation, and/or LCMS) |
|---|---|---|
| B28 | 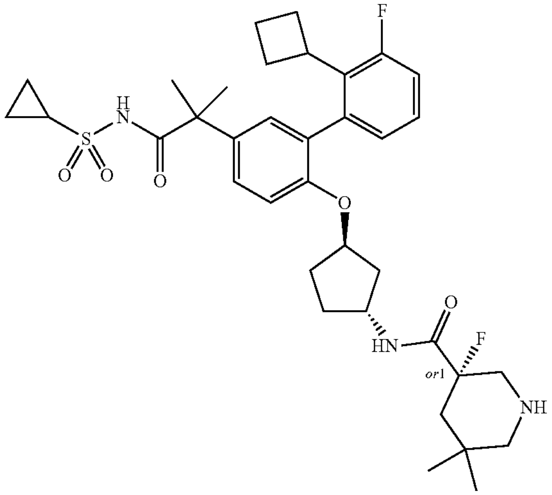 [SMILES: CC1(C)CNC[C@](F)(C(=O)N[C@@H]2CC[C@@H](Oc3ccc(C(C)(C)C(=O)NS(=O)(=O)C4CC4)cc3-c3cccc(F)c3C3CCC3)C2)C1] (3ξ)-N-[(1R,3R)-3-({2'-cyclobutyl-5-[1-(cyclopropanesulfonamido)-2-methyl-1-oxopropan-2-yl]-3'-fluoro[1,1'-biphenyl]-2-yl}oxy)cyclopentyl]-3-fluoro-5,5-dimethylpiperidine-3-carboxamide | $^1$H NMR (400 MHz, MeOD) δ 8.31-8.20 (m, 1H), 7.33 (dd, J = 2.4, 8.7 Hz, 1H), 7.24-7.13 (m, 1H), 7.08-6.96 (m, 3H), 6.87 (dd, J = 5.1, 7.0 Hz, 1H), 4.21-3.97 (m, 1H), 3.56-3.39 (m, 3H), 3.20-3.11 (m, 1H), 3.04-2.92 (m, 2H), 2.41-1.61 (m, 14H), 1.55 (d, J = 7.8 Hz, 6H), 1.50-1.45 (m, 1H), 1.23 (s, 3H), 1.17-1.11 (m, 2H), 1.07 (s, 3H), 1.02-0.95 (m, 2H). $[\alpha]_D^{25}$ = −15.0° (c 0.16, MeOH) LCMS (m/z) $(M + H)^+$: 672.4 |
| B29 | 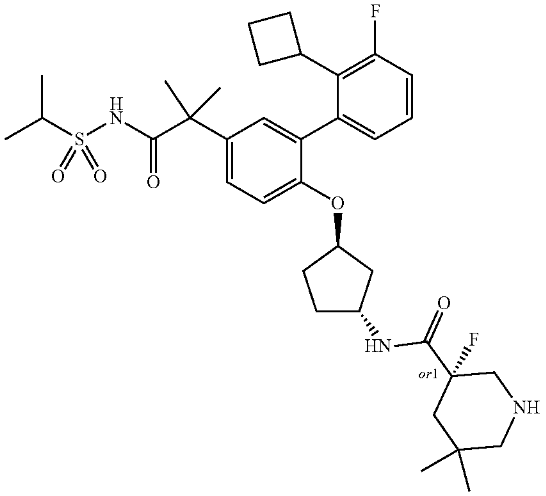 [SMILES: CC(C)S(=O)(=O)NC(=O)C(C)(C)c1ccc(O[C@@H]2CC[C@@H](NC(=O)[C@@]3(F)CNCC(C)(C)C3)C2)c(-c2cccc(F)c2C2CCC2)c1] (3ξ)-N-[(1R,3R)-3-({2'-cyclobutyl-3'-fluoro-5-[2-methyl-1-oxo-1-(propane-2-sulfonamido)propan-2-yl][1,1'-biphenyl]-2-yl}oxy)cyclopentyl]-3-fluoro-5,5-dimethylpiperidine-3-carboxamide | $^1$H NMR (MeOD, 400 MHz) δ 8.5-8.1 (m, 1H), 7.4-7.3 (m, 1H), 7.2-7.1 (m, 1H), 7.1-7.0 (m, 3H), 6.9-6.8 (m, 1H), 4.2-4.0 (m, 1H), 3.8-3.7 (m, 1H), 3.5-3.4 (m, 3H), 3.2-3.1 (m, 1H), 3.0-2.9 (m, 1H), 2.4-1.7 (m, 14H), 1.55 (d, 6H, J = 9.2 Hz), 1.5-1.4 (m, 1H), 1.27 (dd, 6H, J = 4.6, 6.8 Hz), 1.2-1.2 (m, 3H), 1.07 (d, 3H, J = 2.4 Hz). LCMS (m/z) $(M + H)^+$: 674.2 |

TABLE 2-continued

| Ex. | Structure and Name | Characterization Data ($^1$H NMR, optical rotation, and/or LCMS) |
|---|---|---|
| B30 | 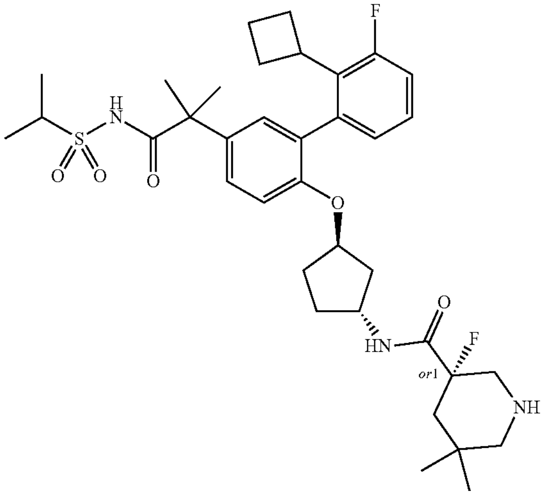 [SMILES: CC(C)S(=O)(=O)NC(=O)C(C)(C)c1ccc(O[C@@H]2CC[C@@H](NC(=O)[C@@]3(F)CNCC(C)(C)C3)C2)c(-c2cccc(F)c2C2CCC2)c1] (3ξ)-N-[(1R,3R)-3-({2'-cyclobutyl-3'-fluoro-5-[2-methyl-1-oxo-1-(propane-2-sulfonamido)propan-2-yl][1,1'-biphenyl]-2-yl}oxy)cyclopentyl]-3-fluoro-5,5-dimethylpiperidine-3-carboxamide | $^1$H NMR (MeOD, 400 MHz) δ 8.5-8.1 (m, 1H), 7.36 (s, 1H), 7.2-7.1 (m, 1H), 7.1-6.9 (m, 3H), 6.9-6.8 (m, 1H), 4.27 (s, 1H), 3.8-3.7 (m, 1H), 3.6-3.4 (m, 3H), 3.12 (br. d, 1H, J = 4.6 Hz), 3.0-2.9 (m, 1H), 2.31 (s, 1H), 2.2-1.7 (m, 13H), 1.55 (d, 6H, J = 9.5 Hz), 1.5-1.4 (m, 1H), 1.28 (dd, 6H, J = 4.6, 6.8 Hz), 1.23 (s, 3H), 1.1-1.1 (m, 3H). LCMS (m/z) (M + H)$^+$: 674.2 |
| B31 | 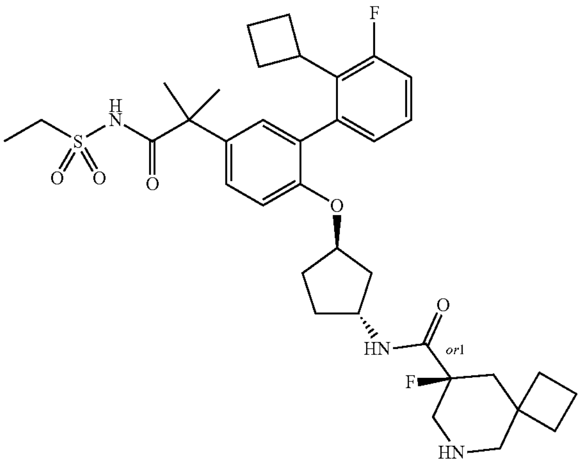 [SMILES: CCS(=O)(=O)NC(=O)C(C)(C)c1ccc(O[C@@H]2CC[C@@H](NC(=O)[C@@]3(F)CNCC4(CCC4)C3)C2)c(-c2cccc(F)c2C2CCC2)c1] (8ξ)-N-[(1R,3R)-3-({2'-cyclobutyl-5-[1-(ethanesulfonamido)-2-methyl-1-oxopropan-2-yl]-3'-fluoro[1,1'-biphenyl]-2-yl}oxy)cyclopentyl]-8-fluoro-6-azaspiro[3.5]nonane-8-carboxamide | First to elute<br>$^1$H NMR (600 MHz, DMSO-$d_6$) δ = 8.11 (br t, J = 8.7 Hz, 1H), 7.27 (dd, J = 2.2, 8.7 Hz, 1H), 7.24-7.16 (m, 1H), 7.13-7.05 (m, 1H), 7.02-6.94 (m, 2H), 6.89-6.84 (m, 1H), 4.79 (br s, 1H), 4.08 (br d, J = 4.7 Hz, 5H), 3.50-3.40 (m, 1H), 3.15-3.10 (m, 2H), 2.25-1.51 (m, 20H), 1.44 (br d, J = 14.5 Hz, 8H), 1.01 (br t, J = 7.4 Hz, 3H).<br>$[\alpha]_D^{22}$ = −8.7 (c 0.1, MeOH)<br>LCMS (m/z) (M + H)$^+$: 672.8 |

TABLE 2-continued

| Ex. | Structure and Name | Characterization Data ($^1$H NMR, optical rotation, and/or LCMS) |
|---|---|---|
| B32 | 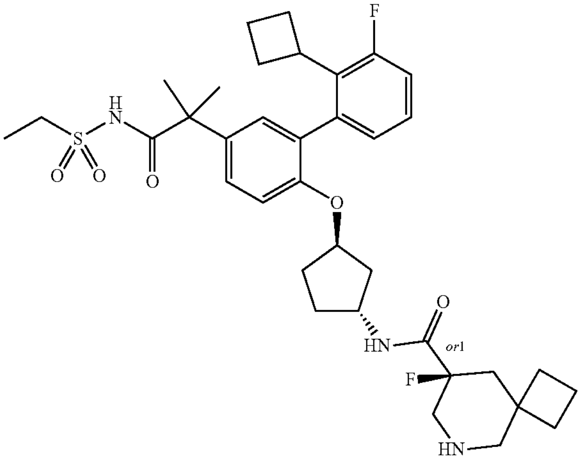 [SMILES: CCS(=O)(=O)NC(=O)C(C)(C)c1ccc(O[C@@H]2CC[C@@H](NC(=O)[C@@]3(F)CNCC4(CCC4)C3)C2)c(-c2cccc(F)c2C2CCC2)c1] (8ξ)-N-[(1R,3R)-3-({2'-cyclobutyl-5-[1-(ethanesulfonamido)-2-methyl-1-oxopropan-2-yl]-3'-fluoro[1,1'-biphenyl]-2-yl}oxy)cyclopentyl]-8-fluoro-6-azaspiro[3.5]nonane-8-carboxamide | Second to elute $^1$H NMR (600 MHz, DMSO-$d_6$) δ = 8.12 (br t, J = 8.9 Hz, 1H), 7.27 (dd, J = 2.0, 8.5 Hz, 1H), 7.23-7.18 (m, 1H), 7.12-7.06 (m, 1H), 7.00-6.95 (m, 2H), 6.90-6.83 (m, 1H), 4.79 (br s, 1H), 4.17-3.95 (m, 2H), 3.49-3.41 (m, 1H), 3.16-3.11 (m, 2H), 2.24-2.14 (m, 1H), 2.13-1.49 (m, 19H), 1.44 (br d, J = 14.9 Hz, 8H), 1.32-1.25 (m, 1H), 1.01 (br t, J = 7.3 Hz, 3H), 0.91-0.78 (m, 2H). $[\alpha]_D^{22}$ = −29.2 (c 0.1, MeOH) LCMS (m/z) $(M + H)^+$: 672.8 |
| B33 | 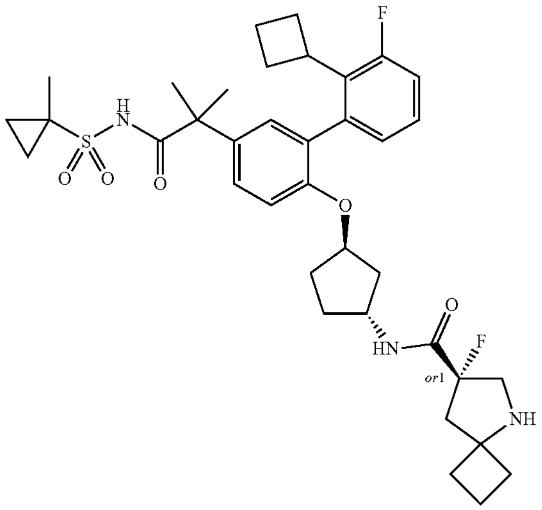 [SMILES: CC(C)(C(=O)NS(=O)(=O)C1(C)CC1)c1ccc(O[C@@H]2CC[C@@H](NC(=O)[C@@]3(F)CNC4(CCC4)C3)C2)c(-c2cccc(F)c2C2CCC2)c1] (7ξ)-N-[(1R,3R)-3-({2'-cyclobutyl-3'-fluoro-5-[2-methyl-1-(1-methylcyclopropane-1-sulfonamido)-1-oxopropan-2-yl][1,1'-biphenyl]-2-yl}oxy)cyclopentyl]-7-fluoro-5-azaspiro[3.4]octane-7-carboxamide | $^1$H NMR (400 MHz, DMSO-$d_6$) δ 11.09-10.66 (m, 1H), 10.05-9.76 (m, 2H), 8.52 (br. t, J = 7.3 Hz, 1H), 7.30-7.18 (m, 2H), 7.11 (dd, J = 8.3, 11.6 Hz, 1H), 7.04 (d, J = 8.6 Hz, 1H), 6.96 (dd, J = 2.6, 3.8 Hz, 1H), 6.88 (dd, J = 2.7, 7.1 Hz, 1H), 4.84 (br. s, 1H), 4.17-3.97 (m, 1H), 3.70-3.59 (m, 1H), 3.59-3.51 (m, 1H), 3.50-3.40 (m, 1H), 2.68-2.56 (m, 1H), 2.54 (br. d, J = 6.8 Hz, 2H), 2.47-2.31 (m, 1H), 2.26-2.07 (m, 4H), 2.03 (td, J = 4.9, 10.3 Hz, 2H), 1.93-1.76 (m, 6H), 1.75-1.63 (m, 2H), 1.57 (br. s, 1H), 1.53-1.50 (m, 3H), 1.48 (s, 3H), 1.46-1.42 (m, 1H), 1.42-1.37 (m, 1H), 1.36-1.30 (m, 1H), 1.25 (s, 3H), 0.88-0.80 (m, 2H). LCMS (m/z) $(M + H)^+$: 684.5 |

TABLE 2-continued

| Ex. | Structure and Name | Characterization Data ($^1$H NMR, optical rotation, and/or LCMS) |
|---|---|---|
| B34 | 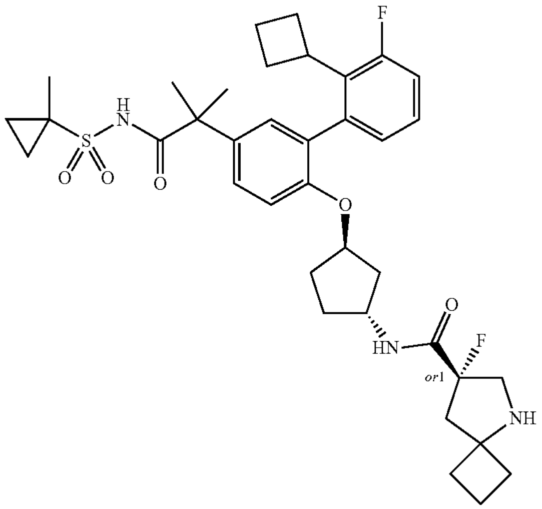 [SMILES: CC(C)(C(=O)NS(=O)(=O)C1(C)CC1)c1ccc(O[C@@H]2CC[C@@H](NC(=O)[C@@]3(F)CNC4(CCC4)C3)C2)c(-c2cccc(F)c2C2CCC2)c1] (7ξ)-N-[(1R,3R)-3-({2'-cyclobutyl-3'-fluoro-5-[2-methyl-1-(1-methylcyclopropane-1-sulfonamido)-1-oxopropan-2-yl][1,1'-biphenyl]-2-yl}oxy)cyclopentyl]-7-fluoro-5-azaspiro[3.4]octane-7-carboxamide | $^1$H NMR (400 MHz, DMSO-$d_6$) δ 11.01-10.74 (m, 1H), 10.05-9.75 (m, 2H), 8.52 (br. t, J = 7.0 Hz, 1H), 7.30-7.18 (m, 2H), 7.11 (dd, J = 8.2, 11.2 Hz, 1H), 7.04 (d, J = 8.8 Hz, 1H), 6.96 (dd, J = 2.5, 5.0 Hz, 1H), 6.88 (d, J = 7.5 Hz, 1H), 4.83 (br. s, 1H), 4.20-3.99 (m, 1H), 3.71-3.51 (m, 2H), 3.50-3.39 (m, 1H), 2.69-2.58 (m, 1H), 2.55 (br. d, J = 10.9 Hz, 1H), 2.53-2.51 (m, 1H), 2.47-2.30 (m, 1H), 2.24-2.14 (m, 3H), 2.13-1.97 (m, 3H), 1.95-1.77 (m, 6H), 1.76-1.64 (m, 2H), 1.64-1.54 (m, 1H), 1.52 (s, 3H), 1.48 (s, 3H), 1.46-1.42 (m, 1H), 1.42-1.36 (m, 1H), 1.36-1.30 (m, 1H), 1.25 (s, 3H), 0.89-0.80 (m, 2H). LCMS (m/z) (M + H)$^+$: 684.3 |
| B35 | 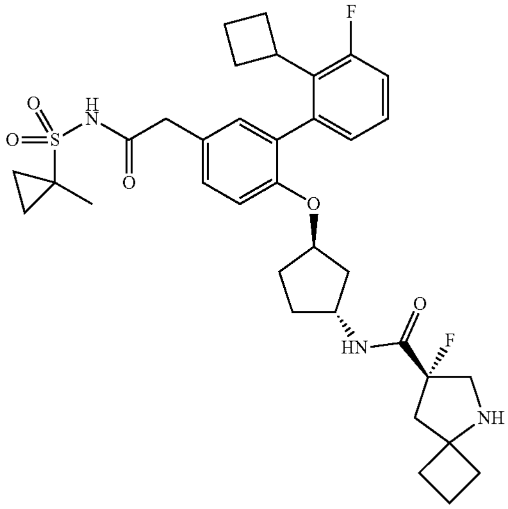 [SMILES: CC1(S(=O)(=O)NC(=O)Cc2ccc(O[C@@H]3CC[C@@H](NC(=O)[C@@]4(F)CNC5(CCC5)C4)C3)c(-c3cccc(F)c3C3CCC3)c2)CC1] (7S)-N-[(1R,3R)-3-({2'-cyclobutyl-3'-fluoro-5-[2-(1-methylcyclopropane-1-sulfonamido)-2-oxoethyl][1,1'-biphenyl]-2-yl}oxy)cyclopentyl]-7-fluoro-5-azaspiro[3.4]octane-7-carboxamide | $^1$H NMR (400 MHz, MeOD) δ = 7.28 (dd, J = 2.2, 8.4 Hz, 1H), 7.16 (dt, J = 5.6, 7.8 Hz, 1H), 7.06 (t, J = 2.4 Hz, 1H), 7.02-6.91 (m, 2H), 6.87 (dt, J = 1.1, 6.7 Hz, 1H), 4.83-4.76 (m, 1H), 4.25-4.05 (m, 1H), 3.54 (s, 2H), 3.52-3.33 (m, 2H), 3.29-3.18 (m, 1H), 2.49-2.29 (m, 3H), 2.26-2.07 (m, 7H), 2.03-1.66 (m, 9H), 1.64-1.54 (m, 1H), 1.49-1.45 (m, 2H), 1.42 (s, 3H), 0.84-0.75 (m, 2H). LCMS (m/z) (M + H)$^+$: 656.4 |

Example C1: (7S)-N-{(1R,3R)-3-[(2'-cyclobutyl-3'-fluoro-5-{1-[(methanesulfonyl)amino]-2-methyl-1-oxopropan-2-yl}[1,1'-biphenyl]-2-yl)oxy]cyclopentyl}-7-fluoro-5-azaspiro[3.4]octane-7-carboxamide

C1

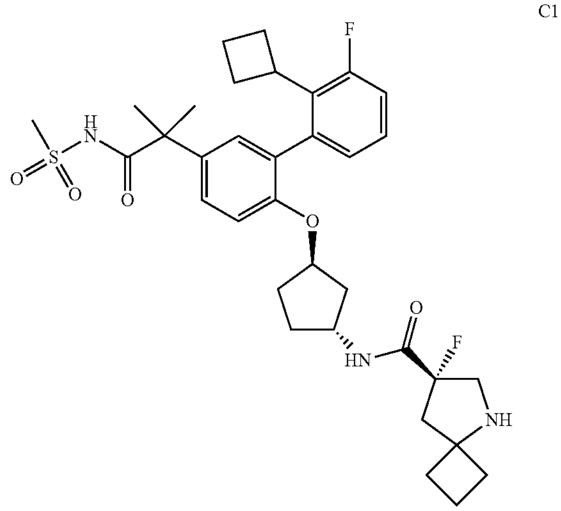 [SMILES: CC(C)(C(=O)NS(C)(=O)=O)c1ccc(O[C@@H]2CC[C@@H](NC(=O)[C@@]3(F)CNC4(CCC4)C3)C2)c(-c2cccc(F)c2C2CCC2)c1]

Example C1 was prepared according to General Method C.

Step 1: tert-butyl (7S)-7-({(1R,3R)-3-[(2'-cyclobutyl-3'-fluoro-5-{1-[(methanesulfonyl)amino]-2-methyl-1-oxopropan-2-yl}[1,1-biphenyl]-2-yl)oxy]cyclopentyl}carbamoyl)-7-fluoro-5-azaspiro[3.4]octane-5-carboxylate (C1a)

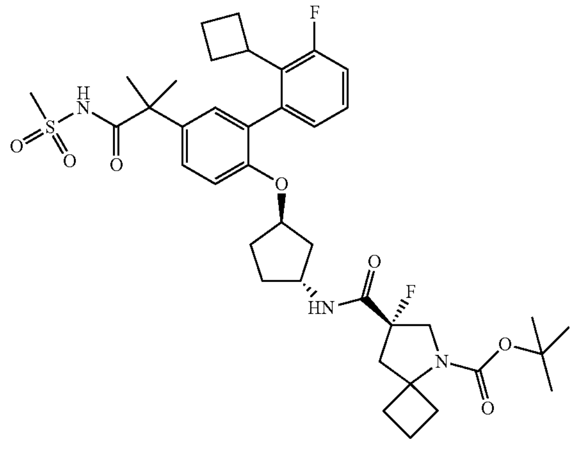 [SMILES: CC(C)(C)OC(=O)N1C[C@](F)(C(=O)N[C@@H]2CC[C@@H](Oc3ccc(C(C)(C)C(=O)NS(C)(=O)=O)cc3-c3cccc(F)c3C3CCC3)C2)CC12CCC2]

To a solution of 2-(6-{[(1R,3R)-3-{[(7S)-5-(tert-butoxycarbonyl)-7-fluoro-5-azaspiro[3.4]octane-7-carbonyl]amino}cyclopentyl]oxy}-2'-cyclobutyl-3'-fluoro[1,1'-biphenyl]-3-yl)-2-methylpropanoic acid (A1e) (53 mg, 0.079 mmol) in DCM (0.79 mL), carbonyldiimidazole (19 mg, 0.12 mmol) was added. The reaction was heated to 40° C. for 1 h, and then methanesulfonamide (19 mg, 0.20 mmol) and 1,8-diazabicyclo[5.4.0]undec-7-ene (48 mg, 48 μL, 0.32 mmol) were added. After 1 h, the reaction was purified by silica gel chromatography (0-100% EtOAc/heptanes) to give tert-butyl (7S)-7-({(1R,3R)-3-[(2'-cyclobutyl-3'-fluoro-5-{1-[(methanesulfonyl)amino]-2-methyl-1-oxopropan-2-yl}[1,1'-biphenyl]-2-yl)oxy]cyclopentyl}carbamoyl)-7-fluoro-5-azaspiro[3.4]octane-5-carboxylate (C1a) (46 mg, 78%) as a white foam. LCMS APCI (+) 644 (M-Boc).

Step 2: (7S)-N-{(1R,3R)-3-[(2'-cyclobutyl-3'-fluoro-5-{1-[(methanesulfonyl)amino]-2-methyl-1-oxopropan-2-yl}[1,1'-biphenyl]-2-yl)oxy]cyclopentyl}-7-fluoro-5-azaspiro[3.4]octane-7-carboxamide (Example C1)

C1

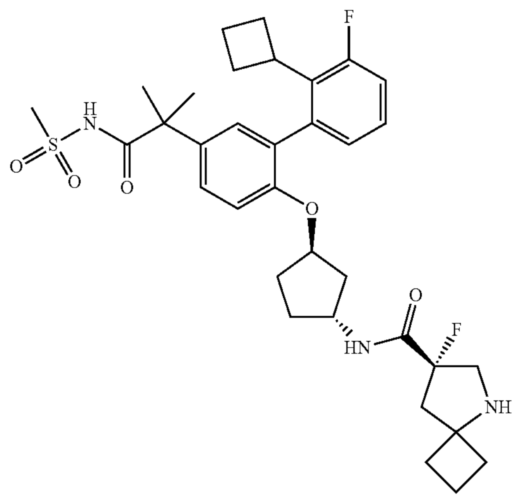

To a solution of tert-butyl (7S)-7-({(1R,3R)-3-[(2'-cyclobutyl-3'-fluoro-5-{1-[(methanesulfonyl)amino]-2-methyl-1-oxopropan-2-yl}[1,1'-biphenyl]-2-yl)oxy]cyclopentyl}carbamoyl)-7-fluoro-5-azaspiro[3.4]octane-5-carboxylate (C1a) (46 mg, 0.062 mmol) in DCM (0.62 mL), HCl (4 N in dioxane, 0.31 mL, 1.2 mmol) was added. After stirring for 2 h at RT, the reaction was concentrated under reduced pressure and the residue was purified by Prep HPLC (Phenomenex Gemini NX C18 150×21.2 mm, 5 um, AXIA Pack column, Mobile phase A: Water+10 mM Ammonium Acetate, Mobile phase B: Acetonitrile, 25-60% B in 8.0 minutes, 40 mL/min) to give (7S)-N-{(1R,3R)-3-[(2'-cyclobutyl-3'-fluoro-5-{1-[(methanesulfonyl)amino]-2-methyl-1-oxopropan-2-yl}[1,1'-biphenyl]-2-yl)oxy]cyclopentyl}-7-fluoro-5-azaspiro[3.4]octane-7-carboxamide (Example C1) (23 mg, 59%). LCMS APCI (+) 644 (M+H). $^1$H NMR (600 MHz, DMSO-d6) δ ppm 8.30-8.19 (m, 1H), 7.25 (dd, J=2.2, 8.7 Hz, 1H), 7.23-7.17 (m, 1H), 7.09 (dd, J=8.5, 11.4 Hz, 1H), 6.98 (dd, J=2.5, 4.0 Hz, 1H), 6.95 (d, J=8.7 Hz, 1H), 6.90-6.85 (m, 1H), 4.79 (br s, 1H), 4.15-4.01 (m, 2H), 3.54-3.41 (m, 1H), 3.27-3.19 (m, 1H), 2.92 (br s, 3H), 2.38-2.24 (m, 2H), 2.22-1.95 (m, 9H), 1.89-1.84 (m, 2H), 1.83-1.77 (m, 2H), 1.75-1.72 (m, 2H), 1.71-1.59 (m, 2H), 1.57-1.44 (m, 2H), 1.42 (s, 3H), 1.40 (s, 3H).

Examples $C_2$-$C_{91}$reported in Table 3 were synthesized with non-critical changes or substitutions to the exemplified procedures for Examples $C_1$ that one skilled in the art would be able to realize. In Example C15, $NH_3$ is used in place of methanesulfonamide. In Examples $C_{19}$ and $C_{20}$, the Suzuki coupling was done last.

TABLE 3

| Ex. | Structure and Name | Characterization Data ($^1$H NMR, optical rotation, and/or LCMS) |
| --- | --- | --- |
| C2 | 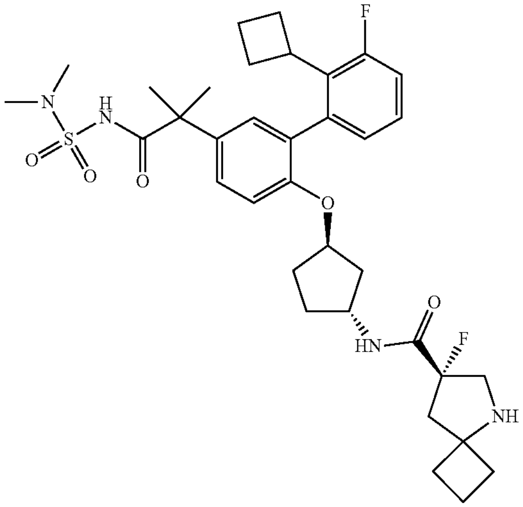 [SMILES: CN(C)S(=O)(=O)NC(=O)C(C)(C)c1ccc(O[C@@H]2CC[C@@H](NC(=O)[C@@]3(F)CNC4(CCC4)C3)C2)c(-c2cccc(F)c2C2CCC2)c1]<br>(7S)-N-{(1R,3R)-3-[(2'-cyclobutyl-5-{1-[(dimethylsulfamoyl)amino]-2-methyl-1-oxopropan-2-yl}-3'-fluorobiphenyl-2-yl)oxy]cyclopentyl}-7-fluoro-5-azaspiro[3.4]octane-7-carboxamide | $^1$H NMR (600 MHz, DMSO-$d_6$) δ 8.17 (br t, J = 9.3 Hz, 1H), 7.27 (dd, J = 2.4, 8.5 Hz, 1H), 7.24-7.17 (m, 1H), 7.13-7.06 (m, 1H), 7.00 (d, J = 8.4 Hz, 1H), 6.96 (dd, J = 2.2, 4.7 Hz, 1H), 6.87 (dd, J = 4.9, 7.1 Hz, 1H), 4.80 (br s, 1H), 4.15-4.08 (m, 2H), 4.07-3.99 (m, 1H), 3.50-3.39 (m, 1H), 2.68 (s, 6H), 2.33-2.15 (m, 3H), 2.14-1.95 (m, 8H), 1.92-1.81 (m, 2H), 1.80-1.70 (m, 4H), 1.69-1.61 (m, 2H), 1.51-1.40 (m, 8H).<br>LCMS (m/z) (M + H)$^+$: 673.2 |
| C3 | 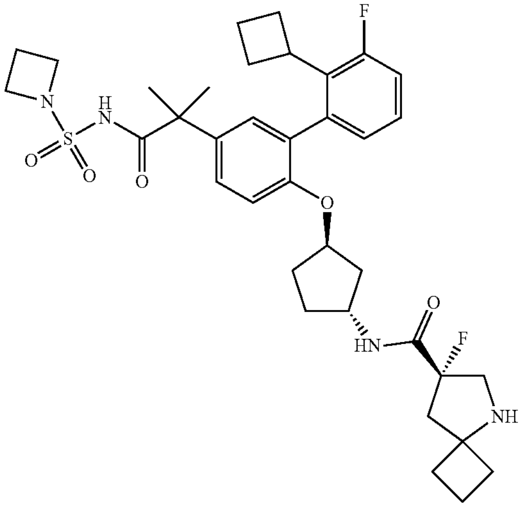 [SMILES: CC(C)(C(=O)NS(=O)(=O)N1CCC1)c1ccc(O[C@@H]2CC[C@@H](NC(=O)[C@@]3(F)CNC4(CCC4)C3)C2)c(-c2cccc(F)c2C2CCC2)c1]<br>(7S)-N-{(1R,3R)-3-[(5-{1-[(azetidin-1-ylsulfonyl)amino]-2-methyl-1-oxopropan-2-yl}-2'-cyclobutyl-3'-fluorobiphenyl-2-yl)oxy]cyclopentyl}-7-fluoro-5-azaspiro[3.4]octane-7-carboxamide | $^1$H NMR (600 MHz, DMSO-$d_6$) δ 8.18 (br s, 1H), 7.35-7.27 (m, 1H), 7.24-7.16 (m, 1H), 7.14-7.05 (m, 1H), 7.05-6.95 (m, 2H), 6.92-6.81 (m, 1H), 4.80 (br s, 1H), 4.18-3.98 (m, 5H), 3.55-3.41 (m, 1H), 3.14-3.05 (m, 1H), 2.38-2.15 (m, 3H), 2.12-1.97 (m, 7H), 1.97-1.84 (m, 4H), 1.81-1.63 (m, 6H), 1.59-1.37 (m, 9H).<br>LCMS (m/z) (M + H)$^+$: 685.1 |

TABLE 3-continued

| Ex. | Structure and Name | Characterization Data ($^1$H NMR, optical rotation, and/or LCMS) |
|---|---|---|
| C4 | 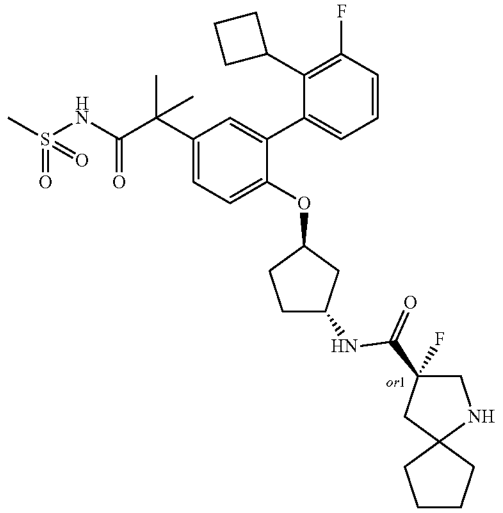 [SMILES: CC(C)(C(=O)NS(C)(=O)=O)c1ccc(O[C@@H]2CC[C@@H](NC(=O)[C@@]3(F)CNC4(CCCC4)C3)C2)c(-c2cccc(F)c2C2CCC2)c1] (3ξ)-N-{(1R,3R)-3-[(2'-cyclobutyl-3'-fluoro-5-{1-[(methanesulfonyl)amino]-2-methyl-1-oxopropan-2-yl}[1,1'-biphenyl]-2-yl)oxy]cyclopentyl}-3-fluoro-1-azaspiro[4.4]nonane-3-carboxamide | $^1$H NMR (400 MHz, DMSO-$d_6$) δ 8.38-8.31 (m, 1H), 7.25 (dd, J = 2.3, 8.7 Hz, 1H), 7.23-7.18 (m, 1H), 7.09 (dd, J = 7.9, 11.4 Hz, 1H), 6.99 (t, J = 2.6 Hz, 1H), 6.95 (d, J = 8.6 Hz, 1H), 6.90-6.85 (m, 1H), 4.81-4.77 (m, 1H), 4.15-4.03 (m, 1H), 3.69-3.49 (m, 4H), 2.89 (br s, 3H), 2.42-2.27 (m, 1H), 2.24-1.96 (m, 5H), 1.92-1.76 (m, 6H), 1.76-1.59 (m, 8H), 1.56-1.43 (m, 2H), 1.40 (br d, J = 8.6 Hz, 6H). $[\alpha]^{22}_D$ = −50.3° (c 0.01, MeOH). LCMS (m/z) (M + H)$^+$: 658.5 |
| C5 | 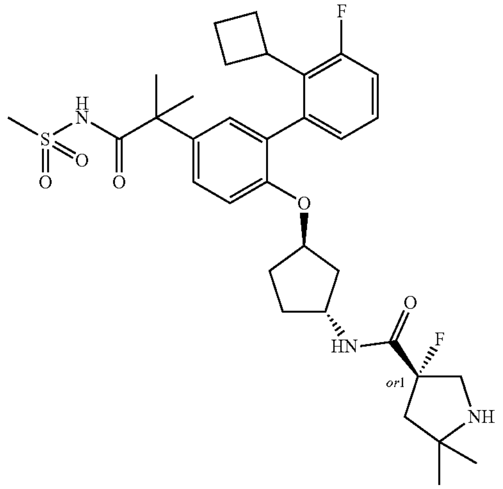 (3ξ)-N-{(1R,3R)-3-[(2'-cyclobutyl-3'-fluoro-5-{1-[(methanesulfonyl)amino]-2-methyl-1-oxopropan-2-yl}[1,1'-biphenyl]-2-yl)oxy]cyclopentyl}-3-fluoro-5,5-dimethylpyrrolidine-3-carboxamide | $^1$H NMR (600 MHz, DMSO-$d_6$) δ 8.26 (br t, J = 8.40 Hz, 1 H) 7.25 (dd, J = 8.67, 2.50 Hz, 1 H) 7.17-7.22 (m, 1 H) 7.08 (dd, J = 11.67, 8.22 Hz, 1 H) 6.98 (dd, J = 4.63, 2.45 Hz, 1 H) 6.95 (d, J = 8.72 Hz, 1 H) 6.87 (ddd, J = 7.54, 4.18, 0.91 Hz, 1 H) 4.78 (br d, J = 2.09 Hz, 1 H) 3.42-3.50 (m, 3 H) 2.90 (br s, 3 H) 2.14-2.25 (m, 2 H) 1.96-2.12 (m, 4 H) 1.84-1.92 (m, 2 H) 1.70-1.83 (m, 3 H) 1.61-1.70 (m, 1 H) 1.43-1.58 (m, 2 H) 1.41 (s, 3 H) 1.39 (s, 3 H) 1.30 (s, 3 H) 1.26 (d, J = 2.27 Hz, 3 H). $[\alpha]^{22}_D$ = −15.1° (c 0.1, MeOH). LCMS (m/z) (M + H)$^+$: 632.1 |

TABLE 3-continued

| Ex. | Structure and Name | Characterization Data ($^1$H NMR, optical rotation, and/or LCMS) |
|---|---|---|
| C6 | 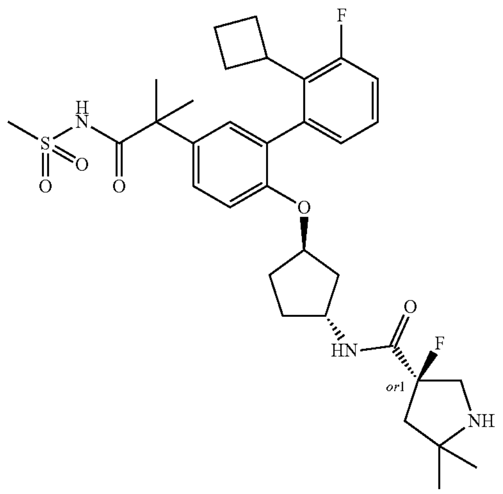 (3ξ)-N-{(1R,3R)-3-[(2'-cyclobutyl-3'-fluoro-5-{1-[(methanesulfonyl)amino]-2-methyl-1-oxopropan-2-yl}[1,1'-biphenyl]-2-yl)oxy]cyclopentyl}-3-fluoro-5,5-dimethylpyrrolidine-3-carboxamide | $^1$H NMR (600 MHz, DMSO-$d_6$) δ 8.27 (br t, J = 8.76 Hz, 1 H) 7.25 (dd, J = 8.63, 2.54 Hz, 1 H) 7.20 (td, J = 7.83, 5.59 Hz, 1 H) 7.06-7.13 (m, 1 H) 6.98 (dd, J = 4.27, 2.54 Hz, 1 H) 6.95 (d, J = 8.72 Hz, 1 H) 6.87 (ddd, J = 7.52, 4.79, 1.14 Hz, 1 H) 4.79 (dt, J = 5.47, 2.76 Hz, 1 H) 3.42-3.53 (m, 3 H) 2.91 (br s, 3 H) 2.14-2.24 (m, 2 H) 1.96-2.13 (m, 4 H) 1.82-1.92 (m, 2 H) 1.69-1.82 (m, 3 H) 1.66 (quin, J = 8.79 Hz, 1 H) 1.43-1.57 (m, 2 H) 1.42 (s, 3 H) 1.39 (s, 3 H) 1.30 (d, J = 3.45 Hz, 3 H) 1.26 (d, J = 5.00 Hz, 3 H). $[\alpha]^{22}_D$ = −21.5° (c 0.1, MeOH). LCMS (m/z) $(M + H)^+$: 632.1 |
| C7 | 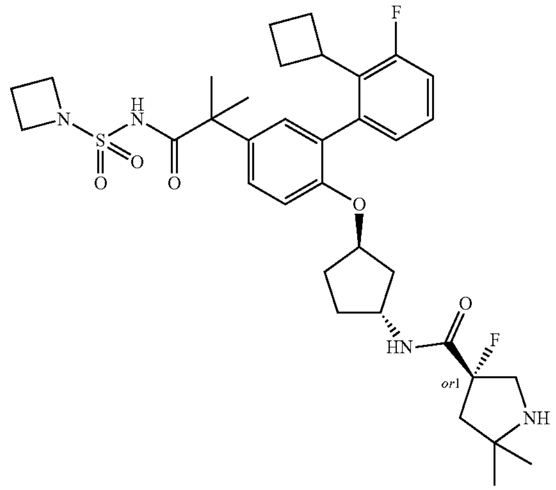 [SMILES: CC1(C)C[C@@](F)(C(=O)N[C@@H]2CC[C@@H](Oc3ccc(C(C)(C)C(=O)NS(=O)(=O)N4CCC4)cc3-c3cccc(F)c3C3CCC3)C2)CN1] (3ξ)-N-{(1R,3R)-3-[(5-{1-[(azetidine-1-sulfonyl)amino]-2-methyl-1-oxopropan-2-yl}-2'-cyclobutyl-3'-fluoro[1,1'-biphenyl]-2-yl)oxy]cyclopentyl}-3-fluoro-5,5-dimethylpyrrolidine-3-carboxamide | $^1$H NMR (600 MHz, DMSO-$d_6$) δ 8.16-8.25 (m, 1 H) 7.31 (dd, J = 8.67, 2.50 Hz, 1 H) 7.21 (td, J = 7.79, 5.68 Hz, 1 H) 7.09 (ddd, J = 11.76, 8.22, 0.91 Hz, 1 H) 7.02 (dd, J = 5.09, 2.54 Hz, 1 H) 6.99 (d, J = 8.72 Hz, 1 H) 6.87 (ddd, J = 7.49, 5.18, 1.14 Hz, 1 H) 4.76-4.83 (m, 1 H) 3.70-3.79 (m, 4 H) 3.43-3.51 (m, 2 H) 1.85-2.23 (m, 10 H) 1.71-1.82 (m, 3 H) 1.62-1.70 (m, 1 H) 1.48 (d, J = 16.26 Hz, 6 H) 1.26 (d, J = 1.82 Hz, 3 H) 1.21 (d, J = 3.36 Hz, 3 H). $[\alpha]^{22}_D$ = −15.4° (c 0.1, MeOH). LCMS (m/z) $(M + H)^+$: 673.0 |

TABLE 3-continued

| Ex. | Structure and Name | Characterization Data ($^1$H NMR, optical rotation, and/or LCMS) |
|---|---|---|
| C8 | 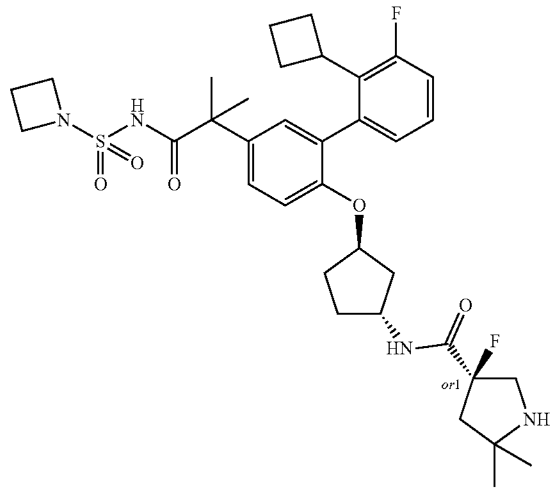 [SMILES: CC1(C)C[C@](F)(C(=O)N[C@@H]2CC[C@@H](Oc3ccc(C(C)(C)C(=O)NS(=O)(=O)N4CCC4)cc3-c3cccc(F)c3C3CCC3)C2)CN1] (3ξ)-N-{(1R,3R)-3-[(5-{1-[(azetidine-1-sulfonyl)amino]-2-methyl-1-oxopropan-2-yl}-2'-cyclobutyl-3'-fluoro[1,1'-biphenyl]-2-yl)oxy]cyclopentyl}-3-fluoro-5,5-dimethylpyrrolidine-3-carboxamide | $^1$H NMR (600 MHz, DMSO-$d_6$) δ m 8.18-8.24 (m, 1 H) 7.32 (dd, J = 8.63, 2.54 Hz, 1 H) 7.22 (td, J = 7.83, 5.68 Hz, 1 H) 7.07-7.12 (m, 1 H) 7.03 (dd, J = 4.90, 2.45 Hz, 1 H) 7.00 (d, J = 8.72 Hz, 1 H) 6.88 (ddd, J = 7.33, 5.97, 1.04 Hz, 1 H) 4.81 (br d, J = 1.73 Hz, 1 H) 4.01-4.06 (m, 1 H) 3.76 (br d, J = 5.63 Hz, 4 H) 3.43-3.52 (m, 2 H) 3.24 (br s, 1 H) 2.15-2.23 (m, 1 H) 2.06-2.14 (m, 2 H) 1.85-2.06 (m, 7 H) 1.63-1.83 (m, 4 H) 1.50 (s, 4 H) 1.47 (s, 4 H) 1.27 (d, J = 3.45 Hz, 3 H) 1.22 (d, J = 5.45 Hz, 3 H). $[\alpha]^{22}_D$ = −18.0° (c 0.1, MeOH). LCMS (m/z) $(M + H)^+$: 673.0 |
| C9 | 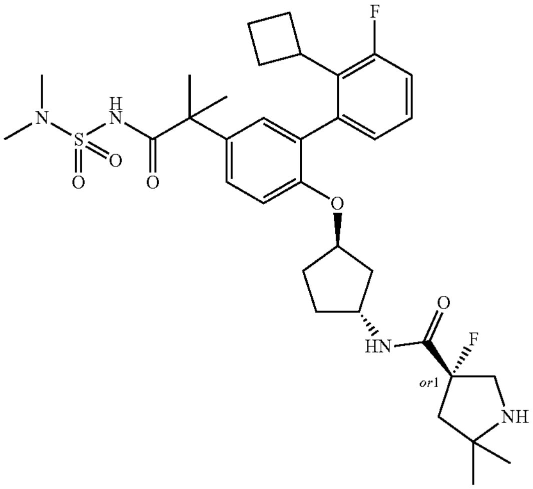 (3ξ)-N-{(1R,3R)-3-[(2'-cyclobutyl-5-{1-[(dimethylsulfamoyl)amino]-2-methyl-1-oxopropan-2-yl}-3'-fluoro[1,1'-biphenyl]-2-yl)oxy]cyclopentyl}-3-fluoro-5,5-dimethylpyrrolidine-3-carboxamide | $^1$H NMR (600 MHz, DMSO-$d_6$) δ 8.11-8.17 (m, 1 H) 7.27 (dd, J = 8.63, 2.54 Hz, 1 H) 7.21 (td, J = 7.86, 5.63 Hz, 1 H) 7.09 (ddd, J = 11.76, 8.22, 0.91 Hz, 1 H) 6.96-7.00 (m, 2 H) 6.86 (ddd, J = 7.49, 5.27, 1.14 Hz, 1 H) 4.77-4.82 (m, 1 H) 3.41-3.49 (m, 1 H) 2.65 (s, 6 H) 1.91-2.24 (m, 6 H) 1.80-1.91 (m, 3 H) 1.62-1.80 (m, 4 H) 1.38-1.56 (m, 7 H) 1.22 (d, J = 2.00 Hz, 3 H) 1.16 (d, J = 3.63 Hz, 3 H). $[\alpha]^{22}_D$ = −19.6° (c 0.1, MeOH). LCMS (m/z) $(M + H)^+$: 661.1 |

TABLE 3-continued

| Ex. | Structure and Name | Characterization Data ($^1$H NMR, optical rotation, and/or LCMS) |
|---|---|---|
| C10 | 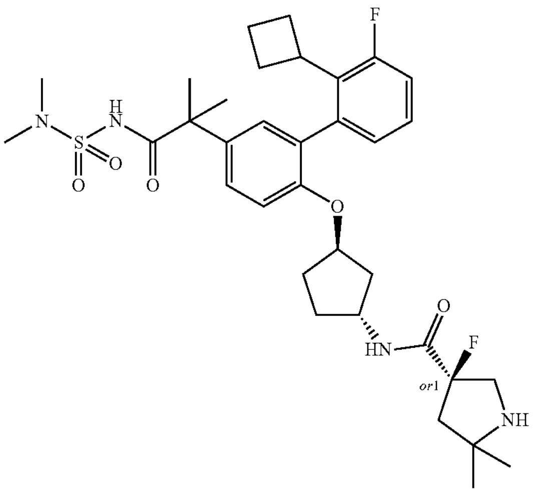 (3ξ)-N-{(1R,3R)-3-[(2'-cyclobutyl-5-{1-[(dimethylsulfamoyl)amino]-2-methyl-1-oxopropan-2-yl}-3'-fluoro[1,1'-biphenyl]-2-yl)oxy]cyclopentyl}-3-fluoro-5,5-dimethylpyrrolidine-3-carboxamide | $^1$H NMR (600 MHz, DMSO-$d_6$) δ 8.14-8.20 (m, 1 H) 7.27 (dd, J = 8.63, 2.54 Hz, 1 H) 7.19-7.23 (m, 1 H) 7.08-7.13 (m, 1 H) 6.99-7.02 (m, 1 H) 6.97-6.99 (m, 1 H) 6.85-6.91 (m, 1 H) 4.78-4.83 (m, 1 H) 4.01-4.06 (m, 1 H) 3.42-3.50 (m, 1 H) 3.19-3.23 (m, 1 H) 2.67 (s, 6 H) 1.94-2.24 (m, 6 H) 1.83-1.94 (m, 3 H) 1.71-1.82 (m, 3 H) 1.63-1.71 (m, 1 H) 1.47 (d, J = 19.71 Hz, 7 H) 1.24 (d, J = 3.72 Hz, 3 H) 1.18 (d, J = 5.81 Hz, 3 H). $[\alpha]^{22}_D$ = −13.6° (c 0.1, MeOH). LCMS (m/z) $(M + H)^+$: 661.1 |
| C11 | 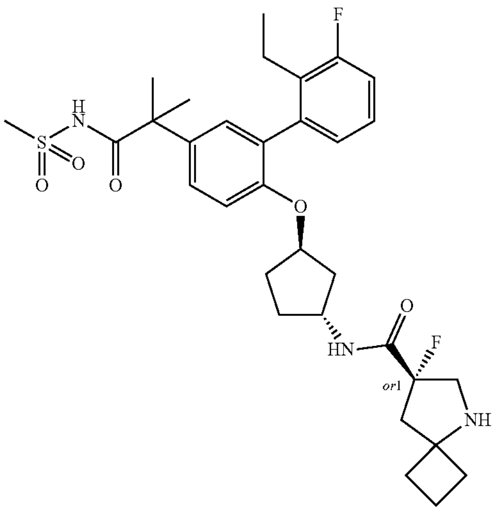 [SMILES: CCc1c(F)cccc1-c1cc(C(C)(C)C(=O)NS(C)(=O)=O)ccc1O[C@@H]1CC[C@@H](NC(=O)[C@@]2(F)CNC3(CCC3)C2)C1] (7ξ)-N-{(1R,3R)-3-[(2'-ethyl-3'-fluoro-5-{1-[(methanesulfonyl)amino]-2-methyl-1-oxopropan-2-yl}[1,1'-biphenyl]-2-yl)oxy]cyclopentyl}-7-fluoro-5-azaspiro[3.4]octane-7-carboxamide | $^1$H NMR (600 MHz, DMSO-$d_6$) δ 8.25 (br d, J = 6.63 Hz, 1 H) 7.26 (dd, J = 8.63, 2.54 Hz, 1 H) 7.22 (td, J = 7.83, 6.04 Hz, 1 H) 7.08-7.14 (m, 1 H) 7.00 (d, J = 2.54 Hz, 1 H) 6.99 (d, J = 8.72 Hz, 1 H) 6.89 (d, J = 7.45 Hz, 1 H) 4.82 (br s, 1 H) 4.07 (sxt, J = 7.50 Hz, 2 H) 3.17 (s, 1 H) 2.96 (s, 3 H) 2.26-2.36 (m, 3 H) 2.14-2.20 (m, 2 H) 1.99-2.12 (m, 3 H) 1.83-1.88 (m, 1 H) 1.73-1.83 (m, 3 H) 1.66-1.73 (m, 1 H) 1.45-1.55 (m, 2 H) 1.42 (br d, J = 9.54 Hz, 6 H) 0.92 (t, J = 7.49 Hz, 3 H). $[\alpha]^{22}_D$ = −21.3° (c 0.1, MeOH). LCMS (m/z) $(M + H)^+$: 618.2 |

TABLE 3-continued

| Ex. | Structure and Name | Characterization Data ($^1$H NMR, optical rotation, and/or LCMS) |
|---|---|---|
| C12 | 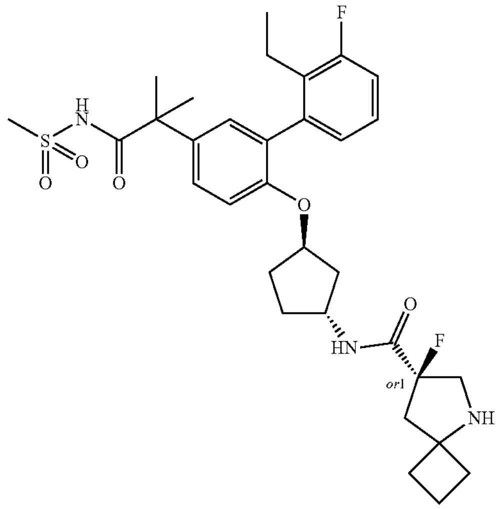 [SMILES: CCc1c(F)cccc1-c1cc(C(C)(C)C(=O)NS(C)(=O)=O)ccc1O[C@@H]1CC[C@@H](NC(=O)[C@]2(F)CNC3(CCC3)C2)C1] (7ξ)-N-{(1R,3R)-3-[(2'-ethyl-3'-fluoro-5-{1-[(methanesulfonyl)amino]-2-methyl-1-oxopropan-2-yl}[1,1'-biphenyl]-2-yl)oxy]cyclopentyl}-7-fluoro-5-azaspiro[3.4]octane-7-carboxamide | $^1$H NMR (400 MHz, DMSO-$d_6$) 8.24 (br, d, J = 6.72 Hz, 1 H) 7.26 (dd, J = 8.67, 2.50 Hz, 1 H) 7.19-7.23 (m, 1 H) 7.08-7.12 (m, 1 H) 6.97-7.01 (m, 2 H) 6.88 (br d, J = 7.54 Hz, 1 H) 4.81 (br dd, J = 4.95, 2.50 Hz, 1 H) 4.02-4.09 (m, 1 H) 2.95 (s, 3 H) 2.25-2.38 (m, 3 H) 2.12-2.21 (m, 2 H) 1.98-2.11 (m, 3 H) 1.64-1.87 (m, 5 H) 1.38-1.54 (m, 8 H) 0.91 (t, J = 7.45 Hz, 3 H). $[\alpha]^{22}_D$ = −23.8° (c 0.1, MeOH). LCMS (m/z) (M + H)$^+$: 618.2 |
| C13 | 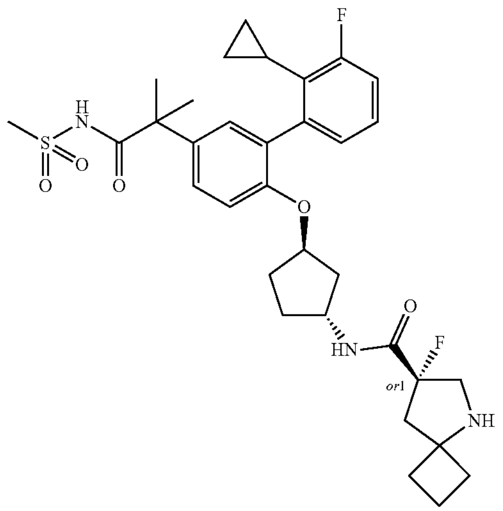 [SMILES: CC(C)(C(=O)NS(C)(=O)=O)c1ccc(O[C@@H]2CC[C@@H](NC(=O)[C@@]3(F)CNC4(CCC4)C3)C2)c(-c2cccc(F)c2C2CC2)c1] (7ξ)-N-{(1R,3R)-3-[(2'-cyclopropyl-3'-fluoro-5-{1-[(methanesulfonyl)amino]-2-methyl-1-oxopropan-2-yl}[1,1'-biphenyl]-2-yl)oxy]cyclopentyl}-7-fluoro-5-azaspiro[3.4]octane-7-carboxamide | $^1$H NMR (600 MHz, DMSO-$d_6$) δ 8.16-8.23 (m, 1 H) 7.30 (dd, J = 8.54, 2.00 Hz, 1 H) 7.19-7.24 (m, 1 H) 7.09 (dd, J = 11.63, 8.36 Hz, 1 H) 6.96-7.01 (m, 2 H) 6.88 (dt, J = 4.27, 3.32 Hz, 1 H) 4.81 (br s, 1 H) 4.05-4.21 (m, 1 H) 2.80-2.89 (m, 1 H) 2.71-2.78 (m, 1 H) 2.24-2.42 (m, 2 H) 2.00-2.23 (m, 5 H) 1.60-1.97 (m, 11 H) 1.38-1.56 (m, 8 H). $[\alpha]^{22}_D$ = −10.3° (c 0.1, MeOH). LCMS (m/z) (M + H)$^+$: 630.0 |

TABLE 3-continued

| Ex. | Structure and Name | Characterization Data ($^1$H NMR, optical rotation, and/or LCMS) |
|---|---|---|
| C14 | 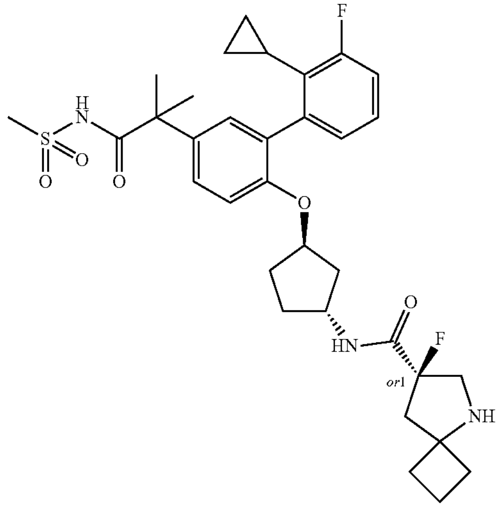 [SMILES: CC(C)(C(=O)NS(C)(=O)=O)c1ccc(O[C@@H]2CC[C@@H](NC(=O)[C@]3(F)CNC4(CCC4)C3)C2)c(-c2cccc(F)c2C2CC2)c1] (7ξ)-N-{(1R,3R)-3-[(2'-cyclopropyl-3'-fluoro-5-{1-[(methanesulfonyl)amino]-2-methyl-1-oxopropan-2-yl}[1,1'-biphenyl]-2-yl)oxy]cyclopentyl}-7-fluoro-5-azaspiro[3.4]octane-7-carboxamide | $^1$H NMR (600 MHz, DMSO-$d_6$) δ 8.22-8.30 (m, 1 H) 7.18-7.27 (m, 2 H) 7.03-7.10 (m, 2 H) 6.91-6.99 (m, 2 H) 4.82 (br s, 1 H) 4.10-4.13 (m, 1 H) 2.25-2.34 (m, 2 H) 2.03-2.21 (m, 5 H) 1.60-1.97 (m, 7 H) 1.35-1.58 (m, 9 H) 0.35-0.68 (m, 4 H). $[\alpha]^{22}_D$ = −23.8° (c 0.1, MeOH). LCMS (m/z) $(M + H)^+$: 630.2 |
| C15 | 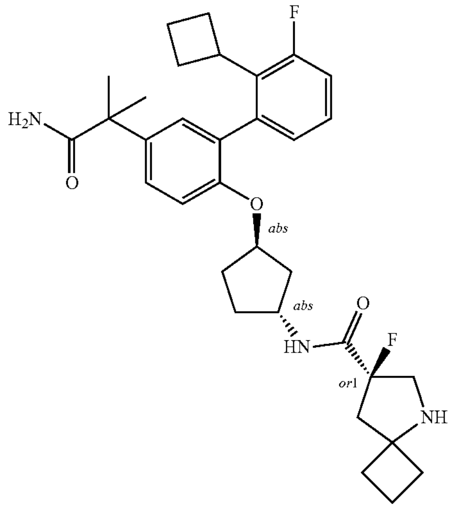 [SMILES: CC(C)(C(N)=O)c1ccc(O[C@@H]2CC[C@@H](NC(=O)[C@]3(F)CNC4(CCC4)C3)C2)c(-c2cccc(F)c2C2CCC2)c1] (7ξ)-N-[(1R,3R)-3-{[5-(1-amino-2-methyl-1-oxopropan-2-yl)-2'-cyclobutyl-3'-fluoro[1,1'-biphenyl]-2-yl]oxy}cyclopentyl]-7-fluoro-5-azaspiro[3.4]octane-7-carboxamide *Can be made by using $NH_3$ in place of methanesulfonamide | $^1$H NMR (400 MHz, DMSO-$d_6$) δ 8.09 (dt, J = 2.6, 7.7 Hz, 1H), 7.28 (dd, J = 2.4, 8.7 Hz, 1H), 7.20 (dt, J = 5.7, 7.9 Hz, 1H), 7.08 (ddd, J = 1.0, 8.2, 11.8 Hz, 1H), 7.00 (t, J = 2.8 Hz, 1H), 6.95 (d, J = 8.8 Hz, 1H), 6.86 (ddd, J = 1.2, 3.6, 7.6 Hz, 1H), 4.77 (br s, 1H), 4.15-3.97 (m, 1H), 3.49-3.41 (m, 1H), 3.11 (ddd, J = 5.6, 12.5, 30.4 Hz, 1H), 3.00 (ddd, J = 5.0, 12.3, 24.0 Hz, 1H), 2.22 (dd, J = 14.1, 31.2 Hz, 1H), 2.21-2.13 (m, 1H), 2.16-2.04 (m, 1H), 2.11-2.04 (m, 1H), 2.05-1.97 (m, 1H), 1.98 (br s, 4H), 1.90-1.83 (m, 1H), 1.87-1.82 (m, 1H), 1.78-1.74 (m, 1H), 1.76-1.71 (m, 2H), 1.78-1.70 (m, 1H), 1.76-1.69 (m, 1H), 1.71-1.66 (m, 1H), 1.69-1.62 (m, 1H), 1.65-1.57 (m, 1H), 1.42 (s, 6H), 1.49-1.38 (m, 1H). LCMS (m/z) $(M + H)^+$: 566.3 |

TABLE 3-continued

| Ex. | Structure and Name | Characterization Data ($^1$H NMR, optical rotation, and/or LCMS) |
|---|---|---|
| C16 | 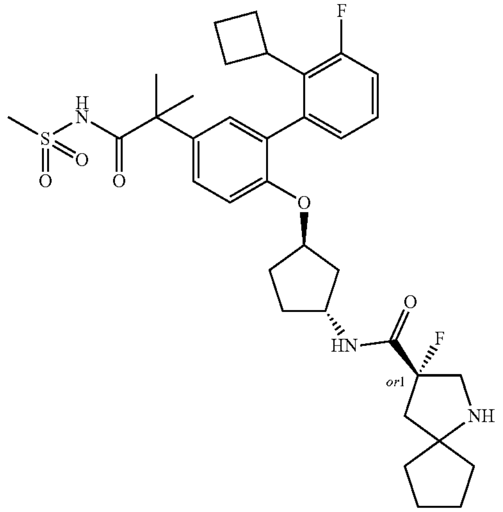 [SMILES: CC(C)(C(=O)NS(C)(=O)=O)c1ccc(O[C@@H]2CC[C@@H](NC(=O)[C@@]3(F)CNC4(CCCC4)C3)C2)c(-c2cccc(F)c2C2CCC2)c1] (3ξ)-N-{(1R,3R)-3-[(2'-cyclobutyl-3'-fluoro-5-{1-[(methanesulfonyl)amino]-2-methyl-1-oxopropan-2-yl}[1,1'-biphenyl]-2-yl)oxy]cyclopentyl}-3-fluoro-1-azaspiro[4.4]nonane-3-carboxamide | $^1$H NMR (400 MHz, DMSO-$d_6$) δ 8.36-8.29 (m, 1H), 7.27-7.23 (m, 1H), 7.23-7.18 (m, 1H), 7.09 (dd, J = 7.9, 11.4 Hz, 1H), 6.99 (t, J = 2.8 Hz, 1H), 6.96 (d, J = 8.6 Hz, 1H), 6.88 (ddd, J = 1.2, 3.1, 7.5 Hz, 1H), 4.82-4.77 (m, 1H), 4.16-4.02 (m, 1H), 3.53-3.37 (m, 4H), 2.97-2.85 (m, 3H), 2.41-2.27 (m, 1H), 2.24-1.97 (m, 5H), 1.94-1.76 (m, 6H), 1.75-1.58 (m, 8H), 1.53-1.44 (m, 2H), 1.41 (d, J = 9.2 Hz, 6H). $[\alpha]^{22}_D$ = −4.80° (c 0.1, MeOH). LCMS (m/z) $(M + H)^+$: 658.3 |
| C17 | 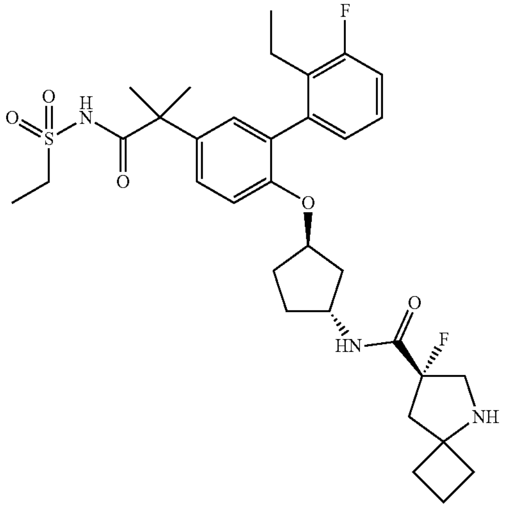 [SMILES: CCc1c(F)cccc1-c1cc(C(C)(C)C(=O)NS(=O)(=O)CC)ccc1O[C@@H]1CC[C@@H](NC(=O)[C@@]2(F)CNC3(CCC3)C2)C1] (7S)-N-[(1R,3R)-3-({5-[1-(ethanesulfonamido)-2-methyl-1-oxopropan-2-yl]-2'-ethyl-3'-fluoro[1,1'-biphenyl]-2-yl}oxy)cyclopentyl]-7-fluoro-5-azaspiro[3.4]octane-7-carboxamide | $^1$H NMR (600 MHz, DMSO-$d_6$) δ 8.01 (br d, J = 6.0 Hz, 1H), 7.28 (dd, J = 2.6, 8.6 Hz, 1H), 7.22 (dt, J = 5.9, 7.9 Hz, 1H), 7.09 (ddd, J = 0.9, 8.5, 10.0 Hz, 1H), 7.06-7.01 (m, 1H), 7.01 (s, 1H), 6.89 (dd, J = 0.8, 7.5 Hz, 1H), 4.89-4.74 (m, 1H), 4.14-4.00 (m, 1H), 3.92-3.72 (m, 1H), 3.46-3.30 (m, 2H), 3.30-3.22 (m, 4H), 2.53-2.50 (m, 1H), 2.43-2.34 (m, 1H), 2.34-2.28 (m, 1H), 2.28-2.22 (m, 1H), 2.15-2.10 (m, 2H), 2.08-1.99 (m, 1H), 1.89-1.79 (m, 1H), 1.82-1.76 (m, 1H), 1.83-1.66 (m, 1H), 1.53-1.45 (m, 8H), 1.10 (t, J = 7.4 Hz, 3H), 0.94 (t, J = 7.4 Hz, 3H). LCMS (m/z) $(M + H)^+$: 632.9 |

TABLE 3-continued

| Ex. | Structure and Name | Characterization Data ($^1$H NMR, optical rotation, and/or LCMS) |
|---|---|---|
| C18 | 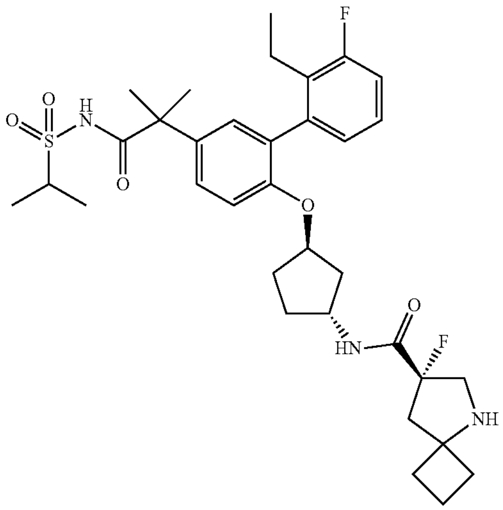 [SMILES: CCc1c(F)cccc1-c1cc(C(C)(C)C(=O)NS(=O)(=O)C(C)C)ccc1O[C@@H]1CC[C@@H](NC(=O)[C@@]2(F)CNC3(CCC3)C2)C1]<br>(7S)-N-[(1R,3R)-3-({2'-ethyl-3'-fluoro-5-[2-methyl-1-oxo-1-(propane-2-sulfonamido)propan-2-yl][1,1'-biphenyl]-2-yl}oxy)cyclopentyl]-7-fluoro-5-azaspiro[3.4]octane-7-carboxamide | $^1$H NMR (600 MHz, DMSO-$d_6$) δ 8.31 (br d, J = 5.8 Hz, 1H), 7.29 (dd, J = 2.5, 8.7 Hz, 1H), 7.27-7.18 (m, 1H), 7.13 (t, J = 9.0 Hz, 1H), 7.04 (d, J = 8.8 Hz, 1H), 7.00 (d, J = 2.4 Hz, 1H), 6.93-6.79 (m, 1H), 4.84 (br s, 1H), 3.67-3.54 (m, 2H), 3.45-3.37 (m, 2H), 2.41-2.33 (m, 2H), 2.34-2.29 (m, 1H), 2.27-2.21 (m, 2H), 2.15-2.09 (m, 2H), 1.93-1.65 (m, 5H), 1.51-1.46 (m, 5H), 1.48 (br d, J = 8.7 Hz, 2H), 1.15 (d, J = 6.9 Hz, 6H), 0.93 (t, J = 7.5 Hz, 3H).<br>LCMS (m/z) (M + H)$^+$: 646.9 |
| C19 | 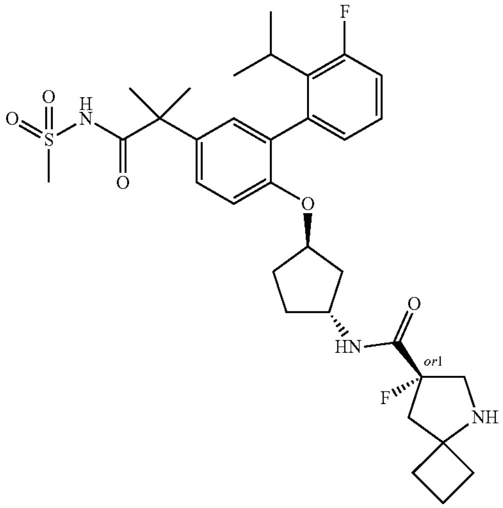 [SMILES: CC(C)c1c(F)cccc1-c1cc(C(C)(C)C(=O)NS(C)(=O)=O)ccc1O[C@@H]1CC[C@@H](NC(=O)[C@@]2(F)CNC3(CCC3)C2)C1]<br>(7ξ)-7-fluoro-N-[(1R,3R)-3-({3'-fluoro-5-[1-(methanesulfonamido)-2-methyl-1-oxopropan-2-yl]-2'-(propan-2-yl)[1,1'-biphenyl]-2-yl}oxy)cyclopentyl]-5-azaspiro[3.4]octane-7-carboxamide | $^1$H NMR (400 MHz, DMSO-$d_6$) δ 8.31-8.22 (m, 1H), 7.29-7.16 (m, 2H), 7.13-7.05 (m, 1H), 7.02-6.97 (m, 1H), 6.96-6.93 (m, 1H), 6.87-6.82 (m, 1H), 4.88-4.73 (m, 1H), 4.14-3.99 (m, 1H), 3.39 (br s, 1H), 3.26-3.18 (m, 2H), 3.02-2.90 (m, 3H), 2.77-2.64 (m, 1H), 2.36-2.32 (m, 1H), 2.29-2.25 (m, 1H), 2.23-1.97 (m, 5H), 1.92-1.85 (m, 1H), 1.84-1.64 (m, 4H), 1.55-1.38 (m, 8H), 1.30-1.21 (m, 3H), 1.13-1.06 (m, 3H).<br>$[\alpha]^{22}_D$ = −6.40° (c 0.1, MeOH).<br>LCMS (m/z) (M + H)$^+$: 632.3 |

TABLE 3-continued

| Ex. | Structure and Name | Characterization Data ($^1$H NMR, optical rotation, and/or LCMS) |
|---|---|---|
| C20 | 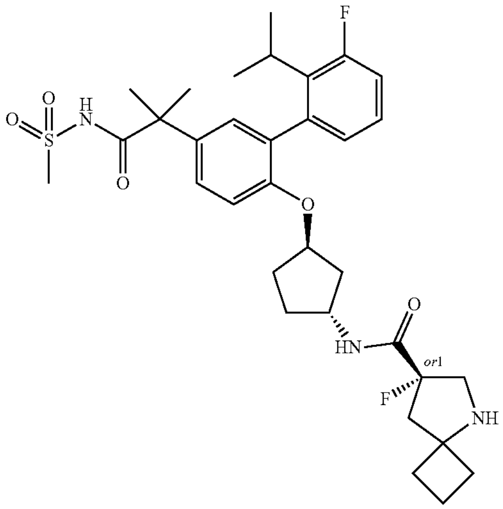 [SMILES: CC(C)c1c(F)cccc1-c1cc(C(C)(C)C(=O)NS(C)(=O)=O)ccc1O[C@@H]1CC[C@@H](NC(=O)[C@@]2(F)CNC3(CCC3)C2)C1] (7ξ)-7-fluoro-N-[(1R,3R)-3-({3'-fluoro-5-[1-(methanesulfonamido)-2-methyl-1-oxopropan-2-yl]-2'-(propan-2-yl)[1,1'-biphenyl]-2-yl}oxy)cyclopentyl]-5-azaspiro[3.4]octane-7-carboxamide | $^1$H NMR (400 MHz, DMSO-$d_6$) δ 8.31-8.22 (m, 1H), 7.29-7.16 (m, 2H), 7.13-7.04 (m, 1H), 7.01-6.92 (m, 2H), 6.84 (br d, J = 7.7 Hz, 1H), 4.86-4.76 (m, 1H), 4.14-4.00 (m, 1H), 3.38 (br d, J = 2.6 Hz, 1H), 3.25 (br s, 2H), 2.95 (s, 3H), 2.76-2.61 (m, 1H), 2.39-2.31 (m, 1H), 2.30-2.25 (m, 1H), 2.23-1.94 (m, 5H), 1.92-1.83 (m, 1H), 1.83-1.65 (m, 4H), 1.56-1.36 (m, 8H), 1.30-1.19 (m, 3H), 1.10 (d, J = 7.1 Hz, 3H). $[\alpha]^{22}_D$ = −10.4° (c 0.1, MeOH). LCMS (m/z) $(M + H)^+$: 632.3 |
| C21 | 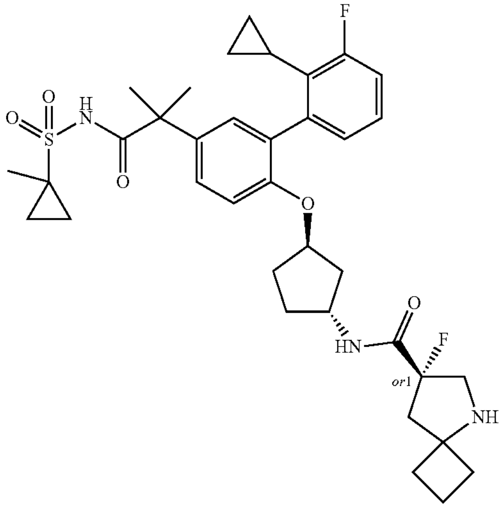 [SMILES: CC(C)(C(=O)NS(=O)(=O)C1(C)CC1)c1ccc(O[C@@H]2CC[C@@H](NC(=O)[C@@]3(F)CNC4(CCC4)C3)C2)c(-c2cccc(F)c2C2CC2)c1] (7ξ)-N-[(1R,3R)-3-({2'-cyclopropyl-3'-fluoro-5-[2-methyl-1-(1-methylcyclopropane-1-sulfonamido)-1-oxopropan-2-yl][1,1'-biphenyl]-2-yl}oxy)cyclopentyl]-7-fluoro-5-azaspiro[3.4]octane-7-carboxamide | $^1$H NMR (600 MHz, DMSO-$d_6$) δ 7.86 (br d, J = 5.4 Hz, 1H), 7.29 (dd, J = 2.5, 8.5 Hz, 1H), 7.25-7.17 (m, 1H), 7.09 (d, J = 2.4 Hz, 1H), 7.07-6.98 (m, 2H), 6.94 (dd, J = 0.9, 7.6 Hz, 1H), 4.82 (tt, J = 3.0, 5.9 Hz, 1H), 4.09 (sxt, J = 7.4 Hz, 1H), 3.31 (br s, 1H), 2.30-2.12 (m, 2H), 2.11-2.00 (m, 5H), 1.93-1.80 (m, 3H), 1.79-1.71 (m, 1H), 1.69-1.61 (m, 2H), 1.58-1.45 (m, 8H), 1.39-1.33 (m, 2H), 1.31-1.28 (m, 3H), 0.77 (br s, 2H), 0.65-0.56 (m, 2H), 0.51-0.44 (m, 2H). $[\alpha]^{22}_D$ = −9.4° (c 0.1, MeOH). LCMS (m/z) $(M + H)^+$: 670.9 |

TABLE 3-continued

| Ex. | Structure and Name | Characterization Data ($^1$H NMR, optical rotation, and/or LCMS) |
|---|---|---|
| C22 | 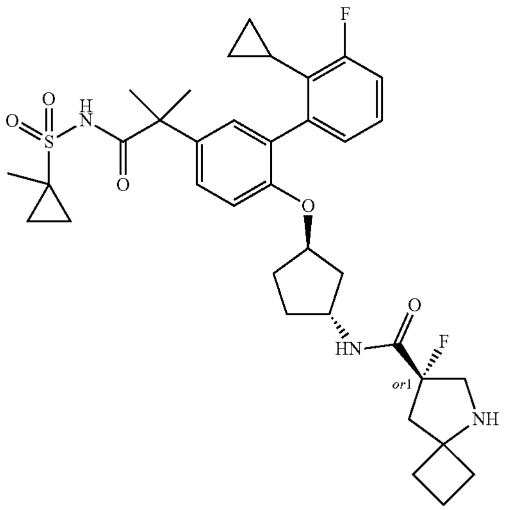 [SMILES: CC(C)(C(=O)NS(=O)(=O)C1(C)CC1)c1ccc(O[C@@H]2CC[C@@H](NC(=O)[C@@]3(F)CNC4(CCC4)C3)C2)c(-c2cccc(F)c2C2CC2)c1] (7ξ)-N-[(1R,3R)-3-({2'-cyclopropyl-3'-fluoro-5-[2-methyl-1-(1-methylcyclopropane-1-sulfonamido)-1-oxopropan-2-yl][1,1'-biphenyl]-2-yl}oxy)cyclopentyl]-7-fluoro-5-azaspiro[3.4]octane-7-carboxamide | $^1$H NMR (600 MHz, DMSO-$d_6$) δ 8.16 (br d, J = 6.1 Hz, 1H), 7.30-7.25 (m, 1H), 7.24-7.20 (m, 1H), 7.10-7.03 (m, 2H), 7.00 (d, J = 8.7 Hz, 1H), 6.96-6.91 (m, 1H), 4.86-4.79 (m, 1H), 4.14-4.08 (m, 1H), 2.29-2.13 (m, 2H), 2.05 (br d, J = 7.9 Hz, 4H), 1.93-1.52 (m, 7H), 1.47 (br s, 7H), 1.31 (br s, 2H), 1.24 (s, 3H), 0.75 (br s, 2H), 0.58-0.35 (m, 3H). $[\alpha]^{22}_D$ = −17.4° (c 0.2, MeOH). LCMS (m/z) $(M + H)^+$: 670.9 |
| C23 | 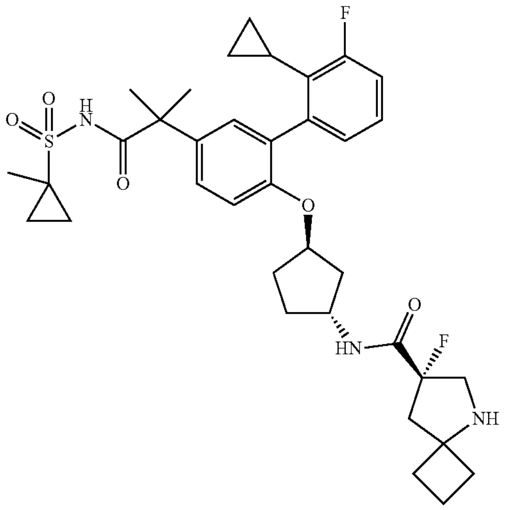 (7S)-N-[(1R,3R)-3-({2'-ethyl-3'-fluoro-5-[2-methyl-1-(1-methylcyclopropane-1-sulfonamido)-1-oxopropan-2-yl][1,1'-biphenyl]-2-yl}oxy)cyclopentyl]-7-fluoro-5-azaspiro[3.4]octane-7-carboxamide | $^1$H NMR (600 MHz, DMSO-$d_6$) δ 8.00 (br d, J = 5.8 Hz, 1H), 7.31 (dd, J = 2.5, 8.7 Hz, 1H), 7.22 (dt, J = 5.8, 7.9 Hz, 1H), 7.13-7.07 (m, 1H), 7.04 (d, J = 8.7 Hz, 1H), 7.02 (d, J = 2.5 Hz, 1H), 6.93-6.87 (m, 1H), 4.91-4.86 (m, 1H), 4.07 (s, 1H), 3.45-3.34 (m, 2H), 3.30-3.24 (m, 2H), 2.40-2.32 (m, 2H), 2.31 (s, 1H), 2.26-2.20 (m, 1H), 2.15-2.09 (m, 2H), 1.90-1.80 (m, 2H), 1.82-1.77 (m, 1H), 1.83-1.77 (m, 1H), 1.77-1.67 (m, 1H), 1.54-1.45 (m, 8H), 1.42-1.33 (m, 2H), 1.31 (s, 3H), 1.29-1.24 (m, 1H), 0.95 (t, J = 7.4 Hz, 3H), 0.82 (d, J = 1.8 Hz, 2H). LCMS (m/z) $(M + H)^+$: 658.9 |

TABLE 3-continued

| Ex. | Structure and Name | Characterization Data ($^1$H NMR, optical rotation, and/or LCMS) |
|---|---|---|
| C24 | 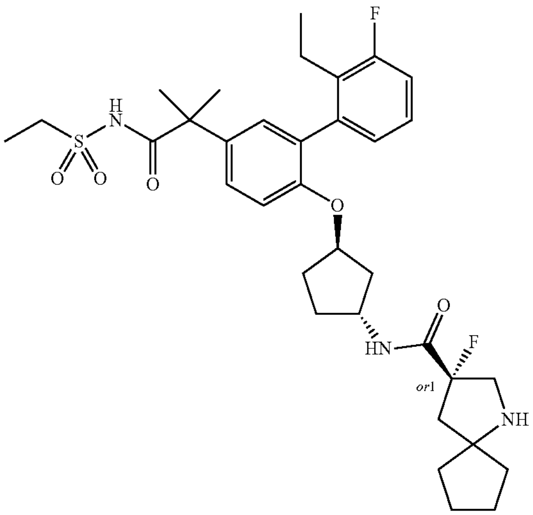 [SMILES: CCc1c(F)cccc1-c1cc(C(C)(C)C(=O)NS(=O)(=O)CC)ccc1O[C@@H]1CC[C@@H](NC(=O)[C@@]2(F)CNC3(CCCC3)C2)C1] (3ξ)-N-[(1R,3R)-3-({5-[1-(ethanesulfonamido)-2-methyl-1-oxopropan-2-yl]-2'-ethyl-3'-fluoro[1,1'-biphenyl]-2-yl}oxy)cyclopentyl]-3-fluoro-1-azaspiro[4.4]nonane-3-carboxamide | $^1$H NMR (600 MHz, DMSO-$d_6$) δ 8.32-8.16 (m, 1H), 7.29 (dd, J = 2.5, 8.6 Hz, 1H), 7.26-7.19 (m, 1H), 7.12 (t, J = 9.2 Hz, 1H), 7.03 (d, J = 2.3 Hz, 1H), 7.00 (br d, J = 8.7 Hz, 1H), 6.92-6.84 (m, 1H), 4.86-4.79 (m, 1H), 4.14-4.03 (m, 3H), 3.16-3.06 (m, 2H), 2.64-2.61 (m, 1H), 2.39 (td, J = 1.8, 3.6 Hz, 1H), 2.37-2.26 (m, 2H), 2.19-1.98 (m, 2H), 1.90-1.84 (m, 1H), 1.83-1.73 (m, 4H), 1.71-1.56 (m, 6H), 1.48-1.37 (m, 7H), 1.02 (br t, J = 7.2 Hz, 3H), 0.93 (t, J = 7.4 Hz, 3H). $[\alpha]^{22}_D$ = −113.7° (c 0.1, MeOH). LCMS (m/z) $(M + H)^+$: 646.9 |
| C25 | 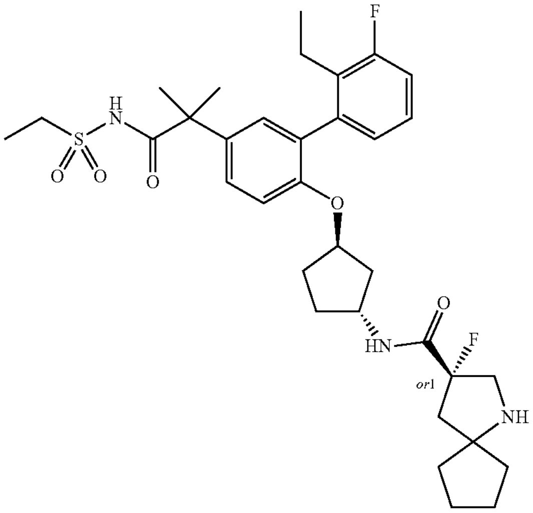 [SMILES: CCc1c(F)cccc1-c1cc(C(C)(C)C(=O)NS(=O)(=O)CC)ccc1O[C@@H]1CC[C@@H](NC(=O)[C@@]2(F)CNC3(CCCC3)C2)C1] (3ξ)-N-[(1R,3R)-3-({5-[1-(ethanesulfonamido)-2-methyl-1-oxopropan-2-yl]-2'-ethyl-3'-fluoro[1,1'-biphenyl]-2-yl}oxy)cyclopentyl]-3-fluoro-1-azaspiro[4.4]nonane-3-carboxamide | $^1$H NMR (600 MHz, DMSO-$d_6$) δ 8.13 (br d, J = 6.4 Hz, 1H), 7.18 (dd, J = 2.5, 8.6 Hz, 1H), 7.14-7.06 (m, 1H), 7.03-6.97 (m, 1H), 6.97-6.93 (m, 3H), 6.91 (d, J = 2.4 Hz, 3H), 6.88 (d, J = 8.6 Hz, 1H), 6.77 (br d, J = 7.4 Hz, 1H), 4.71 (br s, 1H), 3.97 (q, J = 7.3 Hz, 3H), 3.31-3.28 (m, 1H), 3.00 (br s, 1H), 2.28-2.13 (m, 2H), 2.07-1.88 (m, 1H), 1.77-1.60 (m, 5H), 1.58-1.45 (m, 6H), 1.36-1.29 (m, 7H), 0.96-0.87 (m, 1H), 0.84-0.79 (m, 3H). $[\alpha]^{22}_D$ = −77.2° (c 0.1, MeOH). LCMS (m/z) $(M + H)^+$: 646.9 |

TABLE 3-continued

| Ex. | Structure and Name | Characterization Data ($^1$H NMR, optical rotation, and/or LCMS) |
|---|---|---|
| C26 | 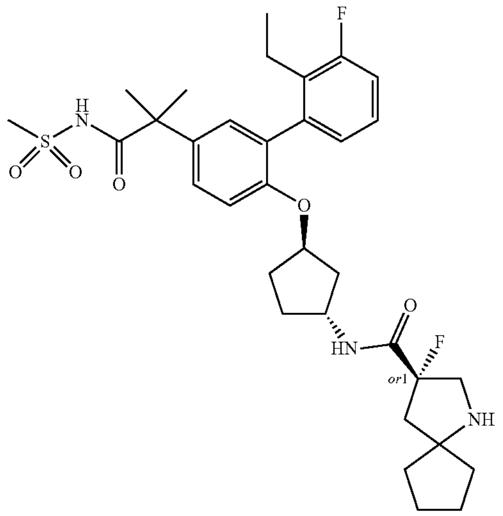 [SMILES: CCc1c(F)cccc1-c1cc(C(C)(C)C(=O)NS(C)(=O)=O)ccc1O[C@@H]1CC[C@@H](NC(=O)[C@@]2(F)CNC3(CCCC3)C2)C1] (3ξ)-N-[(1R,3R)-3-({2'-ethyl-3'-fluoro-5-[1-(methanesulfonamido)-2-methyl-1-oxopropan-2-yl][1,1'-biphenyl]-2-yl}oxy)cyclopentyl]-3-fluoro-1-azaspiro[4.4]nonane-3-carboxamide | $^1$H NMR (600 MHz, DMSO-$d_6$) δ 8.28 (br d, J = 6.8 Hz, 1H), 7.27 (dd, J = 2.5, 8.6 Hz, 1H), 7.24-7.17 (m, 1H), 7.10 (t, J = 9.2 Hz, 1H), 7.01 (d, J = 2.4 Hz, 1H), 7.03-6.99 (m, 1H), 6.97 (d, J = 8.7 Hz, 1H), 6.89 (d, J = 7.4 Hz, 1H), 4.81 (br s, 1H), 4.11-4.06 (m, 2H), 3.48-3.43 (m, 1H), 2.90 (br s, 3H), 2.40-2.28 (m, 2H), 2.21-2.12 (m, 1H), 2.11-1.99 (m, 1H), 1.87-1.74 (m, 5H), 1.72-1.56 (m, 6H), 1.52-1.42 (m, 2H), 1.41 (br s, 3H), 1.40 (br s, 3H), 0.91 (t, J = 7.4 Hz, 3H). $[\alpha]^{22}_D$ = −85.1° (c 0.1, MeOH). LCMS (m/z) $(M + H)^+$: 631.9 |
| C27 | 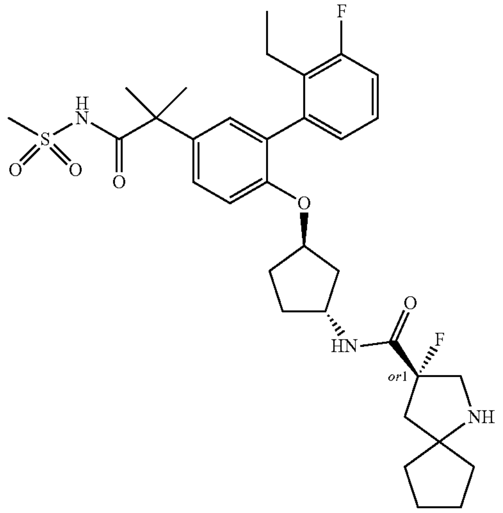 [SMILES: CCc1c(F)cccc1-c1cc(C(C)(C)C(=O)NS(C)(=O)=O)ccc1O[C@@H]1CC[C@@H](NC(=O)[C@@]2(F)CNC3(CCCC3)C2)C1] (3ξ)-N-[(1R,3R)-3-({2'-ethyl-3'-fluoro-5-[1-(methanesulfonamido)-2-methyl-1-oxopropan-2-yl][1,1'-biphenyl]-2-yl}oxy)cyclopentyl]-3-fluoro-1-azaspiro[4.4]nonane-3-carboxamide | $^1$H NMR (600 MHz, DMSO-$d_6$) δ 7.94 (br d, J = 5.6 Hz, 1H), 7.28 (dd, J = 2.5, 8.6 Hz, 1H), 7.22 (dt, J = 5.9, 7.9 Hz, 1H), 7.09 (t, J = 8.9 Hz, 1H), 7.03 (d, J = 2.5 Hz, 1H), 7.00 (d, J = 8.7 Hz, 1H), 6.90 (d, J = 7.4 Hz, 1H), 4.85-4.77 (m, 1H), 4.13-4.02 (m, 1H), 3.84 (br d, J = 4.7 Hz, 2H), 3.42-3.29 (m, 1H), 3.01 (s, 3H), 2.35-2.23 (m, 1H), 2.13-2.01 (m, 2H), 1.93-1.55 (m, 12H), 1.54-1.45 (m, 6H), 1.46-1.41 (m, 2H), 0.94 (t, J = 7.4 Hz, 3H). $[\alpha]^{22}_D$ = −121.0° (c 0.1, MeOH). LCMS (m/z) $(M + H)^+$: 631.9 |

TABLE 3-continued

| Ex. | Structure and Name | Characterization Data ($^1$H NMR, optical rotation, and/or LCMS) |
| --- | --- | --- |
| C28 | 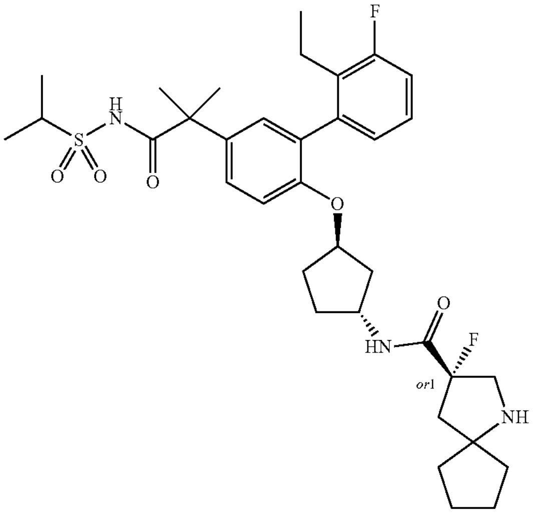 [SMILES: CCc1c(F)cccc1-c1cc(C(C)(C)C(=O)NS(=O)(=O)C(C)C)ccc1O[C@@H]1CC[C@@H](NC(=O)[C@@]2(F)CNC3(CCCC3)C2)C1] (3ξ)-N-[(1R,3R)-3-({2'-ethyl-3'-fluoro-5-[2-methyl-1-oxo-1-(propane-2-sulfonamido) propan-2-yl][1,1'-biphenyl]-2-yl}oxy)cyclopentyl]-3-fluoro-1-azaspiro[4.4]nonane-3-carboxamide | $^1$H NMR (600 MHz, DMSO-$d_6$) δ 7.90 (br d, J = 5.3 Hz, 1H), 7.31 (dd, J = 2.5, 8.7 Hz, 1H), 7.22 (dt, J = 5.9, 7.9 Hz, 1H), 7.12-7.06 (m, 1H), 7.03 (d, J = 2.5 Hz, 1H), 7.01 (d, J = 8.7 Hz, 1H), 6.89 (d, J = 7.4 Hz, 1H), 4.07 (sxt, J = 7.3 Hz, 1H), 3.84 (br d, J = 4.9 Hz, 2H), 3.58 (spt, J = 6.8 Hz, 1H), 3.33-3.24 (m, 1H), 3.15 (br d, J = 13.6 Hz, 3H), 2.32-2.20 (m, 1H), 2.11-1.97 (m, 2H), 1.91-1.76 (m, 3H), 1.75-1.55 (m, 8H), 1.51-1.45 (m, 7H), 1.16 (s, 3H), 1.15 (s, 3H), 0.95 (t, J = 7.4 Hz, 3H). $[\alpha]^{22}_D$ = −76.1° (c 0.1, MeOH). LCMS (m/z) $(M + H)^+$: 660.9 |
| C29 | 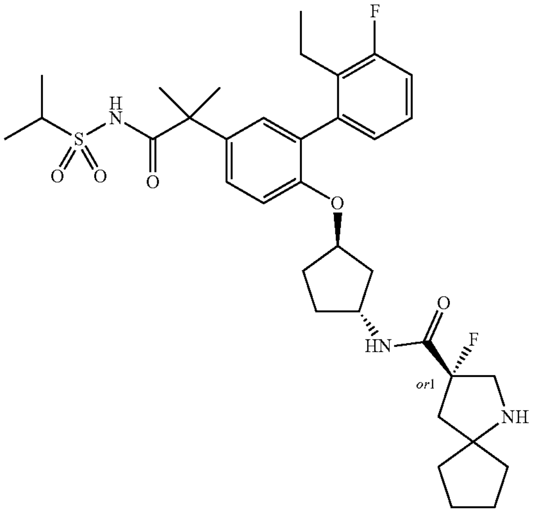 [SMILES: CCc1c(F)cccc1-c1cc(C(C)(C)C(=O)NS(=O)(=O)C(C)C)ccc1O[C@@H]1CC[C@@H](NC(=O)[C@@]2(F)CNC3(CCCC3)C2)C1] (3ξ)-N-[(1R,3R)-3-({2'-ethyl-3'-fluoro-5-[2-methyl-1-oxo-1-(propane-2-sulfonamido)propan-2-yl][1,1'-biphenyl]-2-yl}oxy)cyclopentyl]-3-fluoro-1-azaspiro[4.4]nonane-3-carboxamide | $^1$H NMR (600 MHz, DMSO-$d_6$) δ 7.90 (br d, J = 5.8 Hz, 1H), 7.32 (dd, J = 2.5, 8.6 Hz, 1H), 7.23 (dt, J = 5.9, 7.8 Hz, 1H), 7.10 (t, J = 9.2 Hz, 1H), 7.06-6.96 (m, 2H), 6.90 (d, J = 7.4 Hz, 1H), 4.88-4.77 (m, 1H), 4.08 (sxt, J = 7.3 Hz, 1H), 3.67-3.53 (m, 1H), 3.35-3.23 (m, 2H), 2.49-2.35 (m, 2H), 2.33-2.19 (m, 1H), 2.10-1.99 (m, 2H), 1.93-1.76 (m, 3H), 1.75-1.56 (m, 8H), 1.55-1.40 (m, 8H), 1.17 (s, 3H), 1.15 (s, 3H), 0.96 (t, J = 7.4 Hz, 3H). $[\alpha]^{22}_D$ = −82.1° (c 0.1, MeOH). LCMS (m/z) $(M + H)^+$: 660.9 |

TABLE 3-continued

| Ex. | Structure and Name | Characterization Data ($^1$H NMR, optical rotation, and/or LCMS) |
| --- | --- | --- |
| C30 | 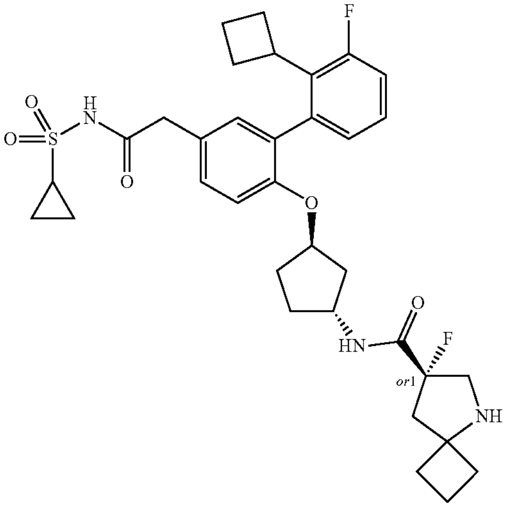 [SMILES: O=C(Cc1ccc(O[C@@H]2CC[C@@H](NC(=O)[C@@]3(F)CNC4(CCC4)C3)C2)c(-c2cccc(F)c2C2CCC2)c1)NS(=O)(=O)C1CC1]<br>(7ξ)-N-[(1R,3R)-3-({2'-cyclobutyl-5-[2-(cyclopropanesulfonamido)-2-oxoethyl]-3'-fluoro[1,1'-biphenyl]-2-yl}oxy)cyclopentyl]-7-fluoro-5-azaspiro[3.4]octane-7-carboxamide | $^1$H NMR (600 MHz, DMSO-$d_6$) δ 8.15 (ddd, J = 2.4, 7.9, 12.8 Hz, 1H), 7.24-7.19 (m, 2H), 7.14-7.06 (m, 1H), 7.01-6.96 (m, 2H), 6.87 (ddd, J = 1.1, 4.0, 7.6 Hz, 1H), 4.81-4.76 (m, 1H), 4.08 (br d, J = 7.1 Hz, 2H), 3.49 (s, 2H), 3.46-3.43 (m, 1H), 3.17-3.12 (m, 3H), 2.88 (s, 1H), 2.21 (br d, J = 1.2 Hz, 3H), 2.12-1.94 (m, 7H), 1.92-1.83 (m, 2H), 1.82-1.60 (m, 6H), 1.58-1.37 (m, 2H), 1.02-0.91 (m, 4H). $[\alpha]^{22}_D$ = −84.1° (c 0.1, MeOH). LCMS (m/z) (M + H)$^+$: 642.9 |
| C31 | 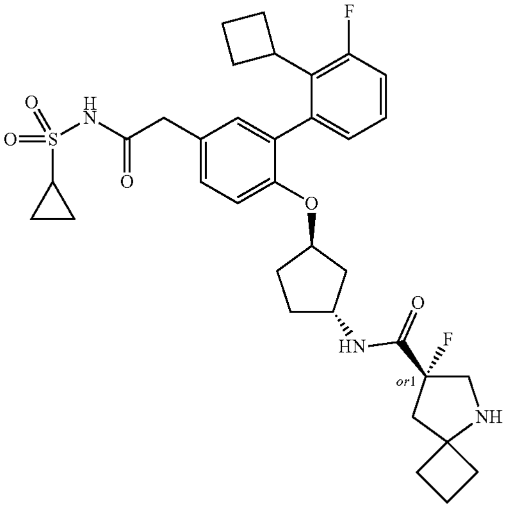 [SMILES: O=C(Cc1ccc(O[C@@H]2CC[C@@H](NC(=O)[C@@]3(F)CNC4(CCC4)C3)C2)c(-c2cccc(F)c2C2CCC2)c1)NS(=O)(=O)C1CC1]<br>(7ξ)-N-[(1R,3R)-3-({2'-cyclobutyl-5-[2-(cyclopropanesulfonamido)-2-oxoethyl]-3'-fluoro[1,1'-biphenyl]-2-yl}oxy)cyclopentyl]-7-fluoro-5-azaspiro[3.4]octane-7-carboxamide | $^1$H NMR (600 MHz, DMSO-$d_6$) δ 8.15 (ddd, J = 2.2, 7.8, 13.2 Hz, 1H), 7.25-7.18 (m, 2H), 7.10 (dd, J = 8.2, 11.7 Hz, 1H), 7.02-6.95 (m, 2H), 6.89-6.83 (m, 1H), 4.83-4.76 (m, 1H), 4.08 (br d, J = 6.7 Hz, 2H), 3.49 (s, 2H), 3.45 (br d, J = 8.4 Hz, 1H), 3.17-3.12 (m, 3H), 2.91-2.86 (m, 1H), 2.25 (br d, J = 12.9 Hz, 9H), 1.92-1.83 (m, 2H), 1.81-1.60 (m, 6H), 1.53-1.25 (m, 3H), 1.02-0.92 (m, 4H). $[\alpha]^{22}_D$ = −83.7° (c 0.1, MeOH). LCMS (m/z) (M + H)$^+$: 642.9 |

TABLE 3-continued

| Ex. | Structure and Name | Characterization Data ($^1$H NMR, optical rotation, and/or LCMS) |
| --- | --- | --- |
| C32 | 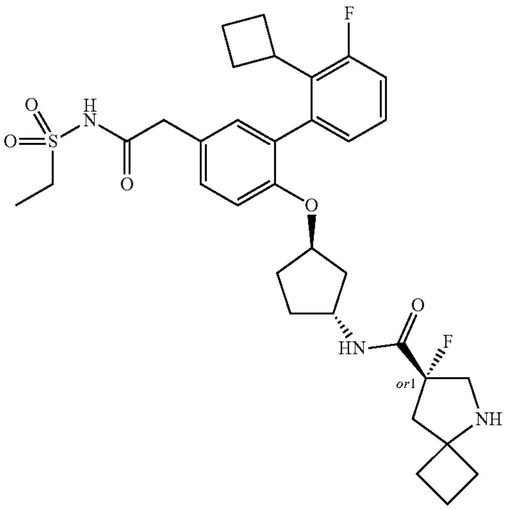 [SMILES: CCS(=O)(=O)NC(=O)Cc1ccc(O[C@@H]2CC[C@@H](NC(=O)[C@@]3(F)CNC4(CCC4)C3)C2)c(-c2cccc(F)c2C2CCC2)c1] (7ξ)-N-[(1R,3R)-3-({2'-cyclobutyl-5-[2-(ethanesulfonamido)-2-oxoethyl]-3'-fluoro[1,1'-biphenyl]-2-yl}oxy)cyclopentyl]-7-fluoro-5-azaspiro[3.4]octane-7-carboxamide | $^1$H NMR (600 MHz, DMSO-$d_6$) δ 8.18-8.11 (m, 1H), 7.25-7.18 (m, 2H), 7.13-7.06 (m, 1H), 7.01-6.96 (m, 2H), 6.88-6.84 (m, 1H), 4.81-4.76 (m, 1H), 4.12-4.01 (m, 2H), 3.48 (s, 2H), 3.44 (br s, 1H), 3.23 (br d, J = 7.4 Hz, 2H), 3.18-3.17 (m, 2H), 2.32-1.92 (m, 10H), 1.91-1.60 (m, 8H), 1.57-1.37 (m, 2H), 1.11 (t, J = 7.4 Hz, 3H). $[\alpha]^{22}_D$ = −102.7° (c 0.1, MeOH). LCMS (m/z) $(M + H)^+$: 630.9 |
| C33 | 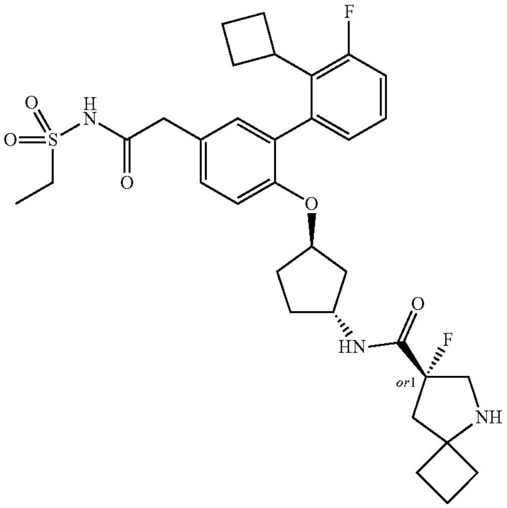 [SMILES: CCS(=O)(=O)NC(=O)Cc1ccc(O[C@@H]2CC[C@@H](NC(=O)[C@@]3(F)CNC4(CCC4)C3)C2)c(-c2cccc(F)c2C2CCC2)c1] (7ξ)-N-[(1R,3R)-3-({2'-cyclobutyl-5-[2-(ethanesulfonamido)-2-oxoethyl]-3'-fluoro[1,1'-biphenyl]-2-yl}oxy)cyclopentyl]-7-fluoro-5-azaspiro[3.4]octane-7-carboxamide | $^1$H NMR (600 MHz, DMSO-$d_6$) δ 8.20-8.09 (m, 1H), 7.27-7.19 (m, 2H), 7.13-7.06 (m, 1H), 7.02-6.95 (m, 2H), 6.90-6.82 (m, 1H), 4.82-4.76 (m, 1H), 4.11-4.01 (m, 1H), 3.48 (br s, 4H), 3.24-3.19 (m, 3H), 3.17 (d, J = 5.3 Hz, 2H), 2.30-1.93 (m, 10H), 1.90-1.61 (m, 8H), 1.56-1.37 (m, 2H), 1.14-1.08 (m, 3H). $[\alpha]^{22}_D$ = −110.1° (c 0.1, MeOH). LCMS (m/z) $(M + H)^+$: 630.9 |

TABLE 3-continued

| Ex. | Structure and Name | Characterization Data ($^1$H NMR, optical rotation, and/or LCMS) |
|---|---|---|
| C34 | 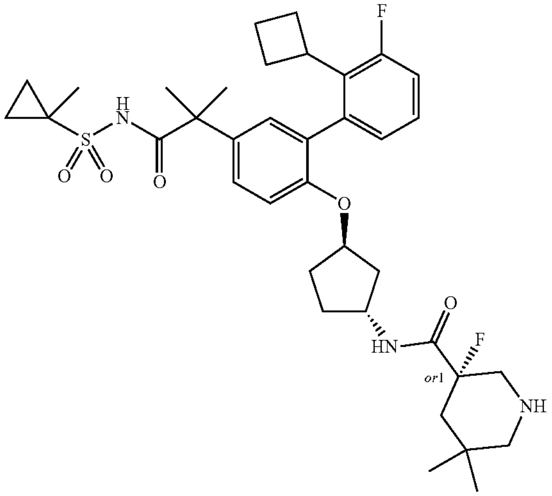 [SMILES: CC1(C)CNC[C@](F)(C(=O)N[C@@H]2CC[C@@H](Oc3ccc(C(C)(C)C(=O)NS(=O)(=O)C4(C)CC4)cc3-c3cccc(F)c3C3CCC3)C2)C1] (3ξ)-N-[(1R,3R)-3-({2'-cyclobutyl-3'-fluoro-5-[2-methyl-1-(1-methylcyclopropane-1-sulfonamido)-1-oxopropan-2-yl][1,1'-biphenyl]-2-yl}oxy)cyclopentyl]-3-fluoro-5,5-dimethylpiperidine-3-carboxamide | $^1$H NMR (400 MHz, MeOD) δ 8.35-8.19 (m, 1H), 7.34 (dd, J = 2.4, 8.6 Hz, 1H), 7.17 (dt, J = 5.5, 7.7 Hz, 1H), 7.07-6.96 (m, 3H), 6.87 (t, J = 7.4 Hz, 1H), 4.25-3.99 (m, 1H), 3.60-3.36 (m, 3H), 3.15 (br. d, J = 12.8 Hz, 1H), 2.96 (dd, J = 1.5, 13.2 Hz, 1H), 2.40-1.59 (m, 14H), 1.45 (s, 9H), 1.36 (s, 3H), 1.22 (s, 3H), 1.07 (d, J = 2.2 Hz, 3H), 0.90-0.79 (m, 2H). LCMS (m/z) $(M + H)^+$: 686.4 $[\alpha]^{25}_D$ = −39.6° (c 0.17, MeOH) |
| C35 | 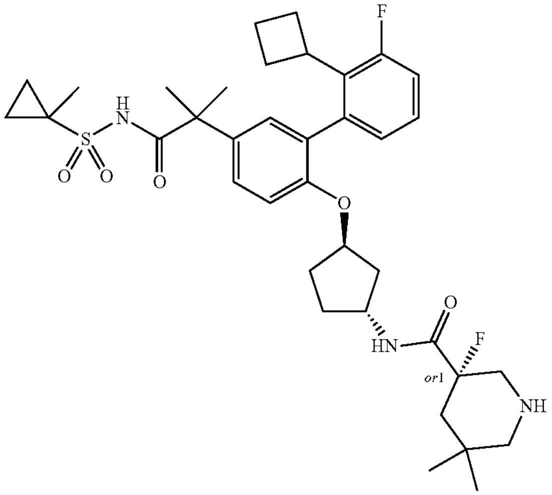 [SMILES: CC1(C)CNC[C@](F)(C(=O)N[C@@H]2CC[C@@H](Oc3ccc(C(C)(C)C(=O)NS(=O)(=O)C4(C)CC4)cc3-c3cccc(F)c3C3CCC3)C2)C1] (3ξ)-N-[(1R,3R)-3-({2'-cyclobutyl-3'-fluoro-5-[2-methyl-1-(1-methylcyclopropane-1-sulfonamido)-1-oxopropan-2-yl][1,1'-biphenyl]-2-yl}oxy)cyclopentyl]-3-fluoro-5,5-dimethylpiperidine-3-carboxamide | $^1$H NMR (400 MHz, MeOD) δ 8.31 (br. t, J = 5.7 Hz, 1H), 7.34 (dd, J = 2.4, 8.6 Hz, 1H), 7.22-7.13 (m, 1H), 7.07-6.97 (m, 3H), 6.91-6.81 (m, 1H), 4.24-4.04 (m, 1H), 3.61-3.37 (m, 3H), 3.15 (br. d, J = 12.5 Hz, 1H), 2.96 (d, J = 12.8 Hz, 1H), 2.38-1.60 (m, 14H), 1.59-1.44 (m, 9H), 1.39 (br. d, J = 4.8 Hz, 3H), 1.23 (s, 3H), 1.07 (s, 3H), 0.91-0.79 (m, 2H). LCMS (m/z) $(M + H)^+$: 686.4 |

TABLE 3-continued

| Ex. | Structure and Name | Characterization Data ($^1$H NMR, optical rotation, and/or LCMS) |
|---|---|---|
| C36 | 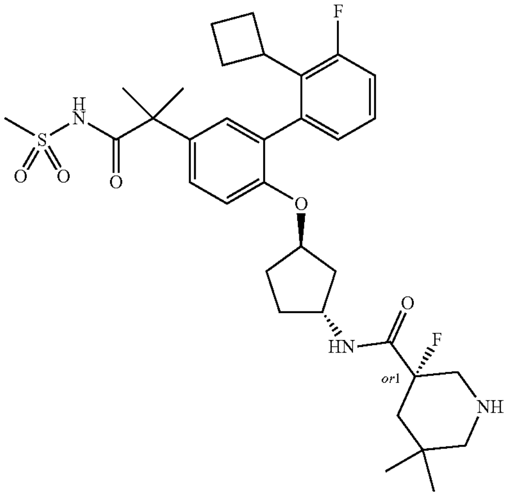 [SMILES: CC1(C)CNC[C@](F)(C(=O)N[C@@H]2CC[C@@H](Oc3ccc(C(C)(C)C(=O)NS(C)(=O)=O)cc3-c3cccc(F)c3C3CCC3)C2)C1]<br>(3ξ)-N-[(1R,3R)-3-({2'-cyclobutyl-3'-fluoro-5-[1-(methanesulfonamido)-2-methyl-1-oxopropan-2-yl][1,1'-biphenyl]-2-yl}oxy)cyclopentyl]-3-fluoro-5,5-dimethylpiperidine-3-carboxamide | $^1$H NMR (400 MHz, MeOD) δ 8.37-8.21 (m, 1H), 7.33 (dd, J = 2.5, 8.7 Hz, 1H), 7.19 (dt, J = 5.5, 7.8 Hz, 1H), 7.07-6.98 (m, 3H), 6.89 (t, J = 7.3 Hz, 1H), 4.25-4.04 (m, 1H), 3.59-3.41 (m, 3H), 3.23 (s, 3H), 3.17 (br. d, J = 12.8 Hz, 1H), 2.98 (dd, J = 1.8, 12.8 Hz, 1H), 2.39-1.64 (m, 14H), 1.58 (s, 3H), 1.55 (s, 3H), 1.52-1.45 (m, 1H), 1.25 (s, 3H), 1.09 (d, J = 2.6 Hz, 3H). LCMS (m/z) (M + H)$^+$: 646.4 |
| C37 | 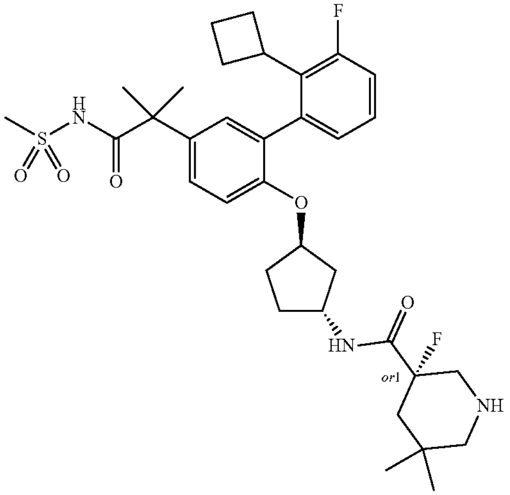 [SMILES: CC1(C)CNC[C@](F)(C(=O)N[C@@H]2CC[C@@H](Oc3ccc(C(C)(C)C(=O)NS(C)(=O)=O)cc3-c3cccc(F)c3C3CCC3)C2)C1]<br>(3ξ)-N-[(1R,3R)-3-({2'-cyclobutyl-3'-fluoro-5-[1-(methanesulfonamido)-2-methyl-1-oxopropan-2-yl][1,1'-biphenyl]-2-yl}oxy)cyclopentyl]-3-fluoro-5,5-dimethylpiperidine-3-carboxamide | $^1$H NMR (400 MHz, MeOD) δ 8.40-8.21 (m, 1H), 7.31 (dd, J = 2.4, 8.6 Hz, 1H), 7.21-7.10 (m, 1H), 7.06-6.95 (m, 3H), 6.87 (dd, J = 4.6, 6.6 Hz, 1H), 4.24-3.99 (m, 1H), 3.62-3.41 (m, 3H), 3.21 (s, 3H), 3.15 (br. d, J = 13.0 Hz, 1H), 2.96 (d, J = 13.2 Hz, 1H), 2.39-1.63 (m, 14H), 1.56 (s, 3H), 1.53 (s, 3H), 1.50-1.41 (m, 1H), 1.23 (s, 3H), 1.07 (s, 3H). LCMS (m/z) (M + H)$^+$: 646.4 |

TABLE 3-continued

| Ex. | Structure and Name | Characterization Data ($^1H$ NMR, optical rotation, and/or LCMS) |
|---|---|---|
| C38 | 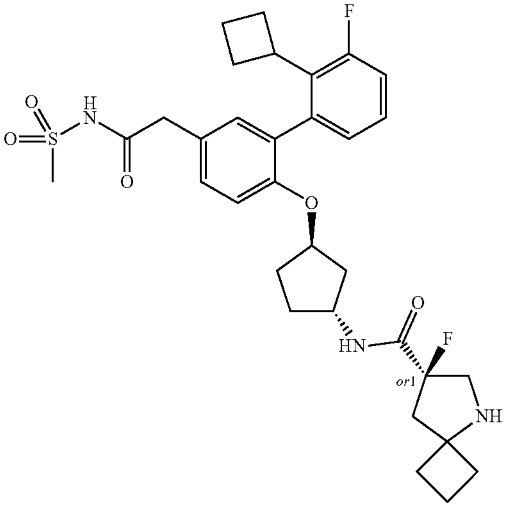 [SMILES: CS(=O)(=O)NC(=O)Cc1ccc(O[C@@H]2CC[C@@H](NC(=O)[C@]3(F)CNC4(CCC4)C3)C2)c(-c2cccc(F)c2C2CCC2)c1] (7ξ)-N-[(1R,3R)-3-({2'-cyclobutyl-3'-fluoro-5-[2-(methanesulfonamido)-2-oxoethyl][1,1'-biphenyl]-2-yl}oxy)cyclopentyl]-7-fluoro-5-azaspiro[3.4]octane-7-carboxamide | First eluting peak $^1H$ NMR (600 MHz, DMSO-$d_6$) δ 8.17 (br. dd, J = 8.4, 9.4 Hz, 1H), 7.23-7.20 (m, 1H), 7.20 (s, 1H), 7.09 (dd, J = 8.2, 10.9 Hz, 1H), 7.00-6.96 (m, 1H), 6.99-6.94 (m, 1H), 6.87 (ddd, J = 1.1, 3.7, 7.5 Hz, 1H), 4.81-4.75 (m, 1H), 4.06-4.00 (m, 1H), 3.49-3.45 (m, 2H), 3.46-3.44 (m, 2H), 3.10 (br. s, 2H), 3.08 (s, 3H), 2.32-2.22 (m, 1H), 2.23-2.17 (m, 2H), 2.07 (br. s, 3H), 2.09-1.99 (m, 3H), 1.88 (br. s, 1H), 1.87 (br. dd, J = 5.5, 7.9 Hz, 1H), 1.80-1.75 (m, 2H), 1.73 (br. d, J = 5.6 Hz, 1H), 1.71 (br. d, J = 4.3 Hz, 1H), 1.70-1.64 (m, 1H), 1.70-1.64 (m, 1H), 1.48-1.39 (m, 2H). $[\alpha]^{22}_D$ = −19.3° (c 0.10, MeOH) LCMS (m/z) $(M + H)^+$: 616.0 |
| C39 | 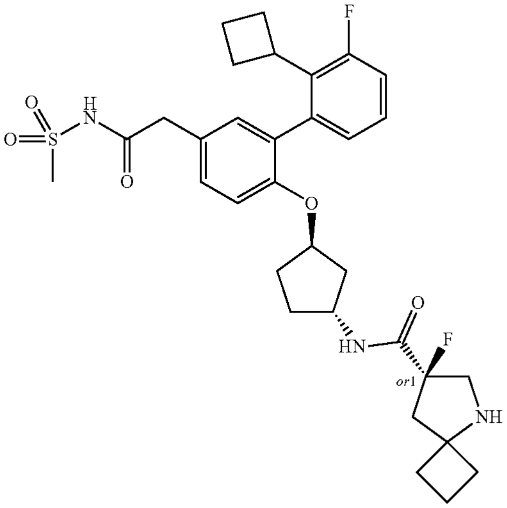 [SMILES: CS(=O)(=O)NC(=O)Cc1ccc(O[C@@H]2CC[C@@H](NC(=O)[C@]3(F)CNC4(CCC4)C3)C2)c(-c2cccc(F)c2C2CCC2)c1] (7ξ)-N-[(1R,3R)-3-({2'-cyclobutyl-3'-fluoro-5-[2-(methanesulfonamido)-2-oxoethyl][1,1'-biphenyl]-2-yl}oxy)cyclopentyl]-7-fluoro-5-azaspiro[3.4]octane-7-carboxamide | Second eluting peak: $^1H$ NMR (600 MHz, DMSO-$d_6$) δ 8.17 (br. dd, J 8.4, 9.4 Hz, 1H), 7.23-7.20 (m, 1H), 7.20 (s, 1H), 7.09 (dd, J = 8.2, 10.9 Hz, 1H), 7.00-6.96 (m, 1H), 6.99-6.94 (m, 1H), 6.87 (ddd, J = 1.1, 3.7, 7.5 Hz, 1H), 4.81-4.75 (m, 1H), 4.06-4.00 (m, 1H), 3.49-3.45 (m, 2H), 3.46-3.44 (m, 2H), 3.10 (br. s, 2H), 3.08 (s, 3H), 2.32-2.22 (m, 1H), 2.23-2.17 (m, 2H), 2.07 (br. s, 3H), 2.09-1.99 (m, 3H), 1.88 (br. s, 1H), 1.87 (br. dd, J = 5.5, 7.9 Hz, 1H), 1.80-1.75 (m, 2H), 1.73 (br. d, J = 5.6 Hz, 1H), 1.71 (br. d, J = 4.3 Hz, 1H), 1.70-1.64 (m, 1H), 1.70-1.64 (m, 1H), 1.48-1.39 (m, 2H). $[\alpha]^{22}_D$ = −11.0° (c 0.10, MeOH) LCMS (m/z) $(M + H)^+$: 616.0 |

TABLE 3-continued

| Ex. | Structure and Name | Characterization Data ($^1$H NMR, optical rotation, and/or LCMS) |
|---|---|---|
| C40 | 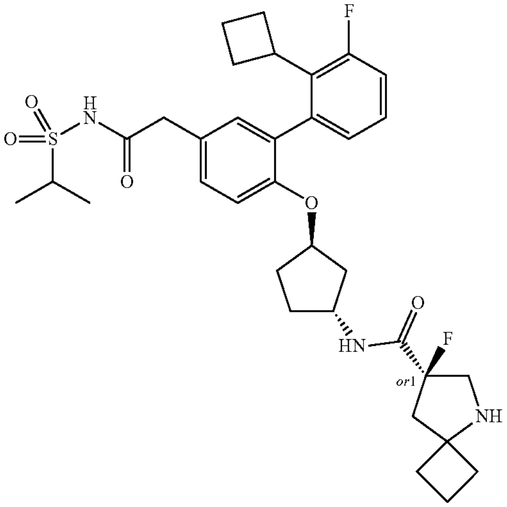 [SMILES: CC(C)S(=O)(=O)NC(=O)Cc1ccc(O[C@@H]2CC[C@@H](NC(=O)[C@]3(F)CNC4(CCC4)C3)C2)c(-c2cccc(F)c2C2CCC2)c1] (7ξ)-N-[(1R,3R)-3-({2'-cyclobutyl-3'-fluoro-5-[2-oxo-2-(propane-2-sulfonamido)ethyl][1,1'-biphenyl]-2-yl}oxy)cyclopentyl]-7-fluoro-5-azaspiro[3.4]octane-7-carboxamide | First eluting peak: $^1$H NMR (600 MHz, DMSO-$d_6$) δ 8.18-8.08 (m, 1H), 7.24-7.20 (m, 1H), 7.23-7.19 (m, 1H), 7.12-7.07 (m, 1H), 7.03-6.98 (m, 1H), 7.00-6.95 (m, 1H), 6.85 (ddd, J = 1.1, 4.2, 7.5 Hz, 1H), 4.79 (br. d, J = 2.8 Hz, 1H), 4.05-4.00 (m, 1H), 3.55-3.51 (m, 1H), 3.49 (s, 2H), 3.43 (br. d, J = 8.2 Hz, 1H), 3.16-3.12 (m, 1H), 3.10-3.03 (m, 1H), 2.30-1.93 (m, 10H), 1.91-1.60 (m, 8H), 1.59-1.37 (m, 2H), 1.18 (d, J = 6.9 Hz, 6H). $[\alpha]^{22}_D$ = −23.9° (c 0.1, MeOH) LCMS (m/z) $(M + H)^+$: 644.04 |
| C41 | 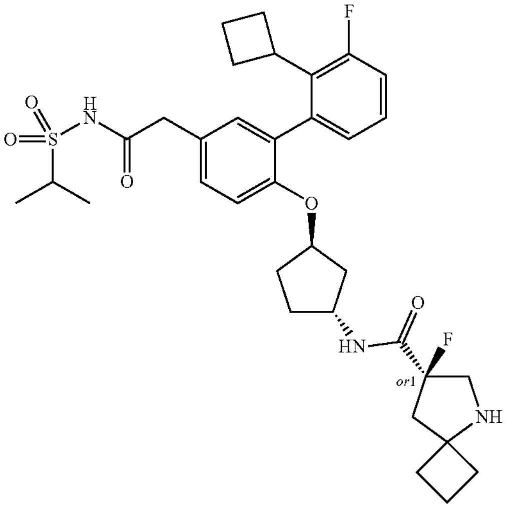 [SMILES: CC(C)S(=O)(=O)NC(=O)Cc1ccc(O[C@@H]2CC[C@@H](NC(=O)[C@]3(F)CNC4(CCC4)C3)C2)c(-c2cccc(F)c2C2CCC2)c1] (7ξ)-N-[(1R,3R)-3-({2'-cyclobutyl-3'-fluoro-5-[2-oxo-2-(propane-2-sulfonamido) ethyl][1,1'-biphenyl]-2-yl}oxy)cyclopentyl]-7-fluoro-5-azaspiro[3.4]octane-7-carboxamide | Second eluting peak: $^1$H NMR (600 MHz, DMSO-$d_6$) δ = 8.14 (ddd, J = 2.3, 7.9, 13.8 Hz, 1H), 7.26-7.20 (m, 1H), 7.24-7.19 (m, 1H), 7.10 (dd, J = 8.2, 11.7 Hz, 1H), 7.04-6.98 (m, 1H), 7.02-6.95 (m, 1H), 6.88-6.83 (m, 1H), 4.79 (br. d, J = 2.7 Hz, 1H), 4.05-4.00 (m, 1H), 3.56-3.51 (m, 1H), 3.51-3.49 (m, 2H), 3.43 (br. d, J = 8.4 Hz, 1H), 3.11-3.04 (m, 2H), 2.30-1.93 (m, 10H), 1.92-1.59 (m, 8H), 1.58-1.37 (m, 2H), 1.18 (d, J = 6.9 Hz, 6H). $[\alpha]^{22}_D$ = −10.4° (c 0.1, MeOH) LCMS (m/z) $(M + H)^+$: 644.02 |

TABLE 3-continued

| Ex. | Structure and Name | Characterization Data ($^1H$ NMR, optical rotation, and/or LCMS) |
|---|---|---|
| C42 | 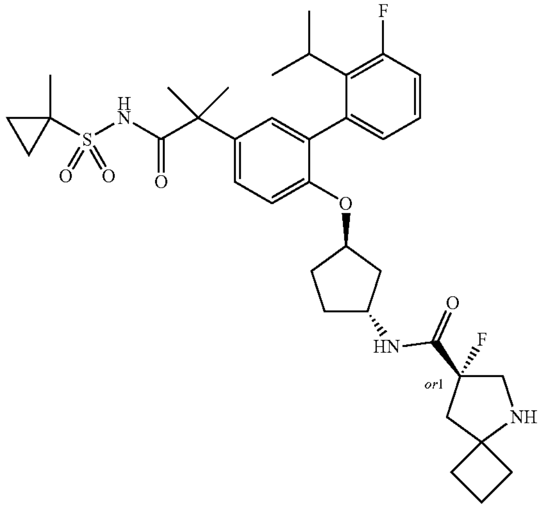 [SMILES: CC(C)c1c(F)cccc1-c1cc(C(C)(C)C(=O)NS(=O)(=O)C2(C)CC2)ccc1O[C@@H]1CC[C@@H](NC(=O)[C@@]2(F)CNC3(CCC3)C2)C1] (7ξ)-7-fluoro-N-[(1R,3R)-3-({3'-fluoro-5-[2-methyl-1-(1-methylcyclopropane-1-sulfonamido)-1-oxopropan-2-yl]-2'-(propan-2-yl)[1,1'-biphenyl]-2-yl}oxy)cyclopentyl]-5-azaspiro[3.4]octane-7-carboxamide | $^1H$ NMR (400 MHz, DMSO-$d_6$) δ 8.24-8.08 (m, 1H), 7.32-7.27 (m, 1H), 7.25-7.18 (m, 1H), 7.15-7.08 (m, 1H), 7.08-7.01 (m, 1H), 6.99-6.92 (m, 1H), 6.89-6.78 (m, 1H), 4.88-4.76 (m, 1H), 4.13-4.03 (m, 1H), 3.20-3.01 (m, 2H), 2.77-2.65 (m, 1H), 2.35-2.15 (m, 3H), 2.13-1.98 (m, 5H), 1.92-1.85 (m, 1H), 1.85-1.56 (m, 5H), 1.53-1.39 (m, 8H), 1.36-1.31 (m, 1H), 1.30-1.22 (m, 7H), 1.14-1.08 (m, 3H), 0.79-0.71 (m, 2H). LCMS (m/z) (M + H)$^+$: 672.5 |
| C43 | 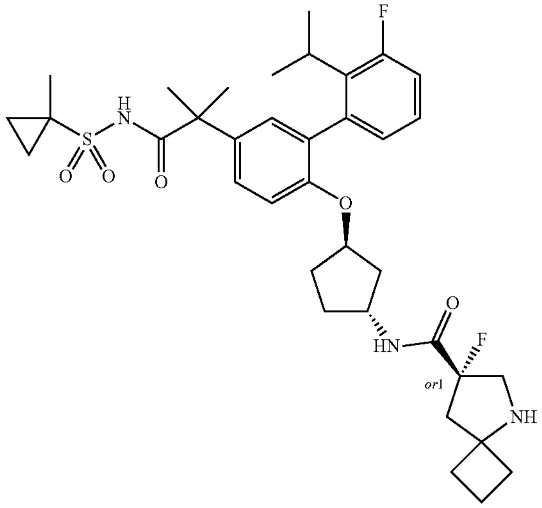 [SMILES: CC(C)c1c(F)cccc1-c1cc(C(C)(C)C(=O)NS(=O)(=O)C2(C)CC2)ccc1O[C@@H]1CC[C@@H](NC(=O)[C@@]2(F)CNC3(CCC3)C2)C1] (7ξ)-7-fluoro-N-[(1R,3R)-3-({3'-fluoro-5-[2-methyl-1-(1-methylcyclopropane-1-sulfonamido)-1-oxopropan-2-yl]-2'-(propan-2-yl)[1,1'-biphenyl]-2-yl}oxy)cyclopentyl]-5-azaspiro[3.4]octane-7-carboxamide | $^1H$ NMR (400 MHz, DMSO-$d_6$) δ 8.29-8.13 (m, 1H), 7.29 (br. d, J = 7.5 Hz, 1H), 7.25-7.16 (m, 1H), 7.15-7.08 (m, 1H), 7.03 (br. d, J = 8.4 Hz, 1H), 6.95 (br. s, 1H), 6.84 (dd, J = 1.4, 7.7 Hz, 1H), 4.87-4.80 (m, 1H), 4.16-4.04 (m, 1H), 3.22-3.05 (m, 2H), 2.71-2.66 (m, 1H), 2.15 (br. d, J = 4.0 Hz, 3H), 2.13-1.96 (m, 5H), 1.91-1.85 (m, 1H), 1.84-1.57 (m, 5H), 1.46 (br. d, J = 8.9 Hz, 8H), 1.34-1.30 (m, 1H), 1.28-1.21 (m, 7H), 1.11 (br. d, J = 7.0 Hz, 3H), 0.80-0.68 (m, 2H). LCMS (m/z) (M + H)$^+$: 672.4 |

TABLE 3-continued

| Ex. | Structure and Name | Characterization Data ($^1$H NMR, optical rotation, and/or LCMS) |
|---|---|---|
| C44 | 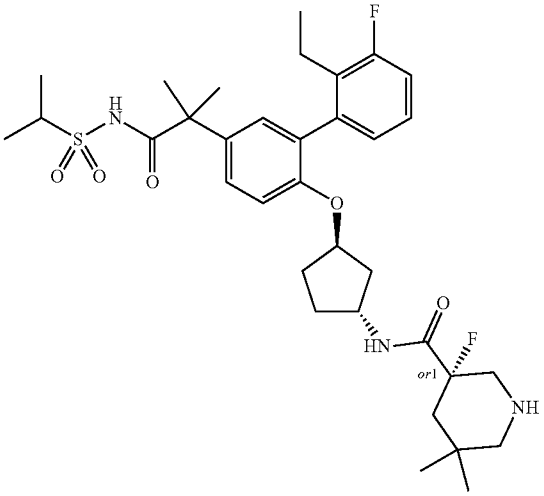 [SMILES: CCc1c(F)cccc1-c1cc(C(C)(C)C(=O)NS(=O)(=O)C(C)C)ccc1O[C@@H]1CC[C@@H](NC(=O)[C@@]2(F)CNCC(C)(C)C2)C1] (3ξ)-N-[(1R,3R)-3-({2'-ethyl-3'-fluoro-5-[2-methyl-1-oxo-1-(propane-2-sulfonamido)propan-2-yl][1,1'-biphenyl]-2-yl}oxy)cyclopentyl]-3-fluoro-5,5-dimethylpiperidine-3-carboxamide | $^1$H NMR (400 MHz, $CDCl_3$) δ 10.84-10.48 (m, 1H), 9.52-9.21 (m, 1H), 7.41-7.28 (m, 2H), 7.22-7.13 (m, 1H), 7.10 (d, J = 1.9 Hz, 1H), 7.07-6.98 (m, 1H), 6.91 (br. d, J = 8.1 Hz, 1H), 6.85 (br. d, J = 7.3 Hz, 1H), 6.77-6.54 (m, 1H), 4.90-4.68 (m, 1H), 4.30-4.07 (m, 1H), 3.83 (td, J = 6.9, 13.7 Hz, 1H), 3.70-3.41 (m, 1H), 3.40-3.11 (m, 2H), 2.84-2.66 (m, 1H), 2.54 (br. dd, J = 6.9, 12.6 Hz, 1H), 2.43-2.25 (m, 1H), 2.24-1.94 (m, 7H), 1.92-1.66 (m, 3H), 1.51-1.39 (m, 1H), 1.39-1.15 (m, 10H), 1.14-1.05 (m, 3H), 1.03 (br. s, 4H). LCMS (m/z) $(M + H)^+$: 648.3 |
| C45 | 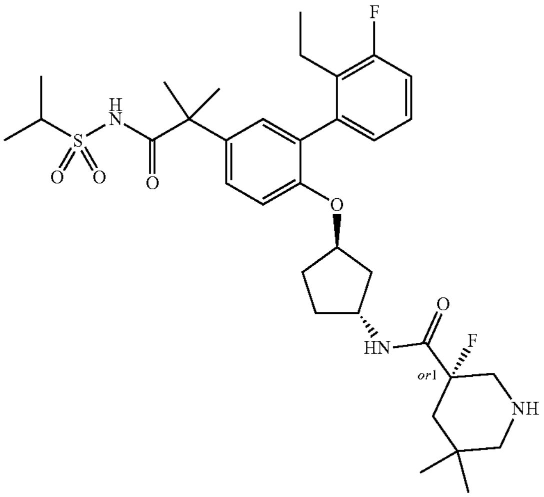 [SMILES: CCc1c(F)cccc1-c1cc(C(C)(C)C(=O)NS(=O)(=O)C(C)C)ccc1O[C@@H]1CC[C@@H](NC(=O)[C@@]2(F)CNCC(C)(C)C2)C1] (3ξ)-N-[(1R,3R)-3-({2'-ethyl-3'-fluoro-5-[2-methyl-1-oxo-1-(propane-2-sulfonamido)propan-2-yl][1,1'-biphenyl]-2-yl}oxy)cyclopentyl]-3-fluoro-5,5-dimethylpiperidine-3-carboxamide | $^1$H NMR (400 MHz, $CDCl_3$) δ 10.92-10.59 (m, 1H), 9.63-9.17 (m, 1H), 7.49-7.37 (m, 1H), 7.34-7.28 (m, 1H), 7.24-7.12 (m, 1H), 7.10 (d, J = 1.6 Hz, 1H), 7.06-6.98 (m, 1H), 6.95-6.89 (m, 1H), 6.89-6.82 (m, 1H), 6.71-6.49 (m, 1H), 4.90-4.69 (m, 1H), 4.24-4.05 (m, 1H), 3.89-3.75 (m, 1H), 3.69-3.47 (m, 1H), 3.43-3.10 (m, 2H), 2.84-2.67 (m, 1H), 2.61-2.46 (m, 1H), 2.42-2.26 (m, 1H), 2.23-1.95 (m, 4H), 1.85 (s, 5H), 1.78 (br. d, J = 12.8 Hz, 2H), 1.50-1.38 (m, 1H), 1.32 (br. s, 9H), 1.10-1.04 (m, 3H), 1.04-0.93 (m, 4H). LCMS (m/z) $(M + H)^+$: 648.4 |

TABLE 3-continued

| Ex. | Structure and Name | Characterization Data ($^1$H NMR, optical rotation, and/or LCMS) |
|---|---|---|
| C46 | 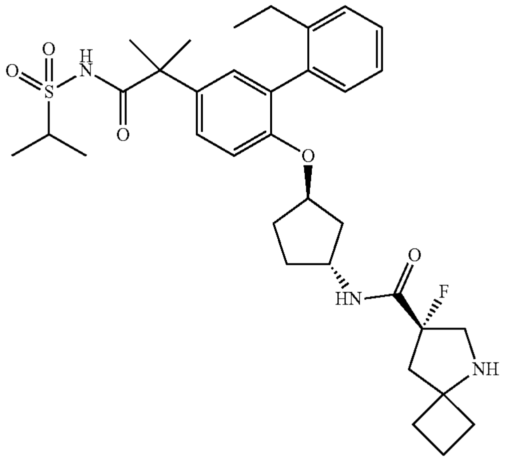 [SMILES: CCc1ccccc1-c1cc(C(C)(C)C(=O)NS(=O)(=O)C(C)C)ccc1O[C@@H]1CC[C@@H](NC(=O)[C@@]2(F)CNC3(CCC3)C2)C1] (7S)-N-[(1R,3R)-3-({2'-ethyl-5-[2-methyl-1-oxo-1-(propane-2-sulfonamido)propan-2-yl][1,1'-biphenyl]-2-yl}oxy)cyclopentyl]-7-fluoro-5-azaspiro[3.4]octane-7-carboxamide | $^1$H NMR (400 MHz, DMSO-$d_6$) δ 11.18-10.80 (m, 1H), 10.27-9.85 (m, 2H), 8.52 (br. d, J = 7.0 Hz, 1H), 7.31-7.23 (m, 3H), 7.23-7.16 (m, 1H), 7.03 (d, J = 9.0 Hz, 2H), 6.98 (d, J = 2.5 Hz, 1H), 4.84 (br. s, 1H), 4.08 (sxt, J = 7.3 Hz, 1H), 3.68-3.50 (m, 3H), 2.68-2.55 (m, 2H), 2.53 (br. s, 1H), 2.49-2.31 (m, 3H), 2.23-2.00 (m, 3H), 1.94-1.73 (m, 5H), 1.49 (br. s, 8H), 1.21-1.11 (m, 6H), 1.02-0.95 (m, 3H). LCMS (m/z) (M + H)$^+$: 628.4 |
| C47 | 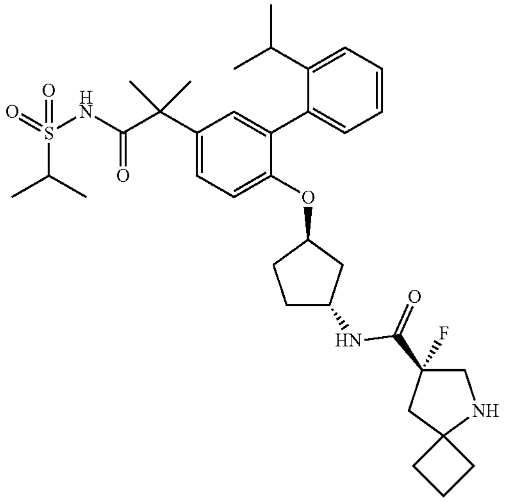 [SMILES: CC(C)c1ccccc1-c1cc(C(C)(C)C(=O)NS(=O)(=O)C(C)C)ccc1O[C@@H]1CC[C@@H](NC(=O)[C@@]2(F)CNC3(CCC3)C2)C1] (7S)-7-fluoro-N-[(1R,3R)-3-({5-[2-methyl-1-oxo-1-(propane-2-sulfonamido)propan-2-yl]-2'-(propan-2-yl)[1,1'-biphenyl]-2-yl}oxy)cyclopentyl]-5-azaspiro[3.4]octane-7-carboxamide | $^1$H NMR (400 MHz, DMSO-$d_6$) δ 11.22-10.69 (m, 1H), 10.33-9.92 (m, 2H), 8.55-8.47 (m, 1H), 7.37-7.24 (m, 3H), 7.17 (t, J = 7.3 Hz, 1H), 7.03 (d, J = 9.0 Hz, 1H), 7.00-6.93 (m, 2H), 4.84 (br d, J = 2.5 Hz, 1H), 4.12-4.02 (m, 1H), 3.67-3.49 (m, 3H), 2.76-2.55 (m, 3H), 2.49-2.36 (m, 2H), 2.23-1.99 (m, 3H), 1.93-1.71 (m, 5H), 1.54-1.47 (m, 6H), 1.47-1.40 (m, 2H), 1.17 (s, 6H), 1.15-1.11 (m, 3H), 0.96 (d, J = 7.0 Hz, 3H). LCMS (m/z) (M + H)$^+$: 642.5 |

TABLE 3-continued

| Ex. | Structure and Name | Characterization Data ($^1$H NMR, optical rotation, and/or LCMS) |
|---|---|---|
| C48 | 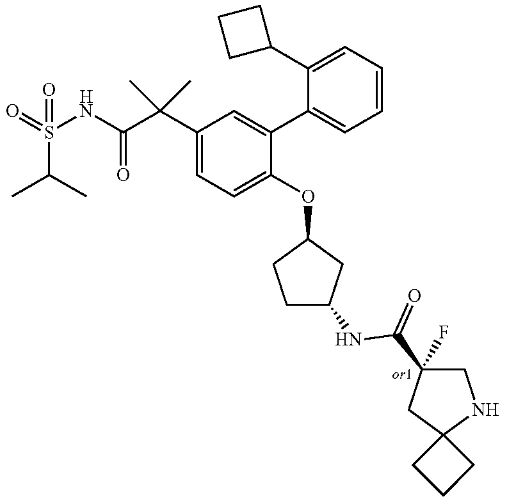 [SMILES: CC(C)S(=O)(=O)NC(=O)C(C)(C)c1ccc(O[C@@H]2CC[C@@H](NC(=O)[C@@]3(F)CNC4(CCC4)C3)C2)c(-c2ccccc2C2CCC2)c1] (7ξ)-N-[(1R,3R)-3-({2'-cyclobutyl-5-[2-methyl-1-oxo-1-(propane-2-sulfonamido)propan-2-yl][1,1'-biphenyl]-2-yl}oxy)cyclopentyl]-7-fluoro-5-azaspiro[3.4]octane-7-carboxamide | First to elute $[\alpha]^{22}_D$ = −100.6° (c 0.1, MeOH) LCMS (m/z) $(M + H)^+$: 654.3 |
| C49 | 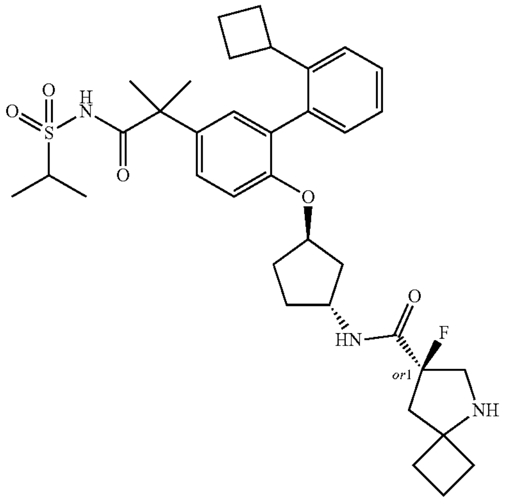 [SMILES: CC(C)S(=O)(=O)NC(=O)C(C)(C)c1ccc(O[C@@H]2CC[C@@H](NC(=O)[C@]3(F)CNC4(CCC4)C3)C2)c(-c2ccccc2C2CCC2)c1] (7ξ)-N-[(1R,3R)-3-({2'-cyclobutyl-5-[2-methyl-1-oxo-1-(propane-2-sulfonamido)propan-2-yl][1,1'-biphenyl]-2-yl}oxy)cyclopentyl]-7-fluoro-5-azaspiro[3.4]octane-7-carboxamide | Second to elute $^1$H NMR (600 MHz, DMSO-$d_6$) δ 7.81 (br d, J = 4.90 Hz, 1 H) 7.40 (d, J = 7.27 Hz, 1 H) 7.36-7.30 (m, 1 H) 7.27 (dd, J = 8.54, 2.54 Hz, 1 H) 7.18 (td, J = 7.45, 1.27 Hz, 1 H) 7.03 (dd, J = 7.54, 1.18 Hz, 1 H) 7.00-6.95 (m, 2 H) 4.77 (dt, J = 5.90, 2.86 Hz, 1 H) 4.12-4.01 (m, 1 H) 3.59 (dt, J = 13.76, 6.83 Hz, 1 H) 3.46 (quin, J = 8.90 Hz, 1 H) 3.23 (br s, 3 H) 3.17 (s, 1 H) 2.32-2.11 (m, 2 H) 2.10-1.88 (m, 9 H) 1.88-1.80 (m, 2 H) 1.81-1.73 (m, 2 H) 1.71-1.61 (m, 2 H) 1.50 (s, 6 H) 1.48-1.40 (m, 2 H) 1.17 (d, J = 6.72 Hz, 6 H). $[\alpha]^{22}_D$ = −20.1° (c 0.1, MeOH) LCMS (m/z) $(M + H)^+$: 654.3 |

TABLE 3-continued

| Ex. | Structure and Name | Characterization Data ($^1$H NMR, optical rotation, and/or LCMS) |
|---|---|---|
| C50 | 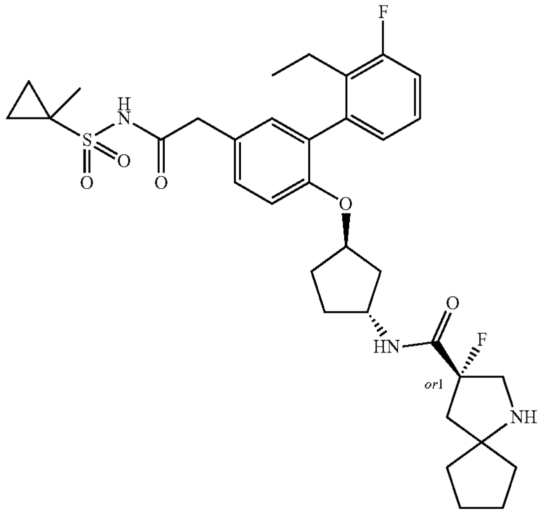 [SMILES: CCc1c(F)cccc1-c1cc(CC(=O)NS(=O)(=O)C2(C)CC2)ccc1O[C@@H]1CC[C@@H](NC(=O)[C@@]2(F)CNC3(CCCC3)C2)C1] (3ξ)-N-[(1R,3R)-3-({2'-ethyl-3'-fluoro-5-[2-(1-methylcyclopropane-1-sulfonamido)-2-oxoethyl][1,1'-biphenyl]-2-yl}oxy)cyclopentyl]-3-fluoro-1-azaspiro[4.4]nonane-3-carboxamide | $^1$H NMR (600 MHz, DMSO-$d_6$) δ 8.16 (br s, 1 H) 7.29-7.18 (m, 2 H) 7.16-7.06 (m, 1 H) 7.03 (d, J = 2.27 Hz, 1 H) 7.00 (d, J = 8.45 Hz, 1 H) 6.87 (br d, J = 7.27 Hz, 1 H) 4.80 (br d, J = 3.18 Hz, 1 H) 4.06 (br d, J = 7.54 Hz, 1 H) 3.28-3.20 (m, 2 H) 3.16 (s, 3 H) 3.15-3.06 (m, 2 H) 2.49-2.46 (m, 1 H) 2.34-2.28 (m, 1 H) 2.28-2.15 (m, 2 H) 2.07-1.96 (m, 2 H) 1.88-1.82 (m, 1 H) 1.81-1.77 (m, 1 H) 1.76 (br s, 1 H) 1.64 (br s, 3 H) 1.61-1.57 (m, 3 H) 1.56-1.49 (m, 2 H) 1.32 (s, 3 H) 1.28 (d, J = 2.18 Hz, 2 H) 0.91 (br t, J = 7.45 Hz, 3 H) 0.76 (d, J = 2.27 Hz, 2 H). LCMS (m/z) $(M + H)^+$: 644.2 |
| C51 | 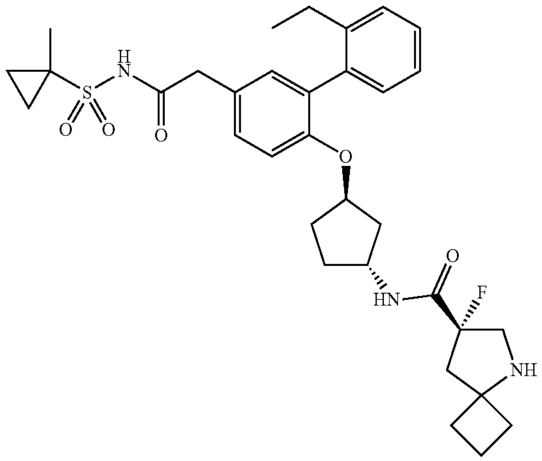 [SMILES: CCc1ccccc1-c1cc(CC(=O)NS(=O)(=O)C2(C)CC2)ccc1O[C@@H]1CC[C@@H](NC(=O)[C@@]2(F)CNC3(CCC3)C2)C1] (7S)-N-[(1R,3R)-3-({2'-ethyl-5-[2-(1-methylcyclopropane-1-sulfonamido)-2-oxoethyl][1,1'-biphenyl]-2-yl}oxy)cyclopentyl]-7-fluoro-5-azaspiro[3.4]octane-7-carboxamide | $^1$H NMR (400 MHz, MeOD) δ 8.50 (s, 1H), 7.31-7.22 (m, 3H), 7.20-7.13 (m, 1H), 7.11-7.02 (m, 2H), 6.96 (d, J = 8.4 Hz, 1H), 4.80 (br s, 1H), 4.22-4.09 (m, 1H), 3.55 (s, 2H), 3.51-3.36 (m, 1H), 3.29-3.19 (m, 1H), 2.55-2.36 (m, 4H), 2.33-2.14 (m, 4H), 2.10-1.61 (m, 7H), 1.53-1.43 (m, 3H), 1.41 (s, 3H), 1.28-1.21 (m, 2H), 1.01 (t, J = 7.6 Hz, 3H), 0.84-0.78 (m, 2H). LCMS (m/z) $(M + H)^+$: 612.3 |

TABLE 3-continued

| Ex. | Structure and Name | Characterization Data ($^1$H NMR, optical rotation, and/or LCMS) |
| --- | --- | --- |
| C52 | 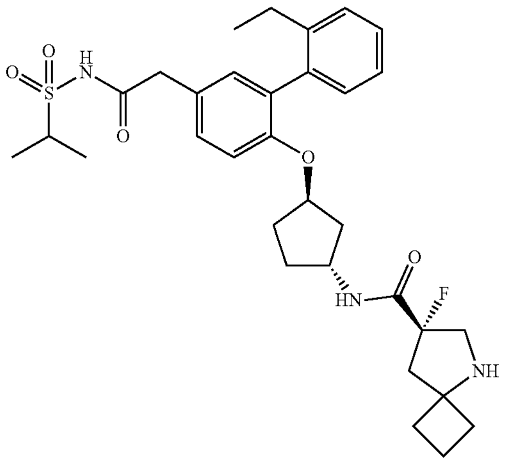 [SMILES: CCc1ccccc1-c1cc(CC(=O)NS(=O)(=O)C(C)C)ccc1O[C@@H]1CC[C@@H](NC(=O)[C@@]2(F)CNC3(CCC3)C2)C1] (7S)-N-[(1R,3R)-3-({2'-ethyl-5-[2-oxo-2-(propane-2-sulfonamido)ethyl][1,1'-biphenyl]-2-yl}oxy)cyclopentyl]-7-fluoro-5-azaspiro[3.4]octane-7-carboxamide | $^1$H NMR (400 MHz, MeOD) δ 7.33-7.21 (m, 3H), 7.20-7.13 (m, 1H), 7.10-7.01 (m, 2H), 6.95 (d, J = 8.6 Hz, 1H), 4.79 (br s, 1H), 4.22-4.09 (m, 1H), 3.63 (td, J = 6.9, 13.7 Hz, 1H), 3.52 (s, 2H), 3.48-3.35 (m, 1H), 3.28-3.19 (m, 1H), 2.57-2.33 (m, 4H), 2.30-2.16 (m, 4H), 2.11-1.56 (m, 7H), 1.53-1.40 (m, 1H), 1.28 (d, J = 6.8 Hz, 6H), 1.01 (t, J = 7.6 Hz, 3H). LCMS (m/z) (M + H)$^+$: 600.5 |
| C53 | 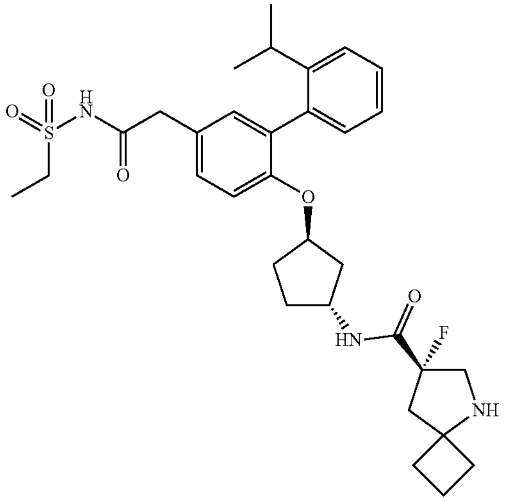 [SMILES: CCS(=O)(=O)NC(=O)Cc1ccc(O[C@@H]2CC[C@@H](NC(=O)[C@@]3(F)CNC4(CCC4)C3)C2)c(-c2ccccc2C(C)C)c1] (7S)-N-[(1R,3R)-3-({5-[2-(ethanesulfonamido)-2-oxoethyl]-2'-(propan-2-yl)[1,1'-biphenyl]-2-yl}oxy)cyclopentyl]-7-fluoro-5-azaspiro[3.4]octane-7-carboxamide | $^1$H NMR (MeOD, 400 MHz) δ 7.4-7.2 (m, 3H), 7.14 (br t, 1H, J = 7.3 Hz), 7.1-7.0 (m, 2H), 6.95 (d, 1H, J = 8.5 Hz), 4.3-4.0 (m, 1H), 3.51 (s, 2H), 3.47 (br dd, 1H, J = 3.3, 15.5 Hz), 3.4-3.3 (m, 1H), 3.3-3.2 (m, 2H), 2.9-2.7 (m, 1H), 2.48 (d, 1H, J = 5.3 Hz), 2.41 (s, 1H), 2.4-1.5 (m, 12H), 1.5-1.4 (m, 1H), 1.3-1.1 (m, 6H), 1.1-1.0 (m, 3H). LCMS (m/z) (M + H)$^+$: 600.2 |

TABLE 3-continued

| Ex. | Structure and Name | Characterization Data ($^1$H NMR, optical rotation, and/or LCMS) |
|---|---|---|
| C54 | 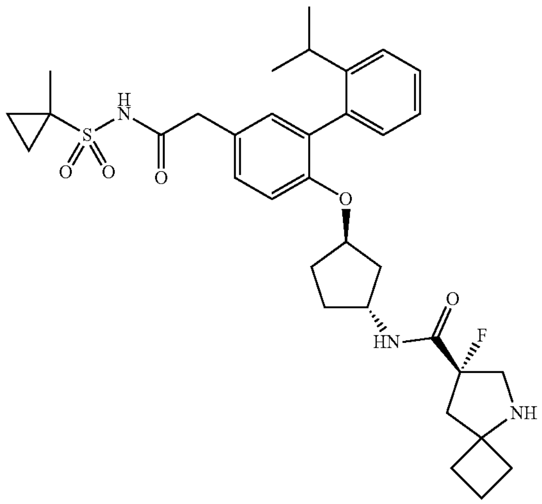 [SMILES: CC(C)c1ccccc1-c1cc(CC(=O)NS(=O)(=O)C2(C)CC2)ccc1O[C@@H]1CC[C@@H](NC(=O)[C@@]2(F)CNC3(CCC3)C2)C1] (7S)-7-fluoro-N-[(1R,3R)-3-({5-[2-(1-methylcyclopropane-1-sulfonamido)-2-oxoethyl]-2'-(propan-2-yl)[1,1'-biphenyl]-2-yl}oxy)cyclopentyl]-5-azaspiro[3.4]octane-7-carboxamide | $^1$H NMR (400 MHz, MeOD) δ 7.35-7.24 (m, 3H), 7.15 (dt, J = 1.3, 7.4 Hz, 1H), 7.06 (s, 1H), 7.04-6.99 (m, 1H), 6.96 (d, J = 8.4 Hz, 1H), 4.83-4.75 (m, 1H), 4.21-4.08 (m, 1H), 3.53 (s, 2H), 3.44-3.34 (m, 1H), 3.28-3.14 (m, 1H), 2.88-2.73 (m, 1H), 2.52-2.31 (m, 2H), 2.29-2.14 (m, 4H), 2.11-1.56 (m, 7H), 1.53-1.43 (m, 3H), 1.41 (s, 3H), 1.19 (dd, J = 5.1, 6.8 Hz, 3H), 1.01 (dd, J = 3.1, 6.9 Hz, 3H), 0.82-0.75 (m, 2H). LCMS (m/z) (M + H)$^+$: 626.4 |
| C55 | 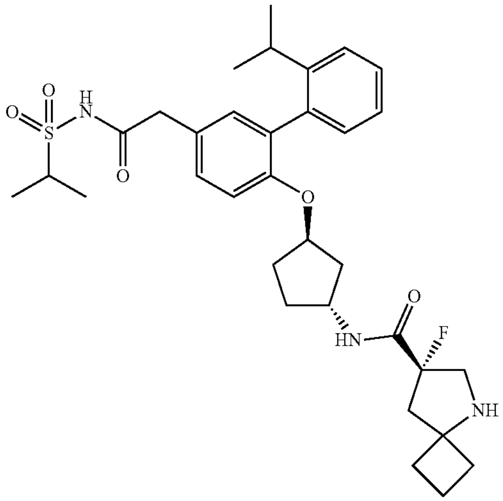 [SMILES: CC(C)c1ccccc1-c1cc(CC(=O)NS(=O)(=O)C(C)C)ccc1O[C@@H]1CC[C@@H](NC(=O)[C@@]2(F)CNC3(CCC3)C2)C1] (7S)-7-fluoro-N-[(1R,3R)-3-({5-[2-oxo-2-(propane-2-sulfonamido)ethyl]-2'-(propan-2-yl)[1,1'-biphenyl]-2-yl}oxy)cyclopentyl]-5-azaspiro[3.4]octane-7-carboxamide | $^1$H NMR (400 MHz, MeOD) δ 7.38-7.21 (m, 3H), 7.18-7.11 (m, 1H), 7.06 (s, 1H), 7.04-6.99 (m, 1H), 6.95 (d, J = 8.4 Hz, 1H), 4.82-4.74 (m, 1H), 4.22-4.05 (m, 1H), 3.63 (td, J = 6.9, 13.7 Hz, 1H), 3.52 (s, 2H), 3.49-3.37 (m, 1H), 3.30-3.21 (m, 1H), 2.80 (ttd, J = 3.2, 6.8, 10.2 Hz, 1H), 2.52-2.36 (m, 2H), 2.34-2.15 (m, 4H), 2.11-1.56 (m, 7H), 1.54-1.38 (m, 1H), 1.27 (d, J = 7.0 Hz, 6H), 1.19 (dd, J = 4.9, 6.8 Hz, 3H), 1.01 (dd, J = 3.2, 6.8 Hz, 3H). LCMS (m/z) (M + H)$^+$: 614.4 |

TABLE 3-continued

| Ex. | Structure and Name | Characterization Data ($^1$H NMR, optical rotation, and/or LCMS) |
|---|---|---|
| C56 | 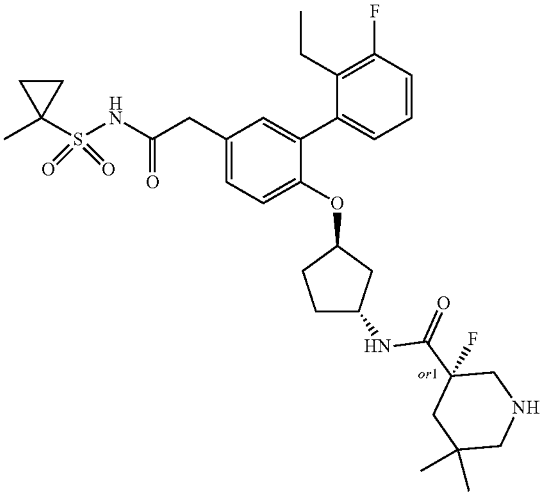 [SMILES: CCc1c(F)cccc1-c1cc(CC(=O)NS(=O)(=O)C2(C)CC2)ccc1O[C@@H]1CC[C@@H](NC(=O)[C@@]2(F)CNCC(C)(C)C2)C1] (3ξ)-N-[(1R,3R)-3-({2'-ethyl-3'-fluoro-5-[2-(1-methylcyclopropane-1-sulfonamido)-2-oxoethyl][1,1'-biphenyl]-2-yl}oxy)cyclopentyl]-3-fluoro-5,5-dimethylpiperidine-3-carboxamide | $^1$H NMR (400 MHz, DMSO-$d_6$) δ 8.10-8.03 (m, 1H), 7.26-7.18 (m, 2H), 7.16-7.07 (m, 1H), 7.05-6.97 (m, 2H), 6.90-6.84 (m, 1H), 4.85-4.76 (m, 1H), 4.07-3.94 (m, 1H), 2.94-2.81 (m, 2H), 2.78-2.65 (m, 1H), 2.37-2.21 (m, 3H), 2.17-1.87 (m, 2H), 1.85-1.36 (m, 8H), 1.34-1.25 (m, 5H), 1.04-0.97 (m, 3H), 0.91 (br t, J = 7.3 Hz, 3H), 0.82-0.74 (m, 5H). $[\alpha]^{23}_D$ = −21.7° (c 0.1, MeOH) LCMS (m/z) $(M + H)^+$: 632.4 |
| C57 | 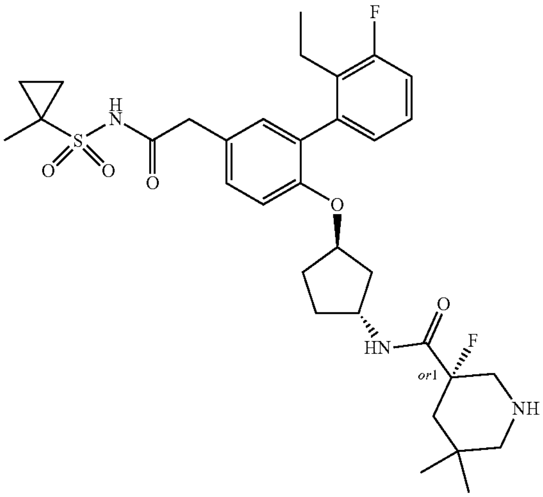 [SMILES: CCc1c(F)cccc1-c1cc(CC(=O)NS(=O)(=O)C2(C)CC2)ccc1O[C@@H]1CC[C@@H](NC(=O)[C@@]2(F)CNCC(C)(C)C2)C1] (3ξ)-N-[(1R,3R)-3-({2'-ethyl-3'-fluoro-5-[2-(1-methylcyclopropane-1-sulfonamido)-2-oxoethyl][1,1'-biphenyl]-2-yl}oxy)cyclopentyl]-3-fluoro-5,5-dimethylpiperidine-3-carboxamide | $^1$H NMR (400 MHz, DMSO-$d_6$) δ 8.13-8.01 (m, 1H), 7.27-7.18 (m, 2H), 7.16-7.07 (m, 1H), 7.05-6.97 (m, 2H), 6.90-6.84 (m, 1H), 4.86-4.75 (m, 1H), 4.07-3.93 (m, 1H), 2.94-2.81 (m, 2H), 2.78-2.65 (m, 1H), 2.39-2.23 (m, 3H), 1.90 (s, 2H), 1.87-1.35 (m, 8H), 1.34-1.26 (m, 5H), 1.04-0.97 (m, 3H), 0.94-0.86 (m, 3H), 0.83-0.76 (m, 5H). $[\alpha]^{23}_D$ = −28.1° (c 0.1, MeOH) LCMS (m/z) $(M + H)^+$: 632.4 |

TABLE 3-continued

| Ex. | Structure and Name | Characterization Data ($^1$H NMR, optical rotation, and/or LCMS) |
|---|---|---|
| C58 | 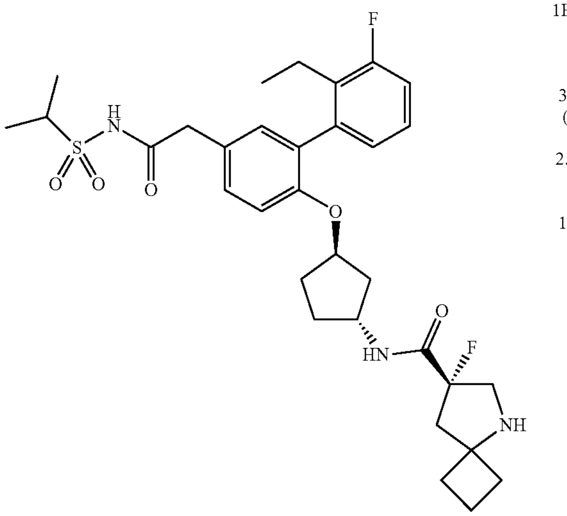 (7S)-N-[(1R,3R)-3-({2'-ethyl-3'-fluoro-5-[2-oxo-2-(propane-2-sulfonamido)ethyl][1,1'-biphenyl]-2-yl}oxy)cyclopentyl]-7-fluoro-5-azaspiro[3.4]octane-7-carboxamide | $^1$H NMR (600 MHz, DMSO-$d_6$) δ 11.68 (br s, 1H), 9.87-9.42 (m, 2H), 8.49 (br s, 1H), 7.27-7.21 (m, 2H), 7.13 (dt, J = 1.0, 9.2 Hz, 1H), 7.05 (d, J = 2.2 Hz, 1H), 7.02 (d, J = 8.4 Hz, 1H), 6.88 (dd, J = 0.9, 7.4 Hz, 1H), 4.86-4.82 (m, 1H), 4.11-4.05 (m, 1H), 3.69-3.58 (m, 2H), 3.59-3.55 (m, 2H), 3.56-3.52 (m, 1H), 2.64-2.57 (m, 1H), 2.52 (s, 1H), 2.49-2.44 (m, 3H), 2.33-2.27 (m, 1H), 2.24-2.16 (m, 2H), 2.11-2.00 (m, 1H), 1.91-1.80 (m, 2H), 1.84-1.79 (m, 2H), 1.82-1.74 (m, 1H), 1.56-1.48 (m, 1H), 1.56-1.43 (m, 1H), 1.22 (d, J = 6.7 Hz, 6H), 0.92 (t, J = 7.4 Hz, 3H). LCMS (m/z) $(M + H)^+$: 618.2 |
| C59 | 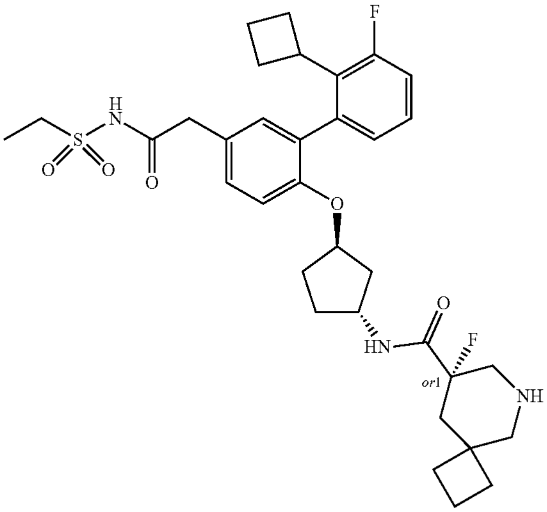 [SMILES: CCS(=O)(=O)NC(=O)Cc1ccc(O[C@@H]2CC[C@@H](NC(=O)[C@@]3(F)CNCC4(CCC4)C3)C2)c(-c2cccc(F)c2C2CCC2)c1] (8ξ)-N-[(1R,3R)-3-({2'-cyclobutyl-5-[2-(ethanesulfonamido)-2-oxoethyl]-3'-fluoro[1,1'-biphenyl]-2-yl}oxy)cyclopentyl]-8-fluoro-6-azaspiro[3.5]nonane-8-carboxamide | $^1$H NMR (400 MHz, DMSO-$d_6$) δ 1.12-1.07 (m, 3 H) 1.26-1.20 (m, 1 H) 1.45-1.39 (m, 1 H) 1.61-1.55 (m, 1 H) 1.79-1.64 (m, 7 H) 1.89-1.83 (m, 4 H) 2.10-1.92 (m, 6 H) 2.23-2.17 (m, 1 H) 2.88-2.85 (m, 1 H) 2.92 (br s, 1 H) 3.03 (br d, J = 12.38 Hz, 1 H) 3.24-3.18 (m, 3 H) 3.47 (s, 2 H) 4.09-3.95 (m, 2 H) 4.82-4.76 (m, 1 H) 6.86 (dd, J = 6.69, 3.44 Hz, 1 H) 7.01-6.95 (m, 2 H) 7.13-7.06 (m, 1 H) 7.26-7.18 (m, 2 H) 8.13-8.06 (m, 1 H) 8.15-8.13 (m, 1 H). $[\alpha]^{23}_D$ = −95.5° (c 0.1, MeOH) LCMS (m/z) $(M + H)^+$: 644.4 |

TABLE 3-continued

| Ex. | Structure and Name | Characterization Data ($^1$H NMR, optical rotation, and/or LCMS) |
| --- | --- | --- |
| C60 | 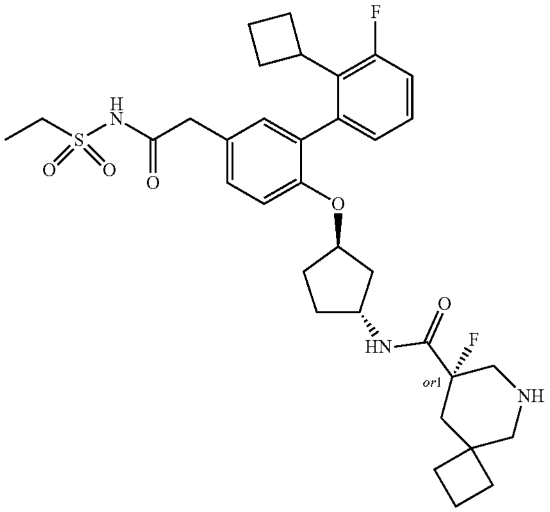 [SMILES: CCS(=O)(=O)NC(=O)Cc1ccc(O[C@@H]2CC[C@@H](NC(=O)[C@@]3(F)CNCC4(CCC4)C3)C2)c(-c2cccc(F)c2C2CCC2)c1] (8ξ)-N-[(1R,3R)-3-({2'-cyclobutyl-5-[2-(ethanesulfonamido)-2-oxoethyl]-3'-fluoro[1,1'-biphenyl]-2-yl}oxy)cyclopentyl]-8-fluoro-6-azaspiro[3.5]nonane-8-carboxamide | $^1$H NMR (400 MHz, DMSO-$d_6$) δ 1.09 (t, J = 7.25 Hz, 3 H) 1.23 (br s, 1 H) 1.43 (br dd, J = 12.01, 6.63 Hz, 1 H) 1.61-1.56 (m, 1 H) 1.80-1.65 (m, 7 H) 1.89-1.82 (m, 4 H) 2.10-1.92 (m, 6 H) 2.23-2.16 (m, 1 H) 2.88-2.83 (m, 1 H) 2.92 (br d, J = 5.38 Hz, 1 H) 3.03 (br d, J = 13.13 Hz, 1 H) 3.23-3.17 (m, 3 H) 3.46 (br s, 2 H) 4.10-3.93 (m, 2 H) 4.83-4.75 (m, 1 H) 6.88-6.82 (m, 1 H) 7.01-6.93 (m, 2 H) 7.13-7.05 (m, 1 H) 7.24-7.18 (m, 2 H) 8.13-8.06 (m, 1 H) 8.14 (s, 1 H). $[\alpha]^{23}_D$ = −16.9° (c 0.10, MeOH) LCMS (m/z) $(M + H)^+$: 644.4 |
| C61 | 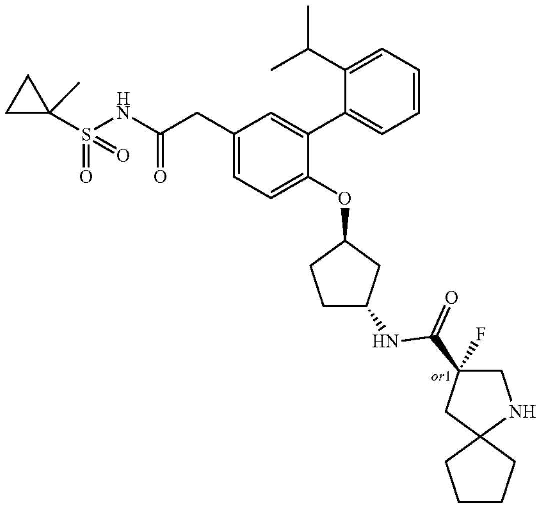 [SMILES: CC(C)c1ccccc1-c1cc(CC(=O)NS(=O)(=O)C2(C)CC2)ccc1O[C@@H]1CC[C@@H](NC(=O)[C@@]2(F)CNC3(CCCC3)C2)C1] (3ξ)-3-fluoro-N-[(1R,3R)-3-({5-[2-(1-methylcyclopropane-1-sulfonamido)-2-oxoethyl]-2'-(propan-2-yl)[1,1'-biphenyl]-2-yl}oxy)cyclopentyl]-1-azaspiro[4.4]nonane-3-carboxamide | $^1$H NMR (600 MHz, DMSO) δ 8.13 (t, J = 7.4 Hz, 1H), 7.33 (d, J = 7.5 Hz, 1H), 7.30 (t, J = 7.5 Hz, 1H), 7.20 (d, J = 8.5 Hz, 1H), 7.16 (t, J = 7.4 Hz, 1H), 7.02-6.94 (m, 3H), 4.78 (s, 1H), 4.05 (p, J = 7.5 Hz, 1H), 3.25-3.20 (m, 1H), 3.11-3.04 (m, 1H), 2.72 (h, J = 6.9 Hz, 1H), 2.21 (dd, J = 32.0, 14.4 Hz, 1H), 2.12-1.93 (m, 2H), 1.87-1.82 (m, 1H), 1.79-1.37 (m, 12H), 1.31 (s, 3H), 1.28 (s, 2H), 1.14 (dd, J = 6.9, 3.7 Hz, 3H), 0.95 (d, J = 6.9 Hz, 3H), 0.78-0.73 (m, 2H). $[\alpha]^{22}_D$ = −11.8° (c 0.10, MeOH) LCMS (m/z) $(M + H)^+$: 640.2 |

TABLE 3-continued

| Ex. | Structure and Name | Characterization Data ($^1$H NMR, optical rotation, and/or LCMS) |
|---|---|---|
| C62 | 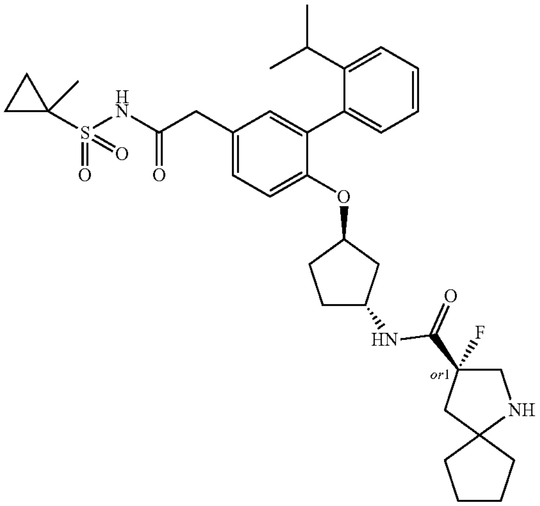 [SMILES: CC(C)c1ccccc1-c1cc(CC(=O)NS(=O)(=O)C2(C)CC2)ccc1O[C@@H]1CC[C@@H](NC(=O)[C@@]2(F)CNC3(CCCC3)C2)C1] (3ξ)-3-fluoro-N-[(1R,3R)-3-({5-[2-(1-methylcyclopropane-1-sulfonamido)-2-oxoethyl]-2'-(propan-2-yl)[1,1'-biphenyl]-2-yl}oxy)cyclopentyl]-1-azaspiro[4.4]nonane-3-carboxamide | $^1$H NMR (600 MHz, DMSO) δ 8.13 (t, J = 7.4 Hz, 1H), 7.33 (d, J = 7.5 Hz, 1H), 7.30 (t, J = 7.5 Hz, 1H), 7.20 (d, J = 8.5 Hz, 1H), 7.16 (t, J = 7.4 Hz, 1H), 7.02-6.94 (m, 3H), 4.78 (s, 1H), 4.05 (p, J = 7.5 Hz, 1H), 3.25-3.20 (m, 1H), 3.11-3.04 (m, 1H), 2.72 (h, J = 6.9 Hz, 1H), 2.21 (dd, J = 32.0, 14.4 Hz, 1H), 2.12-1.93 (m, 2H), 1.87-1.82 (m, 1H), 1.79-1.37 (m, 12H), 1.31 (s, 3H), 1.28 (s, 2H), 1.14 (dd, J = 6.9, 3.7 Hz, 3H), 0.95 (d, J = 6.9 Hz, 3H), 0.78-0.73 (m, 2H). $[\alpha]^{22}_D$ = −19.2° (c 0.10, MeOH) LCMS (m/z) $(M + H)^+$: 640.3 |
| C63 | 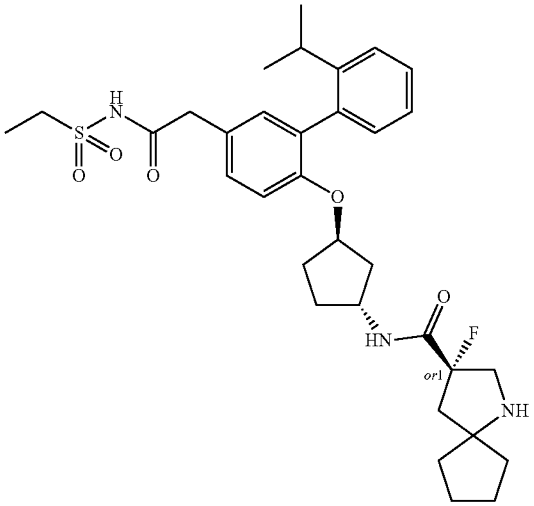 [SMILES: CCS(=O)(=O)NC(=O)Cc1ccc(O[C@@H]2CC[C@@H](NC(=O)[C@@]3(F)CNC4(CCCC4)C3)C2)c(-c2ccccc2C(C)C)c1] (3ξ)-N-[(1R,3R)-3-({5-[2-(ethanesulfonamido)-2-oxoethyl]-2'-(propan-2-yl)[1,1'-biphenyl]-2-yl}oxy)cyclopentyl]-3-fluoro-1-azaspiro[4.4]nonane-3-carboxamide | $^1$H NMR (600 MHz, DMSO-$d_6$) δ 8.17-8.08 (m, 1H), 7.35-7.30 (m, 1H), 7.32-7.27 (m, 1H), 7.18 (br d, J = 8.5 Hz, 1H), 7.15 (br t, J = 7.3 Hz, 1H), 6.98-6.95 (m, 1H), 6.99-6.95 (m, 1H), 6.94-6.91 (m, 1H), 4.78-4.73 (m, 1H), 4.08-4.01 (m, 1H), 3.33 (br s, 2H), 3.24-3.18 (m, 1H), 3.08 (br d, J = 13.5 Hz, 1H), 2.90 (q, J = 7.3 Hz, 2H), 2.76-2.70 (m, 1H), 2.25-2.14 (m, 1H), 2.03-1.93 (m, 1H), 2.09-1.91 (m, 1H), 1.84 (br dd, J = 4.7, 7.6 Hz, 1H), 1.75 (br dd, J = 4.5, 7.2 Hz, 1H), 1.73-1.32 (m, 11H), 1.16-1.11 (m, 3H), 1.15-1.11 (m, 3H), 0.95 (d, J = 6.8 Hz, 3H). $[\alpha]^{22}_D$ = −4.7° (c 0.10, MeOH) LCMS (m/z) $(M + H)^+$: 614.2 |

TABLE 3-continued

| Ex. | Structure and Name | Characterization Data ($^1$H NMR, optical rotation, and/or LCMS) |
| --- | --- | --- |
| C64 | 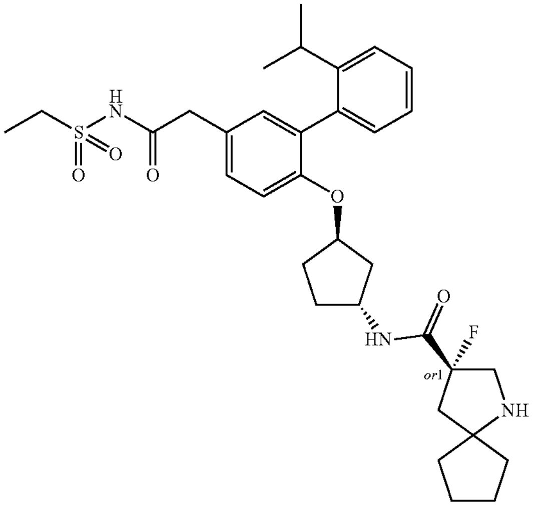 [SMILES: CCS(=O)(=O)NC(=O)Cc1ccc(O[C@@H]2CC[C@@H](NC(=O)[C@@]3(F)CNC4(CCCC4)C3)C2)c(-c2ccccc2C(C)C)c1] (3ξ)-N-[(1R,3R)-3-({5-[2-(ethanesulfonamido)-2-oxoethyl]-2'-(propan-2-yl)[1,1'-biphenyl]-2-yl}oxy)cyclopentyl]-3-fluoro-1-azaspiro[4.4]nonane-3-carboxamide | $^1$H NMR (600 MHz, DMSO-$d_6$) δ 8.17-8.08 (m, 1H), 7.35-7.30 (m, 1H), 7.32-7.27 (m, 1H), 7.18 (br d, J = 8.5 Hz, 1H), 7.15 (br t, J = 7.3 Hz, 1H), 6.98-6.95 (m, 1H), 6.99-6.95 (m, 1H), 6.94-6.91 (m, 1H), 4.78-4.73 (m, 1H), 4.08-4.01 (m, 1H), 3.33 (br s, 2H), 3.24-3.18 (m, 1H), 3.08 (br d, J = 13.5 Hz, 1H), 2.90 (q, J = 7.3 Hz, 2H), 2.76-2.70 (m, 1H), 2.25-2.14 (m, 1H), 2.03-1.93 (m, 1H), 2.09-1.91 (m, 1H), 1.84 (br dd, J = 4.7, 7.6 Hz, 1H), 1.75 (br dd, J = 4.5, 7.2 Hz, 1H), 1.73-1.32 (m, 11H), 1.16-1.11 (m, 3H), 1.15-1.11 (m, 3H), 0.95 (d, J = 6.8 Hz, 3H). $[\alpha]^{22}_D$ = −29.8° (c 0.10, MeOH) LCMS (m/z) (M + H)$^+$: 614.2 |
| C65 | 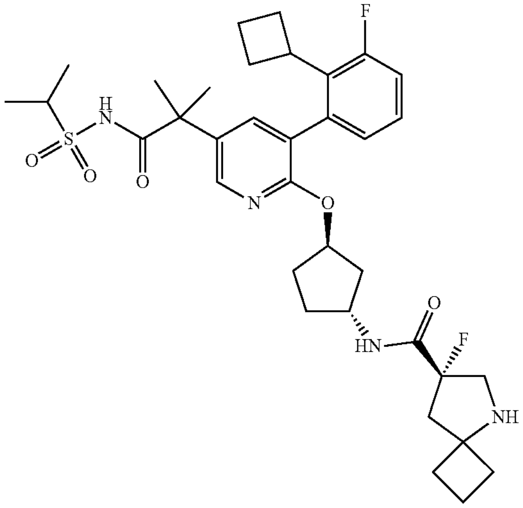 [SMILES: CC(C)S(=O)(=O)NC(=O)C(C)(C)c1cnc(O[C@@H]2CC[C@@H](NC(=O)[C@@]3(F)CNC4(CCC4)C3)C2)c(-c2cccc(F)c2C2CCC2)c1] (7S)-N-[(1R,3R)-3-({3-(2-cyclobutyl-3-fluorophenyl)-5-[2-methyl-1-oxo-1-(propane-2-sulfonamido)propan-2-yl]pyridin-2-yl}oxy)cyclopentyl]-7-fluoro-5-azaspiro[3.4]octane-7-carboxamide *Intermediate 29 was used in the Mitsunobu reaction | $^1$H NMR (600 MHz, DMSO-$d_6$) δ 8.11 (d, J = 2.5 Hz, 1H), 7.83 (br s, 1H), 7.43 (d, J = 2.5 Hz, 1H), 7.22 (dt, J = 5.6, 7.8 Hz, 1H), 7.08 (ddd, J = 0.7, 8.2, 11.8 Hz, 1H), 6.87 (d, J = 7.6 Hz, 1H), 5.48-5.41 (m, 1H), 4.13 (br d, J = 6.4 Hz, 2H), 3.48 (br dd, J = 9.2, 18.3 Hz, 5H), 3.37 (td, J = 6.9, 13.7 Hz, 7H), 2.30-2.19 (m, 1H), 2.18-2.08 (m, 3H), 2.07-1.98 (m, 6H), 1.82-1.59 (m, 5H), 1.55-1.46 (m, 2H), 1.42 (d, J = 1.1 Hz, 6H), 1.04 (d, J = 6.7 Hz, 6H). LCMS (m/z) (M + H)$^+$: 673.9 |

TABLE 3-continued

| Ex. | Structure and Name | Characterization Data ($^1$H NMR, optical rotation, and/or LCMS) |
|---|---|---|
| C66 | 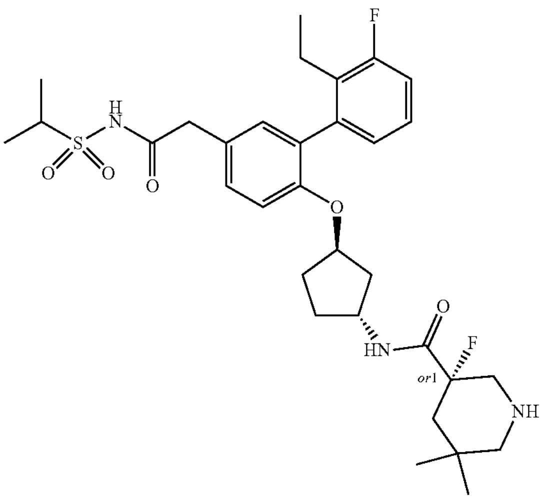 [SMILES: CCc1c(F)cccc1-c1cc(CC(=O)NS(=O)(=O)C(C)C)ccc1O[C@@H]1CC[C@@H](NC(=O)[C@@]2(F)CNCC(C)(C)C2)C1] (3ξ)-N-[(1R,3R)-3-({2'-ethyl-3'-fluoro-5-[2-oxo-2-(propane-2-sulfonamido)ethyl][1,1'-biphenyl]-2-yl}oxy)cyclopentyl]-3-fluoro-5,5-dimethylpiperidine-3-carboxamide | $^1$H NMR (400 MHz, DMSO-$d_6$) δ 8.17-8.01 (m, 1H), 7.29-7.17 (m, 2H), 7.16-7.08 (m, 1H), 7.06-6.96 (m, 2H), 6.91-6.83 (m, 1H), 4.87-4.75 (m, 1H), 4.10-3.92 (m, 1H), 3.57-3.45 (m, 4H), 3.00-2.72 (m, 2H), 2.70-2.52 (m, 2H), 2.42-2.19 (m, 3H), 2.15-1.89 (m, 1H), 1.86-1.29 (m, 7H), 1.19-1.13 (m, 6H), 1.04-0.98 (m, 3H), 0.94-0.86 (m, 3H), 0.83-0.78 (m, 3H). $[\alpha]^{25}_D$ = −88.2° (c 0.10, MeOH) LCMS (m/z) $(M + H)^+$: 620.4 |
| C67 | 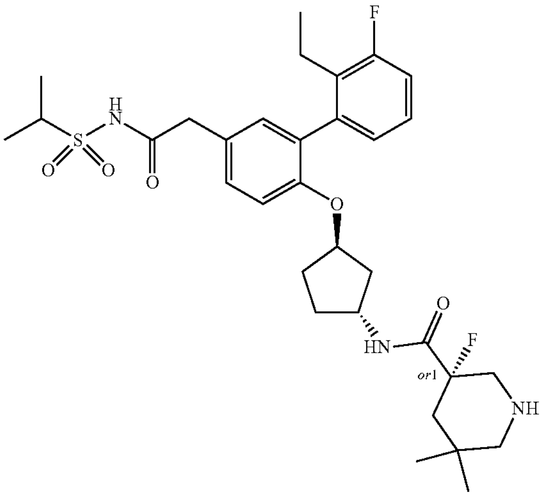 [SMILES: CCc1c(F)cccc1-c1cc(CC(=O)NS(=O)(=O)C(C)C)ccc1O[C@@H]1CC[C@@H](NC(=O)[C@@]2(F)CNCC(C)(C)C2)C1] (3ξ)-N-[(1R,3R)-3-({2'-ethyl-3'-fluoro-5-[2-oxo-2-(propane-2-sulfonamido)ethyl][1,1'-biphenyl]-2-yl}oxy)cyclopentyl]-3-fluoro-5,5-dimethylpiperidine-3-carboxamide | $^1$H NMR (400 MHz, DMSO-$d_6$) δ 8.19-8.01 (m, 1H), 7.31-7.18 (m, 2H), 7.16-7.08 (m, 1H), 7.06-6.95 (m, 2H), 6.92-6.81 (m, 1H), 4.89-4.72 (m, 1H), 4.11-3.91 (m, 1H), 3.56-3.47 (m, 4H), 3.00-2.84 (m, 2H), 2.83-2.52 (m, 2H), 2.48-2.35 (m, 2H), 2.35-2.22 (m, 1H), 2.14-1.93 (m, 1H), 1.88-1.28 (m, 7H), 1.17 (d, J = 6.8 Hz, 6H), 1.05-0.96 (m, 3H), 0.95-0.86 (m, 3H), 0.85-0.77 (m, 3H). $[\alpha]^{25}_D$ = −23.4° (c 0.10, MeOH) LCMS (m/z) $(M + H)^+$: 620.4 |

TABLE 3-continued

| Ex. | Structure and Name | Characterization Data ($^1$H NMR, optical rotation, and/or LCMS) |
|---|---|---|
| C68 | 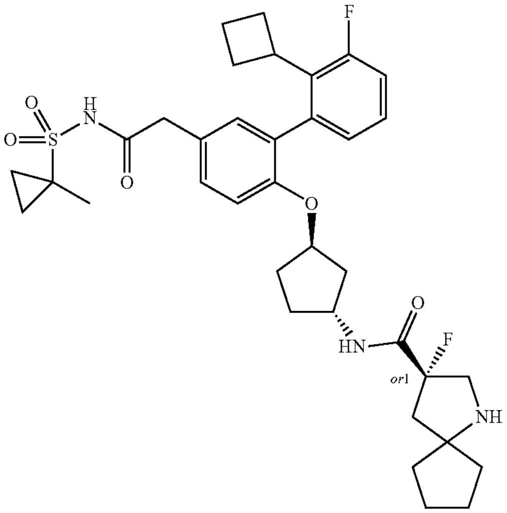 [SMILES: CC1(S(=O)(=O)NC(=O)Cc2ccc(O[C@@H]3CC[C@@H](NC(=O)[C@@]4(F)CNC5(CCCC5)C4)C3)c(-c3cccc(F)c3C3CCC3)c2)CC1] (3ξ)-N-[(1R,3R)-3-({2'-cyclobutyl-3'-fluoro-5-[2-(1-methylcyclopropane-1-sulfonamido)-2-oxoethyl][1,1'-biphenyl]-2-yl}oxy)cyclopentyl]-3-fluoro-1-azaspiro[4.4]nonane-3-carboxamide | $^1$H NMR (400 MHz, DMSO-$d_6$) δ 10.06-9.13 (m, 1H), 8.60-8.48 (m, 1H), 7.26-7.17 (m, 2H), 7.10 (dd, J = 8.3, 11.6 Hz, 1H), 7.04-6.96 (m, 2H), 6.90-6.81 (m, 1H), 4.81 (br d, J = 2.7 Hz, 1H), 4.14-4.01 (m, 1H), 3.79-3.58 (m, 3H), 3.55 (s, 2H), 2.53 (br d, J = 2.1 Hz, 1H), 2.42-2.33 (m, 1H), 2.18 (br dd, J = 6.6, 9.9 Hz, 1H), 2.12-1.95 (m, 5H), 1.94-1.56 (m, 13H), 1.54-1.38 (m, 2H), 1.35 (s, 3H), 1.34-1.27 (m, 2H), 0.89-0.80 (m, 2H). $[\alpha]^{26}_D$ = −77.9° (c 0.10, MeOH) LCMS (m/z) $(M + H)^+$: 670.5 |
| C69 | 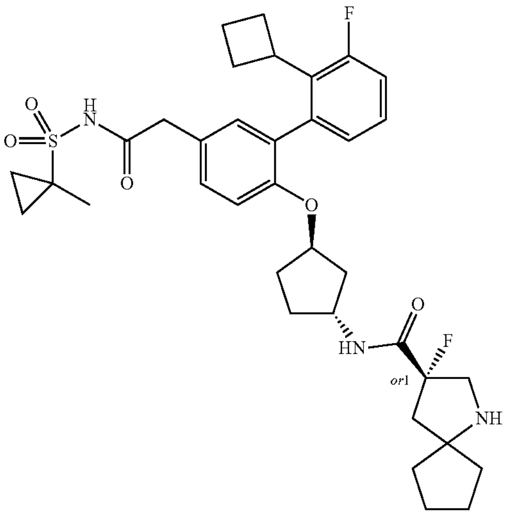 [SMILES: CC1(S(=O)(=O)NC(=O)Cc2ccc(O[C@@H]3CC[C@@H](NC(=O)[C@@]4(F)CNC5(CCCC5)C4)C3)c(-c3cccc(F)c3C3CCC3)c2)CC1] (3ξ)-N-[(1R,3R)-3-({2'-cyclobutyl-3'-fluoro-5-[2-(1-methylcyclopropane-1-sulfonamido)-2-oxoethyl][1,1'-biphenyl]-2-yl}oxy)cyclopentyl]-3-fluoro-1-azaspiro[4.4]nonane-3-carboxamide | $^1$H NMR (400 MHz, DMSO-$d_6$) δ 9.72-9.03 (m, 1H), 8.57-8.51 (m, 1H), 7.26-7.20 (m, 2H), 7.12 (dd, J = 8.3, 11.7 Hz, 1H), 7.04-6.99 (m, 2H), 6.87 (d, J = 7.6 Hz, 1H), 4.83 (br d, J = 2.4 Hz, 1H), 4.15-4.03 (m, 1H), 3.83-3.58 (m, 3H), 3.56 (s, 2H), 2.56 (br s, 1H), 2.44-2.37 (m, 1H), 2.27-2.16 (m, 1H), 2.11-1.96 (m, 5H), 1.94-1.64 (m, 13H), 1.57-1.42 (m, 2H), 1.37 (s, 3H), 1.36-1.32 (m, 2H), 0.92-0.82 (m, 2H). $[\alpha]^{26}_D$ = −50.2° (c 0.10, MeOH) LCMS (m/z) $(M + H)^+$: 670.5 |

TABLE 3-continued

| Ex. | Structure and Name | Characterization Data ($^1$H NMR, optical rotation, and/or LCMS) |
|---|---|---|
| C70 | 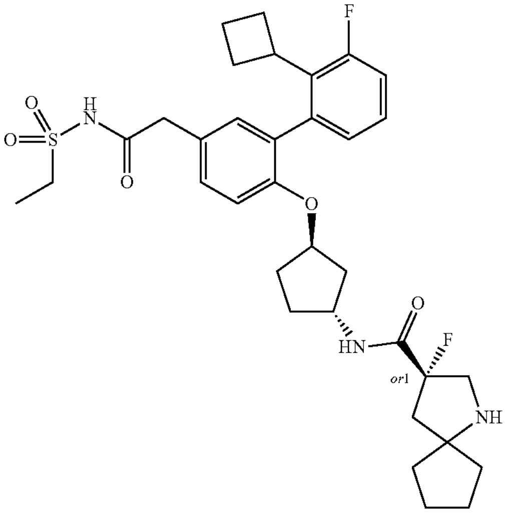 [SMILES: CCS(=O)(=O)NC(=O)Cc1ccc(O[C@@H]2CC[C@@H](NC(=O)[C@@]3(F)CNC4(CCCC4)C3)C2)c(-c2cccc(F)c2C2CCC2)c1] (3ξ)-N-[(1R,3R)-3-({2'-cyclobutyl-5-[2-(ethanesulfonamido)-2-oxoethyl]-3'-fluoro[1,1'-biphenyl]-2-yl}oxy)cyclopentyl]-3-fluoro-1-azaspiro[4.4]nonane-3-carboxamide | $^1$H NMR (400 MHz, DMSO-$d_6$) δ 10.14-9.38 (m, 1H), 8.53 (br t, J = 7.2 Hz, 1H), 7.28-7.17 (m, 2H), 7.16-7.07 (m, 1H), 7.05-6.96 (m, 2H), 6.86 (br d, J = 7.5 Hz, 1H), 4.82 (br s, 1H), 4.18-3.96 (m, 1H), 3.64 (br s, 2H), 3.56 (s, 3H), 3.46-3.39 (m, 1H), 3.31-3.28 (m, 1H), 2.45-2.36 (m, 1H), 2.26-2.16 (m, 1H), 2.14-1.97 (m, 5H), 1.94-1.35 (m, 15H), 1.23 (br s, 1H), 1.14 (t, J = 7.3 Hz, 3H). $[\alpha]^{26}_D$ = −31.5° (c 0.10, MeOH) LCMS (m/z) (M + H)$^+$: 644.4 |
| C71 | 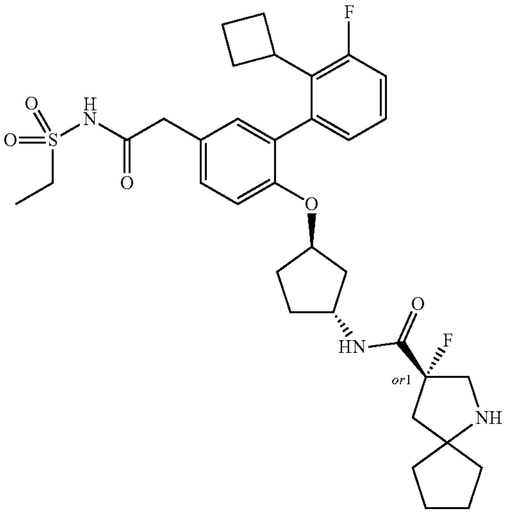 [SMILES: CCS(=O)(=O)NC(=O)Cc1ccc(O[C@@H]2CC[C@@H](NC(=O)[C@@]3(F)CNC4(CCCC4)C3)C2)c(-c2cccc(F)c2C2CCC2)c1] (3ξ)-N-[(1R,3R)-3-({2'-cyclobutyl-5-[2-(ethanesulfonamido)-2-oxoethyl]-3'-fluoro[1,1'-biphenyl]-2-yl}oxy)cyclopentyl]-3-fluoro-1-azaspiro[4.4]nonane-3-carboxamide | $^1$H NMR (400 MHz, DMSO-$d_6$) δ = 10.06-9.34 (m, 1H), 8.54 (br s, 1H), 7.28-7.18 (m, 2H), 7.12 (br dd, J = 8.4, 11.4 Hz, 1H), 7.05-6.97 (m, 2H), 6.87 (br d, J = 7.5 Hz, 1H), 4.83 (br s, 1H), 4.18-3.99 (m, 1H), 3.81-3.60 (m, 2H), 3.57 (s, 3H), 3.49-3.41 (m, 1H), 3.32-3.28 (m, 1H), 2.45-2.36 (m, 1H), 2.20 (br s, 1H), 2.13-1.95 (m, 5H), 1.94-1.36 (m, 15H), 1.24 (br s, 1H), 1.15 (t, J = 7.3 Hz, 3H). $[\alpha]^{26}_D$ = −43.9° (c 0.10, MeOH) LCMS (m/z) (M + H)$^+$: 644.5 |

TABLE 3-continued

| Ex. | Structure and Name | Characterization Data ($^1$H NMR, optical rotation, and/or LCMS) |
|---|---|---|
| C72 | 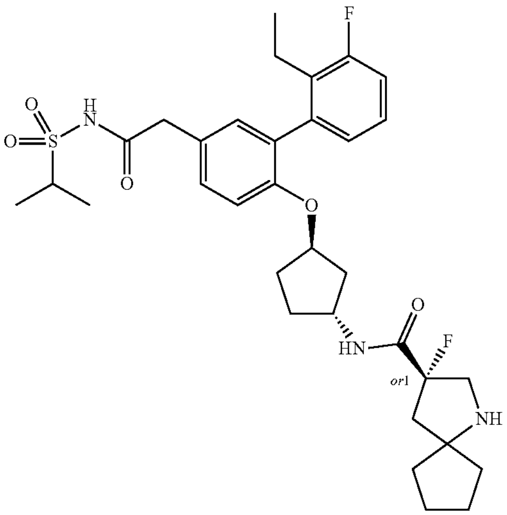 [SMILES: CCc1c(F)cccc1-c1cc(CC(=O)NS(=O)(=O)C(C)C)ccc1O[C@@H]1CC[C@@H](NC(=O)[C@@]2(F)CNC3(CCCC3)C2)C1] (3ξ)-N-[(1R,3R)-3-({2'-ethyl-3'-fluoro-5-[2-oxo-2-(propane-2-sulfonamido)ethyl][1,1'-biphenyl]-2-yl}oxy)cyclopentyl]-3-fluoro-1-azaspiro[4.4]nonane-3-carboxamide | $^1$H NMR (400 MHz, DMSO-$d_6$) δ 10.17-9.34 (m, 1H), 8.61-8.43 (m, 1H), 7.31-7.19 (m, 2H), 7.19-7.09 (m, 1H), 7.08-6.98 (m, 2H), 6.94-6.78 (m, 1H), 4.91-4.78 (m, 1H), 4.19-3.99 (m, 1H), 3.81-3.60 (m, 2H), 3.60-3.48 (m, 4H), 2.45-2.22 (m, 3H), 2.18-1.96 (m, 3H), 1.91-1.61 (m, 10H), 1.59-1.39 (m, 2H), 1.29-1.12 (m, 6H), 1.00-0.80 (m, 3H). $[\alpha]^{27}_D$ = −123.6° (c 0.10, MeOH) LCMS (m/z) $(M + H)^+$: 632.3 |
| C73 | 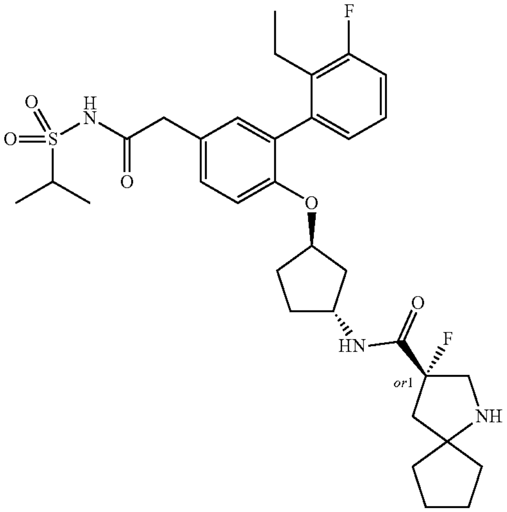 [SMILES: CCc1c(F)cccc1-c1cc(CC(=O)NS(=O)(=O)C(C)C)ccc1O[C@@H]1CC[C@@H](NC(=O)[C@@]2(F)CNC3(CCCC3)C2)C1] (3ξ)-N-[(1R,3R)-3-({2'-ethyl-3'-fluoro-5-[2-oxo-2-(propane-2-sulfonamido)ethyl][1,1'-biphenyl]-2-yl}oxy)cyclopentyl]-3-fluoro-1-azaspiro[4.4]nonane-3-carboxamide | $^1$H NMR (400 MHz, DMSO-$d_6$) δ = 10.08-9.50 (m, 1H), 8.63-8.41 (m, 1H), 7.30-7.20 (m, 2H), 7.18-7.10 (m, 1H), 7.08-6.98 (m, 2H), 6.93-6.78 (m, 1H), 4.94-4.75 (m, 1H), 4.20-3.98 (m, 1H), 3.79-3.62 (m, 2H), 3.62-3.51 (m, 4H), 2.45-2.20 (m, 3H), 2.20-1.99 (m, 3H), 1.94-1.60 (m, 10H), 1.58-1.37 (m, 2H), 1.27-1.17 (m, 6H), 0.99-0.84 (m, 3H). $[\alpha]^{27}_D$ = −88.5° (c 0.10, MeOH) LCMS (m/z) $(M + H)^+$: 632.3 |

TABLE 3-continued

| Ex. | Structure and Name | Characterization Data ($^1$H NMR, optical rotation, and/or LCMS) |
|---|---|---|
| C74 | 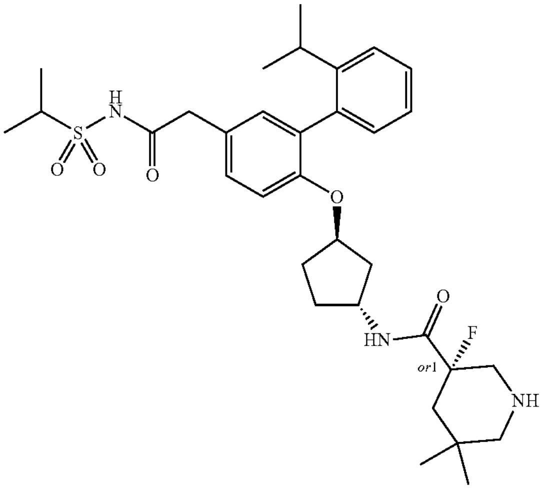 [SMILES: CC(C)c1ccccc1-c1cc(CC(=O)NS(=O)(=O)C(C)C)ccc1O[C@@H]1CC[C@@H](NC(=O)[C@@]2(F)CNCC(C)(C)C2)C1] (3ξ)-3-fluoro-5,5-dimethyl-N-[(1R,3R)-3-({5-[2-oxo-2-(propane-2-sulfonamido)ethyl]-2'-(propan-2-yl)[1,1'-biphenyl]-2-yl}oxy)cyclopentyl]piperidine-3-carboxamide | $^1$H NMR (400 MHz, DMSO-$d_6$) δ 8.13-8.03 (m, 1H), 7.38-7.25 (m, 2H), 7.24-7.12 (m, 2H), 7.04-6.92 (m, 3H), 4.78 (br d, J = 2.38 Hz, 1H), 4.09-3.94 (m, 1 H), 3.55-3.49 (m, 3H) 2.94-2.56 (m, 4H), 2.39 (br d, J = 13.63 Hz, 1H), 2.15-1.90 (m, 1H), 1.88-1.24 (m, 8H) 1.20-1.10 (m, 9H) 1.01 (s, 3H), 0.95 (d, J = 6.63 Hz, 3H) 0.81 (d, J = 2.38 Hz, 3H). LCMS (m/z) $(M + H)^+$: 616.3 |
| C75 | 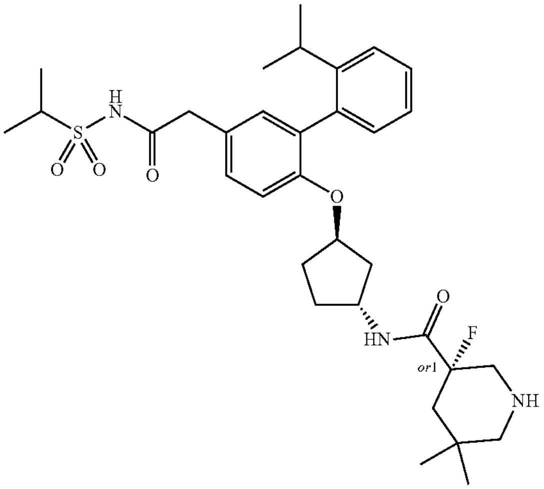 [SMILES: CC(C)c1ccccc1-c1cc(CC(=O)NS(=O)(=O)C(C)C)ccc1O[C@@H]1CC[C@@H](NC(=O)[C@@]2(F)CNCC(C)(C)C2)C1] (3ξ)-3-fluoro-5,5-dimethyl-N-[(1R,3R)-3-({5-[2-oxo-2-(propane-2-sulfonamido)ethyl]-2'-(propan-2-yl)[1,1'-biphenyl]-2-yl}oxy)cyclopentyl]piperidine-3-carboxamide | $^1$H NMR (400 MHz, DMSO-$d_6$) δ 8.15-7.99 (m, 1 H) 7.37-7.26 (m, 2H) 7.24-7.12 (m, 2H) 7.03-6.93 (m, 3H) 4.86-4.73 (m, 1H) 4.11-3.96 (m, 1H) 3.57-3.51 (m, 3H) 2.95-2.56 (m, 4H) 2.38 (br d, J = 13.13 Hz, 1H) 2.14-1.90 (m, 1H) 1.89-1.22 (m, 8H) 1.20-1.11 (m, 9H) 1.01 (s, 3 H) 0.95 (dd, J = 6.82, 1.19 Hz, 3H) 0.82 (s, 3H). LCMS (m/z) $(M + H)^+$: 616.3 |

TABLE 3-continued

| Ex. | Structure and Name | Characterization Data ($^1$H NMR, optical rotation, and/or LCMS) |
|---|---|---|
| C76 | 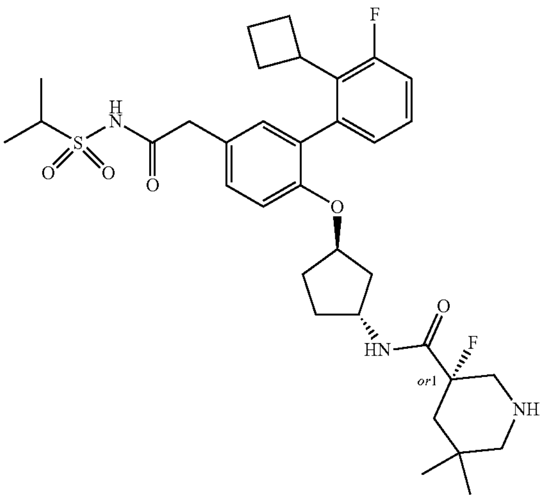 [SMILES: CC(C)S(=O)(=O)NC(=O)Cc1ccc(O[C@@H]2CC[C@@H](NC(=O)[C@@]3(F)CNCC(C)(C)C3)C2)c(-c2cccc(F)c2C2CCC2)c1] (3ξ)-N-[(1R,3R)-3-({2'-cyclobutyl-3'-fluoro-5-[2-oxo-2-(propane-2-sulfonamido)ethyl][1,1'-biphenyl]-2-yl}oxy)cyclopentyl]-3-fluoro-5,5-dimethylpiperidine-3-carboxamide | $^1$H NMR (400 MHz, DMSO-$d_6$) δ 0.99-0.94 (m, 3H) 1.14-1.09 (m, 3H) 1.23-1.19 (m, 6H) 1.51 (s, 2 H) 1.90-1.63 (m, 8H) 2.10-1.95 (m, 3H) 2.24-2.14 (m, 1 H) 3.05-2.89 (m, 2H) 3.47-3.44 (m, 1H) 3.59-3.52 (m, 3 H) 4.13-3.93 (m, 1H) 4.81 (br d, J = 2.38 Hz, 1H) 6.88-6.82 (m, 1H) 7.03-6.97 (m, 1H) 6.98-6.97 (m, 1H) 7.14-7.07 (m, 1 H) 7.25-7.18 (m, 2H) 8.50-8.34 (m, 1 H) 8.80-8.60 (m, 1H) 9.64-9.32 (m, 1H). LCMS (m/z) (M + H)$^+$: 646.3 |
| C77 | 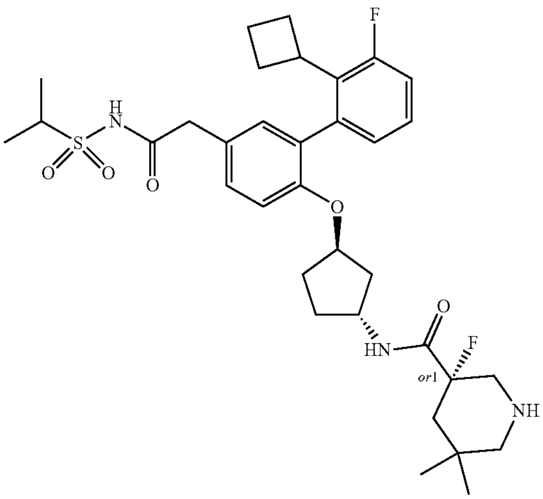 [SMILES: CC(C)S(=O)(=O)NC(=O)Cc1ccc(O[C@@H]2CC[C@@H](NC(=O)[C@@]3(F)CNCC(C)(C)C3)C2)c(-c2cccc(F)c2C2CCC2)c1] (3ξ)-N-[(1R,3R)-3-({2'-cyclobutyl-3'-fluoro-5-[2-oxo-2-(propane-2-sulfonamido)ethyl][1,1'-biphenyl]-2-yl}oxy)cyclopentyl]-3-fluoro-5,5-dimethylpiperidine-3-carboxamide | $^1$H NMR (400 MHz, DMSO-$d_6$) δ 0.96 (s, 3H) 1.12 (s, 3H) 1.21 (d, J = 6.88 Hz, 6H) 1.57-1.39 (m, 2H) 1.90-1.65 (m, 8H) 2.10-1.96 (m, 3H) 2.23-2.14 (m, 1H) 3.04-2.89 (m, 2H) 3.43 (br s, 1H) 3.61-3.52 (m, 3H) 4.15-3.93 (m, 1H) 4.71 (s, 1H) 6.90-6.82 (m, 1H) 7.05-6.97 (m, 2H) 7.16-7.06 (m, 1H) 7.26-7.18 (m, 2H) 8.35 (s, 1H) 8.82-8.58 (m, 1H) 9.59-9.43 (m, 1 H). LCMS (m/z) (M + H)$^+$: 646.3 |

TABLE 3-continued

| Ex. | Structure and Name | Characterization Data ($^1$H NMR, optical rotation, and/or LCMS) |
|---|---|---|
| C78 | 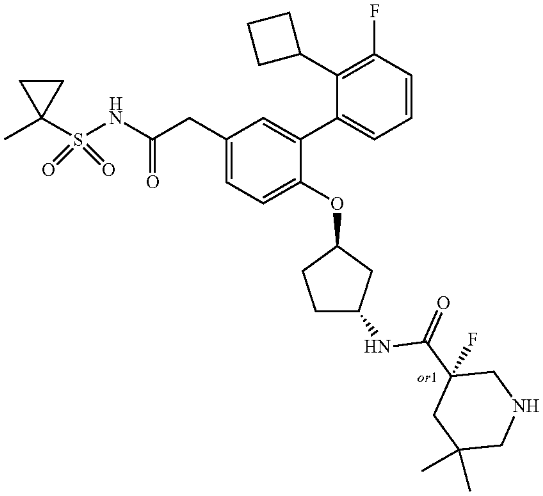 [SMILES: CC1(C)CNC[C@](F)(C(=O)N[C@@H]2CC[C@@H](Oc3ccc(CC(=O)NS(=O)(=O)C4(C)CC4)cc3-c3cccc(F)c3C3CCC3)C2)C1] (3ξ)-N-[(1R,3R)-3-({2'-cyclobutyl-3'-fluoro-5-[2-(1-methylcyclopropane-1-sulfonamido)-2-oxoethyl][1,1'-biphenyl]-2-yl}oxy)cyclopentyl]-3-fluoro-5,5-dimethylpiperidine-3-carboxamide | $^1$H NMR (400 MHz, DMSO-$d_6$) δ 0.90-0.82 (m, 2 H) 0.99-0.92 (m, 3 H) 1.14-1.09 (m, 3 H) 1.37-1.33 (m, 5 H) 1.57-1.42 (m, 2 H) 1.90-1.64 (m, 8 H) 1.97 (br s, 3 H) 2.26-2.14 (m, 1 H) 2.97-2.86 (m, 1 H) 3.05-2.98 (m, 1 H) 3.50-3.35 (m, 3 H) 3.58-3.53 (m, 2 H) 4.05 (br dd, J = 15.45, 7.82 Hz, 1 H) 4.81 (br s, 1 H) 6.89-6.81 (m, 1 H) 7.04-6.97 (m, 2 H) 7.14-7.07 (m, 1 H) 7.26-7.18 (m, 2 H) 8.48-8.33 (m, 1 H) 8.91-8.68 (m, 1 H) 9.76-9.55 (m, 1 H). LCMS (m/z) $(M + H)^+$: 658.3 |
| C79 | 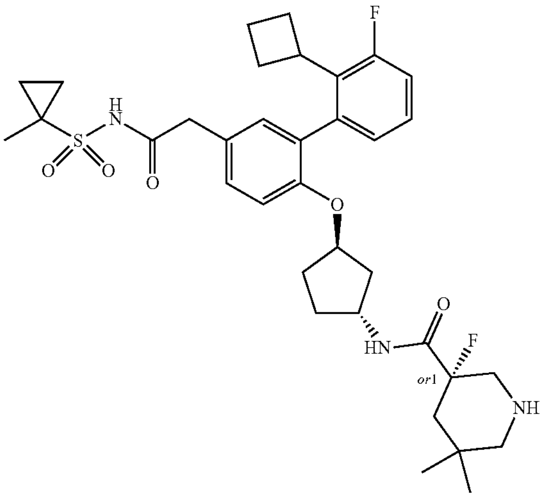 [SMILES: CC1(C)CNC[C@](F)(C(=O)N[C@@H]2CC[C@@H](Oc3ccc(CC(=O)NS(=O)(=O)C4(C)CC4)cc3-c3cccc(F)c3C3CCC3)C2)C1] (3ξ)-N-[(1R,3R)-3-({2'-cyclobutyl-3'-fluoro-5-[2-(1-methylcyclopropane-1-sulfonamido)-2-oxoethyl][1,1'-biphenyl]-2-yl}oxy)cyclopentyl]-3-fluoro-5,5-dimethylpiperidine-3-carboxamide | $^1$H NMR (400 MHz, DMSO-$d_6$) δ 0.89-0.83 (m, 2 H) 0.96 (s, 3 H) 1.14-1.10 (m, 3 H) 1.38-1.32 (m, 5 H) 1.57-1.40 (m, 2 H) 1.91-1.65 (m, 8 H) 1.95 (s, 3 H) 2.24-2.15 (m, 1 H) 2.95-2.89 (m, 1 H) 3.04-2.97 (m, 1 H) 3.48-3.31 (m, 3 H) 3.58-3.53 (m, 2 H) 4.06-4.00 (m, 1 H) 4.85-4.77 (m, 1 H) 6.89-6.83 (m, 1 H) 7.04-6.98 (m, 2 H) 7.15-7.06 (m, 1 H) 7.27-7.18 (m, 2 H) 8.53-8.30 (m, 1 H) 8.93-8.63 (m, 1 H) 9.88-9.62 (m, 1 H). LCMS (m/z) $(M + H)^+$: 658.3 |

TABLE 3-continued

| Ex. | Structure and Name | Characterization Data ($^1$H NMR, optical rotation, and/or LCMS) |
|---|---|---|
| C80 | 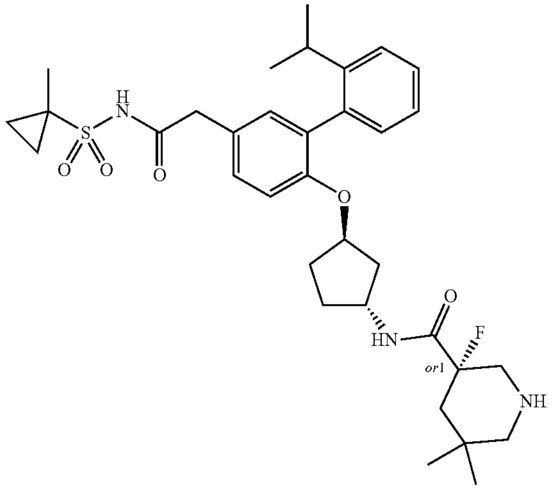 [SMILES: CC(C)c1ccccc1-c1cc(CC(=O)NS(=O)(=O)C2(C)CC2)ccc1O[C@@H]1CC[C@@H](NC(=O)[C@@]2(F)CNCC(C)(C)C2)C1]<br>(3ξ)-3-fluoro-5,5-dimethyl-N-[(1R,3R)-3-{5-[2-(1-methylcyclopropane-1-sulfonamido)-2-oxoethyl]-2'-(propan-2-yl)[1,1'-biphenyl]-2-yl}oxy)cyclopentyl]piperidine-3-carboxamide | $^1$H NMR (400 MHz, DMSO-$d_6$) δ 8.12-8.01 (m, 1 H) 7.39-7.27 (m, 2 H) 7.25-7.13 (m, 2 H) 7.04-6.94 (m, 3 H) 4.80 (br d, J = 3.00 Hz, 1 H) 4.11-3.94 (m, 1 H) 3.51 (s, 2 H) 2.97-2.53 (m, 4 H) 2.41-2.30 (m, 1 H) 2.16-1.90 (m, 1 H) 1.90-1.37 (m, 7 H) 1.35-1.22 (m, 6 H) 1.15 (d, J = 6.75 Hz, 3 H) 1.01 (s, 3 H) 0.96 (dd, J = 6.75, 1.38 Hz, 3 H) 0.82 (s, 5 H).<br>LCMS (m/z) (M + H)$^+$: 628.3 |
| C81 | 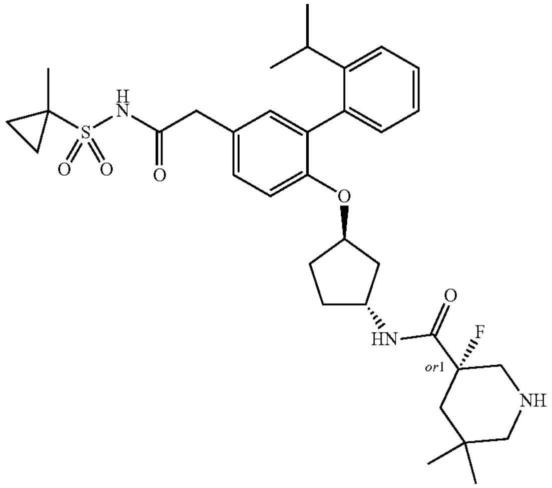 [SMILES: CC(C)c1ccccc1-c1cc(CC(=O)NS(=O)(=O)C2(C)CC2)ccc1O[C@@H]1CC[C@@H](NC(=O)[C@@]2(F)CNCC(C)(C)C2)C1]<br>(3ξ)-3-fluoro-5,5-dimethyl-N-[(1R,3R)-3-({5-[2-(1-methylcyclopropane-1-sulfonamido)-2-oxoethyl]-2'-(propan-2-yl)[1,1'-biphenyl]-2-yl}oxy)cyclopentyl]piperidine-3-carboxamide | $^1$H NMR (400 MHz, DMSO-$d_6$) δ 8.04 (br s, 1H), 7.36-7.29 (m, 2H), 7.22-7.14 (m, 2H), 7.01-6.96 (m, 2H), 4.78 (br s, 1H), 4.09-3.95 (m, 1H), 3.46 (s, 2H), 2.91-2.78 (m, 2H), 2.77-2.66 (m, 2H), 2.35-2.31 (m, 1H), 2.14-1.90 (m, 1H), 1.86-1.64 (m, 4H), 1.63-1.34 (m, 4H), 1.31 (s, 3H), 1.30-1.20 (m, 3H), 1.15 (br d, J = 6.8 Hz, 3H), 1.00 (s, 3H), 0.96 (d, J = 6.8 Hz, 3H), 0.80 (d, J = 2.4 Hz, 3H), 0.77-0.71 (m, 2H).<br>LCMS (m/z) (M + H)$^+$: 628.2 |

TABLE 3-continued

| Ex. | Structure and Name | Characterization Data ($^1$H NMR, optical rotation, and/or LCMS) |
|---|---|---|
| C82 | 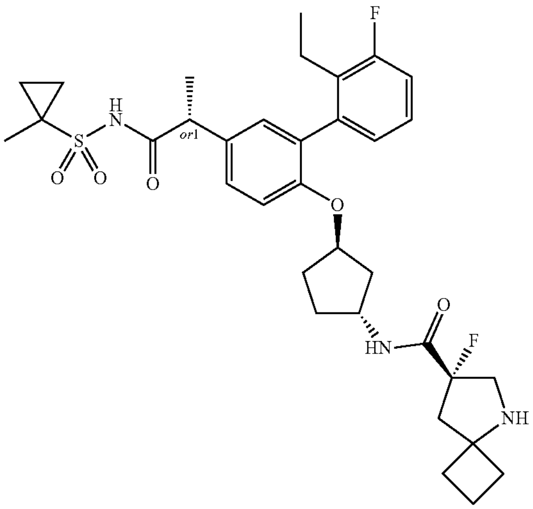 [SMILES: CCc1c(F)cccc1-c1cc([C@@H](C)C(=O)NS(=O)(=O)C2(C)CC2)ccc1O[C@@H]1CC[C@@H](NC(=O)[C@@]2(F)CNC3(CCC3)C2)C1] (7S)-N-[(1R,3R)-3-({2'-ethyl-3'-fluoro-5-[(2ξ)-1-(1-methylcyclopropane-1-sulfonamido)-1-oxopropan-2-yl][1,1'-biphenyl]-2-yl}oxy)cyclopentyl]-7-fluoro-5-azaspiro[3.4]octane-7-carboxamide | $^1$H NMR (400 MHz, MeOD) δ 7.33 (br d, J = 8.6 Hz, 1H), 7.23-7.15 (m, 1H), 7.12 (dd, J = 2.1, 4.5 Hz, 1H), 7.05-6.96 (m, 2H), 6.88 (br d, J = 7.7 Hz, 1H), 4.83-4.77 (m, 1H), 4.21-4.10 (m, 1H), 3.67 (q, J = 6.9 Hz, 1H), 3.50-3.32 (m, 1H), 3.25-3.14 (m, 1H), 2.67-2.51 (m, 1H), 2.50-2.28 (m, 3H), 2.23-1.62 (m, 11H), 1.55-1.38 (m, 6H), 1.31 (d, J = 10.3 Hz, 3H), 1.02-0.91 (m, 3H), 0.83-0.69 (m, 2H). LCMS (m/z) (M + H)$^+$: 644.3 |
| C83 | 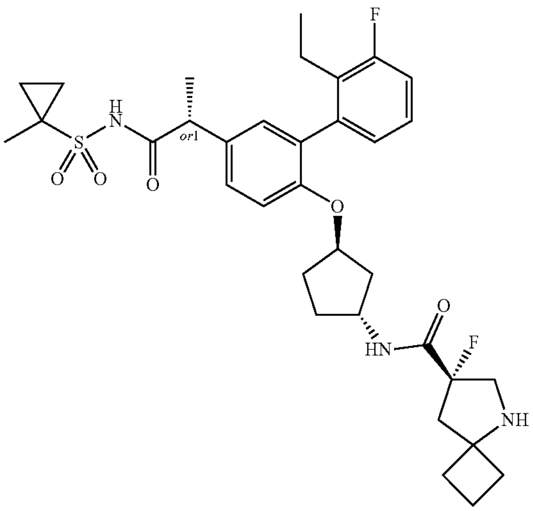 [SMILES: CCc1c(F)cccc1-c1cc([C@@H](C)C(=O)NS(=O)(=O)C2(C)CC2)ccc1O[C@@H]1CC[C@@H](NC(=O)[C@@]2(F)CNC3(CCC3)C2)C1] (7S)-N-[(1R,3R)-3-({2'-ethyl-3'-fluoro-5-[(2ξ)-1-(1-methylcyclopropane-1-sulfonamido)-1-oxopropan-2-yl][1,1'-biphenyl]-2-yl}oxy)cyclopentyl]-7-fluoro-5-azaspiro[3.4]octane-7-carboxamide | $^1$H NMR (400 MHz, MeOD) δ 7.33 (br d, J = 8.6 Hz, 1H), 7.23-7.15 (m, 1H), 7.12 (s, 1H), 7.05-6.95 (m, 2H), 6.88 (dd, J = 7.6, 13.6 Hz, 1H), 4.78 (br s, 1H), 4.22-4.06 (m, 1H), 3.67 (q, J = 6.9 Hz, 1H), 3.51-3.32 (m, 1H), 3.24-3.13 (m, 1H), 2.66-2.50 (m, 1H), 2.46-2.27 (m, 3H), 2.24-1.61 (m, 11H), 1.54-1.39 (m, 6H), 1.32 (d, J = 8.1 Hz, 3H), 0.96 (dt, J = 2.6, 7.3 Hz, 3H), 0.82-0.70 (m, 2H). LCMS (m/z) (M + H)$^+$: 644.3 |

TABLE 3-continued

| Ex. | Structure and Name | Characterization Data ($^1$H NMR, optical rotation, and/or LCMS) |
|---|---|---|
| C84 | 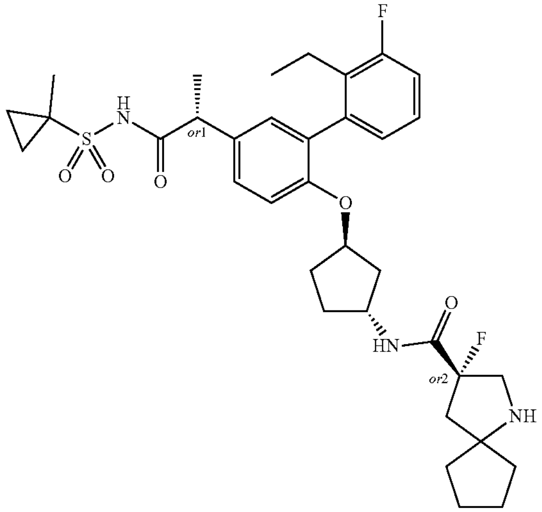 [SMILES: CCc1c(F)cccc1-c1cc([C@@H](C)C(=O)NS(=O)(=O)C2(C)CC2)ccc1O[C@@H]1CC[C@@H](NC(=O)[C@@]2(F)CNC3(CCCC3)C2)C1] (3ξ)-N-[(1R,3R)-3-({2'-ethyl-3'-fluoro-5-[(2ξ)-1-(1-methylcyclopropane-1-sulfonamido)-1-oxopropan-2-yl][1,1'-biphenyl]-2-yl}oxy)cyclopentyl]-3-fluoro-1-azaspiro[4.4]nonane-3-carboxamide | $^1$H NMR (400 MHz, MeOD) δ 7.34 (br d, J = 8.6 Hz, 1H), 7.23-7.15 (m, 1H), 7.12 (br d, J = 2.3 Hz, 1H), 7.06-6.96 (m, 2H), 6.88 (dd, J = 4.0, 7.5 Hz, 1H), 4.83-4.78 (m, 1H), 4.22-4.10 (m, 1H), 3.71-3.63 (m, 1H), 3.51-3.37 (m, 1H), 3.28-3.20 (m, 1H), 2.67-2.50 (m, 1H), 2.44-2.30 (m, 2H), 2.24-1.63 (m, 14H), 1.54-1.38 (m, 6H), 1.31 (d, J = 9.4 Hz, 3H), 0.97 (t, J = 7.5 Hz, 3H), 0.83-0.69 (m, 2H). $[\alpha]^{25}_D$ = −60.0° (c 0.11, MeOH) LCMS (m/z) (M + H)$^+$: 658.3 |
| C85 | 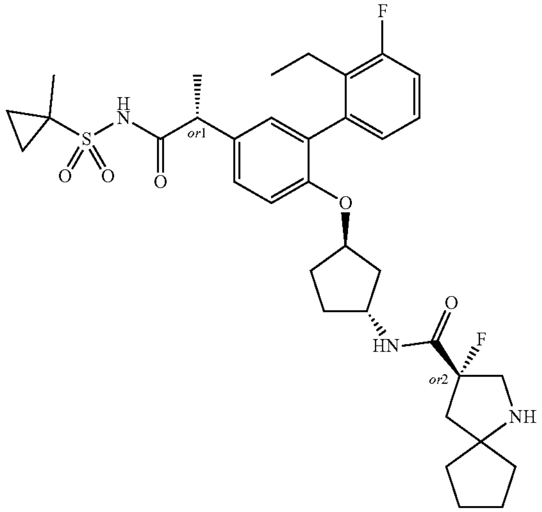 [SMILES: CCc1c(F)cccc1-c1cc([C@@H](C)C(=O)NS(=O)(=O)C2(C)CC2)ccc1O[C@@H]1CC[C@@H](NC(=O)[C@@]2(F)CNC3(CCCC3)C2)C1] (3ξ)-N-[(1R,3R)-3-({2'-ethyl-3'-fluoro-5-[(2ξ)-1-(1-methylcyclopropane-1-sulfonamido)-1-oxopropan-2-yl][1,1'-biphenyl]-2-yl}oxy)cyclopentyl]-3-fluoro-1-azaspiro[4.4]nonane-3-carboxamide | $^1$H NMR (400 MHz, MeOD) δ 7.34 (br d, J = 8.6 Hz, 1H), 7.24-7.15 (m, 1H), 7.12 (br d, J = 3.8 Hz, 1H), 7.06-6.96 (m, 2H), 6.88 (dd, J = 2.8, 7.3 Hz, 1H), 4.83-4.79 (m, 1H), 4.24-4.08 (m, 1H), 3.66 (q, J = 6.6 Hz, 1H), 3.53-3.36 (m, 1H), 3.28-3.19 (m, 1H), 2.56 (td, J = 6.8, 13.9 Hz, 1H), 2.47-2.29 (m, 2H), 2.23-1.62 (m, 14H), 1.54-1.39 (m, 6H), 1.31 (d, J = 9.3 Hz, 3H), 0.97 (t, J = 7.5 Hz, 3H), 0.81-0.71 (m, 2H). $[\alpha]^{25}_D$ = −46.7° (c 0.11, MeOH) LCMS (m/z) (M + H)$^+$: 658.2 |

TABLE 3-continued

| Ex. | Structure and Name | Characterization Data ($^1H$ NMR, optical rotation, and/or LCMS) |
|---|---|---|
| C86 | 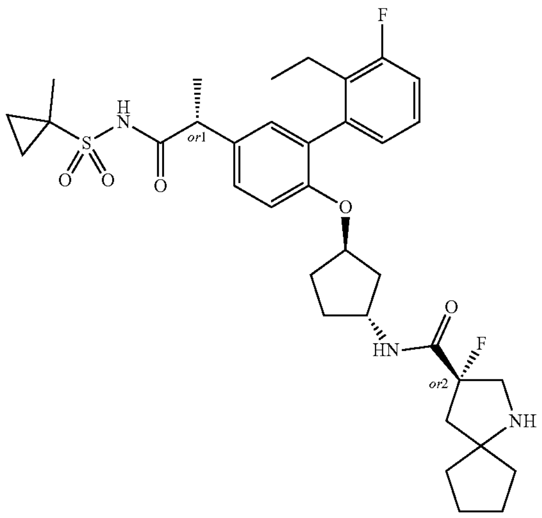 [SMILES: CCc1c(F)cccc1-c1cc([C@@H](C)C(=O)NS(=O)(=O)C2(C)CC2)ccc1O[C@@H]1CC[C@@H](NC(=O)[C@@]2(F)CNC3(CCCC3)C2)C1] (3ξ)-N-[(1R,3R)-3-({2'-ethyl-3'-fluoro-5-[(2ξ)-1-(1-methylcyclopropane-1-sulfonamido)-1-oxopropan-2-yl][1,1'-biphenyl]-2-yl}oxy)cyclopentyl]-3-fluoro-1-azaspiro[4.4]nonane-3-carboxamide | $^1H$ NMR (400 MHz, MeOD) δ 7.34 (br d, J = 8.6 Hz, 1H), 7.24-7.15 (m, 1H), 7.12 (s, 1H), 7.06-6.95 (m, 2H), 6.88 (dd, J = 7.6, 13.4 Hz, 1H), 4.83-4.79 (m, 1H), 4.22-4.10 (m, 1H), 3.66 (q, J = 6.8 Hz, 1H), 3.51-3.36 (m, 1H), 3.28-3.19 (m, 1H), 2.71-2.48 (m, 1H), 2.47-2.28 (m, 2H), 2.24-1.62 (m, 14H), 1.53-1.39 (m, 6H), 1.32 (d, J = 7.6 Hz, 3H), 0.97 (dt, J = 4.3, 7.3 Hz, 3H), 0.82-0.69 (m, 2H). $[\alpha]^{25}_D$ = +69.1° (c 0.11, MeOH) LCMS (m/z) $(M + H)^+$: 658.3 |
| C87 | 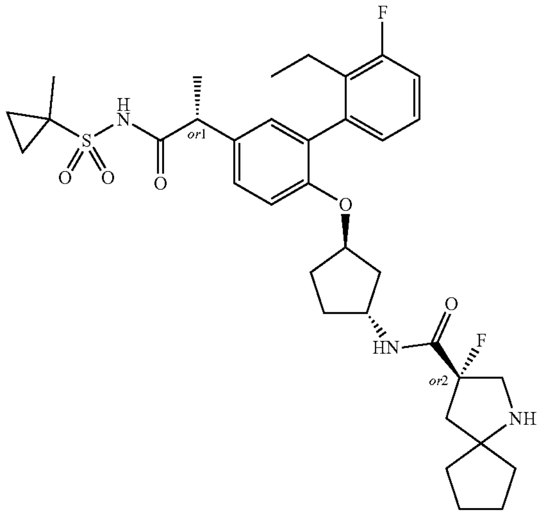 [SMILES: CCc1c(F)cccc1-c1cc([C@@H](C)C(=O)NS(=O)(=O)C2(C)CC2)ccc1O[C@@H]1CC[C@@H](NC(=O)[C@@]2(F)CNC3(CCCC3)C2)C1] (3ξ)-N-[(1R,3R)-3-({2'-ethyl-3'-fluoro-5-[(2ξ)-1-(1-methylcyclopropane-1-sulfonamido)-1-oxopropan-2-yl][1,1'-biphenyl]-2-yl}oxy)cyclopentyl]-3-fluoro-1-azaspiro[4.4]nonane-3-carboxamide | $^1H$ NMR (400 MHz, MeOD) δ 7.34 (br d, J = 8.6 Hz, 1H), 7.23-7.15 (m, 1H), 7.12 (s, 1H), 7.05-6.96 (m, 2H), 6.88 (dd, J = 7.5, 13.4 Hz, 1H), 4.82-4.79 (m, 1H), 4.22-4.10 (m, 1H), 3.66 (q, J = 6.9 Hz, 1H), 3.50-3.37 (m, 1H), 3.27-3.20 (m, 1H), 2.63-2.50 (m, 1H), 2.46-2.31 (m, 2H), 2.24-1.64 (m, 14H), 1.53-1.39 (m, 6H), 1.32 (d, J = 7.8 Hz, 3H), 0.96 (dt, J = 3.6, 7.4 Hz, 3H), 0.80-0.68 (m, 2H). $[\alpha]^{25}_D$ = +61.8° (c 0.11, MeOH) LCMS (m/z) $(M + H)^+$: 658.3 |

TABLE 3-continued

| Ex. | Structure and Name | Characterization Data ($^1$H NMR, optical rotation, and/or LCMS) |
|---|---|---|
| C88 | 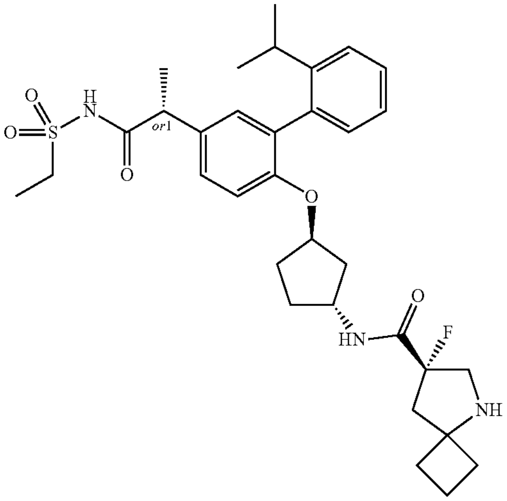 [SMILES: CCS(=O)(=O)NC(=O)[C@H](C)c1ccc(O[C@@H]2CC[C@@H](NC(=O)[C@@]3(F)CNC4(CCC4)C3)C2)c(-c2ccccc2C(C)C)c1] (7S)-N-[(1R,3R)-3-({5-[(2ξ)-1-(ethanesulfonamido)-1-oxopropan-2-yl]-2'-(propan-2-yl)[1,1'-biphenyl]-2-yl}oxy)cyclopentyl]-7-fluoro-5-azaspiro[3.4]octane-7-carboxamide | $^1$H NMR (400 MHz, MeOD) δ 7.37-7.24 (m, 3H), 7.15 (tt, J = 1.7, 7.3 Hz, 1H), 7.10-7.06 (m, 1H), 7.05-6.99 (m, 1H), 6.96 (d, J = 8.6 Hz, 1H), 4.80 (br dd, J = 2.6, 5.2 Hz, 1H), 4.24-4.07 (m, 1H), 3.64 (q, J = 7.0 Hz, 1H), 3.48-3.35 (m, 1H), 3.29-3.18 (m, 3H), 2.78 (quin, J = 6.8 Hz, 1H), 2.53-2.31 (m, 2H), 2.30-1.56 (m, 11H), 1.53-1.44 (m, 1H), 1.42 (d, J = 7.1 Hz, 3H), 1.22-1.10 (m, 6H), 1.02 (t, J = 6.4 Hz, 3H). $[\alpha]^{25}_D$ = −69.1° (c 0.11, MeOH) LCMS (m/z) $(M + H)^+$: 614.3 |
| C89 | 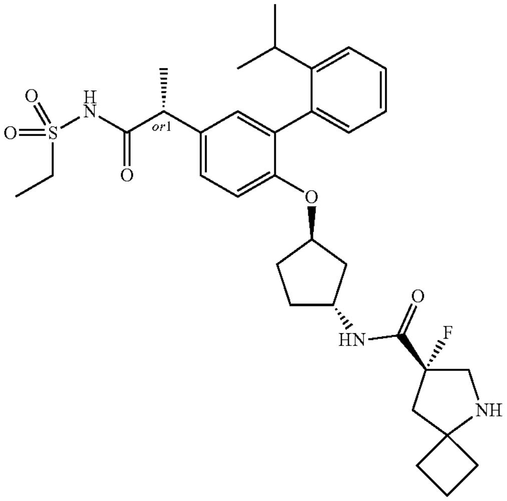 [SMILES: CCS(=O)(=O)NC(=O)[C@H](C)c1ccc(O[C@@H]2CC[C@@H](NC(=O)[C@@]3(F)CNC4(CCC4)C3)C2)c(-c2ccccc2C(C)C)c1] (7S)-N-[(1R,3R)-3-({5-[(2ξ)-1-(ethanesulfonamido)-1-oxopropan-2-yl]-2'-(propan-2-yl)[1,1'-biphenyl]-2-yl}oxy)cyclopentyl]-7-fluoro-5-azaspiro[3.4]octane-7-carboxamide | $^1$H NMR (400 MHz, MeOD) δ 7.36-7.24 (m, 3H), 7.18-7.12 (m, 1H), 7.09 (d, J = 1.8 Hz, 1H), 7.01 (ddd, J = 1.2, 7.5, 11.0 Hz, 1H), 6.96 (d, J = 8.4 Hz, 1H), 4.80 (br d, J = 3.1 Hz, 1H), 4.15 (td, J = 7.6, 15.4 Hz, 1H), 3.64 (q, J = 6.8 Hz, 1H), 3.47-3.34 (m, 1H), 3.28-3.20 (m, 3H), 2.84-2.72 (m, 1H), 2.52-2.32 (m, 2H), 2.29-1.60 (m, 11H), 1.53-1.44 (m, 1H), 1.42 (dd, J = 1.0, 7.0 Hz, 3H), 1.21-1.11 (m, 6H), 1.02 (d, J = 6.8 Hz, 3H). $[\alpha]^{25}_D$ = +18.8° (c 0.11, MeOH) LCMS (m/z) $(M + H)^+$: 614.3 |

TABLE 3-continued

| Ex. | Structure and Name | Characterization Data ($^1$H NMR, optical rotation, and/or LCMS) |
|---|---|---|
| C90 | 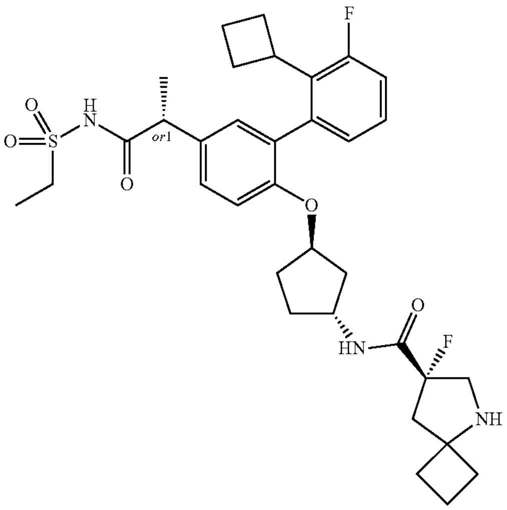 [SMILES: CCS(=O)(=O)NC(=O)[C@H](C)c1ccc(O[C@@H]2CC[C@@H](NC(=O)[C@@]3(F)CNC4(CCC4)C3)C2)c(-c2cccc(F)c2C2CCC2)c1]<br>(7S)-N-[(1R,3R)-3-({2'-cyclobutyl-5-[(2ξ)-1-(ethanesulfonamido)-1-oxopropan-2-yl]-3'-fluoro[1,1'-biphenyl]-2-yl}oxy)cyclopentyl]-7-fluoro-5-azaspiro[3.4]octane-7-carboxamide | $^1$H NMR (DMSO-$d_6$, 400 MHz) δ 8.2-8.1 (m, 1H), 7.3-7.2 (m, 2H), 7.1-7.0 (m, 3H), 6.9-6.8 (m, 1H), 4.9-4.7 (m, 1H), 4.2-4.0 (m, 1H), 3.8-3.6 (m, 2H), 3.21 (br d, 2H, J = 7.3 Hz), 3.2-3.0 (m, 2H), 2.3-1.9 (m, 11H), 1.9-1.6 (m, 9H), 1.6-1.4 (m, 2H), 1.4-1.2 (m, 3H), 1.1-1.0 (m, 3H). LCMS (m/z) (M + H)$^+$: 644.3 |
| C91 | 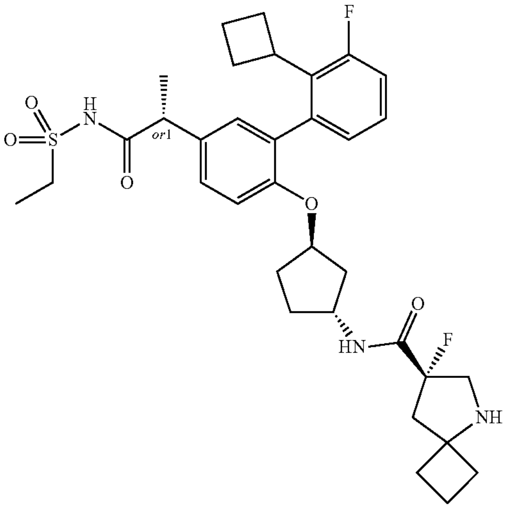 [SMILES: CCS(=O)(=O)NC(=O)[C@H](C)c1ccc(O[C@@H]2CC[C@@H](NC(=O)[C@@]3(F)CNC4(CCC4)C3)C2)c(-c2cccc(F)c2C2CCC2)c1]<br>(7S)-N-[(1R,3R)-3-({2'-cyclobutyl-5-[(2ξ)-1-(ethanesulfonamido)-1-oxopropan-2-yl]-3'-fluoro[1,1'-biphenyl]-2-yl}oxy)cyclopentyl]-7-fluoro-5-azaspiro[3.4]octane-7-carboxamide | $^1$H NMR (DMSO-$d_6$, 400 MHz) δ 8.3-8.1 (m, 1H), 7.3-7.2 (m, 2H), 7.1-7.0 (m, 3H), 6.9-6.8 (m, 1H), 4.9-4.7 (m, 1H), 4.2-4.0 (m, 1H), 3.7-3.6 (m, 2H), 3.20 (br d, 2H, J = 7.3 Hz), 3.2-3.0 (m, 2H), 2.4-1.9 (m, 12H), 1.9-1.8 (m, 2H), 1.8-1.6 (m, 6H), 1.6-1.4 (m, 2H), 1.32 (br t, 3H, J = 6.8 Hz), 1.1-0.9 (m, 3H). LCMS (m/z) (M + H)$^+$: 644.3 |

Example D1: 2-[2'-cyclobutyl-3'-fluoro-6-({(1R, 3R)-3-[(1,4,4-trimethyl-L-prolyl)amino] cyclopentyl}oxy)[1,1'-biphenyl]-3-yl]-2-methylpropanoic acid

D1

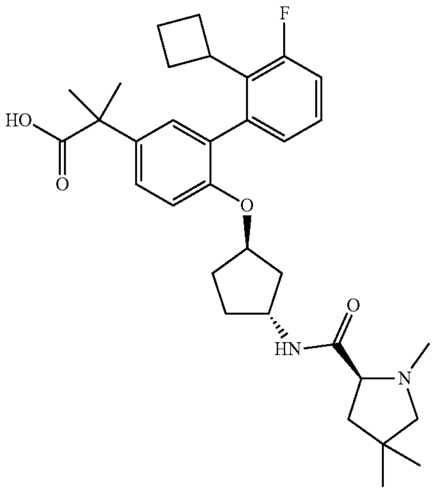

Example D1 was prepared according to General Method D.

Step 1: methyl 2-[2'-cyclobutyl-3'-fluoro-6-({(1R,3R)-3-[(1,4,4-trimethyl-L-prolyl)amino]cyclopentyl}oxy)[1,1'-biphenyl]-3-yl]-2-methylpropanoate (Dia)

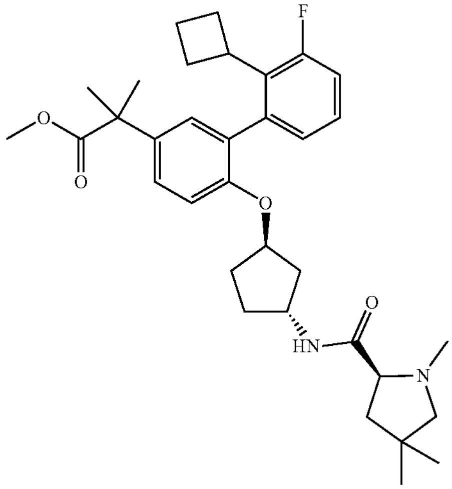

To a solution of 1,4,4-trimethyl-L-proline (35.7 mg, 0.227 mmol) in DMF (2.0 mL), HATU (90.5 mg, 0.238 mmol) was added. After stirring 1 h at 35° C., methyl 2-(6-{[(1R,3R)-3-aminocyclopentyl]oxy}-2'-cyclobutyl-3'-fluoro[1,1'-biphenyl]-3-yl)-2-methylpropanoate (A1c) (100 mg, 0.216 mmol) and DIEA (140 mg, 0.188 mL, 1.08 mmol) were added and the reaction was stirred at 35° C. for 16 h. Additional 1,4,4-trimethyl-L-proline (35.7 mg, 0.227 mmol), HATU (90.5 mg, 0.238 mmol), and DIEA (140 mg, 0.188 mL, 1.08 mmol) was added. After 2 h, the reaction was diluted with EtOAc, washed with water and brine, dried over $Na_2SO_4$, filtered, and concentrated. The residue was purified by silica gel chromatography (0-10% MeOH/DCM) to give methyl 2-[2'-cyclobutyl-3'-fluoro-6-({(1R,3R)-3-[(1,4,4-trimethyl-L-prolyl)amino]cyclopentyl}oxy)[1,1'-biphenyl]-3-yl]-2-methylpropanoate (DIa) (110 mg, 90.0%) as a yellow gum. LCMS APCI (+) 565.1 (M+H). $^1H$ NMR (400 MHz, DMSO-d6) δ=7.29-7.18 (m, 2H), 7.10 (dd, J=8.0, 11.6 Hz, H), 7.01-6.93 (m, 2H), 6.88 (t, J=5.9 Hz, 1H), 4.80 (br s, 1H), 4.13-3.96 (m, 1H), 3.58 (s, 3H), 2.69 (s, 3H), 2.27-1.62 (m, 16H), 1.49 (d, J=9.2 Hz, 6H), 1.07-0.96 (m, 6H).

Step 2: 2-[2'-cyclobutyl-3'-fluoro-6-({(1R,3R)-3-[(1,4,4-trimethyl-L-prolyl)amino]cyclopentyl}oxy)[1,1'-biphenyl]-3-yl]-2-methylpropanoic acid (Example D1)

D1

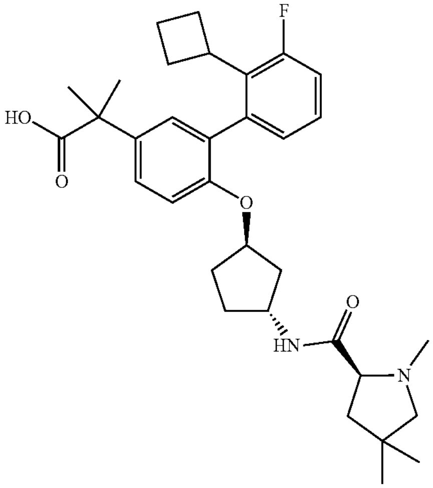

To a solution of methyl 2-[2'-cyclobutyl-3'-fluoro-6-({(1R,3R)-3-[(1,4,4-trimethyl-L-prolyl)amino]cyclopentyl}oxy)[1,1'-biphenyl]-3-yl]-2-methylpropanoate (Dia) (110 mg, 0.195 mmol) in THF (2.0 mL) and water (0.50 mL), LiOH hydrate (40.9 mg, 0.974 mmol) was added. After stirring for 16 h at 35° C., more water (0.50 mL) and LiOH hydrate (40.9 mg, 0.974 mmol) were added. The reaction was stirred at 35° C. for 5 h, and then the temperature was increased to 60° C. and the reaction was stirred for 3 days. The reaction was acidified to pH ~2 with concentrated HCl then extracted with EtOAc (3×). The combined organics were concentrated and the residue was purified by Prep HPLC (Boston Prime C18 150×30 mm, 5 uM, Mobile phase A: Water+0.05% HCl, Mobile phase B: Acetonitrile, 28-68% B in 9.0 minutes, 30 mL/min) to give 2-[2'-cyclobutyl-3'-fluoro-6-({(1R,3R)-3-[(1,4,4-trimethyl-L-prolyl)amino]cyclopentyl}oxy)[1,1'-biphenyl]-3-yl]-2-methylpropanoic acid (Example D1) (48.3 mg, 45.0%) as a white solid. LCMS APCI (+) 551.4 (M+H). $^1H$ NMR (400 MHz, DMSO-d6) δ=12.33 (br s, 1H), 9.77 (br s, 1H), 8.91 (br d, J=4.6 Hz, 1H), 7.30 (dd, J=2.4, 8.6 Hz, 1H), 7.25-7.18 (m, 1H), 7.11 (dd, J=8.1, 11.7 Hz, 1H), 7.04-6.97 (m, 2H), 6.88 (br d, J=7.7 Hz, 1H), 4.84 (br s, 1H), 4.16 (br d, J=6.4 Hz, 1H), 4.04 (qd, J=7.0, 13.4 Hz, 1H), 3.42 (br s, 1H), 2.99 (br t, J=8.9 Hz, 1H), 2.76 (br s, 3H), 2.29 (dd, J=8.6, 13.0 Hz, 1H), 2.24-2.15 (m, 1H), 2.14-1.92 (m, 4H), 1.90-1.62 (m, 7H), 1.46 (d, J=5.1 Hz, 6H), 1.40-1.28 (m, 1H), 1.14 (s, 3H), 1.07 (s, 3H).

Examples D2-D16 reported in Table 4 were synthesized with non-critical changes or substitutions to the exemplified procedures for Example D1 that one skilled in the art would be able to realize.

TABLE 4

| Ex. | Structure and Name | Characterization Data ($^1$H NMR, optical rotation, and/or LCMS) |
|---|---|---|
| D2 | 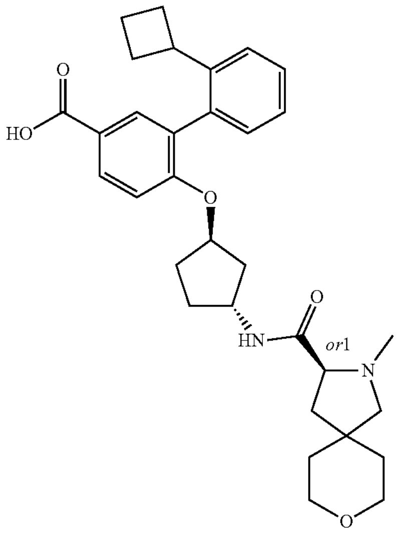 [SMILES: CN1CC2(CCOCC2)C[C@H]1C(=O)N[C@@H]1CC[C@@H](Oc2ccc(C(=O)O)cc2-c2ccccc2C2CCC2)C1] 2'-cyclobutyl-6-{[(1R,3R)-3-{[(3ξ)-2-methyl-8-oxa-2-azaspiro[4.5]decane-3-carbonyl]amino}cyclopentyl]oxy}[1,1'-biphenyl]-3-carboxylic acid | $^1$H NMR (400 MHz, DMSO-d6) δ 7.92 (br d, J = 8.17 Hz, 1 H) 7.60-7.67 (m, 1 H) 7.54-7.59 (m, 1 H) 7.38-7.43 (m, 1 H) 7.34 (t, J = 7.45 Hz, 1 H) 7.21 (t, J = 7.31 Hz, 1 H) 7.11 (br d, J = 8.17 Hz, 1 H) 7.03 (br s, 1 H) 4.93 (br s, 1 H) 3.99-4.09 (m, 1 H) 3.73-3.81 (m, 1 H) 3.52-3.57 (m, 1 H) 3.47 (br s, 3 H) 2.99 (br d, J = 8.63 Hz, 1 H) 2.74 (br s, 1 H) 2.19 (s, 3 H) 2.03-2.11 (m, 2 H) 1.93-1.99 (m, 1 H) 1.82-1.92 (m, 3 H) 1.68-1.81 (m, 5 H) 1.62-1.68 (m, 1 H) 1.53-1.60 (m, 2 H) 1.36-1.51 (m, 5 H). $[a]^{22}_D$ = −41.1° (c 0.1, MeOH). LCMS (m/z) $(M + H)^+$: 533.3 |
| D3 | 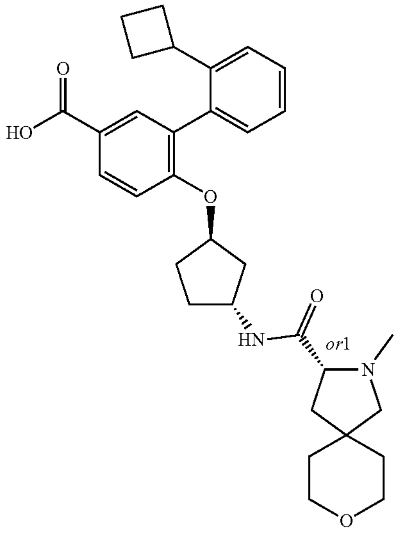 [SMILES: CN1CC2(CCOCC2)C[C@@H]1C(=O)N[C@@H]1CC[C@@H](Oc2ccc(C(=O)O)cc2-c2ccccc2C2CCC2)C1] 2'-cyclobutyl-6-{[(1R,3R)-3-{[(3ξ)-2-methyl-8-oxa-2-azaspiro[4.5]decane-3-carbonyl]amino}cyclopentyl]oxy}[1,1'-biphenyl]-3-carboxylic acid | $^1$H NMR (400 MHz, DMSO-d6) δ = 7.92 (br d, J = 8.17 Hz, 1 H) 7.60-7.67 (m, 1 H) 7.54-7.59 (m, 1 H) 7.38-7.43 (m, 1 H) 7.34 (t, J = 7.45 Hz, 1 H) 7.21 (t, J = 7.31 Hz, 1 H) 7.11 (br d, J = 8.17 Hz, 1 H) 7.03 (br s, 1 H) 4.93 (br s, 1 H) 3.99-4.09 (m, 1 H) 3.73-3.81 (m, 1 H) 3.52-3.57 (m, 1 H) 3.47 (br s, 3 H) 2.99 (br d, J = 8.63 Hz, 1 H) 2.74 (br s, 1 H) 2.19 (s, 3 H) 2.03-2.11 (m, 2 H) 1.93-1.99 (m, 1 H) 1.82-1.92 (m, 3 H) 1.68-1.81 (m, 5 H) 1.62-1.68 (m, 1 H) 1.53-1.60 (m, 2 H) 1.36-1.51 (m, 5 H). $[a]^{22}_D$ = +18.6° (c 0.1, MeOH). LCMS (m/z) $(M + H)^+$: 533.3 |

TABLE 4-continued

| Ex. | Structure and Name | Characterization Data ($^1$H NMR, optical rotation, and/or LCMS) |
|---|---|---|
| D4 | 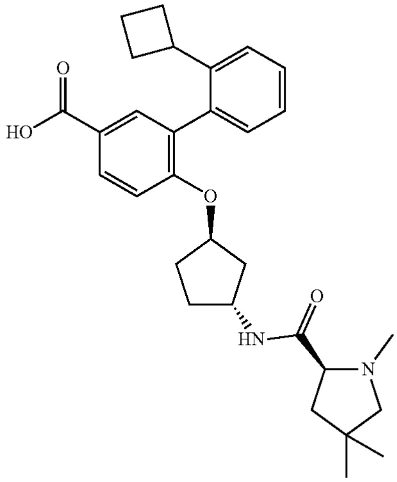 [SMILES: CN1CC(C)(C)C[C@H]1C(=O)N[C@@H]1CC[C@@H](Oc2ccc(C(=O)O)cc2-c2ccccc2C2CCC2)C1] 2'-cyclobutyl-6-({(1R,3R)-3-[(1,4,4-trimethyl-L-prolyl)amino]cyclopentyl}oxy)[1,1'-biphenyl]-3-carboxylic acid | 1H NMR (400 MHz, DMSO-$d_6$) δ 8.18 (s, 1 H) 7.92 (dd, J = 8.62, 2.14 Hz, 1 H) 7.74 (br t, J = 6.54 Hz, 1 H) 7.58 (d, J = 2.20 Hz, 1 H) 7.37-7.43 (m, 1 H) 7.30-7.37 (m, 1 H) 7.21 (t, J = 7.27 Hz, 1 H) 7.11 (d, J = 8.68 Hz, 1 H) 7.04 (br dd, J = 6.97, 3.30 Hz, 1 H) 4.94 (br s, 1 H) 4.06 (dt, J = 15.41, 7.58 Hz, 1 H) 3.37 (br t, J = 8.31 Hz, 1 H) 2.74-2.88 (m, 2 H) 2.23 (s, 3 H) 2.17 (br d, J = 9.05 Hz, 1 H) 1.36-2.10 (m, 14 H) 0.95-1.08 (m, 6 H). LCMS (m/z) $(M + H)^+$: 491.4 |
| D5 | 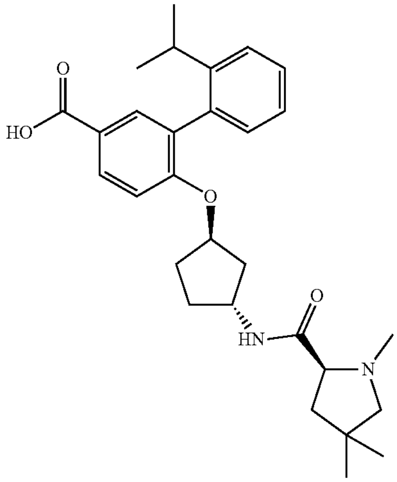 [SMILES: CC(C)c1ccccc1-c1cc(C(=O)O)ccc1O[C@@H]1CC[C@@H](NC(=O)[C@@H]2CC(C)(C)CN2C)C1] 2'-(propan-2-yl)-6-({(1R,3R)-3-[(1,4,4-trimethyl-L-prolyl)amino]cyclopentyl}oxy)[1,1'-biphenyl]-3-carboxylic acid | $^1$H NMR (400 MHz, DMSO-$d_6$, 25° C.): δ = 7.92 (dd, J = 8.6, 2.1 Hz, 1H), 7.66 (t, J = 7.4 Hz, 1H), 7.60 (s, 1H), 7.30-7.40 (m, 2H), 7.19 (t, J = 7.4 Hz, 1H), 7.12 (d, J = 8.6 Hz, 1H), 7.01 (dd, J = 7.4, 3.2 Hz, 1H), 4.89-4.99 (m, 1H), 3.99-4.10 (m, 1H), 2.71-2.77 (m, 2H), 2.64-2.70 (m, 1H), 2.19 (d, J = 1.0 Hz, 3H), 2.03-2.10 (m, 1H), 1.83-1.89 (m, 2H), 1.75-1.81 (m, 2H), 1.38-1.56 (m, 4H), 1.16 (d, J = 6.8 Hz, 3H), 1.05 (d, J = 5.3 Hz, 3H), 0.99 (d, J = 2.8 Hz, 3H), 0.96 ppm (dd, J = 6.8, 3.1 Hz, 3H). LCMS (m/z) $(M + H)^+$: 479.3 |

TABLE 4-continued

| Ex. | Structure and Name | Characterization Data ($^1$H NMR, optical rotation, and/or LCMS) |
|---|---|---|
| D6 | 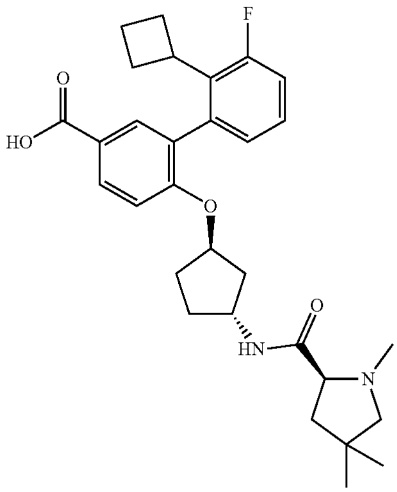 [SMILES: CN1CC(C)(C)C[C@H]1C(=O)N[C@@H]1CC[C@@H](Oc2ccc(C(=O)O)cc2-c2cccc(F)c2C2CCC2)C1] 2'-cyclobutyl-3'-fluoro-6-({(1R,3R)-3-[(1,4,4-trimethyl-L-prolyl)amino]cyclopentyl}oxy)[1,1'-biphenyl]-3-carboxylic acid | $^1$H NMR (400 MHz, DMSO-$d_6$, 26° C.): δ = 7.93 (dd, J = 8.6, 1.7 Hz, 1H), 7.68 (br t, J = 8.9 Hz, 1H), 7.61 (s, 1H), 7.24 (q, J = 7.3 Hz, 1H), 7.08-7.17 (m, 2H), 6.89 (br dd, J = 6.8, 4.9 Hz, 1H), 4.94 (br s, 1H), 3.98-4.13 (m, 1H), 3.36-3.44 (m, 1H), 2.70-2.82 (m, 2H), 2.18-2.25 (m, 4H), 2.10-2.17 (m, 2H), 1.96-2.09 (m, 3H), 1.73-1.92 (m, 6H), 1.38-1.51 (m, 3H), 1.05 (br d, J = 6.8 Hz, 3H), 0.99 ppm (d, J = 3.5 Hz, 3H). LCMS (m/z) (M + H)$^+$: 509.5 |
| D7 | 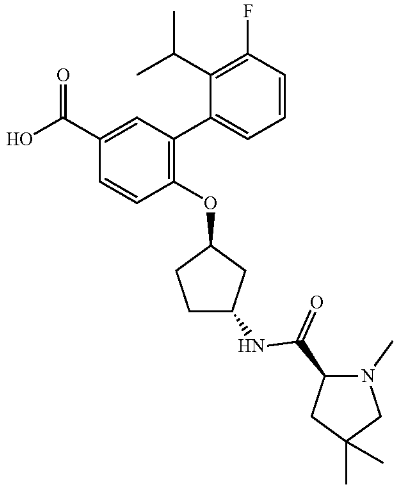 [SMILES: CC(C)c1c(F)cccc1-c1cc(C(=O)O)ccc1O[C@@H]1CC[C@@H](NC(=O)[C@@H]2CC(C)(C)CN2C)C1] 3'-fluoro-2'-(propan-2-yl)-6-({(1R,3R)-3-[(1,4,4-trimethyl-L-prolyl)amino]cyclopentyl}oxy)[1,1'-biphenyl]-3-carboxylic acid | $^1$H NMR (400 MHz, DMSO-$d_6$) δ 8.19 (s, 1 H) 7.96 (dd, J = 8.80, 2.20 Hz, 1 H) 7.68 (t, J = 7.48 Hz, 1 H) 7.59 (s, 1 H) 7.22-7.30 (m, 1 H) 7.10-7.19 (m, 2 H) 6.88 (dd, J = 7.15, 3.19 Hz, 1 H) 4.98 (br s, 1 H) 3.99-4.14 (m, 1 H) 2.72-2.80 (m, 2 H) 2.59 (br d, J = 16.07 Hz, 1 H) 2.20 (d, J = 1.54 Hz, 3 H) 1.94-2.17 (m, 2 H) 1.73-1.92 (m, 4 H) 1.46 (td, J = 12.27, 5.17 Hz, 3 H) 1.27 (br t, J = 4.95 Hz, 3 H) 1.10 (d, J = 6.82 Hz, 3 H) 1.06 (d, J = 5.94 Hz, 3 H) 1.00 (d, J = 2.86 Hz, 3 H). LCMS (m/z) (M + H)$^+$: 497.3 |

TABLE 4-continued

| Ex. | Structure and Name | Characterization Data ($^1$H NMR, optical rotation, and/or LCMS) |
|---|---|---|
| D8 | 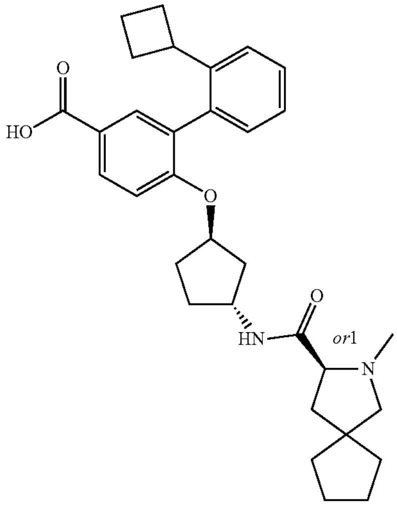 [SMILES: CN1CC2(CCCC2)C[C@H]1C(=O)N[C@@H]1CC[C@@H](Oc2ccc(C(=O)O)cc2-c2ccccc2C2CCC2)C1] 2'-cyclobutyl-6-{[(1R,3R)-3-{[(3ξ)-2-methyl-2-azaspiro[4.4]nonane-3-[carbonyl]amino}cyclopentyl]oxy}[1,1'-biphenyl]-3-carboxylic acid | $^1$H NMR (400 MHz, MeOD) δ 7.98 (dd, J = 2.1, 8.7 Hz, 1H), 7.71 (d, J = 2.0 Hz, 1H), 7.40-7.36 (m, 1H), 7.31 (dt, J = 1.3, 7.5 Hz, 1H), 7.19 (dt, J = 1.1, 7.5 Hz, 1H), 7.07-7.00 (m, 2H), 4.15 (td, J = 7.4, 14.6 Hz, 1H), 3.56-3.42 (m, 1H), 3.14 (d, J = 9.8 Hz, 1H), 2.62 (d, J = 9.8 Hz, 1H), 2.51 (d, J = 2.0 Hz, 3H), 2.31-1.56 (m, 22H), 1.54-1.38 (m, 2H). LCMS (m/z) (M + H)$^+$: 517.5 |
| D9 | 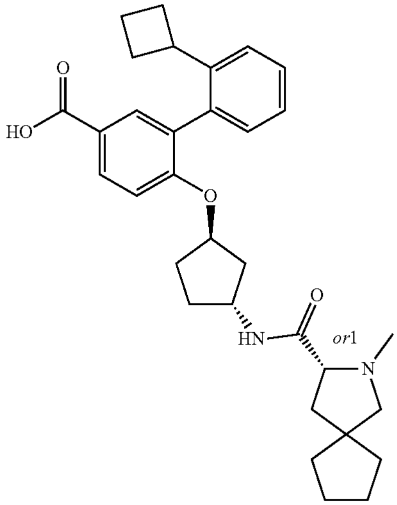 [SMILES: CN1CC2(CCCC2)C[C@@H]1C(=O)N[C@@H]1CC[C@@H](Oc2ccc(C(=O)O)cc2-c2ccccc2C2CCC2)C1] 2'-cyclobutyl-6-{[(1R,3R)-3-{[(3ξ)-2-methyl-2-azaspiro[4.4]nonane-3-carbonyl]amino}cyclopentyl]oxy}[1,1'-biphenyl]-3-carboxylic acid | $^1$H NMR (400 MHz, MeOD) δ 7.98 (dd, J = 2.1, 8.7 Hz, 1H), 7.71 (d, J = 2.0 Hz, 1H), 7.41-7.36 (m, 1H), 7.31 (dt, J = 1.3, 7.4 Hz, 1H), 7.22-7.15 (m, 1H), 7.07-7.00 (m, 2H), 4.23-4.07 (m, 1H), 3.49 (quin, J = 8.7 Hz, 1H), 3.15 (d, J = 10.0 Hz, 1H), 2.63 (d, J = 9.8 Hz, 1H), 2.51 (s, 3H), 2.29-1.56 (m, 22H), 1.54-1.38 (m, 2H). LCMS (m/z) (M + H)$^+$: 517.3 |

TABLE 4-continued

| Ex. | Structure and Name | Characterization Data ($^1H$ NMR, optical rotation, and/or LCMS) |
|---|---|---|
| D10 | 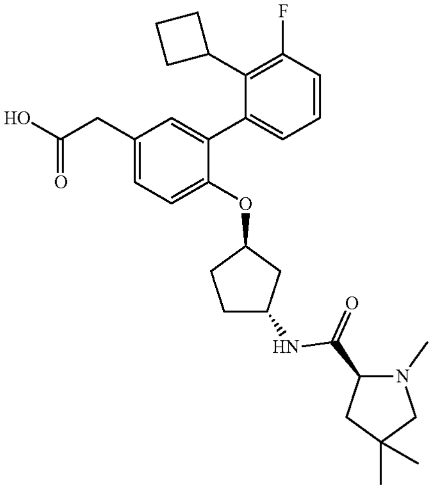 [SMILES: CN1CC(C)(C)C[C@H]1C(=O)N[C@@H]1CC[C@@H](Oc2ccc(CC(=O)O)cc2-c2cccc(F)c2C2CCC2)C1] [2'-cyclobutyl-3'-fluoro-6-({(1R,3R)-3-[(1,4,4-trimethyl-L-prolyl)amino]cyclopentyl}oxy)[1,1'-biphenyl]-3-yl]acetic acid | $^1H$ NMR (400 MHz, DMSO-$d_6$) δ 7.67-7.59 (m, 1H), 7.25-7.16 (m, 2H), 7.13-7.05 (m, 1H), 6.98-6.91 (m, 2H), 6.89-6.83 (m, 1H), 4.81-4.72 (m, 1H), 4.12-3.96 (m, 1H), 2.81-2.71 (m, 2H), 2.26-2.21 (m, 1H), 2.21-2.17 (m, 3H), 2.16-2.02 (m, 4H), 2.01-1.92 (m, 1H), 1.91-1.59 (m, 8H), 1.59-1.27 (m, 4H), 1.08-1.02 (m, 3H), 1.01-0.98 (m, 3H). LCMS (m/z) $(M + H)^+$: 523.2 |
| D11 | 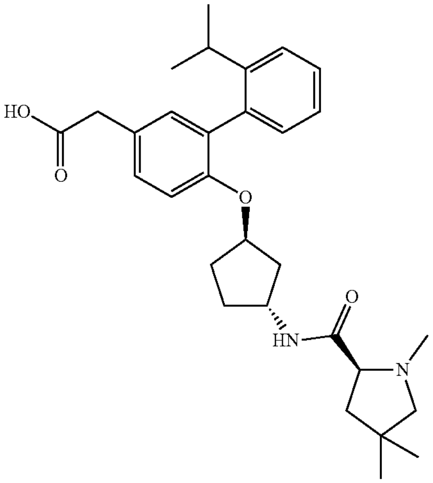 [SMILES: CC(C)c1ccccc1-c1cc(CC(=O)O)ccc1O[C@@H]1CC[C@@H](NC(=O)[C@@H]2CC(C)(C)CN2C)C1] [2'-(propan-2-yl)-6-({(1R,3R)-3-[(1,4,4-trimethyl-L-prolyl)amino]cyclopentyl}oxy)[1,1'-biphenyl]-3-yl]acetic acid | $^1H$ NMR (400 MHz, DMSO-$d_6$) δ 7.60 (s, 1H), 7.38-7.28 (m, 2H), 7.23-7.14 (m, 2H), 7.04-6.90 (m, 3H), 4.84-4.73 (m, 1H), 4.10-3.99 (m, 1H), 3.57-3.49 (m, 2H), 2.80-2.68 (m, 3H), 2.25-2.17 (m, 3H), 2.16-2.11 (m, 1H), 2.10-1.92 (m, 1H), 1.90-1.67 (m, 4H), 1.55-1.29 (m, 3H), 1.21-1.11 (m, 3H), 1.08-1.03 (m, 3H), 1.02-0.93 (m, 6H). LCMS (m/z) $(M + H)^+$: 493.5 |

TABLE 4-continued

| Ex. | Structure and Name | Characterization Data ($^1$H NMR, optical rotation, and/or LCMS) |
|---|---|---|
| D12 | 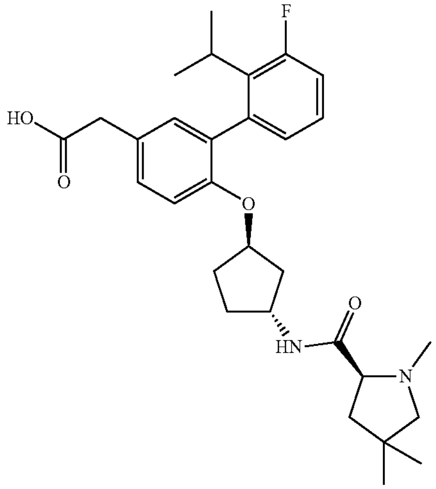 [SMILES: CC(C)c1c(F)cccc1-c1cc(CC(=O)O)ccc1O[C@@H]1CC[C@@H](NC(=O)[C@@H]2CC(C)(C)CN2C)C1] [3'-fluoro-2'-(propan-2-yl)-6-({(1R,3R)-3-[(1,4,4-trimethyl-L-prolyl)amino]cyclopentyl}oxy)[1,1'-biphenyl]-3-yl]acetic acid | $^1$H NMR (400 MHz, DMSO-$d_6$) δ 12.58-11.99 (m, 1H), 7.27-7.18 (m, 2H), 7.15-7.05 (m, 1H), 7.03-6.98 (m, 1H), 6.97-6.93 (m, 1H), 6.88-6.82 (m, 1H), 4.87-4.79 (m, 1H), 4.10-3.97 (m, 1H), 3.53 (s, 2H), 3.42-3.39 (m, 2H), 2.73-2.63 (m, 1H), 2.45-2.18 (m, 3H), 2.16-1.90 (m, 2H), 1.89-1.66 (m, 3H), 1.59 (s, 3H), 1.29-1.23 (m, 3H), 1.13-1.08 (m, 3H), 1.03 (br s, 6H). LCMS (m/z) (M + H)$^+$: 511.4 |
| D13 | 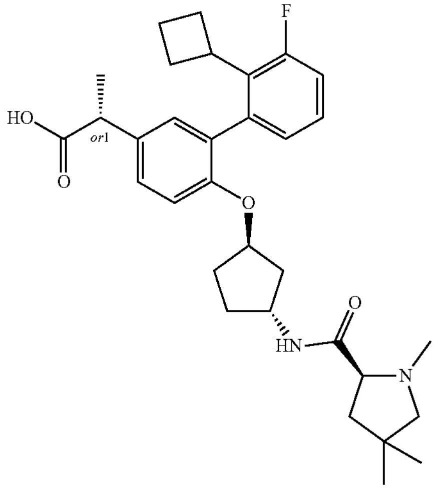 [SMILES: C[C@@H](C(=O)O)c1ccc(O[C@@H]2CC[C@@H](NC(=O)[C@@H]3CC(C)(C)CN3C)C2)c(-c2cccc(F)c2C2CCC2)c1] (2ξ)-2-[2'-cyclobutyl-3'-fluoro-6-({(1R,3R)-3-[(1,4,4-trimethyl-L-prolyl)amino]cyclopentyl}oxy)[1,1'-biphenyl]-3-yl]propanoic acid | $^1$H NMR (400 MHz, MeOD) δ 7.29 (br d, J = 8.4 Hz, 1H), 7.20-7.12 (m, 1H), 7.04 (s, 1H), 7.02-6.92 (m, 2H), 6.91-6.84 (m, 1H), 4.80 (br d, J = 2.6 Hz, 1H), 4.21-4.04 (m, 1H), 3.65 (br d, J = 6.8 Hz, 1H), 3.50 (quin, J = 9.2 Hz, 1H), 3.44-3.35 (m, 1H), 3.09 (br d, J = 10.3 Hz, 1H), 2.58 (br d, J = 9.5 Hz, 1H), 2.53 (d, J = 3.3 Hz, 3H), 2.40-2.26 (m, 1H), 2.24-1.84 (m, 7H), 1.84-1.58 (m, 5H), 1.50-1.38 (m, 4H), 1.12 (d, J = 1.5 Hz, (6H). LCMS (m/z) (M + H)$^+$: 537.5 |

TABLE 4-continued

| Ex. | Structure and Name | Characterization Data ($^1$H NMR, optical rotation, and/or LCMS) |
|---|---|---|
| D14 | 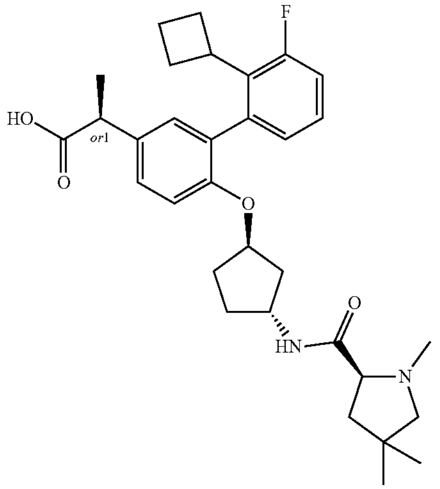 [SMILES: C[C@H](C(=O)O)c1ccc(O[C@@H]2CC[C@@H](NC(=O)[C@@H]3CC(C)(C)CN3C)C2)c(-c2cccc(F)c2C2CCC2)c1] (2ξ)-2-[2'-cyclobutyl-3'-fluoro-6-({(1R,3R)-3-[(1,4,4-trimethyl-L-prolyl)amino]cyclopentyl}oxy)[1,1'-biphenyl]-3-yl]propanoic acid | $^1$H NMR (400 MHz, MeOD) δ 7.29 (br d, J = 8.6 Hz, 1H), 7.20-7.13 (m, 1H), 7.04 (dd, J = 2.4, 4.4 Hz, 1H), 7.02-6.92 (m, 2H), 6.91-6.84 (m, 1H), 4.83-4.76 (m, 1H), 4.23-4.02 (m, 1H), 3.71-3.61 (m, 1H), 3.58-3.39 (m, 2H), 3.12 (dd, J = 2.8, 10.0 Hz, 1H), 2.62 (dd, J = 3.4, 10.2 Hz, 1H), 2.56 (d, J = 4.4 Hz, 3H), 2.38-2.24 (m, 1H), 2.22-1.57 (m, 13H), 1.44 (dd, J = 2.9, 7.0 Hz, 3H), 1.16-1.09 (m, 6H). LCMS (m/z) (M + H)$^+$: 537.5 |
| D15 | 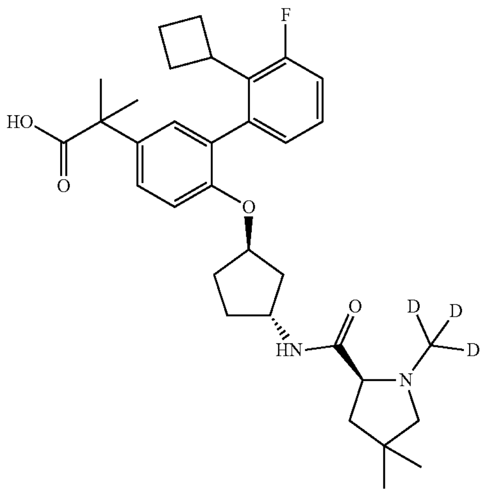 [SMILES: [2H]C([2H])([2H])N1CC(C)(C)C[C@H]1C(=O)N[C@@H]1CC[C@@H](Oc2ccc(C(C)(C)C(=O)O)cc2-c2cccc(F)c2C2CCC2)C1] 2-(2'-cyclobutyl-6-{[(1R,3R)-3-{[4,4-dimethyl-1-($^2H_3$)methyl-L-prolyl]amino}cyclopentyl]oxy}-3'-fluoro[1,1'-biphenyl]-3-yl)-2-methylpropanoic acid *Intermediate 10 was used in the amide coupling | $^1$H NMR (600 MHz, DMSO-$d_6$) δ 7.45-7.79 (m, 1H) 7.30 (dd, J = 8.72, 2.54 Hz, 1H) 7.18-7.26 (m, 1H) 7.09 (dd, J = 11.63, 8.36 Hz, 1H) 6.96-7.03 (m, 2H) 6.82-6.93 (m, 1H) 4.74-4.86 (m, 1H) 3.98-4.04 (m, 1H) 3.39-3.48 (m, 1H) 1.93-2.25 (m, 5H) 1.85-1.93 (m, 2H) 1.60-1.83 (m, 5H) 1.53 (s, 1H) 1.46 (d, J = 7.63 Hz, 7H) 1.32-1.43 (m, 1H) 0.95-1.09 (m, 6 H). LCMS (m/z) (M + H)$^+$: 554.2 |

TABLE 4-continued

| Ex. | Structure and Name | Characterization Data ($^1$H NMR, optical rotation, and/or LCMS) |
|---|---|---|
| D16 | 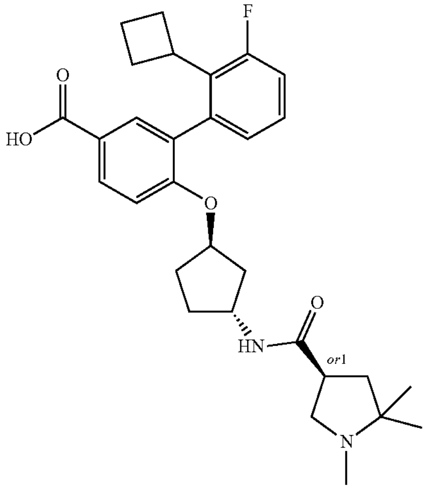 [SMILES: CN1C[C@@H](C(=O)N[C@@H]2CC[C@@H](Oc3ccc(C(=O)O)cc3-c3cccc(F)c3C3CCC3)C2)CC1(C)C]<br>2'-cyclobutyl-3'-fluoro-6-{[(1R,3R)-3-{[(3ξ)-1,5,5-trimethylpyrrolidine-3-carbonyl]amino}cyclopentyl]oxy}[1,1'-biphenyl]-3-carboxylic acid<br>*1-(tert-butoxycarbonyl)-5,5-dimethylpyrrolidine-3-carboxylic acid was used in the amide coupling then the proline was methylated after Boc deprotection using formic acid and formaldehyde | $^1$H NMR (400 MHz, DMSO-$d_6$) δ 8.25 (br t, J = 7.9 Hz, 1H), 7.95 (dd, J = 2.1, 8.7 Hz, 1H), 7.62 (t, J = 2.1 Hz, 1H), 7.31-7.20 (m, 1H), 7.19-7.09 (m, 2H), 6.89 (d, J = 7.5 Hz, 1H), 4.97 (br s, 1H), 4.09-3.93 (m, 1H), 3.13 (br s, 1H), 2.60 (d, J = 3.1 Hz, 3H), 2.29-1.09 (m, 21H).<br>LCMS (m/z) (M + H)$^+$: 509.4 |

Example D17: N-[(1R,3R)-3-({2'-cyclobutyl-3'-fluoro-5-[2-(5-oxo-4,5-dihydro-1,2,4-oxadiazol-3-yl)propan-2-yl][1,1'-biphenyl]-2-yl}oxy)cyclopentyl]-1,4,4-trimethyl-L-prolinamide

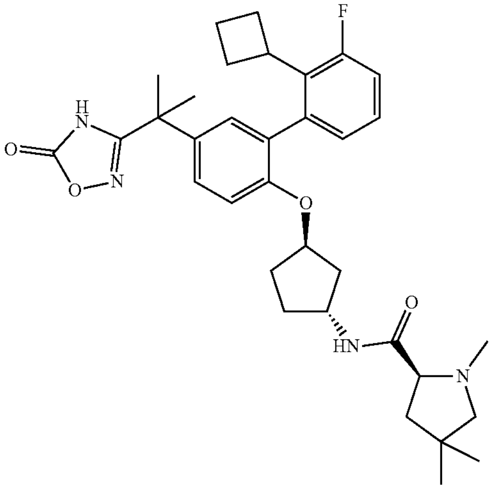 [SMILES: CN1CC(C)(C)C[C@H]1C(=O)N[C@@H]1CC[C@@H](Oc2ccc(C(C)(C)c3noc(=O)[nH]3)cc2-c2cccc(F)c2C2CCC2)C1]

Example D17 was synthesized with non-critical changes or substitutions to the exemplified procedures for Example D1 followed by conversion of the carboxylic acid to the 1,2,4-oxadiazol-5(4H)-one according to literature procedure. [WO2020023356] LCMS APCI (+) 591.3 (M+H).

Example E1: N-{(1R,3R)-3-[(2'-cyclobutyl-3'-fluoro-5-{1-[(methanesulfonyl)amino]-2-methyl-1-oxopropan-2-yl}[1,1'-biphenyl]-2-yl)oxy]cyclopentyl}-1,4,4-trimethyl-L-prolinamide

E1

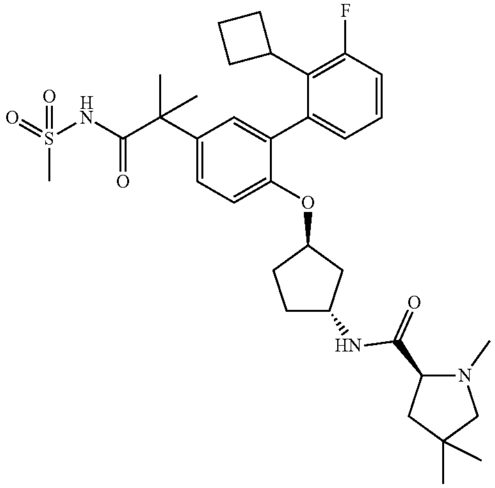

Example E1 was prepared according to General Method E.

To a solution of 2-[2'-cyclobutyl-3'-fluoro-6-({(1R,3R)-3-[(1,4,4-trimethyl-L-prolyl)amino]cyclopentyl}oxy)[1,1'-biphenyl]-3-yl]-2-methylpropanoic acid (Example D1) (6.00 g, 10.9 mmol) in DCM (100 mL), carbonyldiimidazole (2.64 g, 16.3 mmol) was added. The reaction was heated to 40° C. for 1 h, and then methanesulfonamide (2.59 g, 0.20 mmol) and 1,8-diazabicyclo[5.4.0]undec-7-ene (6.63 g, 43.6 mmol) were added. The reaction was complete after 1 h by LCMS. The DCM was removed under reduced pressure, the residue was poured in water and extracted with EtOAc (2×). The combined organics were concentrated, and the crude product was purified by silica gel chromatography (0-10% MeOH/DCM) followed by prep HPLC purification (Boston Prime C18 150×30 mm, 5 uM, Mobile phase A: Water+ 0.05% $NH_3H_2O$+10 mM $NH_4HCO_3$, Mobile phase B: Acetonitrile, 22-62% B in 9.0 minutes, 60 mL/min). The isolated product recrystallized from EtOH/$H_2O$ to give N-{(1R,3R)-3-[(2'-cyclobutyl-3'-fluoro-5-{1-[(methanesulfonyl)amino]-2-methyl-1-oxopropan-2-yl}[1,1'-biphenyl]-2-yl)oxy]cyclopentyl}-1,4,4-trimethyl-L-prolinamide (Example E1) (4.8 g, 70.2%) as a white solid. LCMS APCI (+) 628.3. $^1H$ NMR (400 MHz, DMSO-d6) δ=11.56-10.56 (m, 1H), 7.90 (br s, 1H), 7.30-7.15 (m, 2H), 7.09 (dd, J=8.4, 11.5 Hz, 1H), 7.02-6.92 (m, 2H), 6.90-6.82 (m, 1H), 4.80 (br s, 1H), 4.13-3.96 (m, 1H), 3.54-3.40 (m, 1H), 3.04 (br s, 3H), 2.89 (br s, 1H), 2.35 (br s, 3H), 2.23-1.60 (m, 12H), 1.60-1.32 (m, 9H), 1.11-0.98 (m, 6H).

Examples E2-E11reported in Table 5 were synthesized with non-critical changes or substitutions to the exemplified procedures for Example E1 that one skilled in the art would be able to realize.

TABLE 5

| Ex. | Structure and Name | Characterization Data ($^1H$ NMR, optical rotation, and/or LCMS) |
|---|---|---|
| E2 | 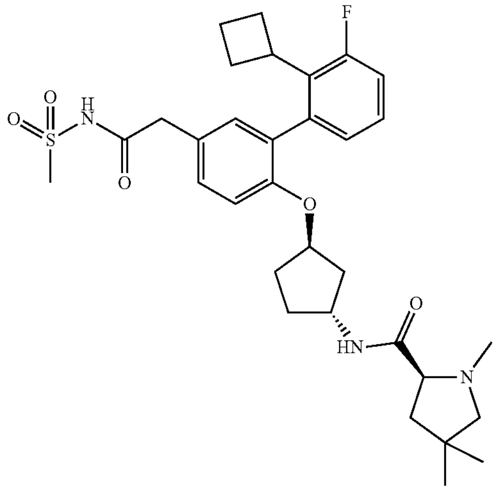 [SMILES: CN1CC(C)(C)C[C@H]1C(=O)N[C@@H]1CC[C@@H](Oc2ccc(CC(=O)NS(C)(=O)=O)cc2-c2cccc(F)c2C2CCC2)C1] N-{(1R,3R)-3-[(2'-cyclobutyl-3'-fluoro-5-{2-[(methanesulfonyl)amino]-2-oxoethyl}[1,1'-biphenyl]-2-yl)oxy]cyclopentyl}-1,4,4-trimethyl-L-prolinamide | $^1H$ NMR (400 MHz, DMSO-$d_6$) δ 7.79 (br s, 1H), 7.27-7.18 (m, 2H), 7.10 (dd, J = 8.1, 11.4 Hz, 1H), 7.01-6.94 (m, 2H), 6.90-6.84 (m, 1H), 4.79 (br s, 1H), 4.13-3.96 (m, 1H), 3.50 (s, 2H), 3.13 (s, 3H), 2.96 (br s, 1H), 2.83 (br d, J = 8.2 Hz, 1H), 2.35-2.14 (m, 6H), 2.12-1.95 (m, 3H), 1.94-1.61 (m, 8H), 1.58-1.30 (m, 3H), 1.10-0.98 (m, 6H). LCMS (m/z) $(M + H)^+$: 600.5 |
| E3 | 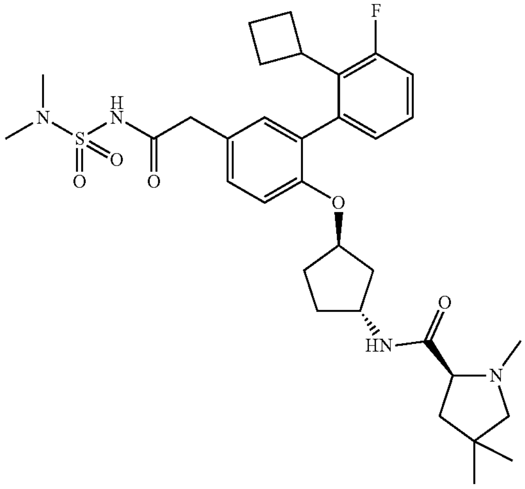 N-{(1R,3R)-3-[(2'-cyclobutyl-5-{2-[(dimethylsulfamoyl)amino]-2-oxoethyl}-3'-fluoro[1,1'-biphenyl]-2-yl)oxy]cyclopentyl}-1,4,4-trimethyl-L-prolinamide | $^1H$ NMR (600 MHz, DMSO-$d_6$) δ 7.61 (br dd, J = 11.63, 8.54 Hz, 1 H) 7.19-7.24 (m, 2 H) 7.09 (dd, J = 11.81, 8.17 Hz, 1 H) 7.00 (t, J = 2.23 Hz, 1 H) 6.96 (d, J = 8.54 Hz, 1 H) 6.84-6.88 (m, 1 H) 6.49 (s, 1 H) 4.77 (dt, J = 5.70, 2.92 Hz, 1 H) 3.98-4.03 (m, 1 H) 3.41 (s, 2 H) 2.72-2.78 (m, 2 H) 2.67 (s, 6 H) 2.20 (d, J = 3.09 Hz, 4 H) 1.94-2.14 (m, 5 H) 1.62-1.88 (m, 8 H) 1.35-1.55 (m, 3 H) 1.04 (d, J = 7.36 Hz, 3 H) 0.99 (d, J = 3.63 Hz, 3 H). LCMS (m/z) $(M + H)^+$: 629.2 |

TABLE 5-continued

| Ex. | Structure and Name | Characterization Data ($^1$H NMR, optical rotation, and/or LCMS) |
|---|---|---|
| E4 | 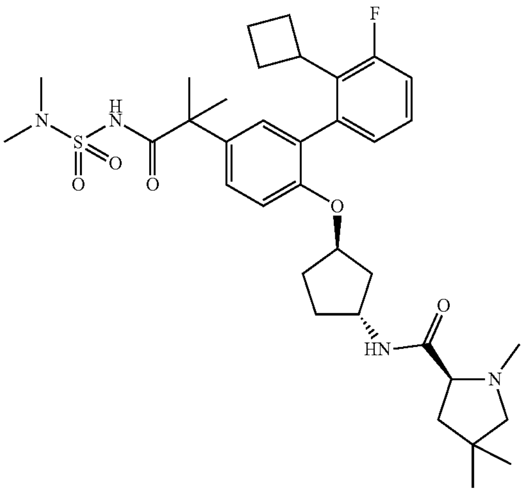 N-{(1R,3R)-3-[(2'-cyclobutyl-5-{1-[(dimethylsulfamoyl)amino]-2-methyl-1-oxopropan-2-yl}-3'-fluoro[1,1'-biphenyl]-2-yl)oxy]cyclopentyl}-1,4,4-trimethyl-L-prolinamide | $^1$H NMR (400 MHz, DMSO-$d_6$) δ (br s, 1 H) 7.64 (br s, 1 H) 7.18-7.30 (m, 2 H) 7.06-7.13 (m, 1 H) 6.93-7.04 (m, 2 H) 6.87 (t, J = 6.82 Hz, 1 H) 4.80 (br s, 1 H) 3.96-4.13 (m, 1 H) 3.44 (br s, 1 H) 2.71 (br s, 7 H) 1.95-2.27 (m, 8 H) 1.60-1.93 (m, 7 H) 1.37-1.54 (m, 8 H) 1.04 (d, J = 5.38 Hz, 3 H) 0.99 (br s, 3 H). LCMS (m/z) (M + H)$^+$: 657.5 |
| E5 | 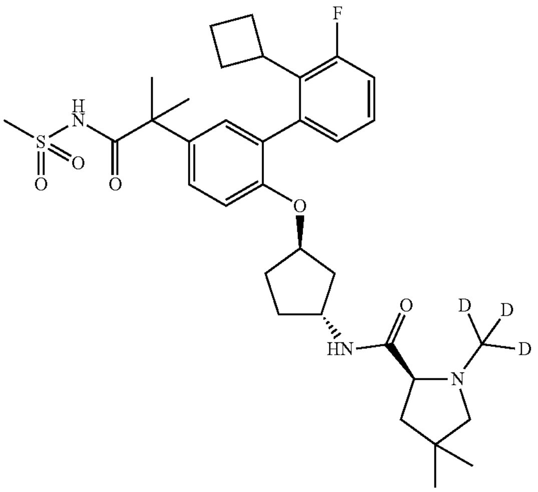 [SMILES: [2H]C([2H])([2H])N1CC(C)(C)C[C@H]1C(=O)N[C@@H]1CC[C@@H](Oc2ccc(C(C)(C)C(=O)NS(C)(=O)=O)cc2-c2cccc(F)c2C2CCC2)C1] N-{(1R,3R)-3-[(2'-cyclobutyl-3'-fluoro-5-{1-[(methanesulfonyl)amino]-2-methyl-1-oxopropan-2-yl}[1,1'-biphenyl]-2-yl)oxy]cyclopentyl}-4,4-dimethyl-1-($^2H_3$)methyl-L-prolinamide | $^1$H NMR (600 MHz, DMSO-$d_6$) δ 8.30-8.74 (m, 1 H) 7.18-7.28 (m, 2 H) 7.06-7.16 (m, 1 H) 7.02 (dd, J = 8.72, 1.45 Hz, 1 H) 6.95 (dd, J = 5.45, 2.54 Hz, 1 H) 6.86-6.91 (m, 1 H) 6.79 (br s, 1 H) 4.76-4.90 (m, 1 H) 3.97-4.12 (m, 1 H) 3.41-3.58 (m, 2 H) 3.18 (s, 3 H) 2.15-2.27 (m, 2 H) 1.93-2.14 (m, 4 H) 1.54-1.92 (m, 10 H) 1.44-1.53 (m, 7 H) 1.30-1.43 (m, 1 H) 1.02-1.16 (m, 6 H). LCMS (m/z) (M + H)$^+$: 631.1 |

TABLE 5-continued

| Ex. | Structure and Name | Characterization Data ($^1H$ NMR, optical rotation, and/or LCMS) |
|---|---|---|
| E6 | 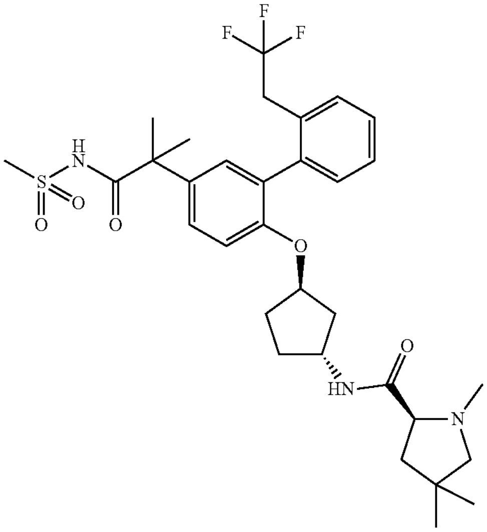 N-[(1R,3R)-3-{[5-{1-[(methanesulfonyl)amino]-2-methyl-1-oxopropan-2-yl}-2'-(2,2,2-trifluoroethyl)[1,1'-biphenyl]-2-yl]oxy}cyclopentyl]-1,4,4-trimethyl-L-prolinamide | $^1H$ NMR (400 MHz, DMSO-$d_6$) δ 12.02-10.55 (m, 1H), 7.91 (br s, 1H), 7.47-7.41 (m, 1H), 7.38 (t, J = 3.6 Hz, 2H), 7.27 (dd, J = 2.3, 8.7 Hz, 1H), 7.20-7.13 (m, 1H), 7.05-6.94 (m, 2H), 4.82 (br s, 1H), 4.14-3.94 (m, 3H), 3.61-3.46 (m, 1H), 3.04 (br s, 3H), 2.55 (s, 2H), 2.33 (br s, 3H), 2.14-1.70 (m, 5H), 1.60-1.34 (m, 9H), 1.08-1.00 (m, 6H). LCMS (m/z) $(M + H)^+$: 638.4 |
| E7 | 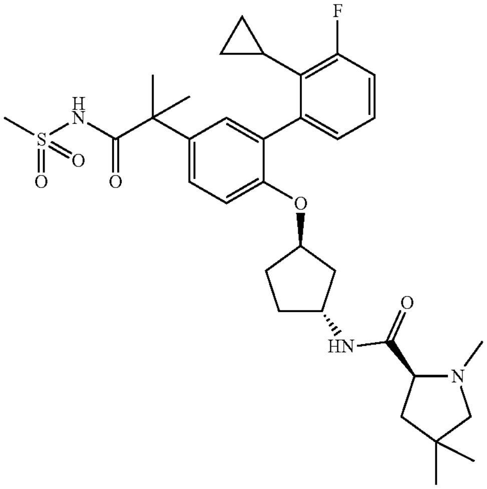 N-{(1R,3R)-3-[(2'-cyclopropyl-3'-fluoro-5-{1-[(methanesulfonyl)amino]-2-methyl-1-oxopropan-2-yl}[1,1'-biphenyl]-2-yl)oxy]cyclopentyl}-1,4,4-trimethyl-L-prolinamide | $^1H$ NMR (600 MHz, DMSO-$d_6$) δ 7.61 (br s, 1 H) 7.25 (br d, J = 9.08 Hz, 1 H) 7.21 (br d, J = 6.18 Hz, 1 H) 7.10 (br d, J = 2.18 Hz, 1 H) 7.01-7.07 (m, 1 H) 6.93 (br d, J = 7.27 Hz, 2 H) 2.75 (br d, J = 6.90 Hz, 2 H) 2.57-2.69 (m, 1 H) 2.20 (br s, 3 H) 2.13 (br d, J = 4.36 Hz, 1 H) 1.74-1.89 (m, 4 H) 1.65 (br t, J = 5.45 Hz, 2 H) 1.28-1.58 (m, 12 H) 1.05 (s, 3 H) 1.00 (br s, 3 H). LCMS (m/z) $(M + H)^+$: 614.2 |

TABLE 5-continued

| Ex. | Structure and Name | Characterization Data ($^1$H NMR, optical rotation, and/or LCMS) |
|---|---|---|
| E8 | 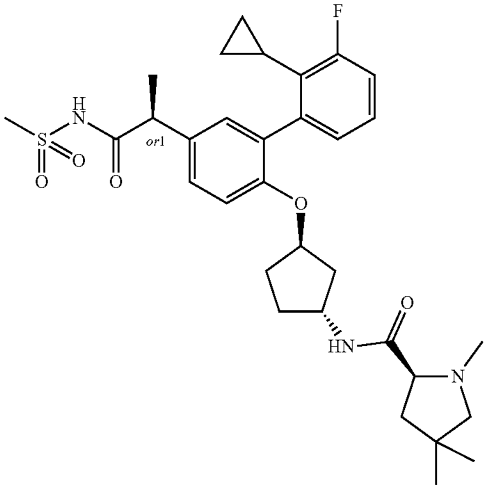 N-{(1R,3R)-3-[(2'-cyclobutyl-3'-fluoro-5-{(2ξ)-1-[(methanesulfonyl)amino]-1-oxopropan-2-yl}[1,1'-biphenyl]-2-yl)oxy]cyclopentyl}-1,4,4-trimethyl-L-prolinamide | $^1$H NMR (400 MHz, DMSO-$d_6$) δ 11.68-11.32 (m, 1H), 7.73 (br s, 1H), 7.27-7.19 (m, 2H), 7.15-6.97 (m, 3H), 6.89 (d, J = 7.5 Hz, 1H), 4.80 (br s, 1H), 4.05 (br dd, J = 7.6, 19.0 Hz, 1H), 3.65 (q, J = 6.6 Hz, 1H), 3.51-3.40 (m, 1H), 3.12 (d, J = 2.5 Hz, 3H), 2.94 (br s, 1H), 2.87-2.79 (m, 1H), 2.31-2.26 (m, 3H), 2.21-1.57 (m, 12H), 1.55-1.27 (m, 6H), 1.10-0.98 (m, 6H). LCMS (m/z) (M + H)$^+$: 614.4 |
| E9 | 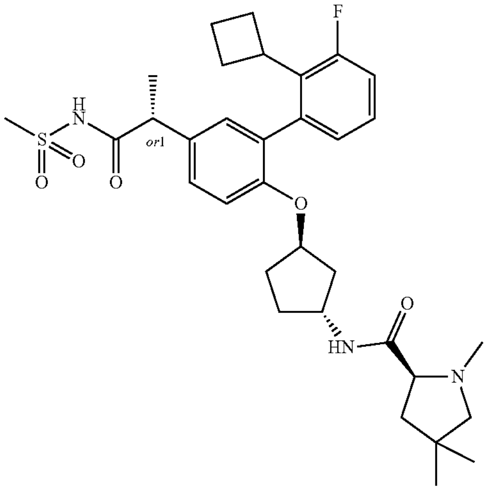 N-{(1R,3R)-3-[(2'-cyclobutyl-3'-fluoro-5-{(2ξ)-1-[(methanesulfonyl)amino]-1-oxopropan-2-yl}[1,1'-biphenyl]-2-yl)oxy]cyclopentyl}-1,4,4-trimethyl-L-prolinamide | $^1$H NMR (400 MHz, DMSO-$d_6$) δ 11.70-11.36 (m, 1H), 7.84-7.62 (m, 1H), 7.27-7.19 (m, 2H), 7.11 (dd, J = 8.1, 11.6 Hz, 1H), 7.06-7.03 (m, 1H), 7.06-6.96 (m, 1H), 6.93-6.85 (m, 1H), 4.80 (br s, 1H), 4.04 (br s, 1H), 3.65 (br d, J = 7.0 Hz, 1H), 3.44 (br d, J = 8.4 Hz, 1H), 3.12 (d, J = 3.9 Hz, 3H), 2.99-2.89 (m, 1H), 2.83 (br d, J = 7.8 Hz, 1H), 2.28 (br s, 3H), 2.20-1.61 (m, 12H), 1.54-1.30 (m, 6H), 1.09-0.97 (m, 6H). LCMS (m/z) (M + H)$^+$: 614.4 |

TABLE 5-continued

| Ex. | Structure and Name | Characterization Data ($^1$H NMR, optical rotation, and/or LCMS) |
|---|---|---|
| E10 | 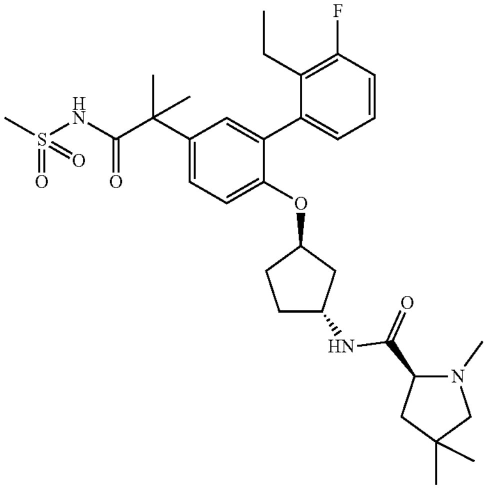 N-{(1R,3R)-3-[(2'-ethyl-3'-fluoro-5-{1-[(methanesulfonyl)amino]-2-methyl-1-oxopropan-2-yl}[1,1'-biphenyl]-2-yl)oxy]cyclopentyl}-1,4,4-trimethyl-L-prolinamide | $^1$H NMR (600 MHz, DMSO-$d_6$) δ 7.62 (br s, 1 H) 7.25-7.29 (m, 1 H) 7.18-7.24 (m, 1 H) 7.10 (br t, J = 9.08 Hz, 1 H) 7.03 (br s, 1 H) 6.95 (br d, J = 4.36 Hz, 1 H) 6.89 (br d, J = 6.90 Hz, 1 H) 4.79 (br s, 1 H) 4.06-4.11 (m, 5 H) 3.98-4.07 (m, 2 H) 2.76 (br d, J = 1.82 Hz, 3 H) 1.97-2.39 (m, 5 H) 1.91 (s, 3 H) 1.69-1.88 (m, 4 H) 1.43-1.57 (m, 3 H) 1.38 (br s, 6 H) 1.05 (s, 3 H) 1.00 (br s, 3 H) 0.92 (br t, J = 7.45 (Hz, 3 H). LCMS (m/z) (M + H)$^+$: 602.2 |
| E11 | 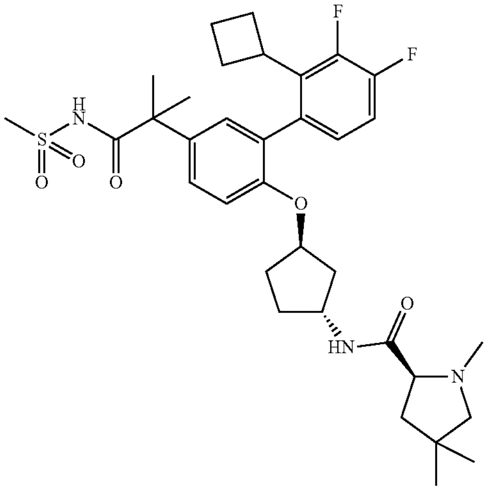 N-{(1R,3R)-3-[(2'-cyclobutyl-3',4'-difluoro-5-{1-[(methanesulfonyl)amino]-2-methyl-1-oxopropan-2-yl}[1,1'-biphenyl]-2-yl)oxy]cyclopentyl}-1,4,4-trimethyl-L-prolinamide | $^1$H NMR (600 MHz, DMSO-$d_6$) δ 7.51-7.92 (m, 1 H) 7.20-7.28 (m, 2 H) 6.94-7.00 (m, 2 H) 6.83-6.90 (m, 1 H) 6.48 (s, 1 H) 4.79 (br s, 1 H) 3.96-4.05 (m, 1 H) 3.44-3.53 (m, 1 H) 2.73-3.09 (m, 4 H) 1.97-2.41 (m, 7 H) 1.83-1.90 (m, 2 H) 1.62-1.83 (m, 5 H) 1.35-1.58 (m, 8 H) 1.05 (d, J = 5.81 Hz, 3 H) 1.02 (br s, 2 H). LCMS (m/z) (M + H)$^+$: 646.1 |

Example F1: [2'-cyclobutyl-3'-fluoro-6-({(1S,3r)-3-[(1,4,4-trimethyl-L-prolyl)amino]cyclobutyl}methoxy)[1,1'-biphenyl]-3-yl]acetic acid

F1

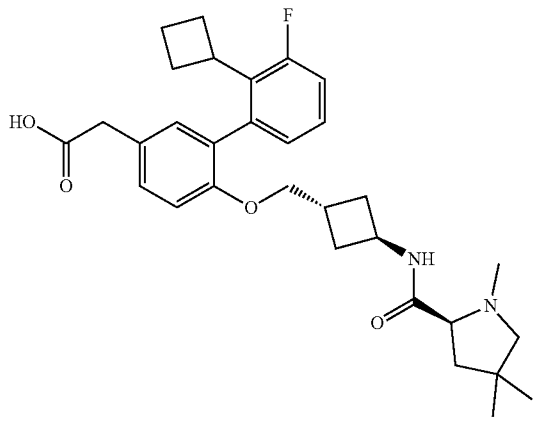

Example F1 was prepared according to General Method F.

Step 1: methyl [3-bromo-4-({(1r,3r)-3-[(tert-butoxycarbonyl)amino]cyclobutyl}methoxy)phenyl]acetate (Fla)

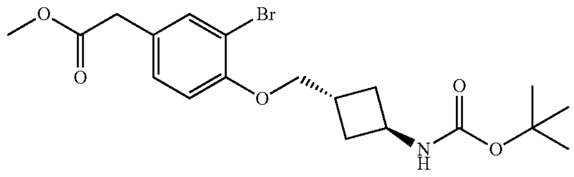 [SMILES: COC(=O)Cc1ccc(OC[C@H]2C[C@H](NC(=O)OC(C)(C)C)C2)c(Br)c1]

A solution of methyl (3-bromo-4-hydroxyphenyl)acetate (725 mg, 2.96 mmol), tert-butyl [(1r,3r)-3-(hydroxymethyl)cyclobutyl]carbamate (714 mg, 3.55 mmol), and triphenylphosphine (1400 mg, 5.32 mmol) in toluene (19.7 mL) was cooled in an ice-water bath, and then diisopropyl azodicarboxylate (1080 mg, 1.050 mL, 5.32 mmol) was added drop-wise. The ice bath was removed and the reaction was stirred overnight. The reaction was then diluted with EtOAc, washed with water and brine, dried over $Na_2SO_4$, filtered, and concentrated under reduced pressure. The residue was purified by silica gel chromatography twice (0-50% EtOAc/heptanes) to give methyl [3-bromo-4-({(1r,3r)-3-[(tert-butoxycarbonyl)amino]cyclobutyl}methoxy)phenyl]acetate (Fla) (673 mg, 53%) as a clear gum. LCMS APCI (+) 328.0, 330.0 (M-Boc). $^1H$ NMR (400 MHz, DMSO-d6) δ ppm 7.48 (d, J=2.08 Hz, 1H) 7.21 (dd, J=8.44, 2.20 Hz, 1H) 7.02-7.10 (m, 2H) 4.86-4.94 (m, 1H) 4.15 (sxt, J=7.65 Hz, 1H) 4.01-4.09 (m, 2H) 3.59-3.62 (m, 5H) 2.01-2.21 (m, 4H) 1.37 (s, 9H).

Step 2: methyl [6-({(1r,3r)-3-[(tert-butoxycarbonyl)amino]cyclobutyl}methoxy)-2'-cyclobutyl-3'-fluoro[1,1'-biphenyl]-3-yl]acetate (F1b)

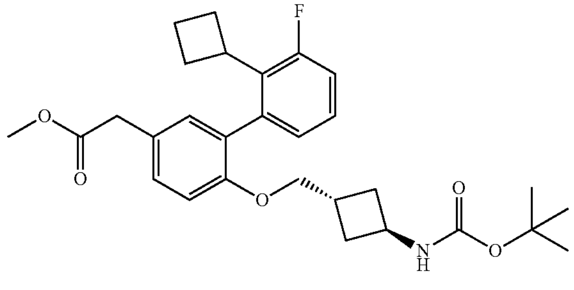 [SMILES: COC(=O)Cc1ccc(OC[C@H]2C[C@H](NC(=O)OC(C)(C)C)C2)c(-c2cccc(F)c2C2CCC2)c1]

A solution of methyl [3-bromo-4-({(1r,3r)-3-[(tert-butoxycarbonyl)amino]cyclobutyl}methoxy)phenyl]acetate (Fla) (673 mg, 0.940 mmol), 2-(2-cyclobutyl-3-fluorophenyl)-4,4,5,5-tetramethyl-1,3,2-dioxaborolane (Intermediate 2) (312 mg, 1.13 mmol), and $Cs_2CO_3$ (922 mg, 2.83 mmol) in 10:1 dioxane:water (6.28 mL) was sparged with $N_2$ for 15 minutes. 1,1'-Bis(di-t-butylphosphino)ferrocene palladium dichloride (61.4 mg, 0.0943 mmol) was added and the reaction was heated to 85° C. for 4 h. The reaction was filtered through celite and the filtrate was diluted with EtOAc, washed with water and brine, dried over $Na_2SO_4$, filtered, and concentrated under reduced pressure. The residue was purified by silica gel chromatography (0-50% EtOAc/heptanes) to give methyl [6-({(1r,3r)-3-[(tert-butoxycarbonyl)amino]cyclobutyl}methoxy)-2'-cyclobutyl-3'-fluoro[1,1'-biphenyl]-3-yl]acetate (F1b) (147 mg, 31%) as a yellow gum. LCMS APCI (+) 398 (M-Boc).

Step 3: methyl (6-{[(1r,3r)-3-aminocyclobutyl]methoxy}-2'-cyclobutyl-3'-fluoro[1,1'-biphenyl]-3-yl)acetate (F1c)

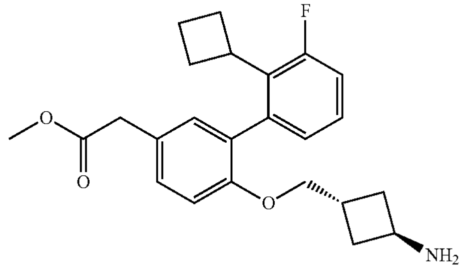 [SMILES: COC(=O)Cc1ccc(OC[C@H]2C[C@H](N)C2)c(-c2cccc(F)c2C2CCC2)c1]

To a solution of methyl [6-({(1r,3r)-3-[(tert-butoxycarbonyl)amino]cyclobutyl}methoxy)-2'-cyclobutyl-3'-fluoro[1,1'-biphenyl]-3-yl]acetate (F1b) (147 mg, 0.295 mmol) in DCM (2.95 mL), HCl (4 N in dioxane, 1.48 mL, 5.91 mmol) was added. After overnight stirring, the reaction was concentrated under reduced pressure and the residue was dissolved in EtOAc, washed with 1 N NaOH and brine, dried over $Na_2SO_4$, filtered, and concentrated under reduced pressure to give methyl (6-{[(1r,3r)-3-aminocyclobutyl]methoxy}-2'-cyclobutyl-3'-fluoro[1,1'-biphenyl]-3-yl)acetate (F1c) (123 mg, 105%) as an orange gum. LCMS APCI (+) 398 (M+H).

Step 4: methyl [2'-cyclobutyl-3'-fluoro-6-({(1S,3r)-3-[(1,4,4-trimethyl-L-prolyl)amino]cyclobutyl}methoxy)[1,1'-biphenyl]-3-yl]acetate (F1d)

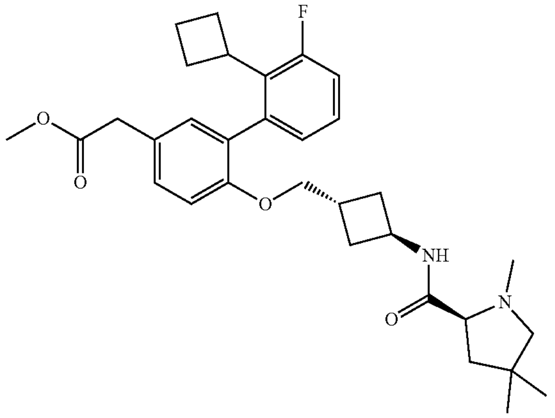

To a solution of methyl (6-{[(1r,3r)-3-aminocyclobutyl]methoxy}-2'-cyclobutyl-3'-fluoro[1,1'-biphenyl]-3-yl)acetate (F1c) (110 mg, 0.277 mmol), 1,4,4-trimethyl-L-proline (65.3 mg, 0.415 mmol), and DIPEA (0.145 mL, 0.830 mmol) in DCM (2.77 mL), HATU (116 mg, 0.304 mmol) was added. After 15 minutes, the reaction was diluted with EtOAc, washed with saturated $Na_2CO_3$ and brine, dried over $Na_2SO_4$, filtered, and concentrated under reduced pressure. The crude product was purified by silica gel chromatography (20-100% EtOAc/heptanes) to give methyl [2'-cyclobutyl-3'-fluoro-6-({(1S,3r)-3-[(1,4,4-trimethyl-L-prolyl)amino]cyclobutyl}methoxy)[1,1'-biphenyl]-3-yl]acetate (F1d) (80 mg, 54%). LCMS APCI (+) 537 (M+H).

Step 5: [2'-cyclobutyl-3'-fluoro-6-({(1S,3r)-3-[(1,4,4-trimethyl-L-prolyl)amino]cyclobutyl}methoxy)[1,1'-biphenyl]-3-yl]acetic acid (Example $F_1$)

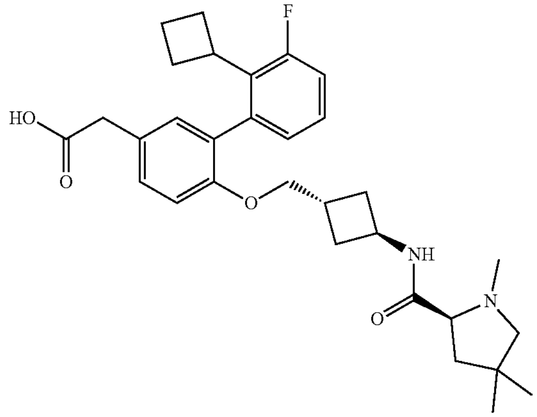 [SMILES: CN1CC(C)(C)C[C@H]1C(=O)N[C@H]1C[C@H](COc2ccc(CC(=O)O)cc2-c2cccc(F)c2C2CCC2)C1]

Example F1

To solution of methyl [2'-cyclobutyl-3'-fluoro-6-({(1S,3r)-3-[(1,4,4-trimethyl-L-prolyl)amino]cyclobutyl}methoxy)[1,1'-biphenyl]-3-yl]acetate (F1d) (33 mg, 0.061 mmol) in MeOH (0.410 mL), NaOH (1 N, 0.307 mL, 0.307 mmol) was added. The mixture was heated to 65° C. overnight. The reaction was cooled to RT, added 0.1 M potassium phosphate buffer (pH 7) and extracted with EtOAc (2×). The organics were combined, dried over $Na_2SO_4$, filtered, and concentrated under reduced pressure. The residue was purified by preparative SFC (Nacalai COSMOSIL 3-hydroxyphenyl 5 μm 20×150 mm Mobile phase A: $CO_2$ Mobile phase B: MeOH 10-50% B in 5.0 minutes, 120 bar, 70 mL/min) to give [2'-cyclobutyl-3'-fluoro-6-({(1S,3r)-3-[(1,4,4-trimethyl-L-prolyl)amino]cyclobutyl}methoxy)[1,1'-biphenyl]-3-yl]acetic acid (Example F1) (15 mg, 47%) as a white solid. LCMS APCI (+) 523 (M+H). $^1$H NMR (600 MHz, DMSO-d6) b ppm 8.01 (br d, J=7.63 Hz, 1H) 7.35-7.43 (m, 2H) 7.26 (dd, J=11.44, 8.54 Hz, 1H) 7.22 (d, J=8.36 Hz, 1H) 7.14 (d, J=1.82 Hz, 1H) 7.07 (d, J=7.27 Hz, 1H) 4.28-4.35 (m, 2H) 4.14-4.19 (m, 1H) 4.06-4.12 (m, 1H) 3.68 (br s, 2H) 3.64 (br t, J=9.08 Hz, 1H) 2.92-2.97 (m, 2H) 2.58 (br d, J=3.27 Hz, 1H) 2.40 (s, 3H) 2.30-2.38 (m, 2H) 2.21-2.29 (m, 1H) 2.01-2.16 (m, 6H) 1.88-1.96 (m, 1H) 1.79-1.88 (m, 1H) 1.64 (dd, J=12.53, 6.72 Hz, 1H) 1.24 (s, 3H) 1.19 (s, 3H).

Examples F2 and F3 reported in Table 6 was synthesized with non-critical changes or substitutions to the exemplified procedures for Example F1 that one skilled in the art would be able to realize.

TABLE 6

| Ex. | Structure and Name | Characterization Data ($^1$H NMR, optical rotation, and/or LCMS) |
|---|---|---|
| F2 | 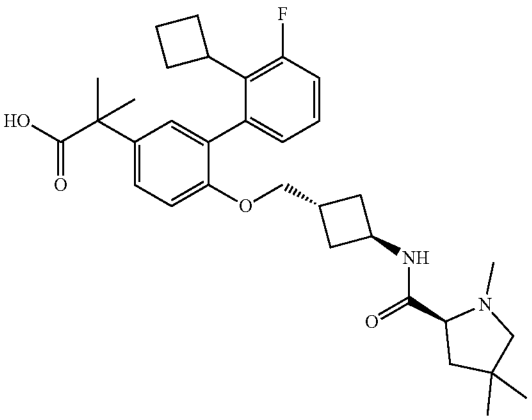 [SMILES: CN1CC(C)(C)C[C@H]1C(=O)N[C@H]1C[C@H](COc2ccc(C(C)(C)C(=O)O)cc2-c2cccc(F)c2C2CCC2)C1] 2-[2'-cyclobutyl-3'-fluoro-6-({(1S,3r)-3-[(1,4,4-trimethyl-L-prolyl)amino]cyclobutyl}methoxy)[1,1'-biphenyl]-3-yl]-2-methylpropanoic acid | $^1$H NMR (400 MHz, DMSO-$d_6$) δ 12.74-11.75 (m, 1H), 7.86 (d, J = 8.0 Hz, 1H), 7.30 (dd, J = 2.5, 8.6 Hz, 1H), 7.20 (dt, J = 5.7, 7.8 Hz, 1H), 7.11-7.03 (m, 2H), 6.98 (d, J = 2.5 Hz, 1H), 6.90 (d, J = 7.3 Hz, 1H), 4.14 (sxt, J = 7.7 Hz, 1H), 4.03-3.88 (m, 2H), 3.49-3.42 (m, 1H), 2.79-2.71 (m, 2H), 2.39 (br d, J = 3.6 Hz, 1H), 2.20 (s, 3H), 2.18-1.80 (m, 11H), 1.79-1.59 (m, 2H), 1.46 (d, J = 5.3 Hz, 6H), 1.07-0.97 (m, 6H). LCMS (m/z) (M + H)$^+$: 551.4 |

TABLE 6-continued

| Ex. | Structure and Name | Characterization Data ($^1$H NMR, optical rotation, and/or LCMS) |
|---|---|---|
| F3 | 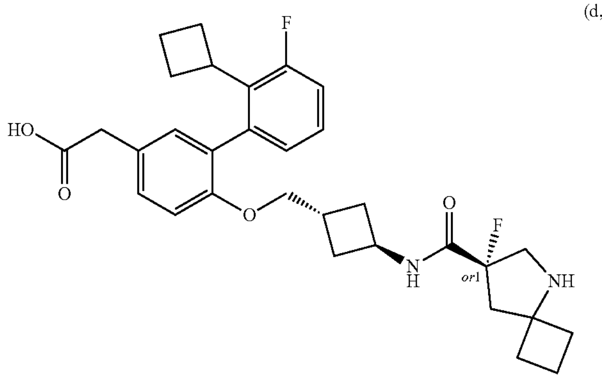 (2'-cyclobutyl-3'-fluoro-6-{[(1r,3r)-3-{[(7ξ)-7-fluoro-5-azaspiro[3.4]octane-7-carbonyl]amino}cyclobutyl]methoxy}[1,1'-biphenyl]-3-yl)acetic acid | $^1$H NMR (400 MHz, MeOD) δ 7.27 (dd, J = 2.2, 8.1 Hz, 1H), 7.14 (dt, J = 5.2, 7.8 Hz, 1H), 7.03 (d, J = 2.4 Hz, 1H), 7.01-6.92 (m, 2H), 6.90 (d, J = 7.3 Hz, 1H), 4.11 (t, J = 7.5 Hz, 1H), 4.01-3.86. LCMS (m/z) (M + H)$^+$: 539.3 |

Example G1: N-[(1r,3S)-3-{[(2'-cyclobutyl-3'-fluoro-5-{2-[(methanesulfonyl)amino]-2-oxoethyl}[1,1'-biphenyl]-2-yl)oxy]methyl}cyclobutyl]-1,4,4-trimethyl-L-prolinamide

G1

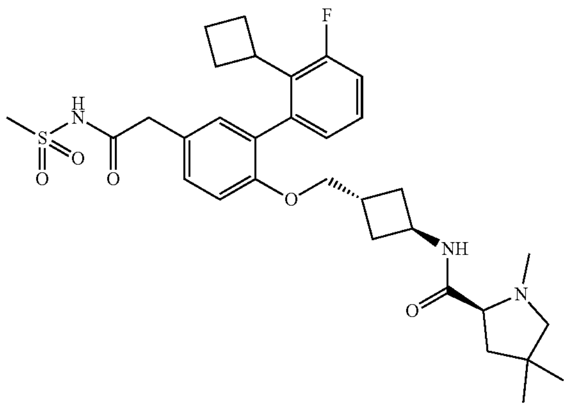

Example G1 was prepared according to General Method G.

To a solution of [2'-cyclobutyl-3'-fluoro-6-({(1S,3r)-3-[(1,4,4-trimethyl-L-prolyl)amino]cyclobutyl}methoxy)[1,1'-biphenyl]-3-yl]acetic acid (Example F1) (50 ing, 0.096 mmol) in THF (0.957 mL), carbonyldiimidazole (23.3 mg, 0.143 mmol) was added. The reaction was stirred for 1 h at RT, then methanesulfonamide (9.10 mg, 0.0957 mmol) and 1,8-diazabicyclo[5.4.0]undec-7-ene (72.8 mg, 0.478 mmol) were added. After 2 hours, the reaction was concentrated and purified by prep HPLC purification (Phenomenex Gemini NX-C18 150×21.2 mm, 5 uM, Mobile phase A: Water+10 mM Ammonium Acetate, Mobile phase B: Acetonitrile, 25-55% B in 12.0 minutes, 2.25 mL/min) to give N-{(1r,3S)-3-[({2'-cyclobutyl-3'-fluoro-5-[2-(methanesulfonamido)-2-oxoethyl][1,1'-biphenyl]-2-yl}oxy)methyl]cyclobutyl}-1,4,4-trimethyl-L-prolinamide (Example G1) (7.0 mg, 12%) as a white solid. LCMS APCI (+) 600.3 (M+H). $^1$H NMR (600 MHz, DMSO-d6) δ ppm 7.84 (br d, J=7.45 Hz, 1H) 7.17-7.23 (m, 2H) 7.04-7.08 (m, 1H) 7.01 (d, J=8.45 Hz, 1H) 6.96 (d, J=2.18 Hz, 1H) 6.89 (d, J=7.54 Hz, 1H) 6.49 (s, 1H) 4.09-4.15 (m, 1H) 3.95-3.99 (m, 1H) 3.85-3.92 (m, 1H) 3.46 (quin, J=9.17 Hz, 1H) 3.34 (br s, 2H) 2.88 (br s, 3H) 2.77 (br d, J=8.81 Hz, 2H) 2.37-2.42 (m, 1H) 2.22 (s, 3H) 2.12-2.20 (m, 2H) 2.08 (quin, J=9.79 Hz, 1H) 1.94-2.02 (m, 3H) 1.83-1.90 (m, 2H) 1.70-1.77 (m, 1H) 1.62-1.68 (m, 1H) 1.46 (dd, J=12.62, 6.81 Hz, 1H) 1.06 (s, 3H) 1.00 (s, 3H).

Examples G2-G5 reported in Table 7 were synthesized with non-critical changes or substitutions to the exemplified procedures for Example G1 that one skilled in the art would be able to realize.

TABLE 7

| Ex. | Structure and Name | Characterization Data ($^1$H NMR, optical rotation, and/or LCMS) |
|---|---|---|
| G2 | 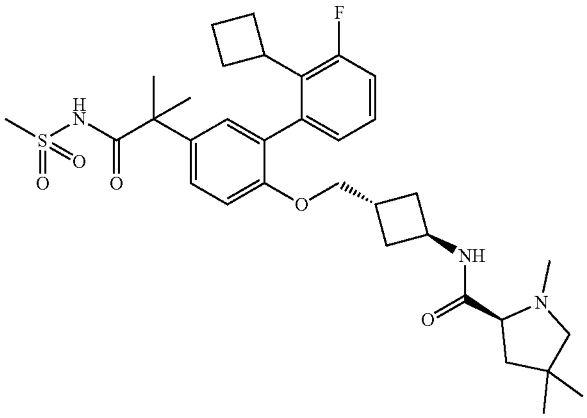 N-[(1r,3S)-3-{[(2'-cyclobutyl-3'-fluoro-5-{1-[(methanesulfonyl)amino]-2-methyl-1-oxopropan-2-yl}[1,1'-biphenyl]-2-yl)oxy]methyl}cyclobutyl]-1,4,4-trimethyl-L-prolinamide | $^1$H NMR (400 MHz, DMSO-$d_6$) δ 11.49-10.78 (m, 1H), 8.02 (br s, 1H), 7.28-7.16 (m, 2H), 7.11-7.02 (m, 2H), 6.95 (d, J = 2.3 Hz, 1H), 6.89 (d, J = 7.1 Hz, 1H), 4.18-4.05 (m, 1H), 4.02-3.86 (m, 2H), 3.49-3.42 (m, 2H), 3.02 (br s, 3H), 2.86 (br s, 1H), 2.44-2.24 (m, 4H), 2.21-1.58 (m, 13H), 1.44 (br d, J = 15.8 Hz, 6H), 1.09-0.99 (m, 6H). LCMS (m/z) (M + H)$^+$: 628.5 |
| G3 | 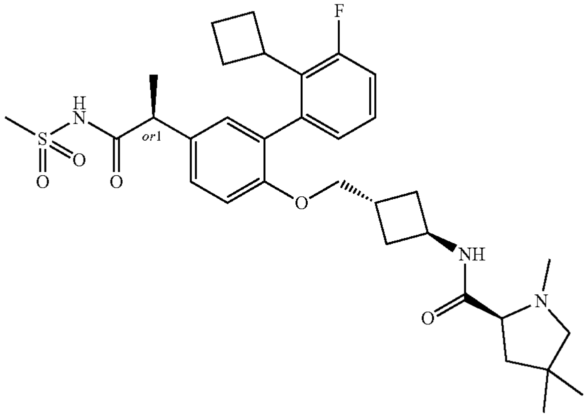 N-[(1r,3S)-3-{[(2'-cyclobutyl-3'-fluoro-5-{(2ξ)-1-[(methanesulfonyl)amino]-1-oxopropan-2-yl}[1,1'-biphenyl]-2-yl)oxy]methyl}cyclobutyl]-1,4,4-trimethyl-L-prolinamide | $^1$H NMR (400 MHz, DMSO-$d_6$) δ 7.98 (br d, J = 8.6 Hz, 1H), 7.30-7.16 (m, 2H), 7.13-6.95 (m, 3H), 6.90 (t, J = 6.9 Hz, 1H), 4.18-4.06 (m, 1H), 4.03-3.87 (m, 2H), 3.69-3.60 (m, 1H), 3.51-3.40 (m, 2H), 3.11 (d, J = 3.7 Hz, 3H), 2.99-2.87 (m, 1H), 2.83 (br d, J = 8.8 Hz, 1H), 2.44-2.36 (m, 1H), 2.28 (s, 3H), 2.26-2.21 (m, 1H), 2.18-1.82 (m, 9H), 1.78-1.57 (m, 2H), 1.52-1.43 (m, 1H), 1.37-1.28 (m, 3H), 1.05 (s, 3H), 1.01 (s, 3H). LCMS (m/z) (M + H)$^+$: 614.4 |
| G4 | 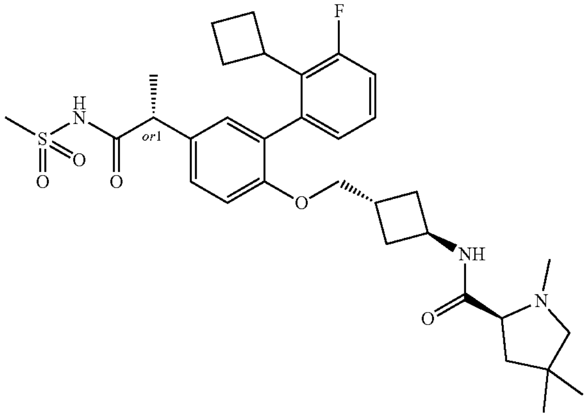 N-[(1r,3S)-3-{[(2'-cyclobutyl-3'-fluoro-5-{(2ξ)-1-[(methanesulfonyl)amino]-1-oxopropan-2-yl}[1,1'-biphenyl]-2-yl)oxy]methyl}cyclobutyl]-1,4,4-trimethyl-L-prolinamide | $^1$H NMR (400 MHz, DMSO-$d_6$) δ 8.01 (br d, J = 7.3 Hz, 1H), 7.28-7.16 (m, 2H), 7.12-6.95 (m, 3H), 6.89 (t, J = 6.8 Hz, 1H), 4.18-4.07 (m, 1H), 4.02-3.87 (m, 2H), 3.66-3.62 (m, 1H), 3.07 (d, J = 3.7 Hz, 3H), 3.00-2.91 (m, 1H), 2.83 (br d, J = 9.2 Hz, 1H), 2.46-2.34 (m, 1H), 2.28 (s, 3H), 2.26-2.20 (m, 1H), 2.18-1.82 (m, 9H), 1.78-1.56 (m, 2H), 1.52-1.43 (m, 1H), 1.36-1.27 (m, 3H), 1.05 (s, 3H), 1.01 (s, 3H). LCMS (m/z) (M + H)$^+$: 614.4 |

TABLE 7-continued

| Ex. | Structure and Name | Characterization Data ($^1$H NMR, optical rotation, and/or LCMS) |
| --- | --- | --- |
| G5 | 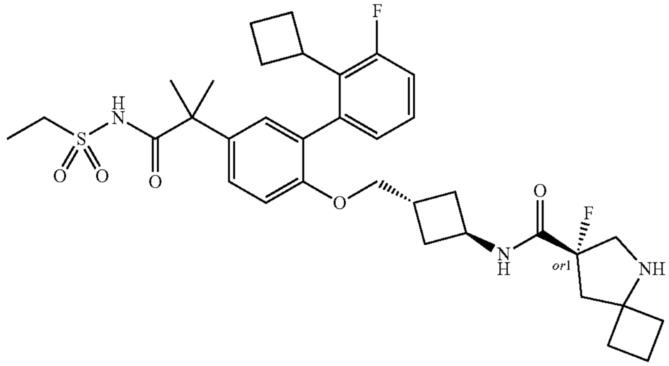 [SMILES: CCS(=O)(=O)NC(=O)C(C)(C)c1ccc(OC[C@H]2C[C@H](NC(=O)[C@@]3(F)CNC4(CCC4)C3)C2)c(-c2cccc(F)c2C2CCC2)c1]<br>(7Rξ)-N-{(1r,3r)-3-[({2'-cyclobutyl-5-[1-(ethanesulfonamido)-2-methyl-1-oxopropan-2-yl]-3'-fluoro[1,1'-biphenyl]-2-yl}oxy)methyl]cyclobutyl}-7-fluoro-5-azaspiro[3.4]octane-7-carboxamide | $^1$H NMR (400 MHz, DMSO-$d_6$) δ 11.32-10.90 (m, 1H), 10.01-9.70 (m, 2H), 8.75 (br d, J = 6.8 Hz, 1H), 7.31-7.25 (m, 1H), 7.24-7.18 (m, 1H), 7.13-7.06 (m, 2H), 6.96 (d, J = 2.3 Hz, 1H), 6.90 (d, J = 7.3 Hz, 1H), 4.21-4.12 (m, 1H), 4.06-3.91 (m, 2H), 3.70-3.55 (m, 2H), 3.47 (quin, J = 9.2 Hz, 1H), 3.39-3.35 (m, 1H), 3.31 (br s, 2H), 2.69-2.55 (m, 2H), 2.47-2.37 (m, 2H), 2.24-2.03 (m, 6H), 1.99-1.63 (m, 8H), 1.57-1.43 (m, 6H), 1.08 (t, J = 7.3 Hz, 3H). LCMS (m/z) (M + H)$^+$: 658.3 |

Example H1: [(1ψ)-2'-cyclobutyl-3'-fluoro-6-({(1R,3R)-3-[(1,4,4-trimethyl-L-prolyl)amino]cyclopentyl}oxy)[1,1'-biphenyl]-2-yl]acetic acid; and Example H2: [(1ψ)-2'-cyclobutyl-3'-fluoro-6-({(1R,3R)-3-[(1,4,4-trimethyl-L-prolyl)amino]cyclopentyl}oxy)[1,1'-biphenyl]-2-yl]acetic acid

H1

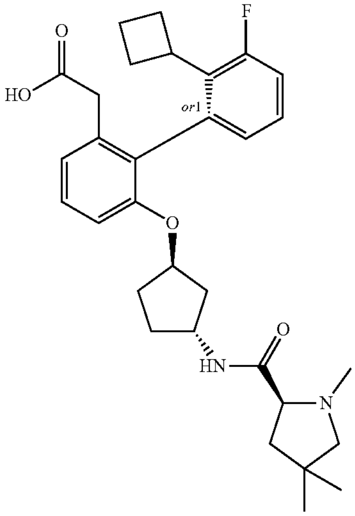

-continued

H2

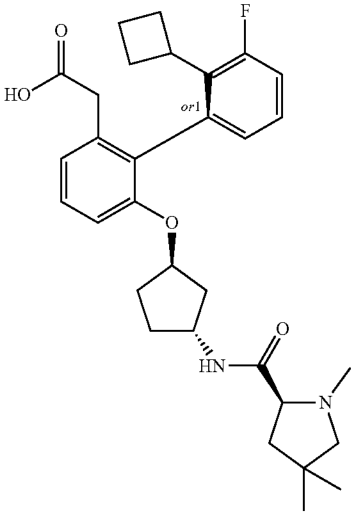

Examples H1 and H2 were prepared according to General Method H.

Step 1: methyl [2-bromo-3-({(1R,3R)-3-[(tert-butoxycarbonyl)amino]cyclopentyl}oxy)phenyl]acetate (H1a)

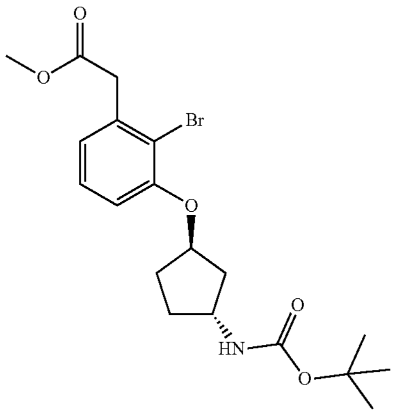 [SMILES: COC(=O)Cc1cccc(O[C@@H]2CC[C@@H](NC(=O)OC(C)(C)C)C2)c1Br]

To a solution of methyl (2-bromo-3-hydroxyphenyl)acetate (Intermediate 6) (300 mg, 1.22 mmol) and tert-butyl ((1R,3S)-3-hydroxycyclopentyl)carbamate (296 mg, 1.47 mmol) in THF (5.0 mL), triphenylphosphine (642 mg, 2.45 mmol) was added followed by diisopropyl azodicarboxylate (495 mg, 2.45 mmol) drop-wise. After 16 h, the reaction was concentrated under reduced pressure and purified by silica gel chromatography (0-50% EtOAc/heptanes) to give methyl [2-bromo-3-({(1R,3R)-3-[(tert-butoxycarbonyl)amino]cyclopentyl}oxy)phenyl]acetate (H1a) (400 mg, 76.3%) as a white solid. LCMS APCI (+) 328.1 and 340.1 (M-Boc). $^1$H NMR (400 MHz, CHLOROFORM-d) b ppm 1.41-1.47 (m, 9H) 1.71-1.84 (m, 1H) 1.88-2.02 (m, 1H) 2.07-2.19 (m, 1H) 2.30 (br s, 1H) 2.32-2.44 (m, 1H) 3.72 (s, 3H) 3.82 (s, 2H) 4.18-4.33 (m, 1H) 4.42-4.60 (m, 1H) 4.80-4.88 (m, 1H) 6.74-6.79 (m, 1H) 6.88 (d, J=7.04 Hz, 1H) 7.19 (t, J=7.81 Hz, 1H).

Step 2: methyl [6-({(1R,3R)-3-[(tert-butoxycarbonyl)amino]cyclopentyl}oxy)-2'-cyclobutyl-3'-fluoro[1,1'-biphenyl]-2-yl]acetate (H1b)

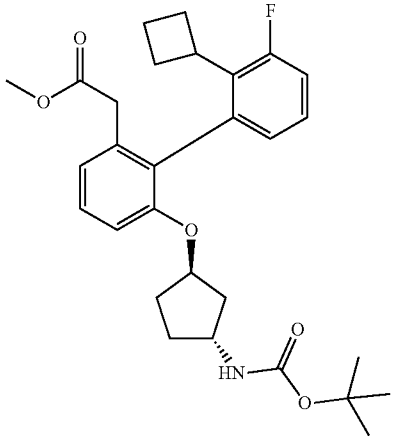 [SMILES: COC(=O)Cc1cccc(O[C@@H]2CC[C@@H](NC(=O)OC(C)(C)C)C2)c1-c1cccc(F)c1C1CCC1]

A solution of methyl [2-bromo-3-({(1R,3R)-3-[(tert-butoxycarbonyl)amino]cyclopentyl}oxy)phenyl]acetate (H1a) (400 mg, 0.75 mmol), 2-(2-cyclobutyl-3-fluorophenyl)-4,4,5,5-tetramethyl-1,3,2-dioxaborolane (Intermediate 2) (248 mg, 0.897 mol), $NaHCO_3$ (188 mg, 2.24 mmol), and Bis(di-tert-butyl(4-dimethylaminophenyl)phosphine)dichloropalladium(II) in 8:1 MeOH:water (9.0 mL) was heated to 70° C. for 16 h. The reaction was concentrated under reduced pressure and the residue was purified by silica gel chromatography (0-50% EtOAc/heptanes) to give methyl [6-({(1R,3R)-3-[(tert-butoxycarbonyl)amino]cyclopentyl}oxy)-2'-cyclobutyl-3'-fluoro[1,1'-biphenyl]-2-yl]acetate (H1b) (330 mg, 89%) as a white solid. LCMS APCI (+) 398.3 (M-Boc).

Step 3: methyl (6-{[(1R,3R)-3-aminocyclopentyl]oxy}-2'-cyclobutyl-3'-fluoro[1,1'-biphenyl]-2-yl)acetate (H1c)

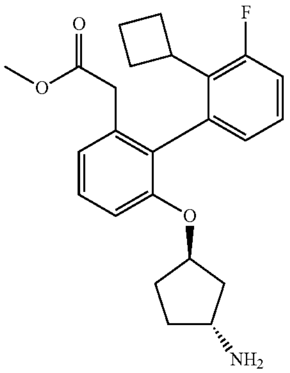 [SMILES: COC(=O)Cc1cccc(O[C@@H]2CC[C@@H](N)C2)c1-c1cccc(F)c1C1CCC1]

To a solution of methyl [6-({(1R,3R)-3-[(tert-butoxycarbonyl)amino]cyclopentyl}oxy)-2'-cyclobutyl-3'-fluoro[1,1'-biphenyl]-2-yl]acetate (H1b) (379 mg, 0.748 mmol) in DCM (5.0 mL), HCl (4 N in dioxane, 2.0 mL, 8.0 mmol) was added at 0° C. After 2 h, the reaction was concentrated under reduced pressure to give methyl (6-{[(1R,3R)-3-aminocyclopentyl]oxy}-2'-cyclobutyl-3'-fluoro[1,1'-biphenyl]-2-yl)acetate (H1c) (374 mg 127%) as a yellow oil. LCMS APCI (+) 398.3 (M+H). $^1$H NMR (400 MHz, CHLOROFORM-d) b ppm 1.69-1.84 (m, 5H) 1.85-1.93 (m, 2H) 2.12-2.22 (m, 2H) 2.26-2.42 (m, 3H) 3.13-3.23 (m, 1H) 3.35 (s, 1H) 3.56-3.58 (m, 3H) 4.79-4.87 (m, 1H) 6.65-6.79 (m, 2H) 6.79-6.84 (m, 1H) 6.95-7.05 (m, 2H) 7.10-7.18 (m, 1H) 8.18 (br s, 3H).

Step 4: methyl [2'-cyclobutyl-3'-fluoro-6-({(1R,3R)-3-[(1,4,4-trimethyl-L-prolyl)amino]cyclopentyl}oxy)[1,1'-biphenyl]-2-yl]acetate (H1d)

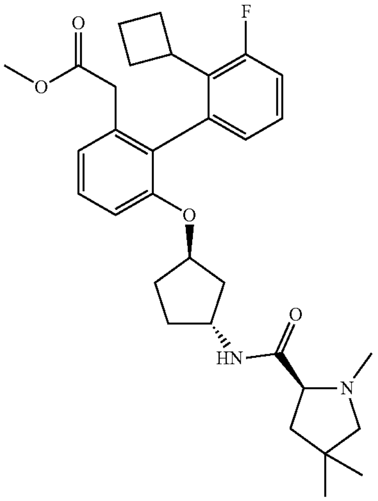

To a solution of methyl (6-{[(1R,3R)-3-aminocyclopentyl]oxy}-2'-cyclobutyl-3'-fluoro[1,1'-biphenyl]-2-yl)acetate (H1c) (200 mg, 0.394 mmol) and 1,4,4-trimethyl-L-proline (68.2 mg, 0.434 mmol) in DCM (7.0 mL), TEA (79.8 mg, 0.789 mmol) was added followed by benzotriazole-1-yl-oxy-tris-pyrrolidino-phosphonium hexafluorophosphate (308 mg, 0.592 mmol). After stirring overnight at RT, water was added then extracted with DCM (3×). The combined organics were washed with water (2×), dried over $Na_2SO_4$, filtered, and concentrated under reduced pressure. The residue was purified by silica gel chromatography (0-10% MeOH/DCM) to give methyl [2'-cyclobutyl-3'-fluoro-6-({(1R,3R)-3-[(1,4,4-trimethyl-L-prolyl)amino]cyclopentyl}oxy)[1,1'-biphenyl]-2-yl]acetate (H1d) (300 mg, 142%) as a yellow oil. LCMS APCI (+) 537.4 (M+H).

Step 5: [(1ψ)-2'-cyclobutyl-3'-fluoro-6-({(1R,3R)-3-[(1,4,4-trimethyl-L-prolyl)amino]cyclopentyl}oxy)[1,1'-biphenyl]-2-yl]acetic acid (Example H1); and [(1ψ)-2'-cyclobutyl-3'-fluoro-6-({(1R,3R)-3-[(1,4,4-trimethyl-L-prolyl)amino]cyclopentyl}oxy)[1,1'-biphenyl]-2-yl]acetic acid (Example H2)

H1

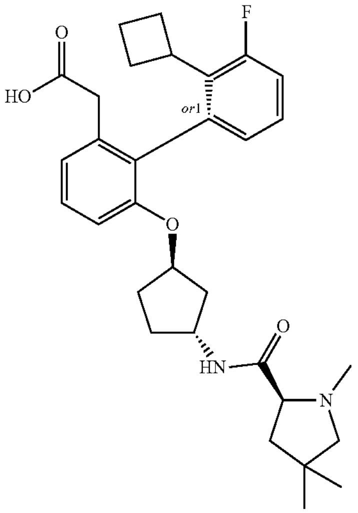

-continued

H2

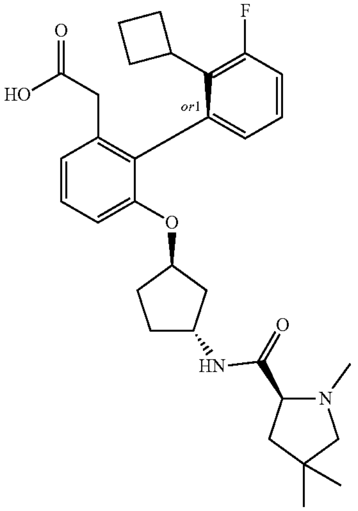

To a solution of methyl [2'-cyclobutyl-3'-fluoro-6-({(1R,3R)-3-[(1,4,4-trimethyl-L-prolyl)amino]cyclopentyl}oxy)[1,1'-biphenyl]-2-yl]acetate (H1d) (300 mg, 0.559 mol) in 10:1 MeOH:water (11 mL), LiOH (2 M, 5.59 mL, 11.2 mmol) was added. After stirring overnight at RT, the reaction was concentrated and the residue was purified by prep HPLC (Xtimate C18 150×40 mm, 5 uM, Mobile phase A: Water+formic acid, Mobile phase B: Acetonitrile, 14-54% B in 9.0 minutes, 60 mL/min) to give [(1P)-2'-cyclobutyl-3'-fluoro-6-({(1R,3R)-3-[(1,4,4-trimethyl-L-prolyl)amino]cyclopentyl}oxy)[1,1'-biphenyl]-2-yl]acetic acid (Example H1) as peak 1 (24.3 mg, 8.32%) as a white solid. LCMS APCI (+) 523.4 (M+H). 1H NMR (400 MHz, METHANOL-d4) 5=7.33-7.24 (m, 1H), 7.21-7.13 (m, 1H), 7.06-6.95 (m, 2H), 6.92-6.87 (m, 1H), 6.84-6.74 (m, 1H), 4.82-4.75 (m, 2H), 4.08 (quin, J=7.2 Hz, 1H), 3.49 (dd, J=7.4, 9.4 Hz, 1H), 3.23-3.16 (m, 1H), 3.14 (d, J=10.3 Hz, 1H), 2.68-2.61 (m, 1H), 2.58 (s, 3H), 2.45-2.24 (m, 2H), 2.22-2.12 (m, 1H), 2.11-1.64 (m, 1OH), 1.63-1.53 (m, 1H), 1.39 (tdd, J=6.2, 8.8, 12.7 Hz, 1H), 1.32-1.19 (m, 1H), 1.13 (d, J=3.6 Hz, 6H). Peak 2 was repurified by prep HPLC (Phenomenex $C_{18}$ $_{75\times30}$ mm, 3 uM, Mobile phase A: Water+$NH_4OH$, Mobile phase B: Acetonitrile, 15-55% B in 9.0 minutes, 60 mL/min) to give [(1M)-2'-cyclobutyl-3'-fluoro-6-({(1R,3R)-3-[(1,4,4-trimethyl-L-prolyl)amino]cyclopentyl}oxy)[1,1'-biphenyl]-2-yl]acetic acid (Example H2) (7.0 mg, 2%) as a white solid. LCMS APCI (+) 523.4 (M+H). 1H NMR (400 MHz, METHANOL-d4) δ=7.36-7.23 (m, 1H), 7.21-7.13 (m, 1H), 7.05-6.95 (m, 2H), 6.91-6.78 (m, 2H), 4.83-4.75 (m, 1H), 4.09-3.98 (m, 1H), 3.29-3.25 (m, 2H), 3.25-3.13 (m, 2H), 3.04-2.97 (m, 1H), 2.47 (s, 1H), 2.44 (s, 3H), 2.42-2.22 (m, 2H), 2.14-1.82 (m, 6H), 1.81-1.57 (m, 5H), 1.47-1.34 (m, 1H), 1.10 (d, J=5.9 Hz, 6H).

Examples H3-H13 reported in Table 8 were synthesized with non-critical changes or substitutions to the exemplified procedures for Examples H1 and H2 that one skilled in the art would be able to realize. For examples H8-H11, MA-12 was used for the amide coupling.

TABLE 8

| Ex. | Structure and Name | Characterization Data ($^1$H NMR, optical rotation, and/or LCMS) |
|---|---|---|
| H3 | 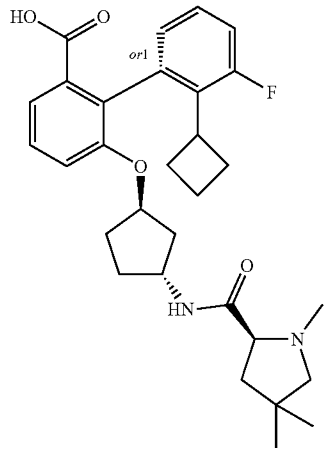 (1ψ)-2'-cyclobutyl-3'-fluoro-6-({(1R,3R)-3-[(1,4,4-trimethyl-L-prolyl)amino]cyclopentyl}oxy)[1,1'-biphenyl]-2-carboxylic acid | 1H NMR (400 MHz, DMSO-d6) δ = 8.16 (s, 1H), 7.64 (br d, J = 8.1 Hz, 1H), 7.44-7.38 (m, 1H), 7.37-7.32 (m, 1H), 7.21-7.11 (m, 2H), 7.04 (dd, J = 8.3, 10.9 Hz, 1H), 6.68 (d, J = 6.6 Hz, 1H), 4.86-4.77 (m, 1H), 4.04-3.94 (m, 1H), 2.81-2.71 (m, 2H), 2.22-2.18 (m, 4H), 2.15 (br t, J = 8.8 Hz, 2H), 2.02-1.91 (m, 2H), 1.89-1.62 (m, 8H), 1.49-1.42 (m, 1H), 1.42-1.27 (m, 2H), 1.06-0.95 (m, 6H). LCMS (m/z) (M + H)$^+$: 509.4 |
| H4 | 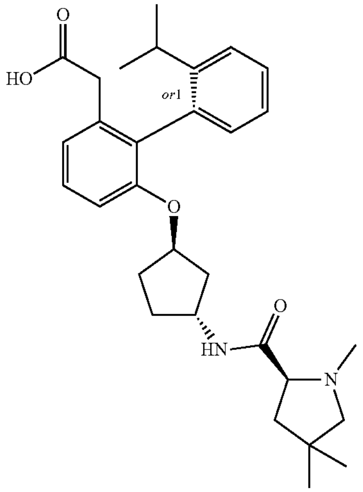 [(1ψ)-2'-(propan-2-yl)-6-({(1R,3R)-3-[(1,4,4-trimethyl-L-prolyl)amino]cyclopentyl}oxy)[1,1'-biphenyl]-2-yl]acetic acid | $^1$H NMR (400 MHz, MeOD) δ 7.40-7.34 (m, 1H), 7.33-7.24 (m, 2H), 7.15 (dt, J = 1.3, 7.4 Hz, 1H), 7.02-6.95 (m, 2H), 6.89 (d, J = 8.1 Hz, 1H), 4.83-4.76 (m, 1H), 4.08 (quin, J = 7.1 Hz, 1H), 3.30-3.14 (m, 3H), 3.00 (d, J = 9.7 Hz, 1H), 2.60 (td, J = 6.9, 13.7 Hz, 1H), 2.47 (s, 1H), 2.44 (s, 3H), 2.14-1.74 (m, 5H), 1.69-1.54 (m, 2H), 1.39 (qd, J = 6.3, 14.9 Hz, 1H), 1.18-1.08 (m, 9H), 1.04 (d, J = 7.0 Hz, 3H). LCMS (m/z) (M + H)$^+$: 493.5 |

TABLE 8-continued

| Ex. | Structure and Name | Characterization Data ($^1$H NMR, optical rotation, and/or LCMS) |
|---|---|---|
| H5 | 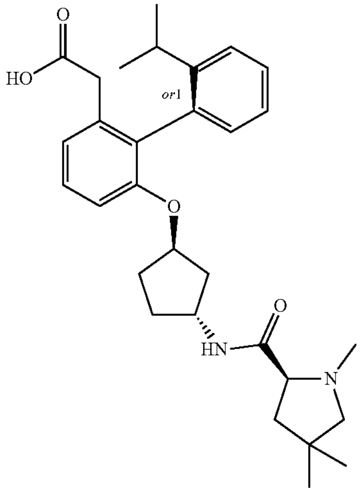 [(1ψ)-2'-(propan-2-yl)-6-({(1R,3R)-3-[(1,4,4-trimethyl-L-prolyl)amino]cyclopentyl}oxy)[1,1'-biphenyl]-2-yl]acetic acid | $^1$H NMR (400 MHz, MeOD) δ 7.38-7.24 (m, 3H), 7.19-7.13 (m, 1H), 6.99 (dd, J = 3.9, 7.6 Hz, 2H), 6.88 (d, J = 7.9 Hz, 1H), 4.83-4.75 (m, 1H), 4.06 (quin, J = 7.4 Hz, 1H), 3.30-3.14 (m, 3H), 3.01 (d, J = 9.7 Hz, 1H), 2.60 (td, J = 6.9, 13.9 Hz, 1H), 2.48 (s, 1H), 2.44 (s, 3H), 2.15-2.04 (m, 2H), 1.97 (br dd, J = 7.8, 13.8 Hz, 1H), 1.91-1.80 (m, 1H), 1.72-1.58 (m, 3H), 1.47-1.36 (m, 1H), 1.18-1.08 (m, 9H), 1.05 (d, J= 6.8 Hz, 3H). LCMS (m/z) (M + H)$^+$: 493.5 |
| H6 | 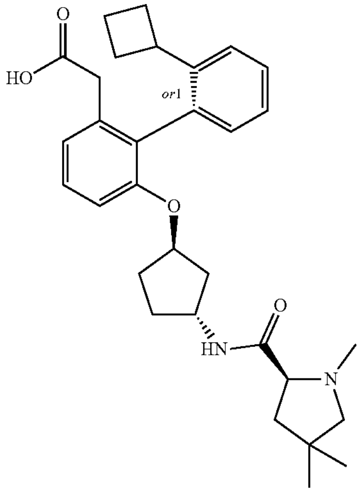 [(1ψ)-2'-cyclobutyl-6-({(1R,3R)-3-[(1,4,4-trimethyl-L-prolyl)amino]cyclopentyl}oxy)[1,1'-biphenyl]-2-yl]acetic acid | $^1$H NMR (400 MHz, $^1$H NMR (400 MHz, DMSO-$d_6$) δ) δ 7.58 (d, J = 8.00 Hz, 1 H) 7.41 (d, J = 7.50 Hz, 1 H) 7.32 (td, J = 7.54, 1.19 Hz, 1 H) 7.26 (t, J = 7.94 Hz, 1 H) 7.17 (td, J = 7.38, 1.13 Hz, 1 H) 6.91-6.94 (m, 1 H) 6.89 (d, J = 8.13 Hz, 1 H) 6.86 (dd, J = 7.57, 1.06 Hz, 1 H) 4.73 (dt, J = 5.57, 2.85 Hz, 1 H) 3.94 (sxt, J = 7.38 Hz, 1 H) 3.24 (s, 1 H) 3.15 (br d, J = 8.63 Hz, 1 H) 2.99 (d, J = 16.13 Hz, 1 H) 2.71-2.77 (m, 2 H) 2.19 (s, 3 H) 2.12 (d, J = 8.88 Hz, 1 H) 1.99-2.06 (m, 1 H) 1.80-2.00 (m, 5 H) 1.57-1.79 (m, 6 H) 1.44 (dd, J = 12.51, 6.75 Hz, 1 H) 1.27-1.40 (m, 2 H) 1.04 (s, 3 H) 0.99 (s, 3 H). LCMS (m/z) (M + H)$^+$: 505.2 |

TABLE 8-continued

| Ex. | Structure and Name | Characterization Data ($^1$H NMR, optical rotation, and/or LCMS) |
|---|---|---|
| H7 | 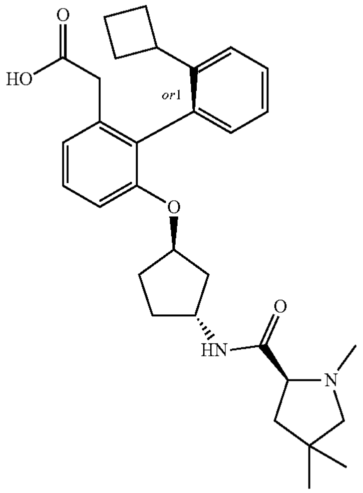 [(1ψ)-2'-cyclobutyl-6-({(1R,3R)-3-[(1,4,4-trimethyl-L-(prolyl)amino]cyclopentyl}oxy)[1,1'-biphenyl]-2-yl]acetic acid | $^1$H NMR (400 MHz, $^1$H NMR (400 MHz, DMSO-$d_6$) δ) δ 11.82 12.12 (m, 1 H) 7.54 (br d, J = 7.63 Hz, 1 H) 7.41 (d, J = 7.50 Hz, 1 H) 7.30-7.36 (m, 1 H) 7.26 (t, J = 7.94 Hz, 1 H) 7.16 (td, J = 7.44, 1.25 Hz, 1 H) 6.84-6.95 (m, 3 H) 4.69-4.77 (m, 1 H) 3.86-3.99 (m, 1 H) 3.22 (d, J = 16.26 Hz, 1 H) 3.10-3.18 (m, 1 H) 3.01 (d, J = 16.26 Hz, 1 H) 2.73 (br d, J = 8.63 Hz, 2 H) 2.18 (s, 3 H) 2.12 (br d, J = 8.75 Hz, 1 H) 1.97-2.05 (m, 2 H) 1.86-1.94 (m, 2 H) 1.80-1.86 (m, 1 H) 1.73-1.79 (m, 1 H) 1.61-1.72 (m, 5 H) 1.40-1.47 (m, 2 H) 1.29-1.39 (m, 1 H) 1.03 (s, 3 H) 0.98 (s, 3 H). LCMS (m/z) (M + H)$^+$: 505.2 |
| H8 | 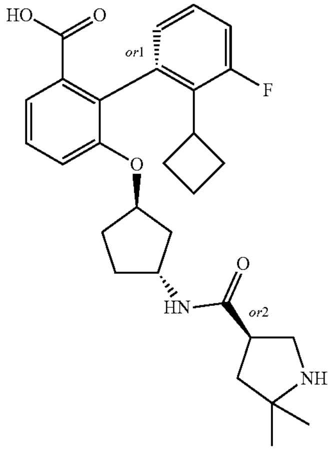 (1ψ)-2'-cyclobutyl-6-{[(1R,3R)-3-{[(3ξ)-5,5-dimethylpyrrolidine-3-carbonyl]amino}cyclopentyl]oxy}-3'-fluoro[1,1'-biphenyl]-2-carboxylic acid | $^1$H NMR (400 MHz, DMSO-$d_6$) δ 12.51 (s, 1H), 9.12-8.76 (m, 1H), 8.16 (d, J = 7.0 Hz, 1H), 7.46-7.39 (m, 1H), 7.38-7.33 (m, 1H), 7.19 (d, J = 7.5 Hz, 1H), 7.17-7.10 (m, 1H), 7.05 (dd, J = 8.4, 10.8 Hz, 1H), 6.68 (d, J = 6.8 Hz, 1H), 4.83 (br s, 1H), 4.02-3.83 (m, 1H), 3.42-3.35 (m, 2H), 3.30-3.24 (m, 1H), 3.16 (quin, J = 8.6 Hz, 1H), 2.29-2.13 (m, 2H), 2.09 (dd, J = 8.7, 13.1 Hz, 1H), 2.04-1.82 (m, 3H), 1.82-1.58 (m, 6H), 1.47-1.21 (m, 8H). LCMS (m/z) (M + H)$^+$: 495.5 |

TABLE 8-continued

| Ex. | Structure and Name | Characterization Data ($^1$H NMR, optical rotation, and/or LCMS) |
|---|---|---|
| H9 | 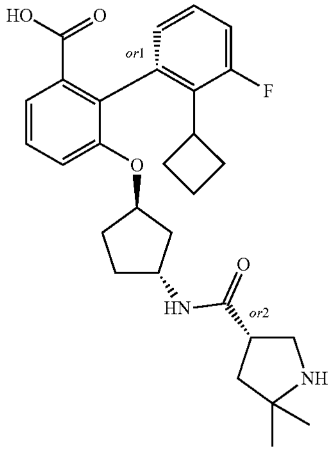 (1ψ)-2'-cyclobutyl-6-{[(1R,3R)-3-{[(3ξ)-5,5-dimethylpyrrolidine-3-carbonyl]amino}cyclopentyl]oxy}-3'-fluoro[1,1'-biphenyl]-2-carboxylic acid | $^1$H NMR (400 MHz, DMSO-$d_6$) δ 12.51 (s, 1H), 9.12-8.76 (m, 1H), 8.16 (d, J = 7.0 Hz, 1H), 7.46-7.39 (m, 1H), 7.38-7.33 (m, 1H), 7.19 (d, J = 7.5 Hz, 1H), 7.17-7.10 (m, 1H), 7.05 (dd, J = 8.4, 10.8 Hz, 1H), 6.68 (d, J = 6.8 Hz, 1H), 4.83 (br s, 1H), 4.02-3.83 (m, 1H), 3.42-3.35 (m, 2H), 3.30-3.24 (m, 1H), 3.16 (quin, J = 8.6 Hz, 1H), 2.29-2.13 (m, 2H), 2.09 (dd, J = 8.7, 13.1 Hz, 1H), 2.04-1.82 (m, 3H), 1.82-1.58 (m, 6H), 1.47-1.21 (m, 8H). LCMS (m/z) (M + H)$^+$: 495.5 |
| H10 | 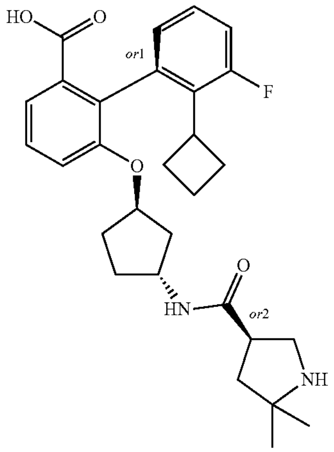 (1ψ)-2'-cyclobutyl-6-{[(1R,3R)-3-{[(3ξ)-5,5-dimethylpyrrolidine-3-[carbonyl]amino}cyclopentyl]oxy}-3'-fluoro[1,1'-biphenyl]-2-carboxylic acid | $^1$H NMR (400 MHz, DMSO-$d_6$) δ 9.04-8.73 (m, 1H), 8.17-8.03 (m, 1H), 7.46-7.38 (m, 1H), 7.39-7.31 (m, 1H), 7.25-7.10 (m, 2H), 7.09-7.00 (m, 1H), 6.73-6.63 (m, 1H), 4.87-4.75 (m, 1H), 3.96-3.79 (m, 1H), 3.23-3.03 (m, 2H), 2.29-1.90 (m, 6H), 1.83-1.55 (m, 8H), 1.54-1.44 (m, 1H), 1.36 (s, 4H), 1.32-1.27 (m, 3H), 1.27-1.21 (m, 1H). LCMS (m/z) (M + H)$^+$: 495.5 |

TABLE 8-continued

| Ex. | Structure and Name | Characterization Data ($^1$H NMR, optical rotation, and/or LCMS) |
|---|---|---|
| H11 | 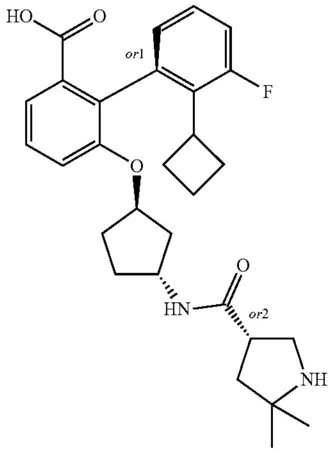 (1ψ)-2'-cyclobutyl-6-{[(1R,3R)-3-{[(3ξ)-5,5-dimethylpyrrolidine-3-carbonyl]amino}cyclopentyl]oxy}-3'-fluoro[1,1'-biphenyl]-2-carboxylic acid | $^1$H NMR (400 MHz, DMSO-$d_6$) δ 12.80-12.06 (m, 1H), 9.15-8.71 (m, 2H), 8.18-8.11 (m, 1H), 7.46-7.39 (m, 1H), 7.39-7.33 (m, 1H), 7.24-7.10 (m, 2H), 7.09-7.01 (m, 1H), 6.72-6.63 (m, 1H), 4.88-4.79 (m, 1H), 3.95-3.79 (m, 1H), 3.22-3.05 (m, 1H), 2.29-2.13 (m, 2H), 2.12-1.91 (m, 3H), 1.85-1.57 (m, 7H), 1.54-1.44 (m, 1H), 1.41-1.35 (m, 3H), 1.33-1.29 (m, 3H), 1.28-1.21 (m, 1H). LCMS (m/z) (M + H)$^+$: 495.5 |
| H12 | 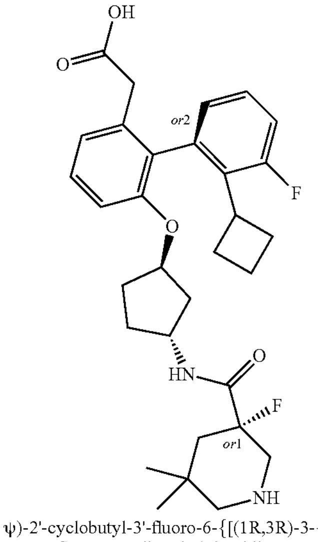 [(1 ψ)-2'-cyclobutyl-3'-fluoro-6-{[(1R,3R)-3-{[(3ξ)-3-fluoro-5,5-dimethylpiperidine-3-carbonyl]amino}cyclopentyl]oxy}[1,1'-biphenyl]-2-yl]acetic acid | $^1$H NMR (400 MHz, DMSO-$d_6$) δ 8.38 (br d, J = 6.6 Hz, 1H), 7.29 (t, J = 7.9 Hz, 1H), 7.24-7.15 (m, 1H), 7.11 (dd, J = 8.0, 11.8 Hz, 1H), 6.93 (t, J = 7.7 Hz, 2H), 6.71 (d, J = 7.0 Hz, 1H), 4.78 (br s, 1H), 3.98-3.87 (m, 1H), 3.44-3.37 (m, 1H), 3.37-3.34 (m, 2H), 3.31 (br s, 1H), 3.28-3.23 (m, 1H), 3.22-3.15 (m, 1H), 3.10 (d, J = 16.1 Hz, 1H), 3.01-2.93 (m, 1H), 2.89-2.82 (m, 1H), 2.33-2.24 (m, 1H), 2.22-2.13 (m, 1H), 2.12-2.02 (m, 1H), 2.00-1.92 (m, 1H), 1.90-1.76 (m, 3H), 1.75-1.66 (m, 5H), 1.49-1.36 (m, 2H), 1.11 (s, 3H), 0.95 (s, 3H). LCMS (m/z) (M + H)$^+$: 541.3 |

TABLE 8-continued

| Ex. | Structure and Name | Characterization Data ($^1H$ NMR, optical rotation, and/or LCMS) |
|---|---|---|
| H13 | 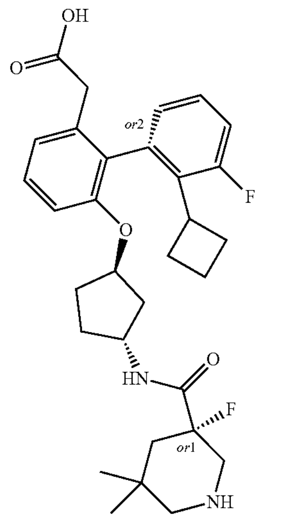 [(1 ψ)-2'-cyclobutyl-3'-fluoro-6-{[(1R,3R)-3-{[(3ξ)-3-fluoro-5,5-dimethylpiperidine-3-carbonyl]amino}cyclopentyl]oxy}[1,1'-biphenyl]-2-yl]acetic acid | $^1H$ NMR (400 MHz, DMSO-$d_6$) δ 8.41 (br d, J = 6.2 Hz, 1H), 7.32 7.26 (m, 1H), 7.20 (dt, J = 5.8, 7.8 Hz, 1H), 7.10 (dd, J = 8.1, 11.7 Hz, 1H), 6.93 (t, J = 7.3 Hz, 2H), 6.73-6.67 (m, 1H), 4.78 (br s, 1H), 4.02-3.89 (m, 1H), 3.43-3.37 (m, 1H), 3.37-3.34 (m, 2H), 3.31 (br s, 1H), 3.29-3.24 (m, 1H), 3.23-3.14 (m, 1H), 3.10 (d, J = 16.3 Hz, 1H), 3.00-2.94 (m, 1H), 2.91-2.84 (m, 1H), 2.25 (br t, J = 9.8 Hz, 1H), 2.20-2.10 (m, 1H), 1.96 (td, J = 5.6, 11.2 Hz, 2H), 1.90-1.76 (m, 5H), 1.74-1.60 (m, 3H), 1.43-1.33 (m, 2H), 1.12 (s, 3H), 0.96 (s, 3H). LCMS (m/z) (M + H)$^+$: 541.3 |

Example I1: N-[(1R,3R)-3-({(1ψ)-2'-cyclobutyl-3'-fluoro-6-[(methanesulfonyl)carbamoyl][1,1'-biphenyl]-2-yl}oxy)cyclopentyl]-1,4,4-trimethyl-L-prolinamide

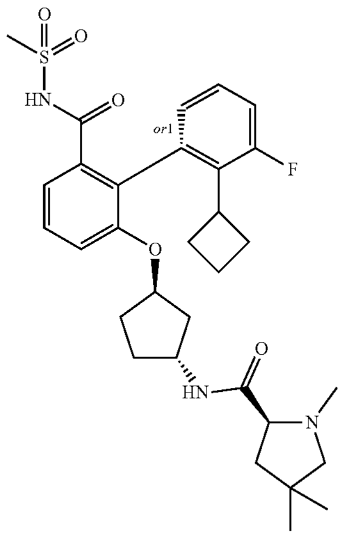

I1

Example I1 was prepared according to General Method I.

To a solution of (1 L)-2'-cyclobutyl-3'-fluoro-6-({(1R, 3R)-3-[(1,4,4-trimethyl-L-prolyl)amino]cyclopentyl}oxy)[1,1'-biphenyl]-2-carboxylic acid (Example H3) (120 mg, 0.236 mmol) and methanesulfonamide (29.2 mg, 0.307 mmol) in DMF (2.5 mL), EDCI (67.8 mg, 0.354 mmol) and DMAP (86.5 mg, 0.708 mmol) were added. The reaction was stirred for 16 h and then purified by prep HPLC purification (Boston Prime C18 150×30 mm, 5 uM, Mobile phase A: Water+$NH_4OH$, Mobile phase B: Acetonitrile, 8-48% B in 9.0 minutes, 30 mL/min) to give N-[(1R,3R)-3-({(1y)-2'-cyclobutyl-3'-fluoro-6-[(methanesulfonyl)carbamoyl][1,1'-biphenyl]-2-yl}oxy)cyclopentyl]-1,4,4-trimethyl-L-prolinamide (Example 11) as a white solid (24.4 mg, 16.9%). LCMS APCI (+) 586.3 (M+H). $^1H$ NMR (400 MHz, DMSO-$d_6$) δ=7.19-7.26 (m, 1H) 7.00-7.08 (m, 2H) 6.84-6.96 (m, 2H) 6.69 (d, J=7.13 Hz, 1H) 4.69 (br s, 1H) 3.94-4.02 (m,1 H) 3.26-3.40 (m, 1H) 2.70-2.81 (m, 2H) 2.40 (s, 3H) 2.09-2.25 (m, 6H) 1.53-2.01 (m, 10H) 1.41 (dd, J=12.63, 6.75 Hz, 1H) 1.25-1.36 (m, 2H) 0.98 (d, J=16.38 Hz, 6H).

Examples I2-I20 reported in Table 9 were synthesized with non-critical changes or substitutions to the exemplified procedures for Example 11 that one skilled in the art would be able to realize.

TABLE 9

| Ex. | Structure and Name | Characterization Data ($^1$H NMR, optical rotation, and/or LCMS) |
|---|---|---|
| I2 | 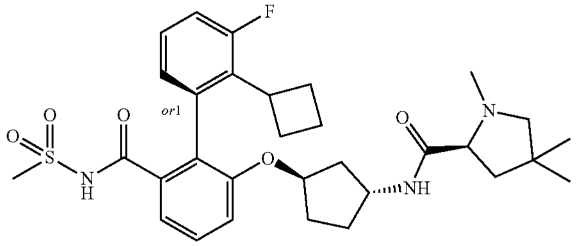<br>N-[(1R,3R)-3-({(1ψ)-2'-cyclobutyl-3'-fluoro-6-[(methanesulfonyl)carbamoyl][1,1'-biphenyl]-2-yl}oxy)cyclopentyl]-1,4,4-trimethyl-L-prolinamide | $^1$H NMR (400 MHz, DMSO-$d_6$) δ 7.91 (br s, 1H) 7.36 (t, J = 7.92 Hz, 1H) 7.01-7.21 (m, 4H) 6.78 (d, J = 7.48 Hz, 1H) 4.82 (br s, 1H) 3.91-4.00 (m, 1H) 2.93 (br s, 1H) 2.74 (br s, 3H) 1.91-2.48 (m, 9H) 1.32-1.85 (m, 9H) 1.01-1.09 (m, 6H). LCMS (m/z) $(M + H)^+$: 586.5 |
| I3 | 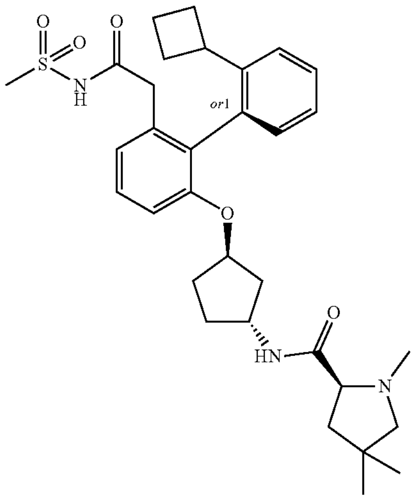<br>N-[(1R,3R)-3-{[(1ψ)-2'-cyclobutyl-6-{2-[(methanesulfonyl)amino]-2-oxoethyl}[1,1'-biphenyl]-2-yl]oxy}cyclopentyl]-1,4,4-trimethyl-L-prolinamide | $^1$H NMR (400 MHz, MeOD δ 7.38 (d, J = 7.9 Hz, 1H), 7.32-7.20 (m, 2H), 7.16 (t, J = 6.9 Hz, 1H), 7.08-7.02 (m, 1H), 6.98 (d, J = 7.5 Hz, 1H), 6.83 (d, J = 8.1 Hz, 1H), 4.73 (br s, 1H), 4.10-3.97 (m, 1H), 3.23 3.06 (m, 2H), 2.92 (s, 3H), 2.89-2.80 (m, 2H), 2.27 (s, 3H), 2.22 (d, J = 9.0 Hz, 1H), 2.11-1.51 (m, 14H), 1.46-1.34 (m, 1H), 1.07 (d, J = 19.6 Hz, 6H).<br>$[\alpha]_D^{22}$ = −0.26° (c 0.1, MeOH).<br>LCMS (m/z) $(M + H)^+$: 582.5 |
| I4 | 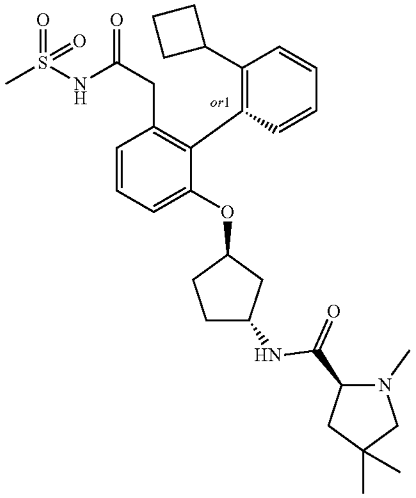<br>N-[(1R,3R)-3-{[(1ψ)-2'-cyclobutyl-6-{2-[(methanesulfonyl)amino]-2-oxoethyl}[1,1'-biphenyl]-2-yl]oxy}cyclopentyl]-1,4,4-trimethyl-L-prolinamide | $^1$H NMR (400 MHz, MeOD δ 7.42 (d, J = 7.7 Hz, 1H), 7.36-7.25 (m, 2H), 7.18 (t, J = 7.2 Hz, 1H), 6.96 (br d, J = 7.9 Hz, 2H), 6.90 (d, J = 8.1 Hz, 1H), 4.77 (br s, 1H), 4.12-4.02 (m, 1H), 3.27-3.15 (m, 3H), 3.04 (s, 3H), 3.00 (br d, J = 9.5 Hz, 1H), 2.43 (br s, 4H), 2.17-1.50 (m, 14H), 1.43-1.33 (m, 1H), 1.10 (d, J = 7.7 Hz, 6H).<br>$[\alpha]_D^{22}$ = −0.98° (c 0.1, MeOH).<br>LCMS (m/z) $(M + H)^+$: 582.5 |

TABLE 9-continued

| Ex. | Structure and Name | Characterization Data ($^1$H NMR, optical rotation, and/or LCMS) |
|---|---|---|
| I5 | 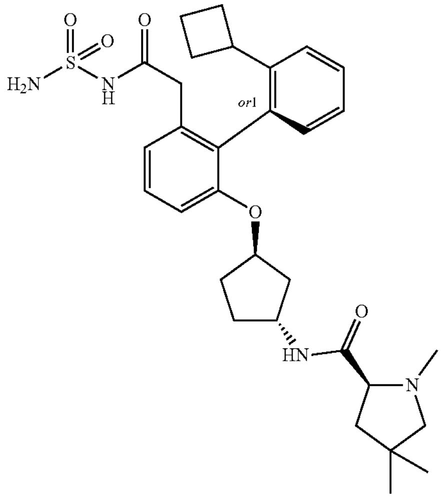 N-[(1R,3R)-3-({(1ψ)-2'-cyclobutyl-6-[2-oxo-2-(sulfamoylamino)ethyl][1,1'-biphenyl]-2-yl}oxy)cyclopentyl]-1,4,4-trimethyl-L-prolinamide | $^1$H NMR (400 MHz, MeOD) δ 7.41 (d, J = 7.6 Hz, 1H), 7.36-7.26 (m, 2H), 7.19 (t, J = 6.9 Hz, 1H), 7.00-6.88 (m, 3H), 4.80 (br s, 1H), 4.16-4.03 (m, 2H), 3.68-3.58 (m, 1H), 3.43 (d, J = 11.4 Hz, 1H), 3.29-3.25 (m, 1H), 3.19-3.13 (m, 1H), 3.06 (d, J = 11.4 Hz, 1H), 2.87 (s, 3H), 2.37 (dd, J = 9.6, 13.3 Hz, 1H), 2.14-1.91 (m, 5H), 1.86-1.56 (m, 7H), 1.42-1.35 (m, 1H), 1.23 (s, 3H), 1.15 (s, 3H). LCMS (m/z) $(M + H)^+$: 583.3 |
| I6 | 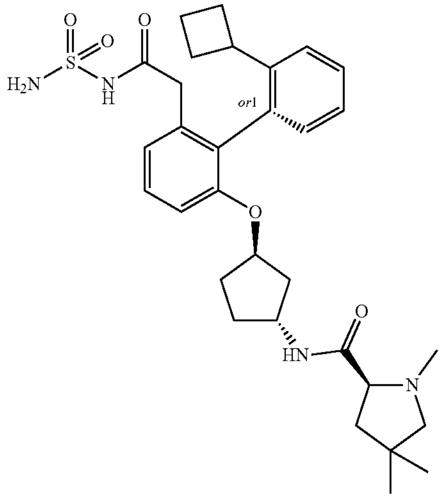 N-[(1R,3R)-3-({(1ψ)-2'-cyclobutyl-6-[2-oxo-2-(sulfamoylamino)ethyl][1,1'-biphenyl]-2-yl}oxy)cyclopentyl]-1,4,4-trimethyl-L-prolinamide | $^1$H NMR (400 MHz, MeOD δ 8.37 (br s, 1H), 7.41 (d, J = 7.8 Hz, 1H), 7.35-7.25 (m, 2H), 7.19 (t, J = 7.1 Hz, 1H), 7.00-6.87 (m, 3H), 4.80 (br s, 1H), 4.16-4.00 (m, 2H), 3.43 (br d, J = 11.1 Hz, 1H), 3.27-3.20 (m, 2H), 3.18-3.12 (m, 1H), 3.05 (br d, J = 11.1 Hz, 1H), 2.87 (s, 3H), 2.41-2.32 (m, 1H), 2.15-1.94 (m, 5H), 1.88-1.78 (m, 3H), 1.76-1.61 (m, 4H), 1.43-1.37 (m, 1H), 1.22 (s, 3H), 1.15 (s, 3H). LCMS (m/z) $(M + H)^+$: 583.3 |

TABLE 9-continued

| Ex. | Structure and Name | Characterization Data ($^1$H NMR, optical rotation, and/or LCMS) |
| --- | --- | --- |
| I7 | 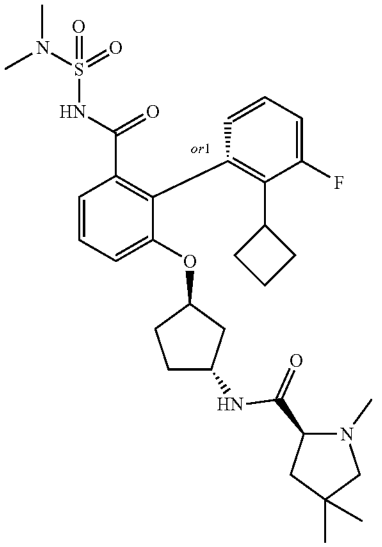 N-[(1R,3R)-3-({(1ψ)-2'-cyclobutyl-6-[(dimethylsulfamoyl)carbamoyl]-3'-fluoro[1,1'-biphenyl]-2-yl}oxy)cyclopentyl]-1,4,4-trimethyl-L-prolinamide | $^1$H NMR (600 MHz, DMSO-$d_6$) δ 11.45 (br s, 1H), 7.69 (br d, J = 6.0 Hz, 1H), 7.39 (t, J = 8.0 Hz, 1H), 7.16 (dt, J = 5.7, 7.8 Hz, 1H), 7.11 (d, J = 8.2 Hz, 1H), 7.08 (dd, J = 0.7, 7.6 Hz, 1H), 7.04 (dd, J = 8.4, 11.7 Hz, 1H), 6.81 (dd, J = 1.0, 7.5 Hz, 1H), 4.81 (tt, J = 3.0, 5.5 Hz, 1H), 4.00 (sxt, J = 7.4 Hz, 1H), 3.38-3.34 (m, 1H), 2.87 (br s, 1H), 2.80 (br d, J = 8.9 Hz, 1H), 2.50 (s, 6H), 2.24 (s, 3H), 2.25-2.19 (m, 1H), 2.23-2.18 (m, 1H), 2.22-2.15 (m, 1H), 2.03-1.98 (m, 1H), 1.99-1.93 (m, 1H), 1.89 (dd, J = 10.0, 13.1 Hz, 1H), 1.87-1.82 (m, 1H), 1.84-1.78 (m, 1H), 1.87-1.77 (m, 1H), 1.75-1.70 (m, 1H), 1.70-1.64 (m, 1H), 1.75-1.62 (m, 1H), 1.47 (dd, J = 6.9, 12.5 Hz, 1H), 1.40-1.35 (m, 1H), 1.37-1.33 (m, 1H), 1.05 (s, 3H), 1.01 (s, 3H). LCMS (m/z) $(M + H)^+$: 615.2 |
| I8 | 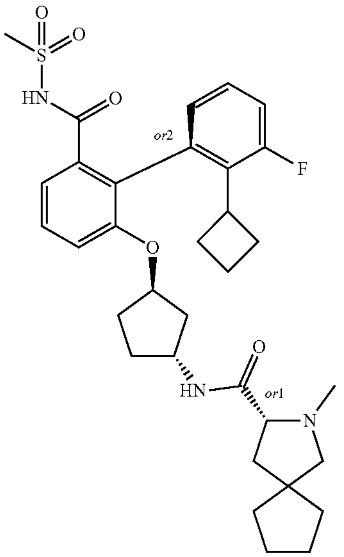 (3ξ)-N-[(1R,3R)-3-({(1ψ)-2'-cyclobutyl-3'-fluoro-6-[(methanesulfonyl)carbamoyl][1,1'-biphenyl]-2-yl}oxy)cyclopentyl]-2-methyl-2-azaspiro[4.4]nonane-3-carboxamide | $^1$H NMR (600 MHz, DMSO-$d_6$) δ 7.44 (br d, J = 7.45 Hz, 1H) 7.25-7.33 (m, 1H) 7.12 (dd, J = 7.63, 1.09 Hz, 1H) 7.04-7.10 (m, 1H) 6.92-7.01 (m, 2H) 6.77 (dd, J = 7.45, 1.09 Hz, 1H) 6.17 (br s, 2H) 4.74 (tt, J = 5.86, 2.86 Hz, 1H) 3.94 (sxt, J = 7.38 Hz, 1H) 3.34-3.46 (m, 2H) 2.62 (s, 3H) 2.28-2.33 (m, 2H) 2.27 (s, 3H) 2.16-2.23 (m, 1H) 1.96-2.08 (m, 3H) 1.80-1.89 (m, 1H) 1.72-1.80 (m, 2H) 1.64-1.71 (m, 3H) 1.58-1.64 (m, 2H) 1.45-1.58 (m, 7 H) 1.32-1.44 (m, 2H). $[\alpha]_D^{22}$ = −31.2° (c 0.1, MeOH). LCMS (m/z) $(M + H)^+$: 612.2 |

TABLE 9-continued

| Ex. | Structure and Name | Characterization Data ($^1$H NMR, optical rotation, and/or LCMS) |
|---|---|---|
| I9 | 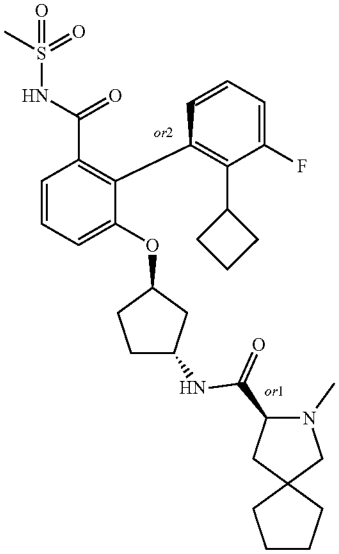 (3ξ)-N-[(1R,3R)-3-({(1ψ)-2'-cyclobutyl-3'-fluoro-6-[(methanesulfonyl)carbamoyl][1,1'-biphenyl]-2-yl}oxy)cyclopentyl]-2-methyl-2-azaspiro[4.4]nonane-3-carboxamide | $^1$H NMR (600 MHz, DMSO-$d_6$) δ 7.58 (s, 1H) 7.39-7.46 (m, 1H) 7.18-7.24 (m, 2H) 7.14 (br d, J = 8.36 Hz, 1H) 7.05-7.11 (m, 1H) 6.89 (dd, J = 7.63, 0.91 Hz, 1H) 4.83-4.90 (m, 1H) 3.97-4.08 (m, 3H) 3.45-3.54 (m, 2H) 2.82 (br s, 3H) 2.39 (s, 3H) 2.27-2.37 (m, 2H) 2.07-2.20 (m, 3H) 1.92-2.00 (m, 1H) 1.81-1.91 (m, 3H) 1.72-1.81 (m, 3H) 1.57-1.73 (m, 8H) 1.45-1.54 (m, 2H). $[\alpha]_D^{22}$ = −76.42° (c 0.1, MeOH). LCMS (m/z) $(M + H)^+$: 612.2 |
| I10 | 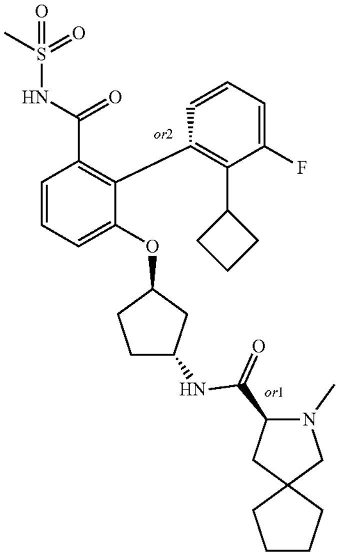 (3ξ)-N-[(1R,3R)-3-({(1ψ)-2'-cyclobutyl-3'-fluoro-6-[(methanesulfonyl)carbamoyl][1,1'-biphenyl]-2-yl}oxy)cyclopentyl]-2-methyl-2-azaspiro[4.4]nonane-3-carboxamide | 1H NMR (600 MHz, DMSO-d6) δ ppm 7.40 (t, J = 7.90 Hz, 1H) 7.10-7.20 (m, 3H) 7.03 (ddd, J = 11.81, 8.17, 1.09 Hz, 1H) 6.81 (dd, J = 7.63, 1.27 Hz, 1H) 4.81 (tt, J = 5.86, 2.86 Hz, 1H) 3.95-4.05 (m, 1H) 3.55-3.59 (m, 1H) 3.49 (t, J = 5.90 Hz, 1H) 3.37 (quin, J = 9.13 Hz, 1H) 3.25-3.30 (m, 1H) 3.20 (br s, 3H) 2.86 (s, 3H) 2.64-2.71 (m, 1H) 2.17-2.30 (m, 2H) 2.00-2.07 (m, 1H) 1.93-1.99 (m, 2H) 1.85-1.92 (m, 2H) 1.80 (ddd, J = 13.81, 7.36, 6.27 Hz, 1H) 1.61-1.77 (m, 8H) 1.54-1.59 (m, 4H) 1.32-1.48 (m, 3H). $[\alpha]_D^{22}$ = −25.8° (c 0.1, MeOH). LCMS (m/z) $(M + H)^+$: 612.1 |

TABLE 9-continued

| Ex. | Structure and Name | Characterization Data ($^1$H NMR, optical rotation, and/or LCMS) |
|---|---|---|
| I11 | 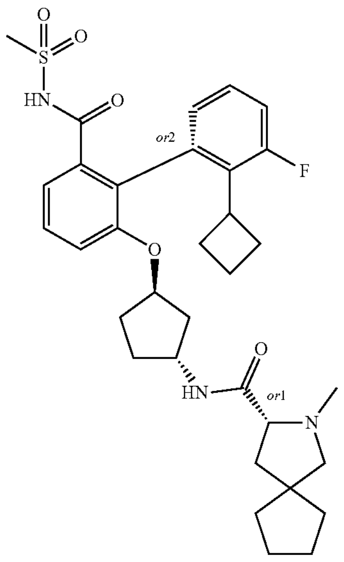 (3ξ)-N-[(1R,3R)-3-({(1ψ)-2'-cyclobutyl-3'-fluoro-6-[(methanesulfonyl)carbamoyl][1,1'-biphenyl]-2-yl}oxy)cyclopentyl]-2-methyl-2-azaspiro[4.4]nonane-3-carboxamide | 1H NMR (600 MHz, DMSO-d6) δ ppm 7.82 (br s, 1H) 7.41 (t, J = 7.99 Hz, 1H) 7.11-7.18 (m, 3H) 7.03 (ddd, J = 11.81, 8.17, 1.09 Hz, 1H) 6.81 (dd, J = 7.54, 1.18 Hz, 1H) 4.82 (tt, J = 5.84, 2.79 Hz, 1H) 3.99-4.01 (m, 1H) 3.36 (dt, J = 18.53, 9.45 Hz, 5H) 3.31 (s, 3H) 2.88 (s, 3H) 2.18-2.29 (m, 2H) 2.10-2.18 (m, 1H) 2.00-2.08 (m, 1H) 1.95-2.00 (m, 1H) 1.89-1.95 (m, 1H) 1.83-1.89 (m, 1H) 1.72-1.83 (m, 3H) 1.65-1.72 (m, 3H) 1.59-1.66 (m, 1H) 1.57 (br d, J = 4.54 Hz, 5H) 1.40-1.47 (m, 2H) 1.33-1.40 (m, 1H). $[\alpha]_D^{22}$ = +11.5° (c 0.1, MeOH). LCMS (m/z) $(M + H)^+$: 612.2 |
| I12 | 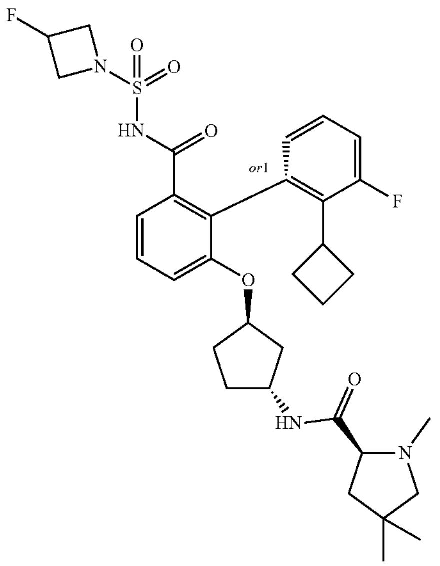 N-[(1R,3R)-3-({(1ψ)-2'-cyclobutyl-3'-fluoro-6-[(3-fluoroazetidine-1-sulfonyl)carbamoyl][1,1'-biphenyl]-2-yl}oxy)cyclopentyl]-1,4,4-trimethyl-L-prolinamide | $^1$H NMR (400 MHz, DMSO-$d_6$) δ 8.20-7.87 (m, 1H), 7.34 (br t, J = 8.0 Hz, 1H), 7.17-6.96 (m, 4H), 6.77 (d, J = 7.5 Hz, 1H), 5.09-4.87 (m, 1H), 4.79 (br s, 1H), 4.04-3.94 (m, 1H), 3.91-3.61 (m, 4H), 3.44-3.35 (m, 1H), 3.01 (br s, 1H), 2.46-2.39 (m, 2H), 2.30-1.27 (m, 17H), 1.06 (s, 6H). LCMS (m/z) $(M + H)^+$: 645.3 |

TABLE 9-continued

| Ex. | Structure and Name | Characterization Data ($^1$H NMR, optical rotation, and/or LCMS) |
|---|---|---|
| I13 | 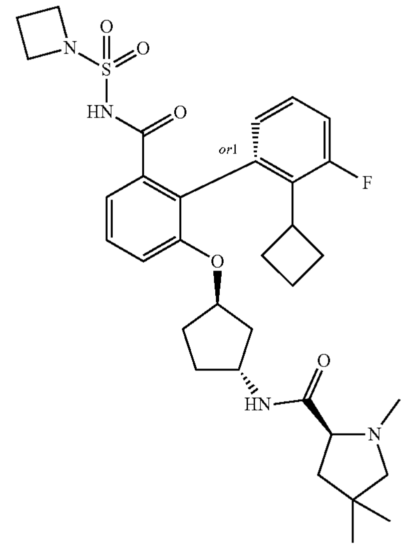 N-[(1R,3R)-3-({(1ψ)-6-[(azetidine-1-sulfonyl)carbamoyl]-2'-cyclobutyl-3'-fluoro[1,1'-biphenyl]-2-yl}oxy)cyclopentyl]-1,4,4-trimethyl-L-prolinamide | $^1$H NMR (400 MHz, DMSO-$d_6$) δ 11.94-10.95 (m, 1H), 8.13 (s, 1H), 7.77 (br s, 1H), 7.40 (br t, J = 7.9 Hz, 1H), 7.21-7.01 (m, 4H), 6.86 (d, J = 7.3 Hz, 1H), 4.82 (br s, 1H), 4.06-3.94 (m, 1H), 3.74-3.52 (m, 4H), 2.83 (br s, 2H), 2.28 (br s, 3H), 2.26-2.12 (m, 3H), 2.03-1.62 (m, 12H), 1.54-1.30 (m, 3H), 1.03 (d, J = 14.3 Hz, 6H), 1.09-0.99 (m, 1H). LCMS (m/z) (M + H)$^+$: 627.5 |
| I14 | 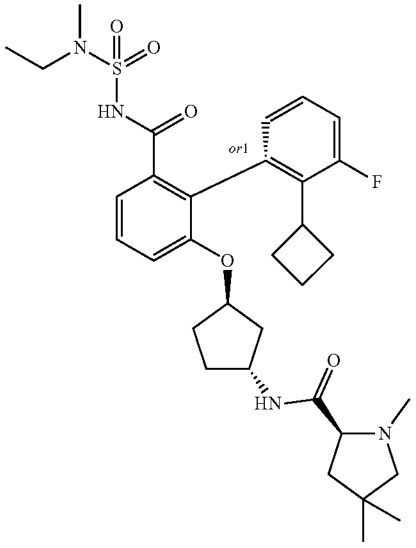 N-[(1R,3R)-3-{[(1ψ)-2'-cyclobutyl-6-{[ethyl(methyl)sulfamoyl]carbamoyl}-3'-fluoro[1,1'-biphenyl]-2-yl]oxy}cyclopentyl]-1,4,4-trimethyl-L-prolinamide | $^1$H NMR (400 MHz, DMSO-$d_6$) δ 11.56 (br s, 1H), 8.14 (s, 1H), 7.70 (br d, J = 6.5 Hz, 1H), 7.40 (t, J = 7.9 Hz, 1H), 7.19-7.10 (m, 2H), 7.09-7.02 (m, 2H), 6.80 (d, J = 7.4 Hz, 1H), 4.81 (br s, 1H), 4.04-3.93 (m, 1H), 2.95-2.74 (m, 4H), 2.53-2.51 (m, 1H), 2.52 (s, 3H), 2.26-2.14 (m, 6H), 2.04-1.61 (m, 10H), 1.50-1.29 (m, 3H), 1.05 (s, 3H), 1.00 (s, 3H), 0.94 (t, J = 7.1 Hz, 3H). LCMS (m/z) (M + H)$^+$: 629.5 |

TABLE 9-continued

| Ex. | Structure and Name | Characterization Data ($^1H$ NMR, optical rotation, and/or LCMS) |
|---|---|---|
| I15 | 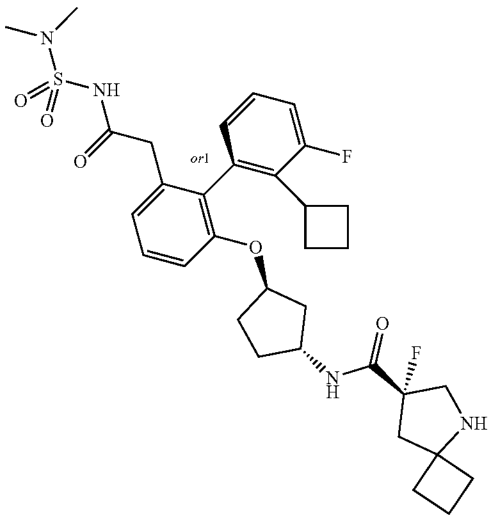 (7S)-N-[(1R,3R)-3-({(1ψ)-2'-cyclobutyl-6-[2-(dimethylsulfamamido)-2-oxoethyl]-3'-fluoro[1,1'-biphenyl]-2-yl}oxy)cyclopentyl]-7-fluoro-5-azaspiro[3.4]octane-7-carboxamide | $^1H$ NMR (400 MHz, DMSO-d6) δ 8.46 (br. d, J = 6.8 Hz, 1H), 7.30 (t, J = 7.9 Hz, 1H), 7.24-7.18 (m, 1H), 7.12 (dd, J = 8.3, 11.3 Hz, 1H), 6.93 (t, J = 8.8 Hz, 2H), 6.68 (d, J = 6.6 Hz, 1H), 4.80 (br. s, 1H), 4.04-3.90 (m, 1H), 3.68-3.48 (m, 2H), 3.38 (d, J = 16.6 Hz, 1H), 3.23-3.14 (m, 2H), 2.70 (s, 6H), 2.65-2.55 (m, 1H), 2.54 (s, 2H), 2.47-2.37 (m, 1H), 2.29-2.13 (m, 4H), 2.11-2.00 (m, 1H), 1.99-1.92 (m, 1H), 1.91-1.79 (m, 3H), 1.77-1.67 (m, 5H), 1.50-1.38 (m, 2H). LCMS (m/z) $(M + H)^+$: 645.3 |
| I16 | 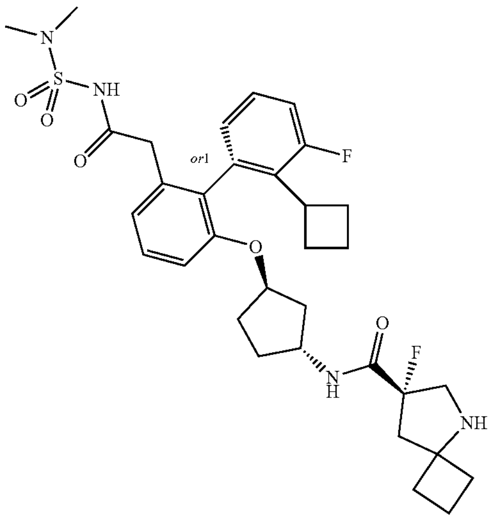 (7S)-N-[(1R,3R)-3-({(1ψ)-2'-cyclobutyl-3'-fluoro-6-[2-oxo-2-(propane-2-sulfonamido)ethyl][1,1'-biphenyl]-2-yl}oxy)cyclopentyl]-7-fluoro-5-azaspiro[3.4]octane-7-carboxamide | $^1H$ NMR (400 MHz, DMSO-d6) δ 8.49 (br. d, J = 7.5 Hz, 1H), 7.29 (t, J = 7.9 Hz, 1H), 7.20 (dt, J = 5.8, 7.7 Hz, 1H), 7.11 (dd, J = 8.1, 11.6 Hz, 1H), 6.93 (t, J = 8.6 Hz, 2H), 6.67 (d, J = 7.4 Hz, 1H), 4.81-4.75 (m, 1H), 4.03-3.93 (m, 1H), 3.69-3.52 (m, 2H), 3.51-3.38 (m, 2H), 3.25 (d, J = 16.8 Hz, 1H), 3.22-3.14 (m, 1H), 2.68-2.55 (m, 1H), 2.55-2.51 (m, 2H), 2.46-2.34 (m, 1H), 2.27-2.11 (m, 4H), 2.02-1.91 (m, 2H), 1.89-1.76 (m, 5H), 1.74-1.59 (m, 3H), 1.46-1.33 (m, 2H), 1.15 (t, J = 6.9 Hz, 6H). LCMS (m/z) $(M + H)^+$: 644.4 |

TABLE 9-continued

| Ex. | Structure and Name | Characterization Data ($^1$H NMR, optical rotation, and/or LCMS) |
|---|---|---|
| I17 | 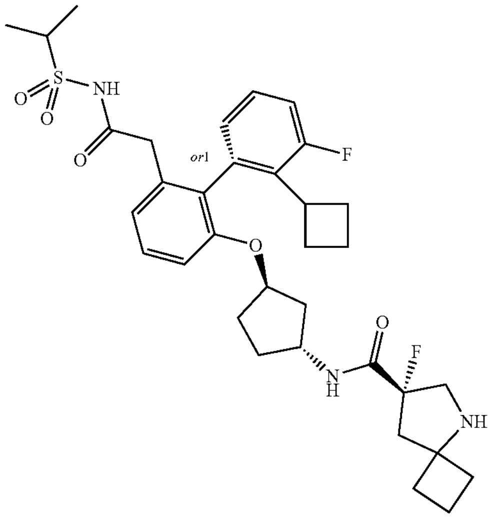 (7S)-N-[(1R,3R)-3-({(1ψ)-2'-cyclobutyl-6-[2-(dimethylsulfamamido)-2-oxoethyl]-3'-fluoro[1,1'-biphenyl]-2-yl}oxy)cyclopentyl]-7-fluoro-5-azaspiro[3.4]octane-7-carboxamide | $^1$H NMR (400 MHz, DMSO-$d_6$) δ 8.52-8.45 (m, 1H), 7.33-7.26 (m, 1H), 7.21 (dt, J = 5.8, 7.8 Hz, 1H), 7.15-7.07 (m, 1H), 6.97-6.89 (m, 2H), 6.67 (dd, J = 0.9, 7.5 Hz, 1H), 4.79 (br. d, J = 2.4 Hz, 1H), 4.06-3.91 (m, 1H), 3.71-3.49 (m, 2H), 3.39 (d, J = 16.6 Hz, 1H), 3.25-3.14 (m, 2H), 2.70 (s, 6H), 2.66-2.56 (m, 1H), 2.56-2.51 (m, 2H), 2.47-2.38 (m, 1H), 2.26-2.11 (m, 4H), 2.00-1.92 (m, 2H), 1.90-1.77 (m, 5H), 1.75-1.61 (m, 3H), 1.47-1.34 (m, 2H). LCMS (m/z) (M + H)$^+$: 645.5 |
| I18 | 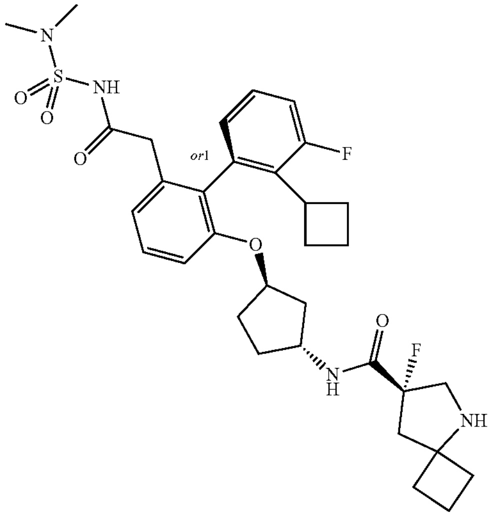 (7S)-N-[(1R,3R)-3-({(1ψ)-2'-cyclobutyl-3'-fluoro-6-[2-oxo-2-(propane-2-sulfonamido)ethyl][1,1'-biphenyl]-2-yl}oxy)cyclopentyl]-7-fluoro-5-azaspiro[3.4]octane-7-carboxamide | $^1$H NMR (400 MHz, DMSO-$d_6$) δ 8.50-8.43 (m, 1H), 7.30 (t, J = 7.9 Hz, 1H), 7.23-7.16 (m, 1H), 7.15-7.08 (m, 1H), 6.93 (t, J = 8.3 Hz, 2H), 6.68 (dd, J = 1.1, 7.5 Hz, 1H), 4.83-4.76 (m, 1H), 4.02-3.91 (m, 1H), 3.70-3.51 (m, 2H), 3.50-3.38 (m, 2H), 3.25 (d, J = 16.8 Hz, 1H), 3.21-3.13 (m, 1H), 2.69-2.58 (m, 1H), 2.54 (s, 1H), 2.40 (d, J = 14.6 Hz, 1H), 2.44-2.36 (m, 1H), 2.30-2.14 (m, 4H), 2.11-2.02 (m, 1H), 1.94 (dt, J = 4.8, 6.0 Hz, 1H), 1.91-1.79 (m, 3H), 1.77-1.66 (m, 5H), 1.50-1.38 (m, 2H), 1.15 (dd, J = 5.3, 6.8 Hz, 6H). LCMS (m/z) (M + H)$^+$: 644.4 |

TABLE 9-continued

| Ex. | Structure and Name | Characterization Data ($^1$H NMR, optical rotation, and/or LCMS) |
| --- | --- | --- |
| I19 | 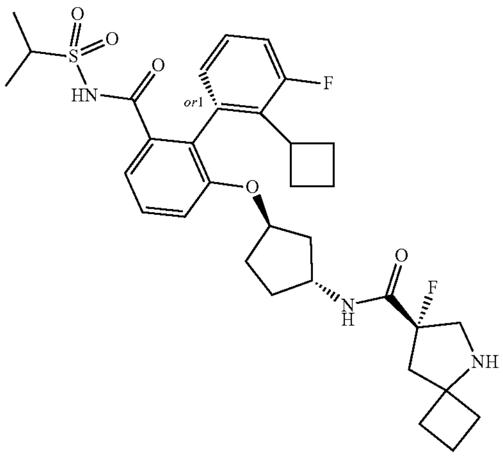 (7S)-N-[(1R,3R)-3-({(1ψ)-2'-cyclobutyl-3'-fluoro-6-[(propane-2-sulfonyl)carbamoyl][1,1'-biphenyl]-2-yl}oxy)cyclopentyl]-7-fluoro-5-azaspiro[3.4]octane-7-carboxamide | $^1$H NMR (400 MHz, DMSO-$d_6$) δ = 8.52 (br. d, J = 7.5 Hz, 1H), 7.48-7.41 (m, 1H), 7.20-7.04 (m, 4H), 6.76 (d, J = 7.3 Hz, 1H), 4.86 (br. s, 1H), 4.04 (qd, J = 7.3, 14.8 Hz, 1H), 3.71-3.46 (m, 3H), 2.66-2.53 (m, 3H), 2.48-2.37 (m, 1H), 2.26-1.58 (m, 16H), 1.51-1.21 (m, 3H), 1.16 (d, J = 6.8 Hz, 3H), 1.10 (d, J = 6.8 Hz, 3H). LCMS (m/z) (M + H)$^+$: 630.5 |
| I20 | 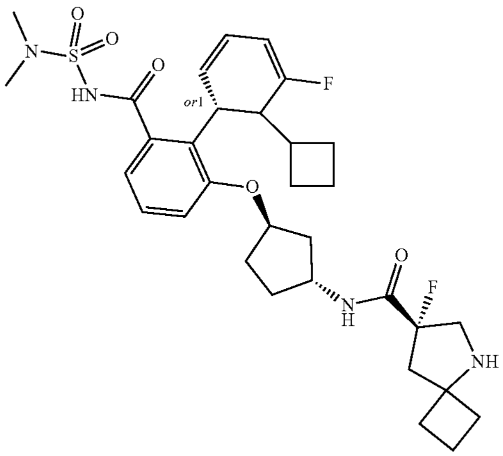 (7S)-N-[(1R,3R)-3-({(1ψ)-2'-cyclobutyl-6-[(dimethylsulfamoyl)carbamoyl]-3'-fluoro[1,1'-biphenyl]-2-yl}oxy)cyclopentyl]-7-fluoro-5-azaspiro[3.4]octane-7-carboxamide | $^1$H NMR (400 MHz, DMSO-$d_6$) δ 11.66 (br. s, 1H), 10.20-9.93 (m, 2H), 8.52 (br. d, J = 7.5 Hz, 1H), 7.47-7.39 (m, 1H), 7.21-7.13 (m, 2H), 7.11-7.03 (m, 2H), 6.82 (dd, J = 0.9, 7.5 Hz, 1H), 4.86 (br. s, 1H), 4.10-3.97 (m, 1H), 3.73-3.41 (m, 3H), 2.73-2.57 (m, 2H), 2.54 (d, J = 0.9 Hz, 6H), 2.47-2.36 (m, 1H), 2.24-2.13 (m, 4H), 2.07-1.61 (m, 11H), 1.49-1.33 (m, 2H). LCMS (m/z) (M + H)$^+$: 631.3 |

Example J1: 4-[2'-cyclobutyl-3'-fluoro-6-({(1R,3R)-3-[(1,4,4-trimethyl -L-prolyl)amino] cyclopentyl}oxy)[1,1'-biphenyl]-3-yl]-1-methyl-1H-pyrazole-3-carboxylic acid

J1

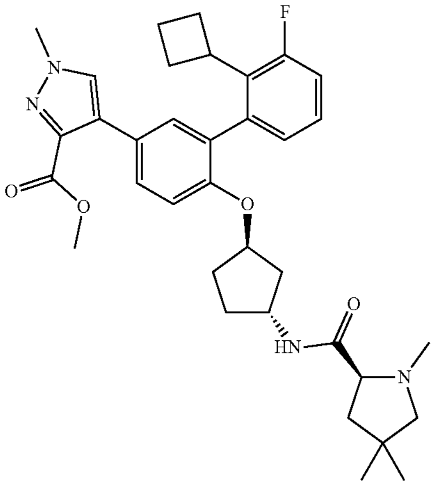

Example J1 was prepared according to General Method J.

Step 1: methyl 4-(3-bromo-4-(((1R,3R)-3-((tert-butoxycarbonyl)amino)cyclopentyl)oxy)phenyl)-1-methyl-1H-pyrazole-3-carboxylate (J1a)

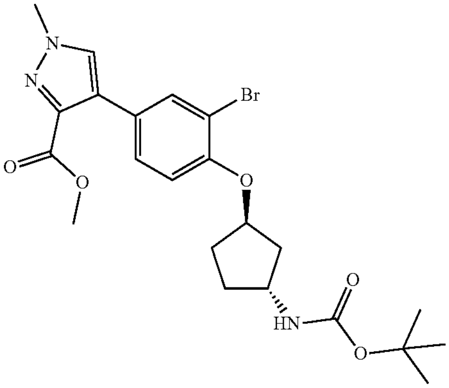 [SMILES: COC(=O)c1nn(C)cc1-c1ccc(O[C@@H]2CC[C@@H](NC(=O)OC(C)(C)C)C2)c(Br)c1]

To a mixture of and methyl 1-methyl-4-(4,4,5,5-tetramethyl-1,3,2-dioxaborolan-2-yl)-1 H-pyrazole-3-carboxylate (in dioxane (4 mL), a solution of K in H was added. Next, Pd(dppf)CI was added, degassed with Ar, and then heated at 50° C. for 4.5 h. The reaction mixture was concentrated and then the residue was diluted into water and extracted with EtOAc (2×). The combined organics were washed with brine, dried over $Na_2SO_4$, filtered, and concentrated. The residue was purified by silica gel chromatography (20-60% EtOAc/PE) to give methyl 4-(3-bromo-4-(((1R,3R)-3-((tert-butoxycarbonyl)amino)cyclopentyl)oxy)phenyl)-1-methyl-1H-pyrazole-3-carboxylate (J1a) (192 mg, 93.6% yield) as yellow oil. LCMS APCI (+) 438.1 (M+H-56).

Step 2: methyl 4-(6-(((1R,3R)-3-((tert-butoxycarbonyl)amino)cyclopentyl)oxy)-2'-cyclobutyl-3'-fluoro-[1,1'-biphenyl]-3-yl)-1-methyl-1H-pyrazole-3-carboxylate (J1b)

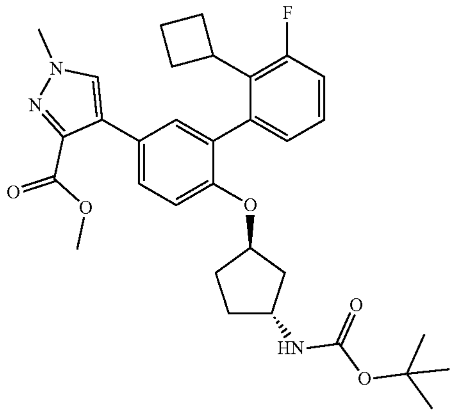 [SMILES: COC(=O)c1nn(C)cc1-c1ccc(O[C@@H]2CC[C@@H](NC(=O)OC(C)(C)C)C2)c(-c2cccc(F)c2C2CCC2)c1]

To a mixture of methyl 4-(3-bromo-4-(((1R,3R)-3-((tert-butoxycarbonyl)amino)cyclopentyl)oxy)phenyl)-1-methyl-1H-pyrazole-3-carboxylate (J1a) (200 mg, 0.405 mmol) and 2-(2-cyclobutyl-3-fluorophenyl)-4,4,5,5-tetramethyl-1,3,2-dioxaborolane (Intermediate 2) (134 mg, 0.485 mmol) in dioxane (5 mL), a solution of K in H was added. Next, Pd(dppf)CI was added, degassed with $N_2$, then heated at 90° C. for 16 h. The reaction mixture was concentrated then the residue was diluted into water and extracted with EtOAc (2×). The combined organics were washed with brine, dried over $Na_2SO_4$, filtered, and concentrated. The residue was purified by silica gel chromatography (20-60% EtOAc/PE) to give methyl 4-(6-(((1R,3R)-3-((tert-butoxycarbonyl)amino)cyclopentyl)oxy)-2'-cyclobutyl-3'-fluoro-[1,1'-biphenyl]-3-yl)-1-methyl-1H-pyrazole-3-carboxylate (J1b) (166.67 mg, 73.1% yield) as a white solid. LCMS APCI (+) 586.3 (M+Na).

Step 3: methyl 4-(6-(((1R,3R)-3-aminocyclopentyl)oxy)-2'-cyclobutyl-3'-fluoro-[1,1'-biphenyl]-3-yl)-1-methyl-1H-pyrazole-3-carboxylate (J1c)

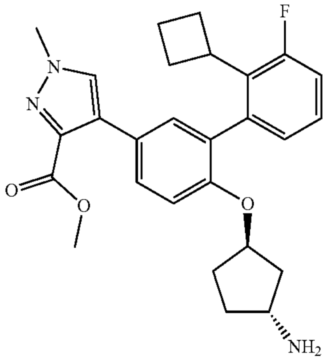 [SMILES: COC(=O)c1nn(C)cc1-c1ccc(O[C@@H]2CC[C@@H](N)C2)c(-c2cccc(F)c2C2CCC2)c1]

To a solution of methyl 4-(6-(((1R,3R)-3-((tert-butoxycarbonyl)amino)cyclopentyl)oxy)-2'-cyclobutyl-3'-fluoro-[1,1'-biphenyl]-3-yl)-1-methyl-1H-pyrazole-3-carboxylate (J1b) (200 mg, 0.355 mmol) in DCM (5 mL), HCl (7 mL, 2 M in dioxane) was added. The reaction was stirred at 20° C. for 1 hour then concentrated to give methyl 4-(6-(((1R,3R)-3-aminocyclopentyl)oxy)-2'-cyclobutyl-3'-fluoro-[1,1'-biphenyl]-3-yl)-1-methyl-1 H-pyrazole-3-carboxylate hydrochloride (J1c) (190 mg, 100% yield) as a yellow solid. LCMS APCI (+) 464.4 (M+H).

Step 4: methyl 4-(2'-cyclobutyl-3'-fluoro-6-(((1R,3R)-3-((S)-1,4,4-trimethylpyrrolidine-2-carboxamido)cyclopentyl)oxy)-[1,1'-biphenyl]-3-yl)-1-methyl-1H-pyrazole-3-carboxylate (J1d)

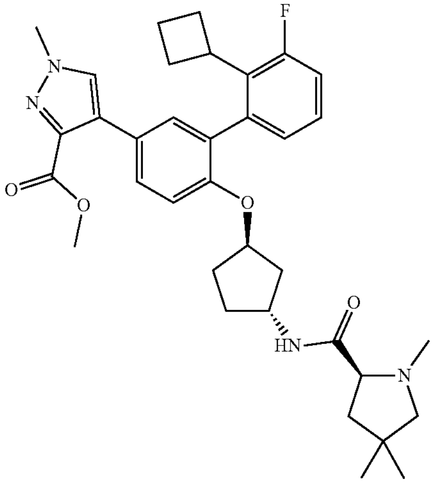 [SMILES: COC(=O)c1nn(C)cc1-c1ccc(O[C@@H]2CC[C@@H](NC(=O)[C@@H]3CC(C)(C)CN3C)C2)c(-c2cccc(F)c2C2CCC2)c1]

To a solution of and methyl in ACN (1 mL), DIPEA (56.7 mg, 0.439 mmol), , and NMI (42.0 mg, 0.512 mmol) were added. Stirred at 25° C. for 3 hours then added more and. The reaction was stirred overnight. The reaction mixture was concentrated and then the residue was diluted into water and extracted with EtOAc (3×). The combined organics were washed with brine, dried over $Na_2SO_4$, filtered, and concentrated. The residue was purified by silica gel chromatography (20-60% EtOAc/PE) to give crude methyl 4-(2'-cyclobutyl-3'-fluoro-6-(((1R,3R)-3-((S)-1,4,4-trimethylpyrrolidine-2-carboxamido)cyclopentyl)oxy)-[1,1'-biphenyl]-3-yl)-1-methyl-1 H-pyrazole-3-carboxylate (J1d) (190 mg, >99% crude yield) as yellow oil. LCMS APCI (+) 562.4 (M-41).

Step 5: 4-(2'-cyclobutyl-3'-fluoro-6-(((1R,3R)-3-((S)-1,4,4-trimethylpyrrolidine-2-carboxamido)cyclopentyl)oxy)-[1,1'-biphenyl]-3-yl)-1-methyl-1H-pyrazole-3-carboxylic acid (Example J1)

J1

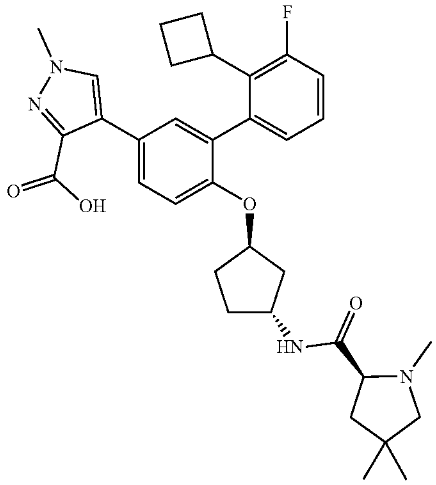

To a solution of methyl 4-(2'-cyclobutyl-3'-fluoro-6-(((1R,3R)-3-((S)-1,4,4-trimethylpyrrolidine-2-carboxamido)cyclopentyl)oxy)-[1,1'-biphenyl]-3-yl)-1-methyl-1H-pyrazole-3-carboxylate (J1d) (190 mg, 0.13 mmol) in THF (4 mL) and water (1 mL), $LiOH \cdot H_2O$ (31.7 mg, 0.757 mmol) was added. The mixture was stirred at 50° C. for 3.5 h. The reaction mixture was concentrated, and the residue was acidified to pH=3-4 with 1 N HCl aqueous then extracted with EtOAc (3×). The combined organics were dried over $Na_2SO_4$, filtered, and concentrated. The residue was purified by prep HPLC (Boston Prime C18 150*30 mm*5 um, Mobile phase A: Water(0.05% $NH_3$H2O+10 mM $NH_4$HCO3), Mobile phase B: Acetonitrile, 24-64% B in 9.0 minutes, 60 mL/min) to give 4-(2'-cyclobutyl-3'-fluoro-6-(((1R,3R)-3-((S)-1,4,4-trimethylpyrrolidine-2-carboxamido)cyclopentyl)oxy)-[1,1'-biphenyl]-3-yl)-1-methyl-1H-pyrazole-3-carboxylic acid Example J1 (6.41 mg, 8.6% yield) as white solid. LCMS APCI (+) 589.3 (M+H). 1H NMR (400 MHz, CD30D) b ppm 7.70 (s, 1H) 7.52 (dd, J=2.2, 8.6 Hz, 1H) 7.28 (t, J=2.1 Hz, 1H) 7.20-7.13 (m, 1H) 7.04-6.89 (m, 3H) 4.24-4.06 (m, 1H) 3.92 (s, 3H) 3.63-3.53 (m, 1H) 3.46-3.35 (m, 1H) 3.13-3.06 (m, 1H) 2.61-2.56 (m, 1H) 2.53 (d, J=3.5 Hz, 3H) 2.40-2.29 (m, 1H) 2.26-2.08 (m, 4H) 2.06-1.61 (m, 9H) 1.52-1.38 (m, 1H) 1.13 (s, 6H).

Examples J2-J16 reported in Table 10 were synthesized with non-critical changes or substitutions to the exemplified procedure for Example J1 that one skilled in the art would be able to realize. In Example J8, the Boc deprotection and amide coupling were done before successive Suzuki couplings.

TABLE 10

| Ex. | Structure and Name | Characterization Data ($^1$H NMR, optical rotation, and/or LCMS) |
|---|---|---|
| J2 | 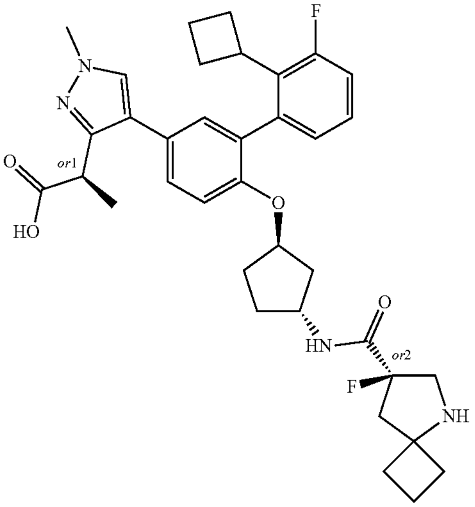 [SMILES: C[C@@H](C(=O)O)c1nn(C)cc1-c1ccc(O[C@@H]2CC[C@@H](NC(=O)[C@]3(F)CNC4(CCC4)C3)C2)c(-c2cccc(F)c2C2CCC2)c1] (2ξ)-2-[4-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-1-methyl-1H-pyrazol-3-yl]propanoic acid | $^1$H NMR (400 MHz, MeOD) δ 7.61-7.54 (m, 1H), 7.39 (td, J = 2.1, 8.4 Hz, 1H), 7.24-7.10 (m, 2H), 7.08-6.87 (m, 3H), 4.27 (s, 1H), 3.93-3.88 (m, 1H), 3.87 (s, 3H), 3.63-3.50 (m, 1H), 3.49-3.38 (m, 1H), 3.27 (br d, J = 7.1 Hz, 1H), 2.52-2.28 (m, 3H), 2.28-2.07 (m, 7H), 2.05-1.56 (m, 10H), 1.53-1.43 (m, 4H). LCMS (m/z) (M + H)$^+$: 633.5 |
| J3 | 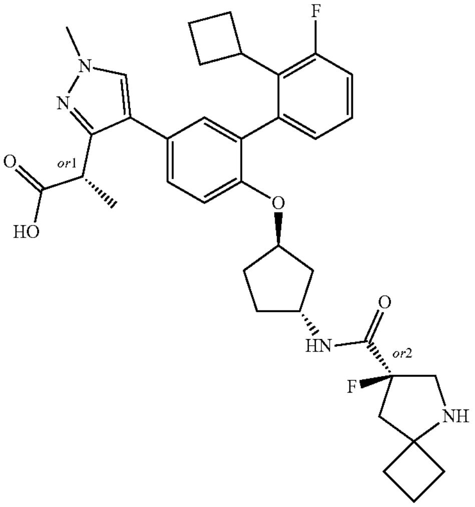 [SMILES: C[C@H](C(=O)O)c1nn(C)cc1-c1ccc(O[C@@H]2CC[C@@H](NC(=O)[C@]3(F)CNC4(CCC4)C3)C2)c(-c2cccc(F)c2C2CCC2)c1] (2ξ)-2-[4-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-1-methyl-1H-pyrazol-3-yl]propanoic acid | $^1$H NMR (400 MHz, MeOD) δ 7.62-7.55 (m, 1H), 7.44-7.34 (m, 1H), 7.23-7.10 (m, 2H), 7.06-6.86 (m, 3H), 4.29-4.06 (m, 1H), 3.97-3.88 (m, 1H), 3.88-3.86 (m, 3H), 3.63-3.39 (m, 1H), 3.29-3.10 (m, 3H), 2.48 (s, 3H), 2.26-2.08 (m, 7H), 2.06-1.55 (m, 10H), 1.48 (t, J = 6.2 Hz, 3H). LCMS (m/z) (M + H)$^+$: 633.5 |

TABLE 10-continued

| Ex. | Structure and Name | Characterization Data ($^1$H NMR, optical rotation, and/or LCMS) |
|---|---|---|
| J4 | 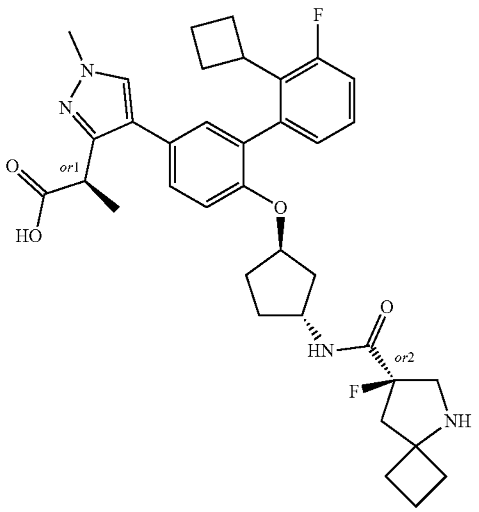 [SMILES: C[C@@H](C(=O)O)c1nn(C)cc1-c1ccc(O[C@@H]2CC[C@@H](NC(=O)[C@]3(F)CNC4(CCC4)C3)C2)c(-c2cccc(F)c2C2CCC2)c1] (2ξ)-2-[4-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-1-methyl-1H-pyrazol-3-yl]propanoic acid | $^1$H NMR (400 MHz, MeOD) δ 7.62-7.57 (m, 1H), 7.44-7.37 (m, 1H), 7.24-7.14 (m, 2H), 7.08-6.90 (m, 3H), 4.29-4.06 (m, 1H), 4.00 (s, 1H), 3.89-3.87 (m, 3H), 3.64-3.50 (m, 1H), 3.49-3.36 (m, 2H), 3.30-3.11 (m, 1H), 2.52 (s, 3H), 2.29-2.11 (m, 7H), 2.09-1.60 (m, 10H), 1.51-1.47 (m, 3H). LCMS (m/z) $(M + H)^+$: 633.5 |
| J5 | 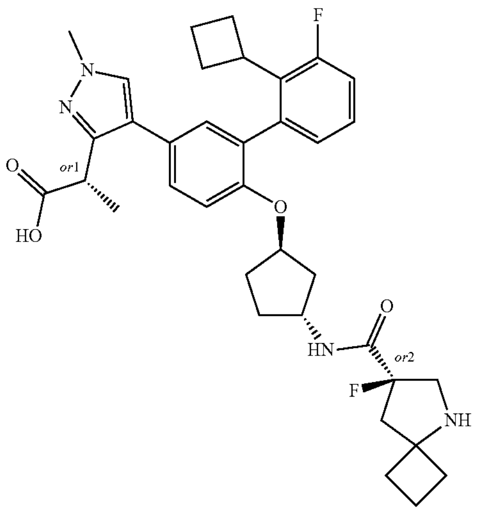 [SMILES: C[C@H](C(=O)O)c1nn(C)cc1-c1ccc(O[C@@H]2CC[C@@H](NC(=O)[C@]3(F)CNC4(CCC4)C3)C2)c(-c2cccc(F)c2C2CCC2)c1] (2ξ)-2-[4-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-1-methyl-1H-pyrazol-3-yl]propanoic acid | $^1$H NMR (400 MHz, MeOD) δ 7.57 (s, 1H), 7.42-7.35 (m, 1H), 7.22-7.11 (m, 2H), 7.04-6.87 (m, 3H), 4.26-4.09 (m, 1H), 3.92-3.88 (m, 1H), 3.88-3.84 (m, 3H), 3.51 (s, 1H), 3.44 (s, 1H), 3.27-3.09 (m, 3H), 2.50-2.28 (m, 3H), 2.25-2.09 (m, 7H), 2.06-1.71 (m, 9H), 1.48 (dd, J = 5.9, 7.0 Hz, 3H). LCMS (m/z) $(M + H)^+$: 633.5 |

TABLE 10-continued

| Ex. | Structure and Name | Characterization Data ($^1H$ NMR, optical rotation, and/or LCMS) |
|---|---|---|
| J6 | 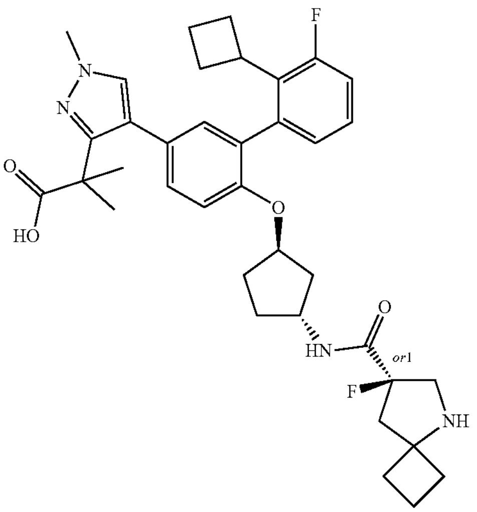 [SMILES: Cn1cc(-c2ccc(O[C@@H]3CC[C@@H](NC(=O)[C@]4(F)CNC5(CCC5)C4)C3)c(-c3cccc(F)c3C3CCC3)c2)c(C(C)(C)C(=O)O)n1] 2-[4-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-1-methyl-1H-pyrazol-3-yl]-2-methylpropanoic acid | $^1H$ NMR (400 MHz, MeOD) δ 7.47-7.44 (m, 1H), 7.26-7.22 (m, 1H), 7.20-7.13 (m, 1H), 7.02-7.00 (m, 1H), 6.99-6.93 (m, 2H), 6.92-6.87 (m, 1H), 4.27-4.08 (m, 1H), 3.86 (s, 3H), 3.62-3.34 (m, 3H), 3.27 (s, 1H), 2.50 (s, 3H), 2.23-2.10 (m, 7H), 2.05-1.55 (m, 10H), 1.48 (s, 3H), 1.45 (s, 3H). LCMS (m/z) (M + H)$^+$: 647.4 |
| J7 | 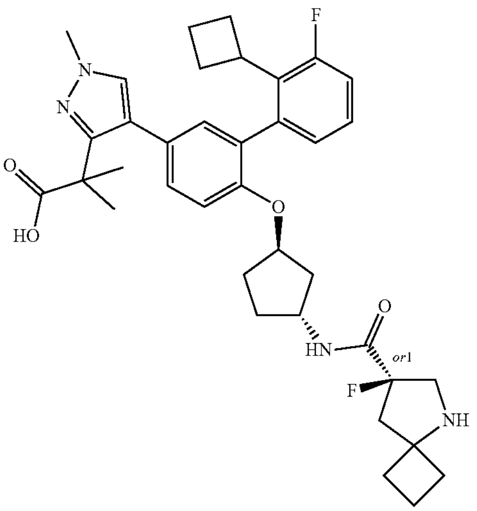 [SMILES: Cn1cc(-c2ccc(O[C@@H]3CC[C@@H](NC(=O)[C@]4(F)CNC5(CCC5)C4)C3)c(-c3cccc(F)c3C3CCC3)c2)c(C(C)(C)C(=O)O)n1] 2-[4-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-1-methyl-1H-pyrazol-3-yl]-2-methylpropanoic acid | $^1H$ NMR (400 MHz, MeOD) δ 7.46-7.45 (m, 1H), 7.28-7.22 (m, 1H), 7.21-7.12 (m, 1H), 7.04-7.00 (m, 1H), 6.99-6.87 (m, 3H), 4.28-4.08 (m, 1H), 3.88-3.85 (m, 3H), 3.61-3.50 (m, 1H), 3.47-3.34 (m, 1H), 3.28-3.17 (m, 1H), 2.49-2.29 (m, 3H), 2.24-2.09 (m, 8H), 2.07-1.68 (m, 10H), 1.48 (s, 3H), 1.45 (s, 3H). LCMS (m/z) (M + H)$^+$: 647.4 |

TABLE 10-continued

| Ex. | Structure and Name | Characterization Data ($^1H$ NMR, optical rotation, and/or LCMS) |
|---|---|---|
| J8 | 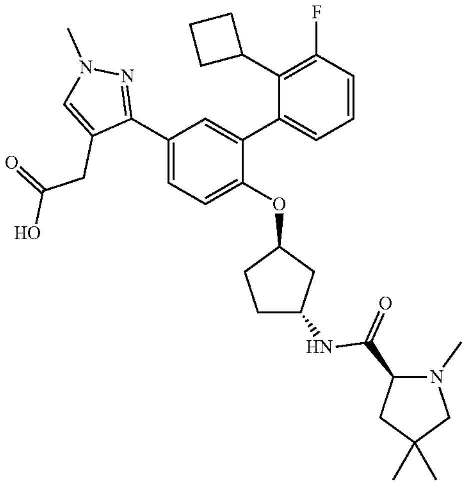 [SMILES: CN1CC(C)(C)C[C@H]1C(=O)N[C@@H]1CC[C@@H](Oc2ccc(-c3nn(C)cc3CC(=O)O)cc2-c2cccc(F)c2C2CCC2)C1] {3-[2'-cyclobutyl-3'-fluoro-6-({(1R,3R)-3-[(1,4,4-trimethyl-L-prolyl)amino]cyclopentyl}oxy)[1,1'-biphenyl]-3-yl]-1-methyl-1H-pyrazol-4-yl}acetic acid | $^1H$ NMR (400 MHz, DMSO-$d_6$) δ = 12.31 (s, 1H), 9.73 (br s, 1H), 8.90-8.61 (m, 1H), 7.86 (s, 1H), 7.33 (br d, J = 2.3 Hz, 1H), 7.25-7.18 (m, 1H), 7.12 (br t, J = 2.1 Hz, 2H), 7.08-7.03 (m, 1H), 6.90 (d, J = 7.5 Hz, 1H), 4.85 (br s, 1H), 4.14-3.93 (m, 1H), 3.79 (s, 3H), 3.59 (br d, J = 2.9 Hz, 2H), 3.53-3.42 (m, 1H), 3.07-2.86 (m, 1H), 2.83-2.69 (m, 2H), 2.27-1.92 (m, 6H), 1.91-1.57 (m, 7H), 1.51-1.20 (m, 3H), 1.16-1.00 (m, 6H). LCMS (m/z) $(M + H)^+$: 603.5 |
| J9 | 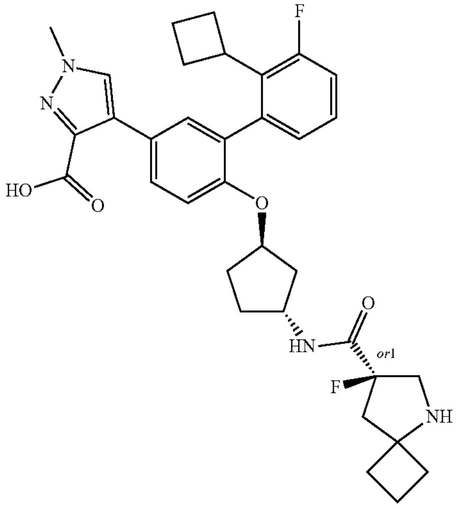 [SMILES: Cn1cc(-c2ccc(O[C@@H]3CC[C@@H](NC(=O)[C@]4(F)CNC5(CCC5)C4)C3)c(-c3cccc(F)c3C3CCC3)c2)c(C(=O)O)n1] 4-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-1-methyl-1H-pyrazole-3-carboxylic acid | $^1H$ NMR (400 MHz, DMSO-$d_6$) δ 8.19-8.11 (m, 1H), 7.96 (s, 1H), 7.46 (dd, J = 2.1, 8.5 Hz, 1H), 7.27 7.18 (m, 2H), 7.10 (dd, J = 8.3, 11.7 Hz, 1H), 7.01 (d, J = 8.3 Hz, 1H), 6.93-6.84 (m, 1H), 4.84 (br s, 1H), 4.16-3.99 (m, 1H), 3.89 (s, 3H), 3.55-3.49 (m, 1H), 3.13-2.95 (m, 2H), 2.32-1.97 (m, 10H), 1.89-1.59 (m, 8H), 1.53-1.35 (m, 2H). $[\alpha]_D^{22}$ = −19.4° (c 0.1, MeOH). LCMS (m/z) $(M + H)^+$: 605.4 |

TABLE 10-continued

| Ex. | Structure and Name | Characterization Data ($^1$H NMR, optical rotation, and/or LCMS) |
|---|---|---|
| J10 | 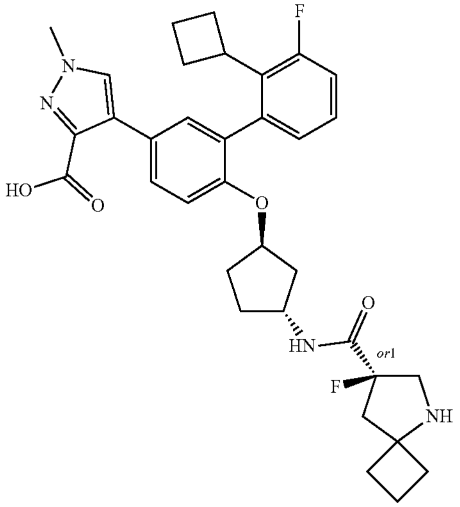 [SMILES: Cn1cc(-c2ccc(O[C@@H]3CC[C@@H](NC(=O)[C@]4(F)CNC5(CCC5)C4)C3)c(-c3cccc(F)c3C3CCC3)c2)c(C(=O)O)n1]<br>4-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-1-methyl-1H-pyrazole-3-carboxylic acid | $^1$H NMR (400 MHz, DMSO-$d_6$) δ 8.18-8.08 (m, 1H), 7.96 (s, 1H), 7.46 (dd, J = 2.2, 8.6 Hz, 1H), 7.28 7.18 (m, 2H), 7.10 (dd, J = 8.1, 11.6 Hz, 1H), 7.01 (d, J = 7.8 Hz, 1H), 6.89 (br d, J = 7.6 Hz, 1H), 4.83 (br s, 1H), 4.20-3.97 (m, 1H), 3.89 (s, 3H), 3.51 (dt, J = 4.5, 8.6 Hz, 1H), 3.16-2.95 (m, 2H), 2.25-1.93 (m, 10H), 1.91-1.59 (m, 8H), 1.55-1.36 (m, 2H).<br>$[\alpha]_D^{22}$ = −12.8° (c 0.1, MeOH).<br>LCMS (m/z) $(M + H)^+$: 605.4 |
| J11 | 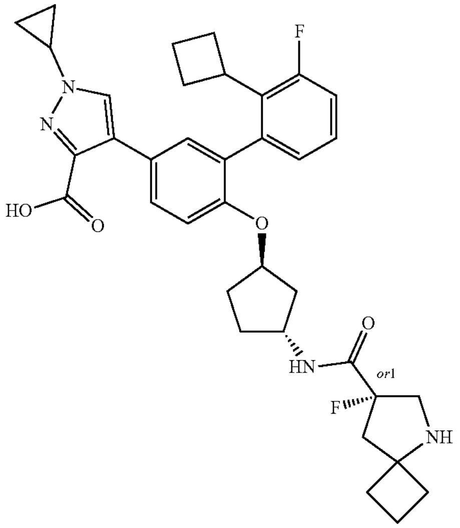 [SMILES: O=C(O)c1nn(C2CC2)cc1-c1ccc(O[C@@H]2CC[C@@H](NC(=O)[C@@]3(F)CNC4(CCC4)C3)C2)c(-c2cccc(F)c2C2CCC2)c1]<br>4-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-1-cyclopropyl-1H-pyrazole-3-carboxylic acid | $^1$H NMR (400 MHz, DMSO-$d_6$) δ 8.15-8.06 (m, 1H), 8.05-8.02 (m, 1H), 7.52-7.44 (m, 1H), 7.25-7.17 (m, 2H), 7.15-7.05 (m, 1H), 7.03-6.97 (m, 1H), 6.93-6.86 (m, 1H), 4.89-4.78 (m, 1H), 4.18-3.98 (m, 1H), 3.83-3.77 (m, 1H), 3.51 (br d, J = 3.4 Hz, 1H), 3.06-2.93 (m, 2H), 2.30-2.12 (m, 3H), 2.11-1.95 (m, 7H), 1.92 (br s, 4H), 1.76-1.42 (m, 6H), 1.19-1.07 (m, 2H), 1.05-0.95 (m, 2H).<br>$[\alpha]_D^{22}$ = −21.5° (c 0.1, MeOH).<br>LCMS (m/z) $(M + H)^+$: 631.3 |

TABLE 10-continued

| Ex. | Structure and Name | Characterization Data ($^1$H NMR, optical rotation, and/or LCMS) |
|---|---|---|
| J12 | 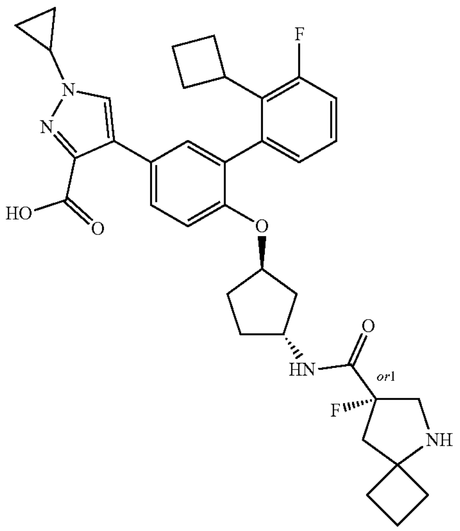 [SMILES: O=C(O)c1nn(C2CC2)cc1-c1ccc(O[C@@H]2CC[C@@H](NC(=O)[C@@]3(F)CNC4(CCC4)C3)C2)c(-c2cccc(F)c2C2CCC2)c1] 4-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-1-cyclopropyl-1H-pyrazole-3-carboxylic acid | $^1$H NMR (400 MHz, DMSO-$d_6$) δ 8.14-8.05 (m, 1H), 8.04-8.02 (m, 1H), 7.50-7.44 (m, 1H), 7.27-7.16 (m, 2H), 7.13-7.05 (m, 1H), 7.02-6.96 (m, 1H), 6.92-6.84 (m, 1H), 4.89-4.76 (m, 1H), 4.14-4.00 (m, 1H), 3.79 (tt, J = 3.7, 7.4 Hz, 1H), 3.52 (br d, J = 8.7 Hz, 1H), 3.07-2.96 (m, 2H), 2.12 (br s, 3H), 2.11-1.93 (m, 7H), 1.90 (br s, 10H), 1.06 (s, 2H), 1.06-0.95 (m, 2H). $[\alpha]_D^{22}$ = −23.5° (c 0.1, MeOH). LCMS (m/z) $(M + H)^+$: 631.3 |
| J13 | 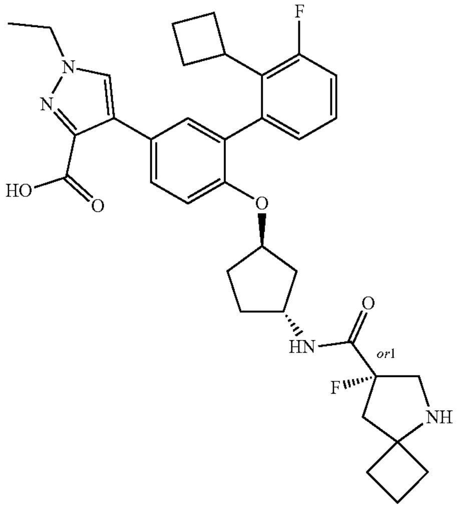 [SMILES: CCn1cc(-c2ccc(O[C@@H]3CC[C@@H](NC(=O)[C@@]4(F)CNC5(CCC5)C4)C3)c(-c3cccc(F)c3C3CCC3)c2)c(C(=O)O)n1] 4-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-1-ethyl-1H-pyrazole-3-carboxylic acid | $^1$H NMR (400 MHz, DMSO-$d_6$) δ 10.14-9.36 (m, 1H), 8.57-8.46 (m, 1H), 8.03 (s, 1H), 7.48 (dd, J = 2.2, 8.6 Hz, 1H), 7.25-7.18 (m, 2H), 7.14-7.07 (m, 1H), 7.02 (d, J = 9.0 Hz, 1H), 6.89 (d, J = 7.3 Hz, 1H), 4.89-4.82 (m, 1H), 4.22-4.03 (m, 3H), 3.72-3.50 (m, 3H), 2.66-2.52 (m, 4H), 2.45 (s, 1H), 2.25-1.99 (m, 6H), 1.96-1.61 (m, 8H), 1.47 (br dd, J = 4.7, 10.2 Hz, 1H), 1.42 (t, J = 7.3 Hz, 3H). $[\alpha]_D^{22}$ = −22.6° (c 0.1, MeOH). LCMS (m/z) $(M + H)^+$: 619.5 |

TABLE 10-continued

| Ex. | Structure and Name | Characterization Data ($^1$H NMR, optical rotation, and/or LCMS) |
|---|---|---|
| J14 | 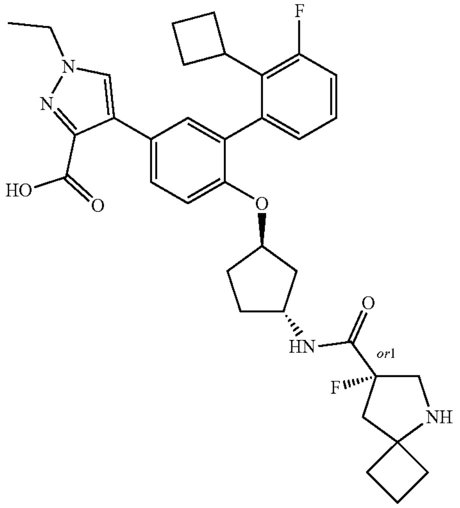 [SMILES: CCn1cc(-c2ccc(O[C@@H]3CC[C@@H](NC(=O)[C@@]4(F)CNC5(CCC5)C4)C3)c(-c3cccc(F)c3C3CCC3)c2)c(C(=O)O)n1] 4-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-1-ethyl-1H-pyrazole-3-carboxylic acid | $^1$H NMR (400 MHz, DMSO-$d_6$) δ 10.23-9.44 (m, 1H), 8.57-8.46 (m, 1H), 8.03 (s, 1H), 7.48 (dd, J = 2.2, 8.4 Hz, 1H), 7.25-7.18 (m, 2H), 7.10 (dd, J = 8.4, 11.2 Hz, 1H), 7.04-7.00 (m, 1H), 6.90 (d, J = 7.3 Hz, 1H), 4.91-4.81 (m, 1H), 4.24-4.00 (m, 3H), 3.50 (br s, 3H), 2.65-2.53 (m, 4H), 2.47-2.38 (m, 1H), 2.26-1.99 (m, 6H), 1.67 (br s, 8H), 1.53-1.45 (m, 1H), 1.42 (t, J = 7.3 Hz, 3H). $[\alpha]_D^{22}$ = −23.9° (c 0.1, MeOH). LCMS (m/z) (M + H)$^+$: 619.3 |
| J15 | 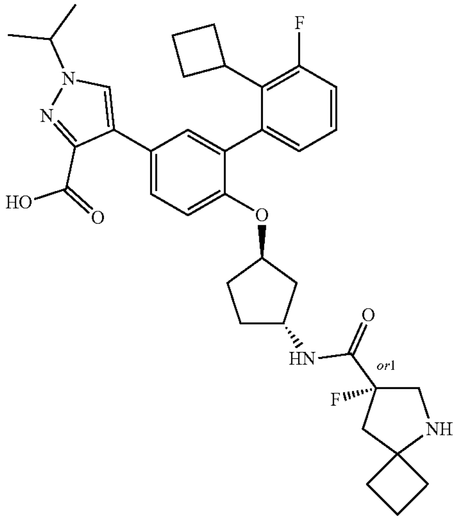 [SMILES: CC(C)n1cc(-c2ccc(O[C@@H]3CC[C@@H](NC(=O)[C@@]4(F)CNC5(CCC5)C4)C3)c(-c3cccc(F)c3C3CCC3)c2)c(C(=O)O)n1] 4-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-1-(propan-2-yl)-1H-pyrazole-3-carboxylic acid | $^1$H NMR (400 MHz, DMSO-$d_6$) δ 10.30-9.15 (m, 1H), 8.50 (br s, 1H), 8.06 (s, 1H), 7.50 (dd, J = 2.2, 8.4 Hz, 1H), 7.25-7.19 (m, 2H), 7.10 (dd, J = 8.4, 11.7 Hz, 1H), 7.02 (d, J = 8.7 Hz, 1H), 6.90 (br d, J = 7.5 Hz, 1H), 4.86 (br s, 1H), 4.57-4.52 (m, 1H), 4.19-4.02 (m, 1H), 3.69-3.50 (m, 3H), 2.63-2.54 (m, 3H), 2.47-2.38 (m, 2H), 2.26-2.04 (m, 6H), 1.96-1.67 (m, 8H), 1.46 (d, J = 6.8 Hz, 7H). $[\alpha]_D^{22}$ = −22.3° (c 0.05, MeOH). LCMS (m/z) (M + H)$^+$: 633.5 |

TABLE 10-continued

| Ex. | Structure and Name | Characterization Data ($^1$H NMR, optical rotation, and/or LCMS) |
|---|---|---|
| J16 | 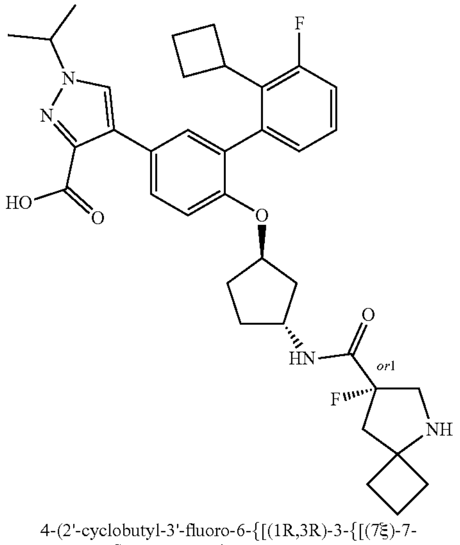 4-(2'-cyclobutyl-3'-fluoro-6-{[(1R,3R)-3-{[(7ξ)-7-fluoro-5-azaspiro[3.4]octane-7-carbonyl]amino}cyclopentyl]oxy}[1,1'-biphenyl]-3-yl)-1-(propan-2-yl)-1H-pyrazole-3-carboxylic acid | $^1$H NMR (400 MHz, DMSO-$d_6$) δ 10.41-9.30 (m, 1H), 8.59-8.44 (m, 1H), 8.06 (s, 1H), 7.49 (dd, J = 2.3, 8.5 Hz, 1H), 7.27-7.18 (m, 2H), 7.10 (dd, J = 8.6, 11.7 Hz, 1H), 7.04-6.98 (m, 1H), 6.90 (d, J = 7.3 Hz, 1H), 4.90-4.82 (m, 1H), 4.54 (td, J = 6.7, 13.4 Hz, 1H), 4.18-4.01 (m, 1H), 3.72-3.51 (m, 3H), 2.54 (br d, J = 4.0 Hz, 4H), 2.46-2.37 (m, 1H), 2.25-1.98 (m, 6H), 1.97-1.63 (m, 8H), 1.45 (d, J = 6.6 Hz, 7H). $[\alpha]_D^{22}$ = −16.6° (c 0.05, MeOH). LCMS (m/z) $(M + H)^+$: 633.5 |

Example K1: 2-[2'-cyclobutyl-3'-fluoro-6-({(1S,3R,4S)-3-hydroxy-4-[(1,4,4-trimethyl-L-prolyl)amino]cyclopentyl}oxy)[1,1'-biphenyl]-3-yl]-2-methylpropanoic acid

K1

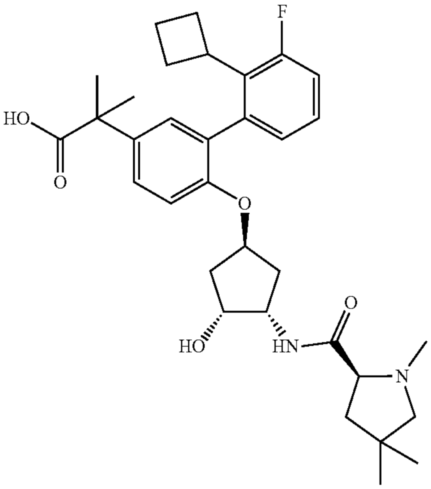

Example K1 was prepared according to General Method K.

Step 1: tert-butyl (3aS,5S,6aR)-5-(2-bromo-4-(1-methoxy-2-methyl-1-oxopropan-2-yl)phenoxy)-2,2-dimethyltetrahydro-2H-cyclopenta[d]oxazole-3(3aH)-carboxylate (K1a)

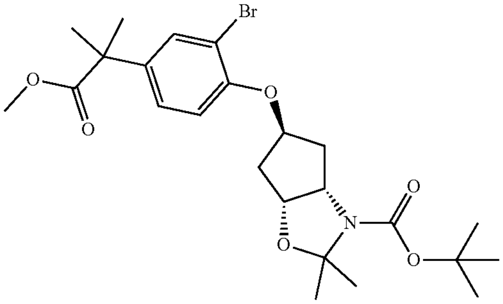 [SMILES: COC(=O)C(C)(C)c1ccc(O[C@@H]2C[C@H]3OC(C)(C)N(C(=O)OC(C)(C)C)[C@H]3C2)c(Br)c1]

To a mixture of methyl 2-(3-bromo-4-hydroxyphenyl)-2-methylpropanoate (Intermediate 1) (326 mg, 1.27 mmol), tert-butyl (3aS,5R,6aR)-5-hydroxy-2,2-dimethyltetrahydro-2H-cyclopenta[d]oxazole-3(3aH)-carboxylate (415 mg, 1.52 mmol), and triphenylphosphine (665 mg, 2.53 mmol) in toluene (6.33 ml) at 23° C., DIAD (499 ul, 2.53 mmol) was added. The mixture was stirred at RT for 75 minutes and then diluted with EtOAc and water. The EtOAc layer was washed with brine, dried over $Na_2SO_4$, filtered, and concentrated under reduced pressure. The residue was purified by silica gel chromatography (0-100% EtOAc/Heptane) to give tert-butyl (3aS,5S,6aR)-5-(2-bromo-4-(1-methoxy-2-methyl-1-oxopropan-2-yl)phenoxy)-2,2-dimethyltetrahydro-2H-cyclopenta[d]oxazole-3(3aH)-carboxylate (K1a) (571 mg, 88%) as a colorless oil. LCMS-ESI(+): M+Na=534/536 @2.73 min, 97% pure. $^1$H NMR (400 MHz, $CDCl_3$) δ ppm 7.51 (br s, 1H) 7.21 (br s, 1H) 6.86 (br d, J=8.31 Hz, 1H) 4.96 (quin, J=5.87 Hz, 1H) 4.68 (br s, 1H) 4.35-4.57 (m, 1H) 3.66 (s, 3H) 2.38 (br d, J=13.94 Hz, 1H)

2.22 (br d, J=6.60 Hz, 1H) 2.08-2.18 (m, 1H) 1.94-2.05 (m, 1H) 1.59 (s, 3H)$_{1.55}$ (s, 6H) 1.47 (br s, 9H).

Step 2: tert-butyl (3aS,5S,6aR)-5-((2'-cyclobutyl-3'-fluoro-5-(1-methoxy-2-methyl-1-oxopropan-2-yl)-[1,1'-biphenyl]-2-yl)oxy)-2,2-dimethyltetrahydro-2H-cyclopenta[d]oxazole-3(3aH)-carboxylate (K1b)

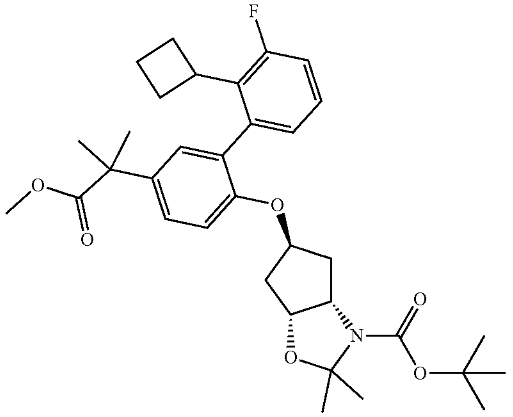 [SMILES: COC(=O)C(C)(C)c1ccc(O[C@@H]2C[C@H]3OC(C)(C)N(C(=O)OC(C)(C)C)[C@H]3C2)c(-c2cccc(F)c2C2CCC2)c1]

A mixture of tert-butyl (3aS,5S,6aR)-5-(2-bromo-4-(1-methoxy-2-methyl-1-oxopropan-2-yl)phenoxy)-2,2-dimethyltetrahydro-2H-cyclopenta[d]oxazole-3(3aH)-carboxylate (K1a) (165 mg, 0.322 mmol), $Cs_2CO_3$ (315 mg, 0.966 mmol), $PdCl_2$(dppf).$CH_2Cl_2$ (13.1 mg, 0.016 mmol), and (2-cyclobutyl-3-fluorophenyl)boronic acid (83.8 mg, 0.419 mmol) in a mixture of 1,4-dioxane (1.00 ml) and water (0.25 ml) was sparged with dry nitrogen for 5 minutes and then heated to 95° C. for 18 hours. The reaction mixture was partitioned between EtOAc and water. The EtOAc layer was washed with brine, dried over $Na_2SO_4$, filtered, and concentrated under reduced pressure. The residue was purified by silica gel chromatography (0-100% EtOAc/Heptane) to give tert-butyl (3aS,5S,6aR)-5-((2'-cyclobutyl-3'-fluoro-5-(1-methoxy-2-methyl-1-oxopropan-2-yl)-[1,1'-biphenyl]-2-yl)oxy)-2,2-dimethyltetrahydro-2H-cyclopenta[d]oxazole-3(3aH)-carboxylate (K1b) (186 mg, 99%) as a colorless oil. $^{1}$H NMR (400 MHz, $CDCl_3$) δ ppm 7.27-7.32 (m, 1H) 7.04-7.18 (m, 2H) 6.94-7.03 (m, 1H) 6.84-6.93 (m, 2H) 4.74-4.87 (m, 1H) 4.45-4.55 (m, 1H) 4.03-4.12 (m, 1H) 3.67 (s, 3H) 3.38-3.52 (m, 1H) 2.28-2.39 (m, 1H) 2.09-2.27 (m, 2H) 1.96-2.04 (m, 1H) 1.83-1.95 (m, 1H) 1.67-1.82 (m, 3H) 1.54-1.59 (m, 14H) 1.42-1.52 (m, 9H). $^{19}$F NMR (376 MHz, $CDCl_3$) δ ppm -114.50 (s, 1 F).

Step 3: methyl 2-(6-(((1S,3S,4R)-3-amino-4-hydroxycyclopentyl)oxy)-2'-cyclobutyl-3'-fluoro-[1,1'-biphenyl]-3-yl)-2-methylpropanoate (K1c)

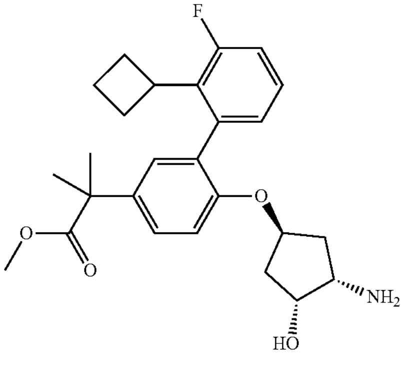 [SMILES: COC(=O)C(C)(C)c1ccc(O[C@@H]2C[C@@H](O)[C@@H](N)C2)c(-c2cccc(F)c2C2CCC2)c1]

To a solution of tert-butyl (3aS,5S,6aR)-5-((2'-cyclobutyl-3'-fluoro-5-(1-methoxy-2-methyl-1-oxopropan-2-yl)-[1,1'-biphenyl]-2-yl)oxy)-2,2-dimethyltetrahydro-2H-cyclopenta[d]oxazole-3(3aH)-carboxylate (K1b) (186 mg, 0.320 mmol) in DCM (2 ml) at 23° C., a 4N solution of HCl in dioxane (1.60 ml, 6.39 mmol) was added. The mixture was stirred 4 hours and then concentrated under reduced pressure and partitioned between EtOAc and saturated $NaHCO_3$(aq). The EtOAc layer was washed with brine, dried over $Na_2SO_4$, filtered, and concentrated to give methyl 2-(6-(((1S,3S,4R)-3-amino-4-hydroxycyclopentyl)oxy)-2'-cyclobutyl-3'-fluoro-[1,1'-biphenyl]-3-yl)-2-methylpropanoate (K1c) (141 mg, 100%) as an amber oil. LCMS-ESI(+)=442.2 (MH+). $^{1}$H NMR (400 MHz, DMSO-d6) δ ppm 7.25 (dd, J=8.62, 2.51 Hz, 1H) 7.17-7.22 (m, 1H) 7.09 (dd, J=11.74, 8.31 Hz, 1H) 6.94 (d, J=2.45 Hz, 1H) 6.92 (d, J=8.68 Hz, 1H) 6.83-6.89 (m, 1H) 4.71-4.81 (m, 1H) 3.72-3.82 (m, 1H) 3.64-3.72 (m, 1H) 3.58 (s, 3H) 3.34-3.45 (m, 1H) 2.93-3.10 (m, 1H) 2.13-2.23 (m, 1H) 2.00-2.12 (m, 2H) 1.89-1.97 (m, 1H) 1.56-1.88 (m, 6H) 1.49 (d, J=8.19 Hz, 6H).

Step 4: methyl 2-(2'-cyclobutyl-3'-fluoro-6-(((1S,3R,4S)-3-hydroxy-4-((S)-1,4,4-trimethylpyrrolidine-2-carboxamido)cyclopentyl)oxy)-[1,1'-biphenyl]-3-yl)-2-methylpropanoate (K1d)

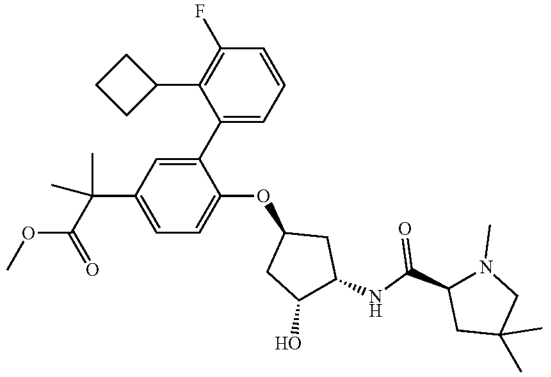

To a solution of (S)-1,4,4-trimethylpyrrolidine-2-carboxylic acid (20.6 mg, 0.131 mmol) in DMF (0.5 ml) cooled in an ice -water bath, HATU (49.9 mg, 0.131 mmol) was added. The mixture was stirred in the ice-bath for 45 minutes. To a solution of methyl 2-(6-(((1S,3S,4R)-3-amino-4-hydroxycyclopentyl)oxy)-2'-cyclobutyl-3'-fluoro-[1,1-biphenyl]-3-yl)-2-methylpropanoate hydrochloride salt (K1c) (41.8 mg, 0.0875 mmol) in DMF (0.5 ml), DIEA (61 ul, 0.350 ml) was added. The amine solution was added to the activated ester and the mixture was stirred at 23° C. for 90 minutes. The reaction mixture was quenched with saturated $NaHCO_3$(aq) then diluted with EtOAc and water. The EtOAc layer was washed with brine, dried over $Na_2SO_4$, filtered, and concentrated under reduced pressure. The residue was purified by silica gel chromatography (0-100% EtOAc/Heptane) and then (0-50% MeOH/EtAOc) to give methyl 2-(2'-cyclobutyl-3'-fluoro-6-(((1S,3R,4S)-3-hydroxy-4-((S)-1,4,4-trimethylpyrrolidine-2-carboxamido)cyclopentyl)oxy)-[1,1-biphenyl]-3-yl)-2-methylpropanoate (K1d) (64 mg, 100%) as a colorless oil. LCMS-ESI(+)=581.3 (MH+). $^{1}$H NMR (400 MHz, CD30D) δ ppm 7.30 (dd, J=8.62, 2.51 Hz, 1H) 7.12-7.21 (m, 1H) 6.94-7.05 (m, 2H) 6.88-6.94 (m, 1H) 6.86 (td, J=7.34, 1.10 Hz, 1H) 4.04-4.17 (m, 4H) 3.65 (s, 3H) 3.46 (br d, J=9.90 Hz, 1H) 2.99 (s, 7H) 2.86 (d, J=0.61 Hz, 6H) 2.46 (br s, 4H) 2.29 (br s, 1H) 2.02-2.21 (m, 5H) 1.60-1.99 (m, 7H) 1.55 (d, J=5.99 Hz, 6H) 1.10 (dd, J=7.76, 2.75 Hz, 6H).

Step 5: 2-(2'-cyclobutyl-3'-fluoro-6-(((1S,3R,4S)-3-hydroxy-4-((S)-1,4,4-trimethylpyrrolidine-2-carboxamido)cyclopentyl)oxy)-[1,1'-biphenyl]-3-yl)-2-methylpropanoic acid (Example K1)

K1

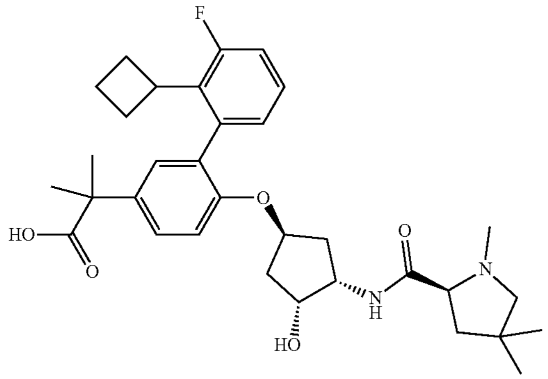

A mixture of methyl 2-(2'-cyclobutyl-3'-fluoro-6-(((1S,3R,4S)-3-hydroxy-4-((S)-1,4,4-trimethylpyrrolidine-2-carboxamido)cyclopentyl)oxy)-[1,1'-biphenyl]-3-yl)-2-methylpropanoate (K1d) (51.0 mg, 0.088 mmol) and $LiOH \cdot H_2O$ (33 mg, 0.79 mmol) in methanol (0.292 ul) was stirred at 60° C. for 21 hours. The mixture was concentrated under reduced pressure and then dissolved in THF (1 ml). A 2 M solution of potassium trimethylsilanoate (87.8 ul, 0.176 mmol) was added and the mixture was heated to 70° C. for 6 hours. The reaction mixture was quenched with acetic acid (54.7 ul, 0.956 mmol) then partitioned between EtOAc and water. The EtOAc layer was washed with brine, dried over $Na_2SO_4$, filtered, and concentrated under reduced pressure. The residue was purified by SFC to give 2-(2-cyclopropyl-3-fluorophenyl)-4,4,5,5-tetramethyl-1,3,2-dioxaborolane (Example K1) (16.6 mg, 33%) as a white solid. $^1H$ NMR (600 MHz, DMSO-d6) δ ppm 7.58 (br d, J=8.36 Hz, 1H) 7.29 (br d, J=8.72 Hz, 1H) 7.17-7.25 (m, 1H) 7.06-7.13 (m, 1H) 6.98 (s, 1H) 6.95 (t, J=7.99 Hz, 1H) 6.88 (dd, J=17.80, 7.63 Hz, 1H) 4.82 (br s, 1H) 4.07 (br d, J=3.27 Hz, 1H) 3.88-4.02 (m, 2H) 3.38-3.49 (m, 1H) 2.71-2.84 (m, 2H) 2.26 (d, J=1.45 Hz, 3H) 2.17 (br d, J=8.72 Hz, 2H) 2.00-2.14 (m, 2H) 1.70-1.99 (m, 8H) 1.59-1.69 (m, 1H) 1.45 (br d, J=7.27 Hz, 8H) 1.03 (d, J=7.27 Hz, 3H) 0.99 (d, J=3.27 Hz, 3H). LCMS ESI (+) 567.1 (M+H).

Examples K2-K8 reported in Table 11 were synthesized with non-critical changes or substitutions to the exemplified procedure for Example K1 including the use of alternate protecting groups that one skilled in the art would be able to realize.

TABLE 11

| Ex. | Structure and Name | Characterization Data ($^1H$ NMR, optical rotation, and/or LCMS) |
|---|---|---|
| K2 | 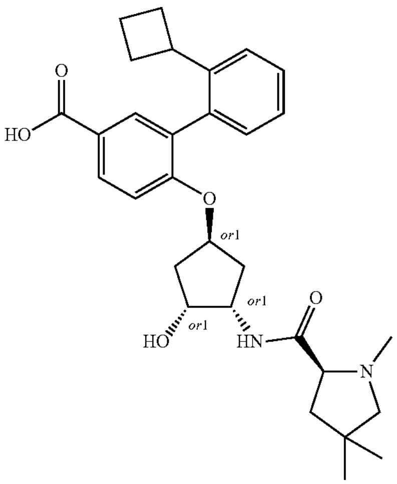 [SMILES: CN1CC(C)(C)C[C@H]1C(=O)N[C@H]1C[C@H](Oc2ccc(C(=O)O)cc2-c2ccccc2C2CCC2)C[C@H]1O] 2'-cyclobutyl-6-({(1ξ,3ξ,4ξ)-3-hydroxy-4-[(1,4,4-trimethyl-L-prolyl)amino]cyclopentyl}oxy)[1,1'-biphenyl]-3-carboxylic acid | $^1H$ NMR (400 MHz, MeOD) δ 7.92 (dd, J = 8.63, 2.25 Hz, 1H) 7.61 (d, J = 2.25 Hz, 1H) 7.28-7.31 (m, 1H) 7.22 (td, J = 7.54, 1.31 Hz, 1H) 7.09 (td, J = 7.44, 1.25 Hz, 1H) 6.91-6.98 (m, 2H) 4.89 (br s, 1H) 3.94-4.08 (m, 2H) 3.29-3.51 (m, 2H) 2.99-3.10 (m, 1H) 2.55-2.62 (m, 1H) 2.51 (s, 3H) 1.57-2.14 (m, 12H) 1.04 (d, J = 3.88 Hz, 6H). $[\alpha]_D^{22}$ = −58.3° (c 0.1, MeOH). LCMS (m/z) $(M + H)^+$: 507.3 |

TABLE 11-continued

| Ex. | Structure and Name | Characterization Data ($^1$H NMR, optical rotation, and/or LCMS) |
|---|---|---|
| K3 | 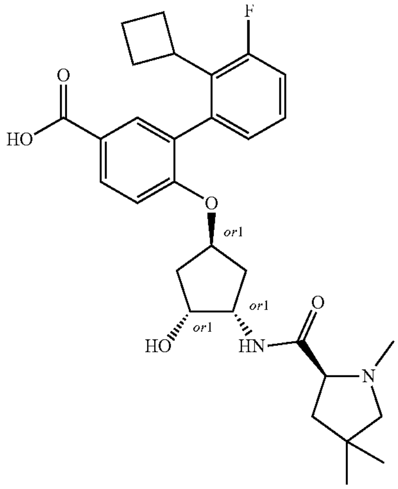 [SMILES: CN1CC(C)(C)C[C@H]1C(=O)N[C@H]1C[C@H](Oc2ccc(C(=O)O)cc2-c2cccc(F)c2C2CCC2)C[C@H]1O] 2'-cyclobutyl-3'-fluoro-6-({(1ξ,3ξ,4ξ)-3-hydroxy-4-[(1,4,4-trimethyl-L-prolyl)amino]cyclopentyl}oxy)[1,1'-biphenyl]-3-carboxylic acid | $^1$H NMR (400 MHz, DMSO-$d_6$) δ 8.01 (br d, J = 8.3 Hz, 1H), 7.65 (s, 1H), 7.36-7.26 (m, 1H), 7.24-7.10 (m, 2H), 6.93 (br dd, J = 3.8, 7.1 Hz, 1H), 5.02 (br s, 1H), 4.05 (br s, 2H), 3.42 (td, J = 9.1, 18.2 Hz, 1H), 3.16 (br s, 1H), 2.74 (br s, 1H), 2.32-2.15 (m, 3H), 2.13-1.93 (m, 4H), 1.89-1.64 (m, 6H), 1.17-1.06 (m, 6H). LCMS (m/z) (M + H)$^+$: 525.5 |
| K4 | 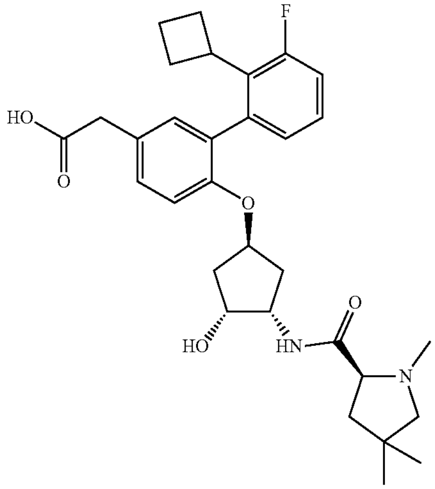 [SMILES: CN1CC(C)(C)C[C@H]1C(=O)N[C@H]1C[C@H](Oc2ccc(CC(=O)O)cc2-c2cccc(F)c2C2CCC2)C[C@H]1O] [2'-cyclobutyl-3'-fluoro-6-({(1S,3R,4S)-3-hydroxy-4-[(1,4,4-trimethyl-L-prolyl)amino]cyclopentyl}oxy)[1,1'-biphenyl]-3-yl]acetic acid | $^1$H NMR (400 MHz, DMSO-$d_6$) δ 12.21 (br s, 1H) 7.59 (br s, 1H) 7.17-7.25 (m, 2H) 7.09 (dd, J = 11.82, 8.19 Hz, 1H) 6.91-6.98 (m, 2H) 6.87 (ddd, J = 10.79, 7.54, 1.19 Hz, 1H) 5.11 (dd, J = 9.63, 4.38 Hz, 1H) 4.80 (br dd, J = 6.69, 3.81 Hz, 1H) 3.86-4.00 (m, 2H) 3.52 (s, 2H) 3.35-3.49 (m, 1H) 2.76 (br d, J = 7.75 Hz, 2H) 2.24-2.29 (m, 3H) 2.12-2.23 (m, 2H) 2.00-2.12 (m, 3H) 1.81-1.97 (m, 3H) 1.61-1.81 (m, 4H) 1.41-1.51 (m, 1H) 1.03 (d, J = 6.38 Hz, 3H) 1.00 (d, J = 3.38 Hz, 3H). LCMS (m/z) (M + H)$^+$: 539.2 |

TABLE 11-continued

| Ex. | Structure and Name | Characterization Data ($^1$H NMR, optical rotation, and/or LCMS) |
| --- | --- | --- |
| K5 | 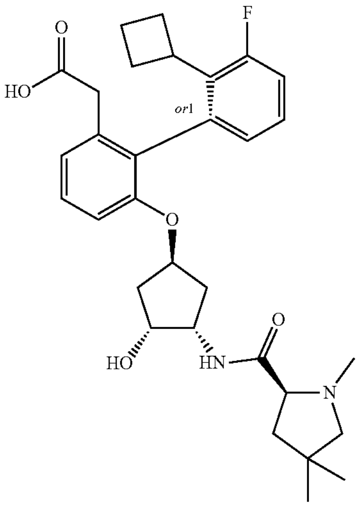 [(1ψ)-2'-cyclobutyl-3'-fluoro-6-({(1S,3R,4S)-3-hydroxy-4-[(1,4,4-trimethyl-L-prolyl)amino]cyclopentyl}oxy)[1,1'-biphenyl]-2-yl]acetic acid | $^1$H NMR (400 MHz, DMSO-$d_6$) δ 7.55 (d, J = 8.38 Hz, 1H) 7.25 (t, J = 7.94 Hz, 1H) 7.15-7.22 (m, 1H) 7.08 (dd, J = 11.88, 8.00 Hz, 1H) 6.95 (br d, J = 7.63 Hz, 1H) 6.84 (d, J = 8.25 Hz, 1H) 6.76 (br d, J = 7.50 Hz, 1H) 4.72-4.81 (m, 1H) 3.88-3.95 (m, 1H) 3.77-3.86 (m, 1H) 3.17-3.23 (m, 2H) 3.03 (br s, 1H) 2.77-2.81 (m, 1H) 2.73-2.76 (m, 1H) 2.26 (s, 3H) 2.06 (ddd, J = 14.54, 6.91, 2.44 Hz, 1H) 1.78-2.00 (m, 6H) 1.64-1.77 (m, 5H) 1.45 (dd, J = 12.57, 5.94 Hz, 1H) 1.02 (s, 3H) 1.00 (s, 3H). LCMS (m/z) $(M + H)^+$: 539.1 |
| K6 | 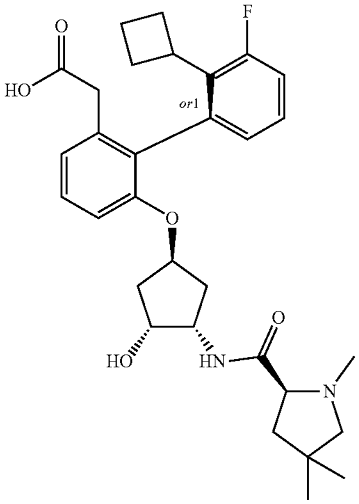 [(1ψ)-2'-cyclobutyl-3'-fluoro-6-({(1S,3R,4S)-3-hydroxy-4-[(1,4,4-trimethyl-L-prolyl)amino]cyclopentyl}oxy)[1,1'-biphenyl]-2-yl]acetic acid | $^1$H NMR (400 MHz, DMSO-$d_6$) δ 7.56 (d, J = 7.88 Hz, 1H) 7.13-7.26 (m, 2H) 7.07 (dd, J = 11.76, 8.13 Hz, 1H) 6.89-6.98 (m, 1H) 6.80 (d, J = 8.13 Hz, 1H) 6.71-6.77 (m, 1H) 4.68-4.77 (m, 1H) 3.80-3.93 (m, 2H) 2.71-2.81 (m, 2H) 2.25 (s, 3H) 2.16 (d, J = 8.88 Hz, 2H) 1.98 (td, J = 7.22, 2.56 Hz, 2H) 1.91 (br dd, J = 12.82, 10.44 Hz, 2H) 1.82 (br dd, J = 8.88, 4.75 Hz, 2H) 1.62-1.73 (m, 2H) 1.58 (dt, J = 14.54, 4.61 Hz, 1H)1.39-1.49 (m, 1H) 1.10-1.23 (m, 2H) 1.03 (s, 3H) 1.00 (s, 3H). LCMS (m/z) $(M + H)^+$: 539.2 |

TABLE 11-continued

| Ex. | Structure and Name | Characterization Data ($^1$H NMR, optical rotation, and/or LCMS) |
|---|---|---|
| K7 | 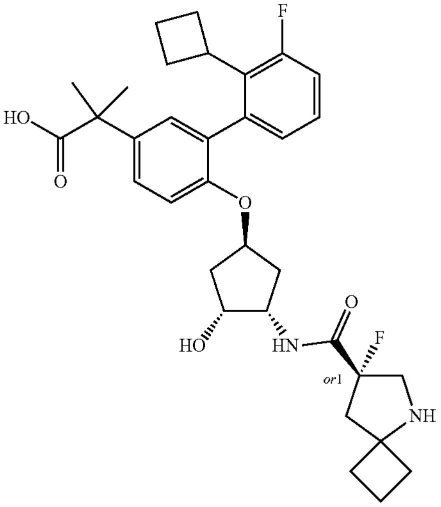 [SMILES: CC(C)(C(=O)O)c1ccc(O[C@@H]2C[C@@H](O)[C@@H](NC(=O)[C@@]3(F)CNC4(CCC4)C3)C2)c(-c2cccc(F)c2C2CCC2)c1] 2-(2'-cyclobutyl-3'-fluoro-6-{[(1S,3S,4R)-3-{[(7ξ)-7-fluoro-5-azaspiro[3.4]octane-7-carbonyl]amino}-4-hydroxycyclopentyl]oxy}[1,1'-biphenyl]-3-yl)-2-methylpropanoic acid | $^1$H NMR (600 MHz, DMSO-$d_6$) δ 7.63 (br s, 1H) 7.30 (br d, J = 8.72 Hz, 1H) 7.17-7.25 (m, 1H) 7.09 (br t, J = 9.63 Hz, 1H) 6.98-7.01 (m, 1H) 6.96 (dd, J = 8.54, 6.36 Hz, 1H) 6.88 (t, J = 7.63 Hz, 1H) 5.06-5.12 (m, 1H) 4.83 (br d, J = 2.54 Hz, 1H) 3.89-4.06 (m, 3H) 3.38-3.48 (m, 2H) 2.31 (br d, J = 1.45 Hz, 2H) 2.10-2.22 (m, 4H) 2.00-2.09 (m, 3H) 1.91-1.99 (m, 2H) 1.62-1.91 (m, 10H) 1.46 (d, J = 7.63 Hz, 9H). LCMS (m/z) $(M + H)^+$: 583.1 |
| K8 | 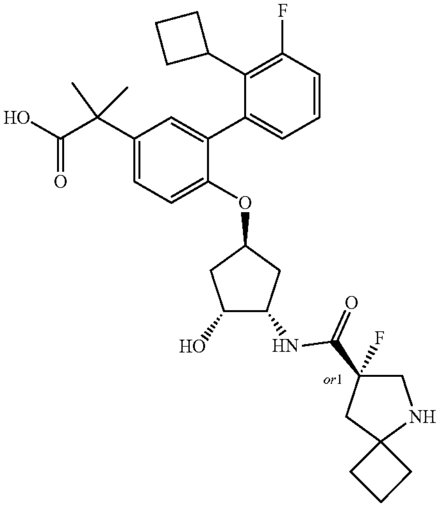 [SMILES: CC(C)(C(=O)O)c1ccc(O[C@@H]2C[C@@H](O)[C@@H](NC(=O)[C@@]3(F)CNC4(CCC4)C3)C2)c(-c2cccc(F)c2C2CCC2)c1] 2-(2'-cyclobutyl-3'-fluoro-6-{[(1S,3S,4R)-3-{[(7ξ)-7-fluoro-5-azaspiro[3.4]octane-7-carbonyl]amino}-4-hydroxycyclopentyl]oxy}[1,1'-biphenyl]-3-yl)-2-methylpropanoic acid | $^1$H NMR (600 MHz, DMSO-$d_6$) δ 7.33-7.41 (m, 1H) 7.30 (br d, J = 8.36 Hz, 1H) 7.17-7.25 (m, 1H) 7.06-7.14 (m, 1H) 6.99 (br s, 1H) 6.93-6.97 (m, 1H) 6.88 (br dd, J = 12.35, 7.63 Hz, 1H) 5.11 (br dd, J = 8.17, 4.18 Hz, 1H) 4.83 (br s, 1H) 3.86-4.06 (m, 3H) 3.43 (dt, J = 17.89, 8.67 Hz, 1H) 2.97-3.22 (m, 2H) 2.19-2.28 (m, 1H) 2.08-2.17 (m, 3H) 2.02-2.07 (m, 2H) 1.94-2.01 (m, 5H) 1.82-1.93 (m, 3H) 1.56-1.80 (m, 7 H) 1.46 (br d, J = 7.27 Hz, 8H). LCMS (m/z) $(M + H)^+$: 583.1 |

Example L1: N-[(1R,3R)-3-({2'-cyclobutyl-3'-fluoro-5-[5-(methanesulfonamido)-3-methyl-1H-pyrazol-1-yl][1,1'-biphenyl]-2-yl}oxy)cyclopentyl]-1,4,4-trimethyl-L-prolinamide

L1

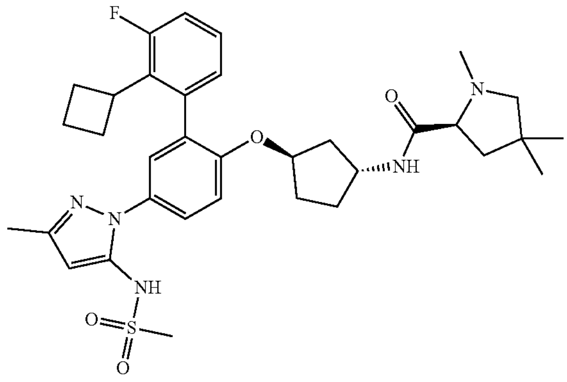

Example L1 was prepared according to General Method L.

Step 1: tert-butyl ((1R,3R)-3-((5-(5-amino-3-methyl-1H-pyrazol-1-yl)-2'-cyclobutyl-3'-fluoro-[1,1'-biphenyl]-2-yl)oxy)cyclopentyl)carbamate (L1a)

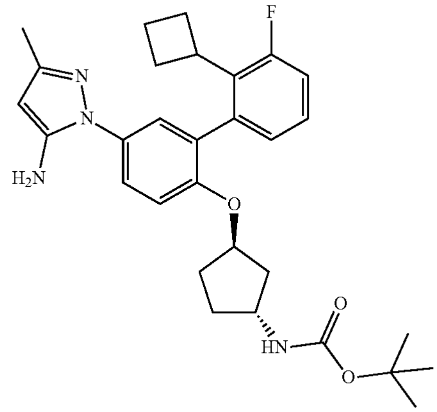 [SMILES: Cc1cc(N)n(-c2ccc(O[C@@H]3CC[C@@H](NC(=O)OC(C)(C)C)C3)c(-c3cccc(F)c3C3CCC3)c2)n1]

To a solution of crude and 2-(2-cyclobutyl-3-fluorophenyl)-4,4,5,5-tetramethyl-1,3,2-dioxaborolane (Intermediate 2) (220 mg, 0.80 mmol) in dioxane (5.0 mL), a solution of Cs in H was added. Next, Pd(dpbpf)CI was added, and the mixture was degassed with $N_2$ and then heated at 80° C. overnight. The reaction was concentrated and the residue was purified by silica gel chromatography (0-40% EtOAc/PE) to give tert-butyl ((1R,3R)-3-((5-(5-amino-3-methyl-1H-pyrazol-1-yl)-2'-cyclobutyl-3'-fluoro-[1,1-biphenyl]-2-yl)oxy)cyclopentyl)carbamate (L1a) (460 mg, >99% crude yield) as a yellow solid. LCMSAPCI (+) 521.1 (M+H). $^1$H NMR (400 MHz, DMSO-$d_6$) δ ppm 7.54-7.45 (m, 1H) 7.30-7.18 (m, 2H) 7.17-7.04 (m, 2H) 7.00-6.92 (m, 1H) 6.91-6.81 (m, 1H) 5.33-5.25 (m, 1H) 5.21-5.09 (m, 2H) 4.85-4.74 (m, 1H) 3.83-3.61 (m, 1H) 3.55-3.40 (m, 1H) 2.31-2.18 (m, 1H) 2.17-2.07 (m, 2H) 2.03 (s, 3H) 1.94-1.61 (m, 6H) 1.58-1.47 (m, 1H) 1.35 (br d, J=4.4 Hz, 10H), 1.20-1.13 (m, 2H).

Step 2: tert-butyl [(1R,3R)-3-({2'-cyclobutyl-3'-fluoro-5-[5-(methanesulfonamido)-3-methyl-1H-pyrazol-1-yl][1,1'-biphenyl]-2-yl}oxy)cyclopentyl]carbamate (L1b)

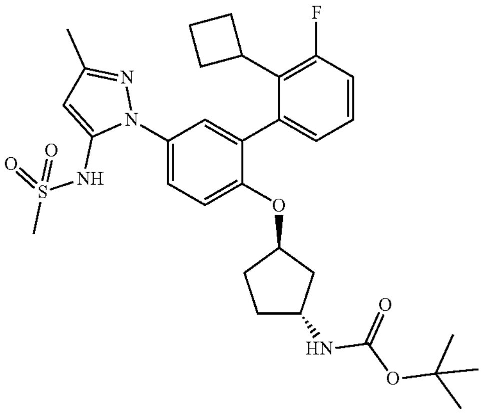 [SMILES: Cc1cc(NS(C)(=O)=O)n(-c2ccc(O[C@@H]3CC[C@@H](NC(=O)OC(C)(C)C)C3)c(-c3cccc(F)c3C3CCC3)c2)n1]

A solution of tert in pyridine (6.0 mL) was cooled in an ice-water bath. Methanesulfonyl chloride (122 mg, 1.07 mmol) and tert-butyldimethylsilyl trfluoromethanesulfonate (376 mg, 1.42 mmol) were added. The ice-bath was removed, and the resulting solution was stirred at 60° C. for 16 hours. The reaction solution was poured into ice-water (20 mL) and extracted with EtOAc (3×). The combined organics were dried over $Na_2SO_4$ and concentrated under reduced pressure. The crude product was purified by prep HPLC (Boston Prime C18 150×30 mm, 5 um, Mobile phase A: Water (0.05% $NH_3H_2O$+10 mM $NH_4HCO_3$), Mobile phase B: Acetonitrile, 25-55% B in 9.0 minutes, 30 mL/min) to give tert-butyl [(1R,3R)-3-({2'-cyclobutyl-3'-fluoro-5-[5-(methanesulfonamido)-3-methyl-1H-pyrazol-1-yl][1,1-biphenyl]-2-yl}oxy)cyclopentyl]carbamate (L1b) (83 mg, 20% yield) as a light yellow solid. LCMS APCI (+) 621.1 (M+Na). $^1$H NMR (400 MHz, DMSO-$d_6$) δ ppm 9.78 (br s, 1H) 7.55-7.49 (m, 1H) 7.31-7.20 (m, 2H) 7.16-7.06 (m, 2H) 6.94-6.83 (m, 2H) 6.30-6.21 (m, 1H) 4.88-4.79 (m, 1H) 3.85-3.64 (m, 1H) 3.55-3.42 (m, 2H) 2.96 (s, 3H), 2.19 (s, 3H) 2.16-1.95 (m, 4H) 1.93-1.41 (m, 8H) 1.35 (s, 9H).

Step 3: N-[1-(6-{[(1R,3R)-3-aminocyclopentyl]oxy}-2'-cyclobutyl-3'-fluoro[1,1'-biphenyl]-3-yl)-3-methyl-1H-pyrazol-5-yl]methanesulfonamide (Lic)

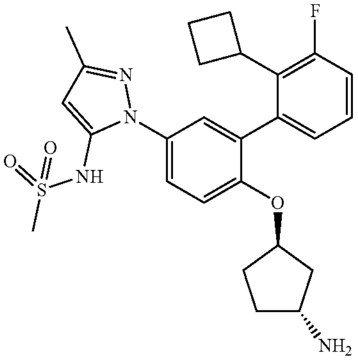 [SMILES: Cc1cc(NS(C)(=O)=O)n(-c2ccc(O[C@@H]3CC[C@@H](N)C3)c(-c3cccc(F)c3C3CCC3)c2)n1]

To a solution of tert in DCM (1.0 mL), HCl (4 N in dioxane, 1.0 mL) was added. After 5 hours, the reaction was concentrated under reduced pressure to give N-[1-(6-{[(1R,3R)-3-aminocyclopentyl]oxy}-2'-cyclobutyl-3'-fluoro[1,1'- biphenyl]-3-yl)-3-methyl-1H-pyrazol-5-yl]methanesulfonamide hydrochloride (Lic) (80 mg, >99% crude yield) as a yellow solid. LCMS APCI (+) 499.0 (M+H).

Step 4: N-[(1R,3R)-3-({2'-cyclobutyl-3'-fluoro-5-[5-(methanesulfonamido)-3-methyl-1H-pyrazol-1-yl][1,1'-biphenyl]-2-yl}oxy)cyclopentyl]-1,4,4-trimethyl-L-prolinamide (Example L1)

L1

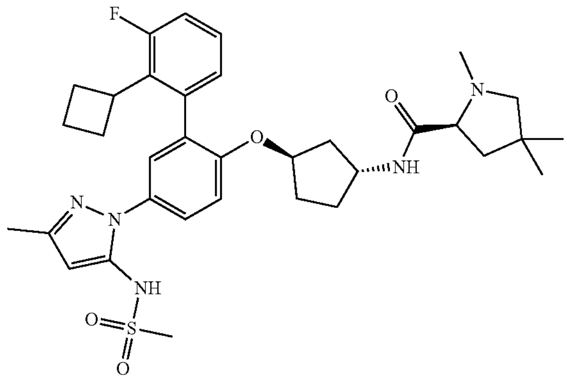

A solution N, EDCI (27.6 mg, 0.14 mmol), 1,4,4-trimethyl-L-proline (22.6 mg, 0.14 mmol), and DMAP (32.0 mg, 0.26 mmol) in DCM (2.5 mL) was stirred for 1 hour at 40° C. The reaction solution was concentrated under reduced pressure and the crude product was purified by prep HPLC (Boston Prime C18 150×30 mm, 5 um, Mobile phase A: Water (0.05% $NH_4OH$+10 mM $NH_4HCO_3$), Mobile phase B: Acetonitrile, 21-51% B in 8.0 minutes, 30 mL/min) to give N-[(1R,3R)-3-({2'-cyclobutyl-3'-fluoro-5-[5-(methanesulfonamido)-3-methyl-1H-pyrazol-1-yl][1,1-biphenyl]-2-yl}oxy)cyclopentyl]-1,4,4-trimethyl-L-prolinamide (Example L1) (39.19 mg, 47% yield) as white solid. LCMSAPCI (+) 638.4 (M+H). $^1$H NMR (400 MHz, DMSO-$d_6$) δ ppm 9.75 (br s, 1H) 7.81 (br s, 1H) 7.61 (br d, J=6.6 Hz, 1H) 7.35 (t, J=2.4 Hz, 1H) 7.29-7.19 (m, 1H) 7.17-7.06 (m, 2H) 6.94-6.89 (m, 1H) 6.14 (s, 1H) 4.86 (br s, 1H) 4.15-3.96 (m, 1H) 3.58-3.45 (m, 1H) 3.04-2.94 (m, 1H) 2.91 (s, 3H) 2.88-2.80 (m, 1H) 2.36-1.97 (m, 11H) 1.97-1.33 (m, 10H) 1.11-0.96 (m, 6H).

Examples L2-L3 reported in Table 12 were synthesized with non-critical changes or substitutions to the exemplified procedure for Example L1 that one skilled in the art would be able to realize.

TABLE 12

| Ex. | Structure and Name | Characterization Data ($^1$H NMR, optical rotation, and/or LCMS) |
|---|---|---|
| L2 | 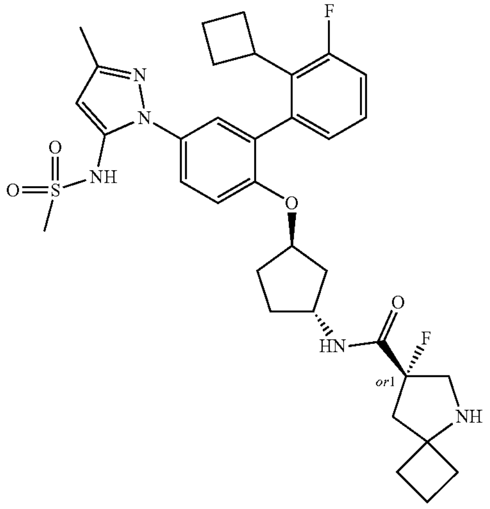 [SMILES: Cc1cc(NS(C)(=O)=O)n(-c2ccc(O[C@@H]3CC[C@@H](NC(=O)[C@@]4(F)CNC5(CCC5)C4)C3)c(-c3cccc(F)c3C3CCC3)c2)n1] (7ξ)-N-[(1R,3R)-3-({2'-cyclobutyl-3'-fluoro-5-[5-(methanesulfonamido)-3-methyl-1H-pyrazol-1-yl][1,1'-biphenyl]-2-yl}oxy)cyclopentyl]-7-fluoro-5-azaspiro[3.4]octane-7-carboxamide | $^1$H NMR (400 MHz, DMSO-$d_6$) δ 10.07-9.70 (m, 3H), 8.58-8.50 (m, 1H), 7.54-7.49 (m, 1H), 7.29 (t, J = 2.3 Hz, 1H), 7.27-7.20 (m, 1H), 7.17-7.09 (m, 2H), 6.93-6.89 (m, 1H), 6.33-6.30 (m, 1H), 4.94-4.87 (m, 1H), 4.10-4.07 (m, 1H), 3.73-3.47 (m, 3H), 3.00 (s, 3H), 2.68-2.55 (m, 3H), 2.49-2.39 (m, 1H), 2.24-2.02 (m, 9H), 1.99-1.40 (m, 10H). LCMS (m/z) (M + H)$^+$: 654.5 |

TABLE 12-continued

| Ex. | Structure and Name | Characterization Data ($^1$H NMR, optical rotation, and/or LCMS) |
|---|---|---|
| L3 | 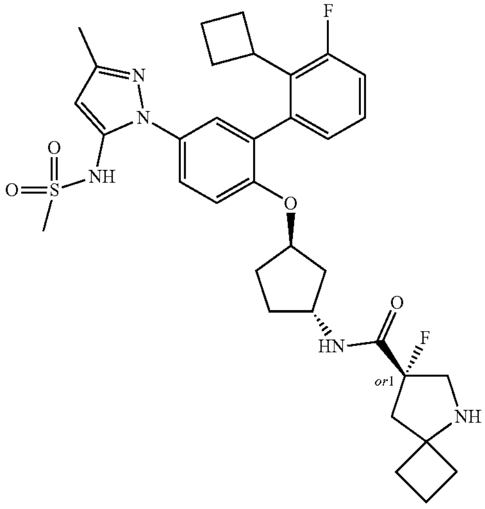 [SMILES: Cc1cc(NS(C)(=O)=O)n(-c2ccc(O[C@@H]3CC[C@@H](NC(=O)[C@@]4(F)CNC5(CCC5)C4)C3)c(-c3cccc(F)c3C3CCC3)c2)n1] (7ξ)-N-[(1R,3R)-3-({2'-cyclobutyl-3'-fluoro-5-[5-(methanesulfonamido)-3-methyl-1H-pyrazol-1-yl][1,1'-biphenyl]-2-yl}oxy)cyclopentyl]-7-fluoro-5-azaspiro[3.4]octane-7-carboxamide | $^1$H NMR (400 MHz, DMSO-$d_6$) δ = 10.20-9.67 (m, 3H), 8.58-8.50 (m, 1H), 7.55-7.49 (m, 1H), 7.29 (t, J = 2.6 Hz, 1H), 7.27-7.20 (m, 1H), 7.17-7.10 (m, 2H), 6.91 (d, J = 7.5 Hz, 1H), 6.31 (s, 1H), 4.95-4.87 (m, 1H), 4.14-4.08 (m, 1H), 3.72-3.46 (m, 3H), 3.05-2.96 (m, 3H), 2.68-2.55 (m, 2H), 2.54 (s, 1H), 2.48-2.39 (m, 1H), 2.24-2.03 (m, 9H), 1.98-1.74 (m, 7H), 1.68-1.43 (m, 3H). LCMS (m/z) $(M + H)^+$: 654.3 |

Metabolite Profile and Deuterated Analogs

The metabolite profile of 2-(2'-cyclobutyl-3'-fluoro-6-{[(1R,3R)-3-{[(7S)-7-fluoro-5-azaspiro[3.4]octane-7-carbonyl]amino}cyclopentyl]oxy}[1,1'-biphenyl]-3-yl)-2-methylpropanoic acid (Example A1) assessed in hepatocytes (mouse, dog, human), recombinant human UGT enzymes, and plasma and urine from dogs. The most significant metabolite observed was glucuronidation of the carboxylic acid group (Acyl glucuronide). Additional metabolites arose from: CYP-mediated oxidation on the cyclobutane ring, the gem-dimethyl group and/or one or both of the biaryl rings. A direct glucose conjugate from UGT enzymes or chemical reaction was also observed.

Deuterated Analogs of Example A1, Example A39, Example D1, and Example E1

The compounds shown in Table 13 include a deuterated analog of 2-(2'-cyclobutyl-3'-fluoro-6-{[(1R,3R)-3-{[(7S)-7-fluoro-5-azaspiro[3.4]octane-7-carbonyl]amino}cyclopentyl]oxy}[1,1'-biphenyl]-3-yl)-2-methylpropanoic acid (Example A1), 2-(2'-cyclobutyl-3'-fluoro-6-{[(1R,3R)-3-{[(7S)-7-fluoro-5-azaspiro[3.4]octane-7-carbonyl]amino}cyclopentyl]oxy}[1,1'-biphenyl]-3-yl)-2-($^2H_3$)methyl($^2H_3$)propanoic acid (Example A44), and prophetic deuterated analogs (PDAs). The PDAs are predicted based on the in vitro metabolic profile of Example A1.

TABLE 13

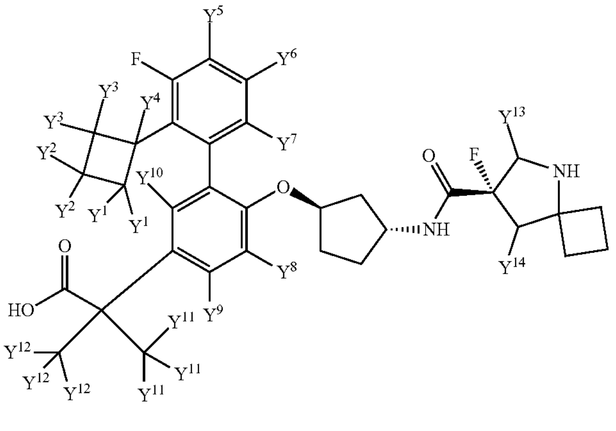

| Example | $Y^1$ | $Y^2$ | $Y^3$ | $Y^4$ | $Y^5$ | $Y^6$ | $Y^7$ | $Y^8$ | $Y^9$ | $Y^{10}$ | $Y^{11}$ | $Y^{12}$ | $Y^{13}$ | $Y^{14}$ |
|---|---|---|---|---|---|---|---|---|---|---|---|---|---|---|
| A1-1 | D | H | H | H | H | H | H | H | H | H | H | H | H | H |
| A1-2 | H | D | H | H | H | H | H | H | H | H | H | H | H | H |

TABLE 13-continued

| | | | | | | | | | | | | | | |
|---|---|---|---|---|---|---|---|---|---|---|---|---|---|---|
| A1-3 | H | H | D | H | H | H | H | H | H | H | H | H | H | H |
| A1-4 | H | H | H | D | H | H | H | H | H | H | H | H | H | H |
| A1-5 | H | H | H | H | D | H | H | H | H | H | H | H | H | H |
| A1-6 | H | H | H | H | H | D | H | H | H | H | H | H | H | H |
| A1-7 | H | H | H | H | H | H | D | H | H | H | H | H | H | H |
| A1-8 | H | H | H | H | H | H | H | D | H | H | H | H | H | H |
| A1-9 | H | H | H | H | H | H | H | H | D | H | H | H | H | H |
| A1-10 | H | H | H | H | H | H | H | H | H | D | H | H | H | H |
| A1-11 | H | H | H | H | H | H | H | H | H | H | D | H | H | H |
| A1-12 | H | H | H | H | H | H | H | H | H | H | H | D | H | H |
| A1-13 (Example A44) | H | H | H | H | H | H | H | H | H | H | D | D | H | H |
| A1-14 | H | H | H | H | H | H | H | H | H | H | H | H | D | H |
| A1-15 | H | H | H | H | H | H | H | H | H | H | H | H | H | D |

The compounds shown in Table 14 are prophetic deuterated analogs of 6-{[(1R,3R)-3-{[(7S)-7-fluoro-5-azaspiro[3,4]octane-7-carbonyl]amino}cyclopentyl]oxy}-2'-(propan-2-yl)[1,1'-biphenyl]-3-carboxylic acid (Example A39). The PDAs are predicted based on an in vitro metabolic identification study performed on Example A39 in a similar manner to Example A1. Table 14

TABLE 14

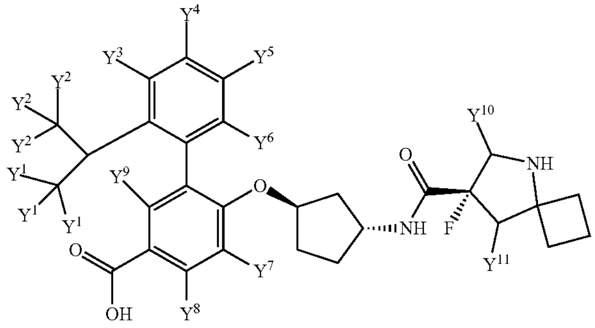

| Example | $Y^1$ | $Y^2$ | $Y^3$ | $Y^4$ | $Y^5$ | $Y^6$ | $Y^7$ | $Y^8$ | $Y^9$ | $Y^{10}$ | $Y^{11}$ |
|---|---|---|---|---|---|---|---|---|---|---|---|
| A39-1 | D | H | H | H | H | H | H | H | H | H | H |
| A39-2 | H | D | H | H | H | H | H | H | H | H | H |
| A39-3 | H | H | D | H | H | H | H | H | H | H | H |
| A39-4 | H | H | H | D | H | H | H | H | H | H | H |
| A39-5 | H | H | H | H | D | H | H | H | H | H | H |
| A39-6 | H | H | H | H | H | D | H | H | H | H | H |
| A39-7 | H | H | H | H | H | H | D | H | H | H | H |
| A39-8 | H | H | H | H | H | H | H | D | H | H | H |
| A39-9 | H | H | H | H | H | H | H | H | D | H | H |
| A39-10 | H | H | H | H | H | H | H | H | H | D | H |
| A39-11 | H | H | H | H | H | H | H | H | H | H | D |

The compounds shown in Table 15 include a deuterated analog of 2-[2'-cyclobutyl-3'-fluoro-6-({(1R,3R)-3-[(1,4,4-trimethyl-L-prolyl)amino]cyclopentyl}oxy)[1,1'-biphenyl]-3-yl]-2-methylpropanoic acid (Example D1), 2-(2'-cyclobutyl-6-{[(1R,3R)-3-{[4,4-dimethyl-1-($^2H_3$)methyl-L-prolyl]amino}cyclopentyl]oxy}-3'-fluoro[1,1'-biphenyl]-3-yl)-2-methylpropanoic acid (Example D15), and PDAs. The PDAs are predicted based on an in vitro metabolic identification study performed on Example D1 in a similar manner to Example A1.

TABLE 15

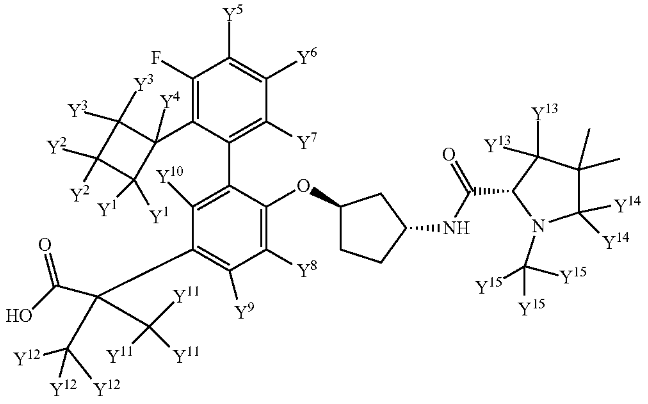

| Example | $Y^1$ | $Y^2$ | $Y^3$ | $Y^4$ | $Y^5$ | $Y^6$ | $Y^7$ | $Y^8$ | $Y^9$ | $Y^{10}$ | $Y^{11}$ | $Y^{12}$ | $Y^{13}$ | $Y^{14}$ | $Y^{15}$ |
|---|---|---|---|---|---|---|---|---|---|---|---|---|---|---|---|
| D1-1 | D | H | H | H | H | H | H | H | H | H | H | H | H | H | H |
| D1-2 | H | D | H | H | H | H | H | H | H | H | H | H | H | H | H |
| D1-3 | H | H | D | H | H | H | H | H | H | H | H | H | H | H | H |
| D1-4 | H | H | H | D | H | H | H | H | H | H | H | H | H | H | H |
| D1-5 | H | H | H | H | D | H | H | H | H | H | H | H | H | H | H |
| D1-6 | H | H | H | H | H | D | H | H | H | H | H | H | H | H | H |
| D1-7 | H | H | H | H | H | H | D | H | H | H | H | H | H | H | H |
| D1-8 | H | H | H | H | H | H | H | D | H | H | H | H | H | H | H |
| D1-9 | H | H | H | H | H | H | H | H | D | H | H | H | H | H | H |
| D1-10 | H | H | H | H | H | H | H | H | H | D | H | H | H | H | H |
| D1-11 | H | H | H | H | H | H | H | H | H | H | D | H | H | H | H |
| D1-12 | H | H | H | H | H | H | H | H | H | H | H | D | H | H | H |
| D1-13 | H | H | H | H | H | H | H | H | H | H | H | H | D | H | H |
| D1-14 | H | H | H | H | H | H | H | H | H | H | H | H | H | D | H |
| D1-15 (Example D15) | H | H | H | H | H | H | H | H | H | H | H | H | H | H | D |

The compounds shown in Table 16 include a deuterated analog of N-{(1R,3R)-3-[(2'-cyclobutyl-3'-fluoro-5-{1-[(methanesulfonyl)amino]-2-methyl-1-oxopropan-2-yl}[1,1T-biphenyl]-2-yl)oxy]cyclopentyl}-1,4,4-trimethyl-L-prolinamide (Example E1), N-{(1R,3R)-3-[(2'-cyclobutyl-3'-fluoro-5-{1-[(methanesulfonyl)amino]-2-methyl-1-oxopropan-2-yl}[1,T1-biphenyl]-2-yl)oxy]cyclopentyl}-4,4-dimethyl-1-($^2H_3$methyl-L-prolinamide (Example E5), and PDAs. The PDAs are predicted based on an in vitro metabolic identification study performed on Example E5 in a similar manner to Example A1.

TABLE 16

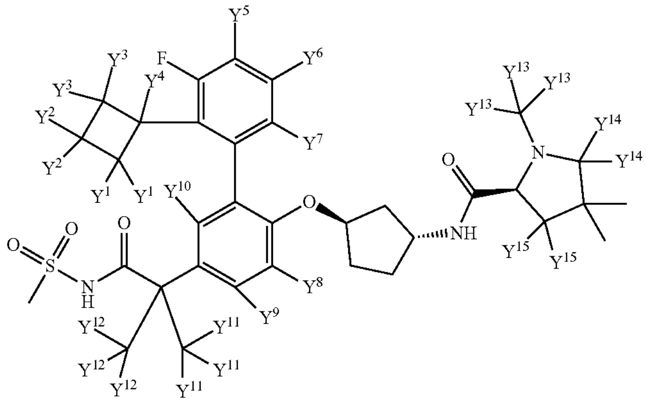

| Example | $Y^1$ | $Y^2$ | $Y^3$ | $Y^4$ | $Y^5$ | $Y^6$ | $Y^7$ | $Y^8$ | $Y^9$ | $Y^{10}$ | $Y^{11}$ | $Y^{12}$ | $Y^{13}$ | $Y^{14}$ | $Y^{15}$ |
|---|---|---|---|---|---|---|---|---|---|---|---|---|---|---|---|
| E1-1 | D | H | H | H | H | H | H | H | H | H | H | H | H | H | H |
| E1-2 | H | D | H | H | H | H | H | H | H | H | H | H | H | H | H |
| E1-3 | H | H | D | H | H | H | H | H | H | H | H | H | H | H | H |
| E1-4 | H | H | H | D | H | H | H | H | H | H | H | H | H | H | H |
| E1-5 | H | H | H | H | D | H | H | H | H | H | H | H | H | H | H |
| E1-6 | H | H | H | H | H | D | H | H | H | H | H | H | H | H | H |

TABLE 16-continued

| | | | | | | | | | | | | | | | |
|---|---|---|---|---|---|---|---|---|---|---|---|---|---|---|---|
| E1-7 | H | H | H | H | H | H | D | H | H | H | H | H | H | H | H |
| E1-8 | H | H | H | H | H | H | H | D | H | H | H | H | H | H | H |
| E1-9 | H | H | H | H | H | H | H | H | D | H | H | H | H | H | H |
| E1-10 | H | H | H | H | H | H | H | H | H | D | H | H | H | H | H |
| E1-11 | H | H | H | H | H | H | H | H | H | H | D | H | H | H | H |
| E1-12 | H | H | H | H | H | H | H | H | H | H | H | D | H | H | H |
| E1-13 (Example E5) | H | H | H | H | H | H | H | H | H | H | H | H | D | H | H |
| E1-14 | H | H | H | H | H | H | H | H | H | H | H | H | H | D | H |
| E1-15 | H | H | H | H | H | H | H | H | H | H | H | H | H | H | D |

General method/reviews of obtaining metabolite profile and identifying metabolites of a compound are described in: DAVLIE, D., et al., "Assessment of Three Human in Vitro Systems in the Generation of Major Human Excretory and Circulating Metabolites," Chemical Research in Toxicology, 2009, 22(2):357-368; KING, R., "Chapter Three—Biotransformations in Drug Metabolism." Drug Metabolism Handbook: Concepts and Applications in Cancer Research, edited by Ala F. Nassar et al., Wiley, 2022, 17-38; WU, Y., et al., "Metabolite Identification in Preclinical and Clinical Phase of Drug Development," Current Drug Metabolism, 2021, 22(11):838-857; GODZIEN, J., et al., "Chapter Fifteen—Metabolite Annotation and Identification." Comprehensive Analytical Chemistry, Elsevier, 2018, 415-445.

Numerous publicly available and commercially available software tools are available to aid in the predictions of metabolic pathways and metabolites of compounds. Examples of such tools include, BioTransformer 3.0 (BIOTRANSFORMER 3.0, "Metabolism Prediction," www.biotransformer.ca. Retrieved Jul. 18, 2024, from URL biotransformer.ca/new) which predicts the metabolic biotransformations of small molecules using a database of known metabolic reactions; MetaSite (MOLECULAR DISCOVERY LTD., "MetaSite," www.moldiscovery.com. Retrieved Jul. 18, 2024, from URL moldiscovery.com/software/metasite/)_which predicts metabolic transformations related to cytochrome P450 and flavin-containing monooxygenase mediated reactions in phase I metabolism; and Lhasa Meteor *Nexus* (LHASA LIMITED, "Metabolite identification and analysis," www.lhasalimited.org. Retrieved Jul. 18, 2024, from URL Ihasalimited.org/products/meteor-*nexus*.htm) offers prediction of metabolic pathways and metabolite structures using a range of machine learning models, which covers phase I and phase II biotransformations of small molecules.

Examples A1-1 to A1-15 in Table 13, examples A39-1 to A39-11 in Table 14, examples D1-1 toD1-15 in Table 15, and examples E1-1 to E1-15 in Table 16 may afford certain therapeutic advantages resulting from greater metabolic stability, for example increased in vivo half-life, reduced dosage requirements, improved drug bioactivation and covalent binding, reduced CYP450 inhibition (competitive or time dependent), or an improvement in therapeutic index or tolerability.

A person with ordinary skill may make additional deuterated analogs of Example A1 with different combinations of $Y^1$-$Y^{14}$ in Table 13, additional deuterated analogs of Example A39 with different combinations of $Y^1$-$Y^{11}$ in Table 14, Example D1 with different combinations of $Y^1$-$Y^{15}$ in Table 15, and additional deuterated analogs of Example E1 with different combinations of $Y^1$-$Y^{15}$ in Table 16. Such additional deuterated analogs may provide similar therapeutic advantages that may be achieved by the deuterated analogs.

Biological Assay Section 1

KAT2A/B Assay Protocol:

A) Compound Preparation

1) Prepare 10 mM stock solutions in 100% DMSO from solid material.
2) Serial dilute 10 mM, 1 mM, 0.1 or 0.01 mM compound stocks 3-fold in 100% DMSO for 11-point dose response.

B) Reagent Preparation

1) Prepare 1× assay buffer containing 40 mM bis tris propane pH 8.0, 10 mM NaCl, 0.5 mM EDTA, and 0.002% Tween-20.
2) Dilute Histone peptide (CPC Scientific) and KAT enzyme together in assay buffer to 1.25×.
3) Dilute AcCoA (Sigma) in assay buffer to 5×.

C) Enzyme Reaction

1) Final reaction conditions for each KAT assay in a 100 ul assay reaction volume:
   i) KAT2A 0.5 nM, 1 uM AcCoA, 5 uM H3 1-21 peptide, 90-minute reaction
   ii) KAT2B 0.5 nM, 1 uM AcCoA, 5 uM H3 1-21 peptide, 90-minute reaction
2) Add 2 ul of diluted compound series to the assay plate (96-well round-bottom polypropylene plates) or 2 ul of DMSO for control wells.
3) Add 11 uL of 10% formic acid to 100% effect (HPE) control wells.
4) Add 80 ul of 1.25× Histone peptide/KAT mix to the assay plate via Multidrop Combi (ThermoFisher). Incubate 15 min at room temperature.
5) Add 20 ul of 5× AcCoA to the assay plate via Multidrop Combi.
6) Stop the reaction after the indicated time with the addition of 11 ul of 10% formic acid via Multidrop Combi.
7) Each reaction was analyzed using Rapid Fire mass spectrometry platform. This methodology leverages an Agilent 6495 triple quadrupole (QQQ) mass spectrometer coupled to a RapidFire model 365 to specifically capture and measure KAT2 acetyltransferase activity, converting AcCoA (substrate) to CoA (product).

D) Rapid Fire Settings

1) Pump1: 6 mM octylammonium acetate, flow rate: 1.5 ml/min; Pump2: 25% acetonitrile, 25% acetone, flow rate: 0.8 ml/min; Pump3: 25% acetonitrile, 25% acetone, flow rate: 0.8 ml/min
2) Aspirate 600 ms; Load Time 4500 ms; Elute Time 8000 ms; Re-equilibrate 600 ms 3) Area under the curve (AUC) for both substrate and product peaks was determined for KAT2 at M.W. 809.6 [Substrate+H]+ and 767.3 [Product+H]+with a +/−1 Da tolerance, respectively.

E) Data Analysis

1) Acetyltransferase activity (% of DMSO control) was calculated by: ((AUCProduct/AUCsubstrate)−AUCHPE)/(AUCZPE−AUCHPE))*100

2) Ki values were determined by fitting the % acetyltransferase activity at each inhibitor concentration to the Morrison equation for tightbinding competitive inhibitors using Pfizer proprietary curve fitting software.

Materials

KAT enzymes were expressed using a baculovirus expression system and purified at Pfizer, La Jolla. Histone H3 (1-21) peptide (ARTKQTARKSTGGKAPRKQLA, SEQ ID NO:3) was purchased from CPC Scientific (Sunnyvale, CA). Acetyl coenzyme A was purchased from Sigma-Aldrich (St. Louis, MO). All other biochemical reagents were purchased from Sigma-Aldrich or ThermoFisher Scientific (Waltham, MA).

KAT Reactions

KAT assays were performed at room temperature in assay buffer containing 1 μM AcCoA, 5 μM histone peptide, 40 mM bis tris propane pH 8.0, 10 mM NaCl, 0.5 mM EDTA 0.002% Tween-20. 80 ul of 1.25× Histone peptide/enzyme mix was added to a 96-well round-bottom polypropylene assay plate containing 2 ul of serially diluted test compound in 100% dimethyl sulfoxide (DMSO). To start the reaction, 20 ul of 5× AcCoA solution was added to the assay plate. KAT assays were terminated after 90 minutes with the addition of 11 ul of 10% formic acid. All assays used histone H3 (1-21) peptide. The final enzyme concentration for each KAT was as follows: KAT2A, 0.5 nM; KAT2B, 0.5 nM. 1). Each reaction was analyzed using Rapid Fire mass spectrometry platform. This methodology leverages an Agilent 6495 triple quadrupole (QQQ) mass spectrometer coupled to a RapidFire model 365 to specifically capture and measure KAT2 acetyltransferase activity, converting AcCoA (substrate) to CoA (product).

Data Processing and Analysis

Area under the curve (AUC) for both substrate and product peaks was determined for KAT2 at M.W. 809.6 [Substrate+H]+ and 767.3 [Product+H]+with a +/−1 Da tolerance, respectively. Acetyltransferase activity (% of DMSO control) was calculated by: $((AUC_{Product}/AUC_{substrate})-AUC_{HPE})/(AUC_{ZPE}-AUC_{HPE}))*100$. Ki values were determined by fitting the % acetyltransferase activity at each inhibitor concentration to the Morrison equation for tight-binding competitive inhibitors using Pfizer proprietary curve fitting software.

KAT2A and KAT2B Ki's are provided in Table 17 below.

TABLE 17

| Compound | KAT2A Ki at 1 μM AcCoA (nM) | KAT2B Ki at 1 μM AcCoA (nM) |
|---|---|---|
| A1 | 0.47 | 2.65 |
| A2 | 2745.86 | N/D |
| A3 | 1438.68 | N/D |
| A4 | 4.12 | N/D |
| A5 | 1801.47 | N/D |
| A6 | 0.54 | 1.21 |
| A7 | 1.25 | N/D |
| A8 | >399.87 | N/D |
| A9 | 0.84 | N/D |
| A10 | >999.88 | N/D |
| A11 | >999.88 | N/D |
| A12 | 1.78 | N/D |
| A13 | 95.98 | N/D |

TABLE 17-continued

| Compound | KAT2A Ki at 1 μM AcCoA (nM) | KAT2B Ki at 1 μM AcCoA (nM) |
|---|---|---|
| A14 | 1.32 | N/D |
| A15 | >999.88 | N/D |
| A16 | 1.39 | 2.43 |
| A17 | >999.88 | N/D |
| A18 | 750.92 | N/D |
| A19 | 2.40 | N/D |
| A20 | 2.53 | N/D |
| A21 | >99.88 | N/D |
| A22 | 0.34 | N/D |
| A23 | 0.57 | 2.85 |
| A24 | 15.38 | N/D |
| A25 | 0.68 | N/D |
| A26 | 29.08 | N/D |
| A27 | 0.16 | N/D |
| A28 | 1.41 | N/D |
| A29 | 0.11 | N/D |
| A32 | 0.84 | N/D |
| A33 | >99.87 | N/D |
| A34 | 0.21 | N/D |
| A35 | >99.88 | N/D |
| A36 | 0.10 | N/D |
| A37 | 0.02 | N/D |
| A38 | 0.02 | N/D |
| A39 | 0.35 | N/D |
| A40 | >99.88 | N/D |
| A42 | 0.41 | N/D |
| A43 | >99.88 | N/D |
| B1 | 80.49 | N/D |
| B2 | 0.13 | 0.13 |
| B3 | 236.44 | N/D |
| B4 | 0.14 | 0.15 |
| B5 | 0.09 | N/D |
| B6 | 746.12 | N/D |
| B7 | 3.78 | N/D |
| B8 | 716 | N/D |
| B9 | 209.03 | N/D |
| B10 | 0.15 | N/D |
| B11 | 516.64 | N/D |
| B12 | 0.18 | N/D |
| B13 | 0.14 | 0.35 |
| B14 | 1.83 | N/D |
| B15 | 660.38 | N/D |
| B16 | 0.08 | N/D |
| B17 | 0.10 | N/D |
| B18 | 16.15 | N/D |
| B19 | 34.67 | N/D |
| B20 | 0.05 | 0.06 |
| B21 | 81.67 | N/D |
| B22 | 0.09 | N/D |
| B23 | >999.88 | N/D |
| B24 | 0.09 | N/D |
| B25 | 72.85 | N/D |
| B26 | 0.06 | N/D |
| B27 | 103.48 | N/D |
| B28 | 0.14 | 0.19 |
| B29 | 221.22 | N/D |
| B30 | 0.09 | N/D |
| B31 | 0.04 | N/D |
| B32 | 0.85 | N/D |
| B33 | 27.60 | N/D |
| B34 | 0.04 | N/D |
| B35 | 0.04 | N/D |
| C1 | 0.43 | N/D |
| C2 | 0.05 | N/D |
| C3 | 0.05 | 0.06 |
| C4 | 0.26 | 0.14 |
| C5 | 0.17 | 0.18 |
| C6 | 2.75 | 14.80 |
| C7 | 0.07 | 0.04 |
| C8 | 13.60 | N/D |
| C9 | 0.06 | 0.17 |
| C11 | 2.22 | N/D |
| C12 | 0.50 | 0.93 |
| C13 | 23.45 | N/D |

TABLE 17-continued

| Compound | KAT2A Ki at 1 μM AcCoA (nM) | KAT2B Ki at 1 μM AcCoA (nM) |
|---|---|---|
| C14 | 1.41 | 5.62 |
| C15 | 1271.53 | N/D |
| C16 | 0.08 | 0.06 |
| C17 | 2748.57 | N/D |
| C18 | 0.10 | 0.31 |
| C19 | 0.12 | 0.80 |
| C20 | 708.10 | N/D |
| C21 | 0.09 | 0.11 |
| C22 | 0.14 | N/D |
| C23 | 6.57 | N/D |
| C24 | 0.34 | 0.22 |
| C25 | 0.14 | 0.55 |
| C26 | 338.06 | N/D |
| C27 | 0.16 | 0.53 |
| C28 | 301.98 | N/D |
| C29 | 0.14 | 0.47 |
| C30 | 237.90 | N/D |
| C31 | 0.02 | N/D |
| C32 | 4.51 | N/D |
| C34 | 321.46 | N/D |
| C35 | 0.14 | N/D |
| C36 | 118.36 | N/D |
| C37 | 0.06 | N/D |
| C38 | 0.09 | N/D |
| C39 | 20.44 | N/D |
| C40 | 0.02 | 0.07 |
| C41 | 4.10 | N/D |
| C42 | >99.88 | N/D |
| C43 | 0.06 | N/D |
| C44 | >99.88 | N/D |
| C45 | 0.11 | N/D |
| C46 | 2.16 | N/D |
| C47 | 0.33 | N/D |
| C48 | 0.21 | N/D |
| C49 | >99.88 | N/D |
| C50 | 0.19 | N/D |
| C51 | 0.40 | N/D |
| C52 | 0.48 | N/D |
| C53 | 0.10 | N/D |
| C54 | 0.04 | N/D |
| C55 | 0.11 | N/D |
| C56 | >99.87 | N/D |
| C57 | 0.05 | N/D |
| C58 | 0.11 | N/D |
| C59 | 12.11 | N/D |
| C60 | 0.04 | N/D |
| C61 | 0.07 | N/D |
| C62 | >99.88 | N/D |
| C63 | 0.08 | N/D |
| C64 | >99.88 | N/D |
| C65 | 0.16 | N/D |
| C66 | 11.79 | N/D |
| C67 | 0.07 | N/D |
| C68 | 13.25 | N/D |
| C69 | 0.04 | N/D |
| C70 | 0.04 | N/D |
| C71 | 0.01 | N/D |
| C72 | 45.36 | N/D |
| C73 | 0.05 | N/D |
| C74 | >99.88 | N/D |
| C75 | 0.17 | N/D |
| C76 | 46.01 | N/D |
| C77 | 0.05 | N/D |
| C78 | 0.08 | N/D |
| C79 | 0.06 | N/D |
| C80 | 0.11 | N/D |
| C81 | 31.15 | N/D |
| C82 | 0.07 | N/D |
| C83 | 0.08 | N/D |
| C84 | >99.88 | N/D |
| C85 | 0.17 | N/D |
| C86 | >99.88 | N/D |
| C87 | 0.07 | N/D |
| C88 | 0.21 | N/D |

TABLE 17-continued

| Compound | KAT2A Ki at 1 μM AcCoA (nM) | KAT2B Ki at 1 μM AcCoA (nM) |
|---|---|---|
| C89 | 0.16 | N/D |
| C90 | 0.05 | N/D |
| C91 | 0.06 | N/D |
| D1 | 4.05 | N/D |
| D2 | 70.26 | 46.78 |
| D4 | 25.07 | N/D |
| D5 | 12.78 | 58.78 |
| D6 | 1.08 | N/D |
| D7 | 3.57 | 6.44 |
| D8 | 925.77 | N/D |
| D9 | 6.76 | N/D |
| D10 | 9.48 | 22.17 |
| D11 | 91.86 | N/D |
| D12 | 12.44 | N/D |
| D13 | 10.76 | N/D |
| D14 | 8.31 | N/D |
| D15 | 8.87 | N/D |
| D17 | 2.64 | N/D |
| E1 | 0.15 | 0.38 |
| E2 | 0.66 | N/D |
| E3 | 0.03 | 0.02 |
| E4 | 0.08 | 0.21 |
| E5 | 0.31 | N/D |
| E6 | 52.96 | N/D |
| E7 | 26.59 | N/D |
| E8 | 0.29 | N/D |
| E9 | 0.21 | N/D |
| E10 | 26.39 | N/D |
| E11 | 1.70 | N/D |
| F1 | 12.88 | N/D |
| F2 | 9.11 | N/D |
| F3 | 2.48 | N/D |
| G1 | 2.55 | N/D |
| G2 | 1.68 | N/D |
| G3 | 2.15 | N/D |
| G4 | 1.30 | N/D |
| G5 | 0.17 | N/D |
| H3 | 18.29 | 32.93 |
| H4 | 42.79 | N/D |
| H5 | 9037.89 | N/D |
| H6 | 35.06 | 63.57 |
| H7 | 1588.13 | N/D |
| H8 | 347.55 | N/D |
| H9 | 33.02 | 114.60 |
| H10 | 26417.96 | N/D |
| H11 | 1102.17 | N/D |
| H12 | >99.88 | N/D |
| I1 | 24.46 | N/D |
| I2 | 1969.24 | N/D |
| I3 | 1432.90 | N/D |
| I4 | 24.17 | N/D |
| I5 | 13.57 | N/D |
| I6 | 387.00 | N/D |
| I7 | 24.45 | N/D |
| I8 | 1364.92 | N/D |
| I9 | 410.80 | N/D |
| I10 | 6.29 | N/D |
| I11 | 163.40 | N/D |
| I12 | 20.59 | 20.29 |
| I13 | 25.04 | N/D |
| I14 | 33.92 | N/D |
| I15 | >99.88 | N/D |
| I16 | 0.03 | N/D |
| I17 | 0.02 | N/D |
| I18 | >99.88 | N/D |
| I19 | 13.71 | N/D |
| I20 | 26.29 | N/D |
| J1 | 0.41 | 0.74 |
| J2 | 61.57 | N/D |
| J3 | 841.61 | N/D |
| J4 | 0.30 | N/D |
| J5 | 0.19 | N/D |
| J6 | >999.88 | N/D |
| J7 | 0.26 | 0.46 |

TABLE 17-continued

| Compound | KAT2A Ki at 1 μM AcCoA (nM) | KAT2B Ki at 1 μM AcCoA (nM) |
|---|---|---|
| J8 | 0.74 | N/D |
| J9 | 2.16 | N/D |
| J10 | 0.27 | 0.49 |
| J11 | 0.08 | N/D |
| J12 | 25.77 | N/D |
| J13 | 0.14 | 0.62 |
| J14 | 284.37 | N/D |
| J15 | 27.33 | N/D |
| J16 | 0.08 | N/D |
| K1 | 0.15 | N/D |
| K2 | 1.21 | N/D |
| K3 | 0.19 | 0.56 |
| K4 | 0.70 | 0.94 |
| K5 | 75.69 | N/D |
| K6 | 1.13 | N/D |
| L1 | 0.16 | N/D |
| L2 | >99.88 | N/D |
| L3 | 0.21 | N/D |

Biological Assay Section 2

Protein Preparation

Molecular Biology—KAT2A: A codon optimized DNA sequence (for expression in insect cells) encoding amino acid residues 1 to 837 (Uniprot Q92830-1) of human KAT2A gene was synthesized by GenScript USA Inc (Piscataway, New Jersey, USA). This was ligated into a modified pFastBac vector designed to encode an N-terminal hexahistidine tag followed by a tobacco etch virus protease (TEV) cleavage site and by the KAT2A sequence. The resulting protein sequence is listed below:

```
                                          (SEQ ID NO.: 1)
MASHHHHHHDYDGATTENLYFQGSMAEPSQAPTPAPAAQPRPLQSPAPA

PTPTPAPSPASAPIPTPTPAPAPAPAAAPAGSTGTGGPGVGSGGAGSGG

DPARPGLSQQQRASQRKAQVRGLPRAKKLEKLGVFSACKANETCKCNGW

KNPKPPTAPRMDLQQPAANLSELCRSCEHPLADHVSHLENVSEDEINRL

LGMVVDVENLFMSVHKEEDTDTKQVYFYLFKLLRKCILQMTRPVVEGSL

GSPPFEKPNIEQGVLNFVQYKFSHLAPRERQTMFELSKMFLLCLNYWKL

ETPAQFRQRSQAEDVATYKVNYTRWLCYCHVPQSCDSLPRYETTHVFGR

SLLRSIFTVTRRQLLEKFRVEKDKLVPEKRTLILTHFPKFLSMLEEEIY

GANSPIWESGFTMPPSEGTQLVPRPASVSAAVVPSTPIFSPSMGGGSNS

SLSLDSAGAEPMPGEKRTLPENLTLEDAKRLRVMGDIPMELVNEVMLTI

TDPAAMLGPETSLLSANAARDETARLEERRGIIEFHVIGNSLTPKANRR

VLLWLVGLQNVFSHQLPRMPKEYIARLVFDPKHKTLALIKDGRVIGGIC

FRMFPTQGFTEIVFCAVTSNEQVKGYGTHLMNHLKEYHIKHNILYFLTY

ADEYAIGYFKKQGFSKDIKVPKSRYLGYIKDYEGATLMECELNPRIPYT

ELSHIIKKQKEIIKKLIERKQAQIRKVYPGLSCFKEGVRQIPVESVPGI

RETGWKPLGKEKGKELKDPDQLYTTLKNLLAQIKSHPSAWPFMEPVKKS

EAPDYYEVIRFPIDLKTMTERLRSRYYVTRKLFVADLQRVIANCREYNP

PDSEYCRCASALEKFFYFKLKEGGLIDK*
```

Molecular Biology—KAT2B: A codon optimized DNA sequence (for expression in insect cells) encoding amino acid residues 2 to 832 (Uniprot Q92831-1) of human KAT2B gene was synthesized by GenScript USA Inc (Piscataway, New Jersey, USA). This was ligated into a modified pFastBac vector designed to encode an N-terminal hexahistidine tag followed by a tobacco etch virus protease (TEV) cleavage site and by the KAT2B sequence. The resulting protein sequence is listed below:

```
                                           (SEQ ID NO: 2)
MASHHHHHHDYDGATTENLYFQGSSEAGGAGPGGCGAGAGAGAGPGALP

PQPAALPPAPPQGSPCAAAAGGSGACGPATAVAAAGTAEGPGGGGSARI

AVKKAQLRSAPRAKKLEKLGVYSACKAEESCKCNGWKNPNPSPTPPRAD

LQQIIVSLTESCRSCSHALAAHVSHLENVSEEEMNRLLGIVLDVEYLFT

CVHKEEDADTKQVYFYLFKLLRKSILQRGKPVVEGSLEKKPPFEKPSIE

QGVNNFVQYKFSHLPAKERQTIVELAKMFLNRINYWHLEAPSQRRLRSP

NDDISGYKENYTRWLCYCNVPQFCDSLPRYETTQVFGRTLLRSVFTVMR

RQLLEQARQEKDKLPLEKRTLILTHFPKFLSMLEEEVYSQNSPIWDQDF

LSASSRTSQLGIQTVINPPPVAGTISYNSTSSSLEQPNAGSSSPACKAS

SGLEANPGEKRKMTDSHVLEEAKKPRVMGDIPMELINEVMSTITDPAAM

LGPETNFLSAHSARDEAARLEERRGVIEFHVVGNSLNQKPNKKILMWLV

GLQNVFSHQLPRMPKEYITRLVFDPKHKTLALIKDGRVIGGICFRMFPS

QGFTEIVFCAVTSNEQVKGYGTHLMNHLKEYHIKHDILNFLTYADEYAI

GYFKKQGFSKEIKIPKTKYVGYIKDYEGATLMGCELNPRIPYTEFSVII

KKQKEIIKKLIERKQAQIRKVYPGLSCFKDGVRQIPIESIPGIRETGWK

PSGKEKSKEPRDPDQLYSTLKSILQQVKSHQSAWPFMEPVKRTEAPGYY

EVIRFPMDLKTMSERLKNRYYVSKKLFMADLQRVFTNCKEYNPPESEYY

KCANILEKFFFSKIKEAGLIDK
```

Baculovirus Production

To produce recombinant protein in insect cells, the Bac-to-Bac baculovirus expression system (ThermoFisher) was utilized. KAT2A and KAT2B plasmids were transformed into *E. coli* DH10Bac competent cells, and plated on agar plates containing 50 ug/mL Kanamycin, 7 ug/mL Gentamicin, 10 ug/mL Tetracycline, and 100 ug/mL Bluo-Gal. Single white colonies were picked and grown to saturation overnight. Recombined viral DNA incorporating KAT2A or KAT2B genes was isolated, and transfected into 4 mL of *Spodoptera frugiperda* (Sf9) insect cells. Cells were cultured for 72 hours at 27° C. High titer virus was generated by two passages of infecting 50 mL culture of Sf9 cells at density of 2E6/mL, culturing them for 72 hours at 27° C., and collecting the supernatant containing amplified virus by centrifugation at 2000×g for 5 minutes. Amplified virus was stored in the presence of 2% fetal bovine serum (FBS) and 50 ug/mL Gentamycin at 4° C. for up to 6 months before being used or discarded.

Protein Expression

Recombinant KAT2A or KAT2B proteins were expressed by infecting 4 L of *Spodoptera frugiperda* (Sf21) insect cells with 8 mL of amplified baculovirus at cell density of 2E6/mL and culturing the cells for 72 hours at 27° C. in flasks. Cell pellets were harvested by centrifugation at 3000×g for 20 minutes and stored at −80° C. for up to 1 month prior to protein purification.

Protein Purification

All purification steps were performed at 4° C. KAT2A or KAT2B recombinant protein purification was initiated by resuspending and solubilizing each cell pellet in Lysis buffer (50 mM Tris pH 8.0, 250 mM NaCl, 0.25 mM TCEP, complete protease inhibitor tablets EDTA-free [Roche]), using a ratio of 4 mL of buffer per 1 g of cells. Cell lysates were then centrifuged at 15,000×g for 1 hour. Supernatants (clarified lysates) were mixed with 5 mL of pre-equilibrated (in Lysis buffer) nickel resin (ProBond, Life Technologies), and allowed to batch bind for 2 hours. The resin was washed with IMAC Wash Buffer (50 mM Tris pH 7.4, 400 mM NaCl, 40 mM imidazole, 0.25 mM TCEP), and bound KAT2A or KAT2B protein eluted with IMAC Elution buffer (50 mM Tris pH 7.4, 400 mM NaCl, 250 mM imidazole, 0.25 mM TCEP). TEV protease (1:100 molar ratio) was added to IMAC-eluted proteins, which were subsequently dialyzed overnight against Dialysis buffer (50 mM Tris pH 7.4, 250 mM NaCl, 40 mM imidazole, 0.25 mM TCEP). Cleaved KAT2A or KAT2B proteins were isolated by passing dialyzed samples over 5 mL of nickel resin pre-equilibrated in Dialysis buffer and collecting the flow-throughs. Protein samples were further purified by passing through a gel filtration chromatography column (Sepax SEC SRT-500) pre-equilibrated in Protein Delivery buffer (25 mM Hepes pH 7.5, 250 mM NaCl, 0.25 mM TCEP). Finally, target proteins were concentrated to 2.5 mg/mL using Amicon Ultra centrifugal filter units (Ultra-15 MWCO 30 kDa), flash-frozen in liquid nitrogen, and stored at -80° C. for up to 6 months.

Acetyltransferase Biochemical Assay

To determine the inhibition of KAT enzymatic activity by test compounds, assay reactions were conducted in a volume of 100 pL in 96-well round-bottom polypropylene assay plate. The reactions were performed in assay buffer (40 mM bis tris propane, pH 8, 10 mM NaCl, 0.5 mM EDTA, 0.002% Tween-20).

Reactions were set up with 1 μM Acetyl coenzyme A, 5 uM of histone H3(1-21) (0.5 nM KAT2A and KAT2B), 11-point, 3× dilution series of the test compounds were prepared in DMSO; a volume of 2 uL was transferred into assay plates before adding enzyme and substrates to start the plate. Positive (no compound, DMSO only, ZPE) and negative (addition of formic acid, HPE) control reactions were included on the same plates and received the same amount of DMSO as the compound treated wells. After adding all reagents, the plates were sealed with adhesive seals and incubated for 90 min at room temperature. Reactions were quenched with 11 ul of 10% formic acid. Each reaction was analyzed using Rapid Fire mass spectrometry platform. This methodology leverages an Agilent 6495 triple quadrupole (QQQ) mass spectrometer coupled to a RapidFire model 365 to specifically capture and measure KAT2 acetyltransferase activity, converting AcCoA (substrate) to CoA (product). Area under the curve (AUC) for both substrate and product peaks was determined for KAT2 at M.W. 809.6 [Substrate+H]+ and 767.3 [Product+H]+with a +/−1 Da tolerance, respectively. Acetyltransferase activity (% of DMSO control) was calculated by: $((AUC_{Product}/AUC_{substrate})-AUC_{HPE})/(AUC_{ZPE}-AUC_{HPE}))*100$. Ki values were determined by fitting the % acetyltransferase activity at each inhibitor concentration to the Morrison equation for tight-binding competitive inhibitors using Pfizer proprietary curve fitting software.

KAT2A Primary Cell-based Screening Assays

Cell Culture (HT1080)

Human fibrosarcoma cell line HT1080 was obtained from American Type Culture Collection (ATCC), Manassas, VA USA, Cat. HT-1080 (ATCC® CCL-121™). Cells were cultured in MEM (Thermo Fisher Scientific/Gibco Life Technologies Cat. #11-095-080) plus 10% (v/v) FBS (Thermo Fisher Scientific/Gibco Life Technologies Cat. #26140-079) and1% Penicillin-Streptomycin (Thermo Fisher Scientific/Gibco Life Technologies Cat. #15070063) at 37° C. in 5% $CO_2$.

H3K9AC Sandwich ELISA Assay

HT1080 cells were trypsinized, cell viability count performed, and cells suspended in complete media at 100,000 cells/ml. Cells were seeded (100 pl/well) into Greiner Bio-One CELLSTAR 96-well polystyrene flat bottom cell culture microplate (Thermo Fisher Scientific Cat. #07-000-162) at a density of 10,000 cells/well. Cells were incubated for 16 hours at 37° C. at 5% $CO_2$. Compound dilution plates were prepared in 96-well, clear U-bottom, polypropylene plates (Corning 3365) in 100% DMSO at 10 mM stock concentration in duplicate, using 10-point serial dilution (1:3). Compounds were diluted to 1:200 in growth medium and 25 μl from intermediate compound plates were added to each well of the cell plates using a Beckman FX liquid handling system such that the highest compound concentration tested was 10 μM final, with a 0.1% final DMSO concentration in the total volume of 125 μl. Plates were incubated for 24 hours at 37° C. and 5% $CO_2$. Plates were centrifuged at 2500 rpm for 5 minutes and medium was removed. 100 μL 0.4N HCL (Thermo Fisher Scientific Cat #SA56-1) was added to each well and plates were shaken for 60 minutes at 4 C to lyse cells. 38 μl 0.4N Sodium phosphase dibasic pH12.5 (Thermo Fisher Scientific Cat #S375-212) containing 2 mM Sodium Butyrate (Millipore TR1008G) and 3 mM Phenylmethanesulfonyl-fluoride (Sigma 93482) was added to each well to neutralize lysates.

Cell lysate plates were mixed for 5 minutes at room temperature on shaker and immediately frozen at −80C overnight. Cell lysates were thawed and 50 pL/well was transferred to ELISA plates (Total Histone H3 mouse (Cell Signaling Technology Cat #14269) mAb-coated Corning 1×8 strip-well, white, 96-well plates (Corning 2485)). After 2 hours room temperature incubation, plates were washed six times with PBS/0.05% Tween Wash Buffer using a BioTek plate washer. 50 μL of Histone H3K9AC rabbit detection mAb (Cell Signaling Technology Cat #9649S) diluted 1:1000 in blocking buffer (Thermo Fisher Scientific Cat #37542) was added to each well and incubated for 2 hours at room temperature. After washing, 50 pL anti-rabbit IgG, HRP-Linked antibody (Cell Signaling Technology Cat #7074) diluted 1:1000 in blocking buffer was added to each well and incubated for 60 minutes at room temperature. Following incubation, plates were washed as described above. 50 μL of luminescent GLO substrate reagent (R&D System Cat #DY993) was added to each well and incubated for 10 minutes at room temperature. Plates were read on the PHERAstar plate reader using the 96-well with Luminescent reading mode. IC50 values were calculated using a four-parameter fit with GraphPad Prism version 9.5.1 or in-house modified IDBS ActivityBase data analyzing package.

Stock compounds were stored as 10 mM compound solution in 100% DMSO at room temperature in the Pfizer Sample Logistic, La Jolla, CA.

Cell Culture (MM.1S)

Human B lymphoblast cell line MM.1S was obtained from American Type Culture Collection (ATCC), Manassas, VA USA, Cat. MM.1S (ATCC® CRL-2974™). Cells were cultured in RPMI (Thermo Fisher Scientific/Gibco Life Technologies Cat. #111875-093) plus 10% (v/v) FBS (Thermo Fisher Scientific/Gibco Life Technologies Cat.

#26140-079) and 1% Penicillin-Streptomycin (Thermo Fisher Scientific/Gibco Life Technologies Cat. #15070063) at 37° C. in 5% $CO_2$.

MM1.S 10 day Proliferation Assay

MM1.S cells were trypsinized cell viability count performed, and cells suspended in complete media at 5,556 cells/ml. Cells were then seeded (90 pl/well) into a 96-well round black/clear bottom, ULA (Ultra-Low Attachment surface plate (Corning cat #4520) at a density of 500 cells/well. Cells were then incubated for 16 hours at 37° C. and 5% $CO_2$. Compound dilution plates were prepared in 96-well, clear U-bottom, polypropylene plates (Corning 3365) in 100% DMSO at 10 mM stock concentration in duplicate wells, using a 10-point serial dilution (1:3 dilutions). Compounds were diluted to 1:100 in growth medium. Then 10 μl of diluted compounds were added to each well of the cell plates using a Beckman FX liquid handling system such that the highest compound concentration tested was 10 μM final, with a 0.1% final DMSO concentration in the total volume of 100 μl. Plates were incubated for 10 total days at 37° C. and 5% COH. Fresh media containing compound was refreshed at 5 days treatment. Finally, the treatment plates were removed from the incubator and 100 μl of CellTiter-Glo Luminescent reagent was added to each well, and plates were equilibrated in the dark for 30 minutes. Plates were read on the PHERAstar plate reader using the 96-well with Luminescent reading mode. $IC_{50}$ values were calculated using a four-parameter fit with GraphPad Prism version 9.5.1 or in house modified IDBS ActivityBase data analyzing package.

Stock compounds were stored as 10 mM compound solution in 100% DMSO at room temperature in the Pfizer Sample Logistic, La Jolla, CA.

The results are shown in Table 18 below:

TABLE 18

| Compound | HT1080 IC50 (nM) | MM.1S IC50 (nM) |
|---|---|---|
| A1 | 8.16 | 45.28 |
| A2 | N/D | N/D |
| A3 | >10000 | N/D |
| A4 | 76.43 | 147.41 |
| A5 | N/D | 7557.38 |
| A6 | 7.67 | 92.43 |
| A7 | 4.45 | 30.88 |
| A8 | N/D | N/D |
| A9 | 11.11 | 135.38 |
| A10 | >1000 | N/D |
| A11 | >1000 | N/D |
| A12 | 28.83 | 367.78 |
| A13 | >1000 | N/D |
| A14 | 4.88 | 157.17 |
| A15 | 295.88 | N/D |
| A16 | 13.43 | 144.11 |
| A17 | N/D | N/D |
| A18 | N/D | N/D |
| A19 | 10.03 | 430.60 |
| A20 | 9.30 | 186.42 |
| A21 | >1000 | >10000 |
| A22 | 4.33 | 101.10 |
| A23 | 6.36 | 60.01 |
| A24 | N/D | N/D |
| A25 | 4.22 | 25.97 |
| A26 | 95.62 | N/D |
| A27 | 7.6 | 26.3 |
| A28 | 53.6 | N/D |
| A29 | >1,000.0 | N/D |
| A30 | >1,000.0 | N/D |
| A31 | 9.3 | N/D |
| A32 | 4.5 | 31.3 |
| A33 | >1,000.0 | N/D |
| A34 | 1.4 | 7.8 |
| A35 | >1,000.0 | N/D |
| A36 | 0.7 | 3.5 |
| A37 | >1,000.0 | N/D |
| A38 | 4.0 | 18.3 |
| A39 | 6.4 | 29.7 |
| A40 | >1,000.0 | >1,000.0 |
| A41 | 3.0 | 9.2 |
| A42 | 8.4 | 37.4 |
| A43 | >1,000.0 | >1,000.0 |
| B1 | 561.60 | N/D |
| B2 | 3.14 | 7.51 |
| B3 | N/D | N/D |
| B4 | 3.12 | 8.38 |
| B5 | 9.93 | 13.35 |
| B6 | >1000 | N/D |
| B7 | 20.91 | 101.70 |
| B8 | >1000 | N/D |
| B9 | N/D | N/D |
| B10 | 15.71 | N/D |
| B11 | N/D | N/D |
| B12 | 1.40 | 14.07 |
| B13 | 1.96 | 38.79 |
| B14 | 49.09 | 552.66 |
| B15 | N/D | N/D |
| B16 | 2.68 | 11.56 |
| B17 | 3.49 | 41.74 |
| B18 | 120.80 | 1266.94 |
| B19 | N/D | N/D |
| B20 | 0.93 | 1.76 |
| B20 | N/D | N/D |
| B22 | 2.38 | 2.51 |
| B24 | 0.9 | N/D |
| B26 | 2.2 | 7.4 |
| B28 | 2.7 | 5.0 |
| B30 | 1.7 | 4.2 |
| B31 | 2.1 | 1.4 |
| B32 | 18.2 | N/D |
| B34 | 3.1 | 8.4 |
| B35 | 0.6 | 1.3 |
| C1 | 18.01 | 36.82 |
| C2 | 3.56 | 5.37 |
| C3 | 3.84 | 6.22 |
| C4 | 1.25 | 5.49 |
| C5 | 10.20 | 12.64 |
| C6 | 89.66 | N/D |
| C7 | 5.79 | 17.53 |
| C8 | 141.82 | N/D |
| C9 | 6.96 | 13.65 |
| C11 | 21.59 | 252.68 |
| C12 | 11.02 | 89.57 |
| C13 | 941.87 | N/D |
| C14 | 17.68 | 63.74 |
| C15 | >1000 | N/D |
| C16 | 23.18 | 81.84 |
| C17 | >1000 | N/D |
| C18 | 2.34 | 30.55 |
| C19 | 5.06 | 66.65 |
| C20 | >1000 | >10000 |
| C21 | 1.11 | 13.69 |
| C22 | 4.49 | 7.80 |
| C23 | 91.76 | N/D |
| C24 | 2.77 | 9.83 |
| C25 | 1.71 | 9.29 |
| C26 | N/D | N/D |
| C27 | 2.62 | 12.77 |
| C28 | N/D | N/D |
| C29 | 1.86 | 7.11 |
| C30 | N/D | N/D |
| C31 | 1.78 | 2.85 |
| C32 | 40.75 | N/D |
| C35 | 3.5 | 7.8 |
| C37 | 3.0 | 11.0 |
| C38 | 6.1 | 10.2 |
| C40 | 1.5 | 3.5 |
| C41 | 39.8 | N/D |
| C43 | 2.8 | 4.2 |
| C44 | >1,000.0 | N/D |

TABLE 18-continued

| Compound | HT1080 IC50 (nM) | MM.1S IC50 (nM) |
|---|---|---|
| C45 | 9.6 | 52.4 |
| C46 | 7.4 | 62.9 |
| C47 | 2.9 | 14.3 |
| C48 | 4.7 | 18.9 |
| C50 | 0.6 | 1.4 |
| C51 | 3.0 | 4.0 |
| C52 | 8.5 | N/D |
| C53 | 7.0 | N/D |
| C54 | 0.9 | 1.4 |
| C55 | 0.8 | 2.5 |
| C56 | >1,000.0 | N/D |
| C57 | 4.1 | 7.6 |
| C58 | 3.4 | 8.1 |
| C59 | 440.5 | N/D |
| C60 | 3.2 | 5.0 |
| C61 | 0.2 | 0.7 |
| C63 | 2.2 | 5.2 |
| C65 | 3.8 | 31.8 |
| C67 | 4.4 | 13.8 |
| C69 | 0.6 | N/D |
| C70 | 73.5 | N/D |
| C71 | 1.0 | N/D |
| C72 | >1,000.0 | N/D |
| C73 | 4.8 | N/D |
| C74 | >1,000.0 | N/D |
| C75 | 4.5 | N/D |
| C76 | 485.2 | N/D |
| C77 | 6.0 | N/D |
| C78 | >1,000.0 | N/D |
| C79 | 3.6 | N/D |
| C80 | 2.6 | N/D |
| C81 | 135.1 | N/D |
| C82 | 8.7 | N/D |
| C83 | 2.4 | N/D |
| C85 | 6.1 | N/D |
| C87 | 1.5 | N/D |
| C88 | 10.3 | N/D |
| C89 | 6.5 | N/D |
| C90 | 3.3 | N/D |
| C91 | 5.4 | N/D |
| D1 | 52.78 | 418.51 |
| D2 | 30.55 | N/D |
| D4 | 88.05 | N/D |
| D5 | 30.36 | N/D |
| D6 | 19.04 | N/D |
| D7 | 45.08 | N/D |
| D8 | N/D | N/D |
| D9 | 67.23 | N/D |
| D10 | 39.18 | 193.37 |
| D11 | 98.54 | 496.77 |
| D12 | 66.59 | N/D |
| D13 | 44.99 | 416.70 |
| D14 | 25.92 | 171.37 |
| D15 | 83.46 | N/D |
| D17 | 14.42 | N/D |
| E1 | 5.06 | 31.46 |
| E2 | 10.77 | 61.35 |
| E3 | 0.84 | 3.82 |
| E4 | 8.38 | 15.92 |
| E5 | 4.83 | 11.95 |
| E6 | 98.96 | 203.44 |
| E7 | 34.18 | 201.63 |
| E8 | 4.76 | 16.45 |
| E9 | 3.89 | 6.32 |
| E10 | 21.32 | 126.34 |
| E11 | 24.20 | 73.38 |
| F1 | 41.53 | 124.69 |
| F2 | 71.19 | 625.41 |
| F3 | 8.5 | 94.5 |
| G1 | 55.20 | N/D |
| G2 | 9.38 | 56.94 |
| G3 | 20.50 | N/D |
| G4 | 30.36 | N/D |
| G5 | 9.5 | 36.2 |
| H3 | 57.18 | 218.67 |
| H4 | 111.79 | 384.85 |

TABLE 18-continued

| Compound | HT1080 IC50 (nM) | MM.1S IC50 (nM) |
|---|---|---|
| H5 | N/D | N/D |
| H6 | 84.25 | 679.07 |
| H7 | 339.61 | N/D |
| H8 | N/D | N/D |
| H9 | 90.03 | N/D |
| H10 | N/D | N/D |
| H11 | N/D | N/D |
| H12 | >1,000.0 | N/D |
| H13 | 9.7 | N/D |
| I1 | 41.86 | N/D |
| I2 | N/D | N/D |
| I3 | >6675.32 | N/D |
| I4 | 23.23 | 248.52 |
| I5 | 58.96 | 88.71 |
| I6 | N/D | N/D |
| I7 | 41.43 | N/D |
| I8 | N/D | N/D |
| I9 | N/D | N/D |
| I10 | 63.77 | 359.33 |
| I11 | 3126.80 | N/D |
| I12 | 6.43 | 122.83 |
| I13 | 24.53 | 237.64 |
| I14 | 18.13 | 69.31 |
| I15 | >1,000.0 | N/D |
| I16 | 5.8 | 31.1 |
| I17 | 0.6 | 1.8 |
| I18 | >1,000.0 | N/D |
| I19 | 7.1 | N/D |
| I20 | 51.9 | N/D |
| J1 | 14.86 | 8.43 |
| J2 | 789.74 | N/D |
| J3 | N/D | N/D |
| J4 | 18.59 | 23.60 |
| J5 | 2.76 | 21.54 |
| J6 | 746.30 | N/D |
| J7 | 3.88 | 20.58 |
| J8 | 2.71 | N/D |
| J9 | 4299.66 | N/D |
| J10 | 19.46 | 51.99 |
| J11 | 8.85 | N/D |
| J12 | >1000 | N/D |
| J13 | 10.24 | N/D |
| J14 | N/D | N/D |
| J15 | 450.63 | N/D |
| J16 | 4.97 | 34.16 |
| K1 | 5.19 | N/D |
| K2 | 28.65 | N/D |
| K3 | 4.29 | 15.88 |
| K4 | 4.56 | 45.63 |
| K5 | 488.57 | N/D |
| K6 | 5.73 | N/D |
| L1 | 7.01 | 55.97 |
| L3 | 6.9 | 43.4 |

It will be apparent to those skilled in the art that various modifications and variations may be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All references cited herein, including patents, patent applications, papers, textbooks, and the like, and the references cited therein, to the extent that they are not already, are hereby incorporated by reference in their entireties. In the event that one or more of the incorporated literature and similar materials differs from or contradicts this application, including but not limited to defined terms, term usage, described techniques, or the like, this application controls.

The invention claimed is:

1. A compound,

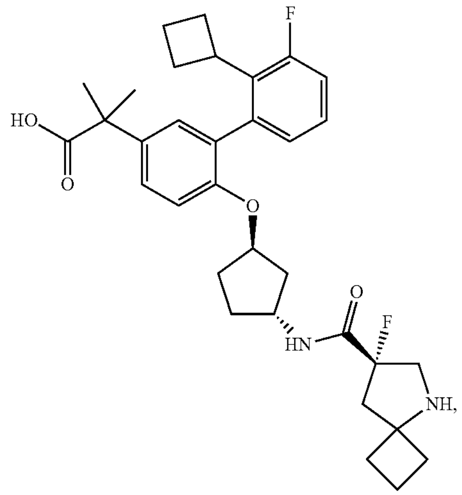 [SMILES: CC(C)(C(=O)O)c1ccc(O[C@@H]2CC[C@@H](NC(=O)[C@@]3(F)CNC4(CCC4)C3)C2)c(-c2cccc(F)c2C2CCC2)c1]

or a pharmaceutically acceptable salt thereof.

2. The compound of claim 1, that is:

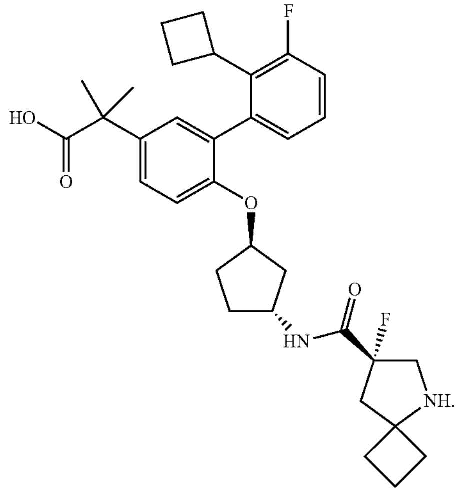 [SMILES: CC(C)(C(=O)O)c1ccc(O[C@@H]2CC[C@@H](NC(=O)[C@@]3(F)CNC4(CCC4)C3)C2)c(-c2cccc(F)c2C2CCC2)c1]

3. The pharmaceutically acceptable salt of the compound of claim 1.

4. A pharmaceutical composition comprising the compound according to claim 1 or a pharmaceutically acceptable salt thereof, and at least one pharmaceutically acceptable excipient.

5. A compound,

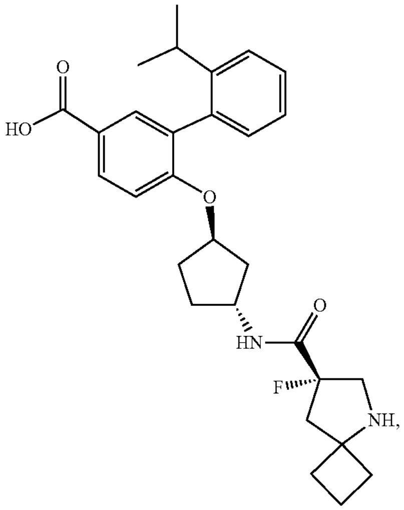 [SMILES: CC(C)c1ccccc1-c1cc(C(=O)O)ccc1O[C@@H]1CC[C@@H](NC(=O)[C@@]2(F)CNC3(CCC3)C2)C1]

or a pharmaceutically acceptable salt thereof.

6. The compound of claim 5, that is:

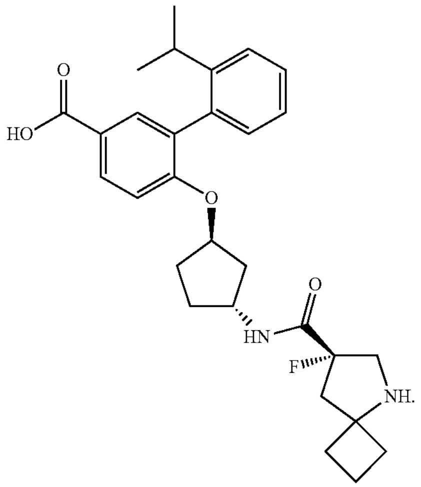 [SMILES: CC(C)c1ccccc1-c1cc(C(=O)O)ccc1O[C@@H]1CC[C@@H](NC(=O)[C@@]2(F)CNC3(CCC3)C2)C1]

7. The pharmaceutically acceptable salt of the compound of claim 5.

8. A pharmaceutical composition comprising the compound according to claim 5, or a pharmaceutically acceptable salt thereof, and at least one pharmaceutically acceptable excipient.

9. A compound,

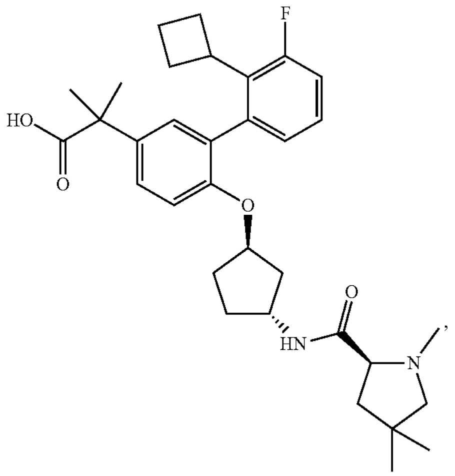 [SMILES: CN1CC(C)(C)C[C@H]1C(=O)N[C@@H]1CC[C@@H](Oc2ccc(C(C)(C)C(=O)O)cc2-c2cccc(F)c2C2CCC2)C1]

or a pharmaceutically acceptable salt thereof.

10. The compound of claim 9, that is:

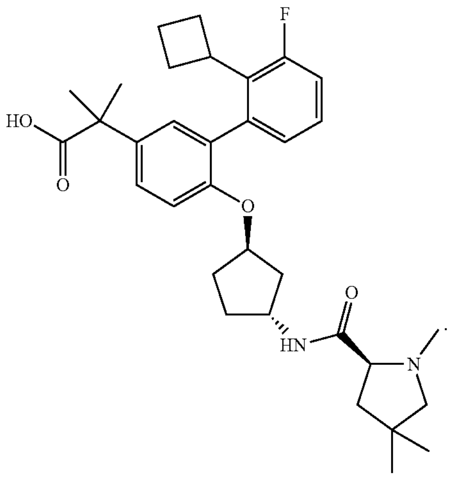 [SMILES: CN1CC(C)(C)C[C@H]1C(=O)N[C@@H]1CC[C@@H](Oc2ccc(C(C)(C)C(=O)O)cc2-c2cccc(F)c2C2CCC2)C1]

11. The pharmaceutically acceptable salt of the compound of claim 9.

12. A pharmaceutical composition comprising the compound according to claim 9, or a pharmaceutically acceptable salt thereof, and at least one pharmaceutically acceptable excipient.

13. A compound,

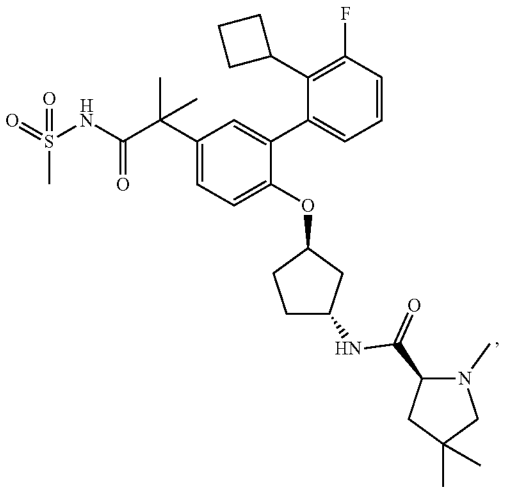 [SMILES: CN1CC(C)(C)C[C@H]1C(=O)N[C@@H]1CC[C@@H](Oc2ccc(C(C)(C)C(=O)NS(C)(=O)=O)cc2-c2cccc(F)c2C2CCC2)C1]

or a pharmaceutically acceptable salt thereof.

14. The compound of claim 13, that is:

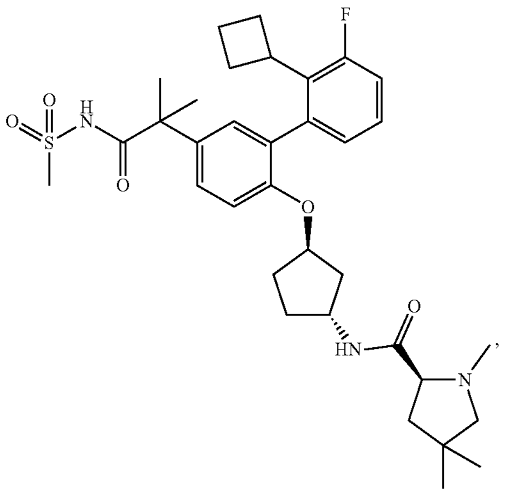 [SMILES: CN1CC(C)(C)C[C@H]1C(=O)N[C@@H]1CC[C@@H](Oc2ccc(C(C)(C)C(=O)NS(C)(=O)=O)cc2-c2cccc(F)c2C2CCC2)C1]

15. The pharmaceutically acceptable salt of the compound of claim 13.

16. A pharmaceutical composition comprising the compound according to claim 13, or a pharmaceutically acceptable salt thereof, and at least one pharmaceutically acceptable excipient.

* * * * *